US012011000B2

(12) United States Patent
Abdelgaffar et al.

(10) Patent No.: US 12,011,000 B2
(45) Date of Patent: Jun. 18, 2024

(54) AFFINITY MOLECULES AND METHODS FOR THEIR USE

(71) Applicant: IMPETUS AGRICULTURE, INC., St. Louis, MO (US)

(72) Inventors: Heba Mohamed Yassen Abdelgaffar, Knoxville, TN (US); Constanze Hahnfeld, Einbeck (DE); Juan Luis Jurat-Fuentes, Knoxville, TN (US); Erik Jongedijk, Einbeck (DE); Jeffrey M. Staub, Wildwood, MO (US); Stefan Meldau, Einbeck (DE)

(73) Assignee: IMPETUS AGRICULTURE, INC., St. Louis, MO (US)

( * ) Notice: Subject to any disclaimer, the term of this patent is extended or adjusted under 35 U.S.C. 154(b) by 0 days.

(21) Appl. No.: 18/346,437

(22) Filed: Jul. 3, 2023

(65) Prior Publication Data
US 2024/0041049 A1 Feb. 8, 2024

Related U.S. Application Data

(63) Continuation-in-part of application No. PCT/US2022/017993, filed on Feb. 25, 2022.

(60) Provisional application No. 63/241,896, filed on Sep. 8, 2021, provisional application No. 63/133,386, filed on Jan. 3, 2021.

(51) Int. Cl.
| | |
|---|---|
| *A01N 63/50* | (2020.01) |
| *A01P 7/04* | (2006.01) |
| *C07K 14/325* | (2006.01) |
| *C07K 16/12* | (2006.01) |
| *C07K 16/28* | (2006.01) |

(52) U.S. Cl.
CPC .............. *A01N 63/50* (2020.01); *A01P 7/04* (2021.08); *C07K 14/325* (2013.01); *C07K 16/1278* (2013.01); *C07K 16/28* (2013.01); *C07K 2317/31* (2013.01); *C07K 2317/569* (2013.01); *C07K 2317/92* (2013.01); *C07K 2319/55* (2013.01)

(58) Field of Classification Search
None
See application file for complete search history.

(56) References Cited

U.S. PATENT DOCUMENTS

| 8,354,371 B2 | 1/2013 | Oppert et al. |
| 2020/0229445 A1 | 7/2020 | Bowen et al. |
| 2020/0308256 A1 | 10/2020 | Yapara et al. |
| 2022/0386594 A1 | 12/2022 | Oren-Benaroya et al. |

FOREIGN PATENT DOCUMENTS

| EP | 3415010 A1 | 12/2018 |
| WO | 2012025602 A1 | 3/2012 |
| WO | 2017015613 A1 | 1/2017 |
| WO | 2022155619 A2 | 7/2022 |

OTHER PUBLICATIONS

International Search Report and Written Opinion, PCTUS2022/017993, filed Feb. 25, 2022, 14 pages, mailed Jul. 25, 2022.
Fitches et al., "Fusion proteins containing insect-specific toxins as pest control agents: snowdrop lectin delivers fused insecticidal spider venom toxin to insect haemolymph following oral ingestion", Journal of Insect Physiology, vol. 50, pp. 61-71 2

FIG. 6

FR1
QVQLQESGGGRSVQSGGSLRLSCAAS

CDR1
GIDVNRNA

FR2
MGWFRQAPGTEREFVAG

CDR2
VRWSDAYTDYADSVK

FR3
GRFTISRDNNKNTVYLQMGSLEAGDTALYYCAA

CDR3
GLLDVQYVRQAAGYSY

FR4
WGQGTQVTVSS

Applicability:

Hundreds of insecticidal proteins
(Cry's, Cyt's, Vip's etc.)

Flexibility

Thousands of membrane proteins
Multispecific affinity molecules

Specificity

Insect-specific sequences as target sites
Reduction of off-target effects

Control

Cry1Ac

Cry1Ac + Nanobody

FIG. 15A

| | | | | | | | | | | | | | | | | | | | | | | | | | | | | End | Organism |
|---|---|---|---|---|---|---|---|---|---|---|---|---|---|---|---|---|---|---|---|---|---|---|---|---|---|---|---|---|---|
| T | N | E | T | K | S | S | A | E | L | Y | F | L | K | T | V | L | Q | Q | K | D | G | I | E | D | G | L | G | 57 | |
| . | . | . | . | . | . | . | . | . | . | . | . | . | . | . | . | . | . | . | . | . | . | . | . | . | G | . | . | 211 | SPODOPTERA FRUGIPERDA |
| . | . | . | . | A | S | . | . | . | . | . | . | . | I | R | . | . | . | . | . | . | . | I | . | . | . | . | . | 211 | SPODOPTERA EXIGUA |
| . | E | K | A | S | . | . | . | . | . | . | . | . | I | . | . | . | . | . | . | . | . | . | . | . | G | . | . | 210 | SPODOPTERA LITURA |
| . | E | K | A | T | . | . | . | . | . | . | . | . | . | . | . | . | . | . | . | . | . | . | . | . | G | . | . | 225 | HELICOVERPA ARMIGERA |
| . | E | K | A | T | . | . | . | . | . | . | . | . | . | . | . | . | . | . | . | . | . | . | . | L | G | . | . | 157 | HELIOTHIS VIRESCENS |
| . | E | N | A | T | . | . | . | . | . | . | . | . | . | . | N | . | . | . | . | . | . | . | . | L | G | . | . | 157 | HELIOTHIS VIRESCENS |
| V | . | G | . | — | . | . | . | . | . | . | . | . | R | . | . | . | . | . | S | . | . | . | . | . | G | . | . | 233 | BOMBYX MANDARINA |
| V | . | G | . | — | . | . | . | . | . | . | . | . | R | . | . | . | . | . | S | . | . | . | . | . | G | . | . | 247 | BOMBYX MANDARINA |
| V | . | G | . | — | . | . | . | . | . | . | . | . | R | . | . | . | . | . | S | . | . | . | . | . | G | . | . | 232 | BOMBYX MANDARINA |
| V | . | G | . | — | . | . | . | . | . | . | . | . | R | . | . | . | . | . | S | . | . | . | . | . | G | . | . | 232 | BOMBYX MORI |
| S | E | N | A | S | . | . | . | . | . | . | . | . | . | . | . | . | . | . | . | . | . | . | . | L | G | . | . | 222 | TRICHOPLUSIA NI |
| . | E | N | A | T | . | . | . | . | . | . | . | . | . | . | N | . | . | . | N | . | . | . | . | L | G | . | . | 229 | HELIOTHIS VIRESCENS |
| . | . | G | . | — | . | . | . | . | . | . | . | . | R | . | . | . | . | . | S | . | . | . | . | . | G | . | . | 219 | MANDUCA SEXTA |
| . | . | . | S | T | . | . | . | . | . | . | F | . | . | . | . | . | . | R | . | R | E | . | . | . | G | . | . | 156 | OSTRINIA FUMACALIS |
| . | . | G | . | — | . | . | . | Q | . | . | . | . | R | . | . | . | . | . | S | . | . | . | . | . | G | . | . | 219 | MANDUCA SEXTA |
| S | P | N | A | S | . | . | . | . | . | . | . | . | . | V | . | . | . | . | . | . | . | I | . | . | G | . | I | 214 | ARCTIA PLANTAGINIS |
| E | . | A | . | — | . | . | . | . | . | . | . | . | . | N | . | . | . | . | S | . | . | . | . | . | G | . | . | 152 | OPEROPHETERA BRUMATA |
| . | E | D | S | . | . | . | . | . | . | . | . | . | I | . | . | . | . | . | S | . | . | . | . | . | G | . | . | 222 | PAPILIO MACHAON |
| L | P | N | A | S | . | . | . | . | . | . | . | . | I | . | . | . | . | R | S | . | . | . | . | . | G | . | . | 202 | ARCTIA PLANTAGINIS |
| L | P | N | A | S | . | . | . | . | . | . | . | . | I | . | . | . | . | R | S | . | . | . | . | . | G | . | . | 202 | ARCTIA PLANTAGINIS |
| . | G | . | P | V | . | . | . | . | . | . | . | . | T | . | . | I | . | K | S | . | . | . | K | . | . | . | I | 168 | HELIOTHIS VIRESCENS |
| Q | G | N | P | V | . | . | . | . | . | . | . | . | T | Q | . | . | . | K | S | . | . | . | K | . | . | . | I | 1,513 | PAPILIO MACHAON |
| . | E | D | S | . | . | . | . | . | . | . | . | . | I | . | . | . | . | . | S | . | . | . | . | . | G | . | . | 903 | PAPILIO MACHAON |
| . | . | . | S | A | . | . | . | . | . | . | . | . | K | N | I | . | . | R | S | . | . | . | . | . | G | . | . | 230 | HYPOSMOCOMA KAHAMA... |
| . | G | . | P | V | . | . | . | . | . | . | . | . | T | . | . | I | . | K | S | . | . | . | H | . | . | . | I | 231 | HELIOTHIS VIRESCENS |
| . | . | V | S | R | . | . | . | . | . | . | . | . | T | . | . | . | . | P | K | . | . | . | . | . | G | . | . | 213 | BICYCLUS ANYNANA |
| . | G | . | P | V | . | . | . | . | . | . | . | . | T | . | . | . | . | . | S | . | . | . | H | . | . | . | . | 231 | HELIOTHIS VIRESCENS |
| . | T | N | A | T | . | . | . | . | . | . | . | . | . | . | . | . | R | . | R | . | N | . | . | . | G | . | . | 225 | CHILO SUPPRESSALIS |
| . | . | . | S | R | . | . | . | . | D | . | . | . | V | E | . | . | . | . | . | P | . | . | . | . | G | . | . | 215 | APHANTOPUS HYPERANTUS |
| I | G | . | P | . | . | . | . | . | . | . | . | . | T | Q | . | I | . | R | S | . | . | . | H | . | . | . | I | 215 | ARCTIA PLANTAGINIS |
| I | G | . | P | . | . | . | . | . | . | . | . | . | T | Q | . | I | . | R | S | . | . | . | H | . | . | . | I | 215 | ARCTIA PLANTAGINIS |
| . | . | . | S | R | . | . | . | . | . | . | . | . | V | H | . | . | . | . | . | N | K | . | L | . | E | . | . | 252 | OSTRINIA FUMACALIS |
| N | . | S | . | . | . | . | . | . | . | . | . | . | . | E | . | . | K | A | . | E | S | . | N | . | . | . | I | 232 | CLUNIO MARINUS |
| Q | . | R | P | I | T | . | . | . | . | . | . | . | T | . | . | I | . | R | S | . | . | . | D | . | . | . | I | 223 | SPODOPTERA EXIGUA |
| . | . | . | . | T | . | . | . | . | F | . | . | T | . | V | I | . | R | E | . | . | S | . | H | . | . | . | I | 92 | RPHAGOLETIS ZOPHYRIA |
| . | . | . | . | T | . | . | . | . | F | . | . | T | . | V | I | . | R | E | . | . | S | . | H | . | . | . | I | 249 | RPHAGOLETIS POMONELLA |
| . | E | N | S | T | . | . | . | . | . | . | . | . | V | . | . | . | . | . | S | . | . | . | . | . | G | . | . | 222 | PAPILIO POLYTES |
| Q | G | N | P | V | G | . | . | . | . | . | . | . | T | Q | . | . | . | R | . | . | . | . | H | . | . | . | I | 845 | PAPILIO XUTHUS |
| . | E | H | S | T | . | . | . | . | . | . | . | . | V | . | . | . | . | . | S | . | . | . | . | . | G | . | . | 235 | PAPILIO XUTHUS |
| . | E | H | S | T | . | . | . | . | . | . | . | . | V | R | . | . | . | . | S | . | . | . | . | . | G | . | . | 240 | VANESSA LAMEAMEA |
| . | E | H | S | T | . | . | . | . | . | . | . | . | V | . | . | . | . | . | S | . | . | . | . | . | G | . | . | 222 | PAPILIO XUTHUS |
| . | . | . | . | T | . | . | . | . | F | . | . | T | . | V | I | . | R | E | R | . | S | . | H | . | . | . | I | 90 | RHAGOLETIS ZEPHYRIA |
| S | S | D | A | R | . | . | . | . | . | . | . | . | . | V | . | I | . | A | R | . | S | . | H | . | . | . | I | 207 | RHAGOLETIS ZEPHYRIA |
| P | . | A | . | — | . | . | . | . | . | . | . | . | I | . | . | . | . | . | S | . | . | . | . | . | G | . | . | 232 | GALLERIA MELLONELLA |
| . | G | . | P | . | . | . | . | . | . | . | . | . | T | Q | . | I | . | R | . | . | . | . | H | . | . | . | . | 223 | TRICHOPLUSIA NI |
| A | . | G | S | R | . | . | . | . | . | . | . | . | V | N | V | . | . | R | Y | . | N | . | D | N | . | . | I | 306 | EUMELA JAPONICA |
| E | . | A | G | — | . | . | . | . | . | . | . | . | I | R | . | . | . | . | S | . | . | . | . | . | G | . | . | 228 | AMYELOIS TRANSITELLA |
| P | S | D | A | R | . | . | . | . | . | . | . | . | . | D | . | I | . | A | . | . | N | . | L | . | . | . | T | 206 | CLUNIO MARINUS |
| N | G | T | L | V | . | . | . | . | . | . | . | . | . | . | . | . | . | K | . | S | . | . | . | D | . | . | I | 221 | PLUTELLA XYLOSTELLA |
| E | . | A | S | — | . | . | . | . | . | . | . | . | I | R | . | . | . | . | S | . | . | . | . | . | G | . | . | 231 | AMYELOIS TRAMSITELLA |
| . | G | . | P | V | . | . | . | . | . | . | . | . | T | . | . | I | . | R | S | . | . | . | H | . | . | . | I | 222 | HELICOVERPA ARMIGERA |

FIG. 15B

| ID | | Pos | Sequence |
|---|---|---|---|
| XP_022830993.1 | (+) | 177 | . . . . . . . . P D . V . . . . . G E V A . N — E . . |
| CAD7099953.1 | (+) | 167 | . . . . A T . R . . . . . N V . . G A T G L D T S A . |
| CAD701567.1 | (+) | 146 | . . . . . Y . R . . . . . . . I D . K K N T . V . T N D |
| XP_004520944.1 | (+) | 193 | . . . . . Y . R . . . . . . . I D . K K N T . V . T N D |
| XP_022130796.1 | (+) | 153 | . . . . A . . . P . . D N . V . . G — Q T E N L N . T |
| XP_023306153.1 | (+) | 206 | F . . . . . F . R . . . . . . . I D . K . K A . D F M Q V |
| XP_037821703.1 | (+) | 207 | . . . . . F . R . . . . . . . I D . K . K A . D F M Q V |
| XP_031772806.1 | (+) | 139 | . . . A K . R . . . . L . I D . S Q Q I . N T N . |
| XP_034477986.1 | (+) | 188 | F . . . . Y . R . . . . . N . D T . Q S . A I . . A |
| XP_037703197.1 | (+) | 128 | . . . . A . . . P . . V N . V . . ———————— . K A |
| XP_037703197.1 | (+) | 168 | . . . . A . . . P . . V N . V . . ———————— . K A |
| XP_037303205.1 | (+) | 168 | . . . . A . . . P . . V N . V . . ———————— . K A |
| XP_034830885.1 | (+) | 161 | . . . . A . . E P G . K . . . V . . G E S V N — I S A . |
| GBP68512.1 | (+) | 192 | . . . . A . . E P G . N E . . . . . G G . S L . S ——— |
| TMW48594.1 | (+) | 201 | . . . . . Y . R . . . . . . . I D . K . . . L . . . S G |
| XP_026488393.1 | (+) | 161 | . . . . A . . D Q S . L N . V . . G E S V N — I T S . |
| XP_015199677.1 | (+) | 163 | . . . . . . . K . . . F N . V . . G E S A . ——— . S B |
| XP_015020622.1 | (+) | 25 | . . . . A T . R D . . . N . I . . E . S D E . N . . L |
| XP_011189038.1 | (+) | 195 | . . . . . Y . R . . . . . V N . . . K V N K S N I F |
| XP_014099642.1 | (+) | 195 | . . . . . Y . R . . . . . I N . . . K V N K S N I F |
| XP_015020623.1 | (+) | 165 | . . . . A T . R D . . . N . I . . E . S D E . N . . L |
| NP_001124343.1 | (+) | 157 | . . . . T Q . L P . . R N . V . . G Q S D N — L T E . |
| XP_028027180.1 | (+) | 195 | . . . . T Q . L P . . R N . V . . G Q S D N — L T E . |
| XP_013107992.1 | (+) | 103 | . . . . . Y . L K . . . . . . I D . K L . S . E S Q N . |
| XP_029409029.1 | (+) | 194 | . I . . . Y . R . . . . . I N . K ——— V N K S N I F |
| XP_020283043.1 | (+) | 166 | . . . . . I . R I . . Q . . . I ——— . I N S N . . V |
| XP_014489453.1 | (+) | 182 | . . . . A . . L . . . . . . S C V N S A G M . N I T V R |
| KDR22766.1 | (+) | 117 | . . . . . T . A . . . D M . F D . K K T E . S . N A S |
| KDR22766.1 | (+) | 703 | . . . . . T . D K . . D M . I D . K K . Y N N S . ——— |
| XP_037361620.1 | (+) | 128 | . . . . . I . H P . . V N . V . . ——————— . K A |
| XP_014367544.1 | (+) | 165 | . . . . A L . D . S . L N . V . . G E A V N — N S S . |
| XP_013107991.1 | (+) | 157 | . . . . . Y . R K . . . . . . I D . K L . S . E S Q N S |
| XP_037303204.1 | (+) | 168 | . . . . . I . H P . . V N . V . . ——————— . H A |
| XP_005168545.1 | (+) | 199 | . V . . . T Y . R . . . . . S . F D . K . . F I I N M . M |
| XP_022130795.1 | (+) | 161 | . . . . A L . D P S . D N . V . . G Q S V N — A S Q . |
| XP_012151996.1 | (+) | 105 | . . . . A K . K . . . . S . I D . G R K M S N N V S . |
| XP_035433139.1 | (+) | 175 | . . . . . . . P D . V . . . V . . G — E V A N S S L . |
| XP_032592356.1 | (+) | 172 | . . . . A T . R P . . . . I N . S . . T N L I A G T |
| XP_012151994.1 | (+) | 105 | . . . . A K . K . . . . S . I D . G R K M S N N V S . |
| EDW02819.1 | (+) | 270 | . . . . A T . R P . . . . I N . S . . T N L I A G T |
| EFN84817.1 | (+) | 154 | . . . . . T . L . . . . . . S C I N S S S V . N I I V R |
| XP_011138894.1 | (+) | 172 | . . . . . T . L . . . . . . S C I N S S S V . N I I V R |
| XP_025157940.1 | (+) | 182 | . . . . . T . L . . . . . . S C I N S S S V . N I I V R |
| GBP42005.1 | (+) | 187 | . . . . A . C D P D . N E . . . . . N N F L . A ——————— |
| XP_012261871.1 | (+) | 156 | . . . . . Y . R . . . . . . S C V A . S S V — S N S N |
| XP_012261870.1 | (+) | 160 | . . . . . Y . R . . . . . . S C V A . S S V — S N S N |
| XP_015590862.1 | (+) | 126 | . . . . . K . . P . . . . V N . G K S E N S T S N V |
| XP_012245180.1 | (+) | 157 | . . . . A K . R . . . A . . V D . S Q K I . S . S M F |
| XP_033187040.1 | (+) | 157 | . . . . A K . R . . . A . . V D . S Q K I . S . S M F |
| XP_033330137.1 | (+) | 157 | . . . . A K . R . . . A . . V D . S Q K I . S . S M F |
| XP_033366390.1 | (+) | 157 | . . . . A K . R . . . A . . V D . S Q K I . S . S M F |
| XP_012171770.1 | (+) | 157 | . . . . A K . R . . . A . . V D . S Q K I . S . S M F |

FIG. 15C

| | | | | | | | | | | | | | | | | | | | | | | | | | | | | | | | | | | | | | | | | | | | | | | | | | | | | | | | | | | | | | | | | | | | | | | |
|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|---|
| I | · | R | P | I | T | · | · | Q | · | · | · | Q | R | · | · | · | R | · | S | · | · | · | · | H | · | · | I | · | 229 | SPODOPTERA LITURA |
| N | · | G | T | L | V | · | · | · | · | · | · | T | · | · | · | · | K | · | S | · | · | · | · | H | · | · | I | · | 222 | PLUTELLA XYLOSTELLA |
| · | · | I | K | T | T | · | · | · | F | · | · | T | · | V | I | · | R | E | · | · | · | S | · | D | · | · | I | · | 203 | CERATITIS CAPITATA |
| · | · | I | K | T | T | · | · | · | F | · | · | T | · | V | I | · | R | E | · | · | · | S | · | D | · | · | I | · | 250 | CERATITIS CAPITATA |
| E | · | G | · | — | — | · | · | · | · | · | · | V | · | · | · | · | R | S | · | D | · | D | N | · | · | I | · | | 205 | PIORIS RAPAE |
| A | · | G | · | V | · | T | · | · | F | · | · | · | I | N | I | I | R | E | · | · | · | · | D | · | D | · | I | · | 265 | LUCILIA CUPRINA |
| A | · | G | · | V | · | T | · | · | F | · | · | · | I | N | I | I | R | E | · | · | · | · | D | · | D | · | I | · | 265 | LUCILIA SERICATA |
| · | S | · | L | R | · | · | · | · | · | · | · | · | V | · | · | · | · | E | · | · | · | S | · | D | · | · | I | · | 201 | APIS FLOREA |
| · | T | V | R | T | T | · | · | · | Y | · | · | T | H | I | I | · | R | E | · | V | D | · | D | · | · | I | · | | 247 | DROSOPHILA INNUBILA |
| A | · | · | S | R | · | · | · | · | Y | · | · | T | Q | · | · | · | R | · | P | · | · | · | · | D | · | · | I | · | 181 | MANDUCA SEXTA |
| A | · | · | S | R | · | · | · | · | Y | · | · | T | Q | · | · | · | R | · | P | · | · | · | · | D | · | · | I | · | 221 | MANDUCA SEXTA |
| A | · | · | S | R | · | · | · | · | Y | · | · | T | Q | · | · | · | R | · | P | · | · | · | · | D | · | · | I | · | 221 | MANDUCA SEXTA |
| A | G | N | P | V | · | · | · | · | · | · | · | S | · | · | · | · | R | R | S | · | · | · | · | H | · | · | I | · | 213 | APHANLOPUS HYPCRANLUS |
| S | · | D | · | · | · | · | · | · | · | · | · | V | · | R | · | · | R | · | I | · | · | · | · | G | · | · | · | · | 245 | EUMELA JAPONICA |
| V | K | T | · | — | — | · | · | · | F | · | · | · | I | N | I | I | R | E | · | · | T | · | D | · | · | I | · | | 259 | SARCOHAGA BULLATA |
| Q | G | N | A | T | · | · | · | · | · | · | · | S | Q | · | · | · | R | · | S | · | · | · | · | H | · | · | I | · | 213 | VANESSA TAMEAMEA |
| S | · | · | · | V | K | · | · | · | · | · | · | T | Q | · | · | · | R | · | S | · | · | · | · | H | · | · | I | · | 218 | AMYELOIS TRANSITELLA |
| N | · | T | D | R | · | · | · | S | · | · | · | Y | V | · | E | · | · | R | E | · | · | Q | · | H | · | · | I | · | 84 | SROSOPHILA MOJAVENSIS |
| · | · | · | S | T | T | · | · | · | F | · | · | T | · | V | I | · | R | E | · | · | · | S | · | D | · | · | I | · | 252 | ZEUGODACUS CUCURBITAE |
| · | · | · | S | T | T | · | · | · | F | · | · | T | · | V | I | · | R | E | · | · | · | S | · | D | · | · | I | · | 252 | BATROCERA OLEAE |
| N | · | T | D | R | · | · | · | S | · | · | · | Y | V | · | E | · | · | R | E | · | · | Q | · | A | · | · | I | · | 224 | DROSOPHILA MOJAVENSIS |
| Q | G | · | A | V | · | · | · | Q | · | · | · | T | E | · | · | · | R | · | S | · | · | · | · | D | · | · | I | · | 210 | BOMBYX MORI |
| Q | · | · | A | V | · | · | · | Q | · | · | · | T | E | · | · | · | R | · | S | · | · | · | · | D | · | · | I | · | 248 | BOMBYX MANDARINA |
| · | A | V | K | · | · | · | · | · | F | · | · | · | I | N | I | · | · | E | · | S | N | · | D | · | · | I | · | | 164 | STOMOXYS CALCITRANS |
| · | · | · | · | T | T | · | · | · | F | · | · | T | · | V | I | · | R | E | · | · | · | S | · | D | · | · | I | · | 251 | BACTROCERA DORSALIS |
| S | · | D | · | R | · | · | · | · | · | · | · | R | · | I | · | · | · | · | · | E | Y | E | S | · | · | · | I | · | 217 | PSEUDOMYRMEX GRACILIS |
| S | · | T | · | R | · | · | · | · | · | · | · | T | · | A | · | · | K | E | · | E | N | · | D | · | · | I | · | | 237 | DINOPONERA QUADRICEPS |
| · | · | Y | · | · | · | · | · | S | · | · | · | Y | · | Y | · | · | N | E | P | · | S | · | · | · | · | · | I | · | 172 | ZOOTERMOPSIS NEVADEMSIS |
| A | · | V | · | · | · | · | · | S | · | · | · | Y | · | Y | · | · | N | E | P | · | S | · | · | · | · | · | V | · | 758 | ZOOTERMOPSIS NEVADEMSIS |
| A | · | · | S | E | · | · | · | · | Y | · | · | T | Q | · | · | · | R | · | P | · | · | · | · | H | · | · | I | · | 181 | MANDUCA SEXTA |
| Q | G | N | P | V | · | · | · | · | · | · | · | T | Q | · | · | · | R | · | S | · | · | · | · | H | · | · | I | · | 217 | PAPILIO NACHAON |
| · | A | V | K | · | · | · | · | · | F | · | · | · | I | N | I | · | · | E | · | S | N | · | D | · | · | I | · | | 218 | STOMOXYS CALCITRANS |
| A | · | · | S | E | · | · | · | · | Y | · | · | T | Q | · | · | · | R | · | P | · | · | · | · | H | · | · | I | · | 221 | MANDUCA SEXTA |
| S | · | · | A | · | · | · | · | · | F | · | · | · | I | N | V | I | · | R | · | · | N | T | · | D | · | · | I | · | 259 | MUSCA DOMESTICA |
| Q | G | N | A | T | · | · | · | · | · | · | · | T | · | V | · | · | R | · | S | N | · | · | · | D | · | · | I | · | 214 | PIERIS RAPAE |
| D | D | Q | H | R | · | · | · | · | · | · | · | · | · | · | · | · | · | E | · | · | S | · | D | · | · | I | · | | 161 | MEGACHILE ROTUNDATA |
| I | D | R | P | I | T | · | · | · | Q | · | · | · | Q | · | V | I | R | · | S | · | · | · | · | H | · | · | I | · | 227 | SPODOPTERA FRUGIPERDA |
| S | · | · | S | D | · | · | · | S | · | · | · | Y | V | · | E | · | · | R | E | · | E | Q | · | A | · | · | I | · | 229 | DROSOPHILA GRIMSHAWI |
| D | D | Q | H | R | · | · | · | · | · | · | · | · | · | · | · | · | · | E | · | · | S | · | D | · | · | I | · | | 161 | MEGACHILE ROTUNDATA |
| S | · | · | S | D | · | · | · | S | · | · | · | Y | V | · | E | · | · | H | E | · | E | Q | · | A | · | · | I | · | 327 | DROSOPHILA GRIMSHAWI |
| H | · | T | · | R | · | · | · | · | · | · | · | T | · | · | · | · | K | E | · | E | N | · | D | · | · | V | · | 211 | HARPEGNATHOS SALTATOR |
| H | · | T | · | R | · | · | · | · | · | · | · | T | · | · | · | · | K | E | · | E | N | · | D | · | · | V | · | 229 | HARPEGNATHOS SALTATOR |
| H | · | T | · | R | · | · | · | · | · | · | · | T | · | · | · | · | K | E | · | E | N | · | D | · | · | V | · | 239 | HARPEGNATHOS SALTATOR |
| D | · | T | · | · | · | · | · | · | · | · | · | V | R | · | · | · | R | · | T | · | · | · | · | G | · | · | V | · | 241 | EUMETA JAPONICA |
| · | T | · | R | N | · | · | · | · | · | · | · | R | R | I | · | · | · | E | A | · | S | · | V | · | · | I | · | | 208 | ATHALIA ROSAE |
| · | T | · | R | N | · | · | · | · | · | · | · | R | R | I | · | · | · | E | A | · | S | · | V | · | · | I | · | | 212 | ATHALIA ROSAE |
| S | K | · | N | R | · | · | · | · | · | · | · | S | · | I | · | · | K | E | · | · | N | · | D | · | · | V | · | 183 | CEPHUS CINCTUS |
| · | K | · | N | R | · | · | · | · | · | · | · | · | V | · | · | · | · | E | · | · | N | · | D | · | · | V | · | | 220 | BOMBUS IMPATIENS |
| · | K | · | N | R | · | · | · | · | · | · | · | · | V | · | · | · | · | E | · | · | N | · | D | · | · | V | · | | 220 | BOMBUS VANCOUVERENSIS |
| · | K | · | N | R | · | · | · | · | · | · | · | · | V | · | · | · | · | E | · | · | N | · | D | · | · | V | · | | 220 | BOMBUS BIFARIUS |
| · | K | · | N | R | · | · | · | · | · | · | · | · | V | · | · | · | · | E | · | · | N | · | D | · | · | V | · | | 220 | BOMBUS VOSNESENKII |
| · | K | · | N | R | · | · | · | · | · | · | · | · | V | · | · | · | · | E | · | · | N | · | D | · | · | V | · | | 220 | BOMBUS TERRESTRIS |

FIG. 15D

NCBI Multiple Sequence Alignment Viewer, Version 1.18.1

| Sequence ID | Start | Alignment |
|---|---|---|
| QUERY 11579 (+) | 1 | |
| XP_035440763.1 (+) | 1,168 | |
| XP_022826291.1 (+) | 1,192 | |
| ADK60914.1 (+) | 1,164 | |
| KAF9406502. (+) | 1,169 | |
| ADV17661.2 (+) | 1,169 | |
| AFJ04291.1 (+) | 1,192 | |
| AEB97395.1 (+) | 1,169 | |
| AFH96949.1 (+) | 1,169 | |
| AGS80251.1 (+) | 1,169 | |
| AEL22856.1 (+) | 1,162 | |
| ABV74206.1 (+) | 1,162 | |
| AFB74171.1 (+) | 1,156 | |
| AAU50668.1 (+) | 1,166 | |
| ABI55359.1 (+) | 1,156 | |
| AFB74174.1 (+) | 1,156 | |
| XP_021195552.1 (+) | 1,156 | |
| ABI55357.1 (+) | 1,156 | |
| ACZ06063.1 (+) | 1,156 | |
| AFB74170.1 (+) | 1,156 | |
| AFC17899.1 (+) | 1,156 | |
| ABF69362.1 (+) | 1,156 | |
| ANZ78200.1 (+) | 1,156 | |
| AKH49609.1 (+) | 1,156 | |
| XP_028026250.1 (+) | 1,148 | |
| AAM69351.2 (+) | 1,156 | |
| AFQ60151.1 (+) | 1,156 | |
| AFB74173.1 (+) | 1,156 | |
| AAV80768.1 (+) | 1,156 | |
| AAK85198.1 (+) | 1,156 | |
| ARQ14731.1 (+) | 403 | |
| ACZ06062.1 (+) | 1,156 | |
| AKH19605.1 (+) | 1,156 | |
| AAQ54935.1 (+) | 1,156 | |
| AFB74172.1 (+) | 1,156 | |
| AVE17268.1 (+) | 1,156 | |
| ABI553/17.1 (+) | 987 | |
| AWJ76614.1 (+) | 1,156 | |
| BAA99404.1 (+) | 1,148 | |
| NP_001037682.1 (+) | 1,148 | |
| AFB74169.1 (+) | 1,156 | |
| BAA99406.1 (+) | 1,148 | |
| ACZ06064.1 (+) | 1,156 | |
| ACY69031.1 (+) | 1,122 | |
| ABI55358.1 (+) | 1,156 | |
| ACY69030.1 (+) | 1,140 | |
| BAA99405.1 (+) | 1,148 | |
| ACZ06065.1 (+) | 1,156 | |

FIG. 16A

| End | Organism |
|---|---|
| 427 | SPODOPTERA FRUGIPERDA |
| 1,694 | SPODOPTERA LITURA |
| 1,617 | SPODOPTERA LITURA |
| 1,589 | SPODOPTERA LITURA |
| 1,595 | SPODOPTERA EXIGUA |
| 1,595 | SPODOPTERA EXIGUA |
| 1,617 | SPODOPTERA LITURA |
| 1,595 | SPODOPTERA EXIGUA |
| 1,595 | SPODOPTERA EXIGUA |
| 1,595 | SPODOPTERA EXIGUA |
| 1,585 | SESARNIA INFERENS |
| 1,585 | SESARNIA NONAGRIOIDES |
| 1,574 | HELICOVERPA ARMIGERA |
| 1,574 | HELICOVERPA ARMIGERA |
| 1,574 | HELICOVERPA ARMIGERA |
| 1,574 | HELICOVERPA ARMIGERA |
| 1,574 | HELICOVERPA ARMIGERA |
| 1,574 | HELICOVERPA ARMIGERA |
| 1,574 | HELICOVERPA ARMIGERA |
| 1,574 | HELICOVERPA ARMIGERA |
| 1,574 | HELICOVERPA ARMIGERA |
| 1,574 | HELICOVERPA ARMIGERA |
| 1,574 | HELICOVERPA ARMIGERA |
| 1,575 | BOMBYX MANDARINA |
| 1,574 | HELICOVERPA ARMIGERA |
| 1,574 | HELICOVERPA ARMIGERA |
| 1,574 | HELICOVERPA ARMIGERA |
| 1,575 | HELIOTHIS VIRESCENS |
| 1,575 | HELIOTHIS VIRESCENS |
| 1,575 | BOMBYX MANDARINA |
| 1,574 | HELICOVERPA ARMIGERA |
| 1,574 | HELICOVERPA ARMIGERA |
| 1,574 | HELICOVERPA ARMIGERA |
| 1,574 | HELICOVERPA ARMIGERA |
| 1,584 | HELICOVERPA PUNCTIGERA |
| 1,574 | HELICOVERPA ARMIGERA |
| 1,574 | HELICOVERPA ARMIGERA |
| 1,569 | BOMBYX MORI |
| 1,569 | BOMBYX MORI |
| 1,574 | HELICOVERPA ARMIGERA |
| 1,569 | BOMBYX MORI |
| 1,574 | HELICOVERPA ARMIGERA |
| 1,574 | HELICOVERPA ARMIGERA |
| 1,574 | HELICOVERPA ARMIGERA |
| 1,574 | HELICOVERPA ARMIGERA |
| 1,569 | BOMBYX MORI |
| 1,571 | HELICOVERPA ARMIGERA |

```
P05068  CR1AC_BACTK  421 PPROGFSHRLSHVSMFRSGFSNSSVSTIRAPMFSWIHRSAEFNNIIASDSITQIPAVKGN 480
P0A370  CR1AB_BACTK  421 PPROGFSHRLSHVSMFRSGFSNSSVSTIRAPMFSWIHRSAEFNNIIPSSQITQIPLTKST 480
B2ZPN5  B2ZPN5_BACTU    1 ------------------------------------------ITQIPAVKAH  10
                                                                    ****.*.

P05068  CR1AC_BACTK  481 FLEN-GSVISGPGFTGGDLVRLNSSGNNIQNRGYIEVPIHFPSTSTRYRVRVRYASVIPI 539
P0A370  CR1AB_BACTK  481 NLGSGTSVVKGPGFTGGDIIRRTSPGQISTLRVNITAP----LSQRYRVRIRYASTTNL 535
B2ZPN5  B2ZPN5_BACTU   11 NLHSGSTVVRGPGFTGGDLLRRTNTGTFADIRVNITGP----LSQRYRVRIRVASTTDL 65
                             *  : *.*   * * ***:******* ****  ******::*::***.**.

P05068  CR1AC_BACTK  540 HLNVWGNSSIFSNTVPATATSLDNLQSSDFGYFESANAFTSSLGN---IVGVRNFSGTA 596
P0A370  CR1AB_BACTK  536 QFHTSIDGRPINQGNFSATMSSGSNLQSGSFRTVGFTTPFNESNGSSVFTLSAHVFNSGN 595
B2ZPN5  B2ZPN5_BACTU   66 QFFTRINGISVNQGNFQRTMNRGGNIESGNFRTAGFSTPFSFSNAQSTFLGTQAFSN-Q 124
                                 :.       * :    ***:.   *    :    *

P05068  CR1AC_BACTK  597 GVIIDRFEFIPVTATLEAEYNLERAQKAVNALFTSTNQLGLKTNVTDYHIDQVSNLVTYL 656
P0A370  CR1AB_BACTK  596 EVYIDRIEFVPAEVTFEAEYDLERAQKAVNELFTSSNQIGLKTDVTDYHIDQVSNLVECL 655
B2ZPN5  B2ZPN5_BACTU  125 EVYIDRIEFVPA------------------------------------------ 136
                          * ****:**.*.
```

FIG. 17A

```
A1E357    A1E357_BACTU       410 PTVRENFINPQNISDRGTANYSQPYESPGLQLKDSETELPEETTERPNYESYSHRLSHIG 469
A0A161VDR8 A0A161VDR8_BACTU  381 EGVEFQNII----------SRSIYRKS--GPIDSFSELPPQDASVSPAIGYSHRLCHAI 427
B2ZPN5    B2ZPN5_BACTU       379 RGVAFQQIGTN--------------HTRIFRNS---GTIDSLDEIPPQDNSGAPWNDYSHVLNHVI 427
                                   *  *:  :            . ****     * ***

A1E357    A1E357_BACTU       470 ILL-------QSRVNVPVYSWTHRSADRTNTIGPNRITQIPMVKASELPQGTIVRGPGF 522
A0A161VDR8 A0A161VDR8_BACTU  428 FLERIS---GPRIAGTVFSWTHRSASPTNETSPSRTIQIPWVKAHTLASGASVIKGPGF 483
B2ZPN5    B2ZPN5_BACTU       428 FVRWPGEIAGSDSWRAPMFSWTHRSADRTNIINPNITIQIPAVKAHNLHSGSTVVRGPGF 497
                                                 ******:. ::  . .*:* ** ***:.   *..* .:****

A1E357    A1E357_BACTU       523 TGGDILRRTNTGGEGPIRVTVNGPLIQRYRIGFRYASTVDFDFFASRGGTIVNNFRLRI 582
A0A161VDR8 A0A161VDR8_BACTU  484 TGGDILRTNSMGELGILRVTFTGRLPQSYVIRFRYASVANRSGTFRYSQPPSYGISFPKI 543
B2ZPN5    B2ZPN5_BACTU       488 TGGDILRRTNTGTFADIRVNITGPLSIQRYRVIRYASTIDLQFFTRINGISVNQGNFQRI 547
                                  ******  *   .  :**.: : * ..  * :****::: .   :* *

A1E357    A1E357_BACTU       583 MNSGDELKYGNEVRRAFTTPETFTQIONIIRTSIQGLSGNGEVYIDKIEIIPVTATEAE 642
A0A161VDR8 A0A161VDR8_BACTU  544 MDAGEPLISRSFAHTLFIPITFSRAQEEFDL-----YI--QSGVYIDRIEFIPVTATEAE 598
B2ZPN5    B2ZPN5_BACTU       548 MNRGGNLESGNFRTAGFSTPFSFSNAQSTFTLGTQAFS--NQEVIIDRIEFVPAEVTFAE 606
                                 *: *  :  ..    . .*:* :.*    :          :::****:*:..  :**

A1E357    A1E357_BACTU       643 VDLERAQEAVNALFINTNPRRLKIIDVDYHIDQVSNLVACLSDEFCLDEKRELLEKVKYA 702
A0A161VDR8 A0A161VDR8_BACTU  599 VDLERAQKAVNALFISTNQLGLKTNVFDYHIDQVSNLVACLSDEFCLDEKRELSEKVKHA 658
B2ZPN5    B2ZPN5_BACTU       607 SDLERAQKAVNALFTSTSQLGLKTNVFGYHIDQVSNLVACLSDEFCLDEKRELSEKVKHA 666
                                 .******:******..*.       . .***************************::*
```

FIG. 17B

AFFINITY MOLECULES AND METHODS FOR THEIR USE

CROSS-REFERENCE TO RELATED APPLICATIONS

This application is a bypass continuation-in-part of International Patent Application PCT/US2022/017993, filed Feb. 25, 2022, which claims priority from U.S. Provisional Application Nos. 63/133,386 filed Jan. 3, 2021, and 63/241,896 filed Sep. 8, 2021 the entire contents of each of which are hereby incorporated by reference.

INCORPORATION BY REFERENCE OF SEQUENCE LISTING

This application contains a Sequence Listing that has been electronically submitted in XML format and is hereby incorporated by reference in its entirety. The XML copy, created on Jul. 3, 2023 and named P14114US02_ST26.txt, is 360,190 bytes in size.

FIELD

This invention relates to the field of insecticidal proteins and their targets, the nucleic acid molecules that encode them, as well as compositions and methods for controlling plant pests.

BACKGROUND

Certain species of microorganisms of the genus *Bacillus* are known to possess pesticidal activity against a range of insect pests. *Bacillus thuringiensis* (Bt) is a gram-positive spore forming soil bacterium characterized by its ability to produce crystalline inclusions that are specifically toxic to certain orders and species of plant pests, including insects, but are harmless to plants and other non-target organisms. For this reason, compositions with *Bacillus thuringiensis* strains, or their insecticidal proteins can be used as environmentally acceptable insecticides to control agricultural insect pests or insect vectors of a variety of human or animal diseases. Crystal (Cry) proteins from *Bacillus thuringiensis* have potent insecticidal activity against predominantly Lepidoptera, Diptera, Coleoptera, Hemiptera and Nematode pests. Based on this property crop plants have been genetically engineered to produce insecticidal proteins from *Bacillus thuringiensis* to thereby exhibit enhanced insect resistance. Sprays and surface applications of microbial insecticides provide an environmentally friendly alternative to synthetic chemical pesticides and can be produced in a cost-effective manner.

A serious threat to the continued efficacy of current insecticidal proteins, such as Cry proteins, whether expressed in transgenic plants or applied over the top on crops or on insect pests, is the evolution of resistance in target pests (Tabashnik et al. 2013, Nat Biotechnol 31, 510-521). At least five different insect species have developed resistance to several Bt toxins, such as Cry toxins, in transgenic crops. The most common resistance mechanism is the reduction in toxin binding to midgut cells, that in different insect species include mutations in Cry toxin receptors such as cadherin, aminopeptidase (APN) and alkaline phosphatase (ALP) (reviewed in Pardo-Lopez et al. 2013, FEMS Microbiol. Rev. 37, 3-22).

Current approaches to address resistance require: (i) identification of new toxins or (ii) targeted modification of existing toxins.

About 952 toxin genes, encoding different entomopathogenic proteinaceous toxins, have been identified and characterized in the Bt strains isolated from different regions of the world (www.lifesci.sussex.ac.uk/Home/Neil_Crickmore/Bt/). The toxins have very different activity spectra against various insect classes and nematodes. Therefore, identifying new toxins against specific targets is tedious, often non-targeted and requires large-scale screens with limited probability of success.

Modifications of existing Cry toxins are mainly limited to specific domains that are required for binding to the target sequence, because other modifications may reduce the stability of the toxins, reduce their specificity or interfere with the mechanisms of toxicity, such as pore formation.

However, neither the development of transgenic plants expressing one or more modified insecticidal toxins, nor developing engineered bacterial strains seems to be flexible enough to allow short-term adjustments to the development of resistances in the insect pest or changes in the pest spectrum. The development of transgenic plants is often very time-consuming and may take up to at least 10 years, thus ruling out modifications or adaptations on a short time scale. Further, and this is true also for bacterial strains that are applied to the surface of plants, alternatives are often missing once a given pest has developed tolerance or even resistance to a certain bacterial toxin.

There remains a need to develop new and effective pest control agents that provide an economic benefit to farmers and that are environmentally acceptable. Particularly needed are control agents that can target to a wider spectrum of insect pests and that efficiently control insect strains that are or could become resistant to existing insect control agents.

SUMMARY OF THE INVENTION

One aspect of the present disclosure encompasses an affinity construct comprising (1) at least one affinity molecule A capable of recognizing, or capable of binding to, or binding to, or being directed to, or being designed to bind to an insect-specific structure in and/or on a target insect, and (2) at least one affinity molecule B capable of binding to, or binding to, or being directed to, or being designed to bind to an insecticidal protein (toxin), wherein the at least one affinity molecule A and the at least one affinity molecule B are optionally separated by a linker L comprising at least one amino acid.

In one aspect, the at least one affinity molecule A of the affinity construct is different from the at least one affinity molecule B.

In some aspects the at least one affinity molecule A of the affinity construct has one or more binding sites (valences) for the same or different insect-specific structures in and/or on a target insect and wherein the at least one affinity molecule B has one or more binding sites (valences) for the same or different insecticidal protein (toxins).

In some aspect the at least one affinity molecule A specifically binds to a receptor, more specifically a membrane-bound receptor, of an inner organ of the target insect.

In some aspects the at least one affinity molecule A specifically binds to a membrane-bound receptor of a digestive tract, of a reproductive organ, or of a nervous system.

In some aspect the affinity construct with at least one affinity molecule A specifically binds to a membrane-bound receptor of a digestive tract, of a reproductive organ, or of a nervous system.

In one aspect the at least one affinity molecule A specifically binds to a fragment from an extracellular loop of NAAT protein.

In one aspect the at least one affinity molecule A specifically binds to a portion of FAW cadherin.

In one aspect the at least the at least one affinity molecule A specifically binds to a portion of integral membrane subunit (Vo) protein complex of the V-ATPase.

In one aspect the at least one affinity molecule A specifically binds to an extracellular loop in ABCC1.

In one aspect the at least one affinity molecule A specifically binds to an extracellular portion of venom dipeptidyl peptidase-4-like isoform X1 or peptide transporter family 1 isoform X1.

In some aspects the insecticidal protein (toxin) is selected from the group consisting of crystal toxins (Cry and Cyt proteins), vegetative insecticidal toxins (Vip proteins), mosquitocidal toxins (Mtx proteins), binary toxins (Bin proteins), Tpp, Mpp, Gpp, App, Spp, Vpa, Vpb, Mcf, Pra, Prb, Xpp, Mpf toxins and secreted insecticidal toxins (Sip proteins), as well as fragments or multimers thereof. In some aspects the insecticidal protein (toxin) is selected from a group consisting of crystal protein toxins derived from *Bacillus thuringiensis*.

In some aspects the at least one affinity molecule A and the at least one affinity molecule B are coupled by a linker sequence L.

In some aspects the at least one affinity molecule A and the at least one affinity molecule B are an affinity mediating molecule selected from the group consisting of a protein, carbohydrate, lipid or nucleotide, or a fragment, derivative or variant of any of these, wherein the at least one affinity molecule A and the at least one affinity molecule B are identical or different.

In some aspects the affinity molecules A and B are not antibodies or a fragment, derivative or variant thereof.

In some aspects the binding protein is selected from the group consisting of affimers (adhirons), affibodies, affilins, affitins, nanofitin, alphabodies (triple helix coiled coil), anticalins, lipocalins, avimers, DARPins (ankyrin repeat), fynomer, kunitz domain pepties, monobodies, adnectins, trinectins, nanoCLAMPs, cellulose/carbohydrate binding molecule (CBM) (for example, dockerins or lectins), centyrins, pronectins, and fibronectin or a fragment, derivative or variant of any of these.

In some aspects the affinity molecule A comprises a naturally occurring or engineered antibody A or a fragment, derivative or variants thereof and the affinity molecule B comprises a naturally occurring or engineered antibody B or a fragment, derivative or variants thereof that are operably connected by the linker L.

In some aspects the antibody A and antibody B of the affinity construct, each is selected from the group consisting of a Fab fragment, a single heavy chain and a single light chain, a single chain variable fragment, a $V_HH$ fragment, CDR3 region and a bispecific monoclonal antibody (diabody).

In some aspects the antibody A and the antibody B, each comprises a single domain antibody or a fragment, derivative or variants thereof, operably connected by the linker L.

In some aspects the antibody A comprises one or more binding sites (valences) for the same membrane-bound receptor of a digestive tract, of a reproductive organ, or of a nervous system of an insect.

In some aspects the antibody A comprises an amino acid sequence selected from any one of SEQ. ID. NOS. 74, 76, 78, 80, 82, 84, 86, 88, 90 and 92.

In some aspects the antibody A comprises a domain that specifically binds to a fragment from an extracellular loop of NAAT protein.

In some aspects the antibody A comprises a domain that specifically binds to a portion of an insect cadherin.

In some aspects the antibody A comprises a domain that specifically binds to a portion of integral membrane subunit (Vo) protein complex of the V-ATPase.

In some aspects the antibody A comprises a domain that specifically binds to an extracellular loop in ABCC1 or ABCC2.

In some aspects the antibody A comprises a domain that specifically binds to an extracellular portion of venom dipeptidyl peptidase-4-like isoform X1 or peptide transporter family 1 isoform X1.

In some aspects the antibody B comprises one or more binding sites (valences) for the same or different insecticidal protein(s) (toxins).

In some aspects the insecticidal protein (toxin) is selected from the group consisting of crystal toxins (Cry and Cyt proteins), vegetative insecticidal toxins (Vip proteins), mosquitocidal toxins (Mtx proteins), Tpp, Mpp, Gpp, App, Spp, Vpa, Vpb, Mcf, Pra, Prb, Xpp, Mpf toxins, binary toxins (Bin proteins), and secreted insecticidal toxins (Sip proteins), as well as fragments or multimers thereof.

In some aspects the insecticidal protein (toxin) comprises a crystal protein toxin derived from *Bacillus thuringiensis*.

In some aspects the antibody B comprises an amino acid sequence selected from any one of SEQ. ID. NOS. 68, 70 and 72.

In some aspects the linker L comprises an amino acid sequence selected from any one of SEQ. ID. NOS. 54, 56, 58, 60, 62 and 64.

In some aspects the affinity construct comprises an amino acid sequence of any one of 96, 98, 100, 102, 104, 106, 108, 110, 112, 114 and 116.

In some aspects the affinity construct comprises an amino acid sequence with at least about 70% sequence identity with any one of SEQ. ID. NOS. 96, 98, 100, 102, 104, 106, 108, 110, 112, 114 and 116.

In some aspects the nucleic acid sequence is at least about 70% identical with any one of SEQ. ID. NOS. 95, 97, 99, 101, 103, 105, 107, 109, 111, 113 and 115.

In some aspects the polynucleotide sequence encoding the amino acid sequence is codon optimized for expression in a selected host cell.

In some aspects the selected host cell is a yeast cell, a bacterial cell, or a plant cell.

In some aspects the first recombinant nucleic acid further comprises a promoter operably linked to the polynucleotide sequence.

In some aspects the promoter comprises a constitutive promoter, an inducible promoter, a plant specific promoter, a plant tissue specific promoter, a CaMV promoter or a microbial promoter.

In some aspects the present disclosure encompasses a transgenic host cell comprising the first recombinant DNA construct.

In some aspects the present disclosure encompasses a transgenic host cell further comprising one or more nucleic acid sequences, each encoding an insecticidal protein (toxin)

that specifically binds to or can be targeted to bind to at least one domain in the at least one affinity molecule B of the affinity construct.

In some aspects the present disclosure encompasses a transgenic host cell wherein the transgenic host cell is a yeast cell, a bacterial cell or a plant cell.

In some aspects the present disclosure encompasses a insecticidal composition comprising the affinity construct as above and at least one insecticidal protein (toxin), wherein the one or more insecticidal protein (toxin) can specifically bind to or can be targeted to bind to at least one domain in the at least one affinity molecule B of the affinity construct.

In some aspects the insecticidal composition further comprises a carrier.

In some aspects the insecticidal composition the carrier may be any one of a powder, a dust, pellets, granules, spray, emulsion, colloid or a solution.

In some aspects the insecticidal composition further comprises an insect food source.

In some aspects the insecticidal composition is specifically toxic to one or more insect pests including insects from orders Isoptera, Blattodea, Orthoptera, Phthiraptera, Thysanoptera, Hemiptera, Hymenoptera, Siphonaptera, Diptera, Coleoptera and Lepidoptera.

In some aspects the insecticidal composition is specifically toxic to one or more insect pests selected from a group consisting of Fall armyworm (FAW, *Spodoptera frugiperda*), Corn earworm (*Helicoverpa zea*, CEW) and Diamond back moth (DBM, *Plutella xylostella*).

In some aspects the present disclosure encompasses the use of the insecticidal compositions as above for preventing damage to a plant, plant part or plant seed by one or more insect pest(s).

In some aspects the present disclosure encompasses a method of preventing damage to a plant, a plant part or plant seed by one or more insect pests, comprising contacting the insect pests with the insecticidal composition as above.

In some aspects the insect pests include insects selected from the orders Isoptera, Blattodea, Orthoptera, Phthiraptera, Thysanoptera, Hemiptera, Hymenoptera, Siphonaptera, Diptera, Coleoptera and Lepidoptera.

In some aspects the present disclosure encompasses an insecticidal kit, comprising the insecticidal composition as above.

In some aspects the insecticidal kit further comprises the host cell producing the affinity construct.

In some aspects the insecticidal kit further comprises the instructions for making and using the kit to prevent damage to a plant, plant part or plant seed by one or more insect pest(s).

In some aspects the present disclosure encompasses a method of protecting a plant or plant parts or plant seeds against one or more insect pest(s) by co-expressing the affinity construct together with one or more insecticidal protein(s) (toxin(s)) in a plant, plant parts or plant seeds, wherein the one or more insecticidal protein (toxin) can specifically bind to or can be targeted to bind to at least one domain in the at least one affinity molecule B of the affinity construct.

In some aspects the present disclosure encompasses a method of protecting a plant or plant parts or plant seeds against one or more insect pest(s) by: a. expressing the affinity construct described above in a plant, plant parts or plant seeds and b. applying the one or more insecticidal protein(s) (toxin(s)) to the plant, plant parts or plant seeds, wherein the one or more insecticidal protein (toxin) can specifically bind to or can be targeted to bind to at least one domain in the at least one affinity molecule B of the affinity construct.

In some aspects the present disclosure encompasses a method of protecting a plant or plant parts or plant seeds against one or more insect pest(s) by: a. applying the affinity construct described above to the plant, plant parts or plant seeds, wherein said affinity construct is expressed in one or more host cell and is applied to said plant, plant parts or plant seeds either in purified form or by applying the microorganism(s) expressing the affinity construct; and b. expressing the one or more insecticidal protein(s) (toxin(s)) in the plant, plant part or plant seed, wherein the one or more insecticidal protein (toxin) can specifically bind to or can be targeted to bind to at least one domain in the at least one affinity molecule B of the affinity construct.

In some aspects the present disclosure encompasses a method of protecting a plant or plant parts or plant seeds against one or more insect pest(s) by: (co-)expressing the affinity construct as described above and one or more insecticidal protein(s) (toxin(s)) in one or more microorganisms and applying the one or more microorganisms (co-) expressing the affinity construct and the one or more insecticidal protein(s) (toxin(s)) either in purified form or together with the respective culture medium/media to a plant, plant parts or plant seeds, wherein the one or more insecticidal protein (toxin) can specifically bind to or can be targeted to bind to at least one domain in the at least one affinity molecule B of the affinity construct, wherein ingestion of the microorganism or culture medium/media by the insect pest causes morbidity to or mortality of the insect pest(s).

In some aspects, the affinity constructs provided herein enhance the activity of Cry1F, Cry1Ab and Cry1Ac against their respective natural target insects as indicated by mortality assays. In some aspects the affinity construct provided herein expands the activity of Cry1F, Cri1Ac and Cry1Ab to previously non-susceptible insects as determined (or as measured) by a mortality assay.

Affinity molecules comprising a single domain antibody comprising the complementarity determining region 1 (CDR1) amino acid sequence, the complementarity determining region 2 (CDR2), and the complementarity determining region 3 (CDR3) amino acid sequence are provided herein. In certain embodiments, the single domain antibodies comprise, consist essentially of, or consist of: (i) the CDR1 amino acid sequence of SEQ ID NO: 138, the CDR2 amino acid sequence of SEQ ID NO: 139, and the CDR3 amino acid sequence of SEQ ID NO: 140 or 141, optionally wherein the single domain antibody comprising the CDR1, CDR2, and CDR3 amino acid sequences binds or specifically binds to an insect gut Nutrient Amino Acid Transporter (NAAT) protein; (ii) the CDR1 amino acid sequence of SEQ ID NO: 135, the CDR2 amino acid sequence of SEQ ID NO: 136, and the CDR3 amino acid sequence of SEQ ID NO: 137, optionally wherein the single domain antibody comprising the CDR1, CDR2, and CDR3 amino acid sequences binds or specifically binds to an insect gut Nutrient Amino Acid Transporter (NAAT) protein; (iii) the CDR1 amino acid sequence of SEQ ID NO: 142, the CDR2 amino acid sequence of SEQ ID NO: 143, and the CDR3 amino acid sequence of SEQ ID NO: 144, optionally wherein the single domain antibody comprising the CDR1, CDR2, and CDR3 amino acid sequences binds or specifically binds to an insect gut Nutrient Amino Acid Transporter (NAAT) protein; (iv) the CDR1 amino acid sequence of SEQ ID NO: 145, the CDR2 amino acid sequence of SEQ ID NO: 146, and the CDR3 amino acid sequence of SEQ ID NO: 147, optionally wherein the single domain antibody comprising the CDR1, CDR2, and CDR3 amino acid sequences binds or specifically binds to an insect gut Nutrient Amino Acid Transporter (NAAT) protein; (v) the CDR1 amino acid sequence of SEQ ID NO: 148, the CDR2 amino acid sequence of SEQ ID NO: 149, and the CDR3 amino acid sequence of SEQ ID NO: 150, optionally wherein the single domain antibody comprising the CDR1, CDR2, and CDR3 amino acid sequences binds or specifically binds to a Cry1F protein; (vi) the CDR1 amino acid sequence of SEQ ID NO: 151, the CDR2 amino acid sequence of SEQ ID NO: 152, and the CDR3 amino acid sequence of SEQ ID NO: 153, optionally wherein the single domain antibody comprising the CDR1, CDR2, and CDR3 amino acid sequences binds or specifically binds to a Cry1F protein; (vii) the CDR1 amino acid sequence of SEQ ID NO: 154, the CDR2 amino acid sequence of SEQ ID NO: 155, and the CDR3 amino acid sequence of SEQ ID NO: 156 or 157, optionally wherein the single domain antibody comprising the CDR1, CDR2, and CDR3 amino acid sequences binds or specifically binds to an insect gut cadherin protein; (viii) the CDR1 amino acid sequence of SEQ ID NO: 158, the CDR2 amino acid sequence of SEQ ID NO: 159, and the CDR3 amino acid sequence of SEQ ID NO: 160, optionally wherein the single domain antibody comprising the CDR1, CDR2, and CDR3 amino acid sequences binds or specifically binds to an insect gut cadherin protein; or (ix) the CDR1 amino acid sequence of SEQ ID NO: 161, the CDR2 amino acid sequence of SEQ ID NO: 162, and the CDR3 amino acid sequence of SEQ ID NO: 163, optionally wherein the single domain antibody comprising the CDR1, CDR2, and CDR3 amino acid sequences binds or specifically binds to a Cry1F protein.

Methods for generating an affinity molecule which binds an insect gut protein comprising immunizing an animal with a composition comprising a polypeptide antigen or a DNA molecule encoding the polypeptide antigen, wherein the polypeptide antigen comprises, consists essentially of, or consisting of an amino acid sequence having at least 80%, 85%, 90%, 95%, 98%, or 100% sequence identity to SEQ ID NO: 30, 31, or 164 to 234 are provided.

Methods for selecting an affinity molecule which binds an insect gut protein comprising: (i) screening an affinity molecule library for a clone which binds to a polypeptide antigen comprising, consists essentially of, or consisting of an amino acid sequence having at least 80%, 85%, 90%, 95%, 98%, or 100% sequence identity to SEQ ID NO:30, 31, or 164 to 234; and (ii) selecting a clone which expresses or comprises the affinity molecule which binds the polypeptide antigen are provided.

BRIEF DESCRIPTION OF THE FIGURES

FIG. 6 shows exemplary GPI-anchored insect midgut proteins as target for single domain antibody-mediated insecticidal protein targeting. Midgut proteins can be isolated and identified via Mass Spectrometry. Proteomic data are screened for proteins with glycosylphophatidyl-inositol (GPI) linked sequence motifs. These proteins are used to produce antibodies, which are then fused to other antibodies raised against insecticidal proteins ("Toxins"). Bimodal antibodies then lead to the accumulation of-insecticidal fusion proteins in the membranes of midguts of target insects, leading to increased target insect mortality.

FIG. 7 provides an example of an amino acid sequence of a $V_HH$ domain from dromedary germline (SEQ ID NO: 28; modified from Harmsen et al. 2000, Mol. Immunol. 37, 579-590 (FR=Framework region, CDR=complementarity-determining region).

FIG. 8 shows increasing affinity of pore-forming toxins via antibodies to membrane proteins increases oligomerization, pore formation and toxicity to exemplify the key concept of the present disclosure.

FIG. 10 shows an overview of the potential applications provided by the present disclosure. The combination of all three boxes offers great potential of the present disclosure for insect pest management.

FIG. 13A shows a graphical representation of the results of ELISA-based binding assays using biotin-labeled solubilized *Plutella* brush border membrane vesicles and NAAT nanobodies.

FIGS. 15A, B, C, and D show a protein sequence alignment of the second extracellular loop of sodium-dependent nutrient amino acid 1-like (NAAT) protein depicting conservation across multiple insect species.

FIGS. 16A, B, C, and D show a protein sequence alignment depicting conservation of Cadherins across multiple insect species.

FIG. 17A shows the sequence alignment of domain 2 of Cry1Ac, Cry1Ab and Cry1F.

FIG. 17B shows the sequence alignment of domain 2 of Cry1B, Cry1 Da and Cry1F.

DETAILED DESCRIPTION

Figure 1:
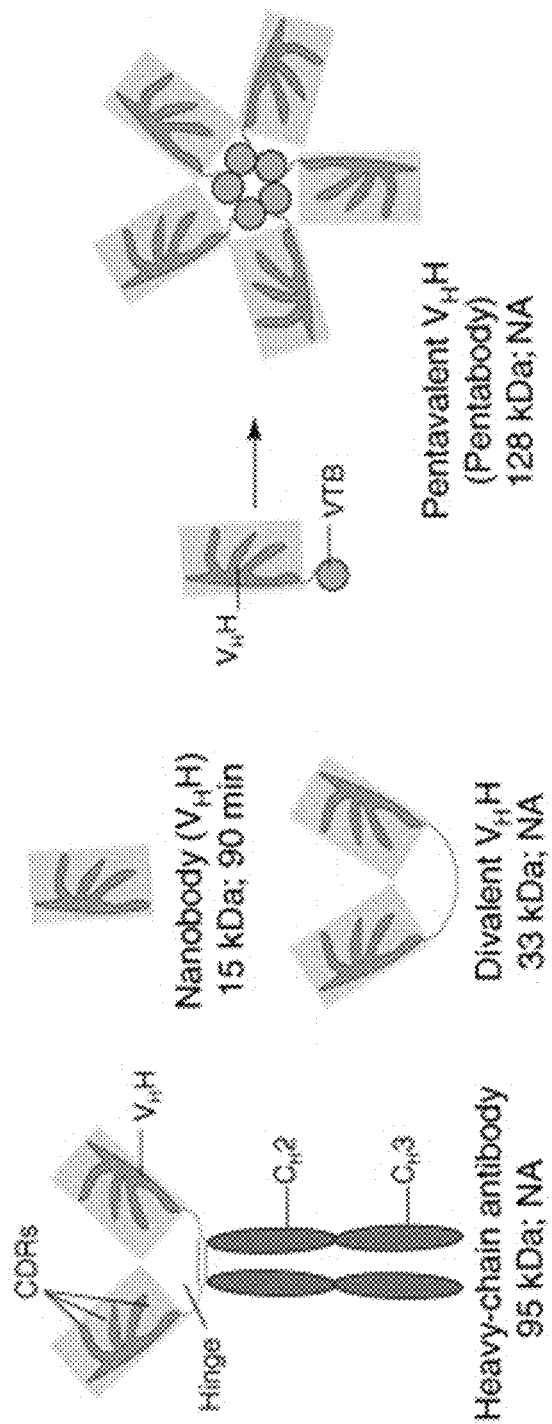
FIG. 1 shows examples of valences of $V_HH$s (nanobodies) (Jain et al., 2007).

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991).

When introducing elements of the present disclosure or the preferred aspects(s) thereof, the articles "a", "an", "the" and "said" are intended to mean that there are one or more of the elements. The terms "comprising", "including" and "having" are intended to be inclusive and mean that there may be additional elements other than the listed elements.

As used herein, the conservative amino acid substitutions or conservatively substituted amino acids are substitutions where one amino acid within one of the following four groups consisting of (1) acidic amino acids; (2) basic amino acids; (3) neutral polar amino acids; and (4) neutral non-polar amino acids is replaced with another amino acid within the same group (e.g., an acidic amino acid is substituted with another acidic amino acid, a basic amino acid is substituted with another basic amino acid, a neutral polar amino acid is replaced with another neutral polar amino acid, or a neutral non-polar amino acid is replaced with another neutral non-polar amino acid). Amino acids within these various groups include: (1) acidic (anionic, negatively charged) amino acids such as aspartic acid and glutamic acid; (2) basic (cationic, positively charged) amino acids such as arginine, histidine, and lysine; (3) neutral polar amino acids such as glycine, serine, threonine, cysteine, cystine, tyrosine, asparagine, and glutamine; (4) neutral nonpolar (hydrophobic) amino acids such as alanine, leucine, isoleucine, valine, proline, phenylalanine, tryptophan, and methionine.

To the extent to which any of the preceding definitions is inconsistent with definitions provided in any patent or non-patent reference incorporated herein by reference, any patent or non-patent reference cited herein, or in any patent or non-patent reference found elsewhere, it is understood that the preceding definition will be used herein.

The present disclosure is drawn to novel affinity constructs and methods for controlling insect pests. The novel affinity constructs of the disclosure comprise at least one affinity molecule A capable of recognizing, or capable of binding to, or binding to, or being directed to, or being designed to bind to, an insect-specific structure in and/or on a target insect, and at least one affinity molecule B capable of binding, or binding to, or is directed to, or is designed to bind to, an insecticidal protein (toxin), wherein the at least one affinity molecule A and the at least one affinity molecule B are optionally separated by a linker L comprising at least one amino acid.

In said novel affinity constructs of the disclosure the at least one affinity molecule A capable of recognizing, or capable of binding to, or binding to, or being directed to, or being designed to bind to, an insect-specific structure in and/or on a target insect is different from the least one affinity molecule B capable of binding to, or binding to, or is directed to, or is designed to bind to, an insecticidal protein (toxin). Thus, the present disclosure encompasses affinity constructs comprising at least one affinity molecule A capable of recognizing, or capable of binding to, or binding to, or being directed to, or being designed to bind to an insect-specific structure in and/or on a target insect, and at least one affinity molecule B capable of binding to, or binding to, or being directed to, or being designed to bind to an insecticidal protein (toxin), wherein the at least one affinity molecule A and the at least one affinity molecule B are different from each other, and wherein the at least one affinity molecule A and the at least one affinity molecule B are optionally separated by a linker L comprising at least one amino acid. The novel affinity constructs comprising at least one affinity molecule A and at least one affinity molecule B can be expressed in a transgenic plant or a microorganism, or be applied as an insecticidal spray, solution or coating to a plant, plant part, plant seed or insect. In both cases, i.e., expression in a transgenic plant or a transgenic microorganism as well as application as an insecticidal spray, solution or coating, the concomitant use of the insecticidal toxin which the at least one affinity molecule B is capable of binding to, or is binding to, or is being directed to, or is being designed to bind to an insecticidal protein (toxin), is required. This means that the insecticidal toxin is either to be co-expressed in the transgenic plant or microorganism or is to be added to the composition containing the affinity construct for the application as a spray, solution, or coating.

The term "specifically toxic" and "specific toxin", as used herein relates to the specific binding demonstrated by compositions described herein, wherein specific binding of a composition to a receptor in a target insect is incapacitating or lethal to that insect, at a measurably higher rate than any incapacity or lethality caused by exposure of generally comparable but non-target insects exposed to the composition. Specific toxicity of a composition relative to a target insect can be determined using any of many means known to those of ordinary skill in the art for quantifying proportion of an insect sample killed or incapacitated, such as by comparative insect counts or quantifying and comparing target and non-target insect damage to control and test plants. A composition that is "specifically toxic" to a target insect, detectably kills or incapacitates a target insect by a factor of at least 1.5-fold, at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold, or at least 20-fold, or more relative to a non-target insect exposed to the same composition. The novel affinity constructs find application in controlling insect pest populations and for producing compositions with insecticidal activity. The novel affinity constructs provided by the present disclosure facilitate the natural function of insecticidal proteins, allow generating new mode of actions by targeting insecticidal proteins to new receptors within the insect pest, and thereby to diminish or overcome insect resistance.

The novel affinity constructs can be generated, for example and as explained in more detail below, by fusing a first affinity molecule or a fragment thereof raised against insect-specific structures (e.g., gut or intestine proteins of target insects) ("affinity molecule A") with a second affinity molecule B raised against an insecticidal protein (toxin) and thus capable of binding to it, wherein the affinity molecule A and the at least one affinity molecule B are optionally separated by a linker L comprising at least one amino acid and wherein the at least one affinity molecule A and the at least one affinity molecule B are identical or different. The term "raised against" as used herein refers to the specific polypeptide sequence that was used as an antigen to raise affinity molecules for example (but not restricted to) antibody, nanobody, sdAb, $V_HH$, CDR3 etc or design binding partners against.

These novel affinity constructs can be formulated in a composition provided by the present disclosure, wherein the composition further comprises an insecticidal protein (toxin). This insecticidal protein (toxin) corresponds to the insecticidal protein (toxin) which the at least one affinity molecule B of the novel affinity construct is capable of binding to, or is binding to, or is being directed to, or is being designed to bind to. Such compositions exhibit insecticidal activity and, hence, find application in controlling insect pest populations.

The insect is exposed to the affinity construct provided by the present disclosure in combination with an insecticidal protein (toxin) the at least one affinity molecule B is capable of binding to, or is binding to, or is being directed to, or is being designed to bind to. This exposure is realized either (a) by co-expression of the affinity construct and the insecticidal protein (toxin) in a transgenic plant upon which the insect pest is generally feeding, or (b) by co-expression of the affinity construct and the insecticidal protein (toxin) in a transgenic microorganism followed by the application of the microorganism either in purified form or together with the respective culture medium/media to a plant, plant parts or plant seeds upon which the insect pest is generally feeding, or (c) by expressing the affinity construct in a transgenic plant, plant part or plant seed and applying the one or more insecticidal protein (toxin) in purified form or by applying an microorganism expressing the insecticidal protein (toxin) to the transgenic plant, plant part or plant seed, or (d) by expressing the affinity construct in one or more microorganism while expressing the insecticidal protein (toxin) in a plant, plant part or plant seed, and applying the affinity construct being expressed in the one or more microorganism in either purified form or by applying the one or more an microorganism expressing the affinity construct to the plant, plant parts or plant seed expressing the insecticidal toxin (protein); or (e) by formulating the affinity construct and the insecticidal protein (toxin) as an insecticidal composition that is then applied to the plant, plant part or plant seed upon which the insect pest is generally feeding.

The present disclosure encompasses the use of the novel affinity constructs (or the novel insecticidal compositions comprising the novel affinity constructs) for protecting a plant, plant part or plant seed against an insect pest. The methods for protecting plants involve transforming plants or microorganisms with one or more nucleic acid sequences encoding a novel affinity construct provided by the present disclosure and an insecticidal protein, wherein the insecticidal protein (toxin) corresponds to the insecticidal protein (toxin) to which the at least one affinity molecule B of the novel fusion protein is B is capable of binding to, or is binding to, or is being directed to, or is being designed to bind to.

Also encompassed by the present disclosure are methods for making the novel affinity constructs (and nucleic acids encoding the affinity constructs), methods of using same as well as methods for protecting plants, plant parts and plant seeds by means of the novel affinity constructs. The methods for protecting plants involve transforming plants or microorganisms with a nucleic acid sequence encoding a novel affinity molecule provided by the present disclosure and/or with a nucleic acid sequence encoding the insecticidal protein (toxin) to which the at least one affinity molecule B of the novel fusion protein is B is capable of binding to, or is binding to, or is being directed to, or is being designed to bind to.

The methods for protecting plants also involve transforming a microorganism with one or more nucleic acid sequences encoding a novel affinity construct provided by the present disclosure and an insecticidal protein, wherein the insecticidal protein (toxin) corresponds to the insecticidal protein (toxin) to which the at least one affinity molecule B of the novel affinity construct B is capable of binding to, or is binding to, or is being directed to, or is being designed to bind to, and applying either the transformed microorganisms or the purified novel affinity construct expressed in the microorganisms to the plant, plant part or plant seed for uptake by a feeding insect pest.

Also encompassed are transgenic plants, plant parts, plant tissues or plant seed thereof as well as transgenic microorganisms expressing the novel affinity constructs and/or the insecticidal protein (toxin) to which the at least one affinity molecule B of the novel affinity construct B is capable of binding to, or is binding to, or is being directed to, or is being designed to bind to.

The Affinity Constructs

The present disclosure in particular provides novel affinity constructs comprising multi-specific affinity molecules directed (1) against known or novel insect-specific structures (e.g., receptors) in/or on the insect pest (the "at least one affinity molecule A") and (2) against an insecticidal protein (toxin) (the "at least one affinity molecule B"). Affinity molecules A and B are combined to bind the insecticidal protein (toxin) on the one hand and to an insect-specific structure (e.g., receptor) on the other hand, thereby increasing the affinity of the insecticidal protein (toxin) to a receptor. This in turn results in (restoration of) binding of the insecticidal protein to its receptor in and/or on the insect pest or to increased activity of the insecticidal protein (toxin). This system provides, amongst others, the advantage that the insecticidal protein (toxin) is not modified itself, therefore decreasing the risk that the insecticidal protein (toxin) may become dysfunctional.

The novel affinity construct provided by the present disclosure exhibits, amongst others, (1) the benefit of more efficient binding of a known insecticidal protein (toxin) to its natural receptors in an insect pest, (2) the benefit of improved targeting of an insecticidal protein (toxin) to both its natural as well as novel receptors in the insect pest, and (3) the benefit of combining multiple mode of actions/site of actions of insecticidal proteins by targeting multiple existing and/or novel receptors in an insect pest. These benefits help to diminish or overcome resistance of an insect pest against the function of an insecticidal protein (toxin), help to expand the range of target insects for a given insecticidal protein (toxin) and help to increase stability of the affinity construct, without being limited thereto. These effects are discussed in more detail in the following.

Efficient Binding of an Insecticidal Protein (Toxin) to its Natural Receptors in the Insect Pest The novel affinity construct provides for efficient binding of insecticidal proteins to the respective natural receptors in the insect pest. This helps to facilitate the function of the insecticidal proteins and will diminish or overcome insect resistance. In particular, the novel affinity construct provided by the present disclosure provides a way of increasing the binding efficiency of insecticidal proteins to insect target structures, in particular target structures of an inner organ of an insect, preferably of the digestive tract, a reproductive organ, or the nervous system, more preferably of such as the gut or intestine. Preferably, such target structures are protein receptors or parts of the brush border membrane.

The digestive system of insects comprises an alimentary canal or gut, which can be divided into three sections: foregut, midgut, and hindgut. The novel affinity construct is particularly useful for binding to receptors in the insect foregut, midgut, and hindgut, but preferred in the insect midgut or insect larva midgut. The novel affinity constructs provided by the present disclosure allow delivering and retaining an insecticidal protein to the (surface of the) insect midgut, in particular delivering the insecticidal protein specifically to the area in the insect's midgut, where the impact of said insecticidal protein affinity-bound to the receptor in and/or on a target insect is maximized. Retaining the insecticidal protein on the (surface of the) insect midgut for example has the effect/advantage that oligomerization and pore formation is improved, thereby improving the toxic effect of the insecticidal protein on the insect and, thus, improving the efficacy of the insecticidal protein in controlling the insect population.

Preferably, the affinity molecule A, exhibits a high-avidity specific binding to receptors present on/in the membrane of epithelial cells of the microvilli of the midgut. The affinity molecules are easily internalized by the insect and are easily attached to the midgut (microvilli) antigens, which is sufficient to retain the insecticidal protein by way of the affinity molecule B comprised in the affinity construct of the present disclosure, thereby increasing the efficacy of an insecticidal protein in controlling the insect population. A correlation between the presence of the affinity construct and insecticidal protein on the one hand and bioactivity against target insects on the other hand can be established for the affinity constructs and the methods of the disclosure.

Improved Targeting of an Insecticidal Protein (Toxin) to Receptors in the Insect Pest The novel affinity construct provided by the present disclosure further serves to improve targeting of insecticidal proteins to insect pests by increasing the target spectrum of a given insecticidal protein (toxin). This is in particular achieved by, for example, restoration of the binding of an insecticidal protein to its natural receptor(s) in an insect to which this insecticidal protein does not bind anymore (e.g., to restore functionality of a given insecticidal protein whose receptor has changed due to mutation and is not binding the protein anymore), and/or by "arming" an insecticidal protein that formerly was not active in a certain insect species due to the fact that a receptor for that protein is missing. In addition, the affinity molecules can be targeted to known and new receptors (e.g., structures at the brush border membrane of insects and others) from any insect species, thereby increasing the spectrum of insecticidal protein (toxins), like, for example, high activity-Cry proteins and other toxins, to insect species that are otherwise not targeted by these insecticidal proteins (toxins). Targeting these toxins to other receptors/structures in, for example, the insect midgut provides a toxic effect against the insect.

Further, the affinity molecules A comprised in the affinity structure of the present disclosure can be designed in different ways to recognize target structures like, for example, receptor(s), in a target insect pest: (1) two or more affinity molecules A may be designed to recognize the same insect-specific structure in and/or om different target insects, (2) two or more affinity molecules A may be designed to recognize the same insect-specific structure in and/or on different target insects, or (3) two or more affinity molecules A may be designed to recognize different insect-specific structures in the same target insect.

Moreover, by using novel small and stable affinity molecules (e.g., VHHs, Affimers and the like) that can bind small epitopes of receptor molecules, one can precisely direct the insecticidal protein (toxin) to the target structure. In addition, once a resistance mode of action of an insect species against a certain toxin is known, the present invention further allows quickly designing affinity molecule/toxin combinations that can robustly overcome resistance.

Facilitation of the Function of an Insecticidal Protein (Toxin) to Diminish or Overcome Insect Resistance The novel ways of increasing the binding efficiency of insecticidal proteins to their insect-specific target structures described herein specifically serve to counteract resistance of insect pests to insecticidal proteins that is caused by reduced binding of the insecticidal protein (toxin) to cells of the digestive system of an insect pest.

The novel affinity constructs provided by the present disclosure facilitate the function of insecticidal proteins and overcome insect resistance. They can be used for producing compositions with insecticidal activity, and find use in controlling, inhibiting growth of or killing, e.g., Isopteran, Blattodean, Orthopteran, Phthirapteran, Thysanopteran, Hymenopteran, Hemipteran, Siphonapteran, Lepidopteran, Coleopteran, Dipteran, and Hemipteran pest populations. Such insecticidal compositions are encompassed by the present disclosure. The present disclosure encompasses controlling, inhibiting growth of or killing pest populations as aforementioned using the novel affinity construct of the present disclosure and an insecticidal protein (toxin), wherein the insecticidal protein (toxin) corresponds to the insecticidal protein (toxin) to which the at least one affinity molecule B of the novel affinity construct is capable of binding, or is binding to, or against which the at least one affinity molecule B is directed to, or designed to bind to. As mentioned elsewhere herein, the affinity construct of the present disclosure comprises at least two affinity molecules, in particular at least one affinity molecule A, capable of binding, binding to, directed to, or designed to bind to an insect-specific structure in and/or on a target insect, and at least one affinity molecule B capable of binding of binding, binding to, directed to, or designed to bind to an insecticidal protein (toxin). Thus, the at least one affinity molecule A is capable of recognizing, or is capable of binding to, or is binding to, or is being directed to, or is being designed to bind to an insect-specific structure (such as, for example, a receptor) in and/or on a target insect, and at least one affinity molecule B is capable of binding to, or is binding to, or is being directed to, or is being designed to bind an insecticidal protein. In such embodiments where more than one of the affinity molecules A is designed to recognize an insect-specific structure (such as, for example, a receptor) in and/or on a target insect at least three general strategies can be applied: (1) the two or more affinity molecules A capable of recognizing, or capable of binding to, or binding to, or being directed to, or being designed to bind to an insect-specific structure in and/or on a target insect can be capable of recognizing, or capable of binding to, or binding to, or being directed to, or being designed to bind to different insect-specific structures in different target insects (i.e., for example, one affinity molecule designed to bind to insect-specific structure T1 in insect X and one affinity molecule designed to bind to insect-specific structure T2 in insect Y, and so on), (2) the two or more affinity molecules A capable of recognizing, or capable of binding to, or binding to, or being directed to, or being designed to bind to an insect-specific structure in and/or on a target insect can capable of recognizing, or capable of binding to, or binding to, or being directed to, or being designed to bind to the same insect-specific structure in and/or on different target insects (i.e., for example, one affinity molecule designed to bind to insect-specific structure T1 in insect X and one affinity molecule designed to bind to insect-specific structure T1 in insect Y, and so on), or (3) the two or more affinity molecules A capable of recognizing, or capable of binding to, or binding to, or being directed to, or being designed to bind to an insect-specific structure in and/or on a target insect can be capable of recognizing, or capable of binding to, or binding to, or being directed to, or being designed to bind to different insect-specific structures in the same target insect (i.e., for example, one affinity molecule designed to bind to insect-specific structure T1 in insect X and one affinity molecule designed to bind to insect-specific structure T2 in insect X, and so on).

Increased Stability of the Affinity Constructs

In addition, the novel affinity constructs provided by the present disclosure are considered to have several other distinct properties. In particular, they exhibit a superior relative stability under adverse conditions (e.g., effective under pH extremes, temperature extremes, etc.), which is of importance to make the insect pest control principle work under the varying harsh conditions in insect digestive tracts (e.g., considering the pH variability within the gut/intestine within insect species and pH variability in gut/intestine between insect species). Conventional insecticidal agents such as conventional insecticidal proteins are way inferior in this respect and are often degraded under even less extreme conditions.

The novel affinity constructs provided by the present disclosure allow delivering and retaining an insecticidal protein to the (surface of the) insect gut, in particular delivering the insecticidal protein specifically to the area in the insect's midgut, where the impact of said insecticidal protein affinity-bound to the receptor in and/or on a target insect is maximized. Retaining the insecticidal protein on the (surface of the) insect midgut, for example, has the effect/advantage that oligomerization and pore formation is improved, thereby improving the toxic effect of the insecticidal protein on the insect and, thus, improving the efficacy of the insecticidal protein in controlling the insect population.

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art. All technical and scientific terms used herein have the same meaning as commonly understood to one of ordinary skill in the art to which this disclosure belongs unless clearly indicated otherwise.

Affinity Molecules

Affinity is an attractive interaction between two molecules, that results in a stable association in which the molecules are in close proximity to each other. In this case molecular binding is without building a covalent bond, hence the association is fully reversible. An affinity mediating molecule is a molecule, which is structured in such a way to mediate an interaction with another molecule in a specific although reversible way. Accordingly, the affinity mediating molecules and in particular the affinity molecules according to the present disclosure are molecules showing binding affinity for a target molecule. Specifically, an affinity molecule A according to the present disclosure is a molecule having binding affinity for an insect-specific structure, preferably for a receptor molecule. Receptor molecules which may be targeted by the at least one affinity molecule A of the present disclosure are described elsewhere herein. Further, an affinity molecule B according to the present disclosure is a molecule having binding affinity for an insecticidal protein (toxin). Insecticidal protein (toxin) molecules which may be targeted by the at least one affinity molecule B of the present disclosure are described elsewhere herein.

In the present disclosure, the affinity construct comprises at least two different affinities. At least one of these least two affinities in said affinity construct is affinity molecule A capable of capable of binding to, or binding to, or being directed to, or being designed to bind to an insect-specific structure, preferably for a receptor molecule, in and/or on a target insect, and at least one of these at least two affinities is affinity molecule B capable of binding to, or binding to, or being directed to, or being designed to bind to an insecticidal protein (toxin), wherein the at least one affinity molecule A and the at least one affinity molecule B are optionally separated by a linker L comprising at least one amino acid. Further, the at least one affinity molecule A has been raised or designed against one or more identical or distinct insect-specific structures (e.g., gut or intestine proteins of target insects) and are thus capable of binding to, or are binding to these insect-specific structures, preferably a receptor molecule. Similarly, the at least one second affinity molecule B has been raised or designed against one or more insecticidal proteins (toxins) and are thus capable of binding to, or are binding to such insecticidal proteins.

Furthermore, the affinity molecules A and B being comprised in the affinity construct are affinity mediating molecule selected from the group comprising a protein, carbohydrate, lipid or nucleotide, or a fragment, derivative or variant of any of these, wherein the at least one affinity molecule A and the at least one affinity molecule B are identical or different. Proteins encompass a non-antibody binding proteins or antibodies or a fragment, derivative or variant thereof. In some embodiments the non-antibody binding protein is selected from the group comprising affimers (adhirons), affibodies, affilins, affitins, nanofitin, alphabodies (triple helix coiled coil), anticalins, lipocalins, avimers, DARPins (ankyrin repeat), fynomer, kunitz domain pepties, monobodies, adnectins, trinectins, nanoCLAMPs, cellulose/carbohydrate binding molecule (CBM) (for example, dockerins or lectins), centyrins, pronectins, and fibronectin or a fragment, derivative or variant of any of these. The antibody is a naturally occurring antibody or a fragment, derivative or variant thereof, in particular a nanobody or an immunoglobulin gamma (IgG) (see FIGS. 1, 2 and 3). The fragment of the naturally occurring antibody can be an antibody fragment selected from the group comprising a Fab fragment, a single heavy chain and a single light chain, a single chain variable fragment, a $V_HH$ fragment, CDR3 region and a bispecific monoclonal antibody (diabody). The Fab fragment can occur as monomer or as a linked dimer, or antibody fragments consisting of a single heavy chain and a single light chain, or consisting of the heavy chain with all three domains, two domains or only on domain of the constant region (the so called crystallizable Fragment Fc) or the single light chain or the so called $V_HH$ or the region facilitating the recognition to the antigen comprising the CDR3 region as will be described in more detail further below. Encompassed are also synthetic affinity molecules like three helix coils. The nucleotide is a RNA aptamer, a SOMAmer or a ribozyme or a fragment, derivative or variant thereof.

In the context of the affinity molecule comprising at least one affinity molecule A and at least one affinity molecule B as described above, "capable of binding to, or binding to, or being directed to, or being designed to bind to an insect-specific structure", preferably for a receptor molecule, in and/or on a target insect encompasses binding of the at least one affinity molecule A to said insect-specific structure, preferably to said receptor molecule, in and/or on a target insect. Thus, in the context of the affinity construct comprising at least one affinity molecule A and at least one affinity molecule B, the at least one affinity molecule A has affinity, more specifically binding affinity, even more specifically specific binding affinity, for an insect-specific structure in and/or on the target insect. Likewise, in the context of the of the affinity construct comprising at least one affinity molecule A and at least one affinity molecule B, the at least one affinity molecule B has affinity, more specifically binding affinity, even more specifically specific binding affinity, for the insecticidal protein (toxin).

As used herein, the terms "specific binding" and "specific binding affinity" when used to characterize any affinity molecule described herein, describes that ability of an affinity molecule to recognize and link to a certain target sequence or structure, i.e., binding partner, such that the linking or binding of the affinity molecule to the target is measurably higher than the binding affinity of the same molecule to a generally comparable, but non-target structure or sequence. The binding affinity of an affinity molecule to target structure or sequence can be determined using any of many means known to those of ordinary skill in the art. A binding domain of an affinity molecule that "specifically binds" to a binding partner, detectably binds the binding partner by a factor of at least 1.5-fold, at least 2-fold, at least 3-fold, at least 4-fold, at least 5-fold, at least 6-fold, at least 7-fold, at least 8-fold, at least 9-fold, at least 10-fold, at least 11-fold, at least 12-fold, at least 13-fold, at least 14-fold, at least 15-fold, at least 16-fold, at least 17-fold, at least 18-fold, at least 19-fold, or at least 20-fold, or more relative to the same molecule binding to a non-target, non-binding partner. The equilibrium dissociation constant (Kd) of any affinity molecule for two or more binding partners can be readily determined and compared to quantify the binding specificity of the affinity molecule of interest with respect to a binding partner, or target of interest. Binding of an affinity molecule to a target structure or sequence can be measured and detected in a variety of ways known in the art, including but not limited to assays using enzymatic or fluorescent labels, radiolabels, gel shift assays, surface plasmon resonance (SPR), biolayer interferometry (BLI), and enzyme linked immunosorbent assays (ELISA). In the context of the affinity construct comprising at least one affinity molecule A and at least one affinity molecule B, the at least one affinity molecule A having affinity, more specifically binding affinity, for an insect-specific structure in and/or on a target insect, is different from the least one affinity molecule B having affinity, more specifically binding affinity, for an insecticidal protein (toxin).

The at least one affinity molecule A of the novel affinity construct may be at least one protein, carbohydrate, lipid or nucleotide, or a fragment, derivative or variant of any of these (or at least two proteins, carbohydrates, lipids or nucleotides, or fragments or derivatives or variants thereof). Preferably, the protein is a non-antibody binding protein or an antibody or a fragment, derivative or variant thereof. More preferred, the non-antibody binding protein is any one of affimers (adhirons), affibodies, affilins, affitins, nanofitin, alphabodies (triple helix coiled coil), anticalins, lipocalins, avimers, DARPins (ankyrin repeat), fynomer, kunitz domain peptides, monobodies, adnectins, trinectins, nanoCLAMPs, cellulose/carbohydrate binding molecule (CBM) (for example, dockerins or lectins), centyrins, pronectins, and fibronectin or a fragment, derivative or variant of any of these. In other embodiments, the antibody is a naturally occurring antibody or a fragment, derivative or variant thereof, in particular a single-domain antibody (sdAb) or a nanobody or an immunoglobulin gamma (IgG) (see FIG. 1 and FIG. 3 for some examples). Preferably, the fragment of the naturally occurring antibody can be an antibody fragment selected from the group comprising a Fab fragment, a single heavy chain and a single light chain, a single chain variable fragment, a $V_HH$ fragment, CDR3 region and a bispecific monoclonal antibody (diabody). The Fab fragment can occur as monomer or as a linked dimer, or antibody fragments consisting of a single heavy chain and a single light chain, or consisting of the heavy chain with all three domains, two domains or only on domain of the constant region (the so called crystallizable Fragment Fc) or the single light chain or the $V_HH$ or the region facilitating the recognition to the antigen comprising the CDR3 region as will be described in more detail further below. Encompassed are also synthetic affinity molecules like three helix coils. In other preferred embodiments, the nucleotide is a RNA aptamer, a SOMAmer or a ribozyme or a fragment, derivative or variant thereof.

In other preferred embodiments, the at least one affinity molecule A of the novel affinity construct, or a fragment or derivative or variant thereof, is at least one protein, carbohydrate, lipid or nucleotide, or a fragment, derivative or variant of any of these (or at least two proteins, carbohydrates, lipids or nucleotides, or fragments or derivatives or variants thereof).

Likewise, in the present disclosure, the at least one affinity molecule B of the novel affinity construct is a non-antibody binding protein or an antibody or a fragment, derivative or variant thereof. More preferred, the non-antibody binding protein is any one of affimers (adhirons), affibodies, affilins, affitins, nanofitin, alphabodies (triple helix coiled coil), anticalins, lipocalins, avimers, DARPins (ankyrin repeat), fynomer, kunitz domain pepties, monobodies, adnectins, trinectins, nanoCLAMPs, cellulose/carbohydrate binding molecule (CBM) (for example, dockerins or lectins), centyrins, pronectins, and fibronectin or a fragment, derivative or variant of any of these. In other embodiments, the antibody is a naturally occurring antibody or a fragment, derivative or variant thereof, in particular a nanobody or an immunoglobulin gamma (IgG). Preferably, the fragment of the naturally occurring antibody can be an antibody fragment selected from the group comprising a Fab fragment, a single heavy chain and a single light chain, a single chain variable fragment, a $V_HH$ fragment, CDR3 region and a bispecific monoclonal antibody (diabody). The Fab fragment can occur as monomer or as a linked dimer, or antibody fragments consisting of a single heavy chain and a single light chain, or consisting of the heavy chain with all three domains, two domains or only one domain of the constant region (the so called crystallizable Fragment Fc) or the single light chain or the $V_HH$ or the region facilitating the recognition to the antigen comprising the CDR3 region as will be described in more detail further below. Encompassed are also synthetic affinity molecules like three helix coils. In other preferred embodiments, the nucleotide is a RNA aptamer, a SOMAmer or a ribozyme or a fragment or derivative or variant thereof. More preferably, the antibody is a single domain antibody (sdAb) or a fragment or derivative or variant thereof.

In other preferred embodiments, the at least one affinity molecule B of the novel affinity constructs, or a fragment or derivative or variant thereof, is at least one alphabody or fragment or derivative or variant thereof (or at least two alphabodies or fragments or derivatives or variants thereof).

In some embodiments, the at least one affinity molecule A and the at least one affinity molecule B being comprised in the affinity construct are separated by a linker L comprising at least one amino acid.

In the context of the affinity construct of the present disclosure comprising at least one affinity molecule A and at least one affinity molecule B, the linker may be any amino acid molecule of variable length (minimum length being 1 amino acid) that serves to link the at least one affinity molecule A and the at least one affinity molecule B and that is not causing steric hindrance between the affinity molecules linked by the linker. Preferably, the linker is a molecule that is used to connect the variable domains of the heavy ($V_H$) and light chains ($V_L$) with their respective non-variable domains of immunoglobulins to construct a single chain antibody (scFv), or to engineer bivalent single chain variable fragments (bi-scFvs) by linking two scFvs. Other examples of suitable linkers to be used in the context of the above-mentioned affinity construct comprising at least one affinity molecule A and at least one affinity molecule B are those used in immunotoxins (see, for example, Huston et al. 1992, Biophys J 62, 87-91; Takkinen et al. 1991). Linkers suitable for use in the context of the above-mentioned affinity construct comprising at least one affinity molecule A and at least one affinity molecule B can also be based on hinge regions of antibody molecules (see, for example, Pack and Plückthun 1992; Pack et al. 1993), or be based on peptide sequences found between structural domains of proteins. Fusions can be made between the multivalent affinity molecules at both sides, the C- and the N-terminus. Linkers suitable for use in the context of the novel affinity construct of the present disclosure are also described elsewhere herein, without being limited thereto.

In the context of the present invention, the affinity constructs comprising at least one affinity molecule A and at least one affinity molecule B, can have different valences as described further below.

In the context of the present invention an affinity construct comprising one affinity molecule A and one affinity molecule B, this affinity construct is the simplest form of the affinity construct of the present disclosure. It represents a bispecific fusion protein, since each affinity molecule A and B recognizes one independent target, respectively, i.e. the target of affinity molecule A and the target of affinity molecule B.

In preferred embodiments, the one or more affinity molecule A and/or the one or more affinity molecule B comprised in the affinity construct of the present disclosure are affinity mediating molecules selected from the group comprising a protein, carbohydrate, lipid or nucleotide, or a fragment, derivative or variant of any of these, wherein the at least one affinity molecule A and the at least one affinity molecule B are identical or different. Preferably, the protein is a non-antibody binding protein or an antibody or a fragment, derivative or variant thereof. More preferred, the non-antibody binding protein is any one of affimers (adhirons), affibodies, affilins, affitins, nanofitin, alphabodies (triple helix coiled coil), anticalins, lipocalins, avimers, DARPins (ankyrin repeat), fynomer, kunitz domain pepties, monobodies, adnectins, trinectins, nanoCLAMPs, cellulose/carbohydrate binding molecule (CBM) (for example, dockerins or lectins), centyrins, pronectins, and fibronectin or a fragment, derivative or variant of any of these. In other embodiments, the antibody is a naturally occurring antibody or a fragment, derivative or variant thereof, in particular a nanobody or an immunoglobulin gamma (IgG). Preferably, the fragment of the naturally occurring antibody can be an antibody fragment selected from the group comprising a Fab fragment, a single heavy chain and a single light chain, a single chain variable fragment, a $V_H$H fragment, CDR3 region and a bispecific monoclonal antibody (diabody). The Fab fragment can occur as monomer or as a linked dimer, or antibody fragments consisting of a single heavy chain and a single light chain or consisting of the heavy chain with all three domains (so called $V_H$H), two domains or only on domain of the constant region (the so called crystallizable Fragment Fc) or the single light chain or the region facilitating the recognition to the antigen comprising the CDR3 region as will be described in more detail further below (see FIG. 4). Encompassed are also synthetic affinity molecules like three helix coils. In other preferred embodiments, the nucleotide is a RNA aptamer, a SOMAmer or a ribozyme or a fragment, derivative or variant thereof.

Figure 5:
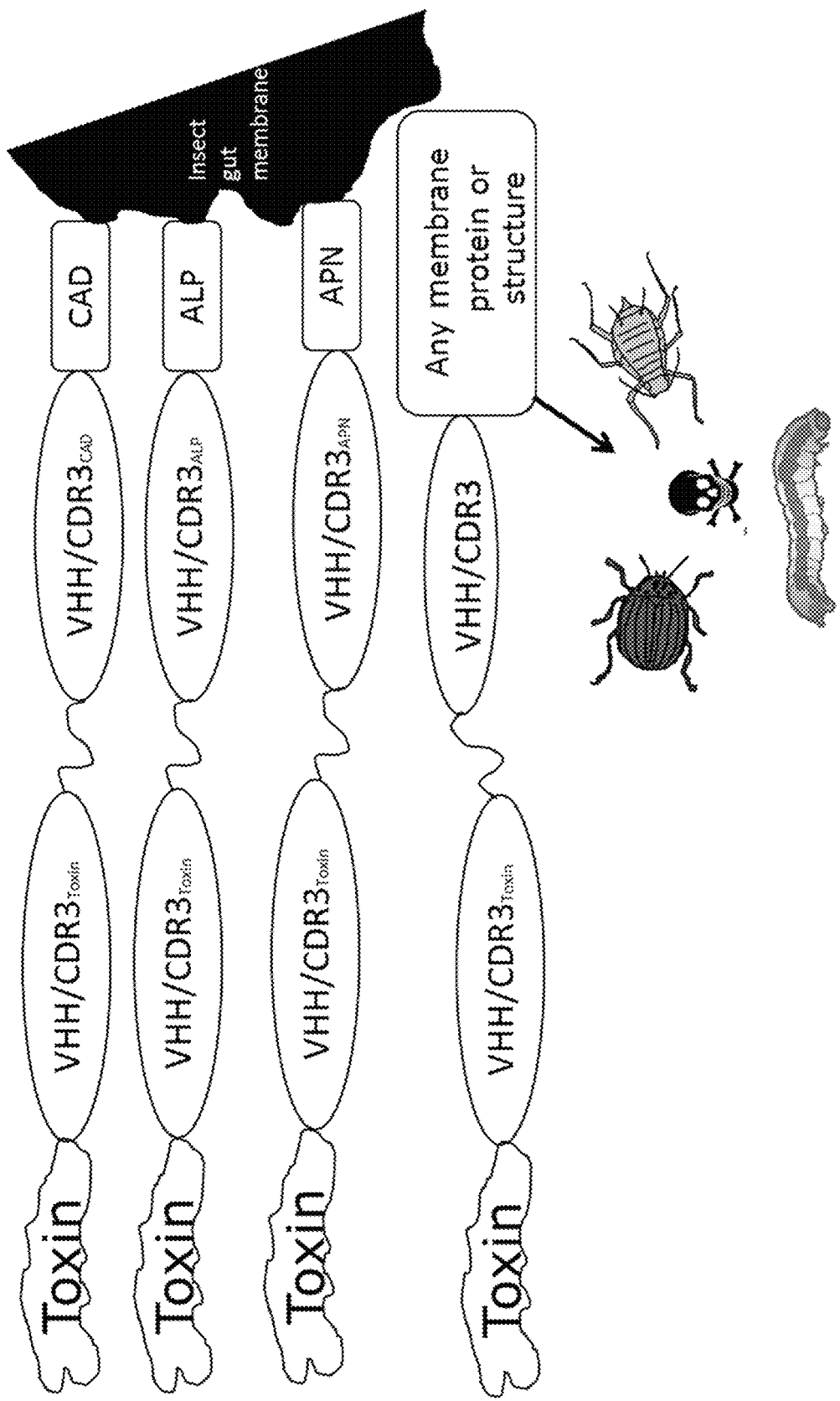
FIG. 5 shows an insecticidal protein (Toxin) supplied with bivalent antibody ($V_HH/CDR3_{Toxin}$-$V_HH/CDR3_{CAD}$) fusion proteins bind with high specificity to insect gut membrane receptors, leading to increased toxicity against target insects (CAD=cadherin, ALP=alkaline phosphatase, APN=aminopeptidase N).
Figure 6:
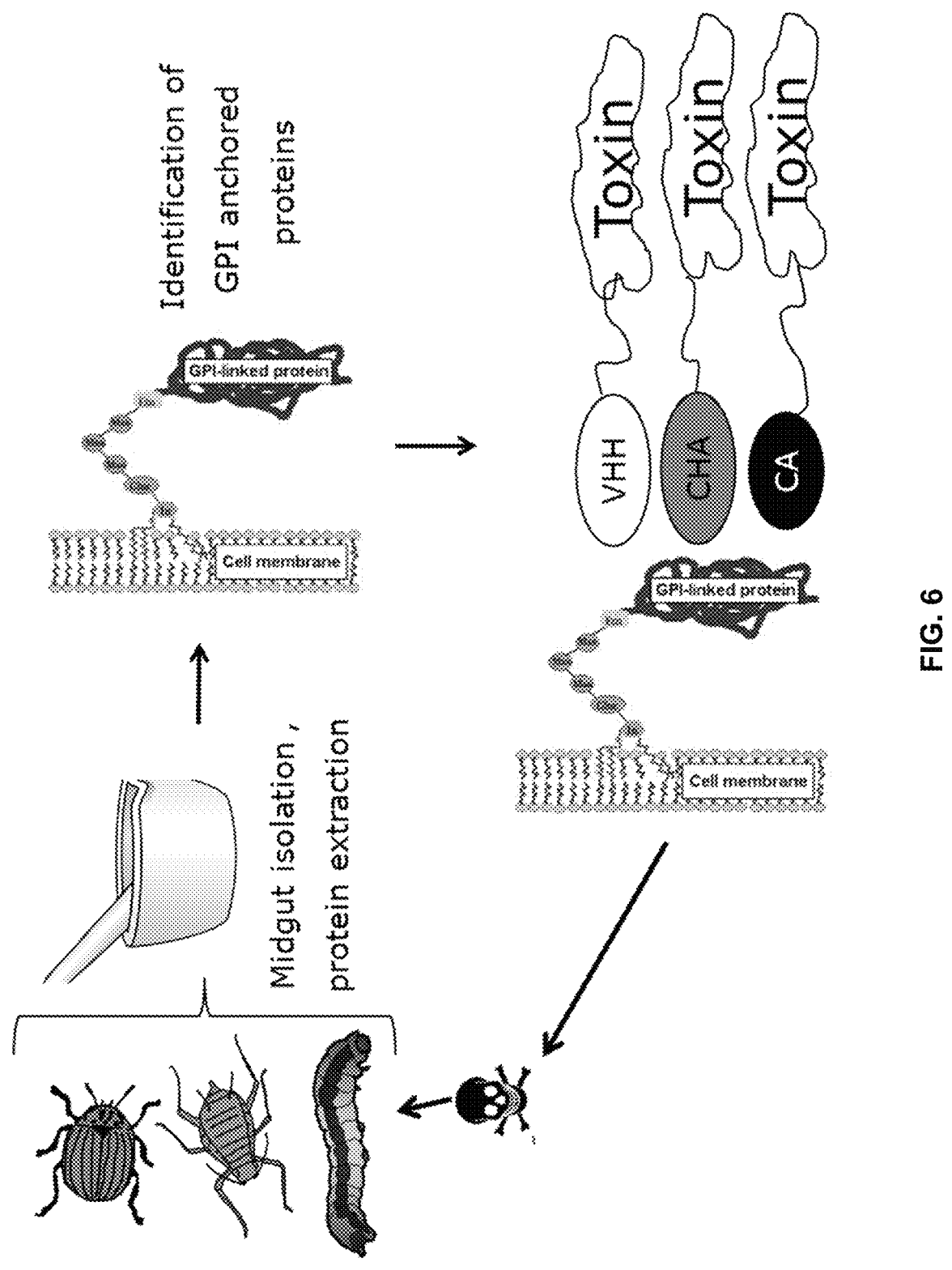

In a further preferred embodiment, the one or more affinity molecule A and/or the one or more affinity molecule B comprised in the affinity construct of the present disclosure are affinity mediating molecules as described above or fragments thereof, wherein at least one of said at least two affinity mediating molecules specifically binds to an inner organ of an insect, preferably to the digestive tract, a reproductive organ or the nervous system, more preferably to the gut or intestine of an insect, and wherein the other of said at least two are affinity mediating molecules binds an insecticidal protein (toxin), wherein the at least two are affinity mediating molecules are optionally separated by a linker L comprising at least one amino acid, and wherein the at least one are affinity mediating molecules specifically binding to the insect-specific structure is different from the least one are affinity mediating molecules binding an insecticidal protein (toxin) (see FIGS. 5 and 6). More preferably, the affinity mediating molecules or fragment thereof specifically binding to an inner organ of an insect, to the digestive tract, a reproductive organ or the nervous system, to the gut or intestine of an insect, specifically binds to a membrane-bound molecule of an inner organ of an insect, preferably of the digestive tract, a reproductive organ or the nervous system, more preferably of the gut or intestine of the insect. Preferably, the membrane-bound molecule is a receptor molecule, preferably an essential receptor molecule, more preferably a receptor molecule for a Cry protein. More preferably, the receptor molecule is selected from the group consisting of cadherin protein receptors, aminopeptidase N protein receptors, alkaline phosphatase protein receptors, ABC transporter protein receptors, chitin synthase B proteins, and 250 kDa protein receptors. In other embodiments the one or more affinity molecule A is targeted against insecticidal structures that in nature do not yet serve as receptors, for example, for insecticidal proteins such as, for example, membrane proteins or proteins that are associated to the membrane or interact with membrane proteins, or to modifications of such proteins (e.g., glycosyl, lipoyl, sumoyl, ubiquitin, phophate residues).

In further preferred embodiments, the affinity construct of the present disclosure comprises one or more affinity molecules A targeted against an insect-specific structure in and/or on a target insect. In that regard, several strategies may by applied if two or more affinity molecules A are incorporated into the affinity construct: (1) the two or more affinity molecules A may be designed to recognize different insect-specific structures in different target insects, (2) the two or more affinity molecules A may be designed to recognize the same insect-specific structure in and/or on different target insects, or (3) the two or more affinity molecules A may be designed to recognize different insect-specific structures in the same target insect.

In some embodiments, where two or more affinity molecules A are present in the affinity construct, the insect-specific structures in and/or on a target insect the at least two affinity molecules A are capable of recognizing, or capable of binding to, or binding to, or being directed to, or being designed to bind to may be identical or distinct. Similarly, in other embodiments, where two or more affinity molecules B are present in the affinity construct, the insecticidal protein (toxins) the at least two affinity molecules B are capable of recognizing, or capable of binding to, or binding to, or being directed to, or being designed to bind to may be identical or distinct.

Similarly, in various embodiments where the affinity construct comprises two or more affinity molecules B targeted against one or more insecticidal proteins (toxins) as mentioned herein, the two or more affinity molecules B are designed according to one of the following three potential strategies (1) the two or more affinity molecules B are capable of recognizing, or capable of binding to, or binding to, or being directed to, or being designed to bind to either the same or different epitopes of the same insecticidal protein (toxin), or (2) the two or more affinity molecules B are capable of recognizing, or capable of binding to, or binding to, or being directed to, or being designed to bind to either the same or different epitopes of different insecticidal proteins (toxins). These strategies include examples where different types of affinity molecule B are employed which are capable of recognizing, or capable of binding to, or binding to, or being directed to, or being designed to bind to the same epitope of the same insecticidal protein (toxin). In such an approach, for example, the first affinity molecule B is a nanobody and the second affinity molecule B is an affimer. In another preferred embodiment where the same epitope of the different insecticidal proteins (toxins) is to be targeted by more than one affinity molecule B, the affinity structure of the present invention is comprising more than one identical affinity molecule B which is capable of recognizing, or capable of binding to, or binding to, or being directed to, or being designed to bind to the same epitope of the different insecticidal proteins (toxins).

In further preferred embodiments, the affinity construct of the present invention is of the structure $(A_mL_nB_o)_pV_q$ and comprises at least one affinity molecule A, at least one affinity molecule B, optionally a linker L that is separating affinity molecules A and B and optionally a linker V. In these embodiments the integer m is at least 1, the integer n 0 or larger, the integer o at least 1, the integer p at least 1, and the integer q 0 or larger, respectively. The linker V may be any amino acid molecule of variable length (minimum length being 1 amino acid) that serves to link two units $A_mL_nB_o$ (in embodiment where more than one of these units are present in the affinity construct) consisting of at least one affinity molecule A, at least one affinity molecule B and optionally a linker L and that prevents steric hindrance between these units linked by the linker V. In all these embodiments the affinity molecules A and B and the Linker L, respectively, are as defined above (see Table 1).

TABLE 1

Non-limiting schematic description of different preferred embodiments of the affinity constructs of the present invention with reference to the structure $(A_mL_nB_o)_pV_q$.

| Affinity structure (example) | Integer m | Integer n | Integer o | Integer p | Integer q | Corresponding formula $(A_mL_nB_o)_pV_q$ |
|---|---|---|---|---|---|---|
| AB | 1 | 0 | 1 | 1 | 0 | $(A_1L_0B_1)_1V_0$ |
| ALB | 1 | 1 | 1 | 1 | 0 | $(A_1L_1B_1)_1V_0$ |
| AAB | 2 | 0 | 1 | 1 | 0 | $(A_2L_0B_1)_1V_0$ |
| AAAB | 3 | 0 | 1 | 1 | 0 | $(A_3L_0B_1)_1V_0$ |
| AALB | 2 | 0 | 1 | 1 | 0 | $(A_2L_1B_1)_1V_0$ |
| ABB | 1 | 0 | 2 | 1 | 0 | $(A_1L_0B_2)_1V_0$ |
| ALBB | 1 | 1 | 2 | 1 | 0 | $(A_1L_1B_2)_1V_0$ |
| AABB | 2 | 0 | 2 | 1 | 0 | $(A_2L_0B_2)_1V_0$ |
| ABAB | 1 | 0 | 1 | 2 | 0 | $(A_1L_0B_1)_2V_0$ |
| ABVAB | 1 | 0 | 1 | 2 | 1 | $(A_1L_0B_1)_2V_1$ |
| ALBVALB | 1 | 1 | 1 | 2 | 1 | $(A_1L_1B_1)_2V_1$ |
| AABVAAB | 2 | 0 | 1 | 2 | 1 | $(A_2L_0B_1)_2V_1$ |
| ABABAB | 1 | 0 | 1 | 3 | 0 | $(A_1L_0B_1)_3V_0$ |

These embodiments cover affinity constructs comprising any combination of one or more units $A_mL_nB_o$ (with the linker L being present (i.e., having an amino acid length of at least 0) or not) which are optionally linked by the linker V.

Preferred Affinity Molecules

The affinity molecules comprised in the affinity construct of the present disclosure as well as fragments or derivatives or variants thereof can be both naturally occurring or naturally produced affinity molecules as well as those produced synthetically, for example through in silico/in vitro combinatorial approaches, in silico/in vitro evolutionary approaches and/or other "synthetic" approaches.

Particularly preferred affinity molecules comprised in the affinity construct of to the present disclosure (including the at least one affinity molecule A and the at least one affinity molecule B of the novel affinity construct) is an affinity mediating molecule selected from the group comprising a protein, carbohydrate, lipid or nucleotide, or a fragment, derivative or variant of any of these. As described already above, an affinity mediating molecule is a molecule, which is structured in such a way to mediate an interaction with another molecule in a specific although reversible way. Accordingly, the affinity mediating molecules and in particular the affinity molecules according to the present disclosure are molecules showing binding affinity for a target molecule.

In various embodiments, proteins emcompass a non-antibody binding proteins or antibodies or a fragment, derivative or variant thereof. In other embodiments the non-antibody binding protein is selected from the group comprising affimers (adhirons), affibodies, affilins, affitins, nanofitin, alphabodies (triple helix coiled coil), anticalins, lipocalins, avimers, DARPins (ankyrin repeat), fynomer, kunitz domain pepties, monobodies, adnectins, trinectins, nanoCLAMPs, cellulose/carbohydrate binding molecule (CBM) (for example, dockerins or lectins), centyrins, pronectins, and fibronectin or a fragment, derivative or variant of any of these.

The present disclosure also encompasses affinity constructs comprising artificial binding moieties/proteins/molecules and antibody mimetics, selected for example from the group consisting of so called affibody molecules, affilins, affimers, affitins, alphabodies, anticalins, avimers, DARPins, Fynomers, Kunitz domain peptides and monobodies that are derived from single domain antibodies or fragments thereof and have the ability to bind specifically to an antigen. Such artificial binding moieties/proteins/molecules and antibody mimetics exhibit the same binding properties/specificities as the single domain antibodies or fragments thereof of the present disclosure. In various embodiments, artificial binding moieties/proteins/molecules and antibody mimetics of the present disclosure are derived from single domain antibodies or fragments thereof that are of shark or camelid origin.

An antibody mimetic may be considered as an organic compound that, like a single domain antibody of the present disclosure, can specifically bind antigens, in particular receptor molecules as described herein. Antibody mimetics according to the present disclosure may be considered as molecules that are synthetically composed of nucleic acids or proteins to produce an artificial antibody. An antibody mimetic can be an artificial peptide with a molar mass of about 3 to 20 kDa. In various embodiments, the antibody mimetic comprises an intrabody, a monobody, a linear peptide, or an alphabody. In preferred embodiments, the antibody mimetic is an alphabody. Alphabodies are small proteins (about 10 kDa molecular weight) engineered to bind to a variety of antigens, and the standard alphabody scaffold contains three alpha-helices connected via glycine/serine-rich linkers. Alphabody sequences were found to fold as antiparallel triple-stranded α-helical coiled-coil structures, thus adopting a previously unknown fold (Desmet et al. 2014, Nature Communications 5:5237, DOI:10.1038/ncomms6237).

In various embodiments of the present disclosure, the affinity construct of the disclosure comprises more than one affinity mediating molecule. For example, the present disclosure encompasses a mixture of single domain antibodies (preferably $V_HH$s of heavy chain-only antibodies) and/or CDR3 loops (molecular stacks).

The antibody is a naturally occurring antibody or a fragment, derivative or variant thereof, in particular a nanobody or an immunoglobulin gamma (IgG).

As used herein, a single domain antibody (sdAb) is an antibody fragment consisting of a monomeric variable domain of an antibody. Thus, in the present disclosure the terms "single domain antibody" and "monomeric variable domain antibody" or "single variable domain antibody" may be used interchangeably. Also, the terms "monomeric variable domain" and "single variable domain" may be used herein interchangeably.

In various embodiments, a single domain antibody is a monomeric variable domain (or a single variable domain) of a heavy chain-only antibody. Heavy chain-only antibodies (hcAbs), also simply called heavy chain antibodies, are found in camelids and cartilaginous fish such as sharks. Heavy chain-only antibodies contain a single variable domain ($V_HH$) and two constant domains ($C_H2$, $C_H3$), i.e., they lack the $C_H1$ constant domain, which is found in a conventional antibody and associates with the light chain and to a lesser degree interacts with the $V_H$ domain. The heavy chain antibodies found in cartilaginous fish were originally designated as "immunoglobulin new antigen receptors" (IgNAR), and the single domain antibody obtained from an IgNAR was originally called "variable new antigen receptor ($V_NAR$) fragment". Like a whole antibody, a single domain antibody is able to bind selectively to a specific antigen. A single domain antibody as used in the present disclosure is a monomeric variable domain of a heavy chain-only antibody as found in camelids or cartilaginous fish, specifically sharks. As used herein, single domain antibodies from heavy chain-only antibodies may also be called $V_HH$ fragments or $V_HH$ domain antibodies or $V_HH$ domains.

In various aspects of the present disclosure, a single domain antibody is any one of a Nanobody™ (also known as nanoantibody; see, for example, www.ablynx.com), an antigen-binding domain of a heavy chain-only antibody, and a $V_HH$, or fragments thereof.

In other aspects of the present disclosure, a single domain antibody encompasses a monomeric variable domain from a conventional Immunoglobulin (Ig), i.e., a monomeric variable domain that is obtained when the dimeric variable domains from a common Ig (e.g., from a mammalian organism such as, e.g., human or mice) have been split into monomers and those are isolated. Thus, in the present disclosure, a single domain antibody encompasses not only a monomeric heavy chain variable domain, but also a monomeric light chain variable domain, or fragments or derivatives or variants thereof. A single domain antibody derived from light chains also specifically binds to target antigens or target epitopes. Thus, in the present disclosure the "single domain antibody" preferably is a "single heavy chain variable domain antibody" or a "single light chain variable domain antibody". In the present disclosure, the terms "single heavy/light chain variable domain antibody" and "monomeric heavy/light chain variable domain antibody" may be used interchangeably.

In various aspects of the present disclosure, the "single domain antibody" can also be called a "Nanobody™" or a "nanoantibody". As used herein, a Nanobody™ (or nanoantibody) is an antibody fragment consisting of a monomeric variable domain of an antibody. Thus, in the present disclosure the terms "single domain antibody" and "Nanobody™" or "nanoantibody" may be used interchangeably. In the present disclosure, "single domain antibody" encompasses not only a monomeric heavy chain variable domain, but also a monomeric light chain variable domain. Preferably, a single domain antibody is a monomeric variable domain of a heavy chain-only antibody as found in camelids and cartilaginous fish such as sharks. Thus, in the present disclosure the single domain antibody or fragment or derivative or variant thereof preferably is of shark or camelid origin.

Single domain antibodies are as specific as regular antibodies. As well, they are isolated using standard procedures such as phage panning, allowing them to be cultured in vitro in high concentrations.

In certain embodiments, affinity molecules comprising a single domain antibody comprising the complementarity determining region 1 (CDR1) amino acid sequence, the complementarity determining region 2 (CDR2), and the complementarity determining region 3 (CDR3) amino acid sequence are provided. In certain embodiments, the CDR1, CDR2, and CDR3 amino acid sequences in the single domain antibodies comprise, consist essentially of, or consist of the CDR1, CDR2, and CDR3 regions of an affinity molecule disclosed herein. In certain embodiments, the CDR1, CDR2, and CDR3 amino acid sequences in the single domain antibodies comprise, consist essentially of, or consist of:

(i) the CDR1 amino acid sequence of SEQ ID NO: 138, the CDR2 amino acid sequence of SEQ ID NO: 139, and the CDR3 amino acid sequence of SEQ ID NO: 140 or 141, optionally wherein the single domain antibody comprising the CDR1, CDR2, and CDR3 amino acid sequences binds or specifically binds to an insect gut Nutrient Amino Acid Transporter (NAAT) protein;

(ii) the CDR1 amino acid sequence of SEQ ID NO: 135, the CDR2 amino acid sequence of SEQ ID NO: 136, and the CDR3 amino acid sequence of SEQ ID NO: 137, optionally wherein the single domain antibody comprising the CDR1, CDR2, and CDR3 amino acid sequences binds or specifically binds to an insect gut Nutrient Amino Acid Transporter (NAAT) protein;

(iii) the CDR1 amino acid sequence of SEQ ID NO: 142, the CDR2 amino acid sequence of SEQ ID NO: 143, and the CDR3 amino acid sequence of SEQ ID NO: 144, optionally wherein the single domain antibody comprising the CDR1, CDR2, and CDR3 amino acid sequences binds or specifically binds to an insect gut Nutrient Amino Acid Transporter (NAAT) protein;

(iv) the CDR1 amino acid sequence of SEQ ID NO: 145, the CDR2 amino acid sequence of SEQ ID NO: 146, and the CDR3 amino acid sequence of SEQ ID NO: 147, optionally wherein the single domain antibody comprising the CDR1, CDR2, and CDR3 amino acid sequences binds or specifically binds to an insect gut Nutrient Amino Acid Transporter (NAAT) protein;

(v) the CDR1 amino acid sequence of SEQ ID NO: 148, the CDR2 amino acid sequence of SEQ ID NO: 149, and the CDR3 amino acid sequence of SEQ ID NO: 150, optionally wherein the single domain antibody comprising the CDR1, CDR2, and CDR3 amino acid sequences binds or specifically binds to a Cry1F protein;

(vi) the CDR1 amino acid sequence of SEQ ID NO: 151, the CDR2 amino acid sequence of SEQ ID NO: 152, and the CDR3 amino acid sequence of SEQ ID NO: 153, optionally wherein the single domain antibody comprising the CDR1, CDR2, and CDR3 amino acid sequences binds or specifically binds to a Cry1F protein;

(vii) the CDR1 amino acid sequence of SEQ ID NO: 154, the CDR2 amino acid sequence of SEQ ID NO: 155, and the CDR3 amino acid sequence of SEQ ID NO: 156 or 157, optionally wherein the single domain antibody comprising the CDR1, CDR2, and CDR3 amino acid sequences binds or specifically binds to an insect gut cadherin protein;

(viii) the CDR1 amino acid sequence of SEQ ID NO: 158, the CDR2 amino acid sequence of SEQ ID NO: 159, and the CDR3 amino acid sequence of SEQ ID NO: 160, optionally wherein the single domain antibody comprising the CDR1, CDR2, and CDR3 amino acid sequences binds or specifically binds to an insect gut cadherin protein; or (ix) the CDR1 amino acid sequence of SEQ ID NO: 161, the CDR2 amino acid sequence of SEQ ID NO: 162, and the CDR3 amino acid sequence of SEQ ID NO: 163, optionally wherein the single domain antibody comprising the CDR1, CDR2, and CDR3 amino acid sequences binds or specifically binds to a Cry1F protein.

In certain embodiments, the affinity molecule will comprise a framework region of a camelid single domain antibody or of a humanized camelid single domain antibody including but not limited to the framework regions set forth in FIG. 7 (FR1, FR2, FR3, and FR4), the affinity molecules set forth herein, or variant thereof (e.g., variants wherein at least one, two, three, or more amino acid residues are substituted or conservatively substituted and/or variants having at least 85%, 90%, 95%, or 98% sequence identity thereto). Such conservative substitutions can include substitutions where an acidic amino acid residue is substituted with another acidic amino acid residue, a basic amino acid residue is substituted with another basic amino acid residue, a polar amino acid residue is substituted with another polar amino acid residue, and/or where a neutral non-polar amino acid residue is substituted with another neutral non-polar amino acid residue. In certain embodiments, the affinity molecule further comprises an amino acid or peptide linker of 1 to 100 amino acids in length, optionally wherein the amino acid or peptide linker comprises a proline-threonine (PT) peptide, a peptide comprising one or more glycine residues, or a peptide comprising glycine and serine residues. In certain embodiments, the affinity molecule is fused (i.e., operably linked) to a Bacillus thuringiensis delta-endotoxin or a modified Bacillus thuringiensis delta-endotoxin. In certain embodiments, the affinity molecule further comprises (e.g., is operably linked to) a second single domain antibody. In certain embodiments, the second single domain antibody comprises: (i) the CDR1 amino acid sequence of SEQ ID NO: 148, the CDR2 amino acid sequence of SEQ ID NO: 149, and the CDR3 amino acid sequence of SEQ ID NO:150; (ii) the CDR1 amino acid sequence of SEQ ID NO: 151, the CDR2 amino acid sequence of SEQ ID NO: 152, and the CDR3 amino acid sequence of SEQ ID NO: 153; or (iii) the CDR1 amino acid sequence of SEQ ID NO: 161, the CDR2 amino acid sequence of SEQ ID NO: 162, and the CDR3 amino acid sequence of SEQ ID NO: 163. In certain embodiments, the affinity molecule comprises: (i) the first single domain antibody comprising the CDR1 amino acid sequence of SEQ ID NO: 138, the CDR2 amino acid sequence of SEQ ID NO: 139, and the CDR3 amino acid sequence of SEQ ID NO: 141; and (ii) the second single domain antibody comprising the CDR1 amino acid sequence of SEQ ID NO: 148, the CDR2 amino acid sequence of SEQ ID NO: 149, and the CDR3 amino acid sequence of SEQ ID NO:150, wherein the first and the second single domain antibodies are operably connected with an amino acid or peptide linker.

Also provided are, compositions comprising the affinity molecules, including but not limited to compositions further comprising a Bacillus thuringiensis delta-endotoxin or a modified Bacillus thuringiensis delta-endotoxin. In certain embodiments, the single domain antibody is fused (i.e., operably linked) to the Bacillus thuringiensis delta-endotoxin or the modified Bacillus thuringiensis delta-endotoxin I in the composition. Methods of preventing damage to a plant, a plant part or plant seed by one or more insect pests in the order Lepidoptera, comprising contacting the insect pests with the compositions or polypeptides comprising the affinity molecules are also provided. the insect pest is Fall Armyworm (FAW; Spodoptera frugiperda), Corn Earworm (CEW; Helicoverpa zea), Diamondback Moth (DBM), or Black Cutworm (BCW; Agrotis epsilon).

Also provided are recombinant nucleic acid molecules comprising a polynucleotide sequence encoding the affinity molecules, optionally wherein the recombinant nucleic acid further comprises a promoter operably linked to the polynucleotide sequence. Transgenic host cells comprising the recombinant nucleic acids, optionally wherein the transgenic host cell is a yeast cell, a bacterial cell, or a plant cell are also provided. Methods of producing an insecticidal formulation comprising the affinity molecules and one or more insecticidal proteins are also provided, optionally wherein the insecticidal protein is a Bacillus thuringiensis delta-endotoxin, a modified Bacillus thuringiensis delta-endotoxin, a Cry1F, Cry1Ab, or Cry1Ac *Bacillus thuringiensis* delta-endotoxin, are provided. In certain embodiments, the methods comprise formulating the affinity molecule and the one or more insecticidal protein(s) (toxin(s)) as an insecticidal formulation, optionally wherein said affinity molecule and said one or more insecticidal protein(s) (toxin(s)) are expressed in one or more microorganism(s) (e.g., a *Bacillus* sp. spore).

Methods of producing a plant or a microorganism comprising the affinity molecules are also provided. In certain embodiments, the methods comprise transforming the plant or microorganism with one or more nucleic acid molecules encoding the affinity molecule. In certain embodiments, the methods comprise transforming a plant or that microorganism comprises or is transformed with one or more nucleic acids encoding an insecticidal protein selected from the group consisting of a Cry1F, Cry1Ab, or Cry1Ac *Bacillus thuringiensis* delta-endotoxin or a modified *Bacillus thuringiensis* delta-endotoxin.

Instead of using entire single domain antibodies ($V_HH$ domains), a binding fragment of the sdAb like the extruding CDR3 loops (complementary determining region; region determining binding affinity) of $V_HH$ domains can be used as affinity molecule in the affinity construct of the present disclosure. The CDR3 loop of certain single domain antibodies has been found to be much longer than that of conventional variable heavy chain ($V_H$) domains (see FIG. 7, for review, see, e.g., S. Muyldermans 2001, Reviews in Molecular Biotechnology 74, 277-302, or M. M. Harmsen et al. 2000, Molecular Immunology 37, 579-590). Thus, the CDR3 loop region of certain single domain antibody possesses the capacity to form long finger-like extensions that can extend into cavities of antigens, e.g., the active site slot of enzymes. The small size of CDR3 loops reduces the risk of conformational changes and steric hindrance when used in fusions with other proteins. CDR3 loops comprise the epitope-recognizing regions of a single domain antibody which recognize and bind to the antigen. These regions are often sufficient for mediating binding to target proteins. Therefore, the present disclosure encompasses not only the use of complete single domain antibodies as affinity molecule in the affinity construct of the present disclosure, but also the use of functional fragments thereof. Such functional fragments are generally the epitope-recognizing regions of a single domain antibody, e.g., the CDR3 loop of an sdAb of the present disclosure, and they are encompassed for use in an affinity construct of the disclosure. In various embodiments, the functional fragment of a single domain antibody or of a fragment thereof of the present disclosure is the CDR3 loop of a single domain antibody. In various embodiments, the CDR3 loop is derived from of a single domain antibody found in camelids and cartilaginous fish such as sharks. In certain embodiments, the CDR3 loop is a CDR3 loop that binds an insect nutrient amino acid transporter protein and comprises, consists essentially of, or consists of the CDR3 amino acid sequence of SEQ ID NO: 137, 140, 141, 144, 147, 150, or 153. In certain embodiments, the CDR3 loop is a CDR3 loop that binds an insect cadherin protein and comprises, consists essentially of, or consists of the CDR3 amino acid sequence of SEQ ID NO: 156, 157, or 160. In certain embodiments, the CDR3 loop is a CDR3 loop that binds a Cry1F Bt endotoxin and comprises, consists essentially of, or consists of the CDR3 amino acid sequence of SEQ ID NO: 163. In certain embodiments, the CDR3 loop consisting essentially of the amino acid sequence of SEQ ID NO: 137, 140, 141, 144, 147, 150, 153, 156, 157, or 160 is a polypeptide that further consists of one, two, or 3 additional amino acids at the N-terminus and/or C-terminus of the CDR3 loop amino acid sequence.

Figure 2A:
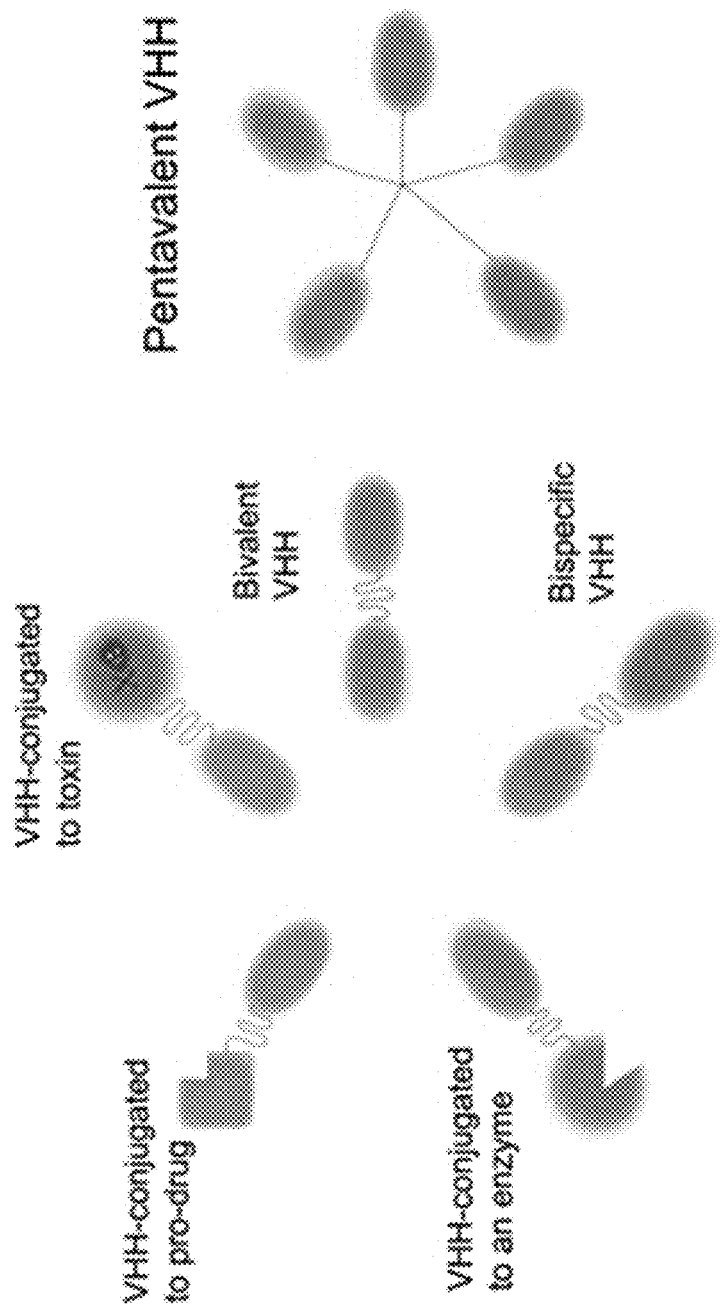
FIG. 2A shows examples for different recombinant $V_HH$s (valences and specificities).
Figure 3:
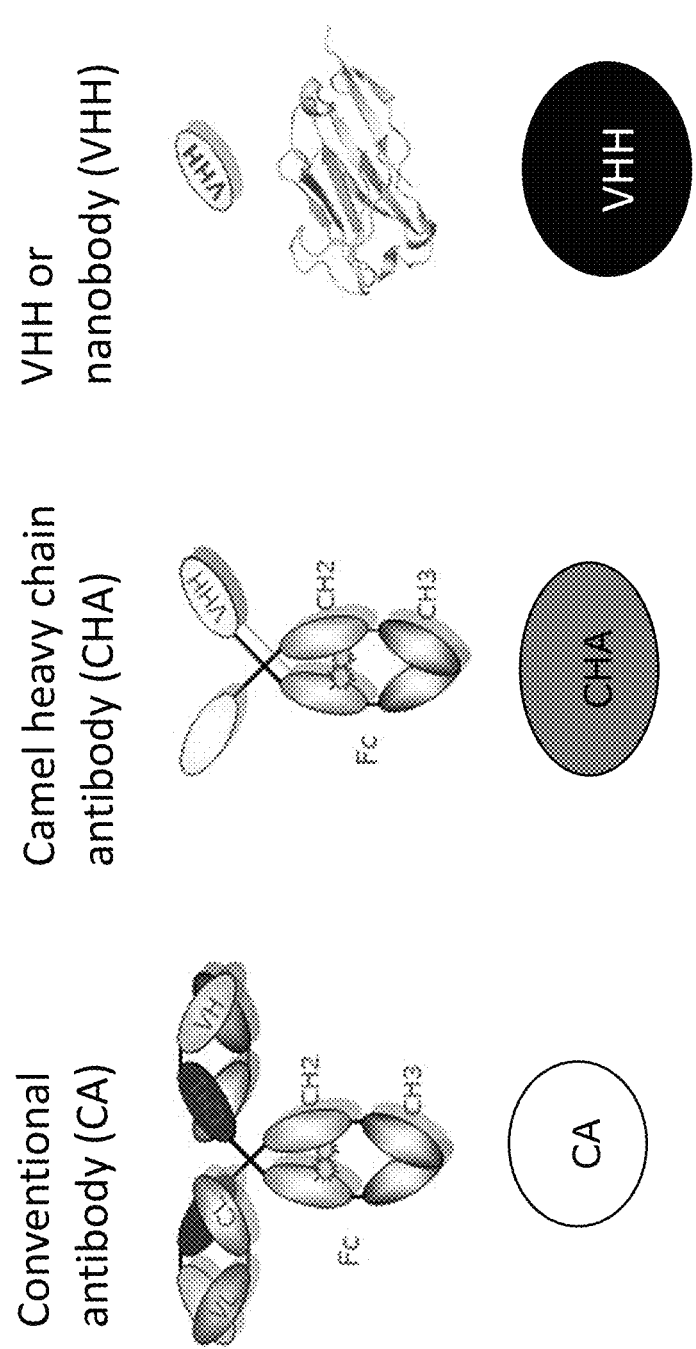
FIG. 3 shows a comparison of the structures of a conventional antibody (CA), a heavy chain antibody of camelid origin (CHA) and of a $V_HH$. For $V_HH$ the protein structure is also provided. Part of the FIG. is modified according to http://www.structuralbiology.be/chaperones.

Affinity molecules provided herein, including entire single domain antibodies ($V_HH$ domains) or a binding fragment of the sdAb like the extruding CDR3 loops (complementary determining region; region determining binding affinity) of $V_HH$ domains, can be fused directly to an insecticidal protein (toxin) (e.g., *Bacillus thuringiensis* delta-endotoxin or a modified *Bacillus thuringiensis* delta-endotoxin), an enzyme, a pro-drug, or a distinct affinity molecule (e.g., FIG. 2A). In certain embodiments, any of the aforementioned or otherwise provided single domain antibodies or CDR3 loops can also be fused directly to an insecticidal protein (toxin). Examples of fusions of other affinity molecules to insecticidal proteins (toxins) which can be adapted to provide direct fusions of affinity molecules provided herein to insecticidal proteins (toxin) include but are not limited to insecticidal proteins (toxins) disclosed in US Patent Application 20170029844, which is incorporated herein by reference in its entirety.

In various embodiments, the single domain antibodies of the affinity constructs provided by the present disclosure are antibody fragments of a $V_HH$ fusion protein, e.g. "one gene encoded single-chain variable domain fragments" and/or "antibody fragments carrying the three CDR loops CDR1, CDR2 and CDR3" and/or "antibody fragments carrying protruding CDR loops ($V_HH$ CDR3 like loops) derived from or inspired by $V_HH$ fragments obtained from camelid/shark single chain antibodies.

A further advantage of the novel affinity construct of the present disclosure is that the single domain antibodies used as affinity molecule(s) can be selected not to trigger any immune responses in mammals and human. This is different to conventional antibodies or antibody fragments, which are less suitable for transgenic plant approaches as anticipated in the present disclosure. Where necessary or appropriate, the nucleic acid sequence of single domain antibodies or fragments thereof that are of animal origin, and in particular of shark or camelid origin, can be modified/adapted for expression in plants as described herein elsewhere. Also encompassed by the present disclosure are plant sequences, more preferred corn sequences, that are homologues of sequences of single domain antibodies or fragments thereof that are of animal origin, and in particular of shark or camelid origin. Thus, the present disclosure encompasses identifying homologues in the plant genome of the sequences of single domain antibodies or fragments thereof of the present disclosure that are of a normal origin and in particular of shark or camelid origin. Such homologous sequences identified in the genome of a plant of interest, preferably in the corn genome, can be used for expression of single domain antibodies or fragments thereof in plants.

In the present disclosure, the single domain antibody or a fragment or derivative or variant thereof, e.g., the CDR3 loop of an sdAb, can be monovalent or multivalent, which means in case of the latter that two or more single domain antibodies or fragments or derivatives or variants thereof are fused or linked with each other. Suitable linker molecules are described elsewhere in the present disclosure. For example, the single domain antibody or fragment or derivative or variant thereof, e.g., the CDR3 loop of an sdAb, can be divalent, trivalent, tetravalent, or multivalent.

The affinity molecules and fragments thereof of the present disclosure can be applied to a plant, or a part or seed thereof. Also, the affinity molecules and fragments thereof of the present disclosure can be expressed in a plant, or a part or seed thereof. Methods of producing synthetic affinity molecules are well known to the person skilled in the art.

Target Binding Structures

The affinity construct of the present disclosure comprises at least two affinity molecules. At least one of these at least two affinity molecules is affinity molecule A capable of recognizing, or capable of binding to, or binding to, or being directed to, or being designed to bind to an insect-specific structure in and/or on a target insect. Further, at least one of these at least two affinity molecules is affinity molecule B capable of binding to, or binding to, or being directed to, or being designed to bind to an insecticidal protein (toxin). The at least one affinity molecule A has been raised or designed against one or more insect-specific structures and is thus capable of binding to or are binding to such structure(s) in the insect pest. Further, the at least one second affinity molecule B has been raised or designed against one or more insecticidal proteins (toxins) and is thus capable of binding to or are binding to such insecticidal protein(s).

The Insect Specific Structures/Receptors:

In various embodiments of the disclosure, the one or more affinity molecule A or a fragment thereof being comprised in the affinity construct of the present disclosure are capable of recognizing, or capable of binding to, or binding to, or being directed to, or being designed to bind specifically to a membrane-bound molecule of an inner organ of an insect, in particular to a membrane-bound molecule of a reproductive organ or the nervous system of an insect.

In preferred embodiments of the disclosure, the one or more affinity molecule A or a fragment thereof being comprised in the affinity construct of the present disclosure are capable of recognizing, or capable of binding to, or binding to, or being directed to, or being designed to bind specifically to a membrane-bound molecule of the digestive tract of an insect, more preferably to a membrane-bound molecule of the gut or intestine of the insect. Preferably, the membrane-bound molecule is a receptor molecule, more preferably an essential receptor molecule, even more preferably a receptor molecule for a Cry protein. Preferably, the receptor molecule is selected from the group consisting of cadherin protein receptors, aminopeptidase N protein receptors, alkaline phosphatase protein receptors, ABC transporter protein receptors, or any other midgut protein that could serve as a potential receptor, such as chitin synthase B proteins, viral docking proteins, 14-3-3 scaffold proteins or any other membrane bound or membrane-associated molecule.

The at least one affinity molecule A being comprised in the affinity construct of the present disclosure are capable of recognizing, or capable of binding to, or binding to, or being directed to, or being designed to bind to receptors of an inner organ of an insect, preferably of the digestive tract, a reproductive organ or the nervous system, but specifically binds to receptors in the midgut or intestine of an insect or insect pest, as described herein above. As mentioned herein above, the digestive system of insects comprises an alimentary canal or gut, which is divided into three sections: foregut, midgut, and hindgut. The hindgut comprises the intestines, more specifically the Malpighian tubule system, which is where much of the diffusion into the insect's body occurs. In various embodiments, the one more affinity molecule A or a fragment thereof is capable of recognizing, or capable of binding to, or binding to, or being directed to, or being designed to bind to receptors in the midgut or intestine of insect larvae. Any specific structure of an inner organ of an insect, preferably of the digestive tract, a reproductive organ or the nervous system, and more preferably of the midgut or intestine of an insect or an insect larva can be targeted in the context of the present disclosure. In various aspects, this insect-specific structure is a specific structure of the midgut of an insect or an insect larva. In various embodiments, the one or more affinity molecule A or a fragment thereof is capable of recognizing, or capable of binding to, or binding to, or being directed to, or being designed to bind to a midgut membrane protein of an insect or an insect larva. In various embodiments, the midgut membrane protein is an insect or insect larva midgut membrane receptor protein. In various embodiments, the insect or insect larva midgut membrane receptor protein is an insect or insect larva midgut membrane receptor for an insecticidal protein from Bt. In various embodiments of the disclosure, the affinity molecule A or a fragment thereof binds to the apical membrane of insect or insect larvae midgut cells.

In preferred embodiments, the one or more affinity molecule A or a fragment thereof, is capable of recognizing, or capable of binding to, or binding to, or being directed to, or being designed to have been raised against or designed to bind and thus bind specifically to Bt toxin receptor proteins of an insect midgut membrane. In various other embodiments, the affinity molecule A of the present disclosure specifically binds insect-specific structures other than the Bt toxin receptor proteins, which other structures include, but are not limited to, any other molecules embedded in or being located on the insect gut membrane. Examples of such structures are insect midgut membrane proteins or insect midgut membrane-bound proteins or proteins attached to the insect midgut membrane, and include, without being limited thereto, receptor proteins other than the *Bacillus thuringiensis* (Bt) toxin receptor proteins.

In the context of the present disclosure, insect-specific receptors can be integral part of membranes of the insect gut or can be attached to these membranes via post-transcriptional modifications, including geranyl-phosphatidyl-inositol (GPI) anchors (see FIG. 6 for schematic of how GPI-anchored insect midgut proteins can be used as targets). Such proteins can be identified from transcriptomic (e.g. RNAseq) or proteomic (e.g., Shotgun proteomics, protein sequencing via Mass Spectrometry) analyses of insect midgut proteins, or via proteomic analysis of fractions enriched in midgut membrane proteins. Membrane proteins can be identified using various protein and nucleic acid sequence analysis software tools. Proteins with GPI anchors can be also identified via web-based tools, including big-PI Predictor (GPI Modification Site Prediction, http://mendel.imp.ac.at/sat/gpi/gpi_server.html).

In various embodiments of the disclosure, the one or more affinity molecule A or a fragment thereof is capable of recognizing, or capable of binding to, or binding to, or being directed to, or being designed to bind to a membrane-bound molecule of the intestine of an insect to be targeted by the affinity construct of the present disclosure. In various embodiments of the disclosure, the one or more affinity molecule A or a fragment thereof is capable of recognizing, or capable of binding to, or binding to, or being directed to, or being designed to bind to a membrane-bound molecule of the intestine of an insect larva. In preferred embodiments, the membrane-bound molecule of the intestine of an insect or insect larva is a membrane-bound receptor molecule. More preferably, the membrane-bound receptor molecule of the intestine of an insect or insect larva is a membrane-bound protein (insect or insect larva midgut membrane protein). More specifically, the membrane-bound receptor molecule is a membrane-bound receptor protein. In preferred embodiments, the membrane-bound receptor molecule or membrane-bound receptor protein is a membrane-bound receptor for an insecticidal protein as described herein. More preferably, the membrane-bound receptor for an insecticidal protein is a membrane-bound receptor for a Cry protein.

In various embodiments, the one or more affinity molecule A of the present disclosure is capable of recognizing, or capable of binding to, or binding to, or being directed to, or being designed to specifically to a molecule attached to or being part of a membrane of the target insect or target insect larva. In various embodiments, the membrane of the target insect or target insect larva is a membrane of the midgut of the target insect or target insect larva. In preferred embodiments, the molecule attached to a membrane of the target insect or target insect larva is a receptor attached to a membrane of the midgut of the target insect or target insect larva. More preferably, the receptor attached to a membrane of the midgut of the target insect or target insect larva is a receptor for an insecticidal protein. Even more preferably, the receptor attached to a membrane of the midgut of the target insect or target insect larva is a receptor for a Cry protein.

In various embodiments of the disclosure, the above-mentioned receptor is a cell surface receptor of a cell of the membrane of the midgut of an insect or insect larva. In various embodiments, the above-mentioned specific structure of the midgut of an insect or insect larva serves as or provides one or more epitopes of a cell surface receptor of insect or insect larva midgut membrane cells. In preferred embodiments, the above-mentioned specific structure of the midgut of an insect or insect larva is the extracellular domain of a receptor protein of insect or insect larva midgut membrane cells. More preferably, the above-mentioned specific structure of the midgut of an insect or insect larva serves as or provides one or more epitopes of the extracellular domain of a receptor protein of insect or insect larva midgut membrane cells. In various aspects, the above-mentioned insect or insect larva midgut membrane receptor is a carbohydrate receptor.

In various embodiments, the above-mentioned receptor for a Cry protein to which one or more affinity molecule A or a fragment thereof of the present disclosure is capable of recognizing, or capable of binding to, or binding to, or being directed to, or being designed to bind, is the receptor of a *B. thuringiensis* Cry protein of any of the 74 major types (classes) of *B. thuringiensis* delta-endotoxins (i.e., the receptor of any of Cry1, Cry2, Cry3, Cry4, Cry5, Cry6, Cry7, Cry8, Cry9, Cry10, Cry11, Cry12, Cry13, Cry14, Cry15, Cry16, Cry17, Cry18, Cry19, Cry20, Cry21, Cry22, Cry23, Cry24, Cry25, Cry26, Cry27, Cry28, Cry29, Cry30, Cry31, Cry32, Cry33, Cry34, Cry35, Cry36, Cry37, Cry38, Cry39, Cry40, Cry41, Cry42, Cry43, Cry44, Cry45, Cry 46, Cry47, Cry49, Cry50, Cry 51, Cry52, Cry53, Cry54, Cry55, Cry56, Cry57, Cry58, Cry59, Cry60, Cry61, Cry62, Cry63, Cry64, Cry65, Cry66, Cry67, Cry68, Cry69, Cry70, Cry71, Cry72, Cry73 or Cry74). In preferred embodiments of the disclosure, the one or more affinity molecule A or a fragment thereof is capable of recognizing, or capable of binding to, or binding to, or being directed to, or being designed to bind to a receptor of a Cry1 or a Cry3 toxin. More preferably, the one nor more affinity molecule A or a fragment thereof is capable of recognizing, or capable of binding to, or binding to, or being directed to, or being designed to bind to a receptor for a Cry1Ac or a Cry3Aa toxin. In various other embodiments of the disclosure, the affinity molecule A or a fragment thereof is capable of recognizing, or capable of binding to, or binding to, or being directed to, or being designed to bind to a receptor of any one of: Cry1Aa (e.g., Cry1Aa1, Accession #M11250), Cry1Ab (e.g., Cry1Ab1, Accession #M13898), Cry1Ab-Iike (Accession #AF327924 or #AF327925 or #AF327926), Cry1Ac (e.g., Cry1Ac1, Accession #M11068), Cry1Ad (e.g., Cry1Ad1, Accession #M73250), Cry1Ae (e.g., Cry1Ae1, Accession #M65252), Cry1Af (e.g., Cry1Af1, Accession #U82003), Cry1Ag (e.g., Cry1Ag1, Accession #AF081248), Cry1Ah (e.g., Cry1Ah1, Accession #AF281866), Cry1Ai (e.g., Cry1Ai1, Accession #AY174873), Cry1A-Iike (Accession #AF327927), Cry1Ba (e.g., Cry1Ba1, Accession #X06711), Cry1Bb (e.g., Cry1Bb1, Accession #L32020), Cry1Bc (e.g., Cry1Bc1, Accession #Z46442), Cry1Bd (e.g., Cry1Bd1, Accession #U70726), Cry1Be (e.g., Cry1Be1, Accession #AF077326), Cry1Bf (e.g., Cry1Bf1, Accession #AX189649), Cry1Bg (e.g., Cry1Bg1, Accession #AY176063), Cry1Ca (e.g., Cry1Ca1, Accession #X07518), Cry1Cb (e.g., Cry1Cb1, Accession #M97880), Cry1Cb-Iike (Accession #AAX63901), Cry1 Da (e.g., Cry1Da1, Accession #X54160), Cry1db (e.g., Cry1db1, Accession #Z22511), Cry1Dc (e.g., Cry1Dc1, Accession #EF059913), Cry1Ea (e.g., Cry1Ea1, Accession #X53985), Cry1Eb (e.g., Cry1Eb1, Accession #M73253), Cry1Fa (e.g., Cry1Fa1, Accession #M63897), Cry1Fb (e.g., Cry1Fb1, Accession #Z22512), Cry1Ga (e.g., Cry1Ga1, Accession #Z22510), Cry1Gb (e.g., Cry1Gb1, Accession #U70725), Cry1Gc (Accession #AAQ52381), Cry1Ha (e.g., Cry1Ha1, Accession #Z22513), Cry1Hb (e.g., Cry1Hb1, Accession #U35780), Cry1H-Iike (Accession #AF182196), Cry1Ia (e.g., Cry1Ia1, Accession #X62821), Cry1Ib (e.g., Cry1Ib1, Accession #U07642), Cry1Ic (e.g., Cry1Ic1, Accession #AF056933), Cry1Id (e.g., Cry1Id1, Accession #AF047579), Cry1Ie (e.g., Cry1Ie1, Accession #AF211190), Cry1If (e.g., Cry1If1, Accession #AAQ52382), Cry1l-like (Accession #190732), Cry1Ja (e.g., Cry1Ja1 (Accession #L32019), Cry1Jb (e.g., Cry1Jb1, Accession #U31527), Cry1Jc (e.g., Cry1Jc1 (Accession #I90730), Cry1Jd (e.g., Cry1Jd1 (Accession #AX189651), Cry1Ka (e.g., Cry1Ka1, Accession #U28801), Cry1La (e.g., Cry1La1, Accession #AAS60191), Cry1-Iike (Accession #190729), Cry2Aa (e.g., Cry2Aa1, Accession #M31738), Cry2Ab (e.g., Cry2Ab1, Accession #M23724), Cry2Ac (e.g., Cry2Ac1, Accession #X57252), Cry2Ad (e.g., Cry2Ad1, Accession #AF200816), Cry2Ae (e.g., Cry2Ae1, Accession #AAQ52362), Cry2Af (e.g., Cry2Af1, Accession #EF439818), Cry2Ag (Accession #ACH91610), Cry2Ah (Accession #EU939453), Cry3Aa (e.g., Cry3Aa1, Accession #M22472), Cry3Ba (e.g., Cry3Ba1, Accession #X17123), Cry3Ca (e.g., Cry3Ca1, Accession #X59797), Cry4Aa (e.g., Cry4Aa1, Accession #00423), Cry4A-like (Accession #DQ078744), Cry4Ba (e.g., Cry4Ba1, Accession #X07423), Cry4Ba-like (Accession #ABC47686), Cry4Ca (e.g., Cry4Ca1, Accession #EU646202), Cry5Aa (e.g., Cry5Aa1, Accession #L07025), Cry5Ab (e.g., Cry5Ab1, Accession #L07026), Cry5Ac (e.g., Cry5Ac1, Accession #I34543), Cry5 Ad (e.g., Cry5Ad1, Accession #EF219060), Cry5Ba (e.g., Cry5Ba1, Accession #U19725), Cry6Aa (e.g., Cry6Aa1, Accession #L07022), Cry6Ba (e.g., Cry6Ba1, Accession #L07024), Cry7Aa (e.g., Cry7Aa1, Accession #M64478), Cry7Ab (e.g., Cry7Ab1, Accession #U04367), Cry7Ba (e.g., Cry7Ba1, Accession #ABB70817), Cry7Ca (e.g., Cry7Ca1, Accession #EF486523), Cry8Aa (e.g., Cry8Aa1, Accession #U04364), Cry8Ab (e.g., Cry8Ab1, Accession #EU044830), Cry8Ba (e.g., Cry8Ba1, Accession #U04365), Cry8Bb (e.g., Cry8Bb1, Accession #AX543924), Cry8Bc (e.g., Cry8Bc1, Accession #AX543926), Cry8Ca (e.g., Cry8Ca1, Accession #U04366), Cry8 Da (e.g., Cry8Da1, Accession #AB089299), Cry8db (e.g., Cry8db1, Accession #AB303980), Cry8Ea (e.g., Cry8Ea1, Accession #AY329081), Cry8Fa (e.g., Cry8Fa1, Accession #AY551093), Cry8Ga (e.g., Cry8Ga1, Accession #AY590188), Cry8Ha (e.g., Cry8Ha1, Accession #EF465532), Cry8Ia (e.g., Cry8Ia1, Accession #EU381044), Cry8Ja (e.g., Cry8Ja1, Accession #EU625348), Cry8-like (Accession #ABS53003), Cry9Aa (e.g., Cry9Aa1, Accession #X58120), Cry9Ba (e.g., Cry9Ba1, Accession #X75019), Cry9Bb (e.g., Cry9Bb1, Accession #AY758316), Cry9Ca (e.g., Cry9Ca1, Accession #Z37527), Cry9 Da (e.g., Cry9Da1, Accession #D85560), Cry9db (e.g., Cry9db1, Accession #AY971349), Cry9Ea (e.g., Cry9Ea1, Accession #AB011496), Cry9Eb (e.g., Cry9Eb1, Accession #AX189653), Cry9Ec (e.g., Cry9Ec1, Accession #AF093107), Cry9Ed (e.g., Cry9Ed1, Accession #AY973867), Cry9-like (Accession #AF093107), Cry10Aa (e.g., Cry10Aa1, Accession #M12662), Cry10A-like (Accession #DQ167578), Cry11Aa (e.g., Cry11Aa1, Accession #M31737), Cry11Aa-like (Accession #DQ166531), Cry11Ba (e.g., Cry11Ba1, Accession #X86902), Cry11Bb (e.g., Cry11Bb1, Accession #AF017416), Cry12Aa (e.g., Cry12Aa1, Accession #L07027), Cry13Aa (e.g., Cry13Aa1, Accession #L07023), Cry14Aa (e.g., Cry14Aa1, Accession #U13955), Cry15Aa (e.g., Cry15Aa1, Accession #M76442), Cry16Aa (e.g., Cry16Aa1, Accession #X94146), Cry17Aa (e.g., Cry17Aa1, Accession #X99478), Cry18Aa (e.g., Cry18Aa1, Accession #X99049),Cry18Ba (e.g., Cry18Ba1, Accession #AF169250), Cry18Ca (e.g., Cry18Ca1, Accession #AF169251), Cry19Aa (e.g., Cry19Aa1, Accession #Y07603), Cry19Ba (e.g., Cry19Ba1, Accession #D88381), Cry20Aa (e.g., Cry20Aa1, Accession #U82518), Cry21Aa (e.g., Cry21Aa1, Accession #I32932), Cry21Ba (e.g., Cry21Ba1, Accession #AB088406), Cry22Aa (e.g., Cry22Aa1, Accession #I34547), Cry22Ab (e.g., Cry22Ab1, Accession #AAK50456), Cry22Ba (e.g., Cry22Ba1, Accession #AX472770), Cry23Aa (e.g., Cry23Aa1, Accession #AAF76375), Cry24Aa (e.g., Cry24Aa1, Accession #U88188), Cry24Ba (e.g., Cry24Ba1, Accession #BAD32657), Cry24Ca (e.g., Cry24Ca1, Accession #AM158318), Cry25Aa (e.g., Cry25Aa1, Accession #U88189), Cry26Aa (e.g., Cry26Aa1, Accession #AF122897), Cry27Aa (e.g., Cry27Aa1, Accession #AB023293), Cry28Aa (e.g., Cry28Aa1, Accession #AF132928), Cry29Aa (e.g., Cry29Aa1, Accession #AJ251977), Cry30Aa (e.g., Cry30Aa1, Accession #AJ251978), Cry30Ba (e.g., Cry30Ba1, Accession #BAD00052), Cry30Ca (e.g., Cry30Ca1, Accession #BAD67157), Cry30 Da (e.g., Cry30Da1, Accession #EF095955), Cry30db (e.g., Cry30db1, Accession #BAE80088), Cry30Ea (e.g., Cry30Ea1, Accession #EU503140), Cry30Fa (e.g., Cry30Fa1, Accession #EU751609), Cry30Ga (e.g., Cry30Ga1, Accession #EU882064), Cry31 Aa (e.g., Cry31Aa1, Accession #AB031065), Cry31Ab (e.g., Cry31Ab1, Accession #AB250923), Cry31Ac (e.g., Cry31Ac1, Accession #AB276125), Cry32Aa (e.g., Cry32Aa1, Accession #AY008143), Cry32Ba (e.g., Cry32Ba1, Accession #BAB78601), Cry32Ca (e.g., Cry32Ca1, Accession #BAB78602), Cry32 Da (e.g., Cry32Da1, Accession #BAB78603), Cry33Aa (e.g., Cry33Aa1, Accession #AAL26871), Cry34Aa (e.g., Cry34Aa1, Accession #AAG50341), Cry34Ab (e.g., Cry34Ab1, Accession #AAG41671), Cry34Ac (e.g., Cry34Ac1, Accession #AAG50118), Cry34Ba (e.g., Cry34Ba1, Accession #AAK64565), Cry35Aa (e.g., Cry35Aa1, Accession #AAG50342), Cry35Ab (e.g., Cry35Ab1, Accession #AAG41672), Cry35Ac (e.g., Cry35Ac1, Accession #AAG50117), Cry35Ba (e.g., Cry35Ba1, Accession #AAK64566), Cry36Aa (e.g., Cry36Aa1, Accession #AAK64558), Cry37Aa (e.g., Cry37Aa1, Accession #AAF76376), Cry38Aa (e.g., Cry38Aa1, Accession #AAK64559), Cry39Aa (e.g., Cry39Aa1, Accession #BAB72016), Cry40Aa (e.g., Cry40Aa1, Accession #BAB72018), Cry40Ba (e.g., Cry40Ba1, Accession #BAC77648), Cry40Ca (e.g., Cry40Ca1, Accession #EU381045), Cry40 Da (e.g., Cry40Da1, Accession #EU596478), Cry41Aa (e.g., Cry41Aa1, Accession #AB116649), Cry41Ab (e.g., Cry41Ab1, Accession #AB116651), Cry42Aa (e.g., Cry42Aa1, Accession #AB116652), Cry43Aa (e.g., Cry43Aa1, Accession #AB115422), Cry43Ba (e.g., Cry43Ba1, Accession #AB115422), Cry43-like (Accession #AB115422), Cry44Aa (Accession #BAD08532), Cry45Aa (Accession #BAD22577), Cry46Aa (Accession #BAC79010), Cry46Ab (Accession #BAD35170), Cry47Aa (Accession #AY950229), Cry48Aa (Accession #AJ841948), Cry48Ab (Accession #AM237207), Cry49Aa (Accession #AJ841948), Cry49Ab (e.g., Cry49Ab1, Accession #AM237202), Cry50Aa (e.g., Cry50Aa1, Accession #AB253419), Cry51Aa (e.g., Cry51Aa1, Accession #DQ836184), Cry52Aa (e.g., Cry52Aa1, Accession #EF613489), Cry53Aa (e.g., Cry53Aa1, Accession #EF633476), Cry54Aa (e.g., Cry54Aa1, Accession #EU339367), and Cry55Aa (e.g., Cry55Aa1, Accession #EU121521). In various embodiments of the disclosure, the one or more affinity molecule A or a fragment thereof is capable of recognizing, or capable of binding to, or binding to, or being directed to, or being designed to bind to a receptor of Cry1Ac, Cry1A.105, Cry2Ab2, Cry3Aa or Cry3Bb1.

In other preferred embodiments of the disclosure, the one or more affinity molecule A or a fragment thereof is capable of recognizing, or capable of binding to, or binding to, or being directed to, or being designed to bind to a receptor of the Cyt toxins of *B. thuringiensis*, preferably to a receptor of the Cyt1 and Cyt2 toxins of *B. thuringiensis*.

In various embodiments of the disclosure, the one or more affinity molecule A or a fragment thereof is capable of recognizing, or capable of binding to, or binding to, or being directed to, or being designed to bind to a receptor of the Cry toxin that is derived from the *B. thuringiensis* strain kurstaki (Btk) HD1, which expresses Cry1Aa, Cry1Ab, Cry1Ac and Cry2Aa proteins, or binds to a receptor of the Cry toxin that is derived from *B. thuringiensis* strain HD73, which produces Cry1Ac (effective in controlling many leaf-feeding lepidopterans that are important crop pests or forest pest defoliators). In various other embodiments of the present disclosure, the one or more affinity molecule A or a fragment thereof is capable of recognizing, or capable of binding to, or binding to, or being directed to, or being designed to bind to a receptor of the Cry toxin that is derived from *B. thuringiensis* var. *aizawai* HD137, which produces slightly different Cry toxins such as Cry1Aa, Cry1Ba, Cry1Ca and Cry1 Da (active against lepidopteran larvae that feed on stored grains). In yet other embodiments of the present disclosure, the one or more affinity molecule A or a fragment thereof is capable of recognizing, or capable of binding to, or binding to, or being directed to, or being designed to bind to a receptor of the Cry toxin that is derived from *B. thuringiensis* var. san diego or *B. thuringiensis* var. *tenebrionis*, which produce Cry3Aa toxin and Cry4A, Cry4B, Cry11A and Cyt1Aa toxins (active against coleopteran pests). In still other embodiments of the present disclosure, the one or more affinity molecule A or a fragment thereof is capable of recognizing, or capable of binding to, or binding to, or being directed to, or being designed to bind to a receptor of a Cry toxin showing toxicity against mosquitoes, like Cry1, Cry2, Cry4, Cry 11, and Cry29. Thus, in one embodiment of the present disclosure, the one or more affinity molecule A or a fragment thereof is capable of recognizing, or capable of binding to, or binding to, or being directed to, or being designed to bind to a receptor of the Cry toxin that is derived from Bt var *israelensis* (Bti.), which has been used worldwide for the control of mosquitoes.

In various embodiments of the present disclosure, the one or more affinity molecule A or a fragment thereof is capable of recognizing, or capable of binding to, or binding to, or being directed to, or being designed to bind to a receptor of the *B. thuringiensis* Cyt1 or Cyt2 toxin. In various other embodiments of the disclosure, the one or more affinity molecule A or a fragment thereof is capable of recognizing, or capable of binding to, or binding to, or being directed to, or being designed to bind to a receptor of the DIG-3 or DIG-I1 toxin, which are N-terminal deletions of alpha-helix 1 and/or alpha-helix 2 variants of Cry proteins such as Cry1A described in U.S. Pat. Nos. 8,304,604 and 8,304,605.

In preferred embodiments of the present disclosure, the one or more affinity molecule A or a fragment thereof is capable of recognizing, or capable of binding to, or binding to, or being directed to, or being designed to bind to a receptor of the Cry proteins that belong to the three-domain Cry (3d-Cry) group, which is the largest family of Cry proteins, with members that show toxicity against different insect orders, such as Hymenoptera, Hemiptera, Lepidoptera, Diptera and Coleoptera. In various embodiments of the present disclosure, the one or more affinity molecule A or a fragment thereof is capable of recognizing, or capable of binding to, or binding to, or being directed to, or being designed to bind to the region of a receptor of a 3d-Cry protein, which is involved in recognition of domain II of a 3d-Cry protein. In various embodiments of the present disclosure, the one or more affinity molecule A or a fragment thereof is capable of recognizing, or capable of binding to, or binding to, or being directed to, or being designed to bind to the region of a receptor of a 3d-Cry protein, which is involved in recognition of domain III of a 3d-Cry protein.

In various other embodiments of the present disclosure, the one or more affinity molecule A or a fragment thereof is capable of recognizing, or capable of binding to, or binding to, or being directed to, or being designed to bind to a receptor of insecticidal lipases including, but not limited to, receptors of lipid acyl hydrolases as described in U.S. Pat. No. 7,491,869, and receptors of cholesterol oxidases such as, for example, from *Streptomyces*.

In other preferred embodiments of the present disclosure, the one or more affinity molecule A or a fragment thereof is capable of recognizing, or capable of binding to, or binding to, or being directed to, or being designed to bind to a receptor of a Vip (vegetative insecticidal protein) toxin from *Bacillus thuringiensis*. More preferably, the one or more affinity molecule A or a fragment thereof is capable of recognizing, or capable of binding to, or binding to, or being directed to, or being designed to bind to a receptor of a Vip1, Vip2 or Vip3 protein. In various embodiments, the one or more affinity molecule A or a fragment thereof is capable of recognizing, or capable of binding to, or binding to, or being directed to, or being designed to bind to a receptor of a Vip protein from *B. thuringiensis*. Preferably, the one or more affinity molecule A or a fragment thereof is capable of recognizing, or capable of binding to, or binding to, or being directed to, or being designed to bind to a receptor of a *B. thuringiensis* Vip1 or a receptor of a Vip2 protein. In various embodiments, the one or more affinity molecule A or a fragment thereof is capable of recognizing, or capable of binding to, or binding to, or being directed to, or being designed to bind to a receptor of a *B. thuringiensis* Vip3 protein. In various embodiments, the one or more affinity molecule A or a fragment thereof is capable of recognizing, or capable of binding to, or binding to, or being directed to, or being designed to bind to a receptor of a *B. thuringiensis* Vip3A protein or a receptor of a *B. thuringiensis* Vip3B protein.

In other embodiments of the present disclosure, the one or more affinity molecule A or a fragment thereof is capable of recognizing, or capable of binding to, or binding to, or being directed to, or being designed to bind to a receptor of a other identified or re-classified insecticidal proteins produced by *B. thuringiensis* including but not limited to Tpp, Mpp, Gpp, App, Spp, Vpa, Vpb, Mcf, Pra, Prb, Xpp, Mpf (see Table 1 of Crickmore et al. 2020, Journal of Invertebrate Pathology, 107438). One recently identified member of Vpb4 insecticidal protein family Vpb4Da2 is particularly active against western corn rootworm (Yin et al. 2020 PLOS one, 15(11): e0242792).

In various embodiments of the present disclosure, the one or more affinity molecule A or a fragment thereof is capable of recognizing, or capable of binding to, or binding to, or being directed to, or being designed to bind to a receptor of an Mtx protein (mosquitocidal toxin). In various other embodiments of the present disclosure, the one or more affinity molecule A or a fragment thereof is capable of recognizing, or capable of binding to, or binding to, or being directed to, or being designed to bind to a receptor of a Bin protein (binary toxin). In various further embodiments of the present disclosure, one or more the affinity molecule A or a fragment thereof is capable of recognizing, or capable of binding to, or binding to, or being directed to, or being designed to bind to a receptor of a Sip protein (secreted insecticidal toxins).

In various embodiments of the present disclosure, the one or more affinity molecule A or a fragment thereof is capable of recognizing, or capable of binding to, or binding to, or being directed to, or being designed to bind to receptors of toxin complex (TC) proteins, obtainable from organisms such as *Xenorhabdus, Photorhabdus* and *Paenibacillus*. In various other embodiments of the present disclosure, the one or more affinity molecule A or a fragment thereof is capable of recognizing, or capable of binding to, or binding to, or being directed to, or being designed to bind to a receptor of spider, snake and scorpion venom proteins.

Methods for identifying receptors of insecticidal proteins are well known in the art (see, Hofmann et. al. (1988, Eur. J. Biochem. 173:85-91; Gill et al. 1995, J. Biol. Chem. 27277-27282) and can be employed to identify and isolate the receptor that recognizes a given insecticidal protein using brush-border membrane vesicles from susceptible insects. Brush-border membrane vesicles (BBMV) of susceptible insects can be prepared according to the protocols listed in the references and separated on SDS-PAGE gel and blotted on a suitable membrane. Labeled insecticidal proteins can be incubated with blotted membrane of BBMV and the insecticidal proteins can be identified with the labeled reporters. Identification of protein band(s) that interact with the insecticidal proteins can be detected by N-terminal amino acid gas phase sequencing or mass spectrometry-based protein identification method (see, Patterson 1998, Current Protocol in Molecular Biology 10(22): 1-24, published by John Wiley & Son Inc). Once the protein is identified, the corresponding gene can be cloned from genomic DNA or cDNA library of the susceptible insects and binding affinity can be measured directly with the insecticidal proteins.

The present disclosure also contemplates affinity molecules A that are capable of recognizing, or capable of binding to, or binding to, or being directed to, or being designed to bind insect-specific structures (such as receptor proteins) in membranes beyond the insect intestine. In various embodiments, targeting of such structures is accomplished by using viral packaging or other packaging means. Relevant insect midgut membranes and feasible receptors sitting in or on such membranes are described in the literature.

The present disclosure also encompasses affinity molecules A that are capable of recognizing, or capable of binding to, or binding to, or being directed to, or being designed to bind insect-specific structures other than the above-mentioned structures, including, but not limited to, protein modifications like, for example, glycosylations, phosphorylations, methylations, acetylations, farnesylations etc., or membrane-lipid modifications like, for example, glycosylations, phosphorylations, specific fatty acids, etc.

Figure 8:
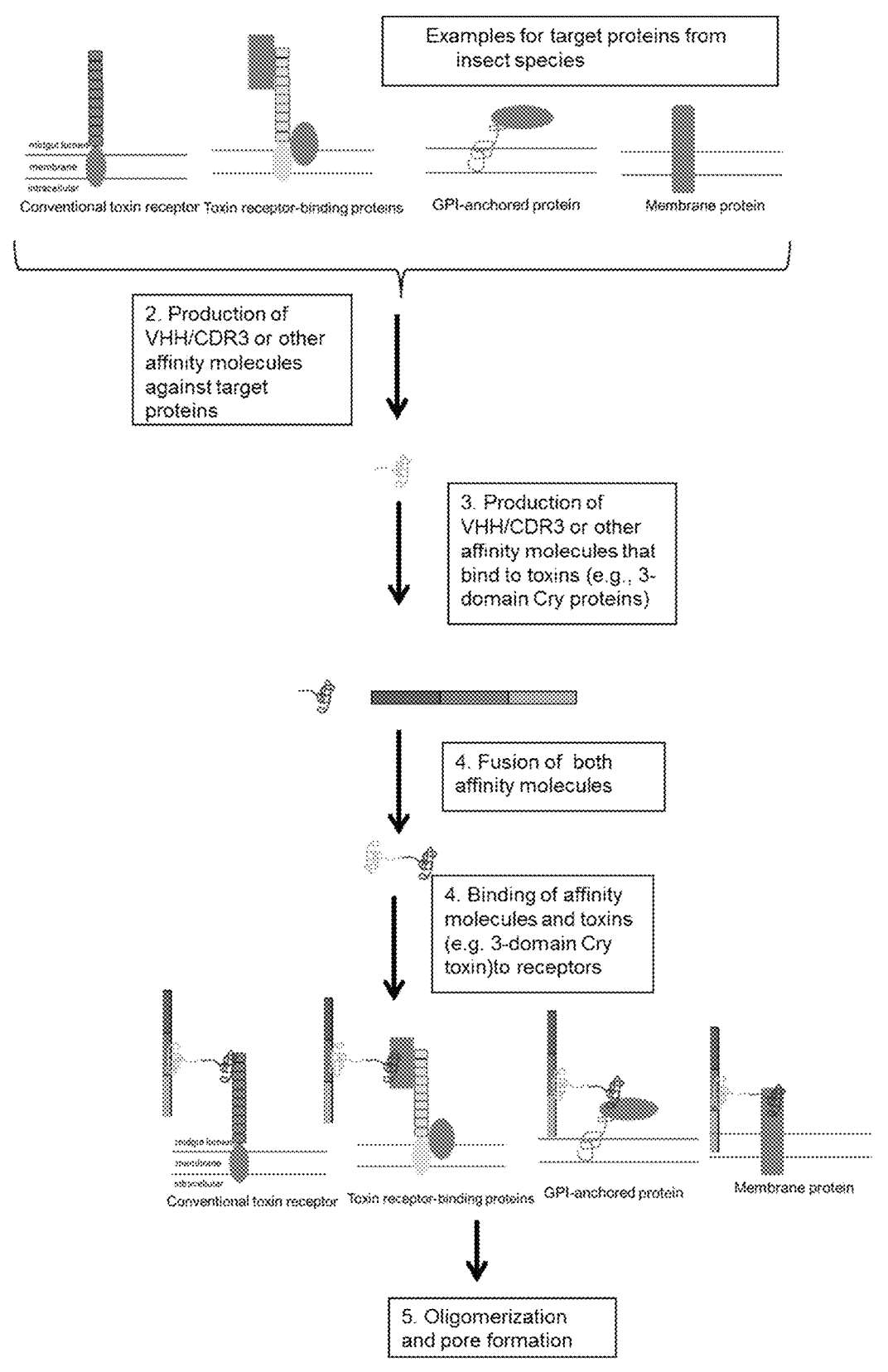

In preferred embodiments of the disclosure, the one or more affinity molecule A or a fragment thereof is capable of recognizing, or capable of binding to, or binding to, or being directed to, or being designed to bind to any one of: cadherin proteins or epitopes thereof; aminopeptidase N proteins or epitopes thereof; alkaline phosphatase proteins or epitopes thereof; ABC transporter proteins or epitopes thereof; 270 kDa glycoconjugate proteins or epitopes thereof; a 250 kDa protein named P252 or epitopes thereof; or any other insect receptor protein that might naturally bind to insecticidal proteins such as Cry proteins. In further embodiments, the one or more affinity molecule A or a fragment thereof is capable of recognizing, or capable of binding to, or binding to, or being directed to, or being designed to bind to insect-structures that do not yet serve as receptors such as, for example, membrane proteins or proteins that are associated to the membrane or interact with membrane proteins, or to modifications of such proteins (e.g., glycosyl, lipoyl, sumoyl, ubiquitin, phosphate residues, see FIG. 8).

In preferred embodiments of the present disclosure, the one or more affinity molecule A or a fragment thereof is capable of recognizing, or capable of binding to, or binding to, or being directed to, or being designed to bind to the *Spodoptera frugiperda* cadherin receptor. Preferably, the one or more affinity molecule A or a fragment is capable of recognizing, or capable of binding to, or binding to, or being directed to, or being designed to bind to the extracellular domain of the *Spodoptera frugiperda* cadherin. The nucleotide and amino acid sequence of the *Spodoptera frugiperda* cadherin is shown in (SEQ ID NOS. 1 and 2) respectively, with amino acids 1-1610 representing the extracellular domain. Additionally, the Cyt toxin binding region of *Spodoptera frugiperda* cadherin is provided in SEQ ID. NOS. 42.

In other preferred embodiments of the present disclosure, the one or more affinity molecule A or a fragment thereof is capable of recognizing, or capable of binding to, or binding to, or being directed to, or being designed to bind to the *Helicoverpa armigera* cadherin receptor. Preferably, the one or more affinity molecule A or a fragment thereof is capable of recognizing, or capable of binding to, or binding to, or being designed to bind to the extracellular domain of the *Helicoverpa armigera* cadherin. The nucleotide and amino acid sequence of the *Helicoverpa armigera* cadherin is presented in SEQ ID. NOS. 3 and 4, with amino acids 1-1583 representing the extracellular domain. In other preferred embodiments of the present disclosure, the one or more affinity molecule A or a fragment thereof is capable of recognizing, or capable of binding to, or binding to, or being directed to, or being designed to thus bind to the *Diabrotica virgifera virgifera* cadherin receptor. Preferably, the one or more affinity molecule A or a fragment thereof is capable of recognizing, or capable of binding to, or binding to, or being directed to, or being designed to bind to the extracellular domain of the *Diabrotica virgifera virgifera* cadherin. The nucleotide and amino acid sequence of the *Diabrotica virgifera virgifera* cadherin is presented in SEQ ID. NOS. 5 and 6, with amino acids 1-1572 representing the extracellular domain. In other preferred embodiments of the present disclosure, the one or more affinity molecule A or a fragment thereof is capable of recognizing, or capable of binding to, or binding to, or being directed to, or being designed to bind to the *Heliothis virescens* cadherin receptor. Preferably, the one or more affinity molecule A or a fragment thereof is capable of recognizing, or capable of binding to, or binding to, or being directed to, or being designed to bind to the extracellular domain of the *Heliothis virescens* cadherin. The nucleotide and amino acid sequence of the *Heliothis virescens* cadherin is presented in SEQ ID. NOS. 7 and 8 respectively with amino acids 1-1583 representing the extracellular domain. In other preferred embodiments, the one or more affinity molecule A or a fragment thereof is capable of recognizing, or capable of binding to, or binding to, or being directed to, or being designed to bind to the *Helicoverpa armigera* chitin synthase B receptor. Preferably, the one or more affinity molecule A or a fragment thereof is capable of recognizing, or capable of binding to, or binding to, or being directed to, or being designed to bind to the extracellular domain of the *Helicoverpa armigera* chitin synthase B. The nucleotide and amino acid sequence of the *Helicoverpa armigera* chitin synthase B is presented in SEQ ID. NOS. 9 and 10 respectively, with amino acids 1048-1242 and 1324-1528 representing the extracellular domain. In still other preferred embodiments of the present disclosure, the one or more affinity molecule A or a fragment thereof is capable of recognizing, or capable of binding to, or binding to, or being directed to, or being designed to bind to the *Spodoptera frugiperda* chitin synthase B receptor. Preferably, the one or more affinity molecule A or a fragment thereof is capable of recognizing, or capable of binding to, or binding to, or being directed to, or being designed to bind to the extracellular domain of the *Spodoptera frugiperda* chitin synthase B. The nucleotide and amino acid sequence of the *Spodoptera frugiperda* chitin synthase B is presented in SEQ ID. NOS. 11 and 12 respectively, with amino acids 1048-1242 and 1321-1523 representing the extracellular domain.

In even other preferred embodiments of the present disclosure, the one or more affinity molecule A or a fragment thereof is capable of recognizing, or capable of binding to, or binding to, or being directed to, or being designed to bind to the *Helicoverpa armigera* aminopeptidase N. Preferably, the one or more affinity molecule A or a fragment thereof is capable of recognizing, or capable of binding to, or binding to, or being directed to, or being designed to bind to the extracellular domain of the *Helicoverpa armigera* aminopeptidase N. The nucleic acid sequence of the *Helicoverpa armigera* aminopeptidase N is provided as SEQ ID NOS. 13 and 14 respectively with amino acids 126-190 representing the extracellular domain.

In other preferred embodiments of the present disclosure, the one or more affinity molecule A or a fragment thereof is capable of recognizing, or capable of binding to, or binding to, or being directed to, or being designed to bind to the *Heliothis virescens* aminopeptidase N. Preferably, the one or more affinity molecule A or a fragment thereof is capable of recognizing, or capable of binding to, or binding to, or being directed to, or being designed to bind to the extracellular domain of the *Heliothis virescens* Aminopeptidase N. The nucleic acid and amino acid sequence of the *Heliothis virescens* Aminopeptidase N is provided as SEQ ID NOS. 15 and 16 respectively with amino acids 126-185 representing the extracellular domain.

In other preferred embodiments of the present disclosure, the one or more affinity molecule A or a fragment thereof is capable of recognizing, or capable of binding to, or binding to, or being directed to, or being designed to bind to the *Helicoverpa armigera* alkaline phosphatase receptor. Preferably, the one or more affinity molecule A or a fragment thereof is capable of recognizing, or capable of binding to, or binding to, or being directed to, or being designed to bind to the extracellular domain of the *Helicoverpa armigera* alkaline phosphatase. The nucleic acid and amino acid sequence of the *Helicoverpa armigera* alkaline phosphatase is provided as SEQ ID NOS. 17 and 18 respectively, with amino acids 192-446 representing the extracellular domain.

In still other preferred embodiments of the present disclosure, the one or more affinity molecule A or a fragment thereof is capable of recognizing, or capable of binding to, or binding to, or being directed to, or being designed to bind to the *Heliothis virescens* alkaline phosphatase receptor. Preferably, the one or more affinity molecule A or a fragment thereof is capable of recognizing, or capable of binding to, or binding to, or being directed to, or being designed to bind to the extracellular domain of the *Heliothis virescens* alkaline phosphatase. The nucleic acid sequence and amino acid sequence of the *Heliothis virescens* alkaline phosphatase is provided as SEQ ID NOS. 19 and 20 respectively, with amino acids 196-450 representing the extracellular domain. In still other preferred embodiments of the present disclosure, the one or more affinity molecule A or a fragment thereof is capable of recognizing, or capable of binding to, or binding to, or being directed to, or being designed to bind to the *Spodoptera frugiperda* alkaline phosphatase receptor. Preferably, the one or more affinity molecule A or a fragment thereof is capable of recognizing, or capable of binding to, or binding to, or being directed to, or being designed to bind to the extracellular domain of the *Spodoptera frugiperda* alkaline phosphatase. The nucleic acid and amino acid sequence of the *Spodoptera frugiperda* alkaline phosphatase is provided as SEQ ID NOS. 21 and 22 respectively, with amino acids 191-451 representing the extracellular domain. In other preferred embodiments of the present disclosure, the one or more affinity molecule A or a fragment thereof is capable of recognizing, or capable of binding to, or binding to, or being directed to, or being designed to bind to the *Heliothis virescens* ABCC2 receptor. Preferably, the one or more affinity molecule A or a fragment thereof is capable of recognizing, or capable of binding to, or binding to, or being directed to, or being designed to bind to the extracellular domain of the *Heliothis virescens* ABCC2 receptor. The nucleic acid and amino acid sequence of the *Heliothis virescens* ABCC2 is provided as SEQ ID NOS. 23 and 24 respectively, with amino acids 1-1339 representing the extracellular domain.

In other preferred embodiments of the present disclosure, the one or more affinity molecule A or a fragment thereof is capable of recognizing, or capable of binding to, or binding to, or being directed to, or being designed to bind to the *Helicoverpa armigera* ABCC2 receptor. Preferably, the one or more affinity molecule A or a fragment thereof is capable of recognizing, or capable of binding to, or binding to, or being directed to, or being designed to bind to the extracellular domain of the *Helicoverpa armigera* ABCC2 receptor. The nucleic acid and amino acid sequence of the *Helicoverpa armigera* ABCC2 is provided as SEQ ID NOS. 25 and 26 respectively, with amino acids 1-1338 representing the extracellular domain.

In various embodiments of the disclosure, the one or more affinity molecule A or a fragment thereof is capable of recognizing, or capable of binding to, or binding to, or being directed to, or being designed to bind to a polypeptide comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or greater identity to the amino acid sequence of the extracellular domain of the *Spodoptera frugiperda* cadherin (Seq ID NOS. 2), with amino acids from 1-1610 representing the extracellular domain. In various embodiments of the disclosure, the one or more affinity molecule A or a fragment thereof is capable of recognizing, or capable of binding to, or binding to, or being directed to, or being designed to bind to a polypeptide comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or greater identity to the amino acid sequence of the extracellular domain of the *Helicoverpa armigera* cadherin (Seq ID NOS. 4), with amino acids from 1-1583 representing the extracellular domain. In various embodiments of the disclosure, the one or more affinity molecule A or a fragment thereof is capable of recognizing, or capable of binding to, or binding to, or being directed to, or being designed to bind to a polypeptide comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or greater identity to the amino acid sequence of the extracellular domain of the *Diabrotica virgifera virgifera* cadherin (Seq ID NOS. 6), with amino acids from 1-1572 representing the extracellular domain. In various embodiments of the disclosure, the one or more affinity molecule A or a fragment thereof is capable of recognizing, or capable of binding to, or binding to, or being directed to, or being designed to bind to a polypeptide comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or greater identity to the amino acid sequence of the extracellular domain of the *Heliothis virescens* cadherin (Seq ID NOS. 8), with amino acids from 1-1583 representing the extracellular domain.

In various embodiments of the disclosure, the one or more affinity molecule A or a fragment thereof is capable of recognizing, or capable of binding to, or binding to, or being directed to, or being designed to bind to a polypeptide comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or greater identity to the amino acid sequence of the extracellular domain of the *Helicoverpa armigera* chitin synthase B (Seq ID NOS. 10), with amino acids from with amino acids 1048-1242 and 1324-1528 representing the extracellular domain. In various embodiments of the disclosure, the one or more affinity molecule A or a fragment thereof is capable of recognizing, or capable of binding to, or binding to, or being directed to, or being designed to bind to a polypeptide comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or greater identity to the amino acid sequence of the extracellular domain of the *Spodoptera frugiperda* chitin synthase B (Seq ID NOS. 12), with amino acids from 1048-1242 and 1321-1523 representing the extracellular domain.

In various embodiments of the disclosure, the one or more affinity molecule A or a fragment thereof is capable of recognizing, or capable of binding to, or binding to, or being directed to, or being designed to bind to a polypeptide comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or greater identity to the amino acid sequence encoded by the nucleotide sequence of the extracellular domain of the *Helicoverpa armigera* aminopeptidase N (Seq ID NOS. 14), with amino acids from 126-190 representing the extracellular domain. In various embodiments of the disclosure, the one or more affinity molecule A or a fragment thereof is capable of recognizing, or capable of binding to, or binding to, or being directed to, or being designed to bind to a polypeptide comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or greater identity to the amino acid sequence encoded by the nucleotide sequence of the extracellular domain of the *Heliothis virescens* Aminopeptidase N (Seq ID NOS. 16), with amino acids from 126-185 representing the extracellular domain. In various embodiments of the disclosure, the one or more affinity molecule A or a fragment thereof is capable of recognizing, or capable of binding to, or binding to, or being directed to, or being designed to bind to a polypeptide comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or greater identity to the amino acid sequence encoded by the nucleotide sequence of the extracellular domain of the *Helicoverpa armigera* alkaline phosphatase (Seq ID NOS. 18), with amino acids from 192-446 representing the extracellular domain.

In various embodiments of the disclosure, the one or more affinity molecule A or a fragment thereof is capable of recognizing, or capable of binding to, or binding to, or being directed to, or being designed to bind to a polypeptide comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or greater identity to the amino acid sequence encoded by the nucleotide sequence of the extracellular domain of the *Heliothis virescens* alkaline phosphatase (Seq ID NOS. 20), with amino acids from 196-450 representing the extracellular domain.

In various embodiments of the disclosure, the one or more affinity molecule A or a fragment thereof is capable of recognizing, or capable of binding to, or binding to, or being directed to, or being designed to bind to a polypeptide comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or greater identity to the amino acid sequence encoded by the nucleotide sequence of the extracellular domain of the *Spodoptera frugiperda* alkaline phosphatase (Seq ID NOS. 22), with amino acids from 191-451 representing the extracellular domain.

In various embodiments of the disclosure, the one or more affinity molecule A or a fragment thereof is capable of recognizing, or capable of binding to, or binding to, or being directed to, or being designed to bind to a polypeptide comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or greater identity to the amino acid sequence encoded by the nucleotide sequence of the extracellular domain of the *Heliothis virescens* ABCC2 (Seq ID NOS. 24), with amino acids from 1-1339 representing the extracellular domain.

In various embodiments of the disclosure, the one or more affinity molecule A or a fragment thereof is capable of recognizing, or capable of binding to, or binding to, or being directed to, or being designed to bind to a polypeptide comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or greater identity to the amino acid sequence encoded by the nucleotide sequence of the extracellular domain of the *Helicoverpa armigera* ABCC2 (Seq ID NOS. 26), with amino acids from 1-1338 representing the extracellular domain.

In various embodiments of the disclosure, the one or more affinity molecule or a fragment thereof comprises an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or greater identity to the amino acid sequence of one of the two $V_HH$ domains (Seq ID NOS. 29), separated by the linker sequence GGGSGGGG and individual domain provided Seq ID NOS. 28.

Further preferred embodiments with regard to the one or more affinity molecule A or a fragment thereof are affinity molecules or a fragment thereof that is/are capable of recognizing, or capable of binding to, or being directed to, or being designed to bind the antigen of the polypeptide selected from the group consisting of the *Spodoptera frugiperda* sodium-dependent nutrient amino acid transporter 1-like protein (SEQ ID NOS. 30 (antigen), 31 (full-length)), the *Spodoptera frugiperda* V-ATPase subunit a protein (SEQ ID NOS. 32 (antigen), 33 (full-length)), the *Spodoptera frugiperda* Cry1Fa domain II protein (SEQ ID NOS. 34), the *Spodoptera frugiperda* cadherin (SEQ ID NOS. 35 antigen, Seq. ID NOS. 2 (full-length)), the *Spodoptera frugiperda* venom dipeptidyl peptidase 4-like isoform X1 protein (SEQ ID NOS. 37 (antigen), 38 (full-length) or the *Spodoptera frugiperda* peptide-transporter family 1 isoform X1 protein (SEQ ID NOS. 39 (antigen), 40 (full-length).

In various embodiments of the disclosure, the one or more affinity molecule A or a fragment thereof is capable of recognizing, or capable of binding to, or binding to, or being directed to, or being designed to bind to a polypeptide comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or greater identity to the amino acid sequence encoded by the nucleotide sequence of the extracellular domain of the *Spodoptera frugiperda* sodium-dependent nutrient amino acid transporter 1-like protein. The extracellular domain (antigen) and full-length sequences are provided as SEQ ID NOS. 30 and 31 respectively.

In various embodiments of the disclosure, the one or more affinity molecule A or a fragment thereof is capable of recognizing, or capable of binding to, or binding to, or being directed to, or being designed to bind to a polypeptide comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or greater identity to the amino acid sequence encoded by the nucleotide sequence of the extracellular domain of the *Spodoptera frugiperda* V-ATPase subunit protein. The extracellular domain and full-length sequences are provided as SEQ ID NOS. 32 (antigen) and 33 respectively.

In various embodiments of the disclosure, the one or more affinity molecule A or a fragment thereof is capable of recognizing, or capable of binding to, or binding to, or being directed to, or being designed to bind to a polypeptide comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or greater identity to the amino acid sequence encoded by the nucleotide sequence of the extracellular domain of the *Spodoptera frugiperda* Cry1Fa domain II protein. The full-length sequence is provided as SEQ ID NOS. 34, with the extracellular domain encompassing the entire sequence.

In various embodiments of the disclosure, the one or more affinity molecule A or a fragment thereof is capable of recognizing, or capable of binding to, or binding to, or being directed to, or being designed to bind to a polypeptide comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or greater identity to the amino acid sequence encoded by the nucleotide sequence of the extracellular domain of the *Spodoptera frugiperda* cadherin protein. The extracellular domain and full-length sequences are provided as SEQ ID NOS. 35 (antigen) and 2 respectively.

In various embodiments of the disclosure, the one or more affinity molecule A or a fragment thereof is capable of recognizing, or capable of binding to, or binding to, or being directed to, or being designed to bind to a polypeptide comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or greater identity to the amino acid sequence encoded by the nucleotide sequence of the extracellular domain of the *Spodoptera frugiperda* venom dipeptidyl peptidase 4-like isoform X1 protein. The extracellular domain and full-length sequences are provided as SEQ ID NOS. 37 (antigen) and 38 respectively.

In various embodiments of the disclosure, the one or more affinity molecule A or a fragment thereof is capable of recognizing, or capable of binding to, or binding to, or being directed to, or being designed to bind to a polypeptide comprising an amino acid sequence having at least 80%, 81%, 82%, 83%, 84%, 85%, 86%, 87%, 88%, 89%, 90%, 91%, 92%, 93%, 94%, 95%, 96%, 97%, 98%, 99% or greater identity to the amino acid sequence encoded by the nucleotide sequence of the extracellular domain of the *Spodoptera frugiperda* peptide-transporter family 1 isoform X1 protein. The extracellular domain and full-length sequences are provided as SEQ ID NOS. 39 (antigen) and 40 respectively.

Insecticidal Proteins

In various embodiments of the disclosure, the one or more affinity molecule B or a fragment thereof being comprised in the affinity construct of the present disclosure is capable of binding to, or binding to, or being directed to, or being designed to bind specifically to one or more proteins that have insecticidal activity against an insect pest.

The insecticidal protein (toxin) against which the above one or more affinity molecule B or a fragment thereof is capable of binding to, or binding to, or being directed to, or being designed to bind exerts its biological activity by contact of the insecticidal protein via the one or more affinity molecule B or a fragment thereof being comprised in the affinity construct of the present invention with a target (receptor) molecule of an inner organ of an insect, preferably of the digestive tract of an insect, a reproductive organ or the nervous system, more preferably of the gut or intestine of an insect.

In various embodiments, the insecticidal protein exerts its biological activity by contact of the protein with an intestine molecule of the insect via the one or more affinity molecule B or a fragment thereof being comprised in the affinity construct of the present invention. This molecule of the intestine generally is a receptor protein. The term insecticidal protein not only includes insecticidal proteins that are active without further processing, but also precursors in an inactive form, which may be activated by inside factors. For example, the insecticidal protein may be a protoxin crystal, which is cleaved inside by a protease so as to provide the toxic monomeric Cry toxin. In case the insecticidal protein is a protoxin, then the affinity molecule B, is directed to or designed to bind to domain(s) in the protoxin that are removed during later protease cleavage of the protoxin so that the affinity-binding of the one or more affinity molecule B or a fragment thereof to the now activated insecticidal protein is maintained.

The activated toxin goes through a complex sequence of binding events including different Cry-binding proteins of the insect gut, finally leading to membrane insertion and pore formation. Cry toxins form pores in the apical membrane of larvae midgut cells, destroying the midgut cells and killing the larvae. Consequently, the activity of insecticidal proteins results in morphological changes of midgut cells after intoxication with the protein toxin.

The interaction of insecticidal proteins with different proteins present in insect midgut cells is a complex process, which involves multiple membrane proteins. The first binding interaction of (activated) insecticidal proteins with membrane proteins serves to concentrate the activated toxin protein in the microvilli membrane of the midgut cells, where the toxin proteins are then able to bind to receptor proteins, which is necessary to trigger the formation of toxin oligomer structures. This process of oligomerization of the toxin proteins finally provides for the formation of the toxin pores, which are essential for the mode of action of the toxins. Mutations in residues of the membrane or receptor proteins of the midgut cells result in loss of toxicity to insects. Such mutations show altered oligomerization or membrane insertion, severely affecting pore formation.

Surprisingly, the novel affinity constructs of the present disclosure overcome the drawbacks of insect resistance that is caused by mutation of membrane and receptor proteins. Further, the novel affinity constructs concentrate the insecticidal protein in the environment in which the insecticidal protein needs to act, e.g. in the microvilli membrane of the midgut cells, and thereby support the process of toxin oligomerization. This provides for an improvement in insecticidal activity of the toxin protein as less insecticidal protein is required for achieving the insecticidal activity. The effects can also be observed with insecticidal compositions of the disclosure comprising a novel affinity construct of the disclosure and an insecticidal protein, wherein the insecticidal protein corresponds to the insecticidal protein the at least one affinity molecule B of the novel affinity construct is capable of binding to, or binding to, or being directed to, or being designed to bind to.

Further, the novel ways described herein improve targeting of insecticidal agents to the insect. Targeting of novel receptors in an insect pest is facilitated to which a certain insect toxin naturally does not bind (e.g., to restore functionality of a given toxin whose natural receptor has changed due to mutation and is not binding anymore the toxin), and/or "arming" of insecticidal proteins is now possible that formerly are not active in a certain insect species due to the fact that its natural receptor is missing. Targeting theses toxins to other receptors in such an insect renders that toxin toxic for the insect. Also surprising is that the novel affinity constructs even work without the affinity molecule A or a fragment thereof being directed to specific membrane proteins, which are the natural target proteins of the insecticidal proteins. The at least one affinity molecule A of the novel affinity construct of the present disclosure may be capable of recognizing, or capable of binding to, or binding to, or being directed to, or being designed to bind to any membrane or receptor protein of the midgut cells.

An alternative way also encompassed herein to address the resistance of insect pests to insecticidal proteins caused by mutations in the receptor proteins is to apply to or express in the plant wild type (i.e., without the mutations conferring resistance against an insecticidal protein) receptor proteins as expressed in the gut of susceptible insects. Upon uptake by the insect these wild type receptor proteins insert themselves into the insect gut either in addition to the mutated receptor proteins or by replacing them. Either way, the presence of wild type receptor proteins allows the insecticidal protein to bind, to insert into the membrane, to form a pore and eventually to kill the insect.

The terms "insecticidal protein" or "insecticidal protein toxin" are intended to encompass proteins (or polypeptides encoding these proteins) the at least one affinity molecule B or a fragment thereof disclosed herein and being comprised in the affinity construct disclosed herein is capable of binding to, or binding to, or being directed to, or being designed to bind and that have toxic activity against one or more insecticidal pests, including, but not limited to, members of the orders Isoptera, Blattodea, Orthoptera, Phthiraptera, Thysanoptera, Hymenoptera, Siphonaptera, Lepidoptera, Diptera, Hemiptera and Coleoptera, or proteins or polypeptides having homology to such an insecticidal or toxic protein. The terms "insecticidal protein toxin" and "insecticidal protein" may be used herein interchangeably.

Referring to the affinity molecule B of the novel affinity construct that is capable of binding, or is binding, or is directed to, or is designed to bind an insecticidal protein (toxin) is intended to mean that the affinity molecule B is capable of binding to, or is binding to, or is directed to, or is designed to bind to a protein or polypeptide that has toxic activity against one or more insecticidal pests, including, but not limited to, members of the orders Isoptera, Blattodea, Orthoptera, Phthiraptera, Thysanoptera, Hymenoptera, Siphonaptera, Lepidoptera, Diptera, Hemiptera and Coleoptera, or proteins or polypeptides having homology to such an insecticidal or toxic protein.

In various embodiments of the present disclosure, the insecticidal protein being part of the novel composition comprising a affinity construct of the disclosure and an insecticidal protein is an insecticidal toxin that is specifically toxic to an insect order of any one of Isoptera, Blattodea, Orthoptera, Phthiraptera, Thysanoptera, Siphonaptera, Lepidoptera, Coleoptera, Hymenoptera, Hemiptera and Diptera. In various embodiments of the present disclosure, the insecticidal protein is an insecticidal toxin that is specifically toxic to an insect family of any one of Crambidae, Noctuidae, Pyralidae, Chrysomelidae, Dynastidae, Elateridae, Melolonthinae, Curcolionidae, Scarabaeidae, Erebonidae, Coccinellidae, Mebidae, or Lamiinae. In various embodiments of the present disclosure, the insecticidal protein has insecticidal activity against an insect pest of the order Lepidoptera, including, but not limited to, *Ostrinia nubilalis* (Europen Corn Borer), *Diatraea grandiosella* (South Western Corn Borer), *Helicoverpa zea* (Corn Earworm), *Agrotis ipsilon* (Black Cutworm), *Agrotis subterranea* (Granulate Cutworm), *Agrotis malefida* (Palesided Cutworm), *Spodoptera frugiperda* (Fall Army worm), *Spodoptera eridania* (Southern Armyworm), *Spodoptera albula* (Gray-Streaked Armyworm), *Spodoptera cosmioides*, *Spodoptera ornithogalli*, *Spodoptera exigua* (Beet Cutworm), *Helicoverpa armigera* (Cotton Bollworm), *Helicoverpa zea* (Corn Earworm), *Heliothis virescens* (Tobacco budworm), *Diatraea saccharalis* (SugarCane Borer), *Diatraea grandiosella* (South Western Corn Borer), *Elasmopalpus lignosellus* (Lesser CornStalk Borer), *Striacosta albicosta* (Western bean cutworm), *Chrysodeixis includens* (Soybean looper), *Pseudaletia sequax* (Wheat armyworm), *Porosagrotis gypaetina, Euxoa bilitura* (Potato Cutworm), *Pseudaletia unipuncta* (True armyworm), *Anticarsia gemmatalis* (Velvetbean caterpillar), *Plathypena scabra* (Green cloverworm), *Elasmopalpus lignosellus* (Lesser CornStalk Borer), *Chrysodeixis includens* (Soybean looper), *Trichoplusia ni* (Cabbage Looper) and *Peridroma saucia* (Variegated Cutworm). In various embodiments of the present disclosure, the insecticidal protein has insecticidal activity against an insect pest of the order Coleoptera including, but not limited to *Diabrotica virgifera virgifera* (Western Corn Rootworm), *Diabrotica barberi* (Northern Corn Rootworm), *Diabrotica speciosa, Diloboderus abderus, Phyllophaga* spp (Scarab beetles), *Listronotus* spp. (Argentine stem weevil), *Cerotoma arcuatus, Popillia japonica* (Japanese beetle), *Colaspis brunnea* (Grape colaspis), *Cerutoma trifurcata* (Bean Leaf Beetle), *Epilachna varivestis* (Mexican bean beetle), *Diabrotica undecimpunctata howardi* (Spotted cucumber beetle), *Epicauta pestifera* (Blister beetles), *Popillia japonica* (Japanese beetle), *Colaspis brunnea* (Grape *colaspis*), *Dectes texanus texanus* (Soybean stem borer), and *Anthonomous grandis* (Boll weevil). In various embodiments of the present disclosure, the insecticidal protein has insecticidal activity against insect pests including, but not limited to *Oscinella frit* (Fruit Fly), *Myzus persicae* (Green Peach Aphid), *Rhopalosiphum maidis* (Corn Leaf Aphid) and *Rhopalosiphum padi* (Bird Cherry-Oat Aphid).

The insecticidal protein that is part of the novel composition comprising an affinity construct of the disclosure together with one or more insecticidal protein(s) can be any protein that is harmful to an insect and that the at least one affinity molecule B being part of the affinity construct is capable of binding to, or is binding to, or is being directed to, or is being designed to bind. Insecticidal proteins have been isolated from organisms including, e.g., *Bacillus* sp. and *Pseudomonas* sp. In various embodiments of the disclosure, the insecticidal protein is derived from *Bacillus* sp. or *Pseudomonas* sp. In various embodiments of the disclosure, the insecticidal protein is derived from *Bacillus thuringiensis*. In various embodiments of the disclosure, the insecticidal protein is an insecticidal crystal protein (ICP). Such ICPs are protein crystals formed during sporulation in some *Bacillus thuringiensis* strains (*Bacillus thuringiensis* produces proteins that aggregate to form crystals). The crystal proteins are toxic to very specific insect pest species. The crystal proteins bind specifically to certain receptors in the insect's intestine or midgut. The Bt ICPs are also known as Bt delta-endotoxins. Delta-endotoxins, which have been isolated from *Bacillus thuringiensis*, include, but are not limited to, the Cry1 to Cry74 classes of delta-endotoxin genes and the Bt cytolytic Cyt genes, in particular Cyt1 and Cyt2. Cyt proteins are toxins mostly found in *Bacillus*

*thuringiensis* strains active against Diptera, although a few exceptions of Cyt proteins active against Coleopteran larvae have been documented. These proteins can synergize Cry activities against mosquitos and black flies.

The insecticidal activity of Cry proteins is well known to one skilled in the art (for review, see, e.g., www.btnomenclature.info, "Insect Midgut and Insecticidal Proteins", Vol 47, Advances in Insect Physiology edited by Tarlochan S. Dhadialla, Sarjeet Gill, August 2014: chapter 2: "Diversity of *Bacillus thuringiensis* Crystal Toxins and Mechanisms of Action": pages 39-87; Academic Press, UK., ISBN: 978-0-12-800197-4, or Pardo-Lopez et al. 2013, FEMS Microbiol Rev 37, 3-22).

Cry proteins are specifically toxic to different insect orders such as Lepidoptera, Coleoptera, Hymenoptera and Diptera. In preferred embodiments of the present disclosure, the insecticidal protein is a Bt Cry protein. In more preferred embodiments of the present disclosure, the insecticidal protein is a Bt Cry toxin that is specifically toxic to an insect order of any of Lepidoptera, Coleoptera, Hymenoptera and Diptera. In other preferred embodiments of the present disclosure, the insecticidal protein is a Bt Cry toxin that is specifically toxic to an insect order of any of Isoptera, Blattodea, Orthoptera, Phthiraptera, Thysanoptera, Siphonaptera, Lepidoptera, Coleoptera, Hymenoptera, Hemiptera and Diptera.

In various embodiments of the disclosure, the insecticidal protein that is part of the novel composition comprising an affinity construct of the disclosure together with one or more insecticidal protein(s) can be any protein that is harmful to an insect and that the at least one affinity molecule B being part of the affinity construct is capable of binding to, or is binding to, or is being directed to, or is being designed to bind, is a protoxin crystal, which is cleaved inside by a protease so as to yield a monomeric Cry toxin. In various embodiments of the disclosure, said insecticidal protein is the monomeric form of an insecticidal toxin. In various embodiments of the disclosure, the insecticidal protein is a monomeric Cry toxin. In various embodiments of the disclosure, the insecticidal protein is the multimeric form of an insecticidal toxin. In various embodiments of the disclosure, the insecticidal protein is a multimeric Cry toxin comprising, e.g., up to, but not limited to, four subunits of a Cry protein.

In preferred embodiments of the present disclosure, the insecticidal protein is a Bt Cry protein. In more preferred embodiments of the present disclosure, the insecticidal protein is a Bt Cry protein of any of the currently 74 major types (classes) of Bt delta-endotoxins (i.e., any of a Cry1, Cry2, Cry3, Cry4, Cry5, Cry6, Cry7, Cry8, Cry9, Cry10, Cry11, Cry12, Cry13, Cry14, Cry15, Cry16, Cry17, Cry18, Cry19, Cry20, Cry21, Cry22, Cry23, Cry24, Cry25, Cry26, Cry27, Cry28, Cry29, Cry30, Cry31, Cry32, Cry33, Cry34, Cry35, Cry36, Cry37, Cry38, Cry39, Cry40, Cry41, Cry42, Cry43, Cry44, Cry45, Cry 46, Cry47, Cry49, Cry50, Cry 51, Cry52, Cry53, Cry54, Cry55, Cry56, Cry57, Cry58, Cry59, Cry60, Cry61, Cry62, Cry63, Cry64, Cry65, Cry66, Cry67, Cry68, Cry69, Cry70, Cry71, Cry72, Cry73 or Cry74 delta-endotoxin). In various embodiments, the insecticidal protein is a Cry1 or a Cry3 protein, more specifically a Cry1 or a Cry3 Bt delta-endotoxin. The Cry1 (Bt delta-) endotoxin is considered to be particularly effective against Lepidoptera, and the Cry3 (Bt delta-) endotoxin is considered to be particularly effective against Coleoptera. The Cry1 or a Cry3 Bt delta-endotoxins are therefore preferred insecticidal proteins in the context of the present invention with Lepidoptera and Coleoptera, respectively, accordingly being preferred insect pest targets according to the present disclosure.

In more preferred embodiments, the insecticidal protein is a Cry1Ac or a Cry3Aa Bt delta-endotoxin. In a preferred embodiment, the insecticidal protein is a Cry1Ac Bt delta-endotoxin. In various other embodiments, the insecticidal protein is a Bt delta-endotoxin of any one of: Cry1Aa (e.g., Cry1Aa1, Accession #M11250), Cry1Ab (e.g., Cry1Ab1, Accession #M13898), Cry1Ab-like (Accession #AF327924 or #AF327925 or #AF327926), Cry1Ac (e.g., Cry1Ac1, Accession #M11068), Cry1Ad (e.g., Cry1Ad1, Accession #M73250), Cry1Ae (e.g., Cry1Ae1, Accession #M65252), Cry1Af (e.g., Cry1Af1, Accession #U82003), Cry1Ag (e.g., Cry1Ag1, Accession #AF081248), Cry1Ah (e.g., Cry1Ah1, Accession #AF281866), Cry1Ai (e.g., Cry1Ai1, Accession #AY174873), Cry1A-Iike (Accession #AF327927), Cry1Ba (e.g., Cry1Ba1, Accession #X06711), Cry1Bb (e.g., Cry1Bb1, Accession #L32020), Cry1Bc (e.g., Cry1Bc1, Accession #Z46442), Cry1Bd (e.g., Cry1Bd1, Accession #U70726), Cry1Be (e.g., Cry1Be1, Accession #AF077326), Cry1Bf (e.g., Cry1Bf1, Accession #AX189649), Cry1Bg (e.g., Cry1Bg1, Accession #AY176063), Cry1Ca (e.g., Cry1Ca1, Accession #X07518), Cry1Cb (e.g., Cry1Cb1, Accession #M97880), Cry1Cb-Iike (Accession #AAX63901), Cry1 Da (e.g., Cry1Da1, Accession #X54160), Cry1db (e.g., Cry1db1, Accession #Z22511), Cry1Dc (e.g., Cry1Dc1, Accession #EF059913), Cry1Ea (e.g., Cry1Ea1, Accession #X53985), Cry1Eb (e.g., Cry1Eb1, Accession #M73253), Cry1Fa (e.g., Cry1Fa1, Accession #M63897), Cry1Fb (e.g., Cry1Fb1, Accession #Z22512), Cry1Ga (e.g., Cry1Ga1, Accession #Z22510), Cry1Gb (e.g., Cry1Gb1, Accession #U70725), Cry1Gc (Accession #AAQ52381), Cry1Ha (e.g., Cry1Ha1, Accession #Z22513), Cry1Hb (e.g., Cry1Hb1, Accession #U35780), Cry1H-Iike (Accession #AF182196), Cry1Ia (e.g., Cry1Ia1, Accession #X62821), Cry1Ib (e.g., Cry1Ib1, Accession #U07642), Cry1Ic (e.g., Cry1Ic1, Accession #AF056933), Cry1Id (e.g., Cry1Id1, Accession #AF047579), Cry1Ie (e.g., Cry1Ie1, Accession #AF211190), Cry1If (e.g., Cry1If1, Accession #AAQ52382), Cry1I-like (Accession #190732), Cry1Ja (e.g., Cry1Ja1 (Accession #L32019), Cry1Jb (e.g., Cry1Jb1, Accession #U31527), Cry1Jc (e.g., Cry1Jc1 (Accession #190730), Cry1Jd (e.g., Cry1Jd1 (Accession #AX189651), Cry1Ka (e.g., Cry1Ka1, Accession #U28801), Cry1La (e.g., Cry1La1, Accession #AAS60191), Cry1-Iike (Accession #190729), Cry2Aa (e.g., Cry2Aa1, Accession #M31738), Cry2Ab (e.g., Cry2Ab1, Accession #M23724), Cry2Ac (e.g., Cry2Ac1, Accession #X57252), Cry2Ad (e.g., Cry2Ad1, Accession #AF200816), Cry2Ae (e.g., Cry2Ae1, Accession #AAQ52362), Cry2Af (e.g., Cry2Af1, Accession #EF439818), Cry2Ag (Accession #ACH91610), Cry2Ah (Accession #EU939453), Cry3Aa (e.g., Cry3Aa1, Accession #M22472), Cry3Ba (e.g., Cry3Ba1, Accession #X17123), Cry3Ca (e.g., Cry3Ca1, Accession #X59797), Cry4Aa (e.g., Cry4Aa1, Accession #00423), Cry4A-like (Accession #DQ078744), Cry4Ba (e.g., Cry4Ba1, Accession #X07423), Cry4Ba-like (Accession #ABC47686), Cry4Ca (e.g., Cry4Ca1, Accession #EU646202), Cry5Aa (e.g., Cry5Aa1, Accession #L07025), Cry5Ab (e.g., Cry5Ab1, Accession #L07026), Cry5Ac (e.g., Cry5Ac1, Accession #I34543), Cry5 Ad (e.g., Cry5Ad1, Accession #EF219060), Cry5Ba (e.g., Cry5Ba1, Accession #U19725), Cry6Aa (e.g., Cry6Aa1, Accession #L07022), Cry6Ba (e.g., Cry6Ba1, Accession #L07024), Cry7Aa (e.g., Cry7Aa1, Accession #M64478), Cry7Ab (e.g., Cry7Ab1, Accession #U04367), Cry7Ba (e.g., Cry7Ba1, Accession #ABB70817), Cry7Ca (e.g., Cry7Ca1, Accession #EF486523), Cry8Aa (e.g., Cry8Aa1, Accession #U04364), Cry8Ab (e.g., Cry8Ab1, Accession #EU044830), Cry8Ba (e.g., Cry8Ba1, Accession #U04365), Cry8Bb (e.g., Cry8Bb1, Accession #AX543924), Cry8Bc (e.g., Cry8Bc1, Accession #AX543926), Cry8Ca (e.g., Cry8Ca1, Accession #U04366), Cry8 Da (e.g., Cry8Da1, Accession #AB089299), Cry8db (e.g., Cry8db1, Accession #AB303980), Cry8Ea (e.g., Cry8Ea1, Accession #AY329081), Cry8Fa (e.g., Cry8Fa1, Accession #AY551093), Cry8Ga (e.g., Cry8Ga1, Accession #AY590188), Cry8Ha (e.g., Cry8Ha1, Accession #EF465532), Cry8Ia (e.g., Cry8Ia1, Accession #EU381044), Cry8Ja (e.g., Cry8Ja1, Accession #EU625348), Cry8-like (Accession #ABS53003), Cry9Aa (e.g., Cry9Aa1, Accession #X58120), Cry9Ba (e.g., Cry9Ba1, Accession #X75019), Cry9Bb (e.g., Cry9Bb1, Accession #AY758316), Cry9Ca (e.g., Cry9Ca1, Accession #Z37527), Cry9 Da (e.g., Cry9Da1, Accession #D85560), Cry9db (e.g., Cry9db1, Accession #AY971349), Cry9Ea (e.g., Cry9Ea1, Accession #AB011496), Cry9Eb (e.g., Cry9Eb1, Accession #AX189653), Cry9Ec (e.g., Cry9Ec1, Accession #AF093107), Cry9Ed (e.g., Cry9Ed1, Accession #AY973867), Cry9-like (Accession #AF093107), Cry10Aa (e.g., Cry10Aa1, Accession #M12662), Cry10A-like (Accession #DQ167578), Cry11Aa (e.g., Cry11Aa1, Accession #M31737), Cry11Aa-like (Accession #DQ166531), Cry11Ba (e.g., Cry11Ba1, Accession #X86902), Cry11Bb (e.g., Cry11Bb1, Accession #AF017416), Cry12Aa (e.g., Cry12Aa1, Accession #L07027), Cry13Aa (e.g., Cry13Aa1, Accession #L07023), Cry14Aa (e.g., Cry14Aa1, Accession #U13955), Cry15Aa (e.g., Cry15Aa1, Accession #M76442), Cry16Aa (e.g., Cry16Aa1, Accession #X94146), Cry17Aa (e.g., Cry17Aa1, Accession #X99478), Cry18Aa (e.g., Cry18Aa1, Accession #X99049), Cry18Ba (e.g., Cry18Ba1, Accession #AF169250), Cry18Ca (e.g., Cry18Ca1, Accession #AF169251), Cry19Aa (e.g., Cry19Aa1, Accession #Y07603), Cry19Ba (e.g., Cry19Ba1, Accession #D88381), Cry20Aa (e.g., Cry20Aa1, Accession #U82518), Cry21Aa (e.g., Cry21Aa1, Accession #I32932), Cry21Ba (e.g., Cry21Ba1, Accession #AB088406), Cry22Aa (e.g., Cry22Aa1, Accession #I34547), Cry22Ab (e.g., Cry22Ab1, Accession #AAK50456), Cry22Ba (e.g., Cry22Ba1, Accession #AX472770), Cry23Aa (e.g., Cry23Aa1, Accession #AAF76375), Cry24Aa (e.g., Cry24Aa1, Accession #U88188), Cry24Ba (e.g., Cry24Ba1, Accession #BAD32657), Cry24Ca (e.g., Cry24Ca1, Accession #AM158318), Cry25Aa (e.g., Cry25Aa1, Accession #U88189), Cry26Aa (e.g., Cry26Aa1, Accession #AF122897), Cry27Aa (e.g., Cry27Aa1, Accession #AB023293), Cry28Aa (e.g., Cry28Aa1, Accession #AF132928), Cry29Aa (e.g., Cry29Aa1, Accession #AJ251977), Cry30Aa (e.g., Cry30Aa1, Accession #AJ251978), Cry30Ba (e.g., Cry30Ba1, Accession #BAD00052), Cry30Ca (e.g., Cry30Ca1, Accession #BAD67157), Cry30 Da (e.g., Cry30Da1, Accession #EF095955), Cry30db (e.g., Cry30db1, Accession #BAE80088), Cry30Ea (e.g., Cry30Ea1, Accession #EU503140), Cry30Fa (e.g., Cry30Fa1, Accession #EU751609), Cry30Ga (e.g., Cry30Ga1, Accession #EU882064), Cry31 Aa (e.g., Cry31Aa1, Accession #AB031065), Cry31Ab (e.g., Cry31Ab1, Accession #AB250923), Cry31Ac (e.g., Cry31Ac1, Accession #AB276125), Cry32Aa (e.g., Cry32Aa1, Accession #AY008143), Cry32Ba (e.g., Cry32Ba1, Accession #BAB78601), Cry32Ca (e.g., Cry32Ca1, Accession #BAB78602), Cry32 Da (e.g., Cry32Da1, Accession #BAB78603), Cry33Aa (e.g., Cry33Aa1, Accession #AAL26871), Cry34Aa (e.g., Cry34Aa1, Accession #AAG50341), Cry34Ab (e.g., Cry34Ab1, Accession #AAG41671), Cry34Ac (e.g., Cry34Ac1, Accession #AAG50118), Cry34Ba (e.g., Cry34Ba1, Accession #AAK64565), Cry35Aa (e.g., Cry35Aa1, Accession #AAG50342), Cry35Ab (e.g., Cry35Ab1, Accession #AAG41672), Cry35Ac (e.g., Cry35Ac1, Accession #AAG50117), Cry35Ba (e.g., Cry35Ba1, Accession #AAK64566), Cry36Aa (e.g., Cry36Aa1, Accession #AAK64558), Cry37Aa (e.g., Cry37Aa1, Accession #AAF76376), Cry38Aa (e.g., Cry38Aa1, Accession #AAK64559), Cry39Aa (e.g., Cry39Aa1, Accession #BAB72016), Cry40Aa (e.g., Cry40Aa1, Accession #BAB72018), Cry40Ba (e.g., Cry40Ba1, Accession #BAC77648), Cry40Ca (e.g., Cry40Ca1, Accession #EU381045), Cry40 Da (e.g., Cry40Da1, Accession #EU596478), Cry41Aa (e.g., Cry41Aa1, Accession #AB116649), Cry41Ab (e.g., Cry41Ab1, Accession #AB116651), Cry42Aa (e.g., Cry42Aa1, Accession #AB116652), Cry43Aa (e.g., Cry43Aa1, Accession #AB115422), Cry43Ba (e.g., Cry43Ba1, Accession #AB115422), Cry43-like (Accession #AB115422), Cry44Aa (Accession #BAD08532), Cry45Aa (Accession #BAD22577), Cry46Aa (Accession #BAC79010), Cry46Ab (Accession #BAD35170), Cry47Aa (Accession #AY950229), Cry48Aa (Accession #AJ841948), Cry48Ab (Accession #AM237207), Cry49Aa (Accession #AJ841948), Cry49Ab (e.g., Cry49Ab1, Accession #AM237202), Cry50Aa (e.g., Cry50Aa1, Accession #AB253419), Cry51Aa (e.g., Cry51Aa1, Accession #DQ836184), Cry52Aa (e.g., Cry52Aa1, Accession #EF613489), Cry53Aa (e.g., Cry53Aa1, Accession #EF633476), Cry54Aa (e.g., Cry54Aa1, Accession #EU339367), and Cry55Aa (e.g., Cry55Aa1, Accession #EU121521). In various embodiments, the insecticidal protein is a Cry1Ac or a Cry3Aa Bt delta-endotoxin.

The Bt Cry toxins that can be used in the context of present disclosure are considered to have in common that they are pore-forming proteins that cause cell lysis by producing an osmotic shock. Cry toxins share less than 40% amino acid identity with proteins from other groups. Although Cry sequences may have low similarities, their 3D structures are quite similar. In various embodiments of the present disclosure, the Cry toxin is derived from *Bacillus thuringiensis* strain kurstaki (Btk) HD1, which expresses Cry1Aa, Cry1Ab, Cry1Ac and Cry2Aa proteins, or from *Bacillus thuringiensis* strain HD73, which produces Cry1Ac (effective in controlling many leaf-feeding Lepidopterans that are important crop pests or forest pest defoliators). In various other embodiments of the present disclosure, the Cry toxin is derived from *B. thuringiensis* var. *aizawai* HD137, which produces slightly different Cry toxins such as Cry1Aa, Cry1Ba Cry1Ca and Cry1 Da (active against Lepidopteran larvae that feed on stored grains). In yet other embodiments of the present disclosure, the Cry toxin is derived from *B. thuringiensis* var. san diego or *B. thuringiensis* var. *tenebrionis*, which produce Cry3Aa toxin and Cry4A, Cry4B, Cry11A and Cyt1Aa toxins (active against Coleopteran pests). In still other embodiments of the present disclosure, the Cry toxin is a Cry toxin showing toxicity against mosquitoes, like Cry1, Cry2, Cry4, Cry 11, and Cry29. Thus, in one embodiment of the present disclosure, the Cry toxin is derived from *B. thuringiensis* var. *israelensis* (Bti), which has been used worldwide for the control of mosquitoes.

In various embodiments of the present disclosure, the insecticidal protein is a Bt Cyt1 or Cyt2 protein. Examples of delta-endotoxins also include, but are not limited to, a DIG-3 or DIG-11 toxin, which are N-terminal deletions of alpha-helix 1 and/or alpha-helix 2 variants of Cry proteins such as Cry1A described in U.S. Pat. Nos. 8,304,604 and 8,304,605. Other Cry proteins are well known to the one of skill in the art (see, for example, Crickmore et al., "Bt toxin nomenclature" (2011), at www.lifesci.sussex.ac.uk/home/Neil_Crickmore/Bt).

The insecticidal Cry proteins produced by Bt are grouped in four different families that are not related in primary sequence, structure and probably neither in their mode of action (Zúniga-Navarrete et al. 2015, Insect Biochemistry and Molecular Biology 59, 50-57). The three-domain Cry (3d-Cry) group is the largest family of Cry proteins, with members that show toxicity against different insect orders, such as Lepidoptera, Diptera and Coleoptera. The 3d-Cry toxins are pore-forming toxins composed of three different domains. Domain I is an alpha-helix bundle that is recognized as the pore-forming domain. Domain II is a beta-prism with exposed loop regions that has been shown to be involved in recognition of larval midgut proteins, while Domain III is a beta-sandwich also involved in recognition of midgut proteins (Zúniga-Navarrete et al. 2015). Thus, domains II and III determine the specificity of Cry toxins. In various embodiments of the present disclosure, the insecticidal protein is a three-domain Cry protein or a variant or fragment thereof, wherein the variant or fragment has insecticidal activity. In other embodiments of the disclosure, the insecticidal protein is the pore-forming domain of a Cry toxin. In various embodiments of the disclosure, the insecticidal protein is the pore-forming domain of a 3d-Cry toxin. In various embodiments of the disclosure, the insecticidal protein is the domain I of a 3d-Cry toxin. In various embodiments of the disclosure, the insecticidal protein is the alpha-helix bundle of a 3d-Cry toxin. In various embodiments of the disclosure, the toxin is a modified toxin, in particular a genetically engineered Cry toxin having a deletion at the N-terminus including the domain I alpha-helix 1.

In various embodiments of the present disclosure, the insecticidal protein is a functional fragment of any insecticidal toxin or protein described herein, wherein such a functional fragment retains insecticidal activity as described herein elsewhere. In other embodiments of the present disclosure, the insecticidal protein is a functional variant of any insecticidal toxin or protein described herein, wherein such a functional variant has insecticidal activity as described herein elsewhere.

The use of Cry proteins as transgenic plant traits is well known to one skilled in the art, and Cry-transgenic plants have regularly received regulatory approval (see, e.g., Sanahuja 2011; (Plant Biotech Journal 9:283-300).

In the present disclosure, insecticidal proteins also include insecticidal lipases including, but not limited to, lipid acyl hydrolases as described in U.S. Pat. No. 7,491,869, and cholesterol oxidases such as those from *Streptomyces*.

Insecticidal proteins also include Vip (vegetative insecticidal proteins) toxins from *Bacillus thuringiensis*, e.g., such as described in U.S. Pat. Nos. 7,615,686 and 8,237,020. Vip toxins are produced during the vegetative growth phase of *B. thuringiensis*. At least Vip toxins Vip1/Vip2 and Vip3 have been characterized in detail and are described in the literature. Descriptions of further Vip proteins are found, for example, at www.lifesci.sussex.ac.uk/home/Neil_Crickmore/Bt/vip.html. In preferred embodiments, the insecticidal protein is a Vip protein from *B. thuringiensis*. In more preferred embodiments, the insecticidal protein according to the disclosure is a Bt Vip1 or a Vip2 protein. In other preferred embodiments, the insecticidal protein is a Bt Vip3 protein. More preferably, an insecticidal protein according to the present disclosure is a Bt Vip3A protein or Bt Vip3B protein.

In various embodiments of the present disclosure, In other embodiments of the present disclosure, the insecticidal proteins include other identified or re-classified insecticidal proteins from *B. thuringiensis* including but not limited to Tpp, Mpp, Gpp, App, Spp, Vpa, Vpb, Mcf, Pra, Prb, Xpp, Mpf (see Table 1 of Crickmore et al. 2020, Journal of Invertebrate Pathology, 107438). One recently identified member of Vpb4 insecticidal protein family Vpb4Da2 is active against western corn rootworm (Yin et al. 2020 PLOS one, 15(11): e0242792).

In various embodiments, the insecticidal protein is a Mtx protein (mosquitocidal toxin), a Bin protein (binary toxin) or a Sip protein (secreted insecticidal toxins).

Insecticidal proteins also include toxin complex (TC) proteins, obtainable from organisms such as *Xenorhabdus*, *Photorhabdus* and *Paenibacillus*. As used herein, insecticidal proteins also include spider, snake and scorpion venom proteins or toxic peptides derived from these proteins.

The present disclosure also encompasses as insecticidal proteins the use of variants of *Bacillus thuringiensis* toxins that bind to receptors which are not natively bound by the corresponding wild-type *Bacillus thuringiensis* toxin. In particular, the present disclosure encompasses compositions comprising an affinity construct of the disclosure and one or more insecticidal protein(s), respectively, which comprise variants of *Bacillus thuringiensis* toxins that can be generated using phage-assisted continuous evolution (PACE) as described in Badran et al. 2016, Nature 533(7601): 58-63.

In various aspects, the insecticidal protein used in the context of the present invention can be fused with other proteins (or protein fragments) when forming the novel insecticidal composition.

The novel composition comprising an affinity construct of the disclosure and one or more insecticidal protein(s) also encompasses modified insecticidal proteins, e.g., insecticidal proteins that have been mutagenized, truncated, or where domains have been swapped (e.g., to enhance efficacy as described by Deist et al. 2014, Toxins, 6:3005-3027; doi:10.3390/toxins6103005). In particular, modified Bt toxins can be a useful option for maintaining Bt toxin activity in resistant insects. Truncated Cry versions may include 5' or 3' truncations, leading to deletions of N- and C-terminal Cry protein domains. Modified toxins that can be used in the context of the affinity constructs in the present disclosure may also include toxins with an altered GC content in their DNA sequence, such as a GC content that mimics eukaryotic genes. These modifications may, e.g., enhance their expression in eukaryotic systems used for the production of crystal Bt protein that can be used in topical application systems in plants according to the present disclosure. These modifications may also enhance the expression of the insecticidal proteins in the context of the present disclosure of transgenic plants or microorganism, or may enhance the co-expression of the affinity construct of the present disclosure and an insecticidal protein in transgenic plants or microorganism in a method for protecting a plant against an insect pest according to the present disclosure.

Modified insect toxins that can be used in the context of the present invention, for example, to form the novel insecticidal compositions comprising an affinity construct of the disclosure and one or more insecticidal protein(s) may also include changes in protease cleavage sites, such as proteins with altered sequences obtained by site-directed mutagenesis or by using genome-editing tools. Furthermore, said modified insecticidal toxins may include proteins that are already chimeric proteins or fusion proteins, consisting of a toxin and another protein or peptide that enables or increases binding of the toxin to the insect target tissue/membrane. Such fusion proteins may include lectins, or specific gut-binding peptides.

In some embodiments the insecticidal proteins, which form part of a novel composition of the disclosure comprising an affinity construct and one or more insecticidal protein (s) have amino acid sequences that are shorter than the full-length sequences, either due to the use of an alternate downstream start site or due to processing that produces a shorter protein having insecticidal activity. Such processing may occur in the target organism after the insecticidal protein is ingested by the pest.

Thus, provided herein are novel isolated or recombinant nucleic acid sequences encoding the novel affinity constructs of the present disclosure. Also provided are the amino acid sequences of the novel affinity constructs of the disclosure. The protein resulting from translation of the genes encoding for the novel affinity constructs in combination with the respective insecticidal protein the at least one affinity molecule B is directed against allows controlling or killing pests that ingest same.

In various embodiments, the affinity construct is soluble in the gut of an insect or an insect larva.

Construction of the Affinity Constructs of the Disclosure

In the context of the affinity constructs comprising at least one affinity molecule A and at least one affinity molecule B, any affinity mediating molecule as defined above (for example, selected from the group comprising a protein, carbohydrate, lipid or nucleotide, or a fragment, derivative or variant of any of these), including monoclonal antibodies as widely applied in medicine and in molecular biology research, may be used (reviewed in Nature Reviews Immunology 10, 285 (2010), FIG. 1). Preferably, the affinity molecule(s) (i.e., the at least one affinity molecule A and/or the at least one affinity molecule B) is/are a protein which is a non-antibody binding protein or an antibody or a fragment, derivative or variant thereof. More preferred, the non-antibody binding protein is any one of affimers (adhirons), affibodies, affilins, affitins, nanofitin, alphabodies (triple helix coiled coil), anticalins, lipocalins, avimers, DARPins (ankyrin repeat), fynomer, kunitz domain pepties, monobodies, adnectins, trinectins, nanoCLAMPs, cellulose/carbohydrate binding molecule (CBM) (for example, dockerins or lectins), centyrins, pronectins, and fibronectin or a fragment, derivative or variant of any of these. In other embodiments, the antibody is a naturally occurring antibody or a fragment, derivative or variant thereof, in particular a nanobody or an immunoglobulin gamma (IgG). Preferably, the fragment of the naturally occurring antibody can be an antibody fragment selected from the group comprising a Fab fragment, a single heavy chain and a single light chain, a single chain variable fragment, a $V_HH$ fragment, CDR3 region and a bispecific monoclonal antibody (diabody). The Fab fragment can occur as monomer or as a linked dimer, or antibody fragments consisting of a single heavy chain and a single light chain, or consisting of the heavy chain with all three domains (so called $V_HH$), two domains or only on domain of the constant region (the so called crystallizable Fragment Fc) or the single light chain or the region facilitating the recognition to the antigen comprising the CDR3 region as will be described in more detail further below. Encompassed are also synthetic affinity molecules like three helix coils. In other preferred embodiments, the nucleotide is a RNA aptamer, a SOMAmer or a ribozyme or a fragment, derivative or variant thereof.

In the context of the affinity construct comprising at least one affinity molecule A and at least one affinity molecule B, the affinity molecules (i.e., the at least one affinity molecule A and/or the at least one affinity molecule B) can be designed in a way to bind more than one target, e.g., two, three, four or even more targets, thus being bispecific, trispecific, tetraspecific or multispecific. With regards to the construction of a multispecific affinity molecule the affinity molecules can be fused directly or by using a linker, which does not interfere with the structure and function of the proteins, or fragments thereof, to be linked.

Affinity construct comprising at least one affinity molecule A and at least one affinity molecule B having the structure (Am-Ln-Bo)p In various embodiments, the novel affinity construct provided by the present disclosure and as described above comprising at least one affinity molecule A, and at least one affinity molecule B, which are optionally separated by a linker L comprising at least one amino acid, may have the structure (Am-Ln-Bo)p. In such embodiments, A is the affinity molecule A or a fragment thereof as described above, B is the affinity molecule B or a fragment thereof as described above, the integer m is at least 1, the integer o is also at least 1, L is a linker comprising or consisting of at least one amino acid, the integer n can be 0 or larger, and the integer p is at least 1. Integers m, n and o can have different values. Embodiments describing specific values of the integers m, n and o are described herein below. Furthermore, the affinity molecule A, the linker L and the affinity molecule B are all covalently bound to form the affinity construct of the structure Am-Ln-Bo. Thus, the present disclosure encompasses a novel affinity construct of the structure Am-Ln-Bo comprising at least one affinity molecule A, at least one affinity molecule B, and optionally at least one linker L, wherein the affinity molecule A or a fragment thereof is capable of recognizing an insect-specific structure in and/or on a target insect, and affinity molecule B or a fragment thereof is capable of binding an insecticidal protein (toxin), and wherein the integer m is at least 1 and the integer o is also at least 1, wherein L is a linker comprising or consisting of at least one amino acid, and wherein the integer n can be 0 or larger, and wherein the integers m, n and o can have different values, and wherein A, L and B are all covalently bound to form said affinity construct. If the integer n is 0 (zero), the affinity molecule A and the affinity molecule B are covalently bound to form the affinity construct of the structure Am-Ln-Bo or Am-Bo, respectively. Several units of the affinity construct Am-Ln-Bo or Am-Bo and be fused together to form affinity molecules of higher order. The integer p indicates how many affinity constructs Am-Ln-Bo or Am-Bo are fused together. For the structure Am-Ln-Bo-Am-Ln-Bo the integer p would be 2, for the structure Am-Ln-Bo-Am-Ln-Bo-Am-Ln-Bo it would be 3 and so on.

The affinity construct of the structure Am-Ln-Bo can be expressed in a transgenic plant or microorganism or be applied as an insecticidal spray/solution to a plant, seed or insect, when applied along with along with an insecticidal protein (toxin), wherein the insecticidal protein (toxin) corresponds to the insecticidal protein (toxin) which the at least one affinity molecule B is (capable of) binding to, or directed to.

In various embodiments of the affinity construct of the disclosure having the structure $A_m$-$L_n$-$B_o$, the integer m may be any one of 1, 2, 3, 4, 5, 6, 7, 8, 9, 10 or more. Preferably, the integer m is any one of 1, 2 and 3, more preferably 1 or 2, and even more preferably the integer m is 1. Furthermore, in various embodiments of the affinity construct of the disclosure having the structure Am-Ln-Bo, the integer o may be any one of 1, 2, 3, 4, 5, 6, 7, 8, 9, 10 or more. Preferably, the integer o is any one of 1, 2 and 3, more preferably 1 or 2, and even more preferably the integer o is 1. Still further, in various embodiments of the affinity construct of the disclosure having the structure $A_m$-$L_n$-$B_o$, the integer n may be any one of 0, 1, 2, 3, 4, 5, 6, 7 8, 9, 10 or more. Preferably, the integer n is any one of 1, 2 and 3, more preferably 1 or 2, and even more preferably the integer n is 1.

In various embodiments, the affinity construct of the disclosure having the structure A1L1-Bo comprises at least one affinity molecule A or a fragment thereof, and at least one affinity molecule B or a fragment thereof, and one linker L comprising or consisting of at least one amino acid, wherein the integer o (and thus the number of affinity molecules B in the affinity construct) is any one of 1, 2 or 3, preferably the integer o is 1 or 2.

In preferred embodiments, the affinity construct of the disclosure having the structure Am-L1-Bo comprises at least one affinity molecule A, at least one affinity molecule B, and one linker L comprising or consisting of at least one amino acid, and wherein the integer m is at least 1 and the integer o is at least 1.

In the present disclosure, the terms "insecticidal protein", "insecticidal toxin", and "insecticidal protein toxin"" may be used interchangeably.

[1] Affinity construct comprising (1) at least one affinity molecule A capable of recognizing, or capable of binding to, or binding to, or being directed to, or being designed to bind to an insect-specific structure in and/or on a target insect, and (2) at least one affinity molecule B capable of binding to, or binding to, or being directed to, or being designed to bind to an insecticidal protein (toxin), wherein the at least one affinity molecule A and the at least one affinity molecule B are optionally separated by a linker L comprising at least one amino acid.

[2] The affinity construct according to [1], wherein the at least one affinity molecule A is different from the at least one affinity molecule B.

[3] The affinity construct according to [1] or [2], wherein the at least one affinity molecule A has one or more binding sites (valences) for the same or different insect-specific structures in and/or on a target insect and wherein the at least one affinity molecule B has one or more binding sites (valences) for the same or different insecticidal protein (toxins).

[4] The affinity construct according to any one of [1] to [3], wherein the at least one affinity molecule A specifically binds to a receptor, more specifically a membrane-bound receptor, of an inner organ of the target insect.

[5] The affinity construct according to any one of [1] to [4], wherein the at least one affinity molecule A specifically binds to a receptor, more specifically a membrane-bound receptor, of the digestive tract, of a reproductive organ or of the nervous system.

[6] The affinity construct according to any one of [1] to [5], wherein the insecticidal protein (toxin) is selected from the group consisting of crystal toxins (Cry and Cyt proteins), vegetative insecticidal toxins (Vip proteins), mosquitocidal toxins (Mtx proteins), binary toxins (Bin proteins), and secreted insecticidal toxins (Sip proteins), as well as fragments or multimers thereof.

[7] The affinity construct according to any one of [1] to [6], wherein the insecticidal protein is derived from *Bacillus thuringiensis.*

[8] The affinity construct according to any one of [1] to [7], wherein the at least one affinity molecule A and the at least one affinity molecule B are an affinity mediating molecule selected from the group comprising a protein, carbohydrate, lipid or nucleotide, or a fragment, derivative or variant of any of these, wherein the at least one affinity molecule A and the at least one affinity molecule B are identical or different.

[9] The affinity construct according to [8], wherein the protein is a non-antibody binding protein or an antibody or a fragment, derivative or variant thereof.

[10] The affinity construct according to [9], wherein the non-antibody binding protein is selected from the group comprising affimers (adhirons), affibodies, affilins, affitins, nanofitin, alphabodies (triple helix coiled coil), anticalins, lipocalins, avimers, DARPins (ankyrin repeat), fynomer, kunitz domain pepties, monobodies, adnectins, trinectins, nanoCLAMPs, cellulose/carbohydrate binding molecule (CBM) (for example, dockerins or lectins), centyrins, pronectins, and fibronectin or a fragment, derivative or variant of any of these.

[11] The affinity construct according to [9], wherein the antibody is naturally-occurring antibody or a fragment, derivative or variant thereof.

[12] The affinity construct according to claim [11], wherein the naturally-occurring antibody or a fragment, derivative or variant thereof is a nanobody or an immunoglobulin gamma (IgG).

[13] The affinity construct according to [12], wherein the fragment of the naturally-occurring antibody is an antibody fragment selected from the group comprising a Fab fragment, a single heavy chain and a single light chain, a single chain variable fragment, a $V_HH$ fragment, CDR3 region and a bispecific monoclonal antibody (diabody).

[14] The affinity construct according to [8], wherein the nucleotide is a RNA aptamer, a SOMAmer or a ribozyme or a fragment, derivative or variant thereof.

[15] An insecticidal composition comprising the affinity construct according to any one of [1] to [5] and at least one insecticidal protein (toxin), wherein the at least one insecticidal protein (toxin) corresponds to the insecticidal protein(s) (toxin(s)), which the at least one affinity molecule B is capable of binding to, or is binding to, or is being directed to, or is being designed to bind to.

[16] Use of the affinity construct according to any one of [1] to [14], or of the insecticidal composition of [15] for protecting a plant, plant part or plant seed against one or more insect pest(s).

[17] A method of protecting a plant or plant parts or plant seeds against one or more insect pest(s) comprising
(a) co-expressing the affinity construct according to any one of [1] to [14] together with one or more insecticidal protein(s) (toxin(s)) in a plant, plant parts or plant seeds, wherein the one or more insecticidal protein(s) (toxin(s)) correspond(s) to the insecticidal protein(s) (toxin(s)) which the at least one affinity molecule B is capable of binding to, or is binding to, or is being directed to, or is being designed to bind to; or
(b) (co-)expressing the affinity construct according to any one of [1] to [14] and one or more insecticidal protein (s) (toxin(s)) in one or more microorganism(s) followed by the application of the one or more microorganism(s) (co-)expressing the affinity construct and the one or more insecticidal protein(s) (toxin(s)) either in purified form or together with the respective culture medium/media to a plant, plant parts or plant seeds, wherein the one or more insecticidal protein(s) (toxin(s)) correspond(s) to the insecticidal protein(s) (toxin(s)) which the at least one affinity molecule B is capable of binding to, or is binding to, or is being directed to, or is being designed to bind to; or (c) expressing the affinity construct according to any one of [1] to [14] in a plant, plant parts or plant seeds and applying the one or more insecticidal protein(s) (toxin(s)) to the plant, plant parts or plant seeds the at least one affinity molecule B comprised in the affinity construct is capable of binding to, or is binding to, or is being directed to, or is being designed to bind to, wherein said one or more insecticidal protein(s) (toxin(s)) are applied in purified form or by applying the microorganism(s) expressing these insecticidal protein(s) (toxin(s)); or (d) expressing the one or more insecticidal protein(s) (toxin(s)) in a plant, plant part or plant seed the at least one affinity molecule B comprised in the affinity construct is capable of binding to, or is binding to, or is being directed to, or is being designed to bind to, and applying the affinity construct according to any one of [1] to [14] to the plant, plant parts or plant seeds, wherein said affinity construct is expressed in one or more microorganism and is applied to said plant, plant parts or plant seeds either in purified form or by applying the microorganism(s) expressing the affinity construct; or (e) applying to the plant or plants parts or plant seeds the insecticidal composition of [15].

[18] A method of producing a plant or a microorganism comprising the affinity construct according to any one of [1] to [14] and one or more insecticidal protein(s) (toxin(s)), the method comprising co-expressing in a plant or microorganism the affinity construct according to any one of [1] to [14] and one or more insecticidal protein(s) (toxin(s)), wherein said one or more insecticidal protein(s) (toxin(s)) correspond(s) to the insecticidal protein(s) (toxin(s)) which the at least one affinity molecule B is capable of binding to, or is binding to, or is being directed to, or is being designed to bind to.

[19] The method of [17(a)] or [18], comprising the step of transforming the plant or microorganism with one or more nucleic acid molecules encoding the affinity construct according to any one of [1] to [14], and one or more nucleic acid molecules encoding the insecticidal protein(s) (toxin(s)), wherein said one or more insecticidal protein(s) (toxin(s)) correspond(s) to the insecticidal protein(s) (toxin(s)) which the at least one affinity molecule B is capable of binding to, or is binding to, or is being directed to, or is being designed to bind to.

[20] A method of producing an insecticidal formulation comprising the affinity construct according to any one of [1] to [14] and one or more insecticidal protein(s) (toxin(s)), the method comprising formulating the affinity construct according to any one of [1] to [14] and one or more insecticidal protein(s) (toxin(s)) as insecticidal formulation, wherein said one or more insecticidal protein(s) (toxin(s)) correspond(s) to the insecticidal protein(s) (toxin(s)) which the at least one affinity molecule B is capable of binding to, or is binding to, or is being directed to, or is being designed to bind to, and wherein said affinity construct and said one or more insecticidal protein(s) (toxin(s)) are expressed in one or more microorganism,

[21] The method of [20], wherein the affinity construct and the one or more insecticidal protein(s) (toxin(s)) being expressed in one or more microorganism are added to the insecticidal composition in either purified form or by adding the microorganism(s) expressing the affinity construct and the one or more insecticidal protein(s).

[22] A plant, plant part or plant seed or a microorganism comprising (i) one or more nucleic acid molecules encoding the affinity molecule according to any one of [1] to [14], and/or one or more nucleic acid molecules encoding one or more insecticidal protein(s) (toxin(s)), wherein said one or more insecticidal protein(s) (toxin(s)) correspond(s) to the insecticidal protein(s) (toxin(s)) which the at least one affinity molecule B is capable of binding to, or is binding to, or is being directed to, or is being designed to bind to; or (ii) one or more vectors comprising the one or more nucleic acid molecules of (i).

[23] A plant, plant part or plant seed, a microorganism or insecticidal formulation, produced or obtainable by the method according to any one of [17] to [21].

In the present disclosure, the affinity molecule or a fragment thereof as described above can be fused to at least a second affinity molecule or fragment thereof. In the present disclosure, an affinity molecule A or a fragment thereof as described above and an affinity molecule B or a fragment thereof as described above can be fused by using a linker, which does not interfere with the structure and function of the two proteins fused or any fragments thereof.

In various embodiments of the disclosure, the novel affinity construct may comprise more than one affinity molecule A or fragments thereof and/or more than one affinity molecule B or fragments thereof. The said more than one insecticidal protein or fragments thereof may be linked by chemical cross-linking.

The affinity constructs of the present disclosure can bind—via one or more affinity molecule(s) B—to insect-specific structures (receptors) that are otherwise not naturally bound, i.e., that are otherwise not target structures (receptors) of the insecticidal protein. The same applies with respect to the insecticidal protein, which is part of the composition of the disclosure comprising a novel affinity construct of the disclosure and an insecticidal protein. This binding to the insect-specific structures (receptors) serves to enrich the insecticidal protein to the gut membrane of the insect, and thereby aids membrane integration and pore formation of the insecticidal protein. It is to be understood that an affinity molecule of the present disclosure may comprise affinities to more than insecticidal protein (toxin). Further, it is also to be understood that a composition of the disclosure comprising a novel affinity construct of the disclosure and an insecticidal protein, may comprise more than one insecticidal protein (toxin). In addition to that it is also to be understood that a transgenic plant according to the present disclosure to which the novel affinity construct of the disclosure is applied may be expressing more than one insecticidal protein (toxin). For example, these more than one insecticidal protein can be (1) several units or copies of the same insecticidal protein, or (2) one or more copies of a particular first insecticidal protein in combination with one or more copies of a particular second insecticidal protein. In case of the latter, it is also considered that the "more than one insecticidal protein" can be one or more copies of a particular first insecticidal protein in combination with one or more copies of a particular third, fourth, fifth etc. insecticidal protein.

Plant Applications

The present disclosure encompasses the use of an affinity construct as described above comprising at least one affinity molecule A and at least one affinity molecule A together with at least one insecticidal protein (toxin), wherein the insecticidal protein (toxin) corresponds to the insecticidal protein (toxin) which the at least one affinity molecule B is capable of binding to, or binding to, or being directed to, or being designed to bind as described above, for protecting a plant against an insect pest.

The use may encompass in general the introduction of the novel affinity construct of the present disclosure comprising at least one affinity molecule A and at least one affinity molecule B into a plant, plant cell or plant seed on one hand or into microorganism on the other hand by means known to the person skilled in the art. The present disclosure also encompasses in general the introduction of the insecticidal protein (toxin), which the at least one affinity molecule B of the novel affinity construct of the present disclosure is capable of binding to, or is binding to, or is being directed to, or being designed to bind to, into a plant, plant cell or plant seed on one hand or into microorganism on the other hand by means known to the person skilled in the art.

In particular, the present disclosure encompasses a method for protecting a plant against an insect pest comprising co-expressing in a plant, plant part or plant seed the affinity construct of the present disclosure comprising at least one affinity molecule A and at least one affinity molecule B together with one or more insecticidal protein (toxin), wherein the one or more insecticidal protein (toxin) correspond(s) to the insecticidal protein (toxin) which the at least one affinity molecule B is capable of binding to, or is binding to, or is being directed to, or is being designed to bind to. In this context, both the affinity construct of the present invention and the one or more insecticidal protein (toxin), which the at least one affinity molecule B is capable of binding to, or is binding to, or is being directed to, or being designed to bind to, are introduced into the plant, plant part or plant seed by means known to the person skilled in the art. Upon expression in the plant, an insect would take up the affinity constructs well as the insecticidal protein(s). The affinity construct is then directed and bound to an insect-specific structure in or on the insect pest via the corresponding at least one affinity molecule A in the affinity construct, which is capable of recognizing, or is capable of binding to, or is binding to, or is binding to, or is being directed to, or is being designed to to bind to an insect-specific structure in and/or on a target insect. The insecticidal activity of the affinity construct is enhanced through the higher binding affinity of the multi-specific affinity molecule to insect-specific structures, preferably to insect receptors.

In a further preferred embodiment of the method for protecting a plant against an insect pest, the affinity construct of the present invention and one or more insecticidal protein(s) (toxin(s)) are co-expressed in one or more microorganism(s) followed by the application of the one or more microorganism(s) co-expressing the affinity construct and the one or more insecticidal protein(s) (toxin(s)) either in purified form or together with the respective culture medium/media to a plant, plant parts or plant seeds. In these embodiments the one or more insecticidal protein(s) (toxin(s)) correspond(s) to the insecticidal protein(s) (toxin(s)) which the at least one affinity molecule B is capable of binding to, or is binding to, or is being directed to, or is being designed to bind to. In this context both the affinity construct of the present invention and the insecticidal protein (toxin), which the at least one affinity molecule B is capable of binding to, or is binding to, or is being directed to, or being designed to bind to, introduced into one or more microorganism(s) by means known to the person skilled in the art. Upon feeding on the plant, plant part or plant seed, an insect would take up the affinity construct applied to the plant material as well as the insecticidal protein(s) expressed in the plant material. The affinity construct is then directed and bound to an insect-specific structure in or on the insect pest via the corresponding at least one affinity molecule A in the affinity construct, which is capable of recognizing, or is capable of binding to, or is binding to, or is being directed to, or is being designed to bind to an insect-specific structure in and/or on a target insect. The insecticidal activity of the affinity construct is enhanced through the higher binding affinity of the multi-specific affinity molecule to insect-specific structures, preferably to insect receptors.

The use also encompasses the introduction of the affinity construct of the present invention into a plant, plant part or plant seed by means known to the person skilled in the art. Such use may encompass applying to a plant, plant part or plant seed that is transformed with the affinity construct of the present invention a formulation comprising the insecticidal protein (toxin), which corresponds to the insecticidal protein (toxin) which the at least one affinity molecule B is capable of binding to, or is binding to, or is being directed to, or being designed to bind, preferably by way of a spray. The spray formulation applied to the plant comprises the insecticidal protein(s) for which the at least one affinity molecule B is capable of binding, or binding to, or being directed to, or being designed to bind to. In another embodiment, the use also encompasses the introduction of the insecticidal protein (toxin), which corresponds to the insecticidal protein (toxin) which the at least one affinity molecule B is capable of binding to, into a plant, plant part or plant seed by means which are known to the person skilled in the art. This particular use further encompasses the introduction of the novel affinity construct of the present disclosure into one or more microorganism(s) by means known to the person skilled in the art and applying the affinity construct to said plant, plant parts or plant seeds either in purified form or by applying the microorganism(s) expressing the affinity construct. Such use may encompass microorganism transformed with the novel affinity construct of the present invention formulated as a composition, preferably formulated as a spray.

In more preferred embodiments, the use encompasses the application of the insecticidal composition or the spray of the present invention comprising the affinity construct of the present disclosure and the insecticidal protein (toxin), which the at least one affinity molecule B is capable of binding to, or is binding to, or is being directed to, or being designed to bind to, to the surface of a plant. Alternatively, the affinity construct of the present disclosure and/or the insecticidal protein (toxin), which the at least one affinity molecule B is capable of binding to, or is binding to, or is being directed to, or being designed to bind to, may be extracted from the microorganism transformed with said affinity construct of the present disclosure and/or said insecticidal protein (toxin) and then formulated as a composition, preferably formulated as a spray. In preferred embodiments, said use encompasses the application of the composition or the spray comprising the affinity construct of the present invention and/or the insecticidal protein (toxin), which the at least one affinity molecule B is capable of binding to, or is binding to, or is being directed to, or being designed to bind to, extracted from the microorganisms to the surface of a plant.

Upon feeding on the plant, an insect would take up the affinity construct of the present disclosure as well as the insecticidal protein(s). The insecticidal protein is then directed and bound to a receptor target in the insect via the corresponding affinity molecule(s) A in the affinity construct, which is capable of recognizing, or capable of binding to, or binding to, or being directed to, or being designed to bind to a receptor in and/or on a target insect. The insecticidal activity of the insecticidal protein is enhanced through the higher binding affinity of the multispecific affinity molecule to insect receptors.

In any of the above embodiments, the plant or the microorganism may preferably be modified by using known genome editing tools for delivery of constructs, through either *Agrobacterium*-mediated transfer, electroporation, micro-projectile bombardment, virus-mediated delivery or sexual cross. The techniques of *Agrobacterium*-mediated transfer, electroporation, micro-projectile bombardment, virus-mediated delivery and sexual cross are well known to the skilled person and corresponding methods are described in the literature. The same holds for genome editing tools like, e.g., TAL Effector Nucleases (TALEN), CRISPR/Cas9 etc.

Genetically Modified (GM) or Gene Edited (GE) Plants

The present disclosure encompasses co-expression of one or more insecticidal protein (toxins) that have been genetically modified (GM) or gene edited (GE) with one or more affinity constructs of the present invention. Preferably, the affinity constructs comprise affinity mediating molecules in crop plants. The skilled artisan will further appreciate that changes can be introduced into the nucleic acid sequences coding for insecticidal proteins by GM or GE approaches thereby leading to changes in the amino acid sequence of the encoded the insecticidal protein (toxin) used in the context of the present invention without altering the biological activity of the proteins. Thus, variant nucleic acid molecules can be created by introducing one or more nucleotide substitutions, additions or deletions into the corresponding nucleic acid sequence disclosed herein, such that one or more amino acid substitutions, additions or deletions are introduced into the encoded protein. Mutations can be introduced by standard techniques, such as site-directed mutagenesis and PCR-mediated mutagenesis. Mutations may also be introduced using genome editing tools like, e.g., Zinc Finger Nucleases, TAL Effector Nucleases (TALEN), and CRISPR/Cas systems, like, for example, CRISPR/Cas9 and CRISPR/cpf1. Specifically, the present disclosure encompasses co-expression of one or more insecticidal proteins (toxins) as disclosed herein, in particular GM/GE insecticidal proteins (toxins) as disclosed herein, with one or more affinity constructs comprising at least one affinity molecule A and at least one affinity molecule B of the present disclosure in crop plants. Example of such GM/GE insecticidal protein (toxin) could be any Bt protein evolved/mutated to have increased affinity to its existing or to novel membrane bound receptor proteins. Example of such insecticidal protein (toxins) that have been gene edited (GE) could be any native protease inhibitor protein evolved/mutated to have increased affinity to its existing or to novel protease receptor proteins.

GM/GE Microbial Sprays & GM/GE Microbial Seed Treatments

The present disclosure encompasses co-expression of one or more insecticidal protein (toxins) that have been genetically modified (GM) or gene edited (GE) as mentioned above, and one or more affinity construct of the present disclosure in currently existing and commercially used *Bacillus thuringiensis* strains expressing Bt toxins.

The present disclosure further encompasses co-expression of one or more insecticidal protein (toxins) that have been genetically modified (GM) or gene edited (GE) as mentioned above, and one or more affinity construct of the present disclosure in other microbes (e.g., *Lactobacillus, Agrobacterium*, plant endophytic microbes such as Azotic's *Gluconacetobacter diazotrophicus*, any other microbes pursued by Biologics companies such as Indigo, AgBiome and the like).

Non-GM *Bacillus thuringiensis*-Based Sprays & Seed Treatments

The present disclosure encompasses co-formulation of one or more *Bacillus thuringiensis* strains each expressing specific (combinations) of Bt toxins with one or more affinity construct of the present disclosure (comprising at least one affinity molecule A and at least one affinity molecule B) in spray or seed formulations. The affinity constructs of the present disclosure are considered to confer increased affinity binding of the respective Bt toxins to their existing or novel membrane bound receptor proteins.

The present disclosure further encompasses co-formulation of one or more purified (and stabilized) Bt toxins or any other type of toxins with one or more affinity construct of the present disclosure (comprising at least one affinity molecule A and at least one affinity molecule B)) in spray or seed formulations. The affinity constructs of the present disclosure are considered to confer increased affinity binding of the respective purified/stabilized Bt toxins and other type of toxins to their existing or novel membrane bound receptor proteins, or existing or novel toxin receptor proteins, respectively. Example of other type of toxins could again be different types of protease inhibitors and their respective protease receptor proteins.

Linker Molecules

The affinity molecules (or fragments thereof) comprised in the affinity constructs of the present invention can be fused directly or by using a (flexible) linker which does not interfere with the structure and function of the proteins (or fragments thereof) to be linked. In various embodiments, the linker (linker L) is a flexible linker. Such flexible linkers may be, for instance, those which are used to fuse the variable domains of the heavy and light chain of conventional immunoglobulins to construct a single chain antibody, scFv, or may be those used to create bivalent bispecific scFvs, or may be those used in immunotoxins. In preferred embodiments, the linker is an amino acid linker, more preferably a flexible amino acid linker. The terms "amino acid(s)" and "amino acid residue(s)" may be used herein interchangeably. In various embodiments, the amino acid linker is a peptide linker, more preferably a flexible peptide linker. Linkers to be used in the present disclosure may also be based on hinge regions found in antibody molecules (Pack et al. 1993, Biotechnology (NY) 11, 1271-1277; Pack and Plückthun, 1992, Biochemistry 31, 1579-1584), or may be based on peptide fragments between structural domains of proteins.

A linker can be used for fusing one affinity molecule or a fragment thereof to another affinity molecule or a fragment thereof to form the affinity construct of the present invention. For example, one affinity molecule A is fused to one affinity molecule B either directly or using linker as described herein.

The term "directly" defines fusions in which the single affinity molecule or a fragment thereof is joined without a linker. As explained herein above, in preferred embodiments, the linker L is an amino acid linker, or a peptide or polypeptide linker. The linking group may be a polypeptide of between 1 and 500 amino acids in length. Preferably, the linking group or linker comprises between 1 and 100 amino acids in length, more preferably between 1 and 50 amino acids in length, still more preferably between 1 and 40, between 1 and 30, between 1 and 20, or between 1 and 10 amino acids in length.

A linker according to the present disclosure may be a flexible linker, which does not interfere with the structure and function of the affinity molecules to be linked. This applies to both the at least two affinity molecules to be fused/linked/joined for generating the novel affinity constructs of the disclosure. Said flexible linkers are, for instance, those which have been used to fuse the variable domains of the heavy and light chain of immunoglobulins to construct a scFv, those used to create bivalent bispecific scFvs or those used in immunotoxins (see, for example, Huston et al. 1992; Takkinen et al. 1991). Linkers can also be based on hinge regions in antibody molecules (Pack and Plückthun, 1992; Pack et al. 1993) or on peptide fragments between structural domains of proteins. Fusions can be made between the multivalent affinity molecules at both sides, the C- and N-terminus.

Further, the linker according to the present disclosure may be a linker which does interfere with the structure and function of one or more affinity molecules to be linked in a positive manner; e.g. by activating the one and/or the other affinity molecule being comprised in the affinity construct in instances where the affinity molecule are not active without the interference of the linker. This activation may, for example, be the results of a change in the 3-dimensional structure that affects the binding efficiency in a positive way.

A linker can be designed as a flexible GGGS-linker of, for example, three distinct lengths (9, 25, 35 amino acids containing glycine for flexibility and serine for solubility), as fusion head-to-tail with a 9 amino acid glycine/serine linker (preferred option) or as hinge-sequence added to the 3' extremity of an affinity molecule.

The linkers joining the at least two affinity molecules of the novel affinity construct of the present disclosure (i.e., the at least one affinity molecule A and the at least one affinity molecule B as described above) are preferably designed to (1) allow the at least two molecules to fold and act independently of each other, (2) not have a propensity for developing an ordered secondary structure which could interfere with the functional domains of the two proteins, (3) have minimal hydrophobic or uncharged characteristic which could interact with the functional protein domains and (4) provide steric separation of the two molecules such that they can interact simultaneously with their corresponding targets or receptors on a single cell or on multiple cells within the target tissue (e.g., the midgut). Typically surface amino acids in flexible protein regions include Gly, Asn and Ser. Virtually any permutation of amino acid sequences containing Gly, Asn and Ser would be expected to satisfy the above criteria for a linker sequence. Other neutral amino acids, such as Thr and Ala, may also be used in the linker sequence. Additional amino acids may also be included in the linkers due to the addition of unique restriction sites in the linker sequence to facilitate construction of the fusions.

In various embodiments the linkers may comprise sequences selected from the group of formulas: (Gly3Ser)n, (Gly4Ser)n, (Gly5Ser)n, (GlynSer)n and (AlaGlySer)n, where n is an integer which can be 1 or more, preferably any one of 1, 2, 3, 4, 5, 6, 7, 8, 9, and 10. The length of the amino acid sequence of the linker can be selected empirically or with guidance from structural information or by using a combination of the two approaches. In various preferred embodiments, the linker comprises a sequence of the formula (Gly4Ser)n, where n is an integer which can be 1 or more, including any one of 1, 2, 3, 4, 5, 6, 7, 8, 9, and 10. Preferably, the integer is 1. Accordingly, in various preferred embodiments, the linker has a sequence GGGGSGGGG (SEQ. ID NOS. 36).

Those skilled in the art will recognize that there are many such sequences that vary in length or composition that can serve as linkers with the primary consideration being that they be neither excessively long nor short. Sequences of affinity structures or affinity molecules of the disclosure capable of folding to biologically active states can be prepared by appropriate selection of the beginning (amino terminus) and ending (carboxyl terminus) positions from within the original polypeptide chain while using the linker sequence as described above.

Valences

The valence is the number of binding sites of a single affinity molecule and therefore the capability of said molecule to recognize a certain target (via its so-called paratope), whereas the region on the target is called the epitope). The presence of more than one valence can improve avidity, which is defined as accumulated strength of multiple binding sites and can exceed the mere sum of its individual binding sites. The human IgG is bi-valent; it consists of an antibody molecule with two binding-sites each for its epitope. The human IgM is dekavalent (deka stands for gr. "ten") because it consists of five bivalent antibody molecules with two binding sites each generating 10 binding sites in total.

Figure 2B:
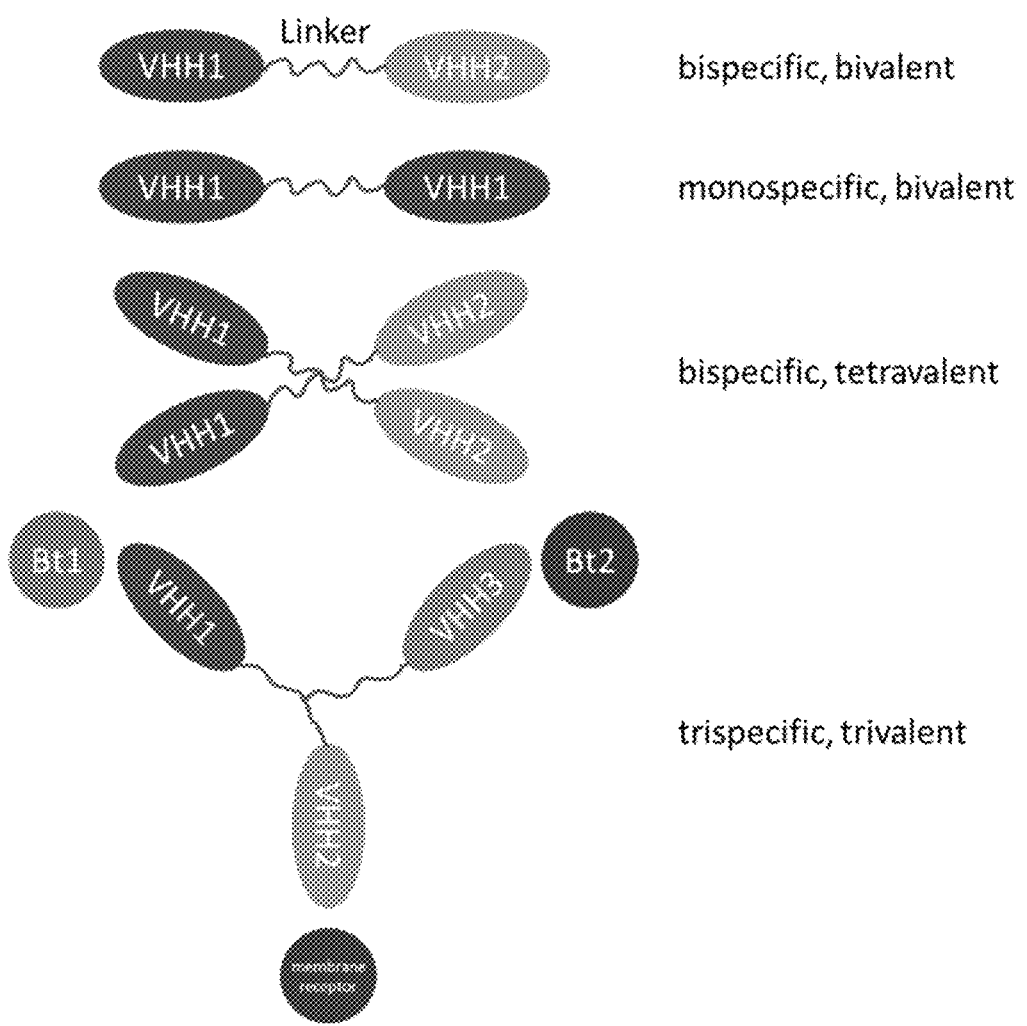
FIG. 2B shows examples for different recombinant $V_HH$s with combination of valences and specificities.

Valences might be of higher order to improve potency and affect avidity, see FIGS. 1 and 2A and 2B. Examples are divalent, trivalent, tetravalent, pentavalent, or multivalent, i.e. having two, three, four, five or many binding sites, respectively (see FIG. 1).

Affinity molecules of the present disclosure, i.e. the one or more affinity molecule A and the one or more affinity molecule B of the present invention, can be designed in a way to bind more than one target, e.g. two, three, four or even more targets, thus being bispecific, trispecific, tetraspecific or multispecific. As an example it should be noted, that an affinity construct of the present invention can have a multitude of affinity molecules; for example two affinity molecules, which are directed at a single epitope of the insect-specific structure, for example an receptor, in or on the insect pest, so that this affinity molecule has one specificity but two valences for this epitope, and additionally contains at least one affinity molecule B which is directed against an epitope of the insecticidal protein. The entire molecule would then be di-specific, i.e. detecting two distinct epitopes, and trivalent, since the affinity molecule has three binding sites in total. Options that may be employed to the affinity molecules of the present disclosure:

Binding
C-terminal to linker: may reduce affinity (Conrath et al. 2001).
N-terminal to linker.
Linker
Flexible GGGS-linker of three distinct lengths (9, 25, 35 amino acids containing glycine for flexibility and serine for solubility).
Fusion head-to-tail with a 9 amino acid glycine/serine linker.
Hinge-sequence added to 3' extremity of $V_HH$ as linker.

Valences: higher valences may improve potency and affect avidity, see FIGS. 1 and 2.

divalent
Trivalent
Tetravalent
Multivalent
Specificity
Bispecific
Trispecific
Tetraspecific Application of Multispecific Affinity Molecules One of the main aspects of the present disclosure is to apply the purified multispecific affinity molecules of the present invention (i.e., the affinity construct comprising at least one affinity molecule A, and at least one affinity molecule B) to the plant (e.g., by spraying) together with the insecticidal protein(s) for which affinity was generated (via affinity molecule B). Upon feeding on the plant, an insect would then take up the affinity molecule(s) (i.e., the affinity construct comprising at least one affinity molecule A and at least one affinity molecule B) as well as the insecticidal protein(s)). The oligomerization capacity and therefore pore formation activity of the insecticidal protein affinity-bound by the affinity construct would be enhanced through higher binding capacities to insect receptors via the multispecific affinity construct.

Alternatively, the multispecific affinity constructs can be easily expressed in plants either alone or together (i.e., by co-expression) with the insecticidal protein. Affinity molecules such as the $V_H$Hs can be readily expressed by transformed plants (Ismaili et al. 2007, Biotechnol Appl Biochem 47, 11-19). Expression in transgenic plants can be done using constitutively active promotors (e.g., 35S promotor or Ubiquitin promotors) or using specific promotors that allow increasing toxin activity in areas that are attacked by the target insects or that can be induced via external cues (e.g., chemically-inducible promotors, heat-inducible promotors).

The invention also includes applying the insecticidal protein to which the affinity molecule B is binding to or is directed to (or intended to bind to) to the plant. The insecticidal protein that is co-applied with the affinity molecule might also be equipped with a tag that is specific for a $V_H$H. Such tags have been described previously (De Genst et al. 2010, J Mol Biol 402, 326-343). However, these tags could be any protein or amino acid sequence, for which a specific antibody or $V_H$H can be produced.

The multispecific affinity constructs can also be introduced to the plant by other means, such as viral vectors, bacteria, injection, grafting, spraying and others.

Figure 4:
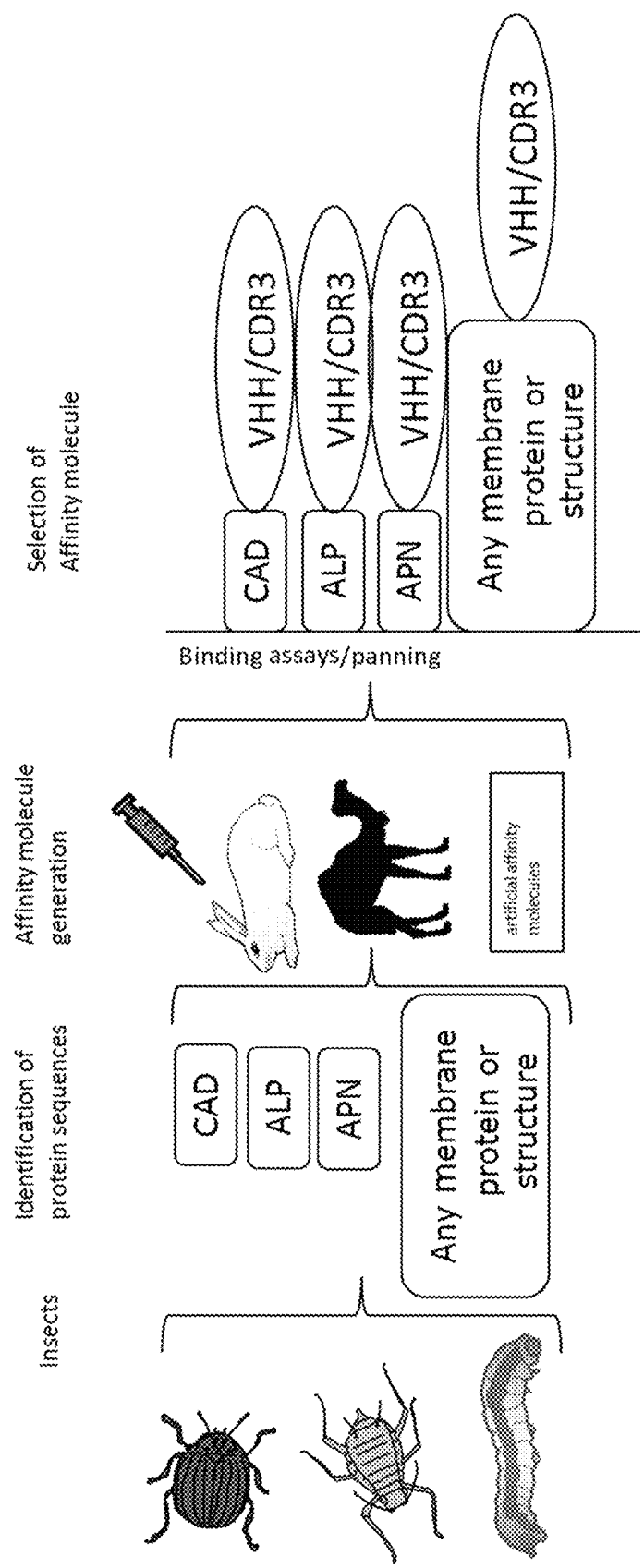
FIG. 4 depicts a schematic overview of a possible procedure to obtain (single domain) antibodies derived from immunization with different insect and bacterial antigens. Examples for insect gut or intestine-derived proteins are CAD=cadherin, ALP=alkaline phosphatase, APN=aminopeptidase N. The procedure shown can be applied to any insect-derived molecule.

Generation of Antibodies, in Particular Single Domain Antibodies, and Alphabodies, Nanobodies and CDR3-Loops Once insect-specific target structures are identified and made available, they can be used to immunize mammals, for example, camelids, as one of the steps to gain affinity molecules of the present invention that bind these insect-specific target structures (see FIG. 4). In certain embodiments, the mammal is a camelid mouse (Xu, et al Nature 595, 278-282 (2021), doi.org/10.1038/s41586-021-03676-z. As a response to immunization with an antigen camelid produce antibodies consisting of two heavy chains and two light chains, but also antibodies consisting of the variable domain of the heavy chain. After the immunization and an optional booster injection, mRNA from white blood cells is produced. The mRNA in its entirety is screened for the mRNA of heavy chain antibodies by reverse transcription and PCR methods. A library consisting of the single domain antibodies with a multitude of clones is therefore generated. In a subsequent screening step phage display or ribosome display is used to isolate antigen binding clones. As an alternative, sharks can be used to generate VNAR (Variable New Antigen Receptor) fragments. Antibodies generated with this technology may be subject to affinity maturation to further increase the antibody affinity. Alternatively, single domain antibodies of the present disclosure may be produced using naïve gene libraries from animals that have not been immunized. Also, single domain antibodies according to the present disclosure may be made from common murine or human IgG having four chains in a similar manner, using gene libraries from immunized or naïve donors and display techniques for the identification of the most specific antigens. Phage display is the most popular method for antibody library generation, including the generation of camelid single domain antibody libraries.

Methods for generating an affinity molecule which binds an insect gut protein comprising immunizing an animal with a composition comprising a polypeptide antigen disclosed herein or a DNA molecule encoding the polypeptide antigen disclosed herein are also provided. In certain embodiments, the polypeptide antigen comprises, consists essentially of, or consists of an amino acid sequence having at least 80%, 85%, 90%, 95%, 98%, or 100% sequence identity to SEQ ID NO: 30, 31, or 164 to 234 and/or comprises a variant of SEQ ID NO: 30, 31, or 164 to 234 wherein at least one, two, three, or more amino acid residues are substituted or conservatively substituted. Such conservative substitutions can include substitutions where an acidic amino acid residue is substituted with another acidic amino acid residue, a basic amino acid residue is substituted with another basic amino acid residue, a polar amino acid residue is substituted with another polar amino acid residue, and/or where a neutral non-polar amino acid residue is substituted with another neutral non-polar amino acid residue. In certain embodiments, the polypeptide antigen comprises, consists essentially of, or consists of an amino acid sequence having at least 80%, 85%, 90%, 95%, 98%, or 100% sequence identity to SEQ ID NO: 32, 35, 39, or 44. In certain embodiments, the polypeptide antigen is any one of about 50, 55, 56, or 57 amino acids in length to any one of about 58, 59, 60, 65, 70, 75, 80, 90, 95, or 100 amino acids in length. In certain embodiments, the polypeptide antigen consisting essentially of the amino acid sequence of SEQ ID NO: 30, 31, 32, 35, 39, 44 or 164 to 234 is a polypeptide that further consists of one, two, or 3 additional amino acids at the N-terminus and/or C-terminus of the polypeptide antigen amino acid sequence. In certain embodiments, immunizing is with a polynucleotide encoding the polypeptide antigen (i.e., DNA vaccination). DNA vaccination methods which can be adapted for use with the polypeptide antigens provided herein include those provided in U.S. Pat. No. 9,260,508, which is incorporated herein by reference in its entirety. In certain embodiments, the composition can further comprise an adjuvant. In certain embodiments, the composition is free of other native (i.e., non-heterologous) insect gut proteins. In certain embodiments, the polypeptide antigen for use in the composition is produced as a recombinant protein in a non-native (i.e., heterologous) host cell distinct from the native (i.e., non-heterologous cell) in which the native polypeptide antigen occurs. In certain embodiments, the heterologous host cell can include but is not limited to a non-native (i.e., heterologous) bacterial, yeast, fungal, or insect cell. In certain embodiments, the composition comprises a non-native whole cell, a virus like particle, or a non-native membrane vesicle where the polypeptide antigen is presented on the surface of a non-native (i.e., heterologous) whole cell, a virus like particle, or a non-native membrane vesicle. Examples of whole cell immunization methods which can be adapted for use with the polypeptide antigens provided herein include those where a cell line which overexpresses the polypeptide antigen is used to immunize an animal (on the world wide web internet site "creative-biolabs.com/antibody-production-by-whole-cell-immunization.html"). Examples of virus-like particles and membrane vesicles which can be adapted for use with the polypeptide antigens provided herein include those respectively disclosed in U.S. Pat. Nos. 9,439,959 and 10,179,167, which are each incorporated herein by reference in their entireties. In certain embodiments, the methods can further comprise: (i) generating a library of complementary DNA (cDNA) clones of mRNAs encoding affinity molecules from the immunized animal; (ii) enriching the library for clones which express an affinity molecule which binds the polypeptide antigen by subjecting the library to one or more rounds of panning the library on the polypeptide antigen to obtain a panned library, optionally wherein the panning is performed at a pH of greater than 9; and/or (iii) comprising screening the library for a clone expressing an affinity molecule which binds to the polypeptide antigen and optionally selecting the clone from the library. In certain embodiments, the polypeptide antigen can further comprise an epitope or other amino acid sequence (e.g., a histidine tag) to facilitate the panning, screening, and/or selection (e.g., by facilitating immobilization on a support). Methods for obtaining nanobodies which can be adapted for use with antigens provided herein include those disclosed herein as well those disclosed in US Patent Applications US20200308256 and US20220386594, both incorporated herein by reference in their entireties.

Methods for selecting an affinity molecule which binds an insect gut protein are also provided herein. In certain embodiments, the methods comprise (i) screening an affinity molecule library for a clone which binds to a polypeptide antigen; and/or (ii) selecting a clone which expresses or comprises the affinity molecule which binds the polypeptide antigen. In certain embodiments, the polypeptide antigen comprises, consists essentially of, or consisting of an amino acid sequence having at least 80%, 85%, 90%, 95%, 98%, or 100% sequence identity to SEQ ID NO: 30, 31, or 164 to 234 and/or comprises a variant of SEQ ID NO: 30, 31, or 164 to 234 wherein at least one, two, three, or more amino acid residues are substituted or conservatively substituted. Such conservative substitutions can include substitutions where an acidic amino acid residue is substituted with another acidic amino acid residue, a basic amino acid residue is substituted with another basic amino acid residue, a polar amino acid residue is substituted with another polar amino acid residue, and/or where a neutral non-polar amino acid residue is substituted with another neutral non-polar amino acid residue. In certain embodiments, the polypeptide antigen comprises, consists essentially of, or consists of an amino acid sequence having at least 80%, 85%, 90%, 95%, 98%, or 100% sequence identity to SEQ ID NO: 32, 35, 39, or 44. In certain embodiments, the polypeptide antigen consisting essentially of the amino acid sequence of SEQ ID NO: 30, 31, 32, 35, 39, 44 or 164 to 234 is a polypeptide that furthers consist of one, two, or 3 additional amino acids at the N-terminus and/or C-terminus of the polypeptide antigen amino acid sequence. In certain embodiments, the polypeptide antigen can further comprise an epitope or other amino acid sequence (e.g., a histidine tag) to facilitate screening and/or selection (e.g., by facilitating immobilization on a support). In certain embodiments, the library which is screened can be either a library is a naïve gene library from an animal that has not been immunized with the polypeptide antigen, a semisynthetic library, or synthetic library or a library is from an animal that has been immunized with the polypeptide antigen. In certain embodiments the library is a phage display library, a ribosome display library, a bacterial display library, or a yeast display library. In certain embodiments, the library is screened with the polypeptide antigen while in other embodiments the library is screened with the polypeptide antigen presented on the surface of a whole cell, a virus like particle, or a non-native membrane vesicle. Methods for screening and selecting for affinity molecules (e.g., nanobodies) which can be adapted for use with antigens provided herein include those disclosed in US Patent Applications US20200308256 and US20220386594, both incorporated herein by reference in their entireties.

Antibodies for use in the affinity constructs of the present disclosure can also be generated by using in silico methodologies which are known one of ordinary skill in the art.

In silico methodologies are also applied with regard to the generation of alphabodies according to the present disclosure. The alphabody scaffold is a computationally designed protein scaffold of about 10 kDa molecular weight and is considered not to have a counterpart in nature. Alphabodies can carry up to 25 variable positions that can be optimized, inter alia, for binding properties. This offers important advantages in the targeting of receptor molecules according to the present disclosure. Alphabodies can be considered as one of the preferred affinity molecules of the present disclosure.

The alphabodies and antibodies, in particular single domain antibodies and fragments thereof, obtained can then be fused or coupled to form an affinity construct of the disclosure, optionally via a linker L as described herein.

Microbial Strains for Use as Host Cells

One aspect of the disclosure pertains to microbial strains that are capable of expressing the novel affinity constructs of the present disclosure. In one embodiment, microbial strains can also be used for producing the novel affinity constructs of the present disclosure comprising at least one affinity molecule A capable of recognizing, or capable of binding to, or binding to, or being directed to, or being designed to bind to an insect-specific structure in and/or on a target insect, and at least one affinity molecule B capable of binding to, or binding to, or being directed to, or being designed to bind to an insecticidal protein (toxin).

The disclosure encompasses a method for expressing in a microbial cell, preferably in a bacterial cell, a yeast cell or a fungal cell, a novel affinity constructs of the disclosure, comprising the steps of: (a) inserting into a microbial cell, preferably into a bacterial cell, a yeast cell or a fungal cell, a nucleic acid sequence comprising in 5' to 3' direction an operably linked recombinant, double-stranded DNA molecule, wherein the recombinant double-stranded DNA molecule comprises (i) a promoter that functions in the microbial cell; (ii) a nucleic acid molecule encoding a affinity construct of the disclosure; and (iii) a 3' non-translated polynucleotide that functions in the microbial cell to cause termination of transcription; (b) obtaining a transformed microbial cell comprising the nucleic acid sequence of step (a) capable of expressing an affinity construct of the disclosure. The disclosure encompasses a microbial cell produced by such a method. The affinity constructs so produced or the microbial cells as such (still comprising the affinity constructs of the present disclosure) can be used in compositions of the present disclosure, in particular in spray compositions provided by the present disclosure. In preferred embodiments, the composition or the spray is applied to the plants, preferably to the leaves or other plant parts where insect pests generally feed, or to plant seeds. The term "microbial strain" or "microbial cell" or "microorganism" as used herein encompasses prokaryotic and eukaryotic microbes. Preferably, the microbial cell is any one of a bacterial cell, a yeast cell or a fungal cell. More preferably, the microbial cell is an endophyte, such as, for example, a bacterial or fungal cell. Even more preferred, the microbial cell is a bacterial cell. Preferably, the bacterial cell is *E. coli.*

Nucleic Acid Molecules, and Variants and Fragments Thereof

Another aspect of the disclosure pertains to recombinant nucleic acid molecules comprising nucleic acid sequences encoding the novel affinity constructs of the present disclosure or biologically active portions thereof.

As used herein, the term "nucleic acid molecule" is intended to include DNA molecules (e.g., recombinant DNA, cDNA, genomic DNA, plastid DNA, mitochondrial DNA) and RNA molecules (e.g., mRNA) and analogs of the DNA or RNA generated using nucleotide analogs. The nucleic acid molecule can be single-stranded or double-stranded, but preferably is double-stranded DNA.

As used herein, an "isolated" nucleic acid molecule (or DNA) refers to a nucleic acid sequence (or DNA) that is no longer in its natural environment, for example in vitro.

As used herein, a "recombinant" nucleic acid molecule (or DNA) refers to a nucleic acid sequence (or DNA) that is in a recombinant bacterial or plant host cell.

In various embodiments, an isolated nucleic acid molecule encoding an insecticidal protein, which forms part of a composition of the disclosure comprising the novel affinity constructs of the present invention and an insecticidal protein (toxin), has one or more changes in the nucleic acid sequence compared to the native or genomic nucleic acid sequence. In various embodiments, the change in the native or genomic nucleic acid sequence includes, but is not limited to: changes in the nucleic acid sequence due to the degeneracy of the genetic code; changes in the nucleic acid sequence due to amino acid substitution, insertion, deletion and/or addition compared to the native or genomic sequence; removal of one or more introns; deletion of one or more upstream or downstream regulatory regions; and deletion of the 5' and/or 3' untranslated region associated with the genomic nucleic acid sequence. In various embodiments, the nucleic acid molecule encoding an insecticidal protein, which forms part of a composition of the disclosure comprising the novel affinity constructs and an insecticidal protein (toxin), is a non-genomic sequence.

A variety of polynucleotides that encode affinity constructs of the present disclosure or related proteins are contemplated. Such polynucleotides are useful for production of the novel affinity constructs in host cells, such as, for example, plant cells or bacterial (microbial) cells, when operably linked to suitable promoter, transcription termination and/or polyadenylation sequences.

Where appropriate, a nucleic acid may be optimized for increased expression in the host cell organism. Thus, where the host organism is a plant, the synthetic nucleic acids can be synthesized using plant-preferred codons for improved expression. See, for example, Campbell and Gowri 1990; Plant Physiol. 92:1-11 for a discussion of host-preferred codon usage. For example, although nucleic acid sequences of the disclosure may be expressed in both monocotyledonous and dicotyledonous plant species, sequences can be modified to account for the specific codon preferences and GC content preferences of monocotyledons or dicotyledons as these preferences have been shown to differ (Murray et al. 1989; Nucleic Acids Res. 17:477-498). Thus, for example the maize-preferred codon for a particular amino acid may be derived from known gene sequences from maize. Methods are available in the art for synthesizing plant-preferred genes. See, for example, Murray, et al. 1989; Nucleic Acids Res. 17:477-498, and Liu H et al. 2010; Mol Bio Rep 37:677-684. Additional sequence modifications are known to enhance gene expression in a cellular host. These include elimination of sequences encoding spurious polyadenylation signals, exon-intron splice site signals, transposon-like repeats, and other well-characterized sequences that may be deleterious to gene expression. The GC content of the sequence may be adjusted to levels average for a given cellular host, as calculated by reference to known genes expressed in the host cell. The term "host cell" as used herein refers to a cell which contains a vector and supports the replication and/or expression of the expression vector is intended. Host cells may be prokaryotic cells, such as *E. coli*, or eukaryotic cells, such as yeast or insect cells or monocotyledonous or dicotyledonous plant cells. An example of a monocotyledonous host cell is a maize host cell.

Polynucleotides that encode an affinity construct of the present disclosure can also be synthesized de novo from a corresponding polypeptide sequence. The sequence of the polynucleotide gene can be deduced from a polypeptide sequence through use of the genetic code. Computer programs such as "BackTranslate" (GCG™ Package, Acclerys, Inc. San Diego, Calif.) can be used to convert a peptide sequence to the corresponding nucleotide sequence encoding the peptide.

Furthermore, synthetic polynucleotide sequences of the disclosure, which encode an affinity construct of the present disclosure, can be designed (for example using codon optimization, which is well known to the skilled person) so that they will be expressed in plants or microbial cells. Methods for synthesizing plant genes to improve the expression level of the protein encoded by the synthesized gene are known in the art. Such methods include the modification of the structural gene sequences of the exogenous transgene, to cause them to be more efficiently transcribed, processed, translated and expressed by the plant. Features of genes that are expressed well in plants include elimination of sequences that can cause undesired intron splicing or polyadenylation in the coding region of a gene transcript while retaining substantially the amino acid sequence of the toxic portion of the insecticidal protein.

A method for obtaining enhanced expression of transgenes in monocotyledonous plants is disclosed, e.g., in U.S. Pat. No. 5,689,052.

Also provided are nucleic acid molecules that encode transcription and/or translation products that are subsequently spliced to ultimately produce a functional insecticidal fusion protein of the present disclosure. Splicing can be accomplished in vitro or in vivo and can involve cis- or trans-splicing. The substrate for splicing can be polynucleotides (e.g., RNA transcripts) or polypeptides. An example of cis-splicing of a polynucleotide is where an intron inserted into a coding sequence is removed and the two flanking exon regions are spliced to generate an insecticidal protein encoding sequence, or an (insecticidal) fusion protein encoding sequence. An example of trans-splicing would be where a polynucleotide is encrypted by separating the coding sequence into two or more fragments that can be separately transcribed and then spliced to form the full-length insecticidal protein encoding sequence, or an insecticidal fusion protein encoding sequence. Thus, in various embodiments the polynucleotides do not directly encode a full-length insecticidal protein or insecticidal fusion protein, but rather encode a fragment or fragments thereof. These polynucleotides can be used to express a functional affinity construct through a mechanism involving splicing, where splicing can occur at the level of polynucleotide (e.g., intron/exon) and/or polypeptide (e.g., intein/extein). This can be useful, for example, in controlling expression of insecticidal activity, in particular in case functional affinity constructs may only be expressed if all required fragments are expressed in an environment that permits splicing processes to generate functional product.

Nucleic acid molecules that are fragments of the nucleic acid sequences encoding affinity constructs of the present disclosure are also encompassed herein. By "fragment" is intended a portion of the nucleic acid sequence encoding an affinity construct of the disclosure. A fragment of a nucleic acid sequence may encode a biologically active portion of an affinity construct of the disclosure, or it may be a fragment that can be used as a hybridization probe or PCR primer. Nucleic acid molecules that are fragments of a nucleic acid sequence encoding an affinity construct of the disclosure comprise at least about 50, 100, 200, 300, 400, 500, 600, 700, 800, 900, 1,000, 1,100, 1,200, 1,300, 1,400, or 1,500 contiguous nucleotides or up to the number of nucleotides present in a full-length nucleic acid sequence encoding an affinity construct of the disclosure, depending upon the intended use. By "contiguous" nucleotide residues are intended that are immediately adjacent to one another. Fragments of the nucleic acid sequences of the disclosure will encode protein fragments that retain the biological activity of the corresponding affinity construct of the disclosure and, hence, retain its ability to bind to one or more insect-specific structure(s) in or on the insect pest as well as to bind one or more insecticidal protein (toxin).

As used herein, the term "insecticidal activity" refers to the activity of a composition of the disclosure comprising the novel affinity construct and an insecticidal protein (toxin), that can be measured by, but is not limited to, mortality, weight loss, stunted growth of the insect pest and other behavioral and physical changes of an insect pest after feeding and exposure for an appropriate length of time. Thus, an organism or substance having insecticidal activity adversely impacts at least one measurable parameter of insect pest fitness. For example, "insecticidal proteins" are proteins that display insecticidal activity by themselves but may also display insecticidal activity in combination with other proteins. The same holds for the insecticidal activity of a composition of the disclosure comprising the novel affinity construct and an insecticidal protein (toxin), which displays insecticidal activity by itself, but may also display insecticidal activity in combination with other proteins.

As used herein, the term "insecticidally effective amount" connotes a quantity of an insecticidal protein applied in combination with the affinity construct of the disclosure that has insecticidal activity when present in the environment of a pest. For each insecticidal protein, the insecticidally effective amount is determined empirically for each insect pest affected in a specific environment.

By "retains activity" is intended that an insecticidal protein has at least about 10%, at least about 30%, at least about 50%, at least about 70%, 80%, 90%, 95% or higher of the insecticidal activity compared to the full-length insecticidal protein alone that is part of the composition of the present invention. In various preferred embodiments, the insecticidal activity is against an Isopteran, Blattodean, Orthopteran, Phthirapteran, Thysanopteran, Hemipteran, Hymenopteran, Siphonapteran, Dipteran, Coleopteran and/or Lepidopteran species. In various preferred embodiments, the insecticidal activity is against a Lepidopteran species. In further preferred embodiments, the insecticidal activity is against a Coleopteran species.

In some embodiments a fragment of a nucleic acid sequence encoding a biologically active portion of an insecticidal protein will encode at least about 15, 25, 30, 50, 75, 100, 125, 150, 175, 200 or 250, contiguous amino acids present in a full-length insecticidal protein.

In various embodiments, the insecticidal protein, which forms part of the composition of the disclosure comprising the novel affinity construct and an insecticidal protein (toxin), may be the core of an insecticidal toxin, preferably the core of a Cry toxin, more preferably the core of a three-domain Cry protein. Thus, in various embodiments, the insecticidal protein is a core toxin, preferably a core toxin of a Cry toxin, more preferably the core of a three-domain Cry protein. The "core" of an insecticidal Cry toxin is a fragment of the insecticidal toxin and may comprise domains I, II and/or III of the insecticidal Cry toxin. A core toxin according to the present disclosure has insecticidal activity as described herein elsewhere.

In various embodiments, an insecticidal protein, which forms part of the composition of the disclosure comprising the novel affinity construct and an insecticidal protein (toxin), has an amino acid sequence comprising at least 80%, 81%, 82%, 83%, 84%, 85%, 86%, 87%, 88%, 89%, 90%, 91%, 92%, 93%, 94%, 95%, 96%, 97%, 98%, 99% or greater identity to the amino acid sequence of the Cry1Ac 3 domain core toxin (SEQ ID NOS. 51), wherein the insecticidal protein has insecticidal activity. In various embodiments, an insecticidal protein, which forms part of the insecticidal composition of the disclosure comprising the novel affinity construct and an insecticidal protein (toxin), has an amino acid sequence comprising at least 80%, 81%, 82%, 83%, 84%, 85%, 86%, 87%, 88%, 89%, 90%, 91%, 92%, 93%, 94%, 95%, 96%, 97%, 98%, 99% or greater identity to the amino acid sequence of the Cry3Ab 3 domain core toxin (SEQ ID NOS. 52), wherein the insecticidal protein has insecticidal activity. In various embodiments, an insecticidal protein, which forms part of the composition of the disclosure comprising the novel affinity construct and an insecticidal protein (toxin), has an amino acid sequence comprising at least 80%, 81%, 82%, 83%, 84%, 85%, 86%, 87%, 88%, 89%, 90%, 91%, 92%, 93%, 94%, 95%, 96%, 97%, 98%, 99% or greater identity to the amino acid sequence of the Vip3Aa toxin (SEQ ID NOS. 53), wherein the insecticidal protein has insecticidal activity.

The "sequence identity" is intended to refer to an amino acid or nucleic acid sequence that has at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to a reference sequence using an alignment program known in the art using standard parameters. In various embodiments the sequence homology/identity is against the full-length sequence of a reference insecticidal protein of the disclosure.

One of skill in the art will recognize that these values can be appropriately adjusted to determine corresponding identity of proteins encoded by two nucleic acid sequences by taking into account codon degeneracy, amino acid similarity, reading frame positioning, and the like. To determine the percent identity of two amino acid sequences or of two nucleic acids, the sequences are aligned for optimal comparison purposes. The percent identity between the two sequences is a function of the number of identical positions shared by the sequences (i.e., percent identity=number of identical positions/total number of positions (e.g., overlapping positions)×100). In one embodiment, the two sequences have the same length. In another embodiment, the comparison is across the entirety of the reference sequence. The percent identity between two sequences can be determined using techniques similar to those described below, with or without allowing gaps. In calculating percent identity, typically exact matches are counted. The determination of percent identity between two sequences can be accomplished using a mathematical algorithm. A non-limiting example of a mathematical algorithm utilized for the comparison of two sequences is the algorithm of Karlin and Altschul 1990; Proc. Natl. Acad. Sci. USA 87:2264, modified as in Karlin and Altschul 1993; Proc. Natl. Acad. Sci. USA 90:5873-5877. Such an algorithm is incorporated into the BLASTN and BLASTX programs of Altschul, et al. 1990; J. Mol. Biol. 215:403. BLAST nucleotide searches can be performed with the BLASTN program, score=100, word length=12, to obtain nucleic acid sequences homologous to insecticidal-like nucleic acid molecules. BLAST protein searches can be performed with the BLASTX program, score=50, word length=3, to obtain amino acid sequences homologous to insecticidal protein molecules. To obtain gapped alignments for comparison purposes, Gapped BLAST (in BLAST 2.0) can be utilized as described in Altschul, et al. 1997; Nucleic Acids Res. 25:3389. Alternatively, PSI-Blast can be used to perform an iterated search that detects distant relationships between molecules. See, Altschul, et al., (1997), supra. When utilizing BLAST, Gapped BLAST, and PSI-Blast programs, the default parameters of the respective programs (e.g., BLASTX and BLASTN) can be used. Alignment may also be performed manually by inspection.

The present disclosure also encompasses nucleic acid molecules encoding variants of either the affinity constructs of the disclosure or the insecticidal protein (toxin) used in the context of the present invention. These "variants" include sequences that encode the affinity constructs of the disclosure or the insecticidal protein (toxin) used in the context of the present invention but that differ conservatively because of the degeneracy of the genetic code as well as those that are sufficiently identical as discussed above. Variant nucleic acid sequences also include synthetically derived nucleic acid sequences that have been generated, for example, by using site-directed mutagenesis but which still encode an (insecticidal) fusion protein of the present disclosure. The present disclosure provides isolated or recombinant polynucleotides that encode any of the affinity constructs or the insecticidal protein (toxin) disclosed herein. Those having ordinary skill in the art will readily appreciate that due to the degeneracy of the genetic code, a multitude of nucleotide sequences encoding either the affinity constructs of the disclosure or the insecticidal protein (toxin) used in the context of the present disclosure exist. The skilled artisan will further appreciate that changes can be introduced by mutation of the nucleic acid sequences thereby leading to changes in the amino acid sequence of the encoded affinity constructs of the disclosure or the insecticidal protein (toxin) used in the context of the present invention, without altering the biological activity of the proteins. Thus, variant nucleic acid molecules can be created by introducing one or more nucleotide substitutions, additions or deletions into the corresponding nucleic acid sequence disclosed herein, such that one or more amino acid substitutions, additions or deletions are introduced into the encoded protein. Mutations can be introduced by standard techniques, such as site-directed mutagenesis and PCR-mediated mutagenesis. Mutations may also be introduced using genome editing tools like, e.g., Zinc Finger Nucleases, TAL Effector Nucleases (TALEN), and CRISPR/Cas systems, like, for example, CRISPR/Cas9 and CRISPR/cpf1. Such variant nucleic acid sequences are also encompassed by the present disclosure.

Proteins and Variants and Fragments Thereof

Insecticidal proteins or polypeptides are encompassed by the present disclosure. By "insecticidal protein", or "insecticidal polypeptide", is intended a protein or polypeptide that retains insecticidal activity against one or more insect pests of, e.g., the Isopteran, Blattodean, Orthopteran, Phthirapteran, Thysanopteran, Hemipteran, Hymenopteran, Siphonapteran, Dipteran, Coleopteran and/or Lepidopteran order. A variety of insecticidal proteins/polypeptides are contemplated.

As used herein, the terms "protein", "peptide molecule" or "polypeptide" includes any molecule that comprises five or more amino acids. It is well known in the art that protein, peptide or polypeptide molecules may undergo modification, including post-translational modifications, such as, but not limited to, disulfide bond formation, glycosylation, phosphorylation or oligomerization. Thus, as used herein, the terms "protein", "peptide molecule" or "polypeptide" includes any protein that is modified by any biological or non-biological process. The terms "amino acid" and "amino acids" refer to all naturally occurring L-amino acids.

A "recombinant protein" is used herein to refer to a protein that is no longer in its natural environment, for example in vitro or in a recombinant bacterial or plant host cell.

In various embodiments of the present disclosure, a fragment of an affinity molecule or antibody as disclosed herein means antigen-binding fragment of an affinity molecule or antigen-binding fragment of an antibody.

In the present disclosure, the terms "fragment", "variant", "derivative" and "analog" when referring to affinity molecules, in particular antibodies, more specifically single domain antibodies, include any "fragment", "variant", "derivative" and "analog" which retain at least some of the affinity properties of the corresponding native affinity molecule. Thus, when referring to antibodies as affinity molecules, in particular single domain antibodies, the terms "fragment", "variant", "derivative" and "analog" describe polypeptide fragments, variants or derivatives, which retain at least some of the antigen-binding properties of the corresponding native antibodies. Thus, polypeptide fragments may also be considered as "biologically active portions" of a polypeptide.

Fragments of affinity molecules (referring to both affinity molecules A and B) of the present disclosure, in particular fragments of polypeptides including fragments of antibodies, include proteolytic fragments, as well as deletion fragments, in addition to specific antibody fragments discussed elsewhere herein. Variants of antibodies and antibody polypeptides of the present disclosure include fragments as described above, and also polypeptides and antibody polypeptides with altered amino acid sequences due to amino acid substitutions, deletions, or insertions. Variants may occur naturally or may be non-naturally occurring. Non-naturally occurring variants may be produced using art-known mutagenesis techniques. Variant polypeptides and antibody polypeptides may comprise conservative or nonconservative amino acid substitutions, deletions or additions. Derivatives of antibodies and antibody polypeptides of the present disclosure are polypeptides, which have been altered so as to exhibit additional features not found on the native polypeptide or antibody polypeptide. Examples include, but are not limited to, fusion proteins. Variant polypeptides may also be referred to herein as "polypeptide analogs". As used herein, a "derivative" of an antibody or antibody polypeptide refers to a subject polypeptide or antibody polypeptide having one or more residues chemically derivatized by reaction of a functional side group. Also included as "derivatives" are those peptides, which contain one or more naturally occurring amino acid derivatives of the twenty standard amino acids. For example, 4-hydroxyproline may be substituted for proline; 5-hydroxylysine may be substituted for lysine; 3-methylhistidine may be substituted for histidine; homoserine may be substituted for serine; and ornithine may be substituted for lysine.

"Fragments" or "biologically active portions" include polypeptide fragments comprising amino acid sequences, which are sufficiently identical to an insecticidal protein disclosed herein that exhibits insecticidal activity. A biologically active portion of an insecticidal protein disclosed herein can be a polypeptide that is, for example, 10, 25, 50, 100, 150, 200, 250 or more amino acids in length. Such biologically active portions can be prepared by recombinant techniques and evaluated for insecticidal activity.

It is well known in the art that polynucleotides encoding a truncated insecticidal protein disclosed herein can be engineered to add a start codon at the N-terminus such as ATG encoding methionine. It is also well known in the art that depending on the host in which the insecticidal protein disclosed herein is expressed the methionine may be partially or completed processed off.

The term variants also refers to proteins or polypeptides having an amino acid sequence that is at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% identical to the parental amino acid sequence.

In some embodiments an insecticidal protein disclosed herein includes variants where an amino acid that is part of a proteolytic cleavage site is changed to another amino acid to eliminate or alter the proteolytic cleavage at that site. This is in particular relevant when protoxins are used as insecticidal proteins in the context of the present disclosure and as discussed elsewhere herein. In some embodiments the proteolytic cleavage is caused by a protease in the insect gut. In other embodiments the proteolytic cleavage is caused by a plant protease in the transgenic plant.

In various embodiments an insecticidal protein disclosed herein has a modified physical property. As used herein, the term "physical property" refers to any parameter suitable for describing the physico-chemical characteristics of a protein. As used herein, "physical property of interest" and "property of interest" are used interchangeably to refer to physical properties of proteins that are being investigated and/or modified. Examples of physical properties include, but are not limited to, net surface charge and charge distribution on the protein surface, net hydrophobicity and hydrophobic residue distribution on the protein surface, surface charge density, surface hydrophobicity density, total count of surface ionizable groups, surface tension, protein size and its distribution in solution, melting temperature, and heat capacity. Examples of physical properties also include, but are not limited to, solubility, folding, stability, in particular pH stability, and digestibility. In various embodiments an insecticidal fusion protein of the disclosure has increased digestibility of proteolytic fragments in an insect gut. Models for digestion by simulated gastric fluids are known to one skilled in the art (Fuchs, R. L. and J. D. Astwood 1996; Food Technology 50: 83-88; Astwood, J. D., et al. 1996; Nature Biotechnology 14: 1269-1273; Fu T J et al. 2002; J. Agric Food Chem. 50: 7154-7160).

Also described herein are means and methods that provide for stability of the affinity construct and the affinity molecules, respectively, such as, for example, single domain antibodies in insect digestive systems. The affinity construct and the affinity molecules of the present disclosure may be degraded by the action of digestive enzymes, including proteases in the insect digestive system. To decrease potential proteolysis of the affinity construct and the affinity molecules in the insect digestive system, the amino acid composition may be changed without changing the binding capacity of the affinity molecules.

As described herein, the single domain antibody or a fragment thereof, e.g., the CDR3 loop of an sdAb, may be modified to provide for stability against proteases, such as the introduction of Cys at selected positions to form an extra disulfide bond. Phage-display panning with single domain antibodies can be performed under conditions that mimic the harsh environment of insect (mid)guts (e.g., pH>9). Other modifications providing for resistance against enzymatic proteolysis are described in the art and are known to the skilled person.

Bacterial genes quite often possess multiple methionine initiation codons in proximity to the start of the open reading frame. Often, translation initiation at one or more of these start codons will lead to generation of a functional protein. These start codons can include ATG codons. However, bacteria such as *Bacillus* sp. also recognize the codon GTG as a start codon, and proteins that initiate translation at GTG codons contain a methionine at the first amino acid. On rare occasions, translation in bacterial systems can initiate at a TTG codon, though in this event the TTG encodes a methionine. Furthermore, it is not often determined a priori which of these codons are used naturally in the bacterium. Thus, it is understood that use of one of the alternate methionine codons may also lead to the generation of insecticidal proteins. Corresponding insecticidal proteins are encompassed in the present disclosure and may be used in the methods of the present disclosure. It will be understood that, when expressed in plants, it will be necessary to alter the alternate start codon to ATG for proper translation.

In another aspect, the affinity constructs of the disclosure may be expressed as a precursor protein with an intervening sequence that catalyzes multi-step, post-translational protein splicing. Protein splicing involves the excision of an intervening sequence from a polypeptide with the concomitant joining of the flanking sequences to yield a new polypeptide.

Polynucleotides encoding an affinity construct of the disclosure may be fused to signal sequences, which will direct the localization of the affinity construct to particular compartments of a prokaryotic or eukaryotic cell and/or direct the secretion of the affinity construct of the disclosure from a prokaryotic or eukaryotic cell. For example, in *E. coli*, one may wish to direct the expression of the affinity construct to the periplasmic space. Further examples of compartments of the plant cell in this regard are chloroplasts, the Golgi apparatus, mitochondria, the nucleus, the endoplasmatic reticulum but also targeting of the extracellular space, targeting of the symplast or the cell wall.

Nucleotide Constructs, Expression Cassettes and Vectors

The use of the term "nucleotide constructs" herein is not intended to limit the embodiments to nucleotide constructs comprising DNA. Those of ordinary skill in the art will recognize that nucleotide constructs, particularly polynucleotides and oligonucleotides, composed of ribonucleotides and combinations of ribonucleotides and deoxyribonucleotides may also be employed as disclosed herein. The nucleotide constructs, nucleic acids, and nucleotide sequences as described herein encompass all complementary forms of such constructs, molecules and sequences. Further, the nucleotide constructs, nucleotide molecules and nucleotide sequences of the disclosure encompass all nucleotide constructs, molecules and sequences, which can be employed in the methods of the disclosure for transforming plants and microorganisms including, but not limited to, those comprised of deoxyribonucleotides, ribonucleotides and combinations thereof. Such deoxyribonucleotides and ribonucleotides include both naturally occurring molecules and synthetic analogues. The nucleotide constructs, nucleic acids, and nucleotide sequences of the disclosure also encompass all forms of nucleotide constructs including, but not limited to, single-stranded forms, double-stranded forms, hairpins, stem-and-loop structures and the like.

A further embodiment relates to a transformed organism such as an organism selected from bacterial or eukaryotic cells. The transformed organism comprises a DNA molecule of the disclosure, an expression cassette comprising the DNA molecule or a vector comprising the expression cassette, which may be stably incorporated into the genome of the transformed organism.

The sequences of the disclosure are provided in DNA constructs for expression in the organism of interest. In various embodiments, the sequences of the disclosure are provided in expression cassettes. The disclosure encompasses an expression cassette comprising an isolated nucleic acid molecule encoding an affinity construct or insecticidal protein of the disclosure. An "expression cassette" as used herein means a DNA construct comprising at least one regulatory sequence operably linked to a polynucleotide encoding an affinity construct of the disclosure. The term "operably linked" as used herein refers to a functional linkage between a promoter and a DNA sequence, wherein the promoter sequence initiates and mediates transcription of the DNA sequence. Generally, "operably linked" means that the nucleic acid sequences being linked are contiguous to join two protein coding regions in the same reading frame. In various embodiments the expression cassette comprises a 5' and a 3' regulatory sequence. In some embodiments the expression cassette comprises a heterologous regulatory sequence. The term "heterologous regulatory sequence" as used herein indicates that the regulatory sequence is not associated with the native or genomic polynucleotide encoding an affinity construct or insecticidal protein of the disclosure. In some embodiments, the expression cassette comprises a regulatory sequence from a plant. In some embodiments the expression cassette comprises a regulatory sequence from the bacterial strain which is used as host for the expression and production of the novel affinity construct and insecticidal proteins of the present disclosure. The expression and production of the novel affinity construct and insecticidal proteins of the present disclosure is discussed elsewhere herein. The construct may additionally contain at least one additional gene to be co-transformed into the organism. Alternatively, the additional gene(s) can be provided on multiple DNA constructs. Such a DNA construct is provided with a plurality of restriction sites for insertion of the nucleotide sequence encoding the affinity construct or insecticidal protein to be under the transcriptional regulation of the regulatory regions. The DNA construct may additionally contain selectable marker genes. An expression cassette will generally include in the 5' to 3' direction of transcription: a transcriptional and translational initiation region (i.e., a promoter), a DNA sequence of the embodiments and a transcriptional and translational termination region (i.e., termination region) functional in the organism serving as a host. The transcriptional initiation region (i.e., the promoter) may be native, analogous, foreign or heterologous to the host organism and/or to the sequence of the embodiments. Additionally, the promoter may be the natural sequence or alternatively a synthetic sequence. The term "foreign" as used herein indicates that the promoter is not found in the native organism into which the promoter is introduced. Where the promoter is "foreign" or "heterologous" to the sequence(s) of the disclosure, it is intended that the promoter is not the native or naturally occurring promoter for the operably linked sequence(s) of the disclosure. Where the promoter is a native or natural sequence, the expression of the operably linked sequence is altered from the wild-type expression, which results in an alteration in phenotype. In various embodiments the expression cassette may also include a transcriptional enhancer sequence. As used herein, the term an "enhancer" refers to a DNA sequence, which can stimulate promoter activity and may be an innate element of the promoter or a heterologous element inserted to enhance the level or tissue-specificity of a promoter.

The expression cassettes may additionally contain 5' leader sequences. Such leader sequences can act to enhance translation. Translation leaders are known in the art. Such constructs may also contain a "signal sequence" or "leader sequence" to facilitate co-translational or post-translational transport of the peptide to certain intracellular structures such as the chloroplast (or other plastid), endoplasmic reticulum or Golgi apparatus. By "signal sequence" is intended a sequence that is known or suspected to result in co-translational or post-translational peptide transport across the cell membrane. In eukaryotes, this typically involves secretion into the Golgi apparatus, with some resulting glycosylation. Insecticidal toxins of bacteria are often synthesized as protoxins, which are proteolytically activated in the gut of the target pest (Chang 1987; Methods Enzymol. 153:507-516). In various embodiments, the signal sequence is located in the native sequence or may be derived from a sequence of the embodiments. By "leader sequence" is intended any sequence that when translated, results in an amino acid sequence sufficient to trigger co-translational transport of the peptide chain to a subcellular organelle. Thus, this includes leader sequences targeting transport and/or glycosylation by passage into the endoplasmic reticulum, passage to vacuoles, plastids including chloroplasts, mitochondria and the like. In preparing the expression cassette, the various DNA fragments may be manipulated so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites or the like. For this purpose, in vitro mutagenesis, primer repair, restriction, annealing, re-substitutions, e.g., transitions and transversions, may be involved. A number of promoters can be used in the practice of the present disclosure. The promoters can be selected based on the desired outcome. The nucleic acids can be combined with constitutive, tissue-preferred, inducible or other promoters for expression in the host organism. Suitable constitutive promoters for use in a plant host cell are known in the art.

Depending on the desired outcome, it may be beneficial to express the gene from an inducible promoter. Of particular interest for regulating the expression of the nucleotide sequences of the disclosure in plants are wound-inducible promoters. Additionally, pathogen-inducible promoters may be employed in the methods of the disclosure and nucleotide constructs of the disclosure. Tissue-preferred promoters can be utilized to target enhanced insecticidal fusion protein expression within a particular plant tissue. Leaf-preferred promoters are known in the art and are also encompassed by the present disclosure. Root-preferred or root-specific promoters are also encompassed and are known and can be selected from the many available from the literature or isolated de novo from various compatible species. "Seed-preferred" promoters include both "seed-specific" promoters (those promoters active during seed development such as promoters of seed storage proteins) as well as "seed-germinating" promoters (those promoters active during seed germination). See, Thompson, et al., 1989; BioEssays 10:108.

Where low level expression is desired, weak promoters will be used. Generally, the term "weak promoter" as used herein refers to a promoter that drives expression of a coding sequence at a low level. The above list of promoters is not meant to be limiting. Any appropriate promoter can be used in the embodiments.

Generally, the expression cassette may comprise a selectable marker gene for the selection of transformed cells. Selectable marker genes are utilized for the selection of transformed cells or tissues. Marker genes include, but are not limited to, genes encoding antibiotic resistance, as well as genes conferring resistance to herbicidal compounds. Any selectable marker gene can be used in the present disclosure.

The disclosure encompasses a recombinant microorganism, comprising an isolated nucleic acid molecule encoding an affinity construct or an insecticidal protein of the disclosure. In various embodiments, the microorganism is any of a bacterium, baculovirus, algae, and fungi. In various embodiments, the microorganism is any of a *Bacillus*, a *Pseudomonas*, a *Clavibacter*, a *Rhizobium*, a *lactobacillus* or *E. coli*. Preferably, the recombinant microorganism is *Bacillus thuringiensis* or *Escherichia coli* or a expression system like, for example, *Saccharomyces cerevisiae* or *Pichia pastoris*.

The disclosure encompasses a method for producing an affinity construct or an insecticidal protein of the disclosure, comprising culturing a microorganism of the disclosure under conditions in which the nucleic acid molecule encoding the affinity construct and/or insecticidal protein, respectively, is expressed. Preferably, the affinity construct and/or insecticidal protein of the present disclosure is either secreted by the microorganism into the culture medium and collected or isolated therefrom, or it is extracted from the microorganism after a period of culture and then formulated into an (insecticidal) composition/formulation according to the present disclosure. The protein can be collected or purified by using a tag, for example, a histidine tag. The most commonly used tag for collecting large amounts of highly purified protein is a poly-histidine tag (His-tag). His-tagged proteins are recombinant proteins designed to include a poly-histidine tail (his-tag) that facilitates purification of the proteins from in vitro expression systems, e.g., from bacterial host strains used for expression of the proteins. The His-tag usually comprises 6-14 histidines and is typically fused to the N- or C-terminal end of a target protein. In some cases, the tag can also be inserted into an exposed loop of the target protein. His-tagged insecticidal fusion proteins and fusion proteins of the present disclosure expressed and subsequently purified by a purification kit for histidine-tagged proteins (such purification kits are commercially available, e.g., from Qiagen or Sigma) are suitable for subsequent use in a composition or formulation, preferably a spray composition or formulation, according to the present disclosure. The disclosure also encompasses a method for producing a microorganism that contains an affinity construct and/or an insecticidal protein, respectively, of the disclosure comprising culturing a microorganism of the disclosure under conditions in which the nucleic acid molecule encoding the affinity construct and/or insecticidal protein, respectively, is expressed, collecting or isolating the microorganism from the culture medium after a period of culture and then formulating the microorganism into an (insecticidal) composition or formulation according to the present disclosure.

Plant Transformation

The novel affinity constructs and/or the insecticidal proteins of the present disclosure can be easily expressed in transgenic plants or in plant cells or be applied as an insecticidal spray/solution to a plant, seed or insect, in particular in agricultural crops or cells thereof. Furthermore, the affinity construct and/or insecticidal protein, respectively, can be readily expressed by transformed plants or plant cells. Also, the novel affinity constructs of the present disclosure can be easily co-expressed with an insecticidal protein in transgenic plants or in plant cells, or can be applied, in combination with an insecticidal protein, as an insecticidal spray/solution to a plant, seed or insect, in particular in agricultural crops or cells thereof, wherein the insecticidal protein corresponds to the insecticidal protein (toxin), which the at least one affinity molecule B of the novel affinity construct is capable of binding to, or is binding to, or is being directed to, or is being designed to bind to.

The present disclosure provides a plant, plant part or plant seed comprising (i) one or more nucleic acid sequences encoding a novel affinity construct of the present disclosure and an insecticidal protein, wherein the insecticidal protein corresponds to the insecticidal protein, against which the at least one of the affinity molecules of the novel affinity construct is binding to, or (i) one or more vectors comprising one or more nucleic acid sequences encoding a novel affinity construct of the present disclosure and an insecticidal protein, wherein the insecticidal protein corresponds to the insecticidal protein (toxin), which the at least one affinity molecule B of the novel affinity construct is capable of binding to, or binding to, or being directed to, or being designed to bind to. The plant may be a monocotyledonous plant or a dicotyledonous plant. The present disclosure also provides parts and seed of such plants.

The methods of the present disclosure involve introducing an affinity construct or a polynucleotide encoding same into a plant. "Introducing" is intended to mean presenting to a plant cell or plant the affinity construct or the polynucleotide encoding same in such a manner that the sequence gains access to the interior of a cell of the plant. The methods of the disclosure do not depend on a particular method for introducing a polynucleotide or polypeptide into a plant; what is relevant is that the polynucleotide or polypeptides gains access to the interior of at least one cell of the plant. Methods for introducing polynucleotide or polypeptides into plants are well known in the art including, but not limited to, stable transformation methods, transient transformation methods and virus-mediated methods.

"Stable transformation" is intended to mean that the nucleotide construct introduced into a plant integrates into the genome of the plant and is capable of being inherited by the progeny thereof. "Transient transformation" is intended to mean that a polynucleotide is introduced into the plant and does not integrate into the genome of the plant or a polypeptide is introduced into a plant. The term "plant" comprises whole plants, plant organs or plant parts (e.g., leaves, stems, roots, etc.), seeds, plant cells, propagules, embryos and progeny of the same. Plant cells can be differentiated or undifferentiated (e.g., callus, suspension culture cells, protoplasts, leaf cells, root cells, phloem cells, and pollen).

The present disclosure encompasses inserting one or more gene constructs comprising one or more nucleic acid sequences, which encode an affinity construct of the disclosure, into the genome of plants, in particular of agricultural crops, or expressing these gene constructs ex planta (e.g., in recombinant bacteria) and applying the purified protein to the plant or the insect pest (e.g., by spraying).

The present disclosure also encompasses inserting one or more gene constructs comprising one or more nucleic acid sequences, which encode a novel affinity construct of the disclosure and an insecticidal protein (wherein the insecticidal protein corresponds to the insecticidal protein (toxin), which the at least one affinity molecule B of the novel affinity construct is binding to, or is binding to, or is being directed to, or is being designed to bind to), into the genome of plants, in particular of agricultural crops, or expressing these gene constructs ex planta (e.g., in recombinant bacteria) and applying the purified proteins to the plant or the insect pest (e.g., by spraying).

When applying the affinity construct to/on the plant, an insect will take up and ingest the affinity construct of the disclosure upon feeding on the plant. In case of applying the novel affinity construct to/on the plant, also an insecticidal protein is applied to/on the plant (wherein the insecticidal protein corresponds to the insecticidal protein (toxin), which the at least one affinity molecule B of the novel affinity construct is binding to, or is being directed to, or is being designed to bind to), so that an insect will take up and ingest both the affinity construct and the insecticidal protein of the disclosure upon feeding on the plant.

When applying the affinity construct and the insecticidal protein directly on the insect pest or the habitat where the insect is living, then the insect pest will take up the affinity construct and the insecticidal protein upon contact. In various aspects of the present disclosure, the gene construct is a vector or a plasmid.

Furthermore, the expression of the affinity construct of the disclosure, and/or an insecticidal protein, in transgenic plants can be achieved using constitutively active promoters (e.g., the 35S promoter or Ubiquitin promoters), or using specific promoters that allow increasing expression of the affinity construct and/or the insecticidal protein in areas that are attacked by the target insects, or that can be induced via external cues (e.g., chemically-inducible promoters, heat-inducible promoters).

Transformation protocols as well as protocols for introducing nucleotide sequences into plants may vary depending on the type of plant or plant cell, i.e., monocot or dicot, targeted for transformation but are widely known in the art. Suitable methods of introducing nucleotide sequences into plant cells and subsequent insertion into the plant genome include, but are not limited to, microinjection, electroporation, *Agrobacterium*-mediated transformation, direct gene transfer and ballistic particle acceleration. Additional transformation procedures can be found, e.g., in Weissinger, et al. 1988, Ann. Rev. Genet. 22:421-477. In various embodiments, the nucleic acid sequences of the disclosure can be provided to a plant using a variety of transient transformation methods. Such transient transformation methods include, but are not limited to, the introduction of the affinity construct and/or insecticidal protein of the disclosure, or variants and fragments thereof, directly into the plant or the introduction of the affinity construct transcript and/or insecticidal protein transcript, into the plant. Such methods include, for example, microinjection or particle bombardment.

Alternatively, polynucleotides encoding affinity constructs and/or insecticidal proteins of the disclosure, or variants and fragments thereof, can be transiently transformed into the plant using techniques known in the art, including, but not limited to, viral vector systems. The affinity construct and/or insecticidal protein of the present disclosure can be introduced to the plant by means including, but not limited to, viral vectors, bacteria, injection, grafting, spraying and the like.

Plant transformation vectors may comprise of one or more DNA vectors needed for achieving plant transformation. For example, it is a common practice in the art to utilize plant transformation vectors that comprise more than one contiguous DNA segment. These vectors are often referred to in the art as "binary vectors". Binary vectors as well as vectors with helper plasmids are often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired).

In general, plant transformation methods involve transferring heterologous DNA into target plant cells (e.g., immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one identifies and proliferates the cells that are transformed with the plasmid vector. Alternatively, transgenic plants can be produced by the use of marker genes that do not rely on antibiotic or herbicide resistance but instead promote regeneration after transformation. Molecular and biochemical methods can then be used to confirm the presence of the integrated heterologous gene of interest into the genome of the transgenic plant. The transformation of plants can be based on the use of a standard *Agrobacterium*-mediated transformation protocol (e.g., as described in Hiei and Komari 1997, Plant Mol Biol 35(1-2): 205-18).

The present disclosure also encompasses marker-free plants that are based on strategies (site-specific recombination, homologous recombination, transposition and co-transformation) that have been developed to eliminate the marker gene efficiently from the nuclear or chloroplast genome soon after selection.

The present disclosure further encompasses marker-free transformation of plants and marker-free plants resulting therefrom, preferably marker-free transformation of monocotyledons and marker-free monocotyledons resulting therefrom. The improvement of the transformation efficiency enables the production of transformed plants with without the need to introduce any selection marker, as discussed in EP2274973A1. The efficiency of transformation can be improved to increase the percentage of transformed cells among non-transformed cells, and this state can be maintained until regeneration of whole plants. A marker-free transformation of plants may be performed according to an *Agrobacterium*-mediated method comprising the steps (a) culturing an *Agrobacterium*-inoculated plant material with a co-culture medium that provides for an enhanced transformation efficiency; and (b) regenerating the tissue obtained in step (a) with a regeneration medium to thereby regenerate a transgenic plant, wherein the method does not contain a marker gene-based selection step.

The cells that have been transformed may be grown or regenerated into plants in accordance with conventional methods. These plants may then be grown, and either pollinated with the same transformed strain or different strains and the resulting hybrid having constitutive or inducible expression of the desired phenotypic characteristic identified. Two or more generations may be grown to ensure that expression of the desired phenotypic characteristic is stably maintained and inherited.

The nucleotide sequences of the disclosure may be provided to the plant by contacting the plant with a virus or viral nucleic acids. Generally, such methods involve incorporating the nucleotide construct of interest within a viral DNA or RNA molecule. Methods for providing plants with nucleotide constructs and producing the encoded proteins in the plants, which involve viral DNA or RNA molecules, are known in the art.

The disclosure further relates to plant-propagating material of a transformed plant of the disclosure including, but not limited to, seeds, tubers, corms, bulbs, leaves, and cuttings of roots and shoots.

The disclosure may be used for transformation of any plant species, including, but not limited to, monocots and dicots. Examples of plants of interest include, but are not limited to, grain plants that provide seeds of interest, e.g., corn (*Zea mays*).

The disclosure encompasses a plant or progeny thereof, comprising one or more nucleic acid molecules encoding an affinity construct of the disclosure and/or an insecticidal protein of the disclosure. The disclosure also encompasses a plant or progeny thereof or plant parts, stably transformed with one or more nucleic acid molecules encoding an affinity construct of the disclosure and/or an insecticidal protein. The disclosure encompasses seed or grain of the plant or progeny thereof of the disclosure, wherein the seed or grain comprises one or more nucleic acid molecules encoding an affinity construct of the disclosure and/or an insecticidal protein. The disclosure also encompasses a biological sample from a tissue or seed of a plant or progeny thereof of the disclosure. In preferred embodiments, the plant is a monocotyledonous plant. In various other preferred embodiments, the plant is a dicotyledonous plant. In various embodiments, the plant is any of barley, corn, oat, rice, rye, sorghum, turf grass, sugarcane, wheat, alfalfa, banana, broccoli, bean, cabbage, canola, carrot, cassava, cauliflower, celery, citrus, cotton, a cucurbit, *eucalyptus*, flax, garlic, grape, onion, lettuce, pea, peanut, pepper, potato, poplar, pine, sunflower, safflower, soybean, strawberry, sugar beet, sweet potato, tobacco, tomato ornamental, shrub, nut, chickpea, pigeon pea, millets, hops, and pasture grasses. More specifically, a plant according to the present disclosure may be any one of barley (*Hordeum vulgare*), sorghum (*Sorghum bicolor*), rye (*Secale cereale*), Triticale, sugar cane (*Saccharum officinarium*), maize (*Zea mays*), foxtail millet (*Setaria italic*), rice (*Oryza sativa*), *Oryza minuta*, *Oryza australiensis*, *Oryza alta*, wheat (*Triticum aestivum*), *Triticum durum*, *Hordeum bulbosum*, purple false brome (*Brachypodium distachyon*), sea barley (*Hordeum marinum*), goat grass (*Aegilops tauschii*), apple (*Malus domestica*), strawberry, sugar beet (*Beta vulgaris*), sunflower (*Helianthus annuus*), Australian carrot (*Daucus glochidiatus*), American wild carrot (*Daucus pusillus*), *Daucus muricatus*, carrot (*Daucus carota*), eucalyptus (*Eucalyptus grandis*), *Erythranthe guttata*, *Genlisea aurea*, woodland tobacco (*Nicotiana sylvestris*), tobacco (*Nicotiana tabacum*), *Nicotiana tomentosiformis*, tomato (*Solanum lycopersicum*), potato (*Solanum tuberosum*), coffee (*Coffea canephora*), grape vine (*Vitis vinifera*), cucumber (*Cucumis sativus*), mulberry (*Morus notabilis*), thale cress (*Arabidopsis thaliana*), *Arabidopsis lyrata*, sand rock-cress (*Arabidopsis arenosa*), *Crucihimalaya himalaica*, *Crucihimalaya wallichii*, wavy bittercress (*Cardamine flexuosa*), peppergrass (*Lepidium virginicum*), sheperd's-purse (*Capsella bursa-pastoris*), *Olmarabidopsis pumila*, hairy rockcress (*Arabis hirsuta*), rape (*Brassica napus*), broccoli (*Brassica oleracea*), *Brassica rapa*, *Brassica juncacea*, black mustard (*Brassica nigra*), radish (*Raphanus sativus*), *Eruca vesicaria sativa*, orange (*Citrus sinensis*), *Jatropha curcas*, cotton (*Gossipium* sp.), soybean (*Glycine max*), and black cottonwood (*Populus trichocarpa*). Preferably, the plant is any one of barley (*Hordeum vulgare*), rye (*Secale cereale*), Triticale, maize (*Zea mays*), rice (*Oryza sativa*), wheat (*Triticum aestivum*), and soybean (*Glycine max*).

In various embodiments, the plant comprises one or more additional transgenic or non-transgenic traits. In various embodiments, the one or more additional transgenic or non-transgenic traits is any of insect resistance, herbicide resistance, fungal resistance, virus resistance or stress tolerance, disease resistance, male sterility, stalk strength, increased yield, modified starches, improved oil profile, balanced amino acids, high lysine or methionine, increased digestibility, improved fiber quality, drought resistance or tolerance, cold resistance or tolerance, salt resistance or tolerance, and increased yield under stress. In various other embodiments, the one or more additional transgenic or non-transgenic traits is any of moisture at harvest, increased sugar content, flowering control, increased biomass, altered secondary plant metabolites, and altered plant-plant interaction abilities (increased crop densities). Non-transgenic traits can be "stacked" in the plant of the present disclosure comprising the insecticidal fusion protein of the disclosure by breeding (so-called breeding stacks). Transgenic traits can be "stacked" in the plant of the present disclosure comprising the insecticidal fusion protein of the disclosure either by molecular means (transformation by more than one genetic constructs or by subsequent transformation (so-called molecular stacks) or breeding (so-called breeding stacks). Both breeding and molecular stacking are described below.

The disclosure also encompasses a plant comprising an expression cassette of the present disclosure. The disclosure also encompasses a plant cell or a plant part or a plant seed comprising an expression cassette of the present disclosure. The disclosure further encompasses a microbial cell comprising an expression cassette of the present disclosure.

The present disclosure encompasses a plant, plant part or plant seed capable of expressing an affinity construct of the disclosure and/or an insecticidal protein. Accordingly, the disclosure also encompasses a method for expressing in a plant, plant part or plant seed an affinity construct of the disclosure and/or an insecticidal protein, comprising the steps of: (a) inserting into a plant cell a nucleic acid sequence comprising in 5' to 3' direction an operably linked recombinant, double-stranded DNA molecule, wherein the recombinant double-stranded DNA molecule comprises (i) a promoter that functions in the plant cell; (ii) one or more nucleic acid molecules encoding an affinity construct of the disclosure and/or an insecticidal protein; and (iii) a 3' non-translated polynucleotide that functions in the cells of the plant to cause termination of transcription; (b) obtaining a transformed plant cell comprising the nucleic acid sequence of step (a); and (c) generating from the transformed plant cell a plant, plant part or plant seed capable of expressing an affinity construct of the disclosure and/or an insecticidal protein. In other embodiments, methods are encompassed wherein in a plant, plant part or plant seed more than one affinity construct of the disclosure and/or more than one insecticidal protein is expressed. The disclosure encompasses a plant, plant part or plant seed produced by such methods. Such a plant, plant part or plant seed may comprise one or more additional transgenic or non-transgenic trait. In various embodiments, the one or more additional transgenic or non-transgenic trait is any one of the one or more additional transgenic or non-transgenic traits mentioned above.

Transformation of Microbes

The novel affinity construct of the present disclosure can be easily co-expressed with an insecticidal protein in transgenic microbial cells, or can be applied, in combination with an insecticidal protein, as an insecticidal spray/solution to a plant, seed or insect, in particular in agricultural crops or cells thereof, wherein the insecticidal protein (toxin) corresponds to the insecticidal protein (toxin) against which the at least one affinity molecule B of the novel affinity construct is capable of binding to, or is binding to, or is being directed to, or is being designed to bind to. Furthermore, the affinity molecules, single domain antibodies can be readily expressed by transformed plants or microbial cells.

The present disclosure provides a microbial cell comprising (i) one or more nucleic acid sequences encoding a novel affinity construct of the present disclosure and/or an insecticidal protein, wherein the insecticidal protein corresponds to the insecticidal protein which the at least one affinity molecule B of the novel affinity construct is capable of binding to, or is binding to, or is being directed to, or is being designed to bind to, or (i) one or more vectors comprising one or more nucleic acid sequences encoding a novel affinity construct of the present disclosure and/or an insecticidal protein, wherein the insecticidal protein corresponds to the insecticidal protein which the at least one affinity molecule B of the novel affinity construct is capable of binding to, or is binding to, or is being directed to, or is being designed to bind to.

The present disclosure also provides a microbial cell comprising a nucleic acid molecule encoding an insecticidal affinity construct of the present disclosure.

In other embodiments, microbial cells are encompassed wherein in these microbial cells more than one affinity construct of the disclosure and/or more than one insecticidal protein is expressed.

The methods of the present disclosure involve introducing a novel affinity construct of the disclosure or a polynucleotide encoding same, and/or an insecticidal protein or a polynucleotide encoding same, into a microbial cell. "Introducing" is intended to mean presenting to a microbial cell the novel affinity construct of the disclosure or a polynucleotide encoding same, and/or an insecticidal protein or a polynucleotide encoding same in such a manner that the sequence gains access to the interior of a microbial cell. The methods of the disclosure do not depend on a particular method for introducing a polynucleotide or polypeptide into a microbial cell; what is relevant is that the polynucleotide or polypeptides gains access to the interior of at least one microbial cell. Methods for introducing polynucleotide or polypeptides into microbial cells are well known in the art including, but not limited to, stable transformation methods, transient transformation methods and virus-mediated methods. The terms "stable transformation", "transient transformation" methods and "virus-mediated transformation" have essentially the same meaning as outline above.

The present disclosure also encompasses inserting one or more gene constructs comprising one or more nucleic acid sequences, which encode a novel affinity construct of the disclosure and/or an insecticidal protein (wherein the insecticidal protein corresponds to the insecticidal protein which the at least one affinity molecule B of the novel affinity construct is capable of binding to, or is binding to, or is being directed to, or is being designed to bind to), into the genome of microbial cells, or expressing these gene constructs ex planta in the recombinant microbial cell and applying the purified proteins or the microbial cells to the plant or the insect pest (e.g., by spraying).

When applying the affinity construct in combination with an insecticidal protein corresponding to the insecticidal protein, which the at least one affinity molecule B of the novel affinity construct is capable of binding to, or is binding to, or is being directed to, or is being designed to bind to or when applying the recombinant microbial cells to/on the plant, an insect will take up and ingest the affinity construct of the disclosure or the recombinant microbial cell upon feeding on the plant. When applying the affinity construct and the corresponding insecticidal protein (toxin) or the recombinant microbial cell directly on the insect pest or the habitat where the insect is living, then the insect pest will take up the affinity construct and the insecticidal protein (toxin) or the recombinant microbial cell of the disclosure upon contact. In various aspects of the present disclosure, the gene construct is a vector or a plasmid.

Furthermore, the expression of the affinity construct of the disclosure and/or of the insecticidal protein (toxin) in transgenic microbial cells can be achieved using constitutively active promoters or using specific promoters that can be induced via external cues (e.g., chemically-inducible promoters, heat-inducible promoters).

Transformation protocols as well as protocols for introducing nucleotide sequences into microbial cells may vary depending on the type of microbial cell, targeted for transformation but are widely known in the art. In various embodiments, the nucleic acid sequences of the disclosure can be provided to a microbial cell using a variety of transient transformation methods. Such methods are known in the art.

The disclosure encompasses a recombinant microbial cell or progeny thereof, comprising a nucleic acid molecule encoding an affinity construct of the disclosure and/or an insecticidal protein, wherein the insecticidal protein corresponds to the insecticidal protein which the at least one affinity molecule B of the novel affinity construct is binding to or directed to. The disclosure also encompasses recombinant microbial cells or progeny thereof stably transformed with a nucleic acid molecule encoding an affinity construct of the disclosure and/or an insecticidal protein, wherein the insecticidal protein corresponds to the insecticidal protein which the at least one affinity molecule B of the novel affinity construct is capable of binding to, or is binding to, or is being directed to, or is being designed to bind to.

The disclosure also encompasses a recombinant microbial cell comprising an expression cassette of the present disclosure.

The present disclosure encompasses a recombinant microbial cell capable of expressing an affinity construct of the disclosure and/or an insecticidal protein, wherein the insecticidal protein corresponds to the insecticidal protein which the at least one affinity molecule B of the novel affinity construct is binding to or directed to. Accordingly, the disclosure also encompasses a method for expressing in a microbial cell an affinity construct of the disclosure and/or an insecticidal protein, wherein the insecticidal protein corresponds to the insecticidal protein which the at least one affinity molecule B of the novel affinity construct is capable of binding to, or is binding to, or is being directed to, or is being designed to bind to, comprising the steps of: (a) inserting into a microbial cell a nucleic acid sequence comprising in 5' to 3' direction an operably linked recombinant, double-stranded DNA molecule, wherein the recombinant double-stranded DNA molecule comprises (i) a promoter that functions in the microbial cell; (ii) a nucleic acid molecule encoding an affinity construct of the disclosure and/or an insecticidal protein, wherein the insecticidal protein corresponds to the insecticidal protein which the at least one affinity molecule B of the novel affinity construct is capable of binding to, or is binding to, or is being directed to, or is being designed to bind to; and (iii) a 3' non-translated polynucleotide that functions in the microbial cell to cause termination of transcription; and (b) obtaining a transformed microbial cell comprising the nucleic acid sequence of step (a) and capable of expressing an affinity construct of the disclosure and/or an insecticidal protein, wherein the insecticidal protein corresponds to the insecticidal protein which the at least one affinity molecule B of the novel affinity construct is capable of binding to, or is binding to, or is being directed to, or is being designed to bind to. The disclosure encompasses a microbial cell produced by such a method.

Evaluation of Plant Transformation

Following introduction of heterologous foreign DNA into plant cells, the transformation or integration of heterologous gene in the plant genome is confirmed by various methods such as analysis of nucleic acids, proteins and metabolites associated with the integrated gene. For example, plant transformation may be confirmed by Southern blot analysis of genomic DNA. PCR analysis is also a rapid method to screen transformed cells, tissue or shoots for the presence of incorporated gene at the earlier stage before transplanting into the soil (Sambrook and Russell, (2001) Molecular Cloning: A Laboratory Manual. Cold Spring Harbor Laboratory Press, Cold Spring Harbor, NY).

The above-described methods for confirming transformation or integration of the heterologous gene(s) in the plant genome can also be applied to microbial cells. The person skilled in the art is aware of respective methods that can be applied to microbial cells.

Stacking of Traits in Transgenic Plant

The present disclosure also encompasses the stacking of multiple affinity constructs of the present disclosure. The stacked affinity constructs of the present disclosure are either directed against the same insect-specific structures, preferably receptors, in or on the same insect pest, are directed against different insect-specific structures, preferably receptors, in or on the same insect pest, or are directed against different insect-specific structures, preferably receptors, in or on different insect pests. The present disclosure also encompasses the stacking of multiple affinity constructs of the present disclosure, wherein the stacked affinity constructs of the present disclosure are either directed against the same insecticidal protein (toxin) or are directed against different insecticidal proteins (toxins). If the stacked insecticidal proteins are directed against the same pest, then there are the following options: (1) the one or more affinity molecule A is the same (stacking would then lead to higher concentrations of the same insecticidal protein), (2) the one or more affinity molecule A is the same but the insecticidal proteins are different while still attacking the same pest (to use, e.g., an abundant receptor to address the pest with different insecticidal mode of actions), (3) the one or more affinity molecule A is different but the insecticidal proteins are the same (to address different receptors with one (insecticidal) mode of action). If the stacked insecticidal proteins are directed against different pests, then there are the following options: (1) the one or more affinity molecule A and insecticidal proteins are the same (stacking would lead to higher concentrations of the same insecticidal protein), (2) the one or more affinity molecule A are the same but the insecticidal proteins are different in order to attack different insect pests (to use, e.g., an abundant receptor to address the pest with different (insecticidal) mode of actions), (3) the one or more affinity molecule A is different but the insecticidal proteins are the same (to address different receptors with one working insecticidal mode of action that affects different insects). Such approaches are also useful to address the probability of resistance to insecticidal proteins.

Transgenic plants may also comprise a stack (or pyramid) of one or more polynucleotides encoding an affinity construct disclosed herein with one or more additional polynucleotides encoding different traits resulting in the production or suppression of multiple polypeptide sequences. Transgenic plants comprising stacks of polynucleotide sequences can be obtained by either traditional breeding methods or through genetic engineering methods or both. These methods include, but are not limited to, crossing individual lines each comprising one or more polynucleotides of interest, transforming a transgenic plant comprising one or more transgenes disclosed herein with a subsequent transgene, and co-transformation of transgenes into a single plant cell. As used herein, the term "stacked" includes having two or more traits present in the same plant (e.g., both traits are incorporated into the nuclear genome, or one trait is incorporated into the nuclear genome and one trait is incorporated into the genome of a plastid, or both traits are incorporated into the genome of a plastid). In one non-limiting example, "stacked traits" comprise a molecular stack where the sequences are physically adjacent to each other. A trait, as used herein, refers to the phenotype derived from a particular sequence or groups of sequences. Co-transformation of genes can be carried out using single transformation vectors comprising multiple genes or genes carried separately on multiple vectors. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. Expression of the sequences can be driven by the same promoter or by different promoters. It is further recognized that polynucleotide sequences can be stacked at a desired genomic location using a site-specific recombination system.

In various embodiments the polynucleotides encoding an affinity construct of the disclosure, alone or stacked with one or more additional insect resistance traits can be stacked with one or more additional transgenic or non-transgenic input traits (e.g., herbicide resistance, fungal resistance, virus resistance or stress tolerance, disease resistance, male sterility, stalk strength, and the like) or transgenic or non-transgenic output traits (e.g., increased yield, modified starches, improved oil profile, balanced amino acids, high lysine or methionine, increased digestibility, improved fiber quality, drought resistance, and the like). Thus, the polynucleotide embodiments can be used to provide a complete agronomic package of improved crop quality with the ability to flexibly and cost effectively control any number of agronomic (insect) pests.

In some embodiments the affinity constructs of the disclosure are useful as part of an insect resistance management strategy in combination (i.e., pyramided or stacked) with other pesticidal or insecticidal proteins or topical application of one or more insecticide to the plant. Provided are methods of controlling Orthopteran, Thysanopteran, Hymenopteran, Dipteran, Lepidopteran, Coleopteran and/or Hemipteran insect infestation(s) in a transgenic plant that promote insect resistance management, comprising expressing in the plant at least two different insecticidal proteins having different modes of action, one of them being part of the insecticidal fusion protein of the disclosure.

Transgenes useful for stacking include but are not limited to: (i) transgenes that confer resistance to insects or disease, (ii) transgenes that confer resistance to a herbicide, (iii) transgenes that confer or contribute to an altered grain characteristic, (iv) genes that control male-sterility, (v) genes that create a site for site specific DNA integration, (vi) genes that affect abiotic stress resistance, (vii) genes that confer increased yield; and (viii) genes that confer plant digestibility.

Use in Insect Pest Control

General methods for employing insecticidal proteins or nucleic acid sequences encoding same in pesticide control or in genetic engineering of organisms that are used as pesticidal agents are known in the art.

Microorganism hosts that are known to occupy the "phytosphere" (phylloplane, phyllosphere, rhizosphere, and/or rhizoplana) of one or more crops of interest may be selected. These microorganisms provide for stable maintenance and expression of the gene expressing an affinity construct of the disclosure, and desirably, provide for improved protection of the affinity construct from environmental degradation and inactivation.

Nucleic acid sequences encoding a novel affinity construct of the disclosure and an insecticidal protein (wherein the insecticidal protein corresponds to the insecticidal protein which the at least one affinity molecule B of the novel affinity construct is capable of binding to, or is binding to, or is being directed to, or is being designed to bind to) can be introduced into a wide variety of microbial hosts. Expression of nucleic acid sequences encoding the novel affinity construct and the insecticidal protein results, directly or indirectly, in the intracellular production and maintenance of the affinity construct and the insecticidal protein. With suitable hosts, e.g., *Pseudomonas*, the microbes can be applied to a place where they will proliferate and be ingested by the insects. The result is a control of the insect pest.

Suitable microorganisms include bacteria, algae, and fungi. Of particular interest are phytosphere bacterial species such as, e.g., *Pseudomonas fluorescens*, Agrobacteria, *Rhizobia* etc. Of particular interest are also root-colonizing bacteria. Nucleic acid sequences encoding affinity constructs of the disclosure and/or insecticidal proteins can be introduced, for example, into the root-colonizing *Bacillus* by means of electro transformation. Furthermore, expression systems can be designed so that affinity constructs of the disclosure and/or insecticidal proteins are secreted outside the cytoplasm of gram-negative bacteria, such as, e.g., *E. coli*.

The novel affinity constructs of the disclosure can be fermented in a bacterial host and the resulting bacteria processed, formulated together with an insecticidal protein, and then used as a microbial spray in the same manner that *Bacillus thuringiensis* strains have been used as insecticidal sprays. Any suitable microorganism can be used for this purpose. Methods of transforming microbial hosts, fermenting same and of collecting, isolating or extracting recombinant proteins from the culture medium or the cultured microbial hosts are well known in the art and also addressed elsewhere herein.

In various embodiments of the methods of controlling insect infestation in a transgenic plant and promoting insect resistance management, the composition of the present disclosure comprising the novel affinity construct and an insecticidal protein (toxin) comprises one or more insecticidal protein(s) insecticidal to insects in the Orthopteran, Thysanopteran, Hemipteran, Hymenopteran, Dipteran, Lepidopteran and/or Coleopteran order of insects. Also provided are means for effective insect resistance management of transgenic plants, comprising co-expressing at high levels in the plants two or more insecticidal proteins toxic to insects, in particular toxic to Orthopteran, Thysanopteran, Hemipteran, Hymenopteran, Dipteran, Lepidopteran and/or Coleopteran insects, but each insecticidal protein exhibiting a different mode of effectuating its inhibiting growth or killing activity.

The disclosure encompasses a method for controlling an insect pest population, comprising contacting the insect pest population with an insecticidally-effective amount of a composition comprising a novel affinity construct of the disclosure and an insecticidal protein, wherein the insecticidal protein corresponds to the insecticidal protein which the at least one affinity molecule B of the affinity construct of the disclosure is capable of binding to, or is binding to, or is being directed to, or is being designed to bind to.

The disclosure further encompasses a method of inhibiting growth or killing an insect pest, comprising contacting the insect pest with an insecticidally-effective amount of a composition comprising a novel affinity construct of the disclosure and an insecticidal protein, wherein the insecticidal protein corresponds to the insecticidal protein which the at least one affinity molecule B of the affinity construct of the disclosure is capable of binding to, or is binding to, or is being directed to, or is being designed to bind to.

The disclosure still further encompasses a method for controlling an insect pest population resistant to a pesticidal protein, comprising contacting the resistant insect pest population with an insecticidally-effective amount of a composition comprising an affinity construct of the disclosure and an insecticidal protein, wherein the insecticidal protein corresponds to the insecticidal protein which the at least one affinity molecule B of the affinity construct of the disclosure is capable of binding to, or is binding to, or is being directed to, or is being designed to bind to is (capable of) binding to or is directed to.

The disclosure further encompasses a method for protecting a plant from an insect pest, comprising expressing in the plant or cell thereof an affinity construct of the disclosure and an insecticidal protein, wherein the insecticidal protein corresponds to the insecticidal protein which the at least one affinity molecule B of the affinity construct of the disclosure is capable of binding to, or is binding to, or is being directed to, or is being designed to bind to.

The disclosure still further encompasses a method for controlling an insect infestation in a transgenic plant and/or providing insect resistance management, comprising expressing in the plant (i) an affinity construct of the disclosure, (ii) a first insecticidal protein, wherein the first insecticidal protein corresponds to the insecticidal protein which the at least one affinity molecule B of the affinity construct of the disclosure is capable of binding to, or is binding to, or is being directed to, or is being designed to bind to, and (iii) at least one additional insecticidal protein, wherein the at least one additional insecticidal protein and the first insecticidal protein have different modes of action. In various embodiments, the insect infestation is an Orthopteran, Thysanopteran, Hemipteran, Hymenopteran, Dipteran, Lepidopteran and/or Coleopteran insect infestation.

The present disclosure provides a method for protecting a plant against an insect pest, comprising the steps: (i) transforming a plant with one or more nucleic acid sequences encoding a novel affinity construct of the present disclosure and an insecticidal protein, wherein the insecticidal protein corresponds to the insecticidal protein, which the at least one affinity molecule B of the affinity construct of the disclosure is capable of binding to, or is binding to, or is being directed to, or is being designed to bind to; and (ii) expressing the affinity construct and the insecticidal protein in the plant. The plant may be a monocotyledonous or a dicotyledonous plant.

The present disclosure further provides a method for increasing the binding efficiency of an insecticidal protein to its receptor, comprising the steps: (i) transforming a plant with one or more nucleic acid sequences encoding a novel affinity construct of the present disclosure and an insecticidal protein, wherein the insecticidal protein corresponds to the insecticidal protein, which the at least one affinity molecule B of the affinity construct of the disclosure is capable of binding to, or is binding to, or is being directed to, or is being designed to bind to; and (ii) expressing the affinity construct and the insecticidal protein in the plant. The plant may be a monocotyledonous or a dicotyledonous plant.

The present disclosure further provides a method for preparing a plant exhibiting resistance against an insect pest, comprising the steps: (i) transforming a plant with one or more nucleic acid sequences encoding a novel affinity construct of the present disclosure and an insecticidal protein, wherein the insecticidal protein corresponds to the insecticidal protein, which the at least one affinity molecule B of the affinity construct of the disclosure is capable of binding to, or is binding to, or is being directed to, or is being designed to bind to; and (ii) expressing the affinity construct and the insecticidal protein in the plant. The plant may be a monocotyledonous or a dicotyledonous plant.

Still further, the present disclosure provides a method for protecting a plant against an insect pest, comprising applying to said plant an insecticidal composition comprising a novel affinity construct of the disclosure and an insecticidal protein, wherein the insecticidal protein corresponds to the insecticidal protein, which the at least one affinity molecule B of the affinity construct of the disclosure is capable of binding to, or is binding to, or is being directed to, or is being designed to bind to. The plant may be a monocotyledonous or a dicotyledonous plant.

Still further, the present disclosure provides the use of (i) an affinity construct of the present disclosure in combination with an insecticidal protein, wherein the insecticidal protein corresponds to the insecticidal protein, which the at least one affinity molecule B of the novel affinity construct is capable of binding to, or is binding to, or is being directed to, or is being designed to bind to, or (ii) one or more nucleic acid sequences encoding a novel affinity construct of the present disclosure and an insecticidal protein, wherein the insecticidal protein corresponds to the insecticidal protein, which the at least one affinity molecule B of the novel affinity construct is capable of binding to, or is binding to, or is being directed to, or is being designed to bind to, or (iii) a vector comprising the said one or more nucleic acid sequences, or (iv) a composition comprising a novel of the present disclosure and an insecticidal protein, wherein the insecticidal protein corresponds to the insecticidal protein, which the at least one affinity molecule B of the novel affinity construct is capable of binding to, or is binding to, or is being directed to, or is being designed to bind to, for protecting a plant against an insect pest. The plant may be a monocotyledonous or a dicotyledonous plant.

In any of the above methods and uses, the plant may preferably be modified by using known genome editing tools for delivery of constructs, either through *Agrobacterium*-mediated transfer, electroporation, micro-projectile bombardment, virus-mediated delivery, or sexual cross. The techniques of *Agrobacterium*-mediated transfer, electroporation, micro-projectile bombardment, virus-mediated delivery and sexual cross are well-known to the skilled person and methods are described in the literature. The same holds for genome editing tools like, e.g., TAL Effector Nucleases (TALEN), CRISPR/Cas9, and CRISPR/cpf1, etc.

Bioassay for Insecticidal Toxins

The final formulation of a composition comprising the novel affinity construct and an insecticidal protein (toxin) of the disclosure can be bioassayed against an accepted international standard using a specific test insect (see, for example, e.g., Baum et al. 2004, (Appl. Environ. Microb., 4889-4898). The standardization allows comparison of different formulations in the laboratory.

Methods for measuring insecticidal activity are well known in the art. See, for example, Dhadialla & Gill 2014, Advances in Insect Physiology, Edition 47, "Insect Midgut and Insecticidal Proteins" Academic Press. Generally, the protein is mixed and used in feeding assays. Such assays can include contacting plants with one or more pests and determining the plant's ability to survive and/or cause the death of the pests.

Methods for Increasing Plant Yield

Methods for increasing plant yield are provided. The methods comprise providing a plant or plant cell expressing one or more polynucleotides encoding a novel affinity construct of the disclosure and/or an insecticidal protein, wherein the insecticidal protein corresponds to the insecticidal protein, which the at least one affinity molecule B of the novel affinity construct is capable of binding to, or is binding to, or is being directed to, or is being designed to bind to, and growing the plant or a seed thereof in a field infested with an insect pest against which the affinity construct in combination with the insecticidal protein has insecticidal activity. In various embodiments, the the affinity construct in combination with the insecticidal protein has insecticidal activity against an Isopteran, Blattodean, Orthopteran, Phthirapteran, Thysanopteran, Hemipteran, Hymenopteran, Siphonapteran, Dipteran, Coleopteran and/or Lepidopteran or nematode pest, and the field is infested with an Isopteran, Blattodean, Orthopteran, Phthirapteran, Thysanopteran, Hemipteran, Hymenopteran, Siphonapteran, Dipteran, Coleopteran, Lepidopteran and/or nematode pest, respectively. As defined herein, the "yield" of the plant refers to the quality and/or quantity of biomass produced by the plant. By "biomass" is intended any measured plant product, including, but not limited to, plant organs that are specifically harvested, e.g., leaves, grain, roots, seeds, stalks, flowers, fruits. An increase in biomass production is any improvement in the yield of the measured plant product. Increasing plant yield has several commercial applications. For example, increasing plant leaf biomass may increase the yield of leafy vegetables for human or animal consumption. Additionally, increasing leaf biomass can be used to increase production of plant-derived pharmaceutical or industrial products, which in case of maize includes, without being limited thereto, food/feedstock, biogas and biofuel. An increase in yield can comprise any statistically significant increase including, but not limited to, at least a 1% increase, at least a 3% increase, at least a 5% increase, at least a 10% increase, at least a 20% increase, at least a 30%, at least a 50%, at least a 70%, at least a 100% or a greater increase in yield as compared to the yield that is obtained from a plant not expressing the insecticidal sequences encoding a novel affinity construct of the disclosure and/or an insecticidal protein (wherein the insecticidal protein corresponds to the insecticidal protein, which the at least one affinity molecule B of the novel affinity construct is capable of binding to, or is binding to, or is being directed to, or is being designed to bind to. In specific methods, plant yield is increased as a result of improved pest resistance of a plant expressing a novel affinity construct of the disclosure and/or an insecticidal protein (wherein the insecticidal protein corresponds to the insecticidal protein, which the at least one affinity molecule B of the novel affinity construct is capable of binding to, or is binding to, or is being directed to, or is being designed to bind to. Expression of the novel affinity construct of the disclosure and/or an insecticidal protein (wherein the insecticidal protein corresponds to the insecticidal protein, which the at least one affinity molecule B of the novel affinity construct is capable of binding to, or is binding to, or is being directed to, or is being designed to bind to results in a reduced ability of an insect pest to infest or feed on the plant, thus improving plant yield.

Compositions

The present disclosure encompasses an (insecticidal) composition comprising an affinity construct of the disclosure which in turn comprises at least one affinity molecule A and at least one affinity molecule B. Preferably, the composition is formulated as a spray.

The present disclosure further encompasses an insecticidal composition comprising an insecticidally-effective amount of the combination of an affinity construct of the disclosure and an insecticidal protein, wherein the insecticidal protein corresponds to the insecticidal protein which the at least one affinity molecule B of the affinity construct of the disclosure is capable of binding to, or is binding to, or is being directed to, or is being designed to bind to.

To address the resistance of insect pests to insecticidal proteins caused by mutations in the receptor proteins the composition may further comprise wild type receptor protein(s) from the gut of the target insect at least one of the at least two affinity molecules A present in the composition is designed to recognize. "Wild type" with regards to the receptor protein means that the receptor protein is in its susceptible form, i.e., without the one or more mutations that in resistant insect pests confer resistance against certain insecticidal proteins. After uptake by the insect pest these wild type receptor proteins insert themselves into the insect gut either in addition to the mutated receptor proteins or by replacing them. Either way, the presence of wild type receptor proteins allows the insecticidal protein to bind, to insert into the membrane, to form a pore and eventually to kill the insect.

The composition may furthermore comprise an agriculturally suitable or agriculturally acceptable component. Examples of such components include water, plant oils, essential oils, emulsifiers, thickeners, suspension agents, dispersion agents, anti-freeze agents, adjuvants, carriers or excipients, and wetting agents. Suitable plant oils for inclusion in the compositions of the present disclosure include canola oil (oilseed rape oil), soybean oil, cottonseed, castor oil, linseed oil and palm oil. Suitable emulsifiers for use in the compositions of the present disclosure include any known agriculturally acceptable emulsifier. In particular, the emulsifier may comprise a surfactant such as: alkylaryl sulphonates, ethoxylated alcohols, polyalkoxylated butyl ethers, calcium alkyl benzene sulphonates, polyalkylene glycol ethers and butyl polyalkylene oxide block copolymers as are known in the art. Nonyl phenol emulsifiers such as Triton N57™ are particular examples of emulsifiers, which may be used in the compositions of the disclosure, as are polyoxyethylene sorbitan esters such as polyoxyethylene sorbitan monolaurate (sold by ICI under the trade name "Tween™"). In some instances, natural organic emulsifiers may be preferred, particularly for organic farming applications. Coconut oils such as coconut diethanolamide is an example of such an compound. Palm oil products such as lauryl stearate may also be used. Examples of thickeners which may be present in the compositions of the present disclosure comprise gums, for example xanthan gum, or lignosulphonate complexes, as are known in the art. Suitable suspension agents that may be included in the compositions of the present disclosure include hydrophilic colloids (such as polysaccharides, polyvinylpyrrolidone or sodium carboxymethylcellulose) and swelling clays (such as bentonite or attapulgite). Suitable wetting agents for use in the compositions of the present disclosure include surfactants of the cationic, anionic, amphoteric or non-ionic type, as is known in the art. The carrier may be any one of a powder, a dust, pellets, granules, spray, emulsion, colloid, and solution. Preferably, the carrier is a spray. Adjuvants that may be used in compositions of the disclosure include antifoam agents, compatibilizing agents, sequestering agents, neutralizing agents and buffers, corrosion inhibitors, spreading agents, sticking agents, dispersing agents, thickening agents, freeze point depressants, antimicrobial agents, and the like. In various embodiments, the composition further comprises one or more herbicides, insecticides, or fungicides.

The disclosure encompasses the application of an affinity construct of the disclosure in combination with an insecticidal protein, wherein the insecticidal protein corresponds to the insecticidal protein, which the at least one affinity molecule B of the affinity construct of the disclosure is capable of binding to, or binding to, or being directed to, or being designed to bind to, in the form of compositions. The disclosure also encompasses the application of the insecticidal proteins of the disclosure in the form of compositions. Such compositions can be applied to the crop area or plant to be treated simultaneously or in succession with other compounds, such as, e.g., adjuvants, cryoprotectants, surfactants, detergents, pesticidal soaps, selective herbicides, etc. Such compositions may also be time-release or biodegradable carrier formulations that permit long-term dosing of a target area following a single application of the formulation.

Methods of applying an agrochemical composition that contains at least one affinity construct of the disclosure include application to plant parts above the ground, as well as seed coating and soil application. In some embodiments, the at least one affinity construct of the disclosure is applied in combination with one or more insecticidal protein, wherein the one or more insecticidal protein corresponds to the insecticidal protein, which the at least one affinity molecule B of the affinity construct of the disclosure is capable of binding to, or binding to, or being directed to, or being designed to bind to. The number of applications and the rate of application depend on the intensity of infestation by the corresponding insecticidal pest. The composition can be used as insecticidal spray, solution or coating or as further routine application, which are familiar to the skilled person for application of compounds to a plant, plant part (tissue) or plant seed. In a further application, the composition in accordance with the invention is used as a pre-treatment for seed. In this regard, the composition is initially mixed with a carrier substrate and applied to the seeds.

The insecticidal composition may be formulated as a powder, dust, pellet, granule, spray, emulsion, colloid, solution or such like, and may be prepared, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, binders or fertilizers. Likewise, the formulations may be prepared into edible "baits" or fashioned into pest "traps" to permit feeding or ingestion of the insecticidal formulation by a target pest.

The insecticidal pest ingests or is contacted with, an insecticidally-effective amount of the insecticidal formulation of the disclosure. By "insecticidally-effective amount" is intended an amount of the insecticidal formulation comprising an affinity construct in combination with an insecticidal protein, which the at least one affinity molecule B of the affinity construct of the disclosure is capable of binding to, or is binding to, or is being directed to, or is being designed to bind to, that is able to kill at least one insecticidal pest or to noticeably reduce pest growth (i.e., cause stunting), feeding or normal physiological development. This amount will vary depending on such factors as, for example, the specific target pests to be controlled, the specific environment, location, plant, crop or agricultural site to be treated, the environmental conditions, and the method, rate, concentration, stability, and quantity of application of the insecticidally-effective polypeptide composition. The formulations may also vary with respect to climatic conditions, environmental considerations, and/or frequency of application and/or severity of pest infestation.

The insecticidal formulation comprising an affinity construct of the disclosure which in turn comprises at least one affinity molecule A and at least one affinity molecule B may be a (standard) commercial formulation containing one or more insecticidal proteins and/or microbes for application on plants, plant parts or plant seeds or on the site where the plant to be protected is growing or sown. Such formulations are either containing the one or more insecticidal protein in purified form or are containing one or more microbes that produce the insecticidal protein (either naturally or via transgenesis). Typically, such formulations are formulations containing Bt protein(s). They may, however, also contain other insecticidal toxins, like, for example, proteins or peptides from spider, scorpions or the like.

Insecticidal Activity

As used herein, insect pests include insects selected from the orders Isoptera, Blattodea, Orthoptera, Phthiraptera, Thysanoptera, Hemiptera, Hymenoptera, Siphonaptera, Diptera, Coleoptera, Lepidoptera, etc., particularly from the orders Lepidoptera and Coleoptera.

The compositions comprising the affinity construct of the disclosure and an insecticidal protein (toxin), wherein the insecticidal protein (toxin) corresponds to the insecticidal protein (toxin) which the at least one affinity molecule B is capable of binding to, or is binding to, or is being directed to, or is being designed to bind to, display entomotoxic activity against insect pests, which may include economically important agronomic, forest, greenhouse, nursery ornamentals, food and fiber, public and animal health, domestic and commercial structure, household and stored product pests.

In various embodiments, the compositions comprising the affinity construct of the disclosure and an insecticidal protein (toxin) of the present disclosure, exhibit insecticidal activity against insect larvae. Of interest are larvae of any of the orders Isoptera, Blattodea, Orthoptera, Phthiraptera, Thysanoptera, Hemiptera, Hymenoptera, Siphonaptera, Diptera, Coleoptera, Lepidoptera, etc., particularly from the orders Lepidoptera and Coleoptera.

Methods for Inhibiting Growth or Killing an Insect Pest and Controlling an Insect Population The present disclosure encompasses methods for inhibiting growth or killing of an insect pest, comprising contacting the insect pest with an insecticidally-effective amount of the combination of an affinity construct of the disclosure and an insecticidal protein, wherein the insecticidal protein corresponds to the insecticidal protein, which the at least one affinity molecule B of the affinity construct of the disclosure is capable of binding to, or is binding to, or is being directed to, or is being designed to bind to.

As used herein, by "controlling an insect pest population" or "controls an insect pest" is intended any effect on an insect pest that results in limiting the damage that the pest causes. Controlling an insect pest includes, but is not limited to, killing the pest, inhibiting development of the pest, altering fertility or growth of the pest in such a manner that the pest provides less damage to the plant, decreasing the number of offspring produced, producing less fit pests, producing pests more susceptible to predator attack or deterring the pests from eating the plant.

In various embodiments methods are provided for controlling an insect pest population resistant to an insecticidal protein, comprising contacting the insect pest population with an insecticidally-effective amount of the combination of an affinity construct of the disclosure, or fragment or variant thereof, and an insecticidal protein or fragment or variant thereof, wherein the insecticidal protein or fragment or variant thereof corresponds to the insecticidal protein, which the at least one affinity molecule B of the affinity construct of the disclosure is capable of binding to, or is binding to, or is being directed to, or is being designed to bind to.

In various embodiments, methods are provided for protecting a plant from an insect pest, comprising expressing in the plant or cell thereof a affinity construct of the disclosure, or fragment or variant thereof, and an insecticidal protein or fragment or variant thereof, wherein the insecticidal protein or fragment or variant thereof corresponds to the insecticidal protein, which the at least one affinity molecule B of the affinity construct of the disclosure is capable of binding to, or is binding to, or is being directed to, or is being designed to bind to.

Insects

As used herein, the term "insect" encompasses in its broad popular sense all species of the superphylum Panarthropoda (classification Systema Naturae, Brands, S. J. (comp.) 1989-2005. Systema Naturae 2000. Amsterdam, The Netherlands, [http://sn2000.taxonomy.nl/]), including the phyla Arthropoda, Tardigrada and Onychophora; it includes all the different phases of the life cycle of the insect, such as, but not limited to eggs, larvae, nymphs, pupae and adults. In the context of the present disclosure, an insect is a living insect, i.e., that, for example, histological preparations of insects are excluded from the present disclosure.

Preferably, the insect belongs to the phylum Arthropoda (including, but not limited to the orders Archaeognatha, Thysanura, Paleoptera and Neoptera, also ticks, mites and spiders), more preferred to the subphylum Hexapoda, even more preferred to the class Insecta, and most preferred to one of the following orders: Isoptera, Blattodea, Orthoptera, Phthiraptera, Thysanoptera, Hemiptera, Hymenoptera, Siphonaptera, Diptera, Coleoptera and Lepidoptera. Most preferred the insect belongs to one of the families of Crambidae, Noctuidae, Pyralidae, Chrysomelidae, Dynastidae, Elateridae, Melolonthinae, Curcolionidae, Scarabaeidae, Erebidae, Coccinellidae, Mebidae, or Lamiinae.

In various aspects, the insect is considered as a pest. As used herein, "pest" is an organism that is detrimental to humans or human concerns, and includes, but is not limited to agricultural pest organisms, household pest organisms, such as cockroaches, ants, etc., and disease vectors, such as malaria mosquitoes. More preferably, said insect is an agricultural pest organism feeding on agricultural crops like corn, soy or cotton. As used herein, a "living insect" refers to the insect as it occurs in its natural habitat.

The agricultural pest insect preferably is a lepidopteran insect selected from the following insects from the order Lepidoptera: *Ostrinia nubilalis* (Europen Corn Borer), *Diatraea grandiosella* (South Western Corn Borer), *Helicoverpa zea* (Corn Earworm), *Agrotis ipsilon* (Black Cutworm), *Agrotis subterranea* (Granulate Cutworm), *Agrotis malefida* (Palesided Cutworm), *Spodoptera frugiperda* (Fall Army worm), *Spodoptera eridania* (Southern Armyworm), *Spodoptera albula* (Gray-Streaked Armyworm), *Spodoptera cosmioides, Spodoptera ornithogalli, Spodoptera exigua* (Beet Cutworm), *Helicoverpa armigera* (Cotton Bollworm), *Helicoverpa zea* (Corn Earworm), *Heliothis virescens* (Tobacco budworm), *Diatraea saccharalis* (SugarCane Borer), *Diatraea grandiosella* (South Western Corn Borer), *Elasmopalpus lignosellus* (Lesser CornStalk Borer), *Striacosta albicosta* (Western bean cutworm), *Chrysodeixis includens* (Soybean looper), *Pseudaletia sequax* (Wheat armyworm), *Porosagrotis gypaetina, Euxoa bilitura* (Potato Cutworm), *Pseudaletia unipuncta* (True armyworm), *Anticarsia gemmatalis* (Velvetbean caterpillar), *Plathypena scabra* (Green cloverworm), *Elasmopalpus lignosellus* (Lesser CornStalk Borer), *Chrysodeixis includens* (Soybean looper), *Trichoplusia ni* (Cabbage Looper) and *Peridroma saucia* (Variegated Cutworm).

Further preferred the agricultural insect pest is a coleopteran insect selected from the following insects from the order Coleopoptera: *Diabrotica virgifera virgifera* (Western Corn Rootworm), *Diabrotica barberi* (Northern Corn Rootworm), *Diabrotica speciosa, Diloboderus abderus, Phyllophaga* spp (Scarab beetles), *Listronotus* spp. (Argentine stem weevil), *Cerotoma arcuatus, Popillia japonica* (Japanese beetle), *Colaspis brunnea* (Grape *colaspis*), *Cerutoma trifurcata* (Bean Leaf Beetle), *Epilachna varivestis* (Mexican bean beetle), *Diabrotica undecimpunctata howardi* (Spotted cucumber beetle), *Epicauta pestifera* (Blister beetles), *Popillia japonica* (Japanese beetle), *Colaspis brunnea* (Grape *colaspis*), *Dectes texanus texanus* (Soybean stem borer), and *Anthonomous grandis* (Boll weevil).

Equally preferred the agricultural insect pest is one of the following, but is not limited to, *Oscinella frit* (Fruit Fly), *Myzus persicae* (Green Peach Aphid), *Rhopalosiphum maidis* (Corn Leaf Aphid) and *Rhopalosiphum padi* (Bird Cherry-Oat Aphid).

It is to be acknowledged that the present disclosure is not limited to the particular nucleic acid molecules, proteins, methodology, protocols, cell lines, genera, and reagents described herein, as such may vary. It is also to be acknowledged that the terminology used herein is for the purpose of describing particular embodiments only and is not intended to be limiting the scope of the present disclosure. The following examples are offered by way of illustration and not by way of limitation.

EXAMPLES

Example 1. Identification and Selection of Insect Structures for Immunization Procedures FIG. 10 provides a schematic of the broad approach to and advantages of development of fusion proteins with insecticidal applications. The steps involve selection of target insecticidal proteins and insect gut membrane targets and developing affinity molecules that recognize epitopes on these targets, fusing the affinity molecules such that the insecticidal proteins can be specifically targeted to defined membrane targets.

Insecticidal Protein for Affinity Molecule Identification

Insecticidal proteins as targets for affinity molecules can be three-domain Cry proteins, such as Cry1Ac or Cry3Ab or Vip3Aa or Cry1F (SEQ ID. NOS. 51, 52, 53 and 34 respectively). Targets can also be domains of such proteins that are known to interact with receptors at the insect gut membrane, such as specific loops in domain 2 of Cry proteins (see Bravo et al. 2013 as example for Cry domains that are involved in binding to membrane proteins). However, the three-dimensional structure of such a purified fragment of the insecticidal protein (e.g. domain 2 loop 1 and 3 of Cry3Ab) might not be the same when compared to the fragment in the native protein. Therefore, using only such partial domains of insecticidal proteins might hamper the identification of affinity molecules. Using native proteins as targets for identification of affinity molecules and the same insecticidal proteins that are mutated in these binding domains is very helpful for the identification of affinity molecules that bind specifically to the natural insect receptor binding domains.

Cry-Receptors

Insect structures for immunization can be proteins or epitopes of proteins that already serve as natural receptors for conventional Cry proteins (see general part of the description). Cadherins are one class of Cry receptors that localize to intercellular adhesion points (Carthew 2005, Current opinion in genetics & development 15, 358-363) and are abundant in the microvilli of midgut epithelia (Chen et al. 2005, Cell and tissue research 321, 123-129). Homologs of cadherins are identified as Cry binding proteins in many insect species, including several important agricultural pests (Flannagan et al., Insect biochemistry and molecular biology 35, 33-40; Jenkins et al. 2001, BMC biochemistry 2, 12; Jurat-Fuentes and Adang 2006, Biochemistry 45, 9688-9695). The extracellular domain of Cadherins contain cadherin repeats and one membrane-proximal extracellular domain (MPED). These cadherin repeats and the extracellular domains present the binding regions for Cry proteins (Gomez et al. 2001, The Journal of biological chemistry 276, 28906-28912; Dorsch et al. 2002, Insect biochemistry and molecular biology 32, 1025-1036; Hua et al. 2004, The Journal of biological chemistry 279, 28051-28056; Xie et al. 2005, The Journal of biological chemistry 280, 8416-8425; Rahman et al. 2012, Applied and environmental microbiology 78, 354-362; Fabrick et al. 2009, The Journal of biological chemistry 284, 18401-18410). Cadherin sequences were isolated from *Spodoptera frugiperda* (Fall army worm, FAW, SEQ ID NOS. 1 (DNA), SEQ ID NOS. 2 (protein)); *Heliothis virescens* (Tobacco budworm, TBW, SEQ ID NOS. 7 (DNA), SEQ ID NOS. 8 (protein)); *Helicoverpa armigera* (Cotton bollworm, CBW, SEQ ID NOS. 7 (DNA), SEQ ID NOS. 8 (protein)) and *Diabrotica virgifera virgifera* (Western Corn Root Worm, WCRW, SEQ ID NOS. 5 (DNA), SEQ ID NOS. 6 (protein)). The extracellular domains are used as epitopes for single domain antibody production.

Membrane Proteins

The binding of Cry proteins to their receptors in insect midguts facilitates insertion and pore formation. One property shared by most Cry receptors is their location at the luminal site of the membrane of insect epithelium midgut cells. It is suggested that creating a membrane-like environment is sufficient to facilitate oligomerization and pore formation of three-domain Cry proteins. This means that targeting Cry proteins to insect gut membrane environments is sufficient to facilitate pore formation of three-domain Cry proteins. Therefore, any membrane-localized protein that can serve as potential Cry receptor could lead to oligomerization and pore formation of Cry proteins, if the Cry proteins are fused to a single domain antibody or a fragment thereof, e.g., the CDR3 loop of an sdAb, raised against luminal epitopes of midgut epithelial proteins. As example for showing the application of this approach, the luminal domains of chitin synthases were used for single domain antibody production. Chitin synthases facilitate the biosynthesis of chitin, which is a dominant molecule of the peritrophic matrix in the midgut of most insect pests. Midgut chitin synthases are expressed during the intermolt stages of feeding larvae and are localized at the apical half of the brush border microvilli formed by the midgut columnar cells (Broehan et al. 2007, The Journal of experimental biology 210, 3636-3643; Zimoch et al. 2002, Cell and tissue research 308, 287-297). The luminal extracellular domains have been used in yeast two hybrid assays for the identification of binding partners (Broehan et al. 2007). The identified proteins also bind in vivo, indicating that expressing these domains in heterologous systems retains their three-dimensional structure. Chitin synthases from *Spodoptera frugiperda* (Fall army worm, FAW, SEQ ID NOS. 11 (DNA) and SEQ ID NOS. 12 (protein)); *Heliothis virescens* (Tobacco budworm, TBW); *Helicoverpa armigera* (Cotton bollworm, CBW, SEQ ID NOS. 9 (DNA) and SEQ ID NOS. 10 (protein)) and *Diabrotica virgifera virgifera* (Western Corn Root Worm, WCRW) are isolated. The extracellular domains are used as epitopes for single domain antibody production.

Other Criteria for Selection of Insect Target Proteins

Cry-susceptible insects get resistant by gaining mutations in Cry-receptor proteins. Such resistances can be detrimental for using other functional Cry proteins (e.g., in stacks) if their mode of action is based on the same receptor binding sites. While fitness costs can greatly influence the rate of resistance evolution, mutations in the target proteins leading to Cry resistance are supposed to be not essential for insect survival. However, by targeting Cry proteins to physiologically essential membrane proteins, resistance establishment can be highly reduced since the fitness of resistant insects is very low. Therefore, the present inventors have selected specific gut epithelial membrane-bound insect structures for immunization procedures that are highly relevant for insect survival, e.g., Chitin synthase 2 (Arakane et al. 2005, Insect molecular biology 14, 453-463).

Target proteins for immunizations might also be proteins that interact with known Cry receptors. These interacting proteins might be membrane-bound or membrane-integral proteins or might be cytosolic proteins. Creating affinity to these target proteins via the single domain antibody technology is considered to increase the probability of (1) interactions between Cry proteins and their natural receptors, and (2) locating the Cry proteins in the vicinity of the plasma membrane.

Toxin Protein Production

The Cry1a gene (SEQ ID NOS. 45) was isolated from the *B. thuringiensis* var. *thuringiensis* T01-328 strain, and the complete gene (2160 bp) was cloned into the pET28a(+) expression vector (Bergamasco et al. 2013, J Invertebr Pathol 112, 152-158). The Vip3Aa gene (SEQ ID NOS. 47) was isolated from the *B. thuringiensis* HD-1 line, and the complete gene (2350 bp) was cloned into the pET SUMO expression vector. Cry3Aa gene (SEQ ID NOS. 46) was isolated from *B. thuringiensis*. The expression vectors added a polyhistidine tag (6 His) to the end of the recombined genes for protein detection and purification. The vectors containing the genes were used to transform competent *E. coli* BL21(DE3) cells by thermal shock (Hanahan 1983, J Mol Biol 166, 557-580) to induce recombinant gene expression.

Cry 1a and Vip3Aa expression was induced by inoculating a pre-culture containing 20 ml LB media and 50 μg/ml kanamycin with a single colony from one of the clones containing the expression vector with the specific gene. The culture was grown at 37° C. and agitated at 250 rpm for 16 h. The pre-culture was transferred to 200 ml of LB media and 50 μg/ml kanamycin and agitated until an $OD_{600}$ of 0.6 was reached. IPTG was then added to a final concentration of 1 mM (Vip3Aa) or 5 mM (Cry1a) to induce expression. The culture was maintained at 25° C. (Vip3Aa) or 30° C. (Cry1a) for 24 h with agitation (190 rpm). Cell lysis and solubilization of the proteins were performed as described by Bergamasco et al., 2013. Gene expression was confirmed by resolving the total protein on a 10% SDS-PAGE gel stained with Coomassie Blue and by Western Blot using an antihistidine antibody (Sigma Aldrich). Lysate from *E. coli* BL21 (DE3) without the gene inserts was used as a negative control. Lysates containing Cry1a (approximately 81 kDa) (Bergamasco et al. 2013) in the lysate were quantified by densitometry via the Bionumerics software (Applied-Maths) and a bovine serum albumin (BSA) standard curve before use in the bioassays and BBMV binding studies (Bergamasco et al. 2013; primary and secondary literature).

Another source for a protocol is: Production of a Bt toxin standard and development of a measuring procedure to assess the amount of the toxin in Bt maize. State Teaching and Research Centre for Agriculture, Viticulture and Horticulture (SLFA), Neustadt. Research Project from BMBF, Förderkennzeichen 0312631 C (2001-2004).

Example 2: Identification of Nanobodies

This disclosure also contemplates immune $V_HH$ libraries obtained from naïve, semisynthetic, or synthetic V repertoires raised against insect target proteins (Goldman et al., 2006, Anal Chem 78, 8245-8255; Monegal et al. 2009, Protein Eng Des Sel 22, 273-280; US Patent Application Publication US20050119455, incorporated herein by reference in its entirety). The term "raised against" as used herein refers to the specific polypeptide sequence that was used as an antigen to raise affinity molecules for example (but not restricted to) antibody, nanobody, $V_HH$, sdAb etc. Target insect antigen or toxin specific nanobodies can be retrieved from immune or other libraries by phage display or any other selection protocol, including bacterial display, yeast display, intracellular 2 hybrid selection (Pellis et al. 2012, Arch Biochem Biophys 526, 114-123; Zolghadr et al. 2008, Mol Cell Proteomics 7, 2279-2287), ribosome display (Yau et al. 2003, J Immunol Methods 281, 161-175), and others (as mentioned in Muyldermans 2013, Annual review of biochemistry 82, 775-797; also in US Patent Application Publications US20050119455 and US20210148928, incorporated herein by reference in their entireties).

$V_HH$ Library Construction and Panning

Lymphocytes can be isolated by Ficoll gradient centrifugation from blood of immunized llamas and total RNA can be isolated, from which cDNA can be prepared. This cDNA can be used as template in a PCR reaction using e.g. primers annealing to the common $C_H2$ exon of the heavy chain llama immunoglobulins and to the leader sequence (5'-GTCCTGGCTGCTCTTCTACAAGG-3' (SEQ ID NOS. 41) and 5'-GGTACGTGCTGTTGAACTGTTCC-3' (SEQ ID NOS. 42), Monegal et al., 2009). PCR products can be separated on an agarose gel and $V_HH$ products (about 600 bp) can be purified. These PCR products can be used as a template for a nested PCR using degenerated primers (e.g., PCR-2 primers: 5'-CCAGCCGGCCATGGCTGAKGTB-CAGCTGGTGGAGTCTGG-3' and 5'-GGACTAGTGCGGCCGCGTGAGGA-GACGGTGACCWGGGT-3' and PCR-3 primers: 5'-AA-CATGCCATGACTCGCGGCTCAACCGGCCATGGCT-GAKGTBCAGCTGCAGGCGTCTGGR GGAGG-3' and 5'-GTTATTATTATTCAGATTATTAGTGCGGCCGCTG-GAGACGGTGACCWGGGTCC-3'; see also Monegal et al. 2009). The PCR product (about 400 bp) can be cloned into suitable vectors (e.g., pHEN4 vector, Arbabi Ghahroudi et al. 1997, FEBS Lett 414, 521-526).

The cloned $V_HH$ library can be expressed preferably on a phage and panned on an antigen (e.g., insect protein) that is immobilized in wells of microtiter plates by passive adsorption (or other methods). The antigen can also be biotinylated and immobilized on streptavidin-coated solid supports (Hoogenboom, 2005, Nat Biotechnol 23, 1105-1116). Two to three rounds of panning are normally sufficient to enrich the clones so that individual clones can be screened for production of antigen-specific nanobodies (e.g., against insect midgut proteins) in a standard enzyme-linked immunosorbent assay (ELISA). After panning (phage display (Hammers and Stanley, 2014, J Invest Dermatol 134, e17), the entire antigen binding fragment of nanobodies (~360 bp) is easily amplified by PCR in one single amplicon (e.g., primers annealing to the common $C_H2$ exon of the heavy chain llama immunoglobulins and to the leader sequence can be used (5'-GTCCTGGCTGCTCTTCTACAAGG-3' (SEQ ID NOS. 41) and 5'-GGTACGTGCTGTTGAACTGTTCC-3', (SEQ ID NOS. 42) Monegal et al. 2009). Small libraries of ~100 individual transformants are representative of the immune $V_HH$ repertoire of B cells present in a Camelid blood sample of ~50 ml. The amino acid sequences of the Nanobodies can be obtained from nucleotide sequencing of the ELISA-positive clones.

Example 3: Determination of Binding Efficiency

Figure 11A:
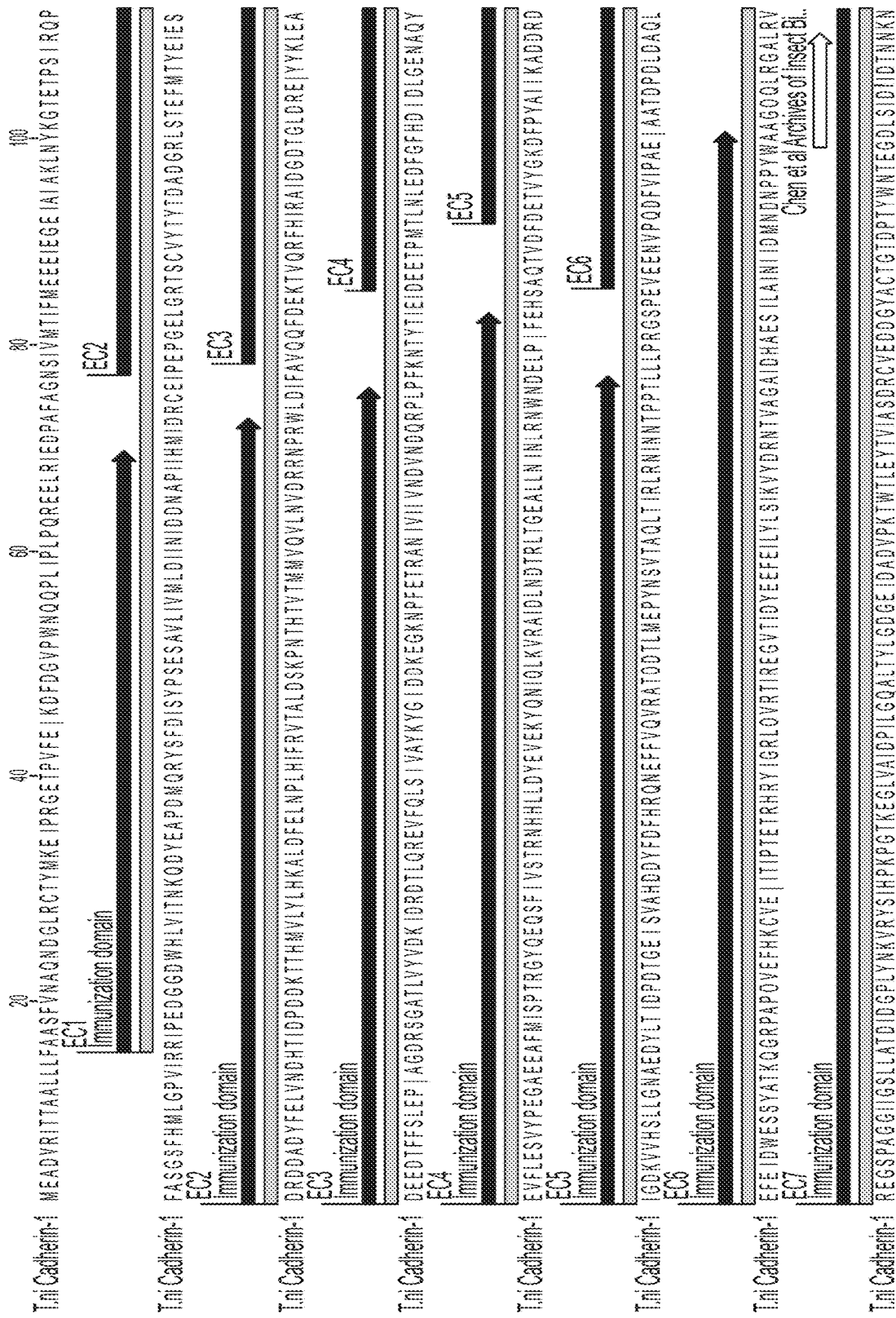
FIGS. 11A and B depict a structure of the Cadherin from *Trichoplusia ni*. Gray arrows indicate the entire extracellular domain that can be used for affinity molecule determination. Black arrows indicate sub-domains with the extracellular domain (EC1-12) and most proximal epidermal domain (MPED). White arrows indicate areas within the cadherin that are bound by Cry toxin (according to Badran et al. 2016, Nature, 533, 58-63, and Chen et al. 2014, Arch. Insect Biochem. Physiol. 86(1), 58-71).
Figure 11B:
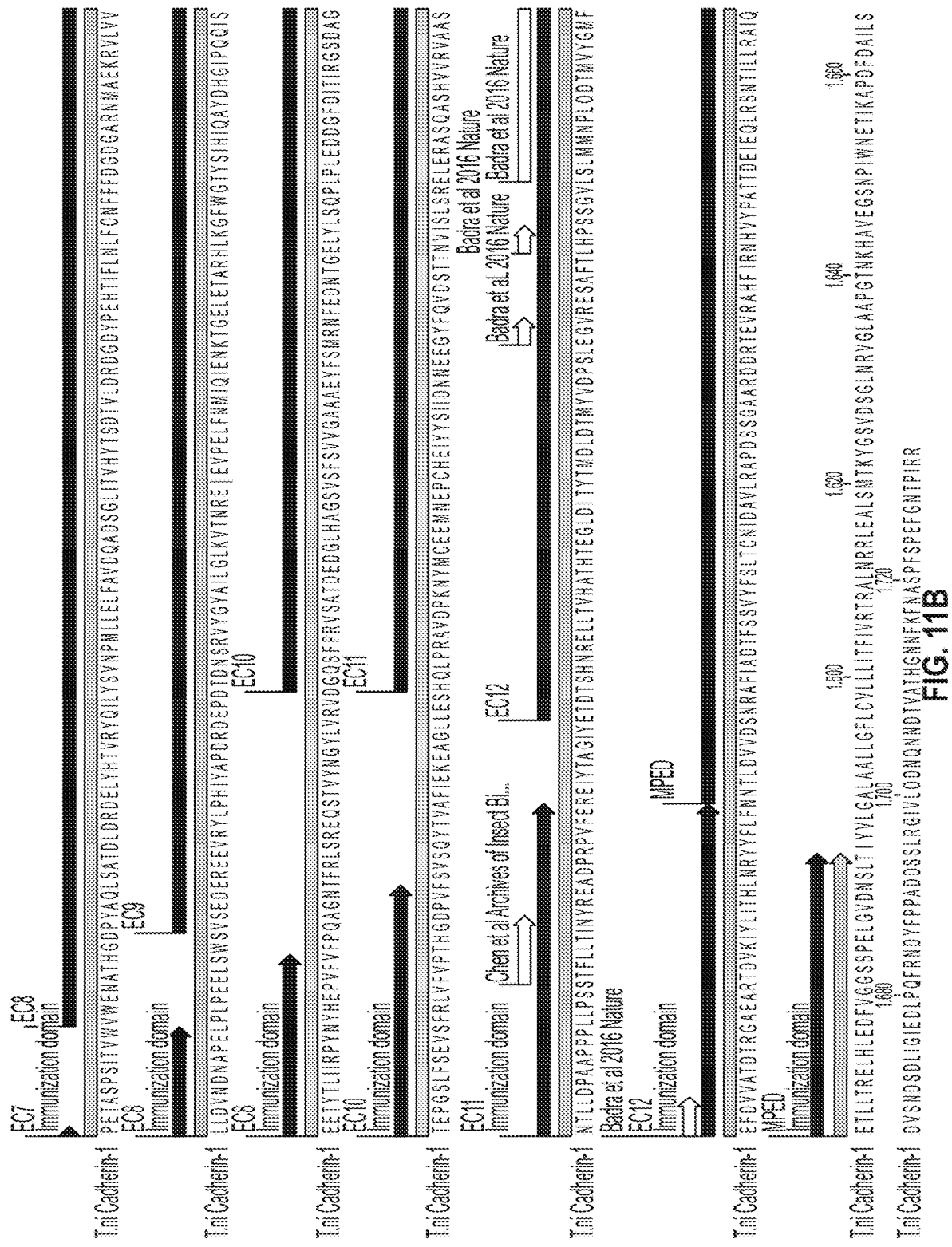
Figure 12:
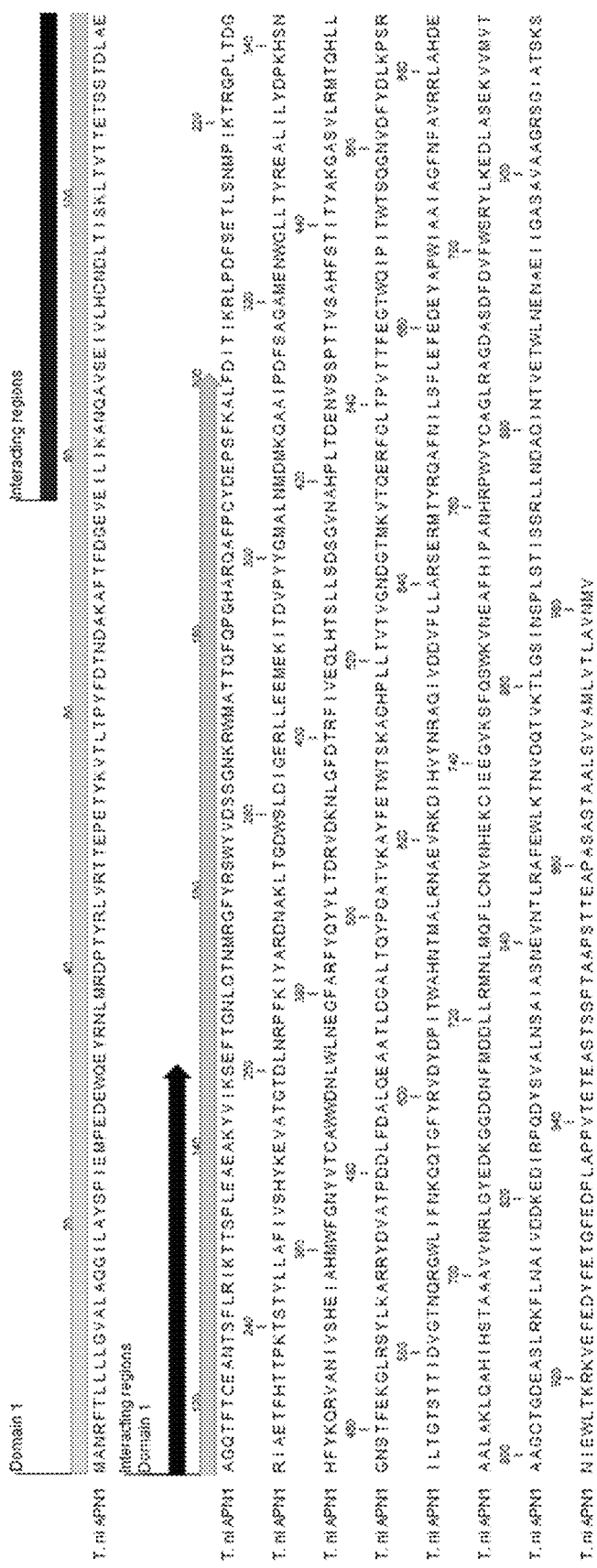
FIG. 12 depicts a structure of the Aminopeptidase N from *Trichoplusia ni* Gray arrows indicate Domain 1, black arrows the Cry-toxin-binding region.

Bacterial cells containing $V_HH$-containing plasmids can be infected with helper phages (e.g., KM13). Phage particles can then be isolated from culture supernatant and used for panning against purified soluble protein constructs. Isolated antigens can be bound via Tags (e.g., GST or Fc fragments) on coated on immunotubes, which are then incubated with the phages. Panning is done with peptides, domains or sub-domains of target insect midgut proteins that bind to insecticidal proteins. In the case of Cadherin, these domains include CR 7, 11 and 12 (see FIGS. 11A, B, C, and D as an example for T. ni cadherin). In addition, the affinity molecules are panned against peptides, domains or sub-domains within the extracellular domain of cadherins that are not usually bound by the toxin, e.g., CR 8-11 or the MPED domain (see FIGS. 11A, B, C, and D) and therefore do not interfere with binding of Cadherin to natural binding sites. The same principle is applied to other natural receptors of toxins (e.g., Cry proteins) such as APN1. Cry1C, for example interacts with a specific region in domain 1 of APN1 (Kaur et al. 2014, Process Biochemistry 49, 688-696). Domain 1 of APN1 could be used for immunization, while peptides from the specific binding region, or peptides outside of the binding region in domain 1 of APN1 could be used for panning, since this will allow new toxin-receptor interactions, without interfering with conventional binding interactions (See FIG. 12).

After several rounds of washing, phages can be eluted and used to infect bacterial cells (e.g., TG1). After infection with helper cells (e.g., KM13) and incubation, phage particles can be isolated and used for additional rounds of panning. Screening of $V_HH$s can be performed via ELISA. For this, Antigens (toxins or insect epitopes) can be bound to reaction tubes and incubated with periplasmic lysates of $V_HH$-containing cultures and binding can be determined calorimetrically (e.g., by using ABTS and measuring absorbance at 405 n). Clones with unique $V_HH$ sequences can then be cloned into vectors containing specific tags (e.g., His-tag) and purified via affinity chromatography.

For example, nanobodies against insect derived proteins with kinetic $k_{on}$ and $k_{off}$ rate constants in the ranges of $10^5$ to $10^6$ $M^{-1}s^{-1}$, and $10^{-2}$ to $10^{-4}$ $s^{-1}$ might be used, however, higher kinetic rate constants are also preferred if a less efficient or transient binding to a specific insect receptor or other protein is needed.

In vitro affinity maturation approaches, such as error-prone PCR, spiked mutagenesis combined with ribosome display (Yau et al. 2005) and Ala scanning-based mutations to identify the critical amino acids for antigen recognition might be used to improve the stability of the domain and/or the affinity for the cognate antigen (Koide et al, 2007, J Mol Biol 373, 941-953). Alternatively, carefully selected mutations at the edge of the paratope can be introduced to affect antigen-Nanobody kinetic and equilibrium affinity values. When combined with a multivariate analysis of the parameterized quantitative descriptors of the mutations and buffers, these methods can be used to propose a quantitative predictive algorithm that models the affinity parameters of all other possible mutants at those positions.

The method described herein includes immunization of Dromedaries or Llamas with proteins, peptides, protein fragments or other chemical structures from insect midgut or other insect tissues as well as toxins. $V_HHs$ libraries can be then obtained from immunized dromedary (or Llama) in the form of phage display vectors. From these immune libraries the antigen-specific $V_HHs$ can be selected (SEQ ID NOS. 28 provides an amino acid sequence of $V_HH$ domain from Dromedary germline, SEQ ID NOS. 29 provides an example of 2 $V_HH$ domains from Dromedary germline, linked by a linker). Small recombinant monomeric nanobodies (15 kDa, about 110 amino acid residues) can be selected that bind the target with 1 nM to 1 mM affinity. Reduced affinity might be preferable if the nanobody-insecticidal agent needs to bind with less specificity or if the interaction with target proteins needs to be transient. Transient interactions might help to concentrate the nanobody-insecticidal agent at specific structures in the insect, including the gut epithelium, as for example in the case of nanobody-Cry combinations, where Cry protein processing and oligomerization lead to the formation of pores in the membrane, finally impairing insect performance. Because of their small size, nanobodies are preferred over conventional antibodies because they can bind specific epitopes that are less immunogenic for conventional antibodies, such as the active sites of enzymes (Muyldermans, 2013). Therefore, nanobodies can target areas or structures that are not accessible to conventional antibodies.

Straightforward identification of antigen-binding $V_HHs$ after immunizing a camelid includes cloning the $V_HH$ repertoire of B cells circulating in blood and panning by phage display (Nguyen et al. 2001, Adv Immunol 79, 261-296). The sequence variability within V domains is localized in three hypervariable (HV) regions surrounded by more conserved framework (FR) regions. The folded V domain comprises nine β-strands (A-B-C-C-C-D-E-F-G), organized in a four-stranded β-sheet and a five-stranded βsheet, connected by loops and by a conserved disulfide bond between Cys23 and Cys94, packed against a conserved Trp. In this architecture, the HV regions are located in the loops H1 to H3 that connect the B-C, the C-C, and the F-G strands, respectively, and that cluster at the N-terminal end of the domain forming a continuous surface, which is complementary to the surface of the epitope, hence its name, complementarity-determining region (CDR, see FIG. 7).).

Example 4: In Vitro Affinity Maturation

In vitro affinity maturation approaches, such as error-prone PCR, spiked mutagenesis combined with ribosome display (Yau et al. 2005, J Immunol Methods 297, 213-224) and Ala scanning-based mutations to identify the critical amino acids for antigen recognition might be used to improve the stability of the domain and/or the affinity for the cognate antigen (Koide et al. 2007, J Mol Biol 373, 941-953). Alternatively, carefully selected mutations at the edge of the paratope can be introduced to affect antigen-$V_HH$ kinetic and equilibrium affinity values. When combined with a multivariate analysis of the parameterized quantitative descriptors of the mutations and buffers, these methods can be used to propose a quantitative predictive algorithm that models the affinity parameters of all other possible mutants at those positions.

Example 5: Construction of Multispecific $V_HHs$

Linker

Affinity molecules (or fragments thereof) can be fused directly or by using a flexible linker which does not interfere with the structure and function of the proteins (or fragments thereof) to be linked. Said flexible linkers are for instance those which have been used to fuse the variable domains of the heavy and light chain of immunoglobulins to construct a scFv, those used to create bivalent bispecific scFvs or those used in immunotoxins (see, for example, Huston et al. 1992; Takkinen et al. 1991). Linkers can also be based on hinge regions in antibody molecules (Pack et al. 1993, Biotechnology (NY) 11, 1271-1277; Pack and Plückthun 1992, Biochemistry 31, 1579-1584) or on peptide fragments between structural domains of proteins.

A linker can be designed as a flexible GGGS-linker of three distinct lengths (9, 25, 35 amino acids containing glycine for flexibility and serine for solubility), as fusion head-to-tail with a 9 amino acid glycine/serine linker (preferred option) or as hinge-sequence added to the 3' extremity of an affinity molecule. Some exemplary linker sequences are provided in SEQ ID NOS 54-65.

Example 6: Application of Multispecific Affinity Molecules

One of the main aspects of the present disclosure is to apply the purified multispecific affinity molecule to the plant (e.g., by spraying), together with the insecticidal protein(s) for which affinity was generated. Upon feeding on the plant, an insect would then take up the affinity molecule(s) as well as the insecticidal protein(s). The oligomerization capacity and therefore pore formation activity of the insecticidal protein would be enhanced through higher binding capacities to insect receptors via the multispecific affinity molecule.

Alternatively, multispecific affinity molecules can be easily expressed in plants also expressing the insecticidal protein. Affinity molecules such as the $V_HH$'s can be readily expressed by transformed plants (Ismaili et al. 2007, Biotechnol Appl Biochem 47, 11-19). Expression in transgenic plants can be done using constitutively active promotors (e.g. 35S promotor or Ubiquitin promotors) or using specific promotors that allow increasing toxin activity in areas that are attacked by the target insects or that can be induced via external cues (e.g. chemically-inducible promotors, heat-inducible promotors).

The invention also includes applying the insect protein to which the affinity molecule is intended to bind to. The insect protein that is co-applied with the affinity molecule might also be equipped with a tag that is specific for a $V_HH$. Such tags have been described previously (De Genst et al. 2010, J Mol Biol 402, 326-343). However, these tags could be any protein or amino acid sequence, for which a specific antibody or $V_HH$ can be produced. The multispecific affinity molecule can also be introduced to the plant by other means, such as viral vectors, bacteria, injection, grafting, spraying and others.

Example 7: Insect Specificity Via Exchanging $V_HH$ or CDR3

$V_HH$ against epitopes from different insects are raised (see Example 1: Insect structures for immunization procedures). By exchanging the $V_HH$ or CDR3 domain between different multispecific affinity molecules, insecticidal proteins are targeted to the membranes of previously non-susceptible insects, thereby creating toxicity to these insects (see FIGS. 4 and 5). Table 2(A-D) provides examples of the use of the approaches for increasing activity of insecticidal proteins and for creating activity of insecticidal proteins in insects, for which the insecticidal protein was not yet active.

Specifically, Table 2A provides the relative activity of native insecticidal proteins against the target insects (FAW=fall armyworm (*Spodoptera frugiperda*), TBW=Tobacco budworm (*Heliothis virescens*), CBW=Cotton bollworm (*Helicoverpa armigera*), WCRW=Western corn rootworm (*Diabrotica virgifera virgifera*), CL=Cabbage looper=*Trichoplusia ni*, Question mark indicates that activity has not been described). As seen from Table 2, different native Cry proteins show varying degrees of activity against different target insects. For instance, Cry3Ac is highly active against CBW but shows no activity against WCRW and CL, and mild activity against FAW. Similarly, Cry3Aa shows no activity against FAW, TBW and CBW but is highly active against WCRW.

TABLE 2A

Relative activity of native insecticidal proteins against the target insects

| Target Insect | Cry1Ac | Cry3Aa | VIP3Aa |
|---|---|---|---|
| FAW | mildly active | not active | active |
| TBW | active | not active | active |
| CBW | highly active | not active | active |
| WCRW | not active | highly active | not active |
| CL | active | not active | highly active |

However, by exchanging the $V_HH$ or CDR3 domain between different multispecific affinity molecules, Cry proteins can be made active against previously non-susceptible species.

Table 2B provides potential activity of Cry1Ac $V_HH$/CDR3$_{Cry1Ac}$-$V_HH$/CDR3$_{insect\text{-}target}$ combinations. $V_HH$/CDR3xxx represents either $V_HH$ or CDR3 loop domains raised against Cry1Ac ($V_HH$/CDR3$_{Cry1Ac}$) or insect-specific epitopes ($V_HH$/CDR3$_{insect\text{-}target}$).

TABLE 2B

Activity of Cry1Ac $V_HH$/CDR3$_{Cry1Ac}$ – $V_HH$/CDR3$_{insect\text{-}target}$ combinations.
Bold letters indicate changes in activity, when compared to Table 2A.

| Target Insect | Cry1Ac + $V_HH$/CDR3$_{Cry1Ac}$ $V_HH$/CDR3$_{FAW}$ | Cry1Ac + $V_HH$/CDR3$_{Cry1Ac}$ $V_HH$/CDR3$_{TBW}$ | Cry1Ac + $V_HH$/CDR3$_{Cry1Ac}$ $V_HH$/CDR3$_{CBW}$ | Cry1Ac + $V_HH$/CDR3$_{Cry1Ac}$ $V_HH$/CDR3$_{WCRW}$ | Cry1Ac + $V_HH$/CDR3$_{Cry1Ac}$ $V_HH$/CDR3$_{CL}$ |
|---|---|---|---|---|---|
| FAW | highly active | mildly active | mildly active | mildly active | mildly active |
| TBW | active | highly active | active | active | active |
| CBW | highly active | highly active | highly active | highly active | highly active |
| WCRW | not active | not active | not active | highly active | active |
| CL | active | Active | active | active | highly active |

As seen from Table 2B3, it is conceivable that Cry1Ac, that previously showed low activity against FAW, can now be highly active against FAW when used in conjunction with $V_HH$/CDR3$_{Cry1Ac}$-$V_HH$/CDR3$_{FAW}$. Surprisingly, WCRW, against which Cry1Ac has no activity, can be made susceptible to Cry1Ac, when used in combination of $V_HH$/CDR3$_{Cry1Ac}$-$V_HH$/CDR3$_{WCRW}$.

Table 2C provides activity of Cry3Aa $V_HH$/CDR3$_{Cry1Ac}$-$V_HH$/CDR3$_{insect\text{-}target}$ combinations. $V_HH$/CDR3xxx represents either $V_HH$ or CDR3 loop domains raised against Cry3Aa ($V_HH$/CDR3$_{Cry3Aa}$) or insect-specific epitopes ($V_HH$/CDR$_{insect\text{-}target}$).

TABLE 2C

Activity of Cry3Aa $V_HH$/CDR3$_{Cry3Aa}$ – $V_HH$/CDR3$_{insect\text{-}target}$ combinations.
Bold letters indicate changes in activity, when compared to Table 2A.

| Target Insect | Cry3Aa + $V_HH$/CDR3$_{Cry3Aa}$ $V_HH$/CDR3$_{FAW}$ | Cry3Aa + $V_HH$/CDR3$_{Cry3Aa}$ $V_HH$/CDR3$_{TBW}$ | Cry3Aa + $V_HH$/CDR3$_{Cry3Aa}$ $V_HH$/CDR3$_{CBW}$ | Cry3Aa + $V_HH$/CDR3$_{Cry3Aa}$ $V_HH$/CDR3$_{WCRW}$ | Cry3Aa + $V_HH$/CDR3$_{Cry3Aa}$ $V_HH$/CDR3$_{CL}$ |
|---|---|---|---|---|---|
| FAW | highly active | not active | mildly active | mildly active | mildly active |
| TBW | not active | highly active | active | active | active |
| CBW | not active | not active | highly active | highly active | highly active |
| WCRW | highly active | highly active | not active | highly active | active |
| CL | ? | ? | active | active | highly active |

Similarly, Table 2D provides activity of Vip3Aa fusion protein. $V_HH/CDR3_{Vip3A}$-$V_HH/CDR_{insect-target}$ combinations. $V_HH/CDR3xxx$ represents either $V_HH$ or CDR3 loop domains raised against Vip3A ($V_HH/CDR3_{VIP3Aa}$) or insect-specific epitopes ($V_HH/CDR3_{insect-target}$).

TABLE 2D

Activity of Cry3Aa Vip3Aa fusion protein. Bold letters indicate changes in activity, when compared to Table 2A.

| Target Insect | Vip3Aa + $V_HH/CDR3_{ViP3Aa}$ $V_HH/CDR3_{FAW}$ | Vip3Aa + $V_HH/CDR3_{ViP3Aa}$ $V_HH/CDR3_{TBW}$ | Vip3Aa + $V_HH/CDR3_{ViP3Aa}$ $V_HH/CDR3_{CBW}$ | Vip3Aa + $V_HH/CDR3_{ViP3Aa}$ $V_HH/CDR3_{WCRW}$ | Vip3Aa + $V_HH/CDR3_{ViP3Aa}$ $V_HH/CDR3_{CL}$ |
|---|---|---|---|---|---|
| FAW | highly active | active | active | active | active |
| TBW | Active | highly active | active | active | active |
| CBW | Active | active | highly active | active | active |
| WCRW | not active | not active | not active | highly active | not active |
| CL | ? | ? | active | active | highly active |

As seen in all these cases, combination of $V_HH$ or CDR3 that specifically recognize and bring together toxins to their insect specific targets can be a powerful tool to generate greater toxicity towards insect pests and indeed to increase the repertoire of insects against which these toxins can be effectively used.

Example 8: Overcoming Resistance in Insects

One of the most common insect resistance mechanisms is based on mutations in domains of proteins that serve as receptors for insecticidal proteins. However, by targeting the insecticidal protein to other domains of known receptors, or to new proteins that are not yet associated with the insecticidal protein, binding of the insecticidal proteins to said other domains of known receptors or to new proteins is able to break this type of resistance.

To test this Cry1Ac was provided with $V_HH/CDR3_{Cry1Ac}$-$V_HH/CDR3_{Chitin\_synthase}$ fusion protein between $V_HH$ or CDR3 loops of $V_HH$ raised against Cry1Ac fused with $V_HH$ or CDR3 loops of $V_HH$ raised against T. ni chitin synthase 2. Wild type and two strains of Cry1Ac-resistant strains of Trichoplus ni (CL=Cabbage looper) were used.

Figure 9:
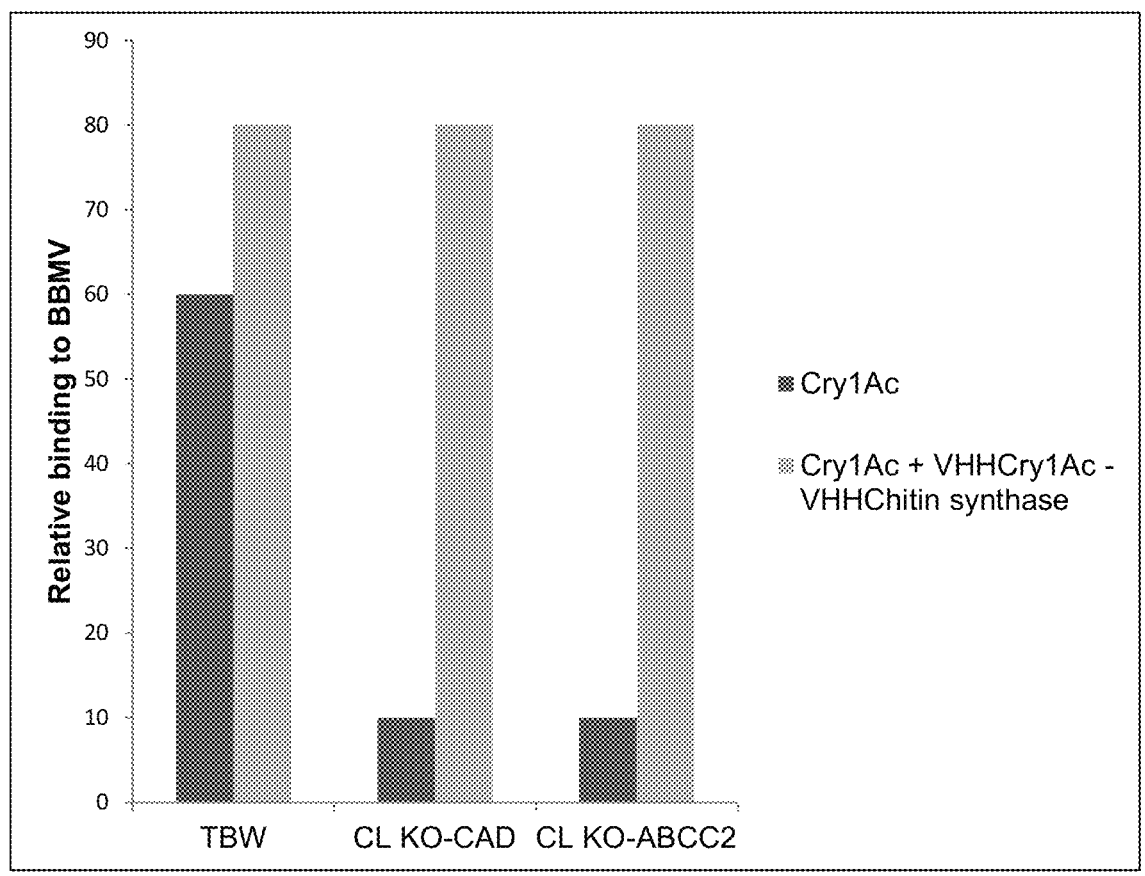
FIG. 9 depicts Cry1Ac combined with $V_HH$ Cry1Ac-$V_HH$ Chitin synthase binds to BBMV of Cry1Ac-resistant *Trichoplusia ni* (Cabbage looper, CL) strains.

Quantitative data for of these experiments are shown in FIG. 9. Targeting Cry1Ac to insect-specific extracellular luminal domains of the gut chitin synthase overcomes resistance in both mutants (see Table 3). This provides further evidence that using the methods disclosed herein, insects previously resistant to these toxins can be made susceptible.

TABLE 3

Targeting Cry1Ac to luminal chitin synthase epitopes using $V_HH$ or CDR3 loops creates susceptibility in two resistant strains of T. ni. Bold letters indicate change in activity when compared to native Cry1Ac toxins in Table 2A.

| Target insect | Cry1Ac | Cry1Ac + $V_HH/CDR3_{Cry1Ac}$ - $V_HH/CDR3_{Chitin\_synthase}$ |
|---|---|---|
| CL | Active | highly active |
| $CL_{KO-CAD}$ | not active | highly active |
| $CL_{KO-ABCC}$ | not active | highly active |

Example 9: Protein Expression Analysis and Feeding Assays

Once the multispecific affinity proteins are cloned into appropriate expression vectors (e.g., vectors that contain a GST-tag, such as pEMBO) the recombinant expression plasmid can be transformed into E. coli strains (e.g., BL21). After appropriate growth in LB medium (e.g., at 37° C. to reach $OD_{600}$ 0.5-0.8) the expression can be induced by IPTG (e.g., for 3 h at 37° C.) and the bacteria can be gained by centrifuging and washing (e.g., with 0.5% NaCl). The bacteria can be mixed and homogenized, and aliquot of the centrifuged supernatant can be treated with loading buffer (boiling for 3-5 min) and protein expression and size can be analyzed SDS-PAGE electrophoresis.

When expression is appropriate, the supernatant mentioned above can be purified with specific kits (e.g., GST-Bind™, Novagen) and analyzed again via SDS-PAGE electrophoresis. After that protein concentration can be determined. Bioassays to determine $LC_{50}$ values are described elsewhere (e.g., Ibargutxi et al. 2006, Appl Environ Microbiol 71(1): 437-442).

Leaf Disc Assays

Leaf punches from a young, fully expanded leaf can be collected using a small paper punch. Leaf punches will not include the leaf midrib. The paper punchers used are cleaned with ethanol between sampling each individual leaf. 128-well assay trays (Bio-Serv) can be half-filled with a 1.5% agar solution (+ perhaps a fungicide). The agar is allowed to harden, and the trays are then be wrapped in plastic and stored at approximately 5° C. Trays will be allowed to reach room temperature before use. Leaf punches are dipped into insecticidal spray formulation and allowed to dry. One leaf punch is placed in each of the wells. One neonate larvae of the appropriate species are placed into each well with a small camel-hair brush. Only healthy, moving neonates are used in the assay. After infestation, wells are sealed with Bio-Serv 16 cell covers. Trays containing larvae are held at 25° C. with 16:8 L:D and 65±5% relative humidity for up to 5 days. The percent leaf area consumed in each well is recorded 3-5 days post-infestation. The actual number of days post-infestation is also recorded. The number of alive and dead insects in the wells per experimental unit is recorded on the same day as the leaf area assessment. Moribund larvae are considered dead. Mortality and weight of larvae are recorded. Other assays are described by Niu et al. 2013, PLoS One 8, e72988; and Olsen and Daly 2000, J Econ Entomol 93, 1293-1299).

Example 10: Expression of Multispecific Affinity Proteins in Plants and Bioassays One aspect of the disclosure is the transformation of plants with genes encoding the multispecific affinity proteins. The transformed plants are resistant to attack by the target pest, when co-expressed or treated with the toxin. The coding sequence of positively tested multispecific affinity proteins is cloned into appropriate vectors for plant transformation (e.g., pBR322, pUC series, M13 mp series, etc.). The resulted plasmid is used for transformation into *E. coli*. The transformed *E. coli* cells are harvested lysed, and plasmid is recovered. After sequence analysis (electrophoresis, digestion analysis, sequencing), the plasmid is used for stable integration into plants. Techniques for plant transformation include (but are not limited to) transformation with T-DNA using *Agrobacterium tumefaciens* or *Agrobacterium rhizogenes* as transformation agent, fusion, injection, biolostics (microparticle bombardment), or electroporation as well as other possible methods. The *Agrobacterium* cells transformed with the appropriate plasmid (e.g., pLHBA, pZFN) containing the insecticidal fusion protein are used for the transformation of plant cells. Plant explants or calli are cultivated with the transformed *Agrobacterium* strains and whole plants are then regenerated from the infected plant material (for example, pieces of leaves, segments of stalks, roots, but also protoplasts or suspension-cultivated cells) in a suitable medium, which may contain antibiotics or biocides for selection. The plants obtained are then tested for the presence and expression of the multispecific affinity. The transgenic plants are used for insect bioassays. Tissues used for insect feeding depend on the target insect. Western corn rootworm (WCR, *Diabrotica virgifera*), for example, can be obtained as eggs and used to infect roots of transgenic and control plants. For this purpose, the soil around the plants is infected with approximately 150-200 WCR eggs and the insects are allowed to feed for 2 weeks, after which a root damage rating can be given to each plant (see Oleson et al. 2005 J Econ Entomol 98, 1-8 for details).

Example 11

Identification of Candidate Fall Armyworm Receptor Targets

The goal of this experiment was to identify gut membrane proteins to be used as targets in development of bispecific affinity molecules for control of fall armyworm (FAW, *Spodoptera frugiperda*). The rationale for target selection was based on identifying proteins with putative high abundance on the surface of midgut cells, with epitopes available on the extracellular surface that were not susceptible to cleavage by phospholipases (avoiding GPI-anchored proteins, "GPI" means glycosylphosphatidylinositol) to promote interaction with affinity molecules and preventing resistance by cleavage and release of target. Presence on the microvillar membranes of midgut cells of FAW was examined by proteomic analysis of midgut brush border membrane vesicle (BBMV) proteins (Silva et al. 2013). Tryptic peptides derived from solubilized BBMV proteins were identified through nano-liquid chromatography coupled to tandem mass spectrometry (nanoLC/MS/MS) and annotated using the FAW TR2012b transcriptome from the Bioinformatics Platform for Agroecosystem Arthropods (BIPAA) and the NCBInr Insecta databases. This proteomic approach also allowed relative quantification of BBMV proteins using the Normalized Spectral Abundance Factor (NASF) quantitative method (Zhang et al. 2010), which considers the normalized spectra and protein length.

Samples of FAW BBMV proteins were prepared and quantified as described elsewhere (Jakka et al. 2016) and solubilized in 1% SDS at room temperature. Solubilized samples were shipped to MS Bioworks (Ann Arbor, MI) for further analysis and processing. Samples (10 μg) were loaded onto a 10% Bis-Tris SDS-PAGE gel (Novex®, Invitrogen) and resolved for approximately 2 cm into the gel. The gel was stained with Coomassie and the area containing the BBMV proteins excised and processed for trypsin digestion, as follows. The gel was first washed with 25 mM ammonium bicarbonate followed by acetonitrile, and then reduced with 10 mM dithiothreitol at 60° C. followed by alkylation with 50 mM iodoacetamide at room temperature. The proteins were digested with trypsin (Promega) at 37° C. for 4 h and reactions quenched with formic acid. The supernatant was analyzed directly without further processing.

Tryptic digests were analyzed by nano LC/MS/MS with a Waters™ NanoAcquity HPLC system interfaced to a Q Exactive™, from ThermoFisher. Peptides were loaded on a trapping column and eluted over a 75 m analytical column at 350 nL/min; both columns were packed with Luna C18 resin (Phenomenex™). A 1 h gradient was employed. The mass spectrometer was operated in data-dependent mode, with MS and MS/MS performed in the Orbitrap at 70,000 FWHM resolution and 17,500 FWHM resolution, respectively. The fifteen most abundant ions were selected for MS/MS. Data were searched using a local copy of Mascot software (Matrix Science) and parsed into the Scaffold software (Proteome Software) for validation and filtering to create a non-redundant list per sample. Data were filtered using a minimum protein value of 99%, a minimum peptide value of 95.5% (PeptideProphet scores, using software from Institute for Systems Biology) and requiring at least two unique peptides per protein.

Searches for matching proteins were performed against an in silico generated FAW proteome and the NCBI (National Center for Biotechnology Information) nr Insecta protein database. The Blast2GO™ v.5.1.13 software (from Biobam) was used to convert all the contigs generated after translating the FAW TR2012b transcriptome in all 6 potential frames to their longest ORF protein sequences. The resulting file (containing 7,785 sequences) was blasted, mapped and annotated in Blast2GO. Proteins containing "membrane" as part of its GO name were then selected and used to manually annotate identified FAW BBMV proteins. The list of proteins identified by matching to NCBInr Insecta was manually curated to eliminate ribosomal and organelle proteins. The lists of identified FAW BBMV proteins by matching to NCBInr Insecta or the translated TR2012b transcriptome were then ranked based on protein abundance using the NASF method (Zhang et al., 2010) and predicted membrane topology as predicted by the TOPCONS consensus prediction tool (https://topcons.cbr.su.se/).

In the list of proteins identified by searching the TR2012b transcriptome, 587 proteins were detected. This list was reduced to 95 proteins, which were selected after increasing probability cutoff and manually deleting proteins not predicted to be associated with the membrane based on GO terms. A second list of 499 proteins was derived using the NCBInr Insecta database for searches. This list was reduced to 345 proteins after manually deleting proteins predicted to be in intracellular organelles and ribosomal proteins.

First Identified Protein:

Based on the critical role of ABC transporters in the activity of some Cry toxins, topologically similar transmembrane proteins with extracellular loops of relevant length were considered as target candidates. Among this group, a protein containing domains from the SLC6 (Solute Carrier Family 6,) family of nutrient transporters expected to direct uptake of nutrients from the gut lumen was identified as sodium-dependent nutrient amino acid transporter 1-like (NAAT) protein. The second extracellular loop in this protein was predicted to consist of 57 aa and used to develop nanobodies. The sequence of the antigenic region of NAAT protein and the full-length protein is shown in SEQ ID NOS. 30 and 31 respectively.

Second Identified Protein

Resistance to Cry 1 toxins is linked to mutations in cadherin in several insects (Rahman, et al. 2012, Park and Kim 2013), yet cadherin is not a functional Cry1F or Cry1Ab toxin receptor in FAW as demonstrated in genetic knockouts not affected in Cry1F susceptibility (Zhang, et al. 2020). Consequently, re-targeting Cry1F to FAW cadherin could allow for the progression of the toxin mode of action. Thus, a FAW cadherin region containing the Cry toxin and membrane proximal domains in other lepidopterans and shown to enhance toxicity in FAW (Rahman et al. 2012) was also selected as a potential target for nanobody development. The sequence of the antigenic region and full-length protein is provided in SEQ ID NOS. 35 and 2 respectively.

Third Identified Protein

As observed in work with lepidopteran BBMV (McNall and Adang, 2003; Krishnamoorthy, et al. 2007; Pauchet, et al. 2009; and Tiewsiri and Wang, 2011), searches with both protein databases identified V-ATPase complex subunits as very abundant proteins in FAW BBMV. Notably, these protein complexes are expected to localize mostly to goblet cells (Wieczorek, et al. 2009), and their detection probably indicates contaminant proteins. Out of the three protein subunits (a, e and c) part of the integral membrane subunit (Vo) protein complex of the V-ATPase, subunit a was predicted to include a lengthy region exposed to the extracellular fluid and thus was selected as candidate for nanobody development. The sequence of the antigenic region and full-length protein are provided in is shown in SEQ ID. NOS. 32 and 33 respectively.

Fourth Identified Protein

Based on the critical role of ABC subfamily C2 (ABCC2) transporters as a receptor for Cry1Fa toxin in FAW (Banerjee, et al. 2017), a member of ABC protein family 1 detected as relatively abundant in FAW BBMV was selected as candidate target. In addition, considering that Cry 1-resistant FAW have truncated ABCC2 proteins, it is possible that resistance could be overcome by targeting Cry1F to bind the remaining ABCC2 in resistant FAW. The longest predicted extracellular loop in ABCC1 was 25 aa long and could be used for nanobody production. The sequence of FAW ABCC1 is provided in SEQ ID NOS. 43, and the extracellular loop is provided in SEQ ID NOS. 44.

Fifth and Sixth Identified Proteins

Additional candidate targets selected based on their topology included a peptidase with a single transmembrane domain followed by a 783 aa long extracellular C terminus (venom dipeptidyl peptidase-4-like isoform X1) SEQ ID NOS. 37 (extracellular domain antigen) and 38 (full-length) and a peptide transporter with transmembrane domains and a 205 aa long extracellular loop (peptide transporter family 1 isoform X1) SEQ ID NOS. 39 (extracellular domain antigen) and 40 (full-length).

Example 12. Cry1F Toxin Core as Antigen for Nanobody Production

The Cry1F toxin is one of the most active *Bacillus thuringiensis* insecticidal proteins against FAW larvae and is produced in transgenic corn as a FAW trait. Initial efforts focused on using protruding loops in domain II of the toxin which determine Cry toxin binding specificity (Dean, et al. 1996; Jurat-Fuentes and Adang, 2001), or the whole domain II as antigens (SEQ ID. NOS. 34). The whole Cry1F toxin core as obtained by trypsinization of the protoxin form was used in the following examples.

Example 13. Expression and Purification of Receptor Antigens in Sf9 Insect Cells Expression of the NAAT and Cadherin antigens in *Spodoptera*-derived Sf9 cells ensured these proteins carry any post-translational modifications similar to the native proteins. For cloning and expression of NAAT, both a GST fusion and His-tag epitope were cloned at the N-terminus of the antigen peptide for affinity purification (SEQ ID NOS. 48). For cloning and expression of cadherin, a His-tag epitope was cloned at the N-terminus for affinity purification (SEQ ID NOS. 49). A Precision Protease (Sigma-Aldrich) cleavage site (NAAT) or TEV (Sigma-Aldrich) cleavage site (cadherin) was cloned immediately upstream of the antigen sequence to enable subsequent purification of the antigen peptide free of any epitope tag.

The NAAT and cadherin antigen constructs were cloned into a baculovirus expression vector and transfected into Sf9 cells.

The fusion proteins were collected by binding to a His-Trap column (Cytiva) via the His-tag on the fusion protein. After elution from the His-Trap column, purified fusion proteins were cleaved overnight with PreScission or TEV Protease to remove the GST and His tags. While the GST fusion was successfully cleaved from NAAT, the His-epitope tag was only partially removed from the Cadherin antigen. NAAT and cadherin antigen peptides were purified over a Superdex 75 size or Superdex 200 (Cytiva) exclusion column, respectively. Peptide mass fingerprinting confirmed the identity of the purified peptides. For the cadherin antigen, aggregation of the peptide could not be avoided. However, when 1 mM EGTA was included in the buffer, aggregation was minimized.

Example 14. Expression and Purification of Cry1Fa Core Toxin for Immunization

The full length Cry1F toxin (SEQ ID NOS. 34) was produced in a recombinant Bt HD-73 mutant strain harboring the pHT315 vector with the cry1F toxin gene under the cry1Ac promoter. For purification, parasporal crystals produced in Bt cultures were solubilized in buffer (50 mM $Na_2CO_3$, 0.1% β-mercaptoethanol, 0.1 M NaCl, pH 10.5) and solubilized Cry1F protoxin purified using anion exchange columns (HiTrap Q HP, GE Healthcare) connected to an AKTA FPLC (GE Healthcare). Protoxin was eluted with a gradient of 1 M NaCl in carbonate buffer (50 mM $Na_2CO_3$, 50 mM $NaHCO_3$ pH 9.8). A single major elution peak was detected and fractions in that peak were pooled, analyzed by SDS-10% PAGE and used in bioassays. Protoxin was activated using bovine trypsin and the activated toxin core was purified following the same anion exchange procedure as the full-length toxin.

Example 15. Design, Production and Purification of a Novel Chimeric Cry Toxin Protein Used for Identification of Cry1F Domain II-Specific Nanobodies A toxin containing domain II of Cry1F and dissimilar domains I and III was needed to affinity-select nanobodies targeting domain II of Cry1F as the most plausible to affect toxin binding to new targets. Comparison of protein sequence identity among selected three-domain Cry toxins identified Cry2A toxins as displaying the lowest sequence identity in both domains I(24%) and III (16%) with the Cry1F toxin core. Consequently, we used comparisons of a Cry2Aa model (1i5 pA in the Protein DataBank) with Cry1F and identified the different toxin domains to design a chimera containing domains I and III of Cry2Aa and domain II of Cry1F (2Aa/1F/2Aa), as provided in SEQ ID NOS. 50. A predicted model of this chimera toxin from Phyre 2 indicates folding similar to the three-domain folding in other Cry toxins.

Example 16. Llama Immunization, $V_HH$ Library Construction and Nanobody Screening Llamas were subcutaneously injected on days 0, 7, 14, 21, 28 and 35, each time with about 100-160 μg of antigen. A different animal was used for injection of each of the three antigens: NAAT, Cadherin, and cry1F. The adjuvant used was Gerbu adjuvant P™ (Gerbu, Germany). On day 40, about 100 ml anticoagulated blood was collected from each llama for lymphocyte preparation.

$V_HH$ antibody libraries were constructed from the llama lymphocytes to screen for the presence of antigen-specific Nanobodies (Nbs). To this end, total RNA from peripheral blood lymphocytes was used as template for first strand cDNA synthesis with an oligo(dT) primer. Using this cDNA, the $V_HH$ encoding sequences were amplified by PCR, digested with SAPI, and cloned into the SAPI sites of the phagemid vector pMECS-GG.

The Nanobody gene cloned in pMECS phagemid vector (Vincke et al., 2012) contains PelB signal sequence at the N-terminus and HA tag and His6 tag at the C-terminus (PelB leader-Nanobody-HA-His6). The PelB leader sequence directs the Nanobody to the periplasmic space of the *E. coli* and the HA and His6 tags can be used for the purification and detection of Nanobody (e.g. in ELISA, Western Blot, etc.).

In pMECS vector, the His6 tag is followed by an amber stop codon (TAG) and this amber stop codon is followed by gene III of M13 phage. In suppressor *E. coli* strains (e.g. TG1), the amber stop codon is read as glutamine and therefore the Nanobody is expressed as fusion protein with protein III of the phage which allows the display of Nanobody on the phage coat for panning. In non-suppressor *E. coli* strains (e. g., WK6), the amber stop codon is read as stop codon and therefore the resulting Nanobody is not fused to protein III.

Example 17. Isolation of Antigen-Specific Nanobodies

For identification of cry1F-specific nanobodies, $V_HH$ libraries were panned on solid-phase coated Cry1Fa antigen (100 μg/ml in 100 mM NaHCO₃ pH 8.2) for 3 rounds. Out of these 285 colonies, 180 colonies scored positive for Cry1Fa. Based on sequence data of the colonies positive on Cry1Fa, 132 different full length Nanobodies were distinguished, belonging to 53 different CDR3 groups (B-cell lineages). Some exemplary monospecific nanobody sequences are provided (Cry1F monospecific nanobody #5: SEQ ID NOS. 67 (DNA), SEQ ID NOS. 72 (protein); #7: SEQ ID NOS. 69 (DNA), SEQ ID NOS. 70 (protein); #51: SEQ ID NOS. 71 (DNA), SEQ ID NOS. 72 (protein)).

For identification of cadherin-specific nanobodies, the $V_HH$ library was panned on solid-phase coated tagless FAW Cadherin antigen (a batch different from the one used for immunization, at 100 μg/ml in 100 mM NaHCO₃ pH 8.2) for 3 rounds. Out of 380 colonies, 324 scored positive for Sp.f Cadherin. Based on sequence data of the colonies positive on Sp.f Cadherin, 121 different full-length Nanobodies were distinguished, belonging to 25 different CDR3 groups (B-cell lineages). Some exemplary selected monospecific nanobody sequences are provided (Cadherin monospecific nanobody #2: SEQ ID NOS. 85 (DNA), SEQ ID NOS. 86 (protein); #43: SEQ ID NOS. 87 (DNA), SEQ ID NOS. 88 (protein); #46: SEQ ID NOS. 89 (DNA), SEQ ID NOS. 90 (protein); #48: SEQ ID NOS. 91 (DNA), SEQ ID NOS. 92 (protein); #50: SEQ ID NOS. 93 (DNA), SEQ ID NOS. 94 (protein).

For identification of NAAT-specific nanobodies, the $V_HH$ library was panned, for 4 rounds, on biotinylated 57NAAT1 like immobilized (at 100 μg/ml in PBS) on streptavidin coated plates. The antigen used for panning carried an AviTag™ (Avidity, LLC) at N-terminus and had been biotinylated in vitro by the supplier at this tag using *E. coli* BirA enzyme. The enrichment for antigen-specific phages was assessed after each round of panning. Based on sequence data of the positive colonies, 4 different full length Nanobodies were distinguished, belonging to 4 different CDR3 groups (B-cell lineages).

The NAAT-specific $V_HH$ library was panned and screened on non-biotinylated 57NAAT1like coated directly (passively) to a well. In total, 380 colonies (95 from round 2, 190 from round 3 and 95 from round 4) were randomly selected and analyzed by ELISA for the presence of antigen-specific nanobodies in their periplasmic extracts. Out of these 380 colonies, 224 colonies scored positive for the target antigen (57NAAT1like). Based on sequence data of the positive colonies, 30 different full length Nanobodies were distinguished, belonging to 24 different CDR3 groups (B-cell lineages). Some exemplary selected monospecific nanobody sequences are provided (NAAT monospecific nanobody #1: SEQ ID NOS. 73 (DNA), SEQ ID NOS. 74 (protein); #2: SEQ ID NOS. 75 (DNA), SEQ ID NOS. 76 (protein); #5: SEQ ID NOS. 77 (DNA), SEQ ID NOS. 78 (protein); #6: SEQ ID NOS. 79 (DNA), SEQ ID NOS. 80 (protein); #10: SEQ ID NOS. 81 (DNA), SEQ ID NOS. 82 (protein); #29: SEQ ID NOS. 83 (DNA), SEQ ID NOS. 84 (protein).

Nanobodies belonging to the same CDR3 group (same B-cell lineage) are very similar and their amino acid sequences suggest that they are from clonally-related B-cells resulting from somatic hypermutation or from the same B-cell but diversified due to RT and/or PCR error during library construction. Nanobodies belonging to the same CDR3 group recognize the same epitope but their other characteristics (e.g. affinity, potency, stability, expression yield, etc.) can be different.

Example 18. Identification of Preferred Cry1F Domain II-Specific Nanobodies

ELISA-based binding assays were performed using biotin-labeled 2Aa/1F/2Aa chimera and nanobodies developed against the Cry1F toxin core (termed Chi nanobodies). Microtiter ELISA plates (Immulon® 2HB 96 well plates, from Thermo Scientific) were coated overnight at room temperature with same amounts of individual Chi proteins in a total volume of 100 μl per well in TSE buffer (0.2 M Tris pH 8, 0.5 M sucrose, 1 mM EDTA). The wells were blocked in 0.5% BSA in PBS buffer (150 μl/well) and then were washed 3 times with binding buffer (0.1% BSA in PBS buffer, pH 7.4). Biotinylated 2Aa/1F/2Aa protein (0.1 μg in 100 μl of binding buffer) was added to each well, and reactions processed for one hour at room temperature with mild agitation. The solutions in each well were discarded and then the wells were washed 3 times with binding buffer for 10 min each. The plates were then incubated with streptavidin conjugated to horseradish peroxidase (1:5,000 dilutions in 100 µl binding buffer) for one hour at room temperature with shaking and then washed as above. Following the final wash, the wells were incubated with 1-step ultra TMB-ELISA substrate (50 µl/well) for 10 min. The reactions were stopped by adding 50 µl of 2 M $H_2SO_4$ and absorbance was measured at 450 nm using a microplate reader (Synergy™ HT from BioTek). Standard curves of two different preparations of biotinylated protein were performed and used for calculation of ng biotinylated protein bound per well. Four biological experiments were performed, each in technical duplicates. The data were analyzed using two-way ANOVA to identify monospecific nanobodies recognizing the 2Aa/1F/2Aa chimera as a proxy for binding to domain II of Cry1F.

Chi nanobodies were further characterized by determining the extent to which each individual nanobody protein can prevent the binding of cry 1F toxin to the FAW BBMV. Microtiter ELISA plates (Immulon 2HB 96 well plates, Thermo Scientific) were coated overnight at room temperature with solubilized Sf BBMV proteins (1.6 µg/well) in a total volume of 100 µl per well of PBS buffer. Two different BBMV preparations were used.

Equal amounts of cry1F nanobodies were mixed with biotinylated Cry1F trypsin activated toxin (0.25 µg/one reaction) in binding buffer. Enough mixtures were made for 7 reactions per nanobody (one reaction volume is 100 µl) in 1.5 ml tubes and the tubes were mixed and incubated at –20° C. for later use.

The ELISA plate wells were blocked in 0.5% BSA in PBS buffer (150 µl/well) for one hour at room temperature and then washed 3 times with binding buffer (0.1% BSA in PBS buffer, pH 7.4). Binding assays were performed by adding the biotinylated Cry1F/nanobody mixes to wells coated with FAW, BBMV proteins, testing each mixture in triplicate wells, and the reactions processed for one hour at room temperature with mild agitation. The reactions in each well were then discarded and each well was washed 3 times with binding buffer for 10 min each. The plates were then incubated with streptavidin conjugated to horseradish peroxidase (1:5,000 dilutions in 100 µl binding buffer) for one hour at room temperature with shaking and then washed as above. Following the final wash, the wells were incubated with 1-step ultra TMB-ELISA substrate for 6 min. The reactions were stopped by adding 2 M $H_2SO_4$ and absorbance was measured at 450 nm using a microplate reader (BioTek Synergy HT). Standard curves to know the amount of biotinylated Cry1F bound to each well were performed. The data are the means from experiments with two different BBMV preparations, each performed in triplicate. The data were analyzed using One Way ANOVA ($p=0.05$). The data show that Domain II-specific nanobodies prevent the majority of cry1F toxin from binding to the BBMV. This result confirmed that cry1F Domain II is required for binding to the native receptor on the BBMV and that the cry1F nanobodies prevent that binding from occurring.

Determining the Binding Affinity of cry1F Domain II-Specific Nanobodies

Binding saturation assays using ELISA of biotinylated Cry1F trypsin activated protein were performed with Cry1F nanobodies previously selected based on their binding to a chimera protein containing domain II of Cry1F (chimera nanobodies). Two different preparations of Cry1F protein were used in this experiment. Microtiter ELISA plates (Immulon 2HB 96 well plates, Thermo Scientific) were coated overnight at room temperature with the same amounts of chimera nanobodies in a total volume of 100 µl per well of TSE buffer. The wells were then blocked in 0.5% BSA in PBS buffer (150 µl/well), followed by washing three times with binding buffer (0.1% BSA in PBS buffer, pH 7.4). Saturation binding assays were performed using increasing concentrations (from 0 to 100 nM) of biotinylated Cry1F protein as ligand. The total reaction volume was 100 µl in binding buffer, and reactions processed for one hour at room temperature with mild agitation. Non-specific binding was determined in separate reactions including 300-fold excess of the homologous unlabeled protein. The reactions in each well were discarded and each well was washed 3 times with binding buffer for 10 min each. The plates were then incubated with streptavidin conjugated to horseradish peroxidase (1:5,000 dilutions in 100 µl binding buffer) for one hour at room temperature with shaking and then washed as above. Following the final wash, the wells were incubated with 1-step ultra TMB-ELISA substrate for 10 min. The reactions were stopped by adding 2 M $H_2SO_4$ and absorbance was measured at 450 nm using a microplate reader (BioTek Synergy HT). Standard curves to know the amount of biotinylated protein represented by a specific A450 were performed for Cry1F biotinylated protein and used to calculate the total and nonspecific binding as ng of biotinylated protein bound per well. Specific binding of each labeled protein was calculated by subtracting non-specific from total binding. The data are the means of experiments performed with two Cry1F preparations, each tested in duplicate. The specific binding data were plotted and analyzed using the SigmaPlot v.11.2 software (Systat Software, San Jose, CA) to obtain the apparent dissociation constant (Kd) and concentration of binding sites ($B_{max}$). The model used is based on the existence of a single binding site. The sequences of cry1F monospecific nanobodies selected from this assay are provided (monospecific nanobody #5: SEQ ID NOS. 67 (DNA), SEQ ID NOS. 72 (protein); #7: SEQ ID NOS. 69 (DNA), SEQ ID NOS. 70 (protein); #51: SEQ ID NOS. 71 (DNA), SEQ ID NOS. 72 (protein).

Example 19. Confirmation of Binding of NAAT and Cadherin Nanobodies to FAW BBMV

ELISA-based binding assays were performed using biotin-labeled solubilized *Spodoptera frugiperda* brush border membrane vesicles (Sf.BBMV) and NAAT nanobodies.

Microtiter ELISA plates (Immulon 2HB 96 well plates, Thermo Scientific) were coated overnight at room temperature with same amounts of NAAT or cadherin proteins in a total volume of 100 µl per well in TSE buffer (0.2 M Tris pH 8, 0.5 M sucrose, 1 mM EDTA). The wells were blocked in 0.5% BSA in PBS buffer (150 µl/well) and then were washed 3 times with binding buffer (0.1% BSA in PBS buffer, pH 7.4). Three different concentrations (0.1 µg, 1:3 and 1:10 dilutions) of biotinylated SfBBMV proteins were examined. The total reaction volume was 100 µl in binding buffer, and reactions processed for one hour at room temperature with mild agitation. The reactions in each well were discarded and then the wells were washed 3 times with binding buffer for 10 min each. The plates were then incubated with streptavidin conjugated to horseradish peroxidase (1:5,000 dilutions in 100 µl binding buffer) for one hour at room temperature with shaking and then washed as above. Following the final wash, the wells were incubated with 1-step ultra TMB-ELISA substrate (50 µl/well) for 10 min. The reactions were stopped by adding 50 µl of 2 M $H_2SO_4$ and absorbance was measured at 450 nm using a microplate reader (BioTek Synergy HT). Standard curves of two different preparations of biotinylated SfBBMV proteins were performed and used for calculation of ng biotinylated protein bound per well. The results are the means of 2 different experiments performed in duplicate (2 biological replicates). The data were analyzed using two-way ANOVA.

The sequences of NAAT monospecific nanobodies chosen for further analysis are provided SEQ ID NOS.: 73, 75, 77, 79, 81, 83, 129, 131, 133 (DNA) and 74, 76, 78, 80, 82, 84, 130, 132, 134 (Protein). The sequences of the various Cadherin monospecific nanobodies chosen for further analysis are provided: SEQ ID NOS. 85, 87, 89, 91, 93, 117, 119, 121, 123, 125, 127 (DNA) and 86, 88, 90, 92, 94, 118, 120, 122, 124, 126, 128 (Protein).

Example 20. Cloning of Bispecific Nanobodies

Bispecific nanobodies were cloned into either the pMECS phagemid vector or the pHEN6c plasmid vector (Conrath et al., 2001). pHEN6 vector carries the PelB signal sequence at the N-terminus and HA epitope tag at the C-terminus and does not carry the gene III of M13 phage. In all cases, bispecific nanobodies are cloned in frame and immediately downstream of the PelB signal sequence (SEQ ID NOS. 66) and consist of a cry1F-specific nanobody (#5, 7 or 51 from Example 19) followed by a short peptide linker, a NAAT- or Cadherin-specific nanobody, and HA-His6 (pMECS) or HA epitope tags (pHEN6). See Table 4 for the combinations of bispecific nanobodies made and tested.

The peptide linkers cloned between the monospecific cry1F and NAAT or Cadherin nanobodies were chosen to optimize the antigen-binding properties and stability of the expressed fusions proteins. To this end, linkers with several different properties, as described below, were tested. See sequences in SEQ ID NOS. 54, 56, 58, 60, 62, 64 (protein) or SEQ ID NOS. 55, 57, 59, 61, 63, 65.

"Rigid" linkers:

PTPTn (Proline-Threonine, SEQ ID NOS. 64 (protein), 65 (DNA))—Proline and threonine amino acids are preferred amino acids found in natural linkers. Proline is a unique amino acid with a cyclic side chain that causes a very restricted conformation. Further, the lack of amide hydrogen on proline may prevent the formation of hydrogen bonds with other amino acids, thereby reducing the potential interaction of the linker with the other protein domains. On the other hand, threonine is a small polar amino acid that may help maintain the stability of the linker structure in the aqueous environment through formation of hydrogen bonds with water (reviewed in Chen et al., 2013).

AEAAAK3 (SEQ ID. NOS. 56 (protein), 57 (DNA)) was chosen as a variation of the natural linker between the lipoyl and E3 binding domains in pyruvate dehydrogenase enzyme and has been used in several fusion proteins, including to tobacco mosaic virus coat protein for overexpression of fusions proteins in tobacco or as a helical linker in transferrin-based fusion proteins in human cells.

Linker 218 as provided in SEQ ID NOS. 54 (protein), 55 (DNA) imparts enhanced proteolytic stability and reduced aggregation characteristics and was used in some exemplary embodiments.

"Flexible" Linkers:

Gly8 (SEQ ID NOS. 62 (protein), 63(DNA) and Gly4Ser1X3 (SEQ ID NOS. 60 (protein), 61(DNA) linkers can increase the accessibility of an epitope to antibodies and improve protein folding. These linkers have also been demonstrated to be stable against proteolytic enzymes, especially important for stability of the fusion protein in the insect gut.

The ESGSVSSEQLAQFRSLD (SEQ ID NOS 58 (protein), 59(DNA) linker has been used for the construction of a bioactive single-chain Fv antibody.

In total, more than 140 combinations of bispecific nanobodies were cloned and tested as shown in Table 4. The amino acid sequences of some exemplary bispecific nanobodies are provided in SEQ. ID. NOS. 96 (#22), 98(#43), 100 (#48), 102 (#49), 104 (#50), 106 (#53), 108 (#62), 110 (#64), 112 (#76), 114 (#85) and 116 (#87) and the nucleotide sequence are SEQ. ID. NOS. 95 (#22), 97 (#43), 99 (#48), 101 (#49), 103 (#50), 105 (#53), 107 (#62), 109 (#64), 111 (#76), 113 (#85) and 115 (#87).

TABLE 4

Listing of bispecific nanobody clone combinations that were synthesized and tested in bioassays. Sequences of some exemplary bispecific nanobodies are provided in the list of sequences and the sequence listing.

| Bispecific Nanobody clone # | cry1F nanobody | Linker | NAAT or Cadherin nanobody |
|---|---|---|---|
| 1 | cry1F#5 (SEQ ID NO. 67 (DNA), 68 (protein)) | 218 (SEQ ID NO. 54 (protein), 55 (DNA)) | NAAT29 (SEQ ID NO. 83 (DNA), 84 (protein)) |
| 2 | cry1F#7 (SEQ ID NO. 69 (DNA), 70 (protein)) | 218 (SEQ ID NO. 54 (protein), 55 (DNA)) | NAAT29 (SEQ ID NO. 83 (DNA), 84 (protein)) |
| 3 | cry1F#5 (SEQ ID NO. 67 (DNA), 68 (protein)) | AEAAAK3 (SEQ ID NO. 56 (protein), 57(DNA)) | NAAT29 (SEQ ID NO. 83 (DNA), 84 (protein)) |
| 4 | cry1F#5 (SEQ ID NO. 67 (DNA), 68 (protein)) | ESGSV (SEQ ID NO. 58 (protein), 59 (DNA)) | NAAT29 (SEQ ID NO. 83 (DNA), 84 (protein)) |
| 5 | Cry1F#51 (SEQ ID NO. 71 (DNA), 72 (protein)) | 218 (SEQ ID NO. 54 (protein), 55 (DNA)) | NAAT29 (SEQ ID NO. 83 (DNA), 84 (protein)) |
| 6 | cry1F#5 (SEQ ID NO. 67 (DNA), 68 (protein)) | Gly4Ser1X3 (SEQ ID NO. 60 (protein), 61 (DNA)) | NAAT29 (SEQ ID NO. 83 (DNA), 84 (protein)) |
| 7 | cry1F#5 (SEQ ID NO. 67 (DNA), 68 (protein)) | Gly8 (SEQ ID NO. 62 (protein), 63 (DNA)) | NAAT29 (SEQ ID NO. 83 (DNA), 84 (protein)) |
| 8 | cry1F#5 (SEQ ID NO. 67 (DNA), 68 (protein)) | PTPT (SEQ ID NO. 64 (protein), 65 (DNA)) | NAAT29 (SEQ ID NO. 83 (DNA), 84 (protein)) |
| 9 | cry1F#7 (SEQ ID NO. 69 (DNA), 70 (protein)) | AEAAAK3 (SEQ ID NO. 56 (protein), 57(DNA)) | NAAT29 (SEQ ID NO. 83 (DNA), 84 (protein)) |
| 10 | Cry1F#51 (SEQ ID NO. 71 (DNA), 72 (protein)) | AEAAAK3 (SEQ ID NO. 56 (protein), 57(DNA)) | NAAT29 (SEQ ID NO. 83 (DNA), 84 (protein)) |

TABLE 4-continued

Listing of bispecific nanobody clone combinations that were synthesized and tested in bioassays. Sequences of some exemplary bispecific nanobodies are provided in the list of sequences and the sequence listing.

| Bispecific Nanobody clone # | cry1F nanobody | Linker | NAAT or Cadherin nanobody |
|---|---|---|---|
| 11 | cry1F#5 (SEQ ID NO. 67 (DNA), 68 (protein)) | 218 ( TABLE 4-continued Listing of bispecific nanobody clone combinations that were synthesized and tested in bioassays. Sequences of some exemplary bispecific nanobodies are provided in the list of sequences and the sequence listing.

| Bispecific Nanobody clone # | cry1F nanobody | Linker | NAAT or Cadherin nanobody |
|---|---|---|---|
| 51 | Cry1F#51 (SEQ ID NO. 71 (DNA), 72 (protein)) | PTPT (SEQ ID NO. 64 (protein), 65 (DNA)) | Cad38 (SEQ ID NO. 121 (DNA), 122 (protein)) |
| 52 | Cry1F#51 (SEQ ID NO. 71 (DNA), 72 (protein)) | PTPT (SEQ ID NO. 64 (protein), 65 (DNA)) | Cad51 (SEQ ID NO. 119 (DNA), 120 (protein)) |
| 53 | Cry1F#51 (SEQ ID NO. 71 (DNA), 72 (protein)) | gly8 (SEQ ID NO. 62 (protein), 63 (DNA)) | Cad46 (SEQ ID NO. 89 (DNA), 90 (protein)) |
| 54 | Cry1F#51 (SEQ ID NO. 71 (DNA), 72 (protein)) | PTPT (SEQ ID NO. 64 (protein), 65 (DNA)) | Cad41 (SEQ ID NO. 127 (DNA), 128 (protein)) |
| 55 | Cry1F#51 (SEQ ID NO. 71 (DNA), 72 (protein)) | gly8 (SEQ ID NO. 62 (protein), 63 (DNA)) | Cad47 (SEQ ID NO. 123 (DNA), 124 (protein)) |
| 56 | Cry1F#51 (SEQ ID NO. 71 (DNA), 72 (protein)) | PTPT (SEQ ID NO. 64 (protein), 65 (DNA)) | Cad43 (SEQ ID NO. 87 (DNA), 88 (protein)) |
| 57 | Cry1F#51 (SEQ ID NO. 71 (DNA), 72 (protein)) | gly8 (SEQ ID NO. 62 (protein), 63 (DNA)) | Cad31 (SEQ ID NO. 125 (DNA), 126 (protein)) |
| 58 | Cry1F#51 (SEQ ID NO. 71 (DNA), 72 (protein)) | PTPT (SEQ ID NO. 64 (protein), 65 (DNA)) | Cad46 (SEQ ID NO. 89 (DNA), 90 (protein)) |
| 59 | Cry1F#51 (SEQ ID NO. 71 (DNA), 72 (protein)) | gly8 (SEQ ID NO. 62 (protein), 63 (DNA)) | Cad49 (SEQ ID NO. 117 (DNA), 118 (protein)) |
| 60 | Cry1F#51 (SEQ ID NO. 71 (DNA), 72 (protein)) | PTPT (SEQ ID NO. 64 (protein), 65 (DNA)) | Cad47 (SEQ ID NO. 123 (DNA), 124 (protein)) |
| 61 | cry1F#7 (SEQ ID NO. 69 (DNA), 70 (protein)) | gly8 (SEQ ID NO. 62 (protein), 63 (DNA)) | NAAT1 (SEQ ID NO. 73 (DNA), 74 (PROTEIN)) |
| 62 | cry1F#7 (SEQ ID NO. 69 (DNA), 70 (protein)) | PTPT (SEQ ID NO. 64 (protein), 65 (DNA)) | NAAT1 (SEQ ID NO. 73 (DNA), 74 (PROTEIN)) |
| 63 | cry1F#7 (SEQ ID NO. 69 (DNA), 70 (protein)) | gly8 (SEQ ID NO. 62 (protein), 63 (DNA)) | NAAT2 (SEQ ID NO. 75 (DNA), 76 (PROTEIN)) |
| 64 | cry1F#7 (SEQ ID NO. 69 (DNA), 70 (protein)) | PTPT (SEQ ID NO. 64 (protein), 65 (DNA)) | NAAT2 (SEQ ID NO. 75 (DNA), 76 (PROTEIN)) |
| 65 | cry1F#7 (SEQ ID NO. 69 (DNA), 70 (protein)) | gly8 (SEQ ID NO. 62 (protein), 63 (DNA)) | NAAT3 (SEQ ID NO. 129 (DNA), 130 (PROTEIN)) |
| 66 | cry1F#7 (SEQ ID NO. 69 (DNA), 70 (protein)) | PTPT (SEQ ID NO. 64 (protein), 65 (DNA)) | NAAT3 (SEQ ID NO. 129 (DNA), 130 (PROTEIN)) |
| 67 | cry1F#7 (SEQ ID NO. 69 (DNA), 70 (protein)) | gly8 (SEQ ID NO. 62 (protein), 63 (DNA)) | NAAT4 (SEQ ID NO. 131 (DNA), 132 (PROTEIN)) |
| 68 | cry1F#7 (SEQ ID NO. 69 (DNA), 70 (protein)) | PTPT (SEQ ID NO. 64 (protein), 65 (DNA)) | NAAT4 (SEQ ID NO. 131 (DNA), 132 (PROTEIN)) |
| 69 | cry1F#7 (SEQ ID NO. 69 (DNA), 70 (protein)) | gly8 (SEQ ID NO. 62 (protein), 63 (DNA)) | NAAT5 (SEQ ID NO. 77 (DNA), 78 (PROTEIN)) |
| 70 | cry1F#7 (SEQ ID NO. 69 (DNA), 70 (protein)) | PTPT (SEQ ID NO. 64 (protein), 65 (DNA)) | NAAT5 (SEQ ID NO. 77 (DNA), 78 (PROTEIN)) |
| 71 | cry1F#7 (SEQ ID NO. 69 (DNA), 70 (protein)) | gly8 (SEQ ID NO. 62 (protein), 63 (DNA)) | NAAT6 (SEQ ID NO. 79 (DNA), 80 (PROTEIN)) |
| 72 | cry1F#7 (SEQ ID NO. 69 (DNA), 70 (protein)) | PTPT (SEQ ID NO. 64 (protein), 65 (DNA)) | NAAT6 (SEQ ID NO. 79 (DNA), 80 (PROTEIN)) |
| 73 | cry1F#7 (SEQ ID NO. 69 (DNA), 70 (protein)) | gly8 (SEQ ID NO. 62 (protein), 63 (DNA)) | NAAT7 (SEQ ID NO. 133 (DNA), 134 (PROTEIN)) |
| 74 | cry1F#7 (SEQ ID NO. 69 (DNA), 70 (protein)) | PTPT (SEQ ID NO. 64 (protein), 65 (DNA)) | NAAT7 (SEQ ID NO. 133 (DNA), 134 (PROTEIN)) |
| 75 | cry1F#7 (SEQ ID NO. 69 (DNA), 70 (protein)) | gly8 (SEQ ID NO. 62 (protein), 63 (DNA)) | NAAT10 (SEQ ID NO. 81 (DNA), 82 (PROTEIN)) |
| 76 | cry1F#7 (SEQ ID NO. 69 (DNA), 70 (protein)) | PTPT (SEQ ID NO. 64 (protein), 65 (DNA)) | NAAT10 (SEQ ID NO. 81 (DNA), 82 (PROTEIN)) |
| 77 | Cry1F#51 (SEQ ID NO. 71 (DNA), 72 (protein)) | gly8 (SEQ ID NO. 62 (protein), 63 (DNA)) | NAAT1 (SEQ ID NO. 73 (DNA), 74 (PROTEIN)) |
| 78 | Cry1F#51 (SEQ ID NO. 71 (DNA), 72 (protein)) | PTPT (SEQ ID NO. 64 (protein), 65 (DNA)) | NAAT1 (SEQ ID NO. 73 (DNA), 74 (PROTEIN)) |
| 79 | Cry1F#51 (SEQ ID NO. 71 (DNA), 72 (protein)) | gly8 (SEQ ID NO. 62 (protein), 63 (DNA)) | NAAT2 (SEQ ID NO. 75 (DNA), 76 (PROTEIN)) |
| 80 | Cry1F#51 (SEQ ID NO. 71 (DNA), 72 (protein)) | PTPT (SEQ ID NO. 64 (protein), 65 (DNA)) | NAAT2 (SEQ ID NO. 75 (DNA), 76 (PROTEIN)) |
| 81 | Cry1F#51 (SEQ ID NO. 71 (DNA), 72 (protein)) | gly8 (SEQ ID NO. 62 (protein), 63 (DNA)) | NAAT3 (SEQ ID NO. 129 (DNA), 130 (PROTEIN)) |
| 82 | Cry1F#51 (SEQ ID NO. 71 (DNA), 72 (protein)) | PTPT (SEQ ID NO. 64 (protein), 65 (DNA)) | NAAT3 (SEQ ID NO. 129 (DNA), 130 (PROTEIN)) |
| 83 | Cry1F#51 (SEQ ID NO. 71 (DNA), 72 (protein)) | gly8 (SEQ ID NO. 62 (protein), 63 (DNA)) | NAAT4 (SEQ ID NO. 131 (DNA), 132 (PROTEIN)) |
| 84 | Cry1F#51 (SEQ ID NO. 71 (DNA), 72 (protein)) | PTPT (SEQ ID NO. 64 (protein), 65 (DNA)) | NAAT4 (SEQ ID NO. 131 (DNA), 132 (PROTEIN)) |
| 85 | Cry1F#51 (SEQ ID NO. 71 (DNA), 72 (protein)) | gly8 (SEQ ID NO. 62 (protein), 63 (DNA)) | NAAT5 (SEQ ID NO. 77 (DNA), 78 (PROTEIN)) |
| 86 | Cry1F#51 (SEQ ID NO. 71 (DNA), 72 (protein)) | PTPT (SEQ ID NO. 64 (protein), 65 (DNA)) | NAAT5 (SEQ ID NO. 77 (DNA), 78 (PROTEIN)) |

TABLE 4-continued

Listing of bispecific nanobody clone combinations that were synthesized and tested in bioassays. Sequences of some exemplary bispecific nanobodies are provided in the list of sequences and the sequence listing.

| Bispecific Nanobody clone # | cry1F nanobody | Linker | NAAT or Cadherin nanobody |
|---|---|---|---|
| 87 | Cry1F#51 (SEQ ID NO. 71 (DNA), 72 (protein)) | gly8 (SEQ ID NO. 62 (protein), 63 (DNA)) | NAAT6 (SEQ ID NO. 79 (DNA), 80 (PROTEIN)) |
| 88 | Cry1F#51 (SEQ ID NO. 71 (DNA), 72 (protein)) | PTPT (SEQ ID NO. 64 (protein), 65 (DNA)) | NAAT6 (SEQ ID NO. 79 (DNA), 80 (PROTEIN)) |
| 89 | Cry1F#51 (SEQ ID NO. 71 (DNA), 72 (protein)) | gly8 (SEQ ID NO. 62 (protein), 63 (DNA)) | NAAT7 (SEQ ID NO. 133 (DNA), 134 (PROTEIN)) |
| 90 | Cry1F#51 (SEQ ID NO. 71 (DNA), 72 (protein)) | PTPT (SEQ ID NO. 64 (protein), 65 (DNA)) | NAAT7 (SEQ ID NO. 133 (DNA), 134 (PROTEIN)) |
| 91 | Cry1F#51 (SEQ ID NO. 71 (DNA), 72 (protein)) | gly8 (SEQ ID NO. 62 (protein), 63 (DNA)) | NAAT10 (SEQ ID NO. 81 (DNA), 82 (PROTEIN)) |
| 92 | Cry1F#51 (SEQ ID NO. 71 (DNA), 72 (protein)) | PTPT (SEQ ID NO. 64 (protein), 65 (DNA)) | NAAT10 (SEQ ID NO. 81 (DNA), 82 (PROTEIN)) |
| 93 | cry1F#7 (SEQ ID NO. 69 (DNA), 70 (protein)) | gly8 (SEQ ID NO. 62 (protein), 63 (DNA)) | Cad2 (SEQ ID NO. 85 (DNA), 86 (protein)) |
| 94 | cry1F#7 (SEQ ID NO. 69 (DNA), 70 (protein)) | gly8 (SEQ ID NO. 62 (protein, 63 (DNA)) | Cad50 (SEQ ID NO. 93 (DNA), 94 (protein)) |
| 95 | cry1F#7 (SEQ ID NO. 69 (DNA), 70 (protein)) | PTPT (SEQ ID NO. 64 (protein), 65 (DNA)) | Cad31 (SEQ ID NO. 125 (DNA), 126 (protein)) |
| 96 | cry1F#7 (SEQ ID NO. 69 (DNA), 70 (protein)) | gly8 (SEQ ID NO. 62 (protein), 63 (DNA)) | Cad38 (SEQ ID NO. 121 (DNA), 122 (protein)) |
| 97 | cry1F#7 (SEQ ID NO. 69 (DNA), 70 (protein)) | gly8 (SEQ ID NO. 62 (protein), 63 (DNA)) | Cad51 (SEQ ID NO. 119 (DNA), 120 (protein)) |
| 98 | cry1F#7 (SEQ ID NO. 69 (DNA), 70 (protein)) | PTPT (SEQ ID NO. 64 (protein), 65 (DNA)) | Cad49 (SEQ ID NO. 117 (DNA), 118 (protein)) |
| 99 | cry1F#7 (SEQ ID NO. 69 (DNA), 70 (protein)) | gly8 (SEQ ID NO. 62 (protein), 63 (DNA)) | Cad41 (SEQ ID NO. 127 (DNA), 128 (protein)) |
| 100 | cry1F#7 (SEQ ID NO. 69 (DNA), 70 (protein)) | PTPT (SEQ ID NO. 64 (protein), 65 (DNA)) | Cad2 (SEQ ID NO. 85 (DNA), 86 (protein)) |
| 101 | cry1F#7 (SEQ ID NO. 69 (DNA), 70 (protein)) | PTPT (SEQ ID NO. 64 (protein), 65 (DNA)) | Cad50 (SEQ ID NO. 93 (DNA), 94 (protein)) |
| 102 | cry1F#7 (SEQ ID NO. 69 (DNA), 70 (protein)) | gly8 (SEQ ID NO. 62 (protein), 63 (DNA)) | Cad43 (SEQ ID NO. 87 (DNA), 88 (protein)) |
| 103 | cry1F#7 (SEQ ID NO. 69 (DNA), 70 (protein)) | PTPT (SEQ ID NO. 64 (protein), 65 (DNA)) | Cad38 (SEQ ID NO. 121 (DNA), 122 (protein)) |
| 104 | cry1F#7 (SEQ ID NO. 69 (DNA), 70 (protein)) | PTPT (SEQ ID NO. 64 (protein), 65 (DNA)) | Cad51 (SEQ ID NO. 119 (DNA), 120 (protein)) |
| 105 | cry1F#7 (SEQ ID NO. 69 (DNA), 70 (protein)) | gly8 (SEQ ID NO. 62 (protein), 63 (DNA)) | Cad46 (SEQ ID NO. 89 (DNA), 90 (protein)) |
| 106 | cry1F#7 (SEQ ID NO. 69 (DNA), 70 (protein)) | PTPT (SEQ ID NO. 64 (protein), 65 (DNA)) | Cad41 (SEQ ID NO. 127 (DNA), 128 (protein)) |
| 107 | cry1F#7 (SEQ ID NO. 69 (DNA), 70 (protein)) | gly8 (SEQ ID NO. 62 (protein), 63 (DNA)) | Cad47 (SEQ ID NO. 123 (DNA), 124 (protein)) |
| 108 | cry1F#7 (SEQ ID NO. 69 (DNA), 70 (protein)) | PTPT (SEQ ID NO. 64 (protein), 65 (DNA)) | Cad43 (SEQ ID NO. 87 (DNA), 88 (protein)) |
| 109 | cry1F#7 (SEQ ID NO. 69 (DNA), 70 (protein)) | gly8 (SEQ ID NO. 62 (protein), 63 (DNA)) | Cad31 (SEQ ID NO. 125 (DNA), 126 (protein)) |
| 110 | cry1F#7 (SEQ ID NO. 69 (DNA), 70 (protein)) | PTPT (SEQ ID NO. 64 (protein), 65 (DNA)) | Cad46 (SEQ ID NO. 89 (DNA), 90 (protein)) |
| 111 | cry1F#7 (SEQ ID NO. 69 (DNA), 70 (protein)) | gly8 (SEQ ID NO. 62 (protein), 63 (DNA)) | Cad49 (SEQ ID NO. 117 (DNA), 118 (protein)) |
| 112 | cry1F#7 (SEQ ID NO. 69 (DNA), 70 (protein)) | PTPT (SEQ ID NO. 64 (protein), 65 (DNA)) | Cad47 (SEQ ID NO. 123 (DNA), 124 (protein)) |
| 113 | cry1F#5 (SEQ ID NO. 67 (DNA), 68 (protein)) | gly8 (SEQ ID NO. 62 (protein), 63 (DNA)) | NAATI (SEQ ID NO. 73 (DNA), 74 (PROTEIN)) |
| 114 | cry1F#5 (SEQ ID NO. 67 (DNA), 68 (protein)) | PTPT (SEQ ID NO. 64 (protein), 65 (DNA)) | NAAT2 (SEQ ID NO. 75 (DNA), 76 (PROTEIN)) |
| 115 | cry1F#5 (SEQ ID NO. 67 (DNA), 68 (protein)) | gly8 (SEQ ID NO. 62 (protein), 63 (DNA)) | NAAT3 (SEQ ID NO. 129 (DNA), 130 (PROTEIN)) |
| 116 | cry1F#5 (SEQ ID NO. 67 (DNA), 68 (protein)) | PTPT (SEQ ID NO. 64 (protein), 65 (DNA)) | NAAT3 (SEQ ID NO. 129 (DNA), 130 (PROTEIN)) |
| 117 | cry1F#5 (SEQ ID NO. 67 (DNA), 68 (protein)) | gly8 (SEQ ID NO. 62 (protein), 63 (DNA)) | NAAT4 (SEQ ID NO. 131 (DNA), 132 (PROTEIN)) |
| 118 | cry1F#5 (SEQ ID NO. 67 (DNA), 68 (protein)) | PTPT (SEQ ID NO. 64 (protein), 65 (DNA)) | NAAT4 (SEQ ID NO. 131 (DNA), 132 (PROTEIN)) |
| 119 | cry1F#5 (SEQ ID NO. 67 (DNA), 68 (protein)) | gly8 (SEQ ID NO. 62 (protein), 63 (DNA)) | NAAT5 (SEQ ID NO. 77 (DNA), 78 (PROTEIN)) |
| 120 | cry1F#5 (SEQ ID NO. 67 (DNA), 68 (protein)) | PTPT (SEQ ID NO. 64 (protein), 65 (DNA)) | NAAT5 (SEQ ID NO. 77 (DNA), 78 (PROTEIN)) |
| 121 | cry1F#5 (SEQ ID NO. 67 (DNA), 68 (protein)) | gly8 (SEQ ID NO. 62 (protein), 63 (DNA)) | NAAT6 (SEQ ID NO. 79 (DNA), 80 (PROTEIN)) |
| 122 | cry1F#5 (SEQ ID NO. 67 (DNA), 68 (protein)) | PTPT (SEQ ID NO. 64 (protein), 65 (DNA)) | NAAT6 (SEQ ID NO. 79 (DNA), 80 (PROTEIN)) |

TABLE 4-continued

Listing of bispecific nanobody clone combinations that were synthesized and tested in bioassays. Sequences of some exemplary bispecific nanobodies are provided in the list of sequences and the sequence listing.

| Bispecific Nanobody clone # | cry1F nanobody | Linker | NAAT or Cadherin nanobody |
|---|---|---|---|
| 123 | cry1F#5 (SEQ ID NO. 67 (DNA), 68 (protein)) | gly8 (SEQ ID NO. 62 (protein), 63 (DNA)) | NAAT7 (SEQ ID NO. 133 (DNA), 134 (PROTEIN)) |
| 124 | cry1F#5 (SEQ ID NO. 67 (DNA), 68 (protein)) | PTPT (SEQ ID NO. 64 (protein), 65 (DNA)) | NAAT7 (SEQ ID NO. 133 (DNA), 134 (PROTEIN)) |
| 125 | cry1F#5 (SEQ ID NO. 67 (DNA), 68 (protein)) | gly8 (SEQ ID NO. 62 (protein), 63 (DNA)) | NAAT10 (SEQ ID NO. 81 (DNA), 82 (PROTEIN)) |
| 126 | cry1F#5 (SEQ ID NO. 67 (DNA), 68 (protein)) | PTPT (SEQ ID NO. 64 (protein), 65 (DNA)) | NAAT10 (SEQ ID NO. 81 (DNA), 82 (PROTEIN)) |
| 127 | cry1F#5 (SEQ ID NO. 67 (DNA), 68 (protein)) | PTPT (SEQ ID NO. 64 (protein), 65 (DNA)) | NAAT1 (SEQ ID NO. 73 (DNA), 74 (PROTEIN)) |
| 128 | cry1F#5 (SEQ ID NO. 67 (DNA), 68 (protein)) | gly8 (SEQ ID NO. 62 (protein), 63 (DNA)) | Cad2 (SEQ ID NO. 85 (DNA), 86 (protein)) |
| 129 | cry1F#5 (SEQ ID NO. 67 (DNA), 68 (protein)) | gly8 (SEQ ID NO. 62 (protein), 63 (DNA)) | Cad50 (SEQ ID NO. 93 (DNA), 94 (protein)) |
| 130 | cry1F#5 (SEQ ID NO. 67 (DNA), 68 (protein)) | PTPT (SEQ ID NO. 64 (protein), 65 (DNA)) | Cad31 (SEQ ID NO. 125 (DNA), 126 (protein)) |
| 131 | cry1F#5 (SEQ ID NO. 67 (DNA), 68 (protein)) | gly8 (SEQ ID NO. 62 (protein), 63 (DNA)) | Cad38 (SEQ ID NO. 121 (DNA), 122 (protein)) |
| 132 | cry1F#5 (SEQ ID NO. 67 (DNA), 68 (protein)) | gly8 (SEQ ID NO. 62 (protein), 63 (DNA)) | Cad51 (SEQ ID NO. 119 (DNA), 120 (protein)) |
| 133 | cry1F#5 (SEQ ID NO. 67 (DNA), 68 (protein)) | PTPT (SEQ ID NO. 64 (protein), 65 (DNA)) | Cad49 (SEQ ID NO. 117 (DNA), 118 (protein)) |
| 134 | cry1F#5 (SEQ ID NO. 67 (DNA), 68 (protein)) | gly8 (SEQ ID NO. 62 (protein), 63 (DNA)) | Cad41 (SEQ ID NO. 127 (DNA), 128 (protein)) |
| 135 | cry1F#5 (SEQ ID NO. 67 (DNA), 68 (protein)) | PTPT (SEQ ID NO. 64 (protein), 65 (DNA)) | Cad2 (SEQ ID NO. 85 (DNA), 86 (protein)) |
| 136 | cry1F#5 (SEQ ID NO. 67 (DNA), 68 (protein)) | PTPT (SEQ ID NO. 64 (protein), 65 (DNA)) | Cad50 (SEQ ID NO. 93 (DNA), 94 (protein)) |
| 137 | cry1F#5 (SEQ ID NO. 67 (DNA), 68 (protein)) | gly8 (SEQ ID NO. 62 (protein, 63 (DNA)) | Cad43 (SEQ ID NO. 87 (DNA), 88 (protein)) |
| 138 | cry1F#5 (SEQ ID NO. 67 (DNA), 68 (protein)) | PTPT (SEQ ID NO. 64 (protein), 65 (DNA)) | Cad38 (SEQ ID NO. 121 (DNA), 122 (protein)) |
| 139 | cry1F#5 (SEQ ID NO. 67 (DNA), 68 (protein)) | PTPT (SEQ ID NO. 64 (protein), 65 (DNA)) | Cad51 (SEQ ID NO. 119 (DNA), 120 (protein)) |
| 140 | cry1F#5 (SEQ ID NO. 67 (DNA), 68 (protein)) | gly8 (SEQ ID NO. 62 (protein), 63 (DNA)) | Cad46 (SEQ ID NO. 89 (DNA), 90 (protein)) |
| 141 | cry1F#5 (SEQ ID NO. 67 (DNA), 68 (protein)) | PTPT (SEQ ID NO. 64 (protein), 65 (DNA)) | Cad41 (SEQ ID NO. 127 (DNA), 128 (protein)) |
| 142 | cry1F#5 (SEQ ID NO. 67 (DNA), 68 (protein)) | gly8 (SEQ ID NO. 62 (protein), 63 (DNA)) | Cad47 (SEQ ID NO. 123 (DNA), 124 (protein)) |
| 143 | cry1F#5 (SEQ ID NO. 67 (DNA), 68 (protein)) | PTPT (SEQ ID NO. 64 (protein), 65 (DNA)) | Cad43 (SEQ ID NO. 87 (DNA), 88 (protein)) |
| 144 | cry1F#5 (SEQ ID NO. 67 (DNA), 68 (protein)) | gly8 (SEQ ID NO. 62 (protein), 63 (DNA)) | Cad31 (SEQ ID NO. 125 (DNA), 126 (protein)) |
| 145 | cry1F#5 (SEQ ID NO. 67 (DNA), 68 (protein)) | PTPT (SEQ ID NO. 64 (protein), 65 (DNA)) | Cad46 (SEQ ID NO. 89 (DNA), 90 (protein)) |
| 146 | cry1F#5 (SEQ ID NO. 67 (DNA), 68 (protein)) | gly8 (SEQ ID NO. 62 (protein), 63 (DNA)) | Cad49 (SEQ ID NO. 117 (DNA), 118 (protein)) |
| 147 | cry1F#5 (SEQ ID NO. 67 (DNA), 68 (protein)) | PTPT (SEQ ID NO. 64 (protein), 65 (DNA)) | Cad47 (SEQ ID NO. 123 (DNA), 124 (protein)) |
| 148 | cry1F#5 (SEQ ID NO. 67 (DNA), 68 (protein)) | gly8 (SEQ ID NO. 62 (protein), 63 (DNA)) | NAAT2 (SEQ ID NO. 75 (DNA), 76 (PROTEIN)) |

Example 21. Purification of Bispecific Nanobodies from *E. coli*

The plasmids expressing bispecific nanobodies were chemically transformed into WK6 *E. coli*. A single colony from each transformation reaction was used. Periplasmic membrane protein extractions were performed in 10 ml of TSE buffer (0.2 M Tris, pH 8, 0.5 M Sucrose and 1 mM EDTA), overnight at 4° C. in end to end shaking to ensure maximum extraction, and the supernatants were extensively dialyzed against PBS pH 7.4 buffer overnight at 4° C. to get rid of EDTA that would interfere with the subsequent purification process.

His-tagged BsNbs were purified using His-Trap-Q-HP columns and 20 mM Tris pH 7.4, 0.3 M NaCl, 20 mM imidazole. Elution of His-tagged BsNbs was performed using 0.5 M imidazole over 10 column volumes. Fractions within the observed peaks were pooled, aliquoted and saved at −20° C. for later use.

Example 22. Bispecific Nanobodies Enhance the Activity of Cry1F Toxin Against FAW Bioassays of Purified BsNb with or without Trypsin Activated Cry1Fa ($LC_{50}$ Dose)

Bioassays with purified BsNbs were performed with or without Cry1Fa toxin. The Cry1F toxin was used at the $LC_{50}$ concentration estimated above. For the bioassays, the BsNb purified proteins were mixed with Cry1Fa toxin in a 3:1 molar ratio (Nb:toxin) in a final volume of 750 μl of autoclaved MilliQ water. The molecular weight of BsNbs used for molarity calculations was ~30 kDa, the amount of BsNb based on a 3:1 molar ratio is 6.33 µM (14.25 µg in 750 µl volume). Mixtures were incubated at room temperature for one hour and then stored on ice until applied on the surface of meridic diet. Once the meridic diet had set and dried in individual wells of 128-cell polystyrene bioassay trays, all treatments were applied on the diet surface, with 16 wells used per one treatment. The buffer used for BsNb extraction and water used for dilutions were used as control treatments. After the treatments had dried on the diet, a single FAW neonate was placed per well and trays incubated at 26±2° C. and 16L:8D photoperiod. Mortality was determined after 7 days of incubation.

The $LC_{50}$ and $LC_{90}$ of trypsin activated Cry1Fa were calculated by Probit analysis from two independent bioassays using the *S. frugiperda* strain from Benzon Inc. The buffer used for BsNb extraction and water used for dilutions were used as control treatments.

Based on bioassay data, numerous bispecific nanobodies enhance the activity of cry1F toxin significantly above its $LC_{50}$ mortality values over several repeated experiments. In several cases, 100% mortality of susceptible wild-type insects was observed. An example of bioassay data is shown in Table 5. Addition of Cry1F toxin to the diet bioassay at the predetermined $LC_{50}$ dose results in 40.6% mortality of the wild-type insects, whereas buffer and water controls have only minimal effect on insects. Likewise, in the absence of cry1F toxin, minimal effects on insects from any of the bispecific nanobodies is observed. In contrast, several bispecific nanobodies (shaded) gave significantly higher insect mortality in this experiment (at least 75% of insects' dead). Furthermore, the average weight of surviving insects is significantly less than insects treated with cry1F toxin alone.

TABLE 5

Bioassay Data

| Wild-type BsNb (see Table 4) | without Cry1Fa | | | with Cry1Fa ($LC_{50}$ dose) | | |
|---|---|---|---|---|---|---|
| | Dead | Live | % Mortality | Dead | Live | % Mortality |
| Bs#45 | 0 | 16 | 0 | 12 | 4 | 75 |
| Bs#46 | 1 | 15 | 6.2 | 10 | 6 | 62.5 |
| Bs#47 | 1 | 15 | 6.2 | 10 | 6 | 62.5 |
| Bs#48 | 0 | 16 | 0 | 12 | 4 | 75 |
| Bs#49 | 2 | 14 | 12.5 | 12 | 4 | 75 |
| Bs#51 | 2 | 14 | 12.5 | 7 | 9 | 43.7 |
| Bs#55 | 0 | 16 | 0 | 7 | 9 | 43.7 |
| Bs#18 | 0 | 16 | 0 | 14 | 2 | 87.5 |
| Bs#33 | 0 | 16 | 0 | 16 | 0 | 100 |
| Cry1Fa ($LC_{50}$) | | | | 13 | 19 | 40.6 |
| Buffer | 1 | 31 | 3.1 | | | |
| $H_2O$ | 1 | 31 | 3.1 | | | |

Cry1F-resistant insect line PR1 that lacks the functional cry1F toxin receptor, ABCC2, has been described (Banerjee et al., 2017). Treatment of cry1F toxin in bioassays using these insects, even at ~20× higher dosage than the $LC_{50}$ in susceptible insects, has no significant effects on insect mortality. Table 3 shows treatment of PR1 insects with several bispecific nanobodies in the presence or absence of cry1F toxin. No effect of the bispecific nanobodies on PR1 insects in any case is seen (see Table 6). These results were repeated with most of the bispecific nanobodies, and no significant mortality was observed in any case. These results indicate that the ABCC2 receptor is apparently important for Cry1F toxicity in PR1 insects. However, since other toxins with different receptors, for instance Cry1Ab and Cry1Ac share sequence similarities with cry1F (FIG. 17A) and similarly Cry1B, Cry1 Da also exhibit sequence similarity with Cry1F (FIG. 17B), these BsNb may be used in conjunction with other toxins to target Cry1F-resistant insects. Furthermore, it may be possible to create a BsNb that binds to the known cry1F binding site in the ABCC2 receptor to restore cry1F insecticidal activity in resistant insects.

TABLE 6

Shows effects of treatment of PR1 insects with bispecific nanobodies

| PR1 BsNb | without Cry1F | | | | with Cry1F (9.5 µg/well) | | | |
|---|---|---|---|---|---|---|---|---|
| | Live | Dead | Total | % mortality | Live | Dead | Total | % mortality |
| Bs#18 | 16 | 0 | 16 | 0 | 16 | 0 | 16 | 0 |
| Bs#19 | 16 | 0 | 16 | 0 | 16 | 0 | 16 | 0 |
| Bs#22 | 15 | 1 | 16 | 6.25 | 15 | 1 | 16 | 6.25 |
| Bs#33 | 15 | 1 | 16 | 6.25 | 16 | 0 | 16 | 0 |

At least 20 bispecific nanobodies, shown in Table 7 gave consistently higher mortality rates in susceptible insects than cry1F toxin alone over multiple experiments; 11 of these (shaded) were chosen for further analysis.

TABLE 7

Some examples of effective bispecifc nanobodies

| BsNb # (see Table 4) | Bispecific nanobody |
|---|---|
| 18 | Nb7-Gly8-NAAT29 |
| 19 | Nb51-Gly8-NAAT29 |
| 22 | Nb51-PTPT-NAAT29 |
| 33 | Nb7-Gly4Ser1X3-NAAT31 |
| 41 | Nb51-gly8-Cad2 |
| 43 | Nb51- PTPT -Cad48 |
| 48 | Nb51- PTPT -Cad2 |
| 49 | Nb51- PTPT -Cad50 |
| 50 | Nb51-gly8-Cad43 |
| 53 | Nb51-gly8-Cad46 |
| 60 | Nb51- PTPT -Cad47 |
| 62 | Nb7- PTPT -NAAT1 |
| 64 | Nb7- PTPT -NAAT2 |
| 69 | Nb7-Gly8-NAAT5 |
| 76 | Nb7- PTPT -NAAT10 |
| 77 | Nb51-Gly8-NAAT1 |
| 78 | Nb51- PTPT -NAAT1 |
| 79 | Nb51-Gly8-NAAT2 |
| 85 | Nb51-Gly8-NAAT5 |
| 87 | Nb51Gly8-NAAT6 |

Example 23. Binding of Cry1F Toxin to Bispecific Nanobody

To prove that the cry1F toxin binds to the bispecific nanobodies, the bispecific nanobody-cry1F complex was analyzed by size exclusion chromatography on an FPLC machine. Bispecific nanobodies were added at various molar ratios compared to cry1F toxin (3:1, 1:1, 0.5:1) and the presence of a complex versus free toxin or free bispecific nanobody was determined over collected fractions that elute from the size exclusion column. Proteins were run on acrylamide gel electrophoresis and stained by Coomassie Blue to visualize proteins.

When bispecific nanobody #64 (as an example) is incubated with cry1F at a 1:1 molar ratio, cry1F and the bispecific nanobody elute in the same fractions, indicating that they are present in a complex. In contrast, if the toxin is added in molar excess, both a complex and excess free toxin are observed, indicating that the excess toxin is not present in a complex. Likewise, when bispecific nanobody was added at 3:1 molar excess over cry1F toxin, both a complex and excess unbound bispecific nanobody were observed. These results show that the bispecific nanobody and cry1F are indeed bound in a complex and indicates that a 1:1 molar ratio is optimal for formation of that complex.

Example 24. Binding of NAAT and Cadherin Nanobodies to Diamondback Moth BBMV The utility of the nanobodies is significantly enhanced if they have activity against multiple insect pests. To determine if the NAAT and cadherin monospecific nanobodies might recognize the cognate receptor protein in other insect species, the 57 amino acid NAAT and 427 amino acid Cadherin antigen sequences were used in a Blast sequence homology search. Using Diamondback moth (DBM; *Plutella xylostella*) as an example, significant amino acid identity was found to be present (see FIGS. 15 and 16) suggesting that the existing nanobodies raised against FAW receptors may also recognize the homologous receptor proteins in *Plutella* and other species. Table 9 shows percent homology of NAAT and Cadherin target sequences to additional insects.

Figure 13A:
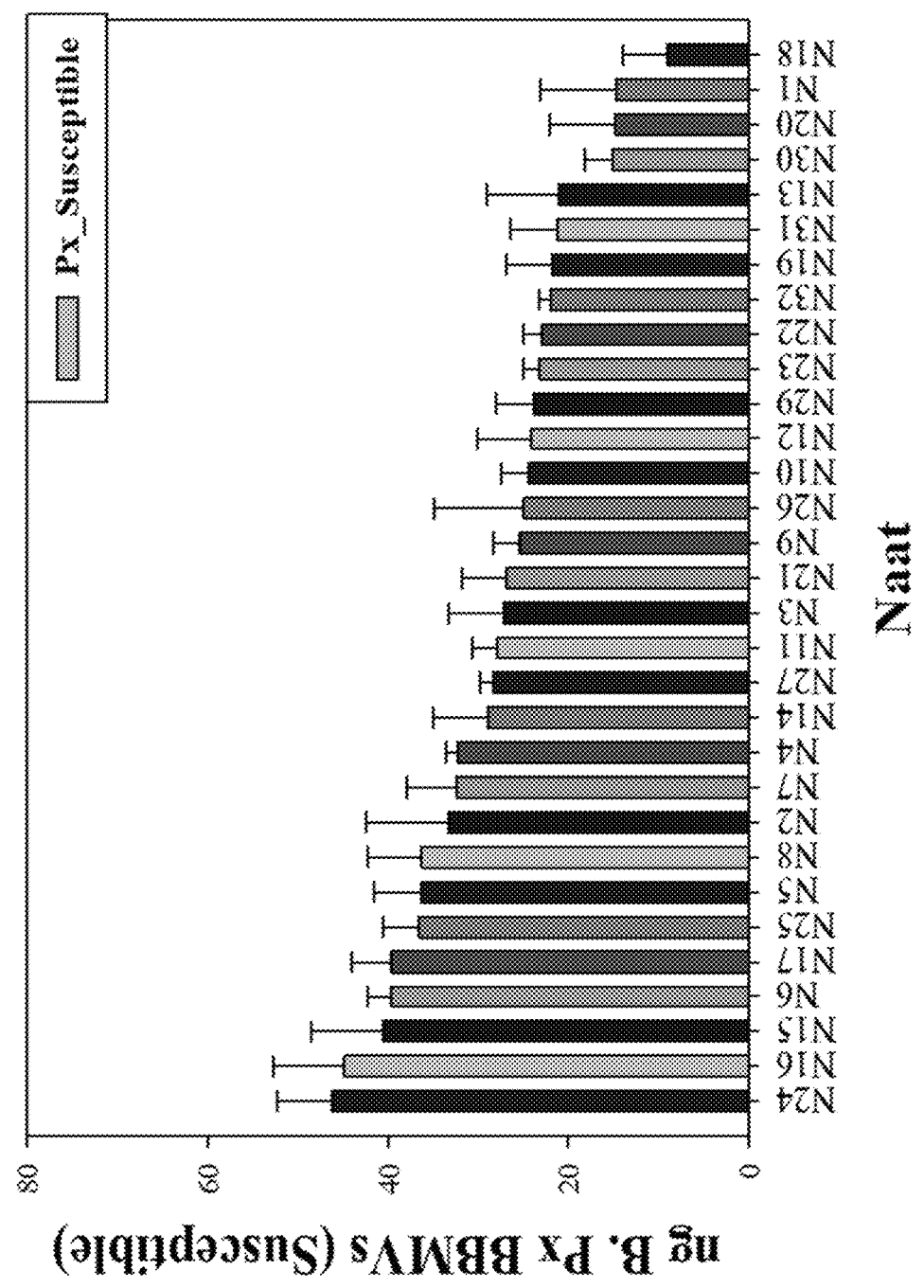
Figure 13A:
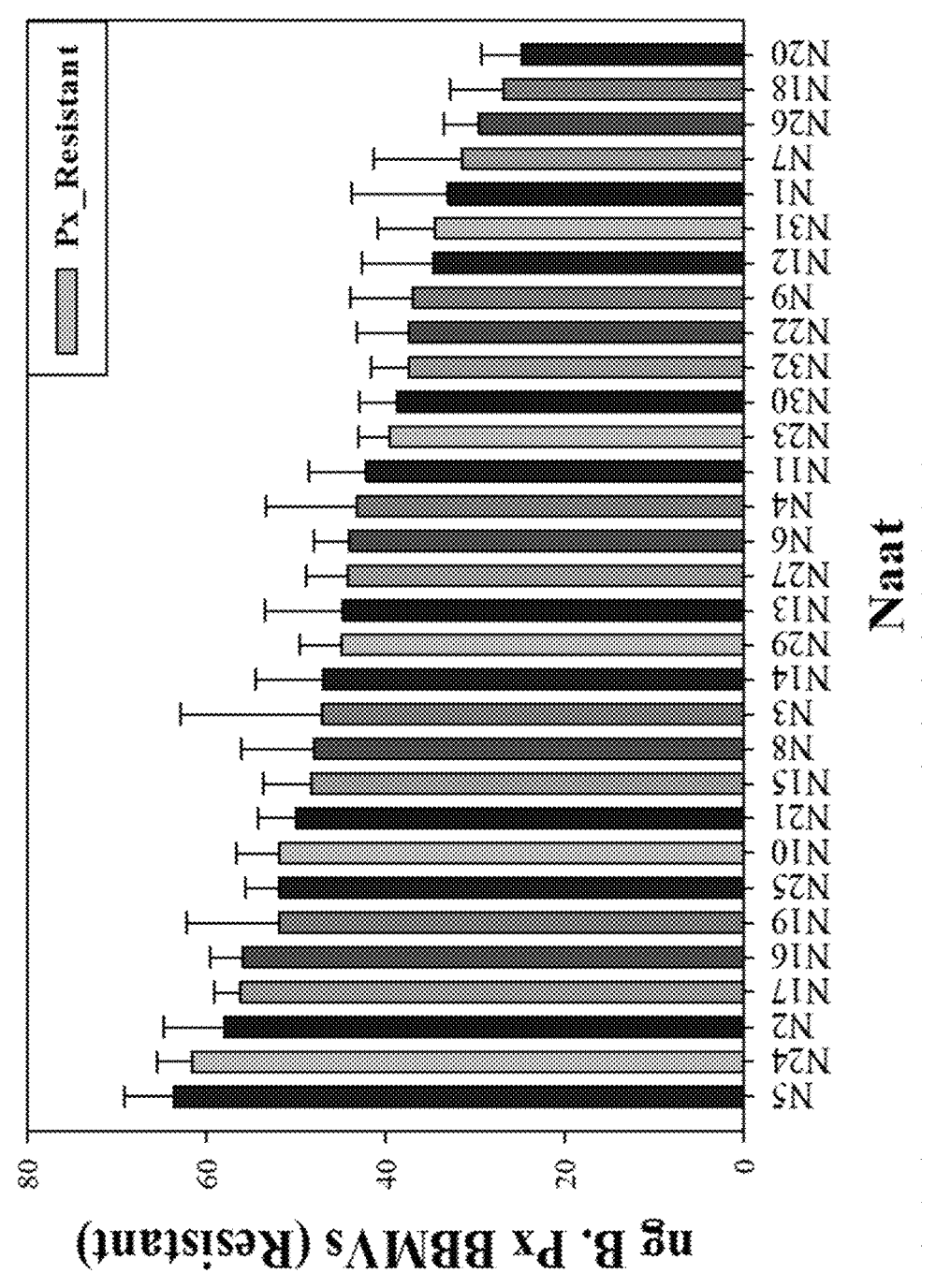
Figure 13B:
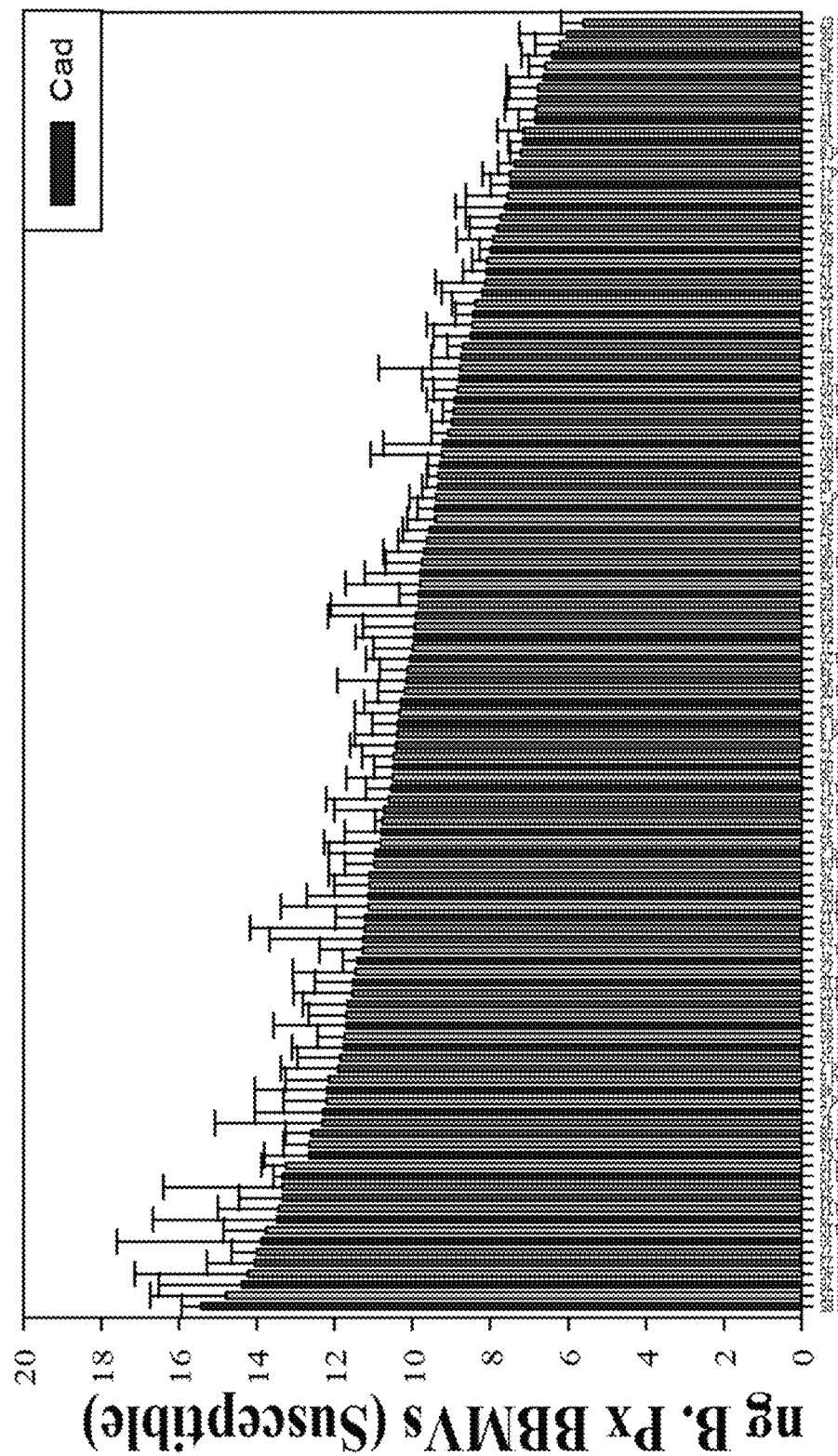
FIG. 13B shows a graphical representation of the results of ELISA-based binding assays using biotin-labeled solubilized *Plutella* brush border membrane vesicles and cadherin nanobodies.
Figure 13B:
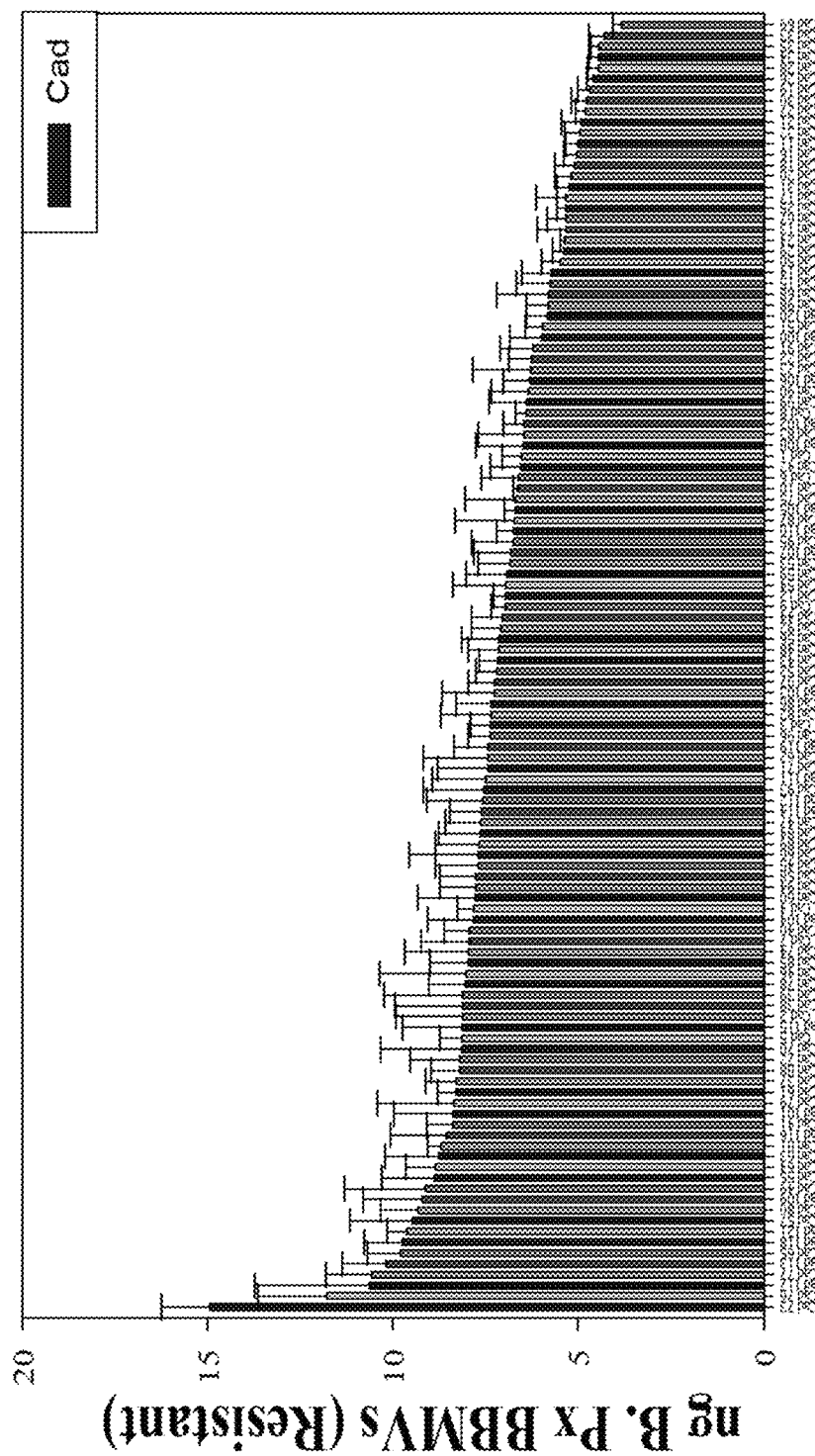

To determine if the existing NAAT and Cadherin nanobodies can recognize Diamondback moth BBMV, ELISA-based binding assays were performed using biotin-labeled solubilized *Plutella* brush border membrane vesicles and NAAT or cadherin nanobodies, using the same methodology as was used for FAW. BBMV derived from *Plutella* insects (Px.BBMV) that are susceptible to cry1F toxin as well as resistant to cry1F toxin were tested. FIGS. 13A and 13B provide results of these ELISA-based assays using NAAT or cadherin monospecific nanobodies respectively. The data given in FIGS. 13A and 13B identify NAAT and Cadherin nanobodies that recognize *Plutella* BBMV in both susceptible and resistant insects, indicating that they have utility in control of those insects.

Example 25. Bioassay to Test Activity Across Plurality of Species and Toxins Similar to recognizing new insects via their gut receptor homology to the antigens that created the bispecific nanobodies, the utility of the nanobodies is also significantly enhanced if they recognize insect toxins with homology to the original Cry1F toxin antigen used to create the nanobodies, with examples of this shown in Table 10. Bioassays with purified bispecific nanobodies (BsNbs) were performed with results in Table 8 shows the study design to test the activity of each of the listed bispecific nanobodies with Cry1F or Cry1Ac or Cry1Ab protein toxins, against Diamondback Moth (DBM), Fall Armyworm (FAW) or Corn Earworm (CEW).

The protein toxins were used at $LC_{50}$. BsNb purified proteins were mixed with the indicated toxin (shown in Table 8) in a 3:1 molar ratio (BsNb:toxin) in a final volume of 75 µl of autoclaved MilliQ water. The molecular weight of BsNbs used for molarity calculations was ~30 kDa, the amount of BsNb based on a 3:1 molar ratio is 6.33 µM (14.25 µg in 75 µl volume). Mixtures were incubated at room temperature for one hour and then stored on ice until applied on the surface of meridic diet. Once the meridic diet had set and dried in individual wells of 128-cell polystyrene bioassay trays, all treatments were applied on the diet surface, with 16 wells used per one treatment. The buffer used for BsNb extraction and water used for dilutions were used as control treatments. After the treatments had dried on the diet, a single DBM, FAW or CEW neonate was placed per well and trays incubated at 26±2° C. and 16L:8D photoperiod. Mortality was determined after 7 days of incubation.

Figure 14:
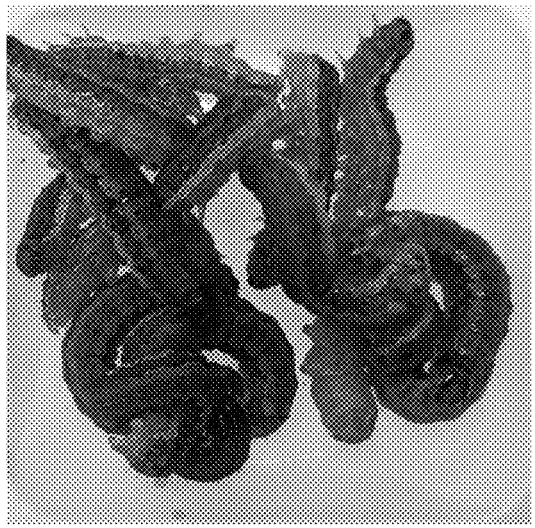
FIG. 14 demonstrates that the worms fed with nanobodies in conjunction with Cry1Ac toxin exhibit greater mortality and morbidity in comparison to worms fed on control diet or on Cry1Ac alone.
Figure 14:
Figure 14:
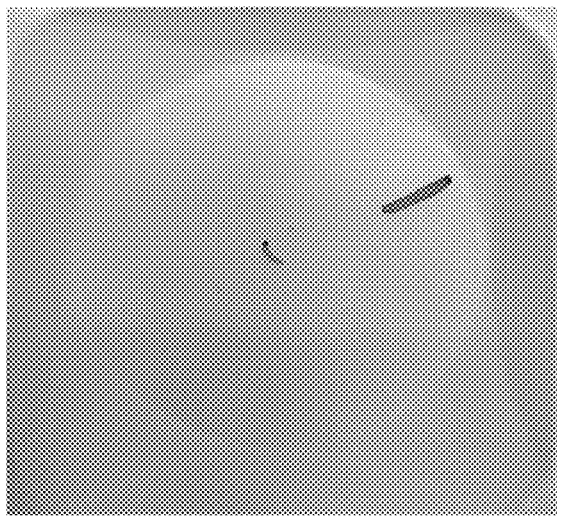

Table 8 shows the outcome of these studies and FIG. 14 shows photographs of one such study. As evident from the FIG. 14 and Table 8, Cry1Ac protein when used in conjunction with the bispecific nanobodies is very effective in killing and stunting FAW larvae. Further the combination is more effective than using Cry1Ac alone. Additionally, numerous bispecific nanobodies enhance the activity of Cry1F toxin significantly above its $LC_{50}$ mortality values across the three species tested. Interestingly, at least one of the BsNbs was also effective in stunting the growth of FAW when used with Cry1Ab. This is surprising since Cry1Ab alone is not effective against FAW. Additionally, multiple bispecific nanobodies generated activity of Cry1F against CEW, another protein not known to effectively control the insect.

TABLE 8

Bioassay Study Design and Outcome ("NT"-non tested, "()"-one replicate, "+"-higher mortality rate over control, "−"-no change over control, "+/−"-higher mortality but the results were inconsistent or not statistically significant.

| BsNb # (see Table 4) | MsNb-Cry-link-target | Cry1F DBM | Cry1F FAW | Cry1F CEW | Cry1Ac FAW | Cry1Ab FAW stunting |
|---|---|---|---|---|---|---|
| 1 | cry1Nb5-218-NAAT29 | NT | − | − | − | − |
| 4 | cry1Nb5-ESGSV-NAAT29 | (+) | +/− | NT | NT | NT |
| 10 | cry1Nb51-AEAAAK3-NAAT29 | NT | + | − | − | − |
| 15 | cry1Nb7-Gly4Ser1x3-NAAT29 | NT | +/− | − | + | − |
| 18 | cry1Nb7-Gly8-NAAT29 | NT | + | − | + | − |
| 21 | cry1Nb7-PTPT-NAAT29 | (+) | +/− | + | NT | NT |
| 39 | cry1Nb7-PTPT-NAAT31 | NT | + | − | + | − |
| 62 | cry1Nb7-PT-NAAT1 | NT | + | − | + | − |
| 64 | cry1Nb7-PT-NAAT2 | − | + | − | + | − |
| 76 | cry1Nb7-PT-NAAT10 | NT | + | +/− | + | + |
| 100 | cry1Nb7-PT-Cad2 | (+) | + | + | NT | NT |
| 108 | cry1Nb7-PT-Cad43 | (−) | +/− | + | NT | NT |

TABLE 8-continued

Bioassay Study Design and Outcome ("NT"-non tested, "()"-one replicate, "+"-higher mortality rate over control, "−"-no change over control, "+/−"-higher mortality but the results were inconsistent or not statistically significant.

| BsNb # (see Table 4) | MsNb-Cry-link-target | Cry1F | | | Cry1Ac | Cry1Ab FAW |
|---|---|---|---|---|---|---|
| | | DBM | FAW | CEW | FAW | stunting |
| 111 | cry1Nb7-Gly8-Cad49 | (+) | + | +/− | NT | NT |
| 112 | cry1Nb7-PT-Cad47 | (+) | +/− | − | NT | NT |

Figure 15A:
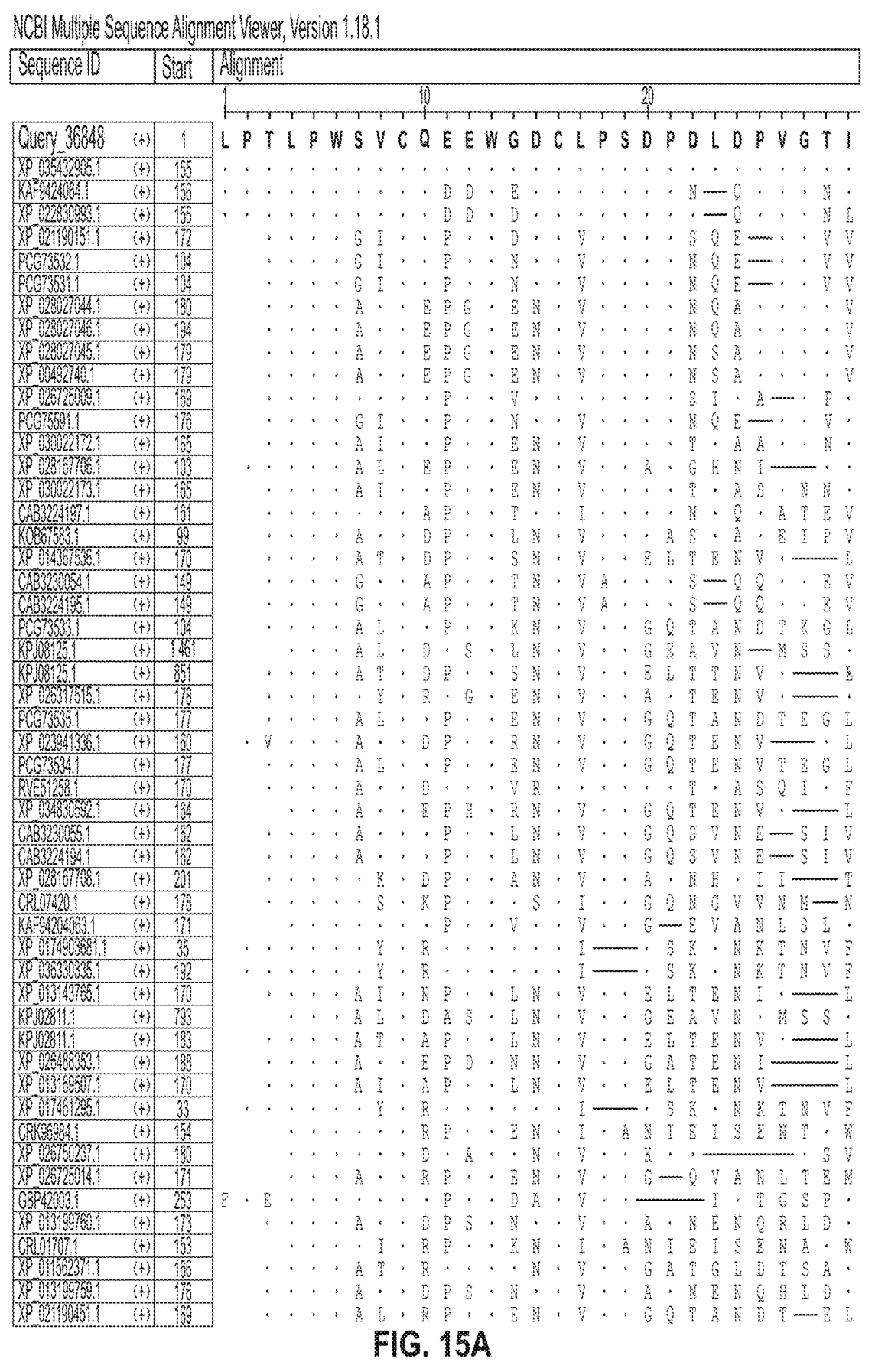
Figure 16C:
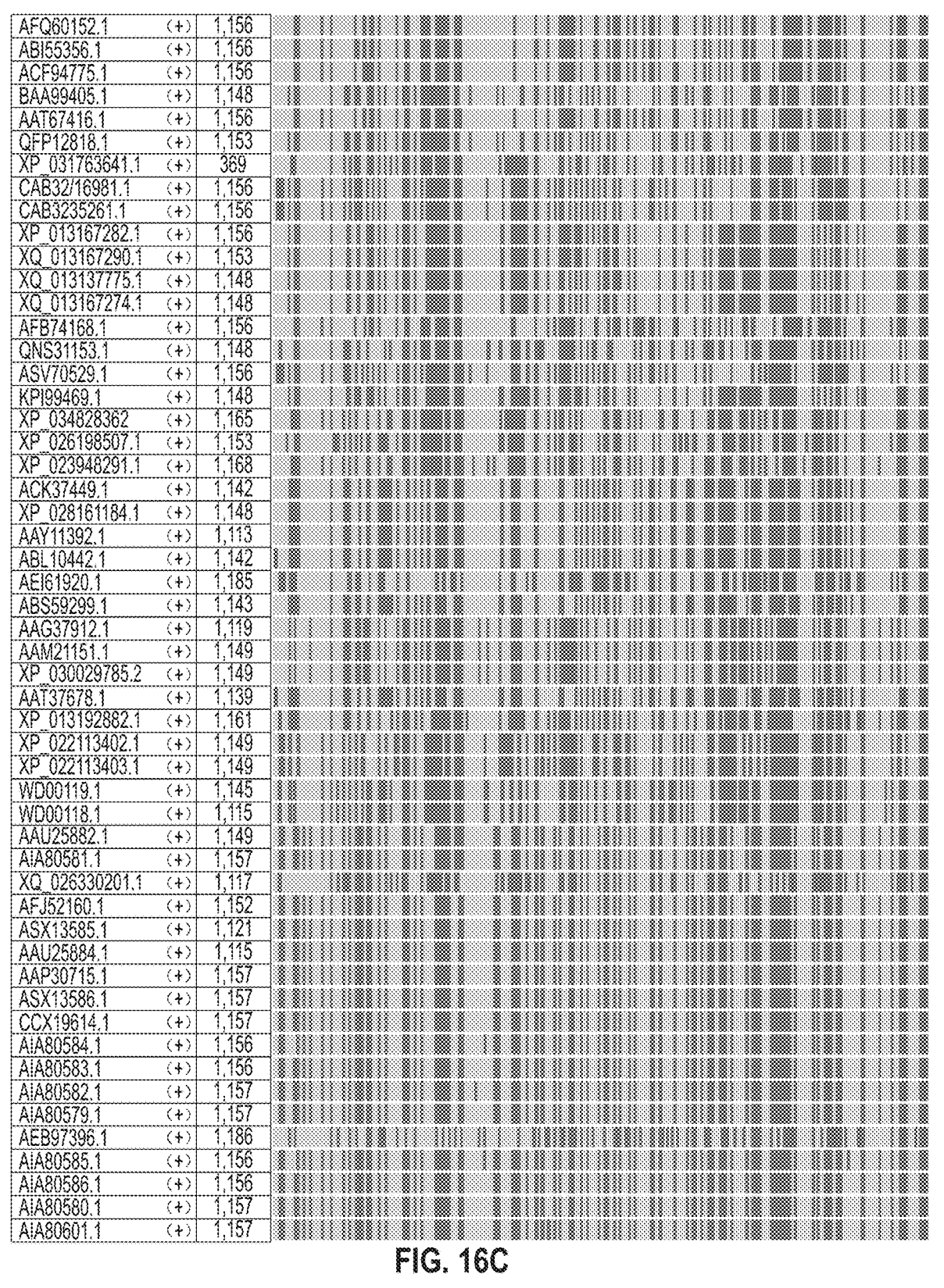
Figure 16D:
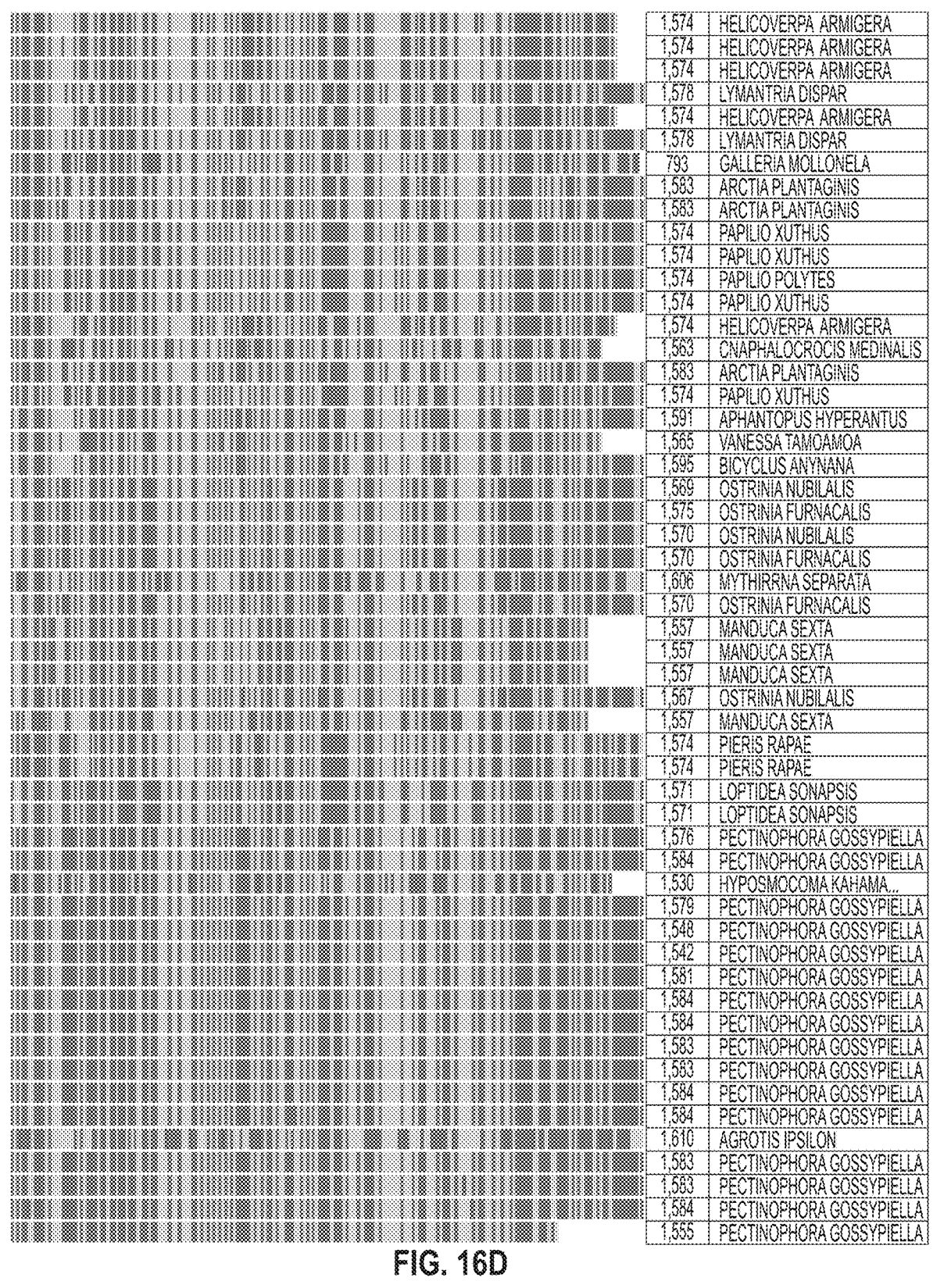

Similarly, bispecific nanobodies with sequences directed to target FAW Cadherins and NAAT sequences were surprisingly also effective against a plurality of other insect pests including DBM and CEW when used with Cry1Ac. This further demonstrates that this approach can be used to target insect strains that are not susceptible to the native toxin. It is noted the selected membrane protein targets show a high degree of sequence conservation across these pests (FIGS. 15 and 16, and Table 9).

TABLE 9

Sequence conservation between membrane proteins (Cadherin and NAAT) across multiple insect species

| Description | Scientific Name (Insect) | Max Score | Total Score | Query Cover | E value | Per. ident | Acc. Len | Accession |
|---|---|---|---|---|---|---|---|---|
| Cadherin | | | | | | | | |
| hypothetical protein SFRUCORN_020876 [Spodoptera frugiperda] | Spodoptera frugiperda | 854 | 854 | 100% | 0 | 99.53 | 1658 | KAG8112339.1 |
| protocadherin Fat 3-like [Spodoptera frugiperda] | Spodoptera frugiperda | 855 | 855 | 100% | 0 | 99.3 | 1734 | XP_035440763.1 |
| hypothetical protein SFRURICE_006703 [Spodoptera frugiperda] | Spodoptera frugiperda | 852 | 852 | 100% | 0 | 99.3 | 1706 | KAF9820681.1 |
| truncated cadherin [Helicoverpa punctigera] | Helicoverpa punctigera | 84.7 | 84.7 | 13% | 2.00 E−16 | 66.67 | 771 | AVE17270.1 |
| truncated cadherin [Helicoverpa armigera] | Helicoverpa armigera | 143 | 143 | 24% | 8.00 E−36 | 66.35 | 1271 | AFB74167.1 |
| cadherin-like protein [Helicoverpa zea] | Helicoverpa zea | 456 | 456 | 97% | 2.00 E−145 | 55.13 | 1730 | AKH49609.1 |
| cadherin [Helicoverpa punctigera] | Helicoverpa punctigera | 449 | 449 | 97% | 7.00 E−143 | 55.11 | 1732 | AVE17268.1 |
| hypothetical protein B5V51_6905 [Heliothis virescens] | Heliothis virescens | 355 | 672 | 97% | 3.00 E−110 | 55.05 | 1304 | PCG67047.1 |
| truncated cadherin [Helicoverpa armigera] | Helicoverpa armigera | 302 | 302 | 64% | 2.00 E−90 | 55.04 | 1441 | AWJ76613.1 |
| E-cadherin [Helicoverpa armigera] | Helicoverpa armigera | 457 | 457 | 97% | 3.00 E−146 | 54.89 | 1672 | AAU50668.1 |
| cadherin-like protein [Helicoverpa zea] | Helicoverpa zea | 453 | 453 | 97% | 2.00 E−144 | 54.89 | 1730 | AKH49605.1 |
| cadherin [Helicoverpa armigera] | Helicoverpa armigera | 457 | 457 | 97% | 1.00 E−145 | 54.65 | 1730 | AFB74170.1 |
| cadherin [Helicoverpa armigera] | Helicoverpa armigera | 454 | 454 | 97% | 8.00 E−145 | 54.42 | 1675 | AFQ60151.1 |
| cadherin-like protein [Ostrinia scapulalis] | Ostrinia scapulalis | 191 | 191 | 38% | 4.00 E−58 | 54.17 | 175 | AGO01049.1 |
| cadherin [Helicoverpa armigera] | Helicoverpa armigera | 447 | 447 | 97% | 1.00 E−142 | 53.94 | 1675 | AFQ60152.1 |

TABLE 9-continued

Sequence conservation between membrane proteins (Cadherin and NAAT) across multiple insect species

| Description | Scientific Name (Insect) | Max Score | Total Score | Query Cover | E value | Per. ident | Acc. Len | Accession |
|---|---|---|---|---|---|---|---|---|
| cadherin-like protein [*Helicoverpa armigera*] | *Helicoverpa armigera* | 446 | 446 | 97% | 1.00 E-141 | 53.94 | 1730 | AAT67416.1 |
| cadherin-like Cry1Ac receptor [*Heliothis virescens*] | *Heliothis virescens* | 455 | 455 | 97% | 4.00 E-145 | 53.92 | 1732 | AAV80768.1 |
| cadherin-like protein [*Heliothis virescens*] | *Heliothis virescens* | 455 | 455 | 97% | 6.00 E-145 | 53.68 | 1732 | AAK85198.1 |
| cadherin [*Helicoverpa armigera*] | *Helicoverpa armigera* | 440 | 440 | 97% | 1.00 E-139 | 53.46 | 1730 | AFB74168.1 |
| cadherin [*Helicoverpa armigera*] | *Helicoverpa armigera* | 181 | 181 | 41% | 1.00 E-48 | 51.67 | 1343 | AEC33256.1 |
| cadherin M1 [*Ostrinia nubilalis*] | *Ostrinia nubilalis* | 412 | 412 | 97% | 1.00 E-129 | 50.12 | 1716 | ACK37449.1 |
| protocadherin Fat 1-like [*Ostrinia furnacalis*] | *Ostrinia furnacalis* | 412 | 412 | 97% | 2.00 E-129 | 50.12 | 1722 | XP_028161184.1 |
| cadherin [*Plutella xylostella*] | *Plutella xylostella* | 380 | 380 | 96% | 3.00 E-119 | 49.64 | 1334 | ABI63545.1 |
| cadherin [*Agrotis ipsilon*] | *Agrotis ipsilon* | 388 | 388 | 96% | 2.00 E-120 | 49.53 | 1760 | AEB97396.1 |
| cadherin [*Ostrinia nubilalis*] | *Ostrinia nubilalis* | 73.2 | 73.2 | 20% | 6.00 E-15 | 49.45 | 95 | AAT48603.1 |
| cadherin-like protein [*Plutella xylostella*] | *Plutella xylostella* | 379 | 379 | 96% | 2.00 E-117 | 49.41 | 1716 | ABU41413.1 |
| cadherin A2 [*Ostrinia nubilalis*] | *Ostrinia nubilalis* | 230 | 230 | 56% | 1.00 E-72 | 49.19 | 242 | ABB03903.1 |
| cadherin [*Plutella xylostella*] | *Plutella xylostella* | 374 | 374 | 96% | 3.00 E-117 | 49.17 | 1334 | ABI63546.1 |
| cadherin [*Ostrinia nubilalis*] | *Ostrinia nubilalis* | 204 | 204 | 48% | 7.00 E-63 | 48.82 | 218 | ADX42727.1 |
| unnamed protein product [*Plutella xylostella*] | *Plutella xylostella* | 372 | 372 | 96% | 6.00 E-117 | 48.57 | 1236 | CAG9135951.1 |
| cadherin [*Ostrinia nubilalis*] | *Ostrinia nubilalis* | 73.6 | 73.6 | 20% | 5.00 E-15 | 48.35 | 95 | AAT48607.1 |
| cadherin [*Ostrinia nubilalis*] | *Ostrinia nubilalis* | 203 | 203 | 48% | 3.00 E-62 | 48.34 | 218 | ADX42726.1 |
| cadherin [*Ostrinia nubilalis*] | *Ostrinia nubilalis* | 70.5 | 70.5 | 20% | 5.00 E-14 | 47.25 | 95 | AAT48610.1 |
| cadherin [*Ostrinia nubilalis*] | *Ostrinia nubilalis* | 166 | 166 | 39% | 1.00 E-46 | 47.06 | 327 | ACK37451.1 |
| cadherin 1 [*Diatraea saccharalis*] | *Diatraea saccharalis* | 378 | 378 | 98% | 4.00 E-117 | 46.6 | 1718 | AFI81418.1 |
| cadherin [*Ostrinia nubilalis*] | *Ostrinia nubilalis* | 68.2 | 68.2 | 20% | 4.00 E-13 | 46.15 | 95 | AAT48604.1 |
| cadherin [*Chrysodeixis includens*] | *Chrysodeixis includens* | 248 | 325 | 96% | 1.00 E-71 | 44.92 | 1956 | QRU95334.1 |
| cadherin-like protein resistant allele r9 [*Helicoverpa armigera*] | *Helicoverpa armigera* | 355 | 355 | 97% | 1.00 E-108 | 43.15 | 1757 | AEE44121.1 |

The invention claimed is:

1. A recombinant nucleic acid molecule comprising a polynucleotide sequence encoding an affinity molecule comprising a first single domain antibody comprising the complementarity determining region 1 (CDR1) amino acid sequence of SEQ ID NO: 138, the complementarity determining region 2 (CDR2) amino acid sequence of SEQ ID NO: 139, and the complementarity determining region 3 (CDR3) amino acid sequence of SEQ ID NO: 140 or 141, wherein the affinity molecule binds an insect gut nutrient amino acid transporter protein.

2. The recombinant nucleic acid molecule of claim 1, further comprising a promoter operably linked to the polynucleotide sequence.

3. A transgenic host cell comprising the recombinant nucleic acid of claim 1.

4. The transgenic host cell of claim 3, wherein the transgenic host cell is a yeast cell, a bacterial cell, or a plant cell.

5. The transgenic host cell of claim 3, wherein the host cell further comprises one or more nucleic acid sequences, each encoding an insecticidal protein derived from Bacillus thuringiensis that specifically binds to or can be targeted to bind to at least one domain in the affinity molecule.

6. A method of producing a plant or a microorganism comprising the recombinant nucleic acid affinity molecule according to claim 1, the method comprising transforming the plant or microorganism with one or more nucleic acid molecules encoding the affinity molecule.

7. The method of claim 6, wherein the plant or microorganism comprises or is transformed with one or more nucleic acids encoding an insecticidal protein comprises a Cry 1F, Cry1Ab, Cry1Ac, or a modified Bacillus thuringiensis delta-endotoxin.

8. The recombinant nucleic acid molecule of claim 1, wherein the affinity molecule further comprises an amino acid or peptide linker of 1 to 100 amino acids in length.

9. The recombinant nucleic acid molecule of claim 8, wherein the amino acid or peptide linker comprises a proline-threonine (PT) peptide, a peptide comprising glycine residues, or a peptide comprising glycine and serine residues.

10. The recombinant nucleic acid molecule of claim 1, wherein the affinity molecule comprises the CDR3 region of the amino acid sequence of SEQ ID NO: 141.

11. The recombinant nucleic acid molecule of claim 1, wherein the single domain antibody is fused to a Bacillus thuringiensis delta-endotoxin or a modified Bacillus thuringiensis delta-endotoxin.

12. The recombinant nucleic acid molecule of claim 1, wherein the affinity molecule further comprises a second single domain antibody comprising: (i) the CDR1 amino acid sequence of SEQ ID NO: 148, the CDR2 amino acid sequence of SEQ ID NO: 149, and the CDR3 amino acid sequence of SEQ ID NO:150; (ii) the CDR1 amino acid sequence of SEQ ID NO: 151, the CDR2 amino acid sequence of SEQ ID NO: 152, and the CDR3 amino acid sequence of SEQ ID NO: 153; or (iii) the CDR1 amino acid sequence of SEQ ID NO: 161, the CDR2 amino acid sequence of SEQ ID NO: 162, and the CDR3 amino acid sequence of SEQ ID NO: 163.

13. The recombinant nucleic acid molecule of claim 12, wherein the affinity molecule further comprises the CDR1 amino acid sequence of SEQ ID NO: 148, the CDR2 amino acid sequence of SEQ ID NO: 149, and the CDR3 amino acid sequence of SEQ ID NO:150.

14. The recombinant nucleic acid molecule of claim 13, wherein the affinity molecule comprises: (i) the first single domain antibody comprising the CDR1 amino acid sequence of SEQ ID NO: 138, the CDR2 amino acid sequence of SEQ ID NO: 139, and the CDR3 amino acid sequence of SEQ ID NO: 141; and (ii) the second single domain antibody comprising the CDR1 amino acid sequence of SEQ ID NO: 148, the CDR2 amino acid sequence of SEQ ID NO: 149, and the CDR3 amino acid sequence of SEQ ID NO: 150, wherein the first and the second single domain antibodies are operably connected with an amino acid or peptide linker.

* * * * *

UNITED STATES PATENT AND TRADEMARK OFFICE
CERTIFICATE OF CORRECTION

| | |
|---|---|
| PATENT NO. | : 12,011,000 B2 |
| APPLICATION NO. | : 18/346437 |
| DATED | : June 18, 2024 |
| INVENTOR(S) | : Heba Mohamed Yassen Abdelgaffar et al. |

It is certified that error appears in the above-identified patent and that said Letters Patent is hereby corrected as shown below:

In the Claims

Column 241, Claim 7, Line 41:
DELETE: "Cry 1F,"
INSERT: --Cry1F,--

Signed and Sealed this
Thirtieth Day of July, 2024

Katherine Kelly Vidal
*Director of the United States Patent and Trademark Office*

SEQUENCE LISTING

```
Sequence total quantity: 234
SEQ ID NO: 1         moltype = DNA  length = 5592
FEATURE              Location/Qualifiers
```

| source | 1..5592 |
| | mol_type = genomic DNA |
| | organism = Spodoptera frugiperda |

SEQUENCE: 1

```
gacattctgt ggtgaaaaca tttttattt attttttct agtggtttgt gggtacagtg   60
taaacatttt ggaatattgt taaagatttc ggaatattgt taaagtattg acagataaag  120
ctgtaacatc actagagaag tgagaactgc aagatcatga gatggcggtc gatgtgcgaa  180
tactgacagc aacattgctg gtactcacca ctgctacagc acagcgagat cgatgtggct  240
acatggtaga aatacccaga ccagacaggc ctgacttccc acctcaaaat tttgacggtt  300
taacatgggc tcagcagcca ctattaccag ctgaggatcg agaagaggtc tgcctcaatg  360
actatgaacc tgatccctgg agcaacaacc atggtgacca gagaatttac atggaggagg  420
agatcgaagg tcccgtagtc attgcgaaaa ttaactacca aggaaacacc cctcctcaaa  480
taagattacc ttttcgtgtt ggtgcagccc acatgcttgg agcagaaatt cgtgaatatc  540
ctgacgcaac tggagactgg tatcttgtaa ttactcaaga gcaggactat gaaactcctg  600
atatgcagag atacacgttc gatgtgagtg tggaaggcca gtcgctggtt gtaacggtga  660
ggctggatat tgtgaacatc gacgacaatg cgcccatcat tgagatgtta gagcctttgca  720
acttaccgga acttgttgaa ccccatgtta cagaatgtaa atatatcgtg tccgacgcag  780
acggtctgat cagtacaagt gttatgagtt atcatataga cagcgagaga gggagacgaaa  840
aagtattcga actgatcaga aaagattatc cgggcgattg gacgaaggtg tatatggttc  900
ttgaattgaa aaaatctctt gattacgaag agaatcctct acacatattc agagtcacgg  960
cttctgattc cttaccaaac aataggaccg tggtcatgat ggttgaagta gagaacgtgg 1020
aacatagaaa tcctcggtgg atggagatct ttgctgtgca acagtttgat gaaaaacagg 1080
cgaaatcgtt cacagtgcga gctattgatg gcgacacggg aatcaataaa cctatattct 1140
atcgtataga aactgaagat gaagacaaag agttcttcag cattgagaac ataggggaag 1200
gcagagacgg tgccagattc cacgtggctc ctatagacag agactacctg aaaagggata 1260
tgtttcatat aagaataatt gcatataaac aaggtagtaa tgacaaagaa ggtgaatcat 1320
cgttcgagac ctcagcaaat gtgacgatta taattaacga tataaatgat cagaggccaa 1380
aacccttcca taaagaatac acgatctcca taatggaaga aactgcgatg accttagatt 1440
tgcaagagtt tggtttccat gaccgtgaca ttggtcccca cgctcagtac gacgttcact 1500
tagagagtat acagccagag ggggcccata ccgcttcta catcgcccct gaagaaggtt 1560
accaggccca gtctttcacc ataggtacta gaatccataa catgttggat tatgaagatg 1620
acgactacag accaggaata aagctaaagg cagtagcaat tgacagacac gataacaatc 1680
acattgggga agcaattatt aacattaacc ttatcaattg gaatgatgag ctacctatat 1740
tcgacgagga cgcctacaac gtgacatttg aggagacggt cggtgatggc ttccacattg 1800
gtaaataccg ggctaaagac agagacatcg gtgacatagt cgagcactcg atattgggca 1860
acgctgcaaa cttcctgaga attgacatag atactggaga tgtgtacgtg tcacgggacg 1920
attactttga ttatcaaaga cagaacgaaa tcatagttca gattctggct gttgatacac 1980
taggtttacc tcagaacagg gctaccacac agctcacgat attttggaa gacatcaaca 2040
acacgccacc tatactgcga ctgccacgtt ccagtccaag tgtagaagag aacgttgaag 2100
tcgggcaccc gattaccgag gggctaacgg cgacagaccc agacaccaca gccgatttac 2160
acttcgagat cgattgggac aattcttacg ctacgaagca gggcaccaat ggacccaaca 2220
ctgcagacta ccacgatgc gtagaaatcc tgacggtata cccagatcct gacaatcacg 2280
ggagagctga gggtcacttg gtggcacgtg aggtcagtga tggcgtgacc atcgattacg 2340
agaagtttga ggtgctgtac ctcgtcgtca gggtgataga tcgcaacact gtcattggcc 2400
ctgattatga cgaagcaatg ctgacggtga cgataatcga tatgaacgac aactggccga 2460
tatgggccga caacacgctg cagcagacac tgcgcgtgcg cgagatggcc gacgaaggag 2520
tcatcgtcgg tacactgctc gccaccgact tggatgacgc tctctacaac cgagtccgct 2580
acaccatggt ccccatcaag gacactcctg atgacctaat agcgatcaac tacgtcaccg 2640
gtcagctgac tgtgaacaag gggcaagcaa ttgacgcaga tgatccacct cgcttctacc 2700
tgtattacaa ggtcactgcc agcgataagt gctctcttga cgattcttc cctgtgtgcc 2760
cacctgaccc cacttactgg aataccgagg gagagatagc gatcgcgata accgatacag 2820
acaacaaaat tccacgcgcg gaaacagata tgttccctag tgaaaagcgc atctatgaga 2880
acacacccaa tggtaccaag atcacgacga tcatcgctag tgaccaggac agagatcgac 2940
caaataacgc gctgacgtac agaatcaact acgcattcaa ccacaggctg gagaacttcc 3000
tcgcagtgga ccctgatact ggtgaactgt ttgtccactt caccactagc gaagtgttgg 3060
acagagacgg agaggaaccg gagcatagga tcatcttcac catcgtcgat aacttggaag 3120
gcgctgagaa tggcaatcag aacacaatct ccacggaggt gcgtgtttata ctgcttgata 3180
taaacgacaa taagccggaa ctaccaattc ctgatggcga attttggacc gttccgaag 3240
gtgaagtgga gggaaaacgc aattccaccag agattccgac acacgacaga gatgaaccat 3300
tcaacgacaa ctctcgcgtg ggatatgaaa ttcgatcgat caaattgatc aatagagaca 3360
tcgagcttcc tcaagatcca ttcaaaataa taacgattga tgatctcgat acctggaaat 3420
tcgttggaga gttggagact accatggacc ttagaggata ctgggaacc tatgatgtcg 3480
agatacgtgc gtttgaccac ggtttcccga tgctggattc attcgagacc taccaactaa 3540
ccgtcaggcc atacaacttc cattcaccgg tgtttgtt cccaactcct ggctcaacca 3600
tcaggctttc tagggagcgt gctatagtca atggtatgct ggctctggct aatatccgca 3660
gcggagagtt cctcgacaga ctctctgcca ctgatgaaga tgggctacac gcaggcagag 3720
taactttctc catagctgga aacgatgaag ctgcggaata tttcaatgtg ttgaacgacg 3780
gtgacaactc agcaatgctc acgctgaagc aagcattgcc cgctggcgtc cagcagtttg 3840
agttggttat tcgggccacg gacggcggga cggagccggg acctaggagt acgactgct 3900
ccgtcactgt ggtgtttgtg atgacgcagg gagacccgt gttcgacgag aacgcagctt 3960
ctgtccgctt cgttgaaaag gaagctggta tgtcggaaaa gttcagctg cctcaggccg 4020
atgaccccaa aaactacagg tgtatggacg actgccatac catctactac tctatcgttg 4080
atggcaacga tggtgaccac ttccgcgtgg agccggagac taacgtgatc tatttgctga 4140
agccgctgga ccgcagccaa caggagcagt acagggtggt ggtgggcgct tccaacagc 4200
ctggcggcac ctccaccttg tcctcctcac tcctcaccgt caccatcggc gttcgagaag 4260
caaaccctag accgatcttc gaaagtgaat tttacacagc tggcgtctta cacaccgata 4320
gcatacacaa ggagctcgtt tacctggcgg caaaacattc agaagggctt cctatcgtct 4380
actcgataga tcaagaaacc atgaaaatag acgagtcgtt gcaaacagtt gtggaggacg 4440
ccttcgacat taactctgca accggagtca tatcgctgaa cttccagcca acatctgtca 4500
```

```
tgcacggcag tttcgacttc gaggtggtgg ctagtgacac gcgtggagcg agtgatcgag 4560
caaaagtgtc aatttacatg atatcgactc gcgttagagt agccttcctg ttctacaaca 4620
cggaagctga agttaacgag agaagaaatt tcattgcaca aacgttcgcc aacgcgtttg 4680
gtatgacatg taacatagac agcgtgctgc cggctaccga cgccaacggc gtgattcgcg 4740
aggggtacac agaactccag gctcacttca tacgagacga ccagccggtg ccagccgact 4800
atattgaggg attatttacg gaactcaata cattgcgtga catcagagag gtactgagta 4860
ctcagcaatt gacgctactg gactttgcgg cgggagggtc ggcagtgctg cccggcggag 4920
agtacgcgct agcggtgtac atcctcgccg gcatcgcagc gttactcgcc gtcatctgtc 4980
tcgctctcct catcgctttc ttcattagga accgaacact gaaccggcgc atcgaagctc 5040
tcacaatcaa agatgttcct acggacatcg agccaaacca cgcgtcagta gcagtgctaa 5100
acattaacaa gcacacagaa cctggttcca atcccttcta taacccggat gttaagacac 5160
ctaacttcga cactataagc gaagtatccg atgacctgct tgatgtcgaa gacttggaac 5220
agtttggaaa ggattacttc ccacccgaaa acgaaattga gagcctgaat tttgcacgta 5280
accccatagc gacacacggg aacaactttg gcgtaaactc aagcccctcc aacccagagt 5340
tctccaactc ccagtttaga agttaaacta aatacacttt tatcacttgc atagacttat 5400
gtatttaata attttacatt ttttacatta aatataaatg ttttatatgt aataatagtg 5460
tgataaaatg tacgtaacaa tcaacatagc tgttgtaggt cgtaaataa catactcgta 5520
atgtataagt gttatgttta tatatagaaa taaaaatatt aaatattaaa aaaaaaaaaa 5580
aaaaaaaaaa aa                                                    5592

SEQ ID NO: 2           moltype = AA   length = 1742
FEATURE                Location/Qualifiers
source                 1..1742
                       mol_type = protein
                       organism = Spodoptera frugiperda
SEQUENCE: 2
MAVDVRILTA TLLVLTTATA QRDRCGYMVE IPRPDRPDFP PQNFDGLTWA QQPLLPAEDR   60
EEVCLNDYEP DPWSNNHGDQ RIYMEEEIEG PVVIAKINYQ GNTLIGVSVV LPPQIRLPFR  120
VGAAHMLGAE IREYPDATGD WYLVITQRQD YETPDMQRYT FDVSVEGQSL VVTVRLDIVN  180
IDDNAPIIEM LEPCNLPELV EPHVTECKYI VSDADGLIST SVMSYHIDSE RGDEKVFELI  240
RKDYPGDWTK VYMVLELKKS LDYEENPLHI FRVTASDSLP NNRTVVMMVE VENVEHRNPR  300
WMEIFAVQQF DEKQAKSFTV RAIDGDTGIN KPIFYRIETE DEDKEFFSIE NIGEGRDGAR  360
FHVAPIDRDY LKRDMFHIRI IAYKQGDNDK EGESSFETSA NVTIIINDIN DQRPEPFHKE  420
YTISIMEETA MTLDLQEFGF HDRDIGPHAQ YDVHLESIGP EGAHTAFYIA PEEGYQAQSF  480
TIGTRIHNML DYEDDDYRPG IKLKAVAIDR HDNNHIGEAI ININLINWND ELPIFDEDAY  540
NVTFEETVGD GFHIGKYRAK DRDIGDIVEH SILGNAANFL RIDIDTGDVY VSRDDYFDYQ  600
RQNEIIVQIL AVDTLGLPQN RATTQLTIFL EDINNTPPIL RLPRSSPSVE ENVEVGHPIT  660
EGLTATDPDT TADLHFEIDW DNSYATKQGT NGPNTADYHG CVEILTVYPD PDNHGRAEGH  720
LVAREVSDGV TIDYEKFEVL YLVVRVIDRN TVIGPDYDEA MLTVTIIDMN DNWPIWADNT  780
LQQTLRVREM ADEGVIVGTL LATDLDGPLY NRVRYTMVPI KDTPDDLIAI NYVTGQLTVN  840
KGQAIDADDP PRFYLYYKVT ASDKCSLDEF FPVCPPDPTY WNTEGEIAIA ITDTNNKIPR  900
AETDMFPSEK RIYENTPNGT KITTIIASDQ DRDRPNNALT YRINYAFNHR LENFFAVDPD  960
TGELFVHFTT SEVLDRDGEE PEHRIIFTIV DNLEGAGDGN QNTISTEVRV ILLDINDNKP 1020
ELPIPDGEFW TVSEGEVEGK RIPPEIHAHD RDEPFNDNSR VGYEIRSIKL INRDIELPQD 1080
PPFKIITIDDL DTWKFVGELE TTMDLRGYWG TYDVEIRAFD HGFPMLDSFE TYQLTVRPYN 1140
FHSPVFVFPT PGSTIRLSRE RAIVNGMLAL ANIASGEFLD RLSATDEDGL HAGRVTFSIA 1200
GNDEAAEYFN VLNDGDNSAM LTLKQALPAG VQQFELVIRA TDGGTEPGPR STDCSVTVVF 1260
VMTQGDPVFD DNAASVRFVE KEAGMSEKFQ LPQADDPKNY RCMDDCHTIY YSIVDGNGDG 1320
HFAVEPETNV IYLLKPLDRS QQEQYRVVVA ASNTPGGTST LSSSLLTVTI GVREANPRPI 1380
FESESEFYTAGV LHTDSIHKEL VYLAAKHSEG LPIVYSIDQE TMKIDESLQT VVEDAFDINS 1440
ATGVISLNFQ PTSVMHGSFD FEVVASDTRG ASDRAKVSIY MISTRVRVAF LFYNTEAEVN 1500
ERRNFIAQTF ANAFGMTCNI DSVLPATDAN GVIREGYTEL QAHFIRDDQP VPADYIEGLF 1560
TELNTLRDIR EVLSTQQLTL LDFAAGGSAV LPGGEYALAV YILAGIAALL AVICLALLIA 1620
FFIRNRTLNR RIEALTIKDV PTDIEPNHAS VAVLNINKHT EPGSNPFYNP DVKTPNFDTI 1680
SEVSDDLLDV EDLEQFGKDY FPPENEIESL NFARNPIATH GNNFGVNSSP SNPEFSNSQF 1740
RS                                                              1742

SEQ ID NO: 3           moltype = DNA   length = 5193
FEATURE                Location/Qualifiers
source                 1..5193
                       mol_type = genomic DNA
                       organism = Helicoverpa armigera
SEQUENCE: 3
atggcagtcg acgtgagaat attcacggca gcggttttta tactcgctgc tcacttcact   60
ttcgcacaag attgtagcta catggtagca ataccagac cagagcgacc agattttcca  120
agtcaaaatt tcgatggaat accatggagt cagtatccct tgataccagt ggagggtaga  180
gaagacgtgt gtatgaacga gttcgagcca ggtaaccaaa accctgttac cgtcatcttc  240
atggaagagg agatcgaagg ggatgtggcc atcgcacggc tcaactatcg aggtaccaat  300
actccgacca ttgtatctcc atttagcttt ggtactttta acatgttggg gccggtcata  360
cgtagaatac ctgagaatgg tggtgactgg catctcgtca ttacacagga acaggactac  420
gagacaccag gtatgcagca gtacatcttc gacgtgaggg tagacgacga accccctggtg  480
gccacggtca tgcttctcat cgtcaacatt gatgacaacg atcctatcat acagatgttc  540
gagccttgtg atattccgga acgcgtgaa acaggcatca catcatgcaa gtatacagtc  600
agcgatgctg acggtgagat cagtactcgc ttcatgagt tcgaaattca agcgatcga  660
gacgatgacg aatattcga actcgtcagg gaaaatatac aaggacagtg gatgtatgtt  720
catatgagag ttcacgtcaa aaaacctctt gactacgagg aaaacccgct acatttgttt  780
agagttacag cttatgattc cctaccaaac acacatacag taacaatgat ggtgcaagta  840
gagaacgttg agaacagacc gccgcgatgg gtggagatat ttgctgtcca gcagttcgat  900
gagaagacgg agcggtcctt cagggttcga gccatcgatg tgatacagg aatcgataaa  960
```

-continued

```
cctatcttct ataggatcga aacagaagaa ggagaggaaa acttgttcag cattcaaaca   1020
atggaaggtg gtcgagaagg agcttggttt aacgttgctc caatagacag agacactctt   1080
gagaaggaag ttttccacgt gtccataata gcgtacaaat atggtgataa tgacgtggaa   1140
ggcagttcgt cgttccagtc gaaaaccgat gtggtcatca tcgtgaacga tgtcaatgat   1200
caggctccgt tgcctttccg ggaagagtat tccattgaaa ttatggagga aactgcgatg   1260
acactgaact tagaagactt tgggttccac gatagagatc ttggtcctca cgcccaatac   1320
acagtgcacc tagagagcat ccatcccccc cgagctcacg aggcgttcta catagcaccg   1380
gaggtgggct accagcgcca gtccttcatc atgggcacgc agaaccatca catgctggac   1440
tttgaagtgc cggagttcca gaatatacaa ctgagggcta tagcgataga catggacgat   1500
cccaaatggg ttggtattgc gataatcaac attaaactga tcaactggaa cgatgagctg   1560
ccgatgttcg agagtgacgt gcaaaccgtc agcttcgacg agacagaggg cgctggcttc   1620
tatgtggcca ctgttgtggc gaaggaccgg gatgttggtg ataaagtcga acactctcta   1680
atgggtaacg cagtaagcta cctgaggatc gacaaggaaa ccggcgagat attcgtcaca   1740
gaaaacgaag ctttcaacta tcacagacag aacgaactct ttgtgcagat acgagctgat   1800
gacacattag gcgagccata caacaccaac actacccagt tggtgatcaa gctgcgggat   1860
attaacaaca ctcctcctac gctcagactg cctcgcgcca ctccgtcagt ggaagagaac   1920
gtgcccgacg ggtttgtgat ccccacacaa ctgaacgcca cggaccccga cactacagcc   1980
gagctgcgct tcgagatcga ctgggagaac tcctatgcca ccaagcagga acggaatact   2040
gactctaagg agtatatagg ttgtatagaa atcgagacga tacccgaa tataaaccag   2100
cgcggcaacg ccatcggccg cgtggtggtg cgagagatcc gggacggcgt caccatagac   2160
tatgagatgt ttgaagtgct atatctgacg gtcattgtga gggatctcaa cactgttatt   2220
ggggaagacc atgatatttc cacattcaca atcacaataa tagacatgaa cgacaaccct   2280
cccctgtggg tggaaggcac cctcactcaa gagttccgcg tgcgagaggt cgcagcctca   2340
ggagtcgtta taggatccgt actgctact gatatcgacg gaccgctgta taatcaagtg   2400
cagtatacta taactcccag actcgatact ccagaagacc tagtggacat agacttcaac   2460
acgggtcaga tctccgtgaa gttacaccaa gctatagatg cagacgagcc gccgcgtcca   2520
aacctctact acaccgtcat agctagtgac aagtgtgacc tcctcactgt cactgggtgt   2580
cctcctgacc ctacctactt tgggacgccg ggagagatca cgatccacat aacgacacg   2640
aacaacaagg tgcctcaagt ggaagacgac aagttcgagg cgacggtgta catctacgag   2700
ggcgcgacg acggagaaca cgtcgtgcag atctacgcg gcgatctcga tagagatgaa   2760
atctaccaca aagtgagcta ccagatcaac tacgcgatca actccgtct ccgcgacttc   2820
ttcgagatgg aacctggagac aggcctggtg tacgtcaaca caccgccgg cgagctgctg   2880
gacagggacg gcgacgagcc cacacatcgc atcttcttca atgtcatcga taacttctat   2940
ggagaaggag atggcaaccg caatcagaac gagacacaag tattggtagt attgctggac   3000
atcaacgaca actatccaga actgcctgaa acaatcccat gggctatctc tgagagctta   3060
gagcagggtg agcgagtacc gccagaaatc ttcgcccggg accgcgatga acccggaaca   3120
gacaactccc gcgtcgccta cgccatcacc ggtcttacca gcaccgaccg ggacatacaa   3180
gtgcctgatc tcttcaacat gatcaccata gagagggaca ggggaattga tcaaactgga   3240
atacttgagg cagctatgga tttgcggggc tattgggga cttatgaaat tgatatacag   3300
gcgtacgacc atggcatacc tcgaaggatt tcaaatcaga agtacccgct ggtcatcaga   3360
ccttacaact tccacgaccc agtgttcgtg ttccctcaac ctggatctac tatcagactg   3420
gcaaggagc gagcagtagt caacggtata ctggccacag tggacggcga atttctggac   3480
agaatcgtcg ccaccgacga agatggttta gaagctgaac ttgttacatt ctctatcgag   3540
ggagatgatg aagatgctca gttcttcgac gtgttgaacg atggagtgaa ctcgggcgct   3600
ctcacccctca cgcggctctt ccctgaagat ttccgagagt tccaggtgac gattcgtgct   3660
acggacggtg gaactgagcc tggtccaagg agtacggact gtgcggtgac cgtagtgttt   3720
gttcccacac agggagaccc cgtgttcgag gaaagtacct acacggtgc ttttgttgaa   3780
aaagatgagg gtatggagga gagggcagaa ttacctcgcg cctcagatcc gaggaacatc   3840
atgtgtgaag atgactgtca cgacacctat tacagcattg ttggaggcaa ttcgggtgaa   3900
cacttcagag tagaccctcg taccaacgtg ctgaccctcg tgaagccgct ggaccgctcc   3960
gaacaggaga cacacaccct catcatcgga gccagcaaga ctcccaaccc ggccgccgtc   4020
ctgcaggctt ctacactcac tgtcactgtt aatgttcgag aagcgaaccc gcgaccagtg   4080
ttccagagag cactctacac agctggcatc tctgctggcg atttcatcga aagaaatctg   4140
ctgactgtag tagcgacaca ttcagaaggt ctgcccatca cttacactct gatacaagag   4200
tccatggaag cagaccccac actcgaagct gttcaggagt cagccttcat cctcaaccct   4260
gagactggag tcctgtcact caacttccag ccaaccgccg ccatgcatgg catgtttgag   4320
ttcgaagtcg aagccactga ttcaaggaga gaaactgccc gcacggaagt gaaggtgtac   4380
gtgatatcgg accgcaaccg agtgttcttc acgttcaata acccgctgcc tgaagtcaca   4440
cccaggaag atttcatagc ggagacgttc acggcattct tcggcatgac gtgcaacatc   4500
gaccagacgt ggtgggccag cgacccgtc accggcgcca ccaggacga ccagactgaa   4560
gtcagggctc atttcatcag ggacgactta cccgtgcctg ctgaggagat tgaacagtta   4620
cgcggtaacc caactctagt aaatagcatc aacgagccc tagaagaaca gaacctgcag   4680
ctggccgacc tgttcacggg cgagacgccc atcctgggcg tgacgcgca ggcgcgagct   4740
ctgtacgcgc tggcggcggt ggctgctgca ctcgcgctga ttgtagttgt gctgcttatt   4800
gtgttctttg ttaggactag gactctgaac cggcgcttgc aagctctatc catgaccaag   4860
tacagttcgc aagactcggg gctgaaccgc gtgggtctgg cggcgccggg caccaacaag   4920
cacgccgtcc agggctccaa ccccatctgg aacgaaacgt tgaaggctcc agactttgat   4980
gctcttagtg agcagtcata cgactcagac ctgatcctca tcgaagactt gccgcagttc   5040
aggaacgact acttcccgcc tgaagagggc agctccatgc ggagtgtcgt caatgaacac   5100
gtgcctgaat caatagcgaa ccataacaac aacttcgggt tcaactctac tcccttcagc   5160
ccagagttcg cgaacacaca gttcggaaga taa                               5193
```

SEQ ID NO: 4      moltype = AA  length = 1730
FEATURE           Location/Qualifiers
source            1..1730
                  mol_type = protein
                  organism = Helicoverpa armigera
SEQUENCE: 4
MAVDVRIFTA AVFILAAHFT FAQDCSYMVA IPRPERPDFP SQNFDGIPWS QYPLIPVEGR   60

```
EDVCMNEFEP GNQNPVTVIF MEEEIEGDVA IARLNYRGTN TPTIVSPFSF GTFNMLGPVI    120
RRIPENGGDW HLVITQRQDY ETPGMQQYIF DVRVDDEPLV ATVMLLIVNI DDNDPIIQMF    180
EPCDIPERGE TGITSCKYTV SDADGEISTR FMRFEISSDR DDDEYFELVR ENIQGQWMYV    240
HMRVHVKKPL DYEENPLHLF RVTAYDSLPN THTVTMMVQV ENVENRPPRW VEIFAVQQFD    300
EKTERSFRVR AIDGDTGIDK PIFYRIETEE GEENLFSIQT MEGGREGAWF NVAPIDRDTL    360
EKEVFHVSII AYKYGDNDVE GSSSFQSKTD VVIIVNDVND QAPLPFREEY SIEIMEETAM    420
TLNLEDFGFH DRDLGPHAQY TVHLESIHPP RAHEAFYIAP EVGYQRQSFI MGTQNHHMLD    480
FEVPEFQNIQ LRAIAIDMDD PKWVGIAIIN IKLINWNDEL PMFESDVQTV SFDETEGAGF    540
YVATVVAKDR DVGDKVEHSL MGNAVSYLRI DKETGEIFVT ENEAFNYHRQ NELFVQIRAD    600
DTLGEPYNTN TTQLVIKLRD INNTPPTLRL PRATPSVEEN VPDGFVIPTQ LNATDPDTTA    660
ELRFEIDWEN SYATKQGRNT DSKEYIGCIE IETIYPNINQ RGNAIGRVVV REIRDGVTID    720
YEMFEVLYLT VIVRDLNTVI GEDHDISTFT ITIIDMNDNP PLWVEGTLTQ EFRVREVAAS    780
GVVIGSVLAT DIDGPLYNQV QYTITPRLDT PEDLVDIDFN TGQISVKLHQ AIDADEPPRQ    840
NLYYTVIASD KCDLLTVTGC PPDPTYFGTP GEITIHITDT NNKVPQVEDD KFEATVYIYE    900
GADDGEHVVQ IYASDLDRDE IYHKVSYQIN YAINSRLRDF FEMDLETGLV YVNNTAGELL    960
DRDGDEPTHR IFFNVIDNFY GEGDGNRNQN ETQVLVVLLD INDNYPELPE TIPWAISESL   1020
EQGERVPPEI FARDRDEPGT DNSRVAYAIT GLTSTDRDIQ VPDLFNMITI ERDRGIDQTG   1080
ILEAAMDLRG YWGTYEIDIQ AYDHGIPRRI SNQKYPLVIR PYNFHDPVFV FPQPGSTIRL   1140
AKERAVVNGI LATVDGEFLD RIVATDEDGL EAGLVTFSIA GDDEDAQFFD VLNDGVNSGA   1200
LTLTRLFPED FREFQVTIRA TDGGTEPGPR STDCAVTVVF VPTQGEPVFE ESTYTVAFVE   1260
KDEGMEERAE LPRASDPRNI MCEDDCHDTY YSIVGGNSGE HFRVDPRTNV LTLVKPLDRS   1320
EQETHTLIIG ASDTPNPAAV LQASTLTVTV NVREANPRPV FQRALYTAGI SAGDFIERNL   1380
LTVVATHSEG LPITYTLIQE SMEADPTLEA VQESAFILNP ETGVLSLNFQ PTAAMHGMFE   1440
FEVEATDSRR ETARTEVKVY VISDRNRVFF TFNNPLPEVT PQEDFIAETF TAFFGMTCNI   1500
DQTWWASDPV TGATRDDQTE VRAHFIRDDL PVPAEEIEQL RGNPTLVNSI QRALEEQNLQ   1560
LADLFTGETP ILGGDAQARA LYALAAVAAA LALIVVVLLI VFFVRTRTLN RRLQALSMTK   1620
YSSQDSGLNR VGLAAPGTNK HAVEGSNPIW NETLKAPDFD ALSEQSYDSD LIGIEDLPQF   1680
RNDYFPPEEG SSMRGVVNEH VPESIANHNN NFGFNSTPFS PEFANTQFGR             1730

SEQ ID NO: 5           moltype = DNA   length = 5371
FEATURE                Location/Qualifiers
source                 1..5371
                       mol_type = genomic DNA
                       organism = Diabrotica virgifera
SEQUENCE: 5
agagcatatc gaaagataat aaagttaatc acaggtataa aacttttttc atgaaatctg     60
taaaatattt agcactaaac tatttgtttt tgtgagagtt acaagtgaga gggtgttttg    120
taaatgatgt ggattgtttg atacccttaa aaaacatcaa aaatggctac gagaaatcta    180
tgtttatgta tgcttatttg gatgccactc tttgagggca tagttggcag cgtcgccttt    240
ggcattgcac aaattcctgg tggtaaggca acagtagaag atttgaaaaa agggaaatac    300
ttacttaaca tggaagaaaa taatcatggc ggcgtaatac caactccact tttactatt    360
acaggggtgg acaacactga ttgtcctaac ttgaatgttg aatttactca aggcatgaag    420
tttaagtttt cgattaatga aagttgtata ttctatgctg aacagacatt tgactacgaa    480
tcgaatgaaa gatcatacaa tttcagaatt tcaaagtccg taaatgacga gatagatatt    540
gcattcagta tcaaaaatat cgatgatgaa cctccacaat taggaacgtt taaatgcaac    600
tttaatgaac aattagacta tagtcttgat gacacaccat gcaatactac attgcatgat    660
cccgacggat ggctggcaca agagaaaatt ttaatattca tcgacactga gatgaagat    720
atattcgcaa ttgatttgcg aaagcctcta ccaaatgata ctgggacaga cacctacgtt    780
tttatgtatc tcttaaagca acttaattat gaggatacca attttatca gtttacagtg    840
caagcaaatg attctggagg taatctttca ccacaagaaa gtgctgtggt aaatgttatc    900
aacattagaa gtagacctcc aaaatggtca aaaataactt tatttgatca atttgacgaa    960
ctgaccgaac aagattacga tatacaagct ttagatggag atactggaat tcatgcagat   1020
atttgttatg caaactaggt gaagatttaa ccagacaatt acataaacgt cagtaccgat   1080
aaaaccaata aaaaaggcca tattcacgtt aatcccattg atagagataa ggatgatcta   1140
acactatacc attttaacat ttctgcctat gttttgtgatg ccccagacta ttttactgta   1200
aatacagtgc agtattacat catcgatatt gacaataatc ctcccaggat agttgaaaat   1260
gttggggatg acgaaagaa cacaacattt gacgatgata cgaccataaa aatgttaca   1320
ctaagttatt tggaaaatta ttcgagatcg tataatttta gcacaaccat tacagataga   1380
gatacgggcg aaaacgcgca attcactgta agtctcgaaa atgttgaggg ttctacggtt   1440
gattatacac aaccctatct aatagtaccg gacaatgctt acaagacagg atcattcata   1500
ataagcgtga aaaataagac cttcctggat ttcgagaacg acacttggaa aaagcattcc   1560
tattatgttg tttccaatgg aaaaaaagac aaatcaaaga ctgacagaat gttaatatca   1620
gtctcactag aagactataa cgatgaactt cctattttcg agaaagaatc atacacaaca   1680
gaaataaatg agactgttgc gaacggcact caaatactat acacccatgc aacagacaga   1740
gatgcagaag atttcgaact gaaaatgaat atagttggaa cttatgctga gaataggcta   1800
agtattgata aagatggaaa tattaaagta gaggtagtca atgccttcga ttacgatgtc   1860
ttaaattctg tgtatttcca gtaaccgca acagataagg ttaatcatgt gactagagta   1920
ccagtaacga ttaacatttt ggatgttaat aatgaagctc ccgtaataaa tcaagtggac   1980
catatacaaa tcgaagaaaa ccaacaaaac ggtagtgtgc taaatgtaac aataacagct   2040
acggatgtag ataccacggc taatctgact gctactataa attgggaaga ttccaaagtt   2100
accaaaacta atggtgctgt agtaaaaact gacgctgtaa taaaagctat gcaattttta   2160
gagatagaaa atacacaaac agatgacggt ctggaaatga aactaaaggt aataaataat   2220
aatgacgata atccagacaa gccagatttt gaaacttctcg atacattgta tttaagtata   2280
gttgttgaag accgtaagtg acctcgtgat tttgaacaaa atcgatatc agaaggtcaa   2340
attgtcatca atatccttga tgttaacgat aatccaccat attttccacc ttctaatgat   2400
gacactcgac aggtccagga aatgtctctg aaaggagtat cggttggctc cataaaagct   2460
gtcgatgttg atttgaattc agaaattacc taccattgca cgcccgaata tgaaaagttt   2520
gactgggtcg atgtaaatct tacaactggc gccaatactg taagaacgaa taacaagtt   2580
gacgcagaca cagacaaaac gtattatttc aactatactt gttgggctca tgatggtgtg   2640
```

-continued

```
ttcttttcca aaccgttaga catctcaatc tatgtcatcg acacaaacaa cgaagtgcct  2700
gtaatagatt ttccaaatga agtacacgta aaggaaaaat cacttataga tacagtaatt  2760
aaaaagattg ttacaagtga tttagataga gatgagccgt ttcgtactgt aaactgtaat  2820
tttgcaagcg atactgatcc agactgtcaa atagaattct atattgatac caatgttctt  2880
aaagtgaaaa gaaataaaac tcttgatcgt gataaggaga gaaaaacata tcctttgtcta 2940
tttgagtgct tggataatcc tttaaatgtt cgatcccaag gacaaaataa agccaataaa  3000
agctttacta taatattgga tgatataaat gatcatgcac ctgtgcttat gacgaaggac  3060
ctacaatgtt ctgaaaattt gaataaggac ggcgaagtag gagagggcat aataggagaa  3120
gatattgatg atggtgataa tgctaaaata gattttctg tgttaagtat cgttgataag   3180
gaaaccaaaa atgacattca agaatctttt aatatttcta aaattgatag tgattatgta  3240
ttgaacgata cattgaagaa agtgcatctt atagccttcg aagatctcaa aggaaaatat  3300
ggaacgtatg aagtcacttt acacatgcat gacgaaggag atccaatgca gacaacagat  3360
ccggatccaa ctttaacact tacaattgaa aaatggaatt accaaacacc aagtataata  3420
tttcctgaaa acgatcaaac atacattgtc ctatcggatc aacaacctgg tcaaccattg  3480
gcactgttta acaacactgg aactttcaaat actttgcccg attttagtgc aacagatggt  3540
gaaacgaagg actattctaa gtgggatgtg aaattttctt atacgcagac taattatgaa  3600
gatgataaaa ttttcgtgat agaccatata cagccgtgcg tttctcaact acaagtcagc  3660
aaacatttca actcggatct agtacgaagt aaaaagtata agctaactat tacagccagt  3720
gttaaggatg gagcagaaca ggaaggtgaa gcaggttact cgacatcagc aaatataagt  3780
atagttttcc tcaacaacga cgctcagccg atctttcaaa atagtgactg gagtgtatca  3840
tttgttgaat tcaatacaac acaacctgcg aaacctttgg aagaacaggc tgagtatgag  3900
aacacgaaag gaggacttcc tatctattac catttctaat ccgaaaaacca gacccttttca 3960
aaatattttg aggttgatga gacgtccggt gatttatcgg ttataggaaa tcttacctat  4020
gattatgatc aagatatatc gtttcacata gttgcttcga atgactcaca agtcagaatg  4080
ttggatccac gatccagtct aaatgttact gttaattttc ttccacgtaa ccgcagagct  4140
cctcagtgga aaagtaccaa attctttgga gcagttatgc ctacattcgt aactgggaac  4200
ctcatagtca ccgctcaagc tcatgacgac gattatatcg atcaacaacg cggattaacg  4260
tgttctatat ctagtgagat taaccgaatt ggggaaggat tagataaaat aataggcgaa  4320
ccatttatt tgagcactga aaatgatgcc gccaaaatat ttttggactt tacagtgcag   4380
actacaatga ccggtcgatt tgaatttaaa atcaaagtag aggacaatag agatgactac  4440
ggcaatggtc catttgaaag tgaagctgat acaacaatat ttattattac taaagacaac  4500
accgttgatt tcaattttta caacgatatt gaggatgttc aggacagaga aacaccgatg  4560
ttaaaaataa tatccgatat agtgggatat gatgcatatc gtcaaaatat agatacagta  4620
acaaatagcg gtctcgttag gaccagagca aggctttatt tcattgacag taaaagcagc  4680
cgtcggttgc aactcactaa aagtcccgca gacagtggat tcgaactggt taatagtgaa  4740
acaatattaa acatagtgac caatgtgaac accttccaaa atctggccag caccttgaga  4800
agtgaacaaa aactgaacct cgacagcttt gaaacgaatt ccaaatccgg caacagcgaa  4860
gcagcactca gagcttggtt gatcggagtg tccgtggtct tggggatctt ggtcttgctt  4920
ttactaatca cttaatact aaaaaccaga cagttaagta acagaattaa aaaactaact  4980
acccccaat ttggttctca agagtctgga cttaacagga tgggcataaa tgcacccacc  5040
accaacaagc atgccatcga aggaacaaat ccagtataca ataataacga aatcaagaag  5100
ccaaaaaata tgaacgattt tgatactcac agcataagaa gcggtgattc tgatttggtt  5160
ggaatagaaa caaacccaga gtttgactac aacttcacaa ctaacgagga taaaactaca  5220
tatctctaaa ctattttat aataatctta tgtctagctt aagttggtct taatagatat  5280
taatgtaatc tgatttaact ataattgtat tataagtatt aaatatgtat aaaatataaaca  5340
cttattagat ccaaaaaaaa aaaaaaaaaa a                                  5371
```

```
SEQ ID NO: 6           moltype = AA  length = 1688
FEATURE                Location/Qualifiers
source                 1..1688
                       mol_type = protein
                       organism = Diabrotica virgifera
SEQUENCE: 6
MATRNLCLCM LIWMPLFEGI VGDVAFGIAQ IPGGKATVED LKKGKYLLNM EENNHGGVIP    60
TPLFTITGVD NTDCPNLNVE FTQGMKFKFS INESCIFVAE QTFDYESNER SYNFRISKSV   120
NDEIDIAFSI KNIDDEPPQL GTFKCNFNEQ LDYSLDDTPC NTTLHDPDGW LAQEKILIFI   180
DTKDEDIFAI DLRKPLPNDT GTDTYVFMYL LKQLNYEDTN FYQFTVQAND SGGNLSPQES   240
AVVNVINIRS RPPKWSKITL FDQFDELTEQ DYDIQALDGD TGIHADICYA KLGEDLPDNY   300
INVSTDKTNK KGHIHVNPID RDKDDLTLYH FNISAYVCDA PDYFTVNTVQ YYIIDIDNNP   360
PRIVENVGDD GKNTTFDDDN DHKNVTLSYL ENYSRSYNFS TTITDRDTGE NAQFTVSLEN   420
VEGSTVDYTQ PYLIVPDNAY KTGSFIISVK NKTFLDFEND TWKKHSYYVV SNGKKDKSKT   480
DRMLISVSLE DYNDELPIFE KESYTTEINE TVANGTQILY THATDRDAED FELKMNIVGT   540
YAENRLSIDK DGNIKVEVVN AFDYDVLNSV YFQVTATDKV NHVTRVPVTI NILDVNNEAP   600
VINQVDHIQI EENQQNGVVL NVTITATDVD TTANLTATIN WEDSKVTKTN GAVVKTDAVI   660
KAMQFLEIEN TQTDDGLEMK LKVINNNDDN PDKPDFETFD TLYLSIVVED RNTDPDFEQN   720
RYTEGQIVIN ILDVNDNPPY FPPSNDDTRQ VQEMSLKGVS VGSIKAVDVD LNSEITYHCT   780
PEYEKFDWVD VNLTTGAITV KNDKQVDADT DKTYYFNYTC WAHDGVFFSK PLDISIYVID   840
TNNEVPVIDF PNEVHVKEKS LIDTVIKKIV TSDLDRDEPF RTVNCNFASD TDPDCQIEFY   900
IDTNVLKVKR NKTLDRDKGR KTYPCLFECL DNPLNVRSQG QNKANKSFTI ILDDINDHAP   960
VLMTKDLQCS ENLNKDGEVG EGIIGEDIDD GDNAKIDFSV LSIVDKETKN DIQESFNISK  1020
IDSDYVLNDT LKKVHLIAFE DLKGKYGTYE VTLHMHDEGD PMQTTDPDPT LTLTIEKWNY  1080
QTPSIIFPEN DQTYIVLSDQ QPGQPLALFN NTGTSNTLPD FSATDGETKD YSKWDVKFSY  1140
TQTNYEDDKI FVIDHIQPCV SQLQVSKHFN SDLVRSKKYK LTITASVKDG AEQEGEAGYS  1200
TSANISIVFL NNDAQPIFQN SDWSVSFVEF NTTQPAKPLE EQAEYENTKG GLPIYYHFYS  1260
ENQTLSKYFE VDETSGDLSV IGNLTYDYDQ DISFHIVASN DSQVRMLDPR SSLNVTVNFL  1320
PRNRRAPQWK STKFFGAVMP TFVTGNLIVT AQAHDDDYID QQRGLTCSIS SEINRIGEGL  1380
DKIIGEPFYL STENDAAKIF LDFTVQTTMT GRFEFKIKVE DNRDDYGNGP FESEADTTIF  1440
IITKDNTVDF QFYNDIEDVQ DRETPMLKII SDIVGYDAYR QNIDTVTNSG LVRTRARLYF  1500
IDSKSSRRLQ LTKSPADSGF ELVNSETILN IVTNVNTFQN LASTLRSEQK LNLDSFETNS  1560
```

KSGNSEAALR AWLIGVSVVL GILVLLLLIT LILKTRQLSN RIKKLTTPQF GSQESGLNRM   1620
GINAPTTNKH AIEGTNPVYN NNEIKKPKNM NDFDTHSIRS GDSDLVGIEN NPEFDYNFNT   1680
NEDKTTYL                                                            1688

SEQ ID NO: 7            moltype = DNA   length = 5277
FEATURE                 Location/Qualifiers
source                  1..5277
                        mol_type = genomic DNA
                        organism = Heliothis virescens
SEQUENCE: 7
atggcagtcg acgtgagaat agtaacggca gcggtattga ttctcgctgc taatttaact   60
ttcgcgcaag attgttccta tatggtagca attcccagac cagagcgacc tgactttcct   120
aatcaaaatt tcgaaggagt accatggagt cagaaccccc tgttaccagc ggaggatagg   180
gaagatgtgt gcatgaacgc gtttgatcca agtgccttga accccgtcac cgtcatcttc   240
atggaggagg agatcgaagg ggacgtggcc attgccaggc ttaactaccg aggtaccaat   300
actccgaccg tggtaactcc atttaacttt ggtaccttcc acttgttggg gccggtcata   360
cgtaggatcc ccgagcaagg gggggactgg catcttgtta ttacgcagag caggactat   420
gagaccccga acatgcagca gtatatcttc aacgtgagag tagaggatga gcccaggaa   480
gccactgtga tgctcatcat tgtcaacatc gacgacaacg ctcctatcat acagatgttc   540
gagccttgtg acattcctga cacggcgaaa ccggcacca cagaatgcaa gtacgtagtg   600
agcgatgctg acggcgagat cagcacacgt ttcatgacgt ttgaaatcga gagcgatcga   660
aacgacgaag aatatttcga actcgtgaga gagaatatca agggacagtg gatgtacgtc   720
catatgaggc ttatactcaa caaacctctt gactatgagg aaaacccgct gcatttgttt   780
agagttacag ctttggattc cctaccaaac gttcatacag tgacgatgat ggtgcaagtc   840
gagaacatag agagcagacc accgcggtgg atggagacct cgccgtgca gcagttcgat   900
gagaagacag cacaagcctt cagggttcga gccatcgatg gagacacggg aatcgataaa   960
cctattttct ataggattga aactgaagaa agcgagaaag atttgttcag tgttgaaaaca  1020
ataggagctg tcgagaagg tgcttggttt aaagtcgctc caatagacag agacactctt   1080
gaaaaggaag ttttccacgt gtctctaata gcgtacaaat atggcgacaa tgacgtgaa   1140
ggaagttcgt cattcgagtc gaaaaccgat atcgtcatta ttgtgaacga cgtgaatgat   1200
caggcgccgg tgcctttccg tccttcatac ttcattgaaa ttatgaggaa aactgcgatg   1260
acattgaatt tagaggactt tggtttccac gatagagatc ttggtccgca cgcgcagtac   1320
acggtacacc tggagagcat ctcccggcg ggagcgcacg aggcgttcta catcgcgccg   1380
gaggtgggct accagcgaca gtccttcatc gtcggcacgc agaaccatca catgctggac   1440
ttcgaagtgc cagagttcca gaagataca cttagggcag tagccataga catggacgat   1500
cccaggtggg ttggtatcgc gattataaac attaacctga tcaactggaa cgatgagctg   1560
ccgatcttcg agcacgatgt gcagactgtg accttcaagg agacggaggg cgctggcttc   1620
cgggtcgcca ctgttctggc aaaggacagg gatattgatg atagagtcga acattctcta   1680
atgggcaacg cagtgaatta cctgagtatc gacaaagaca ccggtgacat cctcgtgaca   1740
attgacgatg cattcaacta tcacagacag aacgagctct tgtgcagat acgagctgac   1800
gacacgttgg gagagccgta taatacgaac actgcccaac tggtgataca gctgcaagac   1860
atcaataaca cacctccaac gctcagactg ccccgcacga ctccgtcagt ggaagagaac   1920
gtgccgacgg ggttcgtgat ccccaccgag ctgcacgcct ccgacccccga caccaccgcc   1980
gagctgcgct tcagcatcga ctgggacact tcctatgcca ccaagcaggg cagggatgct   2040
gatgctaagg agtttgttaa ttgcatagaa atcgagacgg tataccgaa cttgaacgac   2100
cgaggcaccg ccatcggccg cgtggtggtt cgcgagatcc gggaacacgt cactatagac   2160
tacgagatgt tcgaggtgct gtacctcacc gtcagggtca ggatctcaa cacggtcatt   2220
ggagacgact atgatatatc aacattcacg atcataataa tagacatgaa cgacaaccct   2280
ccgctgtggg tggaaggcac gctgacgcag gagttccgcg tgcgagaggt cgccgcctca   2340
ggagttgtta taggatccgt actcgccact gatattgatg gacctcttta taatcaagtg   2400
cggtatacca tcactcctag attagacact ccagaagacc tagtggagat cgacttcaat   2460
tcgggtcaga tctcagtgaa gaagcaccag gctatcgacg cggacgagcc gccgcgccag   2520
cacctctact gcaccgtggt cgccagcgac aagtgcgacc tgctctctgt cgacgtctgt   2580
ccgcctgacc ctaactactt caacacaccg ggtgaaataa cgatccacat aacagacacg   2640
aacaacaagg tgcctcagt ggaggaggac aagttcgaca aaaccgtcta tatctacgag   2700
ggcgcggagg acggagaaca agtcgtgcag ctcttcgcca gcgatctgga tagagatgaa   2760
atctaccaca aagtgagcta ccagaccaac tacgcgatca accctcgtct ccgcgacttc   2820
ttcgaggtag acctggagac cggtctggtg tacgtcaaca cacgccggg ggagaagctc   2880
gaccgggacg gcgatgacac cacgcatcgg atcttcttca acgtcatcga taacttctat   2940
ggggaaggag acggcaaccg gaaccaggac gagacccaag tgttagtggt gctgttggac   3000
atcaacgaca actatccgga actgcctgag ggtctctcat gggatatctc tgagagcttg   3060
ctacaggtg tccgtgtaac cccagatatc ttcgccccgg accgcgacga gcccggcacc   3120
gacaactccc gcgtggcgta cgacatcgtc agcctcacgc ccaccgacag ggacatcaca   3180
cttcctcaac tcttcaccat gatccctata gagaaggaca catcca ccagatgaca   3240
gaactggaga ccgctatgga tttaagaggc tattgggca cttatgaaat acatgtcaag   3300
gcatacgacc atggagtacc tcaaaggatt tcctacgaga agtacccgct agttataaga   3360
ccttacaact tccacgatcc tgtgtttgtg ttccctcaac tggaatgac tatcagactc   3420
gcgaaggagc gagcagtagt gaacggcgtg ctggcgacag tggacggcga gttcctggag   3480
cgaatcgtcg ctaccgacga ggacggctta cacgctcgga ttgtcacctt ctctatctcg   3540
ggagatgatg aggcgttgca gtacttcgac gtgtttaacg acggagtgaa cttaggtgcg   3600
ctgaccatca cgcagctctt ccctgaagac ttccgagagt tcaggtgac gattcgtgct   3660
acggatggtg gtacgagcc tggtccaagg agtacggact gcaccgtcac cgtagtgttt   3720
gttcctacgc agggagagcc tgtgttcgag acaagcacct cacggtcgc ttttattgag   3780
aaagatgtcg gtatggagga acgggctacg ctgcctctcg ccaaggacc cggaacata   3840
atgtgtgaag atgattgtca cgacacctat tacagcattg ttggaggcaa ctcgatgggc   3900
cactttgcag tggaccccca gtccaacgag ctgttcctgc tgacaccgct ggaccgcgcg   3960
gagcaggaga cgcacaccct catcatcggc gccagcgact cgcccagccc ggccgccgtg   4020
ctgcaggctt ccaccctcac tgttactgtc aatgttcgag aagcaaatcc gcggccagtg   4080
ttccagagcg ctctgtacac agccggcatc tccaccctcg acaccatcaa cagagctctg   4140

-continued

```
ctgacactac acgcgacaca ttcagaaggc ctgcccgtga cctacacgct gatacaagac    4200
tccatggaag ctgactccac actgcaagct gtgcaggaga cagccttcaa cctcaaccct    4260
cagactggag tgctgaccct caacttccag ccaactgcct ccatgcacgg catgtttgag    4320
ttcgatgtga tggctattga tacagtggga gaaaccgcac gcaccgaagt gaaggtgtac    4380
ctgatatccg accgcaacag agtgttcttc acgttcatga acacgctcga ggaagtcgaa    4440
ccgaatgagg atttcatggc ggagacattt accctgttct tcggcatgcg gtgcaacatc    4500
gaccagacgc tgcccgccag tgaccccgcc accggcgccg ccaggacga ccagaccgaa    4560
gtcagggcac acttcatacg cgacgacctg cctgtgccgg ctgaggagat cgaacagttg    4620
cgcggtaatc caaccctagt ggcgacaatc cagaacgccc tgcaggagga gaacctgaac    4680
ctggccgacc tgttcacggg cgagactccc atcctgggcg gcgaggcgca ggcgcgggcg    4740
gtgtacgcgc tggcggcggt ggcggctgcg ctcgcgctgc tctgtgtcgt actgcttata    4800
ctcttcttca tcaggactag ggccctcaac cgtcgcctgg aagctctctc catgaccaag    4860
tatagttccc aagactcagg actaaaccgc gtgggtctgg cggcgccggg caccaacaag    4920
cacgcggtgg agggctccaa ccccatctgg aacgaaaccc tcaaggcacc ggactttgat    4980
gctcttagcg agcagtcgta cgactcggac ctaatcggca ttgaagactt gccgcagttc    5040
aggaacgact acttccgcc tgacgaggag agctccatgc ggggagtcgt caatgaacac    5100
atgcctggag ctaattcagt agcaaaccat aacaataact tcgggttcaa cgctaccccc    5160
tttagcccga agttcgcgaa ctcgcagctc agaagataaa atattatagt attttttata    5220
caatattata tagaagtgat ataacgcact aaaatttacc tataagtatg ggcgaag       5277

SEQ ID NO: 8           moltype = AA   length = 1732
FEATURE                Location/Qualifiers
source                 1..1732
                       mol_type = protein
                       organism = Heliothis virescens
SEQUENCE: 8
MAVDVRIVTA AVLILAANLT FAQDCSYMVA IPRPERPDFP NQNFEGVPWS QNPLLPAEDR     60
EDVCMNAFDP SALNPVTVIF MEEEIEGDVA IARLNYRGTN TPTVVTPFNF GTFHLLGPVI    120
RRIPEQGGDW HLVITQRQDY ETPNMQQYIF NVRVEDEPQE ATVMLIIVNI DDNAPIIQMF    180
EPCDIPEHGE TGTTECKYVV SDADGEISTR FMTFEIESDR NDEEYFELVR ENIQGQWMYV    240
HMRLILNKPL DYEENPLHLF RVTALDSLPN VHTVTMMVQV ENIESRPPRW METFAVQQFD    300
EKTAQAFRVR AIDGDTGIDK PIFYRIETEE SEKDLFSVET IGAGREGAWF KVAPIDRDTL    360
EKEVFHVSLI AYKYGDNDVE GSSSFESKTD IVIIVNDVND QAPVPFRPSY FIEIMEETAM    420
TLNLEDFGFH DRDLGPHAQY TVHLESISPA GAHEAFYIAP GEVGYQRQSFI VGTQNHHMLD    480
FEVPEFQKIQ LRAVAIDMDD PRWVGIAIIN INLINWNDEL PIFEHDVQTV TFKETEGAGF    540
RVATVLAKDR DIDDRVEHSL MGNAVNYLSI DKDTGDILVT IDDAFNYHRQ NELFVQIRAD    600
DTLGEPYNTN TAQLVIQLQD INNTPPTLRL PRTTPSVEEN VPDGFVIPTE LHASDPDTTA    660
ELRFSIDWDT SYATKQGRDA DAKEFVNCIE IETVYPNLND RGTAIGRVVV REIREHVTID    720
YEMFEVLYLT VRVTDLNTVI GDDYDISTFT IIIIDMNDNP PLWVEGTLTQ EFRVREVAAS    780
GVVIGSVLAT DIDGPLYNQV RYTITPRLDT PEDLVEIDFN SGQISVKKHQ AIDADEPPRQ    840
HLYCTVVASD KCDLLSVDVC PPDPNYFNTP GEITIHITDT NNKVPRVEED KFDETVYIYE    900
GAEDGEQVVQ LFASDLDRDE IYHKVSYQTN YAINPRLRDF FEVDLETGLV YVNNTAGEKL    960
DRDGDEPTHR IFFNVIDNFY GEGDGNRNQD ETQVLVVLLD INDNYPELPE GLSWDISESL   1020
LQGVRVTPDI FAPDRDEPGT DNSRVAYDIV SLTPTDRDIT LPQLFTMITI EKDRGIDQTG   1080
ELETAMDLRG YWGTYEIHVK AYDHGVPQRI SYEKYPLVIR PYNFHDPVFV FPQPGMTIRL   1140
AKERAVVNGV LATVDGEFLE RIVATDEDGL HAGVVTFSIS GDDEALQYFD VFNDGVNLGA   1200
LTITQLFPED FREFQVTIRA TDGGTEPGPR STDCTVTVF VPTQGEPVFE TSTYTVAFIE   1260
KDAGMEERAT LPLAKDPRNI MCEDDCHDTY YSIVGGNSMG HFAVDPQSNE LFLLTPLDRA   1320
EQETHTLIIG ASDSPSPAAV LQASTLTVTV NVREANPRPV FQSALYTAGI STLDTINRAL   1380
LTLHATHSEG LPVTYTLIQD SMEADSTLQA VQETAFNLNP QTGVLTLNFQ PTASMHGMFE   1440
FDVMAIDTVG ETARTEVKVY LISDRNRVFF TFMNTLEEVE PNEDFMAETF TLFFGMRCNI   1500
DQTLPASDPA TGAARDDQTE VRAHFIRDDL PVPAEEIEQL RGNPTLVATI QNALQEENLN   1560
LADLFTGETP ILGGEAQARA VYALAAVAAA LALLCVVLLI LFFIRTRALN RRLEALSMTK   1620
YSSQDSGLNR VGLAAPGTNK HAVEGSNPIW NETLKAPDFD ALSEQSYDSD LIGIEDLPQF   1680
RNDYFPPDEE SSMRGVVNEH MPGANSVANH NNNFGFNATP FSPEFANSQL RR           1732

SEQ ID NO: 9           moltype = DNA   length = 4587
FEATURE                Location/Qualifiers
source                 1..4587
                       mol_type = genomic DNA
                       organism = Helicoverpa armigera
SEQUENCE: 9
atggcgacga aacccaagac tcctgggttc acaggtttgg gagatgacag cgaagacgag      60
tcggagtaca ctccgcttta tgacgacgtc gacgatttag aacaaagaac agctcaagaa    120
acaaaaggat ggaatttgtt ccgagaactc cccgtgaaga aggagagcgg tccatggcg     180
tccacagcat ggatcgacac cagtgtcaag atccctcaagt ttctggcata catcaccata    240
tttgtcgtcg tactcggatc tgctgttatt tctaaaggca ctctcctttt tatcacttct    300
caacttaaga agggcaaaca tatcactcat tgtaacaggg cattagcttt agatcaacag    360
tttataacag tccactcttt ggaggagcgc gtgacatggc tatgggcagc cttcataatg    420
ttcagtttcc cggaggtggg cgtattctta agatctgtca ggatatgctt cttcaaaacc    480
gctctgaagc ctacattcct tcactttctt gcgtctatag taatagaaac cctgcacact    540
gttggaattg cgatgctcgt tctgatcatt ctgcccgaac tagatgtcgt taaaggcaca    600
atgttgatga atgcgatgtg cttcgtgcca gggctcctga acgccctctc gagagacmga    660
aatgagcgcc gatatgtttg gaagtcatg ttagacgtac tggcgatctc cggccaagct    720
actgccttcg tagtctggcc tctccttaaa ggcgatacta ttctatggac tattccggta    780
gcttgcgtgt tgtttcact cggctggtgg gaaaacttcg tcggcagctc ggatcaacaa    840
tggtcagtcc tccgacctct tcaagarctt cgagatggtt taaaaagrac tcgttattac    900
acgcagagag ttgtgtcwgt atggaagata tttatattca tgtgctgcat tttgatatct    960
ttggaaatac aacatgatga yccttttgct ttcttcacaa aactcaccac tggttttgcc   1020
```

-continued

```
gaccgcttct acatcgtaca tgaggttcaa gcagttcgag atgagttcga aggcttcttg   1080
ggctacgcag tgaagggatt aacgttagaa ataccagctt catggtctac cccactatgg   1140
gtggtcctca tccaagtgtt ggccgcatac gtttgtttcg gagccagtaa attcgcctgt   1200
aaaatcctca ttcagaactt cagctttaca tttgcactga gcctcgtagg accrgtcact   1260
attaacttct tgattgccgc atgcgggatg aggaatgcaa acccttgtgc tttttaccgc   1320
actatacctg attacttgtt cttcgatatt ccaccggtgt acttcctaaa cgagttcgta   1380
gtacgcgaga tgtcrtgggt wtggttgctg tggatagtct cccaagcttg ggtgactgct   1440
cacacktggc agccgcggtg tgagcgactc gckgcyactg acaaactgtt cgccaaacct   1500
tggtactgca gcgcggtgat agaccagtcg ctgttgttga ataggaccaa ggatgacgac   1560
actgatatag cgttagagga cctcaaaggt ttggatgcag atgctgattc tatagttagc   1620
ggggaaaaag tttcaaagga tgtcaaggcm tctgacagta taacaaggat ctacgtrtgt   1680
gcaactatgt ggcacgaaac gaaagaagaa atgatggagt tcttgaaatc tatttttccgt   1740
ctcgacgaag atcagagcgc tcgaagggtt gcacagaagt acttgggcat tgtcgatcct   1800
gattactatg aactagaagt gcacattttc atggatgacg cgtttgaggt gtccgatcat   1860
agttcggaag attcgcaagt gaatcgtttc gtcacgtgcc tcgtagacac tatygaygag   1920
gctgcytcag argtccayct cacaaacgtr agattaagac cccctaagaa gtaccccacc   1980
ccatacggcg gccgactygt atggacacts ccaggaaaga acaaaatgat ttgccatctm   2040
aaagacaagt ccaaaatcag acacaggaaa agatggctc aggtgatgta catgtactat   2100
ttccttggtc aycgtttgat ggacttgccr atctctgtgg atcgcaagga ggttatcgct   2160
gagaaytactt atttgttggc tytggatggy gacattgact tyaagccgat agccgtcacc   2220
ttgctgattg atctcatgaa gaaggayaag aacttrggag cagcgtgygg acgtatccat   2280
cctgtgggct ctggcttcat ggcttggtat caaatgtcag agtacgctat tggtcattgg   2340
ctgcaaaagg cgacggaaca catgatcggc tgcgtactct gtagtcctgg atgcttctct   2400
ctgttcagag gaaaggcttt gatggacgac aacgtcatga agaaatacac tttgacttct   2460
cacgaagccc gacattacgt acaatatgat caaggtgagg accgttggct gtgcacatta   2520
ctactacaac gcggctaccg agtcgagtac tctgccgacc ccgatgcgta cacgcactgt   2580
ccggaacaat tcgacgagtt cttcaaccag cgacgacgat gggtaccctc tactatggcc   2640
aacatattcg atctgctggc rgatgctaar cgraccatct cgataaatga taatatttcc   2700
acgctttata ttatgtatca gtctatgctt atgttcggta caatcctcgg ccccggcact   2760
atattcctga tgatggtggg agcgatgaac gccatcctca agagcgat gtccaacgcg   2820
ctcatactca acttggtgcc cattctcata ttcatcgtag tctgtatgac ttgcaagtct   2880
gaaacgcagc tattcctggc gagcttgata acatgcgcat acgcaatggt gatgatgtta   2940
gtcatagtgg ggatagtcct tcaaatcgtc gaggacggat ggctggcccc gtccagtttg   3000
ttcacggcg tcatattcgg gacttttctc gtgacggcrg ccccttcatcc vcaggagatc   3060
atatgtttgc tgtatctaac tgtgtactat gtgaccattc cgagtatgta catgttgctc   3120
attatatact cgctgtgcaa tctcaacaac gtgtcgtggg gaactaggga ggtggtgcag   3180
aagaaaacgc taaggaaat ggaacaagaa cgcaaagaag cagaagaagc taagaagaag   3240
atggacgaga agagcataca gaagtggttc ggcaagagtg atgagaccag cggctccttg   3300
gagatgagtg tggctggtct gttcaagtgt atgtgctgca ccaatcctaa ggaccacaag   3360
gaggatctgc atctgctgca gattgctaca gccatcgaga agattgataa gagattggaa   3420
gcgctcggtg cacctcccga agagactgag ccgttgaatc gtcgccggtc ttcagctgta   3480
ttacgtcgac agtcgttaga cccgctcgcc agagtgccgg agtacgaaga gagcgatgta   3540
tccagcgacg tacctaggga cgagcgtgac gatcttatca acccgtactg gatagaagac   3600
gtgaatcttc agaagggtga agtagacttc ctgaccacgg cggagactga gttctggaag   3660
gatctgatcg atgtatactt gaggcccatt gatgaaaaca aacaggaact ggaacgtatc   3720
aaaacgacct tgaagaatct tcgcgacaag agcgtgttcg cgttcgtaat gctgaactct   3780
ttgttcgtgc tgatgatctt cctgctgcaa ctcaaccagg atcagctgca cttcaagtgt   3840
cccttcggac agtcagccag tatagagtac gatgatcaga tgaatgtgtt ccacataaca   3900
caagactacc tgaccctgga gccgatcggg tcgctgttca tcatattctt cgggtccatc   3960
atcatcatcc agttcaccgc tatgctgttc catcgactcg gcacgctcac gcatctgctg   4020
tccaatgttc agctcaactg gtacttcact aagaagcgaa acgacatgtc acaacaacgcg   4080
ctaatagagt ctcgagcact agaaatagcc aaagaccttc aacgcctgaa cacagatgac   4140
ctagaaaagc gtgacaacaa ccaacacgtg agcagaagga agaccataca taacttagag   4200
aaagggaagg atactaagca gagcgttgtg aatcttgacg ccaacttcaa gaggaggctt   4260
actatactgc aaaatgggga tgctgaactg atctcccgcc taccatccct gggaggaacc   4320
acagcgacgc gacgagctac tctacgtgct ctcaaaacca gacgcgactc cgtggtggcc   4380
gagcgccgcc gctcacagat gcaagcccga gactccacca cagacttcat gttcaactcg   4440
cccggcgcgt tggaggatct gggcagtcgg gcgtcggttg gagcgtacgt gaatcgtggc   4500
tacgagcctg cgctcgatag cgaagtggag gacacgccgc ctcctccgag aaggtccacc   4560
gtgcgcttcc aggaccatta cgcgtga                                      4587

SEQ ID NO: 10          moltype = AA  length = 1528
FEATURE                Location/Qualifiers
source                 1..1528
                       mol_type = protein
                       organism = Helicoverpa armigera
SEQUENCE: 10
MATKPKTPGF TGLGDDSEDE SEYTPLYDDV DDLEQRTAQE TKGWNLFREL PVKKESGSMA    60
STAWIDTSVK ILKFLAYITI FVVVLGSAVI SKGTLLFITS QLKKGKHITH CNRALALDQQ   120
FITVHSLEER VTWLWAAFIM FSFPEVGVFL RSVRICFFKT ALKPTFLHFL ASIVIETLHT   180
VGIAMLVLII LPELDVVKGT MLMNAMCFVP GLLNALSRDR NERRYVWKIM LDVLAISGQA   240
TAFVWPLLK GDTILWTIPV ACVFVSLGWW ENFVGSSDQQ WSVLRPLQEL RDGLKRTRYY   300
TQRVVSVWKI FIFMCCILIS LEIQHDDPFA FFTKLTTGFA DRFYIVHEVQ AVRDEFEGFL   360
GYAVKGLTLE IPASWSTPLW VVLIQVLAAY VCFGASKFAC KILIQNFSFT FALSLVGPVT   420
INFLIAACGM RNANPCAFYR TIPDYLFFDI PPVYFLNEFV VREMSWVWLL WIVSQAWVTA   480
HTWQPRCERL AATDKLFAKP WYCSAVIDQS LLLNRTKDDD TDIALEDLKG LDADADSIVS   540
GEKVSKDVKP SDSITRIYVC ATMWHETKEE MMEFLKSIFR LDEDQSARRV AQKYLGIVDP   600
DYYELEVHIF MDDAFEVSDH SSEDSQVNRF VTCLVDTIDE AASEVHLTNV RLRPPKKYPT   660
PYGGRLVWTL PGKNKMICHL KDKSKIRHRK RWSQVMYMYY FLGHRLMDLP ISVDRKEVIA   720
```

```
ENTYLLALDG DIDFKPIAVT LLIDLMKKDK NLGAACGRIH PVGSGFMAWY QMFEYAIGHW    780
LQKATEHMIG CVLCSPGCFS LFRGKALMDD NVMKKYTLTS HEARHYVQYD QGEDRWLCTL    840
LLQRGYRVEY SAASDAYTHC PEQFDEFFNQ RRRWVPSTMA NIFDLLADAK RTISINDNIS    900
TLYIMYQSML MFGTILGPGT IFLMMVGAMN AITQMSMSNA LILNLVPILI FIVVCMTCKS    960
ETQLFLASLI TCAYAMVMML VIVGIVLQIV EDGWLAPSSL FTAVIFGTFF VTAALHPQEI   1020
ICLLYLTVYY VTIPSMYMLL IIYSLCNLNN VSWGTREVVQ KKTAKEMEQE RKEAEEAKKK   1080
MDEKSIQKWF GKSDETSGSL EMSVAGLFKC MCCTNPKDHK EDLHLLQIAT AIEKIDKRLE   1140
ALGAPPEETE PLNRRRSSAV LRRQSLDPLA RVPEYEESDV SSDVPRDERD DLINPYWIED   1200
VNLQKGEVDF LTTAETEFWK DLIDVYLRPI DENKQELERI KTDLKNLRDK SVFAFVMLNS   1260
LFVLMIFLLQ LNQDQLHFKW PFGQSASIEY DDQMNVFHIT QDYLTLEPIG SLFIIFFGSI   1320
IIIQFTAMLF HRLGTLTHLL SNVQLNWYFT KKPDDMSDNA LIESRALEIA KDLQRLNTDD   1380
LEKRDNNQHV SRRKTIHNLE KGKDTKQSVV NLDANFKRRL TILQNGDAEL ISRLPSLGGT   1440
TATRRATLRA LKTRRDSVVA ERRRSQMQAR DSTTDFMFNS PGALEDLGSR ASVGAYVNRG   1500
YEPALDSEVE DTPPPPRRST VRFQDHYA                                     1528

SEQ ID NO: 11            moltype = DNA   length = 4572
FEATURE                  Location/Qualifiers
source                   1..4572
                         mol_type = genomic DNA
                         organism = Spodoptera frugiperda
SEQUENCE: 11
atggcgagac caagaccttta tggttttagg gctttagatg aggagagtga tgacaattcg    60
gagttgactc cgttgcacga tgataatgat gacctaggac aaagaacagc tcaagaggca   120
aaaggatgga atctgtttcg agagattccg gtgaagaagg agagtgggtc tatgcctca    180
actgccggga tagacttcag tgtaaagatc cttaaagtcc tggcgtatat ttttatattt   240
ggcatagtgc tcggatctgc ggttgtgtct aagggtagc tgcttttttat cacatcacaa   300
ctgaaaaagg gcaaagcaat cgttcactgt aatagacagt tagaactgga caagcagttt   360
ataacaatcc attcgttgca agagcgtgtg acgtggctat gggcagcctt catagcattc   420
agtattccag aagttggcgt tttcttgaga tcagtcagaa tatgcttctt caaaacagca   480
ccgaagcctt ctgtttttaca gttttttgacg gccttcgtga tagacaccct tcatacaata   540
ggcattggat tactggtgct tttcatcctg ccagaattga acgtggttaa ggaacaatg    600
ctaatgaatg ctatgtgctt catgcctgga atactaaacg ctgtgaccag agaccgcacg   660
gactctcgat acatgttgaa aatggcacta gatgtactag ctatctccgc tcaagccacc   720
gcgttcgtcg tctggcctct gctaaaaggc gttagtatgc tctgacgat tcctgtcga    780
tgcgtattca tctcactcgg atggtgggaa aatttcgtcg gcgtatcgg aaaacaatga    840
ccagtcctgg aacctgtaca agaacttcgt gacaatttaa agaagactcg ttactacaca   900
cagagggtgt tgtctttgtg aagatattc atattcatgt gttgcatcct gatatctttg   960
gcggcacaag atgacagccc gctttctttc ttcacggagt ttgctactgg atttggtgag  1020
cgcttctaca aagttcatga ggttcgagcg atacaggacg aatttgaagg tttcctgggc  1080
tacaaaatta tggacttata cttcgatcaa atgccagcgg catgggccac cccactgtgg  1140
gtggtgctga tccaggtcct ggcttcttta gtctgtttta tggcaagttt gtctgcctgc  1200
aagattctga tacaaaactt cagctttaca tttgcgttga gtcttgttgg acctgtcacc  1260
atcaacttgt tgatttggct ttgcggcgag aggaacgcag atccctgcgc atatagtaat  1320
acgataccag attatctgtt cttcgacata ccaccggtgt atttcctgaa ggagtttgtg  1380
gtgaaagaga tgtcgtggat ttggttgctg tggctggtgt cgcaggcgtg ggtgacggcc  1440
cacaactggc gctcccggggc cgagcgtctc gccgccagcg acaagctctt caacaggcct  1500
tggtactgca gcccgtcct cgacgtctcc atgctgttga acagaaccaa gaatgaagaa  1560
gcggaaataa cgatagagga tctaaaagaa acagagagtg agggtgggtc tatgatgagc  1620
ggatttgaag caaagaaaga cataaagcct tctgacaaca ttacgaggat atatgtctgc  1680
gcgactatg gcacgaaac gaaagaagaa atgatggact tcttgaagtc tatcctgcgt  1740
ttcgatgagg atcagagcgc gcgtcgcgtc gcacagaagt acttgggcat tgtagatcgt  1800
gattactatg aactcgaagt acacatcttc atggacgatg ctttcgaagt gtcggaccac  1860
agcgcggacg actcgaaagt gaatcccttc gtgacgtgtc tcgtggagac tgtcgacgag  1920
gctgcttcag aggtccatct caccaacgtg aggttgaggc caccgaagaa attccccaca  1980
ccgtacggcg gccgactggt ctggactctc ccaggaaaga acaaaatgat atgccacctc  2040
aaagacaagt ccaaaatacg acacaggaaa agatggtctc aagtgatgta catgtactac  2100
ctattgggcc accgcctgat ggacgtgccg atctcagtgg accgcaagga agtcatcgca  2160
gggaacacct acttactggc tttggacggc gacattgact tcaaaccgac agcagtcacg  2220
ttactaatcg atttgatgaa gaaggataag aatttaggag cagcgtgcgg gcgcatccat  2280
cctgtgggct caggcttcat ggcatggtat caaatgttcg agtacgctat tggtcattgg  2340
ctgcaaaagg cgactgaaca catgattggc tgtgtactct gtagccctgg atgcttctcc  2400
ctcttcagag gaaaggcttt gatggacgac aacgttatga gaaatatac cttaacttcc  2460
cacgaggcac gacactatgt gcaatacgat caaggcgagg accgttggtg cacgctactg  2520
ctgcagcgcg gtaccgcgt ggagtacagc gcggtgtcgc acgcgtacac gcactgccc    2580
gagcacttcg acgagttctt caaccagcgc cgccgctggg tgccctccac gctcgccaac  2640
atcttcgacc tgctcggcag cgccaagctc accgtcaagt ccaacgacaa catctccacc  2700
ctctatatag tctatcagtt catgttgata gtgggtacgg tgttgggtcc cggcacgatc  2760
ttcctgatga tgggggggagc catgaacgcc atcattcaga tcagcaacgc gtacgcgatg  2820
atgttgaacc tcgtaccact cgtcatcttc cttatagtct tgatgacttg tcagtcaaag  2880
acgcagctct tcctcgctaa cctcataaca tgcgcatacg caatggtgat gatgatcgtg  2940
atagtgggga tagttctgca gatagtggag gatggatggc tggctccgtc cagtatgttc  3000
acagctttaa tattcggtac attcttcgtc accgcggcac tacacccgca agagatcaaa  3060
tgtttgttgt tcatagcagt gtactatgta accatcccta gtatgtacat gttgttgatc  3120
atatactcca tctgtaatct caacaacgta tcctgggag ccaggggagac accgcagaag  3180
aaaactgcta aggaaatgga aatgaacag aaggaagcag aagagcgaa gaaaaaatg    3240
gagagtcagg gtttgaagaa gttgtttgcc aagggagaag agaagagtgg ttcgttagag  3300
ttcagtgtgt cgggcctgtt gcgatgtatg tgctgcacca atccagagga tcataaggac  3360
gatctcaaca tgatgcagat ctcacacgcg ttggagaaga taaataagag attggatcaa  3420
ctcgatgtcc ctccctgagcc gacccaccag ccctcgcatc cgcacacaca cgtggagacg  3480
```

-continued

```
gtcggtgttc gtgattacga agacagcgag atttccactg aaattcctaa ggaagaacga   3540
gacgacctga ttaacccta ctggatcgag gacgtggaac tccagaaggg cgaggtagac    3600
ttcctcacca ccgctgagac caacttctgg aaggatgtca tcgatgaata cttactgcct   3660
attgatgagg acaagcgtga aattgaacgt ataagaaaag atttgaagaa cttgcgagat   3720
aagatggtgt ttgcgttcgt gatgttgaac tctctgttcg tgctcgtcat cttcctgctg   3780
cagctcagcc aggaccagct gcacttcaag tggccattcg gacagaagtc cagcatggag   3840
tacgataatg atatgaatat gttcatcata acccaagact acttaacgct ggaacctatc   3900
ggtttcgtgt tcctcctgtt cttcggctcc atcatcatga tccagttcac cgccatgttg   3960
ttccatcgcc tggacacgct ggcccatctg ctgtccacca ccaagctgga ttggtatttc   4020
agtaagaagc cggacgacct atcagacgat gcgctaatag actcttgggc gttgacaata   4080
gcgaaggatc ttcaacgtct gaacaccgac gacttggata aacgaaataa caacgaacac   4140
gtgtccagga ggaagaccat atataacttg gagaaaggga aggaaaccaa accggctgtt   4200
atcaacctcg atgccaacgc caagaggaga ttgactatcc tgcagaatga agactcagaa   4260
ttgatctccc gcctgccatc tctgggacct aatttgtcga ctcgtcgtgc cacggtgcgt   4320
gcaataaaca ctcgacgcgc atctgtcatg gcggagcgac gcaggtctca gttccaagcg   4380
cgaccttccg ggggatcata catgtataat aaccctcaaa acacgattca gctggacgat   4440
atggtcgggg ggccgtcgac gtcggagtg tacgtgaacc gagggtacga gcccgccctg    4500
gacagcgaca tcgaggacac gcccgtgccc accagacgat ccgttgtaca cttcaccgac   4560
catttcgcgt ga                                                       4572
```

| SEQ ID NO: 12 | moltype = AA   length = 1523 |
|---|---|
| FEATURE | Location/Qualifiers |
| source | 1..1523 |
| | mol_type = protein |
| | organism = Spodoptera frugiperda |

SEQUENCE: 12

```
MARPRPYGFR ALDEESDDNS ELTPLHDDND DLGQRTAQEA KGWNLFREIP VKKESGSMAS     60
TAGIDFSVKI LKVLAYIFIF GIVLGSAVVS KGTLLFITSQ LKKGKAIVHC NRQLELDKQF    120
ITIHSLQERV TWLWAAFIAF SIPEVGVFLR SVRICFFKTA PKPSVLQFLT AFVVDTLHTI   180
GIGLLVLFIL PELDVVKGTM LMNAMCFMPG ILNAVTRDRT DSRYMLKMAL DVLAISAQAT   240
AFVVWPLLKG VSMLWTIPVA CVFISLGWWE NFVGDIGKQW PVLEPVQELR DNLKKTRYYT   300
QRVLSLWKIF IFMCCILISL AAQDDSPLSF FTEFATGFGE RFYKVHEVRA IQDEFEGFLG   360
YKIMDLYFDQ MPAAWATPLW VVLIQVLASL VCFMASLSAC KILIQNFSFT FALSLVGPVT   420
INLLIWLCGE RNADPCAYSN TIPDYLFFDI PPVYFLKEFV VKEMSWIWLL WLVSQAWVTA   480
HNWRSRAERL AASDKLFNRP WYCSPVLDVS MLLNRTKNEE AEITIEDLKE TESEGGSMMS   540
GFEAKKDIKP SDNITRIYVC ATMWHETKEE MMDFLKSILR FDEDQSARRV AQKYLGIVDP   600
DYYELEVHIF MDDAFEVSDH SADDSKVNPF VTCLVETVDE AASEVHLTNV RLRPPKKFPT   660
PYGGRLVWTL PGKNKMICHL KDKSKIRHRK RWSQVMYYY LLGHRLMDVP ISVDRKEVIA   720
GNTYLLALDG DIDFKPTAVT LLIDLMKKDK NLGAACGRIH PVGSGFMAWY QMFEYAIGHW   780
LQKATEHMIG CVLCSPGCFS LFRGKALMDD NVMKKYTLTS HEARHYVQYD QGEDRWCTLL   840
LQRGYRVEYS AVSDAYTHCP EHFDEFFNQR RRWVPSTLAN IFDLLGSAKL TVKSNDNIST   900
LYIVYQFMLI VGTVLGPGTI FLMMGGAMNA IIQISNAYAM MLNNLVPLVIF LIVCMTCQSK   960
TQLFLANLIT CAYAMVMMIV IVGIVLQIVE DGWLAPSSMF TALIFGTFFV TAALHPQEIK   1020
CLLFIAVYYV TIPSMYMLLI IYSICNLNNV SWGTRETPQK KTAKEMEMEQ KEAEEAKKKM   1080
ESQGLKKLFA KGEEKSGSLE FSVAGLLRCM CCTNPEDHKD DLNMMQISHA LEKINKRLDQ   1140
LDVPPEPTHQ PSHPHTHVET VGVRDYEDSE ISTEIPKEER DDLINPYWIE DVELQKGEVD   1200
FLTTAETNFW KDVIDEYLLP IDEDKREIER IRKDLKNLRD KMVFAFVMLN SLFVLVIFLL   1260
QLSQDQLHFK WPFGQKSSME YDNDMNMFII TQDYLTLEPI GFVFLLFFGS IIMIQFTAML   1320
FHRLDTLAHL LSTTKLDWYF SKKPDDLSDD ALIDSWALTI AKDLQRLNTD DLDKRNNNEH   1380
VSRRKTIYNL EKGKETKPAV INLDANAKRR LTILQNEDSE LISRLPSLGP NLATRRATVR   1440
AINTRRASVM AERRRSQFQA RPSGGSYMYN NPQNTIQLDD MVGGPSTSGV YVNRGYEPAL   1500
DSDIEDTPVP TRRSVVHFTD HFA                                           1523
```

| SEQ ID NO: 13 | moltype = DNA   length = 2862 |
|---|---|
| FEATURE | Location/Qualifiers |
| source | 1..2862 |
| | mol_type = genomic DNA |
| | organism = Helicoverpa armigera |

SEQUENCE: 13

```
atgggtgcca aaatgttgct tcccaccgta ttctgcatcc tcctgggatc catagcggcc     60
attcctcaag aggacttcag gtccaacttg gagtggctg actacagcac caacttagac    120
gagccggcgt accgtctgcg tgatgtggtc tatcctactg atgtcaacct ggatctggat   180
gtctacctaa accacctgaa cttctctgga cttgtacaga ttgatgttca agtacgagag   240
aacaatttac gccaaattgt tcttccaccaa aaggtggttt ccatcactgg agtgaatgtt   300
gtcggaccta acggcccagt tcctctccaa ttcccccacc cttataccac tgatgattac   360
tatgagatcc ttctcatcaa cttggaccag cccatcaaca ttggcaacta ctccatcgcc   420
atcagataca atggccagat caatgctaac cctcttgacc gaggttttta cagaggctac   480
tatccacctga acaatgaatt gagggtctac gccaccaacc agttccagcc ttaccacgca   540
aggaaggcct tccccttgct cgatgaaccc caattcaaat cccgctacac tatctccatt   600
actcgcgaca ccagtctgtc tccatcgtac tccaacatgg ctattagaag cgcccaaagc   660
attagtacct cccgtattcg cgaaaacttc tacactacgc ccatcatctc cgcctatctg   720
gtcgctttcc acgtcagtga cttcgtctcc actgaataca ccagcaccga tgccaaaccc   780
ttcagtatta tctcccgcca aggtgccacg aaccagcacc aatatgctgc tgaaatcggt   840
cttaagataca caacgaact cgatgactac tttggcatca agtaccatga gatgggacaa   900
ggtgctttga tgaagaatga ccacatcgct cttcctgact tccccctcgg tgctatggag   960
aactggggaa tggttaacta cagggaagcc tacctcttgt acgacgaaaa caacaccaac   1020
ttgaacaaca agatttttcat cgctaccatc atggctcacg aattgggaca caaatggttc   1080
ggtaacctcg tcacttgctt ctggtggagc aaccttggc ttaacgagtc tttcgccagc    1140
ttcttcgaat acttcggcgc tcactgggct gatcccgctc tagagttaga tgaccagttt   1200
```

-continued

```
gtcgttgact acgtgcacag cgctctcaac tctgacgcca gccagtacgc cactcccatg  1260
aaccacaccg acgtcgtgga caatgactcc atcacctccc acttcagtgt taccagctac  1320
gctaagggag cttccgtcct taagatgatg gaacatttcg ttggatggag gaccttcaga  1380
aacgctctca gatactactt gagaaacaac gagtacgaca tcggtttccc cgttgatatg  1440
tacacggctt tcaagcaagc agtcgctgaa gattttactt tccaacgtga tttccctaat  1500
gttgacgttg gcgcagtatt cgacagctgg gtccagaacc ctggctctcc cgtcatcaac  1560
gttgcccgta acaataacac aggtgtcatc actgtcaacc agcaacgtta cgtgctctcc  1620
ggcgctgttg cctcaacgac gtggcacatt cctctcacct ggactcaaca tggctccctc  1680
aacttcaaca gcaccaggcc tagcaccgtc cttagcgatg agattggcac catcaacgct  1740
gcatctggag accacttcgt cattttcaac attgcccaat ctggtctgta ccgtgtcaac  1800
tacgacacca acaactggca gttgcttgct tcatacctga agagcaacaa cagacagaac  1860
attcacaagc tgaacagagc tcagatcgtc aacgacatct tgtacttcgt gcgttctaac  1920
agcatcaaca ggactctcgc ttttgatgtc ctcgacttct tgagggatga gaccgattac  1980
tacgtatgga atggagctct tacccagatc gactggatcc ttcgtcgcct tgaacacttg  2040
cctaccgctc atgctgcttt ctctgaatac atcctcgagc tcatgaacac ggttatcaat  2100
caccttggct ataacgagca cagtaccgac tctacctcca caatcctcaa ccgtatgcag  2160
atcatgaact acgcttgcaa ccttggacac agtggctgca tttctgacag tttagacaaa  2220
tggaggcagc accgtgctaa cgtatctaac ttggtaccag taaatctccg tcgttacgtt  2280
tactgcgttg gtcttcgtga gggtaacgaa actgactaca actacctgta tagcgtgtac  2340
aattcttcag agaacactgc tgacatggtt gttatcctcc gcgccctcgc ttgcaccaag  2400
catcagcctt ctcttgagca ctacttgcaa cagtccatgt acaacgacaa agttcgtatc  2460
cacgaccgca ccaacgcgtt ctccttcgct ctgcaaggca accctgagaa ccttcccatc  2520
gttctgaact tcctctacaa caactttgcc gctatcaggg aaacgtacgg aggtgttgcc  2580
cgtctcaata tttgcctcaa cgctattgcg gcattcttga ctgactacca gaccatcact  2640
cagttccaaa cttgggtgta ctccaaccaa ttggagctgg ttggctctgt cggcgttgga  2700
aataacgtcg tcgccgccgc cttgaacaat ctcacttggg gcaacggcgc agctgttgaa  2760
attgtcaact tcctcaactc tagaagcggt tccaccacca tccttgcttc ttcaatcctc  2820
atcttagcag ccatgcttct acaaatgttc cgctaagatg tc                     2862

SEQ ID NO: 14           moltype = AA  length = 951
FEATURE                 Location/Qualifiers
source                  1..951
                        mol_type = protein
                        organism = Helicoverpa armigera
SEQUENCE: 14
MGAKMLLPTV FCILLGSIAA IPQEDFRSNL EWSDYSTNLD EPAYRLRDVV YPTDVNLDLD  60
VYLNHLNFSG LVQIDVQVRE NNLRQIVLHQ KVVSITGVNV VGPNGPVPLQ FPHPYTTDDY  120
YEILLINLDQ PINIGNYSIA IRYNGQINAN PLDRGFYRGY YHLNNELRVY ATTQFQPYHA  180
RKAFPCFDEP QFKSRYTISI TRDTSLSPSY SNMAIRSAQD ISTSRIRENF YTTPIISAYL  240
VAFHVSDFVS TEYTSTDAKP FSIISRQGAT NQHQYAAEIG LKITNELDDY FGIQYHEMGQ  300
GALMKNDHIA LPDFPSGAME NWGMVNYREA YLLYDENNTN LNNKIFIATI MAHELGHKWF  360
GNLVTCFWWS NLWLNESFAS FFEYFGAHWA DPALELDDQF VVDYVHSALN SDASQYATPM  420
NHTDVVDNDS ITSHFSVTSY AKGASVLKMM EHFVGWRTFR NALRYYLRNN EYDIGFPVDM  480
YTAFKQAVAE DFTFQRDFPN VDVGAVFDSW VQNPGSPVIN VARNNNTGVI TVNQQRYVLS  540
GAVASTTWHI PLTWTQHGSL NFNSTRPSTV LSDEIGTINA ASGDHFVIFN IAQSGLYRVN  600
YDTNNWQLLA SYLKSNNRQN IHKLNRAQIV NDILYFVRSN SINRTLAFDV LDFLRDETDY  660
YVWNGALTQI DWILRRLEHL PTAHAAFSEY ILELMNTVIN HLGYNEHSTD STSTILNRMQ  720
IMNYACNLGH SGCISDSLDK WRQHRANVSN LVPVNLRRYV YCVGLREGNE TDYNYLYSVY  780
NSSENTADMV VILRALACTK HQPSLEHYLQ QSMYNDKVRI HDRTNAFSFA LQGNPENLPI  840
VLNFLYNNFA AIRETYGGVA RLNICLNAIA AFLTDYQTIT QFQTWVYSNQ LELVGSVGVG  900
NNVVAAALNN LTWGNGAAVE IVNFLNSRSG STTILASSIL ILAAMLLQMF R           951

SEQ ID NO: 15           moltype = DNA  length = 3014
FEATURE                 Location/Qualifiers
source                  1..3014
                        mol_type = genomic DNA
                        organism = Heliothis virescens
SEQUENCE: 15
atgggtgcca aaatgttgct tcccaccgtg ttttgtatcc ttctgggatc catagcagcc  60
attcctcaag aggacttcag gtcgaacttg gagtgggctg actacagcac caatttagac  120
gagccggcgt accgtctccg tgatgtggtg taccctactg atgtcaacct ggatctggac  180
gtgtacctcg atgaactaag gttcaatgga ttggtacaga ttgatgtcga agtacgagag  240
aacgatttac gtcaaattgt tcttcatcag aaggtcgtct caatcaacgc tgttaacgtt  300
gtcggaccca acggtccagt cggtctacag ttcccatacc cttacaccac tgatgattac  360
tacgagatcc tcctcatcaa cctggctgag cccatcaaca tcggcaacta ctccatcacc  420
atcagataca acggccagat caatgataac cctatcgaca gaggtttcta caaaggctac  480
tattacctga acaatgaatt gaggctctac gccaccacac agttccagcc ttaccacgcc  540
aggaaggcct tcccgtgctt cgacgagccc caattcaaat cccgcttcac tatctccatc  600
actcgtgcca gcagcctgtc tccttcatac tccaacatgg ctatcagcaa cactcaaatc  660
cttggtgccc gtactcgcga aactttccat cctacgccca tcatctccgc ctacctggtt  720
gctttccacg tcagtgactt cgtcgccact gaatacacca gcaccgatgc caaacccttc  780
agtattatct cccgccaagg tgtcacagac cagcacgaat atgccgctga gatcggtctc  840
aagatcacca acgagcttga tgactactta ggcatccagt accatgagat gggacaaggt  900
accctgatga agaatgacca cattgctctt cctgacttcc cctccggtgc tatggagaac  960
tggggaatgg taaactacag ggaggcttac cttttgtacg acgctaacaa caccaactta  1020
aacaataaga ttttcatcgc taccatcatg gctcacgagc tgggacacaa atggttcggt  1080
aacctcgtca cctgcttctg gtggagcaac ctttggctaa acgagtcttt cgccagcttt  1140
ttcgaatacc ttggtgctca ctgggctgat cccgctctag agttagatga ccagtttgtc  1200
gtcgactacg tacacagcgc tctcaattct gacgccagtc aattcgccac ccctatgaac  1260
```

-continued

```
catgtcgacg ttgtggacaa cgactcaatc accgcccact tcagtgtcac tagctacgct   1320
aagggcgctt ccgtcttag gatgatggaa cacttcgttg gatcgaggac cttcagaaat    1380
gccctcagat attacttgag aaacaacgag tatagtatag gtttcccgt tgatatgtac    1440
gcggctttca agcaagccgt ctctgaagat tttaccttcg aacgtgattt ccccggtatt   1500
gacgttggag cagtattcga cacctgggtc cagaacccgg gatctcccgt cttgaacgtt   1560
gcccgtaaca gcaacactgg tgtcatcagt gtcagccagg aacgctatgt gctctcgggc   1620
gctgtagctc cagcgttgtg gcagattcct ctcaccttga ctcaaaatgg ctccctcaac   1680
tttgagaaca ccagacctag cttggtcctt actacccaga gccagaatat caacggtgcc   1740
tctgcagata actttgttat tttcaacaat gctcagtccg gtctgtaccg tgttaactac   1800
gacacaaaca actggcagtt gcttgcttca tacctgaaga gcaacaacag agagaacatt   1860
cacaagctga acagagccca gatcgtcaac gatgtcttga acttcgtgcg ttccaacagc   1920
atcaacagaa ccctcgcttt tgaagttctc gacttcttga gagatgagac cgattactat   1980
gtatggaacg gagctcttac ccagatcgac tggatccttc gtcgccttga gcatttgccg   2040
gctgccatg ctgctttctc tgaatacatc cttgatctca tgagcacggt catcaaccac   2100
cttggttaca atgagcagag tactgactcc acctccacaa tcctcaaccg aatgcagatc   2160
atgaactatg cctgcaatct tggacacagt ggttgcattg ctgacagttt agacaaatgg   2220
aggcagcacc gtgagaaccc gaataacttg gtgccagtga atctccgtcg ttacgtgtac   2280
tgcgtcggtc tgcgtgaagg caacgaaact gactacagct acttgttcag cgtgtacaat   2340
tcctcagaga acaccgctga catggttgtg atactccgcg ctctcgcctg caccaaacac   2400
cagccatctc ttgagcacta tctgcaagag tccatgtaca cgacaaaat ccgtatccac    2460
gaccgtacaa atgcattctc cttcgctctg caaggcaacc tgagaaccct tcccatcgtc   2520
cttaacttcc tctacaacaa cttttgccgct atcagggaaa cgtatggagg tgtggcccgt   2580
ctcaatctgt gcatcaacgc aatccctgca ttcttgactg actaccagac tattactcag   2640
ttccaatctt gggtatacgc aaaccaattg gcgttggttg gttcattcaa caatggcgtt   2700
agcgtcgtca acaccgcctt ggataacctt acttggggca acggtgctgc tgttgagatc   2760
gtcaatttcc tcaactacaa gagtgcatcc ccctccatcc ttgcttcttc catcctcatc   2820
ttagcagcta tgctcgtaca aatgttccgc taaggtgtct cattctaagt cgttacactt   2880
cacataattc taatttaagt ttatctattt tgttttatac aatcgttccg tcgttttgtt   2940
tatggttgtg aagtatttat tgtagattta ttgataataa atgttctttt gtaaagaaaa   3000
aaaaaaaaaa aaaa                                                     3014

SEQ ID NO: 16           moltype = AA  length = 950
FEATURE                 Location/Qualifiers
source                  1..950
                        mol_type = protein
                        organism = Heliothis virescens
SEQUENCE: 16
MGAKMLLPTV FCILLGSIAA IPQEDFRSNL EWADYSTNLD EPAYRLRDVV YPTDVNLDLD     60
VYLDELRFNG LVQIDVEVRE NDLRQIVLHQ KVVSINAVNV VGPNGPVGLQ FPYPYTTDDY   120
YEILLINLAE PINIGNYSIT IRYNGQINDN PIDRGFYKGY YYLNNELRLY ATTQFQPYHA   180
RKAFPCFDEP QFKSRFTISI TRASSLSPSY SNMAISNTQI LGARTRETFH PTPIISAYLV   240
AFHVSDFVAT EYTSTDAKPF SIISRQGVTD QHEYAAEIGL KITNELDDYL GIQYHEMGQG   300
TLMKNDHIAL PDFPSGAMEN WGMVNYREAY LLYDANNTNL NNKIFIATIM AHELGHKWFG   360
NLVTCFWWSN LWLNESFASF FEYLGAHWAD PALELDDQFV VDYVHSALNS DASQFATPMN   420
HVDVVDNDSI TAHFSVTSYA KGASVLRMME HFVGSRTFRN ALRYYLRNNE YSIGFPVDMY   480
AAFKQAVSED FTFERDFPGI DVGAVFDTWV QNRGSPVLNV ARNSNTGVIS VSQERYVLSG   540
AVAPALWQIP LTLTQNGSLN FENTRPSLVL TTQSQNINGA AQSGLYRVNY              600
DTNNWQLLAS YLKSNNRENI HKLNRAQIVN DVLNFVRSNS INRTLAFEVL DFLRDETDYY   660
VWNGALTQID WILRRLEHLP AAHAAFSEYI LDLMSTVINH LGYNEQSTDS TSTILNRMQI   720
MNYACNLGHS GCIADSLDKW RQHRENPNNL VPVNLRRYVY CVGLREGNET DYSYLFSVYN   780
SSENTADMVV ILRALACTKH QPSLEHYLQE SMYNDKIRIH DRTNAFSFAL QGNPENLPIV   840
LNFLYNNFAA IRETYGGVAR LNLCINAIPA FLTDYQTITQ FQSWVYANQL ALVGSFNNGV   900
SVVNTALDNL TWGNGAAVEI VNFLNYKSAS PSILASSILI LAAMLVQMFR              950

SEQ ID NO: 17           moltype = DNA  length = 2133
FEATURE                 Location/Qualifiers
source                  1..2133
                        mol_type = genomic DNA
                        organism = Helicoverpa armigera
SEQUENCE: 17
agcgacttta ctggttcagt tagaatcgcg atggtgacac tgttcccgta cgtagtggcg     60
gtgctgtgcg gcgcgacgag cgcgcgcgcc cactggctgc atcccgcggc gccggccgcc    120
gccagccgcg ccgagacctc tgccaactac tgggcgcaag acgcgcaggc cgccatcaac    180
gctcgcctgg aacgagttga aagcgtgaag aaagcgcgca acgtcatcat gttcctgggc    240
gacggcatgt cggtgcccac gctcgccgcc gcgcgcacgc tgctcgggca gcgcaagggc    300
aaaacgggag aggagacaaa gttgcatttc gagactttcc ccacaatcgg attagtgaag    360
acgtactgtg tggacgccca gattgcagac tccgcatgta ctgccacagc gtatttgtgt    420
ggtgtaaaaa ataactatgg cgcatagcc gtagacggca cggtacgccg aggagactgt     480
caagccgctt caaacactgc gacacacgtc gagtcctacg ggagtgggc gctcgctgac    540
ggacgagatg tcgtattgt gacgacgact cgtatcactc acgcgtctcc ggcggggcacg    600
ttcgcgaaga cggcgaaccg cacctgggag aacgacggtg aagtgtcgca gatgggcttg    660
gacgccaagg actgccctga catcgcgcat cagttggtac accatcatcc cggtaacaag    720
ttcaaggtta ttttggtgg tggcaagcgt gccttttttgc caaatactga acaggacgaa    780
aaaggtaaag atgtagaaag gatagacaac cgcaatctca tcaaagaagg aggatgat     840
aaggtttctc gtaatgtcag ccatcaatat gtttggcacc gcgagcagct aatgcgtcta    900
aaggaggacc tgcctgaata catgttggga ctgttcgaga gcagtcatat gacctatcac    960
ttgaaatcag accctcagtc tgaacccact ctcgctgaac taacagaggt ggcaattcgg    1020
tcattaagac gcaatgagaa gggattcttc ctgttcgtgg agggggggcg catcgaccac   1080
gcgcaccacg acaacctggt ggagctcgca ctcgacgaga cgctggagat ggacaaggcc   1140
```

-continued

```
gtggccaccg ccacgaagat gctctcagag gacgactcgc tcatcgtggt cactgccgac    1200
cacgcacacg tcatgacttt caatggctac tctaactgtg gtcataacat cctcgggccc    1260
tccagggatg tcggactaga caatgtgcct tacatgacgc taacgtacgc caatgggacc    1320
ggattccgtc cacacgttaa cgacattaga ccagatgtta cccttgagcc aaactatcgc    1380
accctggact gggagtcgca cgtggacgtg ccgctggtgg acgagacgca cggcggcgca    1440
gacgtggccg tgttcgcgcg cgggccgcac cactccatgt tcacggggct gtacgagcag    1500
agccagctgc cgcacctcat ggcctacgcc gcctccatcg gccccggccg gcacgcctgc    1560
gccagtgccg cgcacttgcc tagcgcgcac ttcttcgtag ctctgctcgc tctattcact    1620
tccattttac tgcgataata tttattaatt gaaatagctt taataaagtt tcatacttaa    1680
tagtcatcat tacgttgaca agcagatctg taatgttgtg aaataaaagt aaaagttatc    1740
atttaacata cgaaaaataa agttcacata gacatttgta aacaatacaa gattgataga    1800
cgttatttat ttacgatttc tgtacataca taggtacaca taataaatac gaaaggaaag    1860
aaattaaatg taatcgattt tggagttgag ctaattaata accatgttgt taatattgcg    1920
agtttcattg gccacgtgct gcatatctac attgtttgaa cacatcttct aggtcttgaa    1980
gcactgcagt tgttgccatt tattgcgtat catgttgttt acaatactta aaatattgaa    2040
ccttttcat tattaaacaa tatgaactgt aaaaaaaaaa aaaaaaaaaa aaaaaaaaaa     2100
aaaaaaaaaa aaaaaaaaaa aaaaaaaaaa aaa                                 2133

SEQ ID NO: 18         moltype = AA  length = 535
FEATURE               Location/Qualifiers
source                1..535
                      mol_type = protein
                      organism = Helicoverpa armigera
SEQUENCE: 18
MVTLFPYVVA VLCGATSARA HWLHPAAPAA ASRAETSANY WAQDAQAAIN ARLERVESVK    60
KARNVIMFLG DGMSVPTLAA ARTLLGQRQG KTGEETKLHF ETFPTIGLVK TYCVDAQIAD   120
SACTATAYLC GVKNNYGAIG VDGTVRRGDC QAASNTATHV ESIAEWALAD GRDVGIVTTT   180
RITHASPAGT FAKTANRTWE NDGEVSQMGL DAKDCPDIAH QLVHHHPGNK FKVIFGGGKR   240
AFLPNTEQDE KGSYGRRIDN RNLIKEWEDD KVSRNVSHQY VWHREQLMRL KEDLPEYMLG   300
LFESSHMTYH LKSDPQSEPT LAELTEVAIR SLRRNEKGFF LFVEGGRIDH AHHDNLVELA   360
LDETLEMDKA VATATKMLSE DDSLIVVTAD HAHVMTFNGY SNCGHNILGP SRDVGLDNVP   420
YMTLTYANGP GFRPHVNDIR PDVTLEPNYR TLDWESHVDV PLVDETHGGD DVAVFARGPH   480
HSMFTGLYEQ SQLPHLMAYA ACIGPGRHAC ASAAHLPSAH FFVALLALFT SILLR         535

SEQ ID NO: 19         moltype = DNA  length = 1680
FEATURE               Location/Qualifiers
source                1..1680
                      mol_type = genomic DNA
                      organism = Heliothis virescens
SEQUENCE: 19
cagttagtgc gatcgcgatg atgtcgctgt accagtgcct actggccgtg ctgtgctgtg     60
cggcgtgcgc gcgcgcccac tggttccacc ccgcagcgac ggcgggtcgc gcggcggcca    120
ccactcgcgt cgagacttct gccaactatt gggtgcaaga tgcgcaggca gccatcgacg    180
ctcgcctggc gcaagtggag agcgtgaaga agcgcgtaa cgtcatcatg ttcctgggcg    240
acggcatgtc cgtgcccacg ctggccgccg cgcgcacgct gctaggtcag cgccaaggga    300
acacaggaga ggagactaag ttgcatttcg agactttcc cacaatcgga ctagtgaaga    360
catactgtgt ggacgctcga attgcagact ccgcatgtac tgccacgacg tatttgtgtg    420
gtgtaaagaa taattatggt gctattggcg tagacgccac ggtacggcgc ggagactgcc    480
agacagcttc aaacactgcc actcacgtcg agtccatcgc ggagtgggcg ctcgcggacg    540
gacgagatgt cggtatcgtg acgacgacgc gtattactca cgcgtctcca gcgggcacat    600
tcgcgaagac tgcgaaccgc acctgggaga acgacggaga agtatcgcaa atgggattga    660
acgctaagga ctgccctgac atcgctcatc agttggtaca ccaccatccc ggtaacaagt    720
tcaaggttat ttttggaggt ggcaagcgcg ccttttttgcc aaacactgaa caggatgaaa    780
aagggtctta cggtaggagg ttagacaacc gcaaccttat caaagagtgg gagaatgata    840
aagtgtctcg taatgtgagt catcaatatg tttggaatcg cgaacaactg atgagcctaa    900
atgacgacct gccagagtac atgttgggct tgttcgagag tagtcatatg acatatcaca    960
tgaaatcaga tcctcagtct gaacctactc tcgctgaact aacagagttg gcgattcggt    1020
cattgcggcg caatgaaaag ggattcttcc tgttcgtgga gggcggacgc atcgaccacg    1080
cgcaccacga caacctggtg gagctcgcgc tcgatgagac gctggagatg gacaaggccg    1140
tggcgaccgc cacgcagctg ctgtcggagg acgactcgct cattgtggtc accgccgacg    1200
acgcacacgt catgactttc aatgctact ctaaccgtgg ccgtgacatc ttggggcct     1260
ccagggatgt tgatctagac aacgtaccttt acatgacgct aacgtatgcc aatggacctg    1320
gatttcgttc gcacgtgaac gacattcgac cagatgttac agctgagtca aactaccgct    1380
ctctgactg ggagtcgcac gtggacgtgc cgctggagga cgagacgcac ggcggcgacg    1440
acgtggccgt gttcgcgcgc gggccgcgcc actccatgtt cacggggctg tacgagcaga    1500
gccagctgcc gcacctcatg gcctacgcg cctgcatcgg ccccgccga cacgcctgcg    1560
tcagcgccgc gcacttgccc accgcgcact tctttattgc tctgtttgct ctattcaccc    1620
cgattttact aaaataataa ttatttagaa tttacatcat aaaaaaaaaa aaaaaaaaaa    1680

SEQ ID NO: 20         moltype = AA  length = 539
FEATURE               Location/Qualifiers
source                1..539
                      mol_type = protein
                      organism = Heliothis virescens
SEQUENCE: 20
MMSLYQCLLA VLCCAACARA HWFHPAATAG RAAATTRVET SANYWVQDAQ AAIDARLAQV    60
ESVKKARNVI MFLGDGMSVP TLAAARTLLG QRQGNTGEET KLHFETFPTI GLVKTYCVDA   120
QIADSACTAT AYLCGVKNNY GAIGVDATVR RGDCQTASNT ATHVESIAEW ALADGRDVGI   180
VTTTRITHAS PAGTFAKTAN RTWENDGEVS QMGLNAKDCP DIAHQLVHHH PGNKFKVIFG   240
```

```
GGKRAFLPNT EQDEKGSYGR RLDNRNLIKE WENDKVSRNV SHQYVWNREQ LMSLNDDLPE    300
YMLGLFESSH MTYHMKSDPQ SEPTLAELTE LAIRSLRRNE KGFFLFVEGG RIDHAHHDNL    360
VELALDETLE MDKAVATATQ LLSEDDSLIV VTADHAHVMT FNGYSNRGRD ILGPSRDVDL    420
DNVPYMTLTY ANGPGFRSHV NDIRPDVTAE SNYRSLDWES HVDVPLEDET HGGDDVAVFA    480
RGPHHSMFTG LYEQSQLPHL MAYAACIGPG RHACVSAAHL PTAHFFIALF ALFTPILLK     539

SEQ ID NO: 21             moltype = DNA   length = 1626
FEATURE                   Location/Qualifiers
misc_feature              1182..1183
                          note = n is a, c, g, or t
source                    1..1626
                          mol_type = genomic DNA
                          organism = Spodoptera frugiperda
SEQUENCE: 21
atgaggtcgc tactgactta cctagtggcc gccgtggtgg tggcggcgtg tgtccgcggg     60
gaccggtacc accccgcgga ccccggcagc agagctgaca ccgttgcgaa ccgtgccgag    120
acctcagcca actactgggc ccaagaagcg caggctgcaa tcaatgcccg gctgcgcac    180
aaggagagcg tgaagaaggc gcgcaacgtg gtcatgttcc tgggcgacgg catgtccgtg    240
cccacgctcg ccgccgcgcg gacgctgctc ggccagcgcc gcgggcacac cggcgaggag    300
gataaactgc atttgaaac attcccacc gttggattga ctaagacgta ttgcgtgaac     360
gctcagatcc cagactccgc gtgcactgct actgcgtact tatgtggtgt caaaacaact    420
tacggagcta ttggagtgaa tgcggaggtg ccacggacgg gctgcgaggc gtccaccgac    480
accagccgac acgtggagtc catcgcggag tgggcgctgg ccgacggccg cgacgctggt    540
atcgtgacga cgacgcgcat caccacgcg tcgccggccg gcgtgtacgc caaggtggcg     600
gaccgcaact gggagcacaa ccaggcgtg gagaacgatg gcttcgacac ggacaagtgc     660
ccggatatcg cactgcagct cgtgcataag caccccgcga ataaactcaa ggttatttta    720
ggcggaggaa gactaaactt tttgccaat gatgtgaaaa acgaagaagg ggtatatgga     780
aaccgaacag cagccgcaa cctcatcgaa gaatgggcac aagacaagga agatcgtaaa    840
gttactcata aatatgtttg gaatcgtgag cagctgatga gtcttaaaga tgatcttcct    900
gagtaccttt taggacttt cgaaagtaat catcttcagt acaacatgca ggcagatcct    960
aatactgagc ccacgctgac tgagctaact gagatagcaa tcaagtcgct aagtaraaac   1020
gagaaaggtt tttttcctgt cgtggaaggc ggtcgtatcg accacgcgca ccatcgcaac   1080
tgggtagagc tagcgctgga cgagaccctg gagatggacg aggccgtcgc gcgcgccgcc   1140
gagctgctcc ccgaggacga ctcgcccatt gtggtcacac cnnaccactc ccacgtcatg   1200
gcttacaatg gatactcggc ccgtggacat gacatcctcg gcccttccag agacttggac   1260
ctggacggga tgccttacat gacgctgtcg tacaccaacg ggcccggctt ccgttcgcat   1320
atgaacggta tacgcccga tgtcaccgct gaagacggtt tcggagaaga cgaatggttg    1380
gctcatgtag atgttccgtt gatagacgag acgcacggcg gggacgacgt ggcggtgttc   1440
gcgcgcgggc cgcaccactc catgttcacg gggctgtacg agcagagcca gctgccgcac   1500
ctcatggccgt acgccgcctg catcggcccc ggcagacacg cctgcagcgg cgccgcgcat  1560
gcgctggccc agcctgtgct gctgctctct ctccttgtac tgctcacttc actattccaa   1620
caatga                                                              1626

SEQ ID NO: 22             moltype = AA    length = 541
FEATURE                   Location/Qualifiers
SITE                      339
                          note = misc_feature - Xaa can be any naturally occurring
                           amino acid
SITE                      395
                          note = misc_feature - Xaa can be any naturally occurring
                           amino acid
source                    1..541
                          mol_type = protein
                          organism = Spodoptera frugiperda
SEQUENCE: 22
MRSLLTYLVA AVVVAACVRG DRYHPADPGS RADTVANRAE TSANYWAQEA QAAINARLAH     60
KESVKKARNV VMFLGDGMSV PTLAAARTLL GQRRGHTGEE DKLHFETFPT VGLTKTYCVN    120
AQIPDSACTA TAYLCGVKTT YGAIGVNAEV PRKGCEASTD TSRHVESIAE WALADGRDAG    180
IVTTTRITHA SPAGVYAKVA DRNWEHNQAV ENDGFDTDKC PDIALQLVHK HPGNKLKVIL    240
GGGRLNFLPN DVKDEEGVYG NRTDSRNLIE EWAQDKEDRK VTHKYVWNRE QLMSLKDDLP    300
EYLLGLFESN HLQYNMQADP NTEPTLTELT EIAIKSLSXN EKGFFLFVEG GRIDHAHHRN    360
WVELALDETL EMDEAVARAA ELLPEDDSPI VVTAXHSHVM AYNGYSARGH DILGPSRDLD    420
LDGVPYMTLS YTNGPGFRSH MNGIRPDVTA EDGFGEDEWL AHVDVPLIDE THGGDDVAVF    480
ARGPHHSMFT GLYEQSQLPH LMAYAACIGP GRHACSGAAH ALAQPVLLLS LLVLLTSLFQ    540
Q                                                                   541

SEQ ID NO: 23             moltype = DNA   length = 4020
FEATURE                   Location/Qualifiers
source                    1..4020
                          mol_type = genomic DNA
                          organism = Heliothis virescens
SEQUENCE: 23
atgggcgtag aaaataagaa taatgtacaa aatgcggaag gcgcggccct caagacttac     60
aagaaaccga acattttatc tcgtatattt ctttggtgga tgtgtccggt gctcataact    120
ggtaacagaa gaaacgtaga agaatcagat ctaataccgc ccagtaattt atataattca    180
gaaagacaag gagaatatct agaaagatac tggttacaag aaatagaaaa tgcaacaaat    240
gaaaatcggg agccatcgct atggaaggcg ttgcaaaggg cctactggtt atcctatatg    300
ccaggagcca tttatgtctt aattcaatca gcagccagga cgtatcagcc gttgtttatt   360
gctcagctac tgacgtactg gtcggtcgat agtgaaatga ctcagcaaga cgctgggctg    420
```

-continued

```
tatgcgctag ccatgctggg actgaacttc gtctccatga tgtgtcagca ccacaacaac  480
ttgtttgtga tgcggttcag tttgaaagtc aaggttgctt gttcttcact cttgtataqq  540
aagttgctcc gcatgactca agtgtcggta agtgaagtcg caggtggaaa gttggtaaac  600
ttgctgtcca acgacatcac gaggttcgac tacgcattca tgttcctgca ctacttgtgg  660
atagtgccta tccaagtggc cgtagtcttg tacttcttgt gggatgctgc tgggtttgca  720
ccttttgttg gtctctttgg agttgtccta ttgattttac cacttcaagc cggtttgacg  780
agactcacat ctattgtaag gcgtgagaca gccaagagga cggataggcg aattaaactt  840
atgagtgaaa ttatcaatgg tattcaggtc attaaaatgt acgcttggga gaaacccttc  900
cagctagtgg tgaaggcggc tcgtgccttt gaaatgagtg ctctcaggaa gtccatcttc  960
attaggagta ccttcctcgg gttcatgttg ttcactgagc ggagtatcat gtttgtcaca 1020
gtattgacac tcgcactcac aggcactatg attactgcta ccacgatata tcccattcag 1080
cagtacttca gtattattca atttaatgta acgctagtca ttcctatggc aatcgcaagt 1140
ttatccgaga tgatggtgtc tatagaacgt atccaaggat tcctcagttt ggatgagcgg 1200
tccgacatgc aagtgactcc taaaatgaat ggctccaata acagcacttt gttcaaaagc 1260
aagaaggcac cacttgaaat aagcatcgtg ccaaagaaat actcgcctag cgaagttacg 1320
gttgcaagag aagtgcagga tgatcccagc caggtggact atcctataag actcaacaaa 1380
ataaacgcat cgtggaccgg caatgatact ccttcagaga tgacacttaa aaatatatcc 1440
ttacgtatac gtaaaggcaa attgtgtgct atcattgtc ctgtgggttc cggaaagaca 1500
tctctgcttc agctactctt aaaagaatta ccgatgacta gtggcacact ggacgtgtca 1560
ggaagattgt cttacgcttg tcaggagtcg tggctgttcc ccggcacagt gcgagaaaac 1620
attttgtttg gcctagatta tgaagccaca aaatacaaag aggtttgcaa ggtgtgttcg 1680
ttactgccag acttcaaaca gttcccgtat ggtgacttgt ctttagtggg ggagcgagga 1740
gtatccctgt ctggaggtca aagagccaga atcaatttga ccagagcaat ttatcgtgag 1800
gccgatattt acttgctgga tgatccccta tccgcagtgg atgcaaatgt aggcagacaa 1860
ctgtttgatg gctgcatcaa aggctacctt tctggacgaa cttgcgtctt ggtcacccat 1920
cagatccatt acctcaaagc tgctgatttt attgtactcc ttaatgaggg ttccatcgag 1980
aacatgggca cgtatgacga gctggtcaag acaggaaccg agttctcgat gctgctatcc 2040
aaccaagaaa gtgaagcaac tgaaaacgaa atgaaagagc gaccatcatt gctgcgagga 2100
atatcaaaaa tctcaattaa gagcgacgac cacgatgcgg atcagaaggc gcaagtacga 2160
gaggcaggag agagcgcaac aggcagcttg aagtgggagg tggtgctgaa gtacctgagc 2220
tccgtcgaat cgtggtgtct ggtgttcatg gctttcctcg cgctgctgat cacgcaaggc 2280
gctgccacta cgtctgacta ttggctgagt ttctggacta atcaagtgga ttcttatgaa 2340
caatcattgc ctgatggcgc cgaaccagat actgacatga acgcacaaat tggtttactt 2400
acaactgccc agtacctata cgtgtacggc ggagttatat tggctgtaat aatcatgaca 2460
ctcgtcagga tcacaggttt cgtagcgatg acaatgcgag cctctcaaaa tctccacaac 2520
actatttacg aaaaattgat tgtgacagta atgagattct ttgataccaa tccttctggt 2580
cgtgtcctga acaggttctc aaaagacatg ggtgccatgg atgagcttct acctcgcagt 2640
cttttagaaa cagttcagat gtatctgtcg ctgaccagca tcttggtgct aaacgccaca 2700
gcattgccct ggacgctcat acctacctcc gtattgatag tcatcttcgt gttcatgttg 2760
agatggtacc tgaatacagc tcaggctgtc aaacgattgg aaggaacaac caagagtcct 2820
gtatttggaa tgattaattc cactatttct ggacttcga ctatcaggag ttcgggttcc 2880
cagtttagac agatgagatt attttgacgaa gcgcagaatc tccacacaag tgctttccac 2940
acattcttg gcggttctac ggcattttgga ttgtatctcg atactttgtg tttgatctac 3000
ctcggagttg tcatgtcaat tttcattttg ggcgactttg gtgatttgat cgcagtagga 3060
agcgtcggtc tggccgtcag tcagtccatg gtgctcacca tgatgttgca gatgacagct 3120
aggtttacag ctgacttctt gggacaaatg acggcagtag agagggtgct ggagtacacc 3180
cagctaccca tggagactaa tatggagcaa ggaccaacta cccgccaaa agaatggcct 3240
aatgctggca gagtgacgtt ctcaaatgtg tacctgaatt attctgtgga agacccacca 3300
gtgctaaagg acttgaactt tgaaattcaa agccggttgga aggttggagt tgtaggccga 3360
acgggagccg gcaaatcatc gctcattgcg gctctgttcc ggcttaccga cataactggc 3420
agcatcaaaa ttgacggcgt ggacacagaa ggattagcca aaaagctttt gagatcgaaa 3480
atatcaataa ttccacaaga gccggtcctc ttctccgcta ctctgcgtta aattttggat 3540
ccgttcgacg attacagtga cgaagatatt tggagggctc tggaacaggt ggaactaaaa 3600
gaaggaatac cggcacttga ttataaagtg gctgaaggtg gtactaactt ctccatggga 3660
cagcgtcagt tggtatgctt ggctcgtgct attttacgct ctaacaaaat actcatcatg 3720
gacgaagcca cagctaatgt cgatcctcag acggacgctt tgattcaaaa gacgatccgt 3780
cgtcaattcg cgtcgtgcac ggtgctgacc atcgcgcatc gactgaacac catcatggac 3840
tccgaccgag tgctggtcat ggaccagggc gaggtcgccg agttcgatca cccacacatc 3900
ttgctcagca accccaacag caagttcttc tctatggtca gagagaccgg agaaagcatg 3960
acgaagacct taatggaggt cgcgaagact aaatacgata gtgataataa ggaggcttag 4020
```

```
SEQ ID NO: 24        moltype = AA  length = 1339
FEATURE              Location/Qualifiers
source               1..1339
                     mol_type = protein
                     organism = Heliothis virescens
SEQUENCE: 24
MGVENKNNVQ NAEGAALKTY KKPNILSRIF LWWMCPVLIT GNRRNVEESD LIPPSNLYNS    60
ERQGEYLERY WLQEIENATN ENREPSLWKA LQRAYWVSYM PGAIYVLIQS AARTYQPLLF   120
AQLLTYWSVD SEMTQQDAGL YALAMLGLNF VSMMCQHHNN LFVMRFSLKV KVACSSLLYR   180
KLLRMTQVSV SEVAGGKLVN LLSNDITRFD YAFMFLHYLW IVPIQVAVVL YFLWDAAGFA   240
PFVGLFGVVL LILPLQAGLT RLTSIVRRET AKRTDRRIKL MSEIINGIQV IKMYAWEKPF   300
QLVVKAARAF EMSALRKSIF IRSTFLGFML FTERSIMFVT VLTLALTGTM ITATTIYPIQ   360
QYFSIIQFNV TLVIPMAIAS LSEMMVSIER IQGFLSLDER SDMQVTPKMN GSNNSTLFKS   420
KKAPLEISIV PKKYSPSEVT VAREVQDDPS QVDYPIRLNK INASWTGNDT PSEMTLKNIS   480
LRIRKGKLCA IIGPVSGKT SLLQLLLKEL PMTSGTLDVS GRLSYACQES WLFPGTVREN   540
ILFGLDYEAT KYKEVCKVCS LLPDFKQFPY GDLSLVGERG VSLSGGQRAR INLARAIYRE   600
ADIYLLDDPL SAVDANVGRQ LFDGCIKGYL SGRTCVLVTH QIHYLKAADF IVVLNEGSIE   660
NMGTYDELVK TGTEFSMLLS NQESEATENE MKERPSLLRG ISKISIKSDD HDADQKAQVQ   720
```

```
EAEERATGSL KWEVVLKYLS SVESWCLVFM AFLALLITQG AATTSDYWLS FWTNQVDSYE  780
QSLPDGAEPD TDMNAQIGLL TTAQYLYVYG GVILAVIIMT LVRITGFVAM TMRASQNLHN  840
TIYEKLIVTV MRFFDTNPSG RVLNRFSKDM GAMDELLPRS LLETVQMYLS LTSILVLNAT  900
ALPWTLIPTS VLIVIFVFML RWYLNTAQAV KRLEGTTKSP VFGMINSTIS GLSTIRSSGS  960
QFRQMRLFDE AQNLHTSAFH TFFGGSTAFG LYLDTLCLIY LGVVMSIFIL GDFGDLIAVG 1020
SVGLAVSQSM VLTMMLQMTA RFTADFLGQM TAVERVLEYT QLPMETNMEQ GPTNPPKEWP 1080
NAGRVTFSNV YLNYSVEDPP VLKDLNFEIQ SGWKVGVVGR TGAGKSSLIA ALFRLTDITG 1140
SIKIDGVDTE GLAKKLLRSK ISIIPQEPVL FSATLRYNLD PFDDYSDEDI WRALEQVELK 1200
EGIPALDYKV AEGGTNFSMG QRQLVCLARA ILRSNKILIM DEATANVDPQ TDALIQKTIR 1260
RQFASCTVLT IAHRLNTIMD SDRVLVMDQG EVAEFDHPHI LLSNPNSKFF SMVRETGESM 1320
TKTLMEVAKT KYDSDNKEA                                              1339

SEQ ID NO: 25           moltype = DNA   length = 4017
FEATURE                 Location/Qualifiers
source                  1..4017
                        mol_type = genomic DNA
                        organism = Helicoverpa armigera
SEQUENCE: 25
atgggcgtag aaaataagaa taatgtacaa aatgcggaag gtccggcccg caagacttac   60
aaaagaccga acattttatc ccgtatattt ctctggtgga tgtgtcctgt gctcataact  120
ggtaacaaaa gaaatgtaga agaatcagat cttataccgc ccagtaattt atataattca  180
gaaagacaag gagaatatct tgaaagatac tggttggcag agatagaaaa tgcaacaatt  240
gaaaatcgag agccatcact ttggaaggca ttacgaaagg cctactgggt ctcctatatg  300
ccaggagcta ttttatcat cattcaatct gcagccagga cgtatcagcc gctgttgttt  360
tctcagcttt tgtcgtactg gtcagtggac agtgaaatga ctcagcaaga cgctggcctg  420
tatgctctcg ccatgctggg actgaacttc gtctctatga tgtgtcagca ccacaacaca  480
ttgtttgtga tgcggttcag tttaaaagtc aaggttgcct gttcttcgct cttgtatagg  540
aagttgctcc gcatgaccca agtgtcagta ggtgaggtgg ctggtggaaa gttggtgaac  600
ttgctgtcca acgatatcac gaggttcgac tacgccttca tgttccttca ctacttgtgg  660
atcgtgccta tccaagtggc tgtttgtctta tacttcttgt gggaagctgc tggctttgcg  720
cccttcgtcg gtctgtttgg agtcgttata ctgattttac cactgcaagc tggcttgacg  780
aaactcacaa ctgttgtaag acgtgagacg gctaagagaa cggacaggcg aattaaacta  840
atgagtgaaa ttattggtgg tattcaggtc attaaaatgt acgcttggga gaaacccttc  900
cagtcagttg tgaaagcagc ccgtgccttc gaaatgggtg ccctccaggaa gtccatcttc  960
atcaggagta ctttcctagg gttcatgttg tcactgaaa gaagcatcat gtttgtcaca 1020
gtgttgacac tcgctctcac aggcactatg attactgcta ccacgatata tcctattcaa 1080
cagtacttca gtattattca gtttaacgta acactgatca ttcctatggc aatcgcaagt 1140
tattccgaga tgatggtgtc catagaacgt atccaggat tccttagttt ggacgagcgg 1200
tcagacatgc aagtgactcc aaaaatgaat ggatctaaca ataacttt gtttaaatcc 1260
aagaagtcac cacttgaagt aggcatcgtg cctaaaaaat actccaccaag cgaagttatg 1320
gctgcaaagg agatgcagga tgatcctacc cagatggact atcctatcag actcaacaaa 1380
gtaagcgcat cctggaccgg cagcaatagt tcttcagaaa tgacacttaa gaatatatcg 1440
ttgcgtatac gtaaaggaaa atttgtgtgct atcattgtc ctgtggggtc cggaaagacg 1500
tctctactgc aactgctgtt aaaagaatta ccattgaaca gtggtacact tgacgtgagt 1560
gggaagatgt cctacgcttg tcaagagtcc tggctgttcc cggcacagt gcgagaaaac 1620
atttgtttg gcctaactta cgaacccaca aaatacaagg aggtttgcaa ggtgtgttcg 1680
ttactgccga atttcaagca gttcccgtat ggtgacctgt ccttggtggg agagaggga 1740
gtatccttgt caggtggtca aagagccagg atcaatttgg ccagagcaat ttatcgtgag 1800
gccgacattt acttgctgga tgatcctcta tctgcagtgg acgctaatgt aggcagacaa 1860
ctgtttgacg gctgcatcaa aggctacctc actggaagaa cgtgcgtctt ggtcacccat 1920
cagatccatt acctcaaagc tgctgatttt attgtagtcc ttaatgaggt ctccgtcgag 1980
aatatgggca cgtatgatga gctggtgaag acaggaactg agttctcaat gctgctatcc 2040
aaccaagaaa atgacgcaac tgaaaacgaa agaaagatc gaccagcaat gatgcgagga 2100
atatcaaaaa tctcagttaa gagcgacacc gaaatggaac agaaggctca aatacggag 2160
gcagagggaa gagcgacagg tagcttgaag ttcgaggtgg tgctcaagta tctgagctca 2220
gtccagtcct ggtgtctggt gttcacggcg ttcctggtgc tgctgatcac gcaaggcgct 2280
gccaccacgg ccgactattg gttgagtttc tggactaatc aagtggattc ttatgaacaa 2340
tcgttgcctg atggcgttga tccagatact gacatgaatg cacaaattgg tttacttaca 2400
actgcccagt acctatacgt ttttggtgga gtttatattgg ctttgatagt catgaccctc 2460
gtcagaatca cagctttcgt agcgatgaca atgcgagctt ctcaaaatct tcacaacact 2520
atttacgaaa aattgattgt gactgtaatg agatttttcg atactaatcc atctggtcgt 2580
gtcctgaaca ggttctcaaa agacatgggt gctatgatg agcttctacc tcgcagtctt 2640
ttagaaacaa ttcagatgta tctgtctctg accagcgtgt tggtgctaaa cgccacagca 2700
ttgccctggg cgctcattcc tacctccgtg ttgattgtca tcttcgtgtt catgttgaga 2760
tggtacctga atactgctca ggctgtgaaa cgtttggaag cacaaccaa gagtcctgta 2820
tttggaatga ttaactccac tatttctgga ctctccacta tcagaagttc tggttcccag 2880
gatagacaga tgaaattgtt tgacgaagcg cagaatctcc acacagtgc tttccacaca 2940
ttcttcggcg gttctacggc atttgcactg tatctcgata ctttgtgttt gttctctccc 3000
ggagttgtca tgtcaatctt catttttggc gactttgtgg atttgatcgc ggtgggaagc 3060
gtcggtctgg ccgtcagtca gtccatggtg ctgaccatga tgttgcagat ggcagccagg 3120
tttacagctg acttctgggg acaaatgacg gcagtggaga gagtgctgga gtacaccaaa 3180
ctacccacgg aaaccaatat ggaacaagga ccaactaacc caccaaaaga atggcccagt 3240
gctggtagag tgacgttctc aaatgtgtac ctgaattatt ccatggaaga cccaccggtg 3300
gtgaaggact taggcttga aattcaaagc ggttgagttgt tggagttgt aggcagaact 3360
ggagccggca gtcatcact catcgcggct ttgttccggc ttagcgacat aagcggcagc 3420
atcaaaattg acggcgtgga caccgaagga ttagccaaaa agactttgag atcgaaaata 3480
tcaattattc cacaagaacc ggtgctgttc tcggctactc tgcgatacaa tttgatcca  3540
ttcgacgatt acagcgacga cgatatttgg agggcgttga acaggtgga attaaaagaa  3600
ggaataccgg ctttagactt taaggtcgct gaaggtggta ctaacttctc tatgggacaa  3660
```

```
cgtcaactgg tgtgcttggc gcgtgccatt cttcggtcta ataaaatact catcatggac   3720
gaagctaccg ctaatgtcga tcctcagacg gacgctttga tccaaaagac gatccgtcgc   3780
cagttcgcgt cgtgcacggt gctcaccatc gcgcatcgac tgaacaccat catggactcc   3840
gaccgagtgc tggtcatgga ccagggcgag gtggccgagt cgaccaccc ccacatcttg    3900
ctcagcaacc ccaatagcaa gttcttctct atggtccggg agacaggaga aagcatgaca   3960
aggaccttaa tggaggtcgc taaggccaaa tatgatagtg ataataagga ggcttaa      4017

SEQ ID NO: 26           moltype = AA  length = 1338
FEATURE                 Location/Qualifiers
source                  1..1338
                        mol_type = protein
                        organism = Helicoverpa armigera
SEQUENCE: 26
MGVENKNNVQ NAEGPARKTY KRPNILSRIF LWWMCPVLIT GNKRNVEESD LIPPSNLYNS   60
ERQGEYLERY WLAEIENATI ENREPSLWKA LRKAYWVSYM PGAIFIIQS  AARTYQPLLF   120
SQLLSYWSVD SEMTQQDAGL YALAMLGLNF VSMMCQHHNT LFVMRFSLKV KVACSSLLYR   180
KLLRMTQVSV GEVAGGKLVN LLSNDITRFD YAFMFLHYLW IVPIQVAVVL YFLWEAAGFA   240
PFVGLFGVVI LILPLQAGLT KLTTVVRRET AKRTDRRIKL MSEIIGGIQV IKMYAWEKPF   300
QLVVKAARAF EMGALRKSIF IRSTFLGFML FTERSIMFVT VLTLALTGTM ITATTIYPIQ   360
QYFSIIQFNV TLIIPMAIAS YSEMMVSIER IQGFLSLDER SDMQVTPKMN GSNNNTLFKS   420
KKSPLEVGIV PKKYSPSEVM AAKEMQDDPT QMDYPIRLNK VSASWTGSNS SSEMTLKNIS   480
LRIRKGKLCA IIGPVGSGKT SLLQLLLKEL PLNSGTLDVS GKMSYACQES WLFPGTVREN   540
ILFGLTYEPT KYKEVCKVCS LLPDFKQFPY GDLSLVGERG VSLSGGQRAR INLARAIYRE   600
ADIYLLDDPL SAVDANVGRQ LFDGCIKGYL TGRTCVLVTH QIHYLKAADF IVVLNEGSVE   660
NMGTYDELVK TGTEFSMLLS NQENDATENE KKDRPAMMRG ISKISVKSDT EMEQKAQIQE   720
AEERATGSLK FEVVLKYLSS VQSWCLVFTA FLVLLITQGA ATTADYWLSF WTNQVDSYEQ   780
SLPDGVDPDT DMNAQIGLLT TAQYLYVFGG VILALIVMTL VRITAFVAMT MRASQNLHNT   840
IYEKLIVTVM RFFDTNPSGR VLNRFSKDMG AMDELLPRSL LETIQMYLSL TSVLVLNATA   900
LPWTLIPTSV LIVIFVLMLR WYLNTAQAVK RLEGTTKSPV FGMINSTISG LSTIRSSGSQ   960
DRQMKLFDEA QNLHTSAFHT FFGGSTAFAL YLDTLCLFYL GVVMSIFILG DPFGDLIPVGS  1020
VGLAVSQSMV LTMMLQMAAR FTADFLGQMT AVERVLEYTK LPTETNMEQG PTNPPKEWPS  1080
AGRVTFSNVY LNYSMEDPPV LKDLSFEIQS GWKVGVVGRT GAGKSSLIAA LFRLSDISGS  1140
IKIDGVDTEG LAKKTLRSKI SIIPQEPVLF SATLRYNLDP FDDYSDDDIW RALEQVELKE  1200
GIPALDFKVA EGGTNFSMGQ RQLVCLARAI LRSNKILIMD EATANVDPQT DALIQKTIRR  1260
QFASCTVLTI AHRLNTIMDS DRVLVMDQGE VAEFDHPHIL LSNPNSKFFS MVRETGESMT  1320
RTLMEVAKAK YDSDNKEA                                                1338

SEQ ID NO: 27           moltype = DNA  length = 795
FEATURE                 Location/Qualifiers
misc_feature            480
                        note = n is a, c, g, or t
source                  1..795
                        mol_type = other DNA
                        note = SYNTHESIZED
                        organism = synthetic construct
misc_feature            411
                        note = v is a, c, or g
SEQUENCE: 27
aggtccaact gcaggagtct gggggaggct cggtgcagtc tggagggtct ctgagactct   60
cctgtgcagc ctctggatac accatcacta atagttaccg catggcctgg ttccgccagg   120
ctccagggaa ggagcgcgag ggggtcgcag ctatcaatag tggtggttct acaacatacg   180
cagactccgt gaagggccga ttcaccatct cccaagacaa cgcccagaac acgctgtatt   240
tgcagatgaa cagcctgaaa gccgaggaca cggccatgta ttactgtgcg gaggaggagg   300
aagaggagga ggaggaggca gggcgcgtac agtggtggcc tgtactacgc gcgctgaacg   360
aggatgatta tctctactgg ggccagggga cccaggtcac cgtctcctca vcaggtgcag   420
ctgcaggagt cggggggaga ctcggtgcag gctggagggt ctctgagact cgcctgtgcn   480
gcctcggcct ctggcactc cgtgtgtgtg ggtgggtgg gctggttccg cccggctccc     540
gggcgggagc gcgggggggt cgccgttgtt tctgttcctg gtggtggttc cttctttggc   600
ggcgacgtgg ggggccgatt ttccctctcc ccggaccacg cccagaacag ggtgtatccg   660
caaatgaaca gtctgaaacc tgaggacact gccatgtact attgcgcagc gcgcaatgcg   720
ggggggcgtt ttcggccttc ggccaatggt gggtataatt attggggcca ggggacccag   780
gtcaccgtct cctca                                                    795

SEQ ID NO: 28           moltype = AA  length = 125
FEATURE                 Location/Qualifiers
source                  1..125
                        mol_type = protein
                        organism = Camelus dromedarius
SEQUENCE: 28
QVQLQESGGR SVQSGGSLRL SCAASGIDVN RNAMGWFRQA PGTEREFVAG VRWSDAYTDY   60
ADSVKGRFTI SRDNNKNTVY LQMGSLEAGD TALYYCAAGL LDVQYVRQAA GYSYWGQGTQ   120
VTVSS                                                              125

SEQ ID NO: 29           moltype = AA  length = 265
FEATURE                 Location/Qualifiers
source                  1..265
                        mol_type = protein
                        note = SYNTHESIZED
                        organism = synthetic construct
```

```
SEQUENCE: 29
QVQLQESGGG SVQSGGSLRL SCAASGYTIT NSYRMAWFRQ APGKEREGVA AINSGGSTTY    60
ADSVKGRFTI SQDNAQNTLY LQMNSLKAED TAMYYCAAGR VQWWPVLRAL NEDDYLYWGQ   120
GTQVTVSSGG GGSGGGGQVQ LQESGGDSVQ AGGSLRLACA ASASGYSVCV GWVGWFRPAP   180
GRERGGVAVV SVPGGGSFFG GDVGGRFSLS PDHAQNTVYP QMNSLKPEDT AMYYCAARNA   240
GGRFRPSANG GYNYWGQGTQ VTVSS                                        265

SEQ ID NO: 30           moltype = AA  length = 57
FEATURE                 Location/Qualifiers
source                  1..57
                        mol_type = protein
                        organism = Spodoptera frugiperda
SEQUENCE: 30
LPTLPWSVCQ EEWGDCLPSD PDLDPVGTIT NETKSSAELY FLKTVLQQKD GIEDGLG       57

SEQ ID NO: 31           moltype = AA  length = 635
FEATURE                 Location/Qualifiers
source                  1..635
                        mol_type = protein
                        organism = Spodoptera frugiperda
SEQUENCE: 31
MKMSLRLTLK TVKMSGETNN GFDASPEDGK AAALNDKSLV NGANEKSPEK KDEPERAVWG    60
NQIEFLMSCI ATSVGLGNVW RFPFVAYQNG GGAFLIPYII VLLLIGKPMY YLECVLGQFS   120
SKNSVTVWSL SPAMKGAGYA TALGCGYILS YYVSIVALCL YYLAMSFLPT LPWSVCQEEW   180
GDCLPSDPDL DPVGTITNET KSSAELYFLK TVLQQKDGIE DGLGLPIWYL VVCLFGSWFI   240
IFVIVSRGVK SSGKAAYFLA LFPYVVMLIL LITTSILPGA GTGILFFLTP QWDKLIELDV   300
WYAAVTQVFF SLSVCTGAII MFSSYNGFRQ NVYRDAMIVT TLDTFTSLLS GFTIFGILGN   360
LAYELDKDVD DVTGSAGTGL AFISYPDAIS KTFQPQLFAV LFFLMMTVLG IGSAVALLST   420
INTVMMDAFP RIKTIYMSAF CCTIGFAIGL IYVTPGGQYI LELVDYFGGT FLILFCAIAE   480
IIGVFWIYGL ENLCLDIEYM LGVKTSFYWR CCWGVIMPAM MITVFIYALA TSETLKFGED   540
YYYPTAGYVA GYMMLFVGVA FVPISIGLTM YKNKTGDCAE TAKRSFRPKE SWGPREEFER   600
LNWIEFRREA EAERAQKRTS WLQHIRYSLF GGYRR                             635

SEQ ID NO: 32           moltype = AA  length = 352
FEATURE                 Location/Qualifiers
source                  1..352
                        mol_type = protein
                        organism = Spodoptera frugiperda
SEQUENCE: 32
MGAMFRSEEM ALCQLFIQPE AAYTSVSELG EAGSVQFRDL NPDVNAFQRK FVNEVRRCDE    60
MERKLRYIEA EVHKDGVHIP AVKEAPRAPN PREIIDLEAH LEKTENEILE LSHNAVNLKQ   120
NYLELTELRH VLEKTEAFFI AQEEIGMDSM TKSLISDETG QQAATRGRLG FVAGVVNRER   180
VPAFERMLWR ISRGNVFLRR AELDKPLEDP ATGNEIYKTV FVAFFQGEQL KSRIKKVCSG   240
FHASLYPCPP SNTERQDMVK GVRTRLEDLN MVLNQTSDHR QRKALADGSN ACGSSIPSFL   300
NCIETDEEPP TFNRTNRFTR GFQNLIDAYG VASYRECNPA LYTTITFPFL FA           352

SEQ ID NO: 33           moltype = AA  length = 788
FEATURE                 Location/Qualifiers
source                  1..788
                        mol_type = protein
                        organism = Spodoptera frugiperda
SEQUENCE: 33
MGAMFRSEEM ALCQLFIQPE AAYTSVSELG EAGSVQFRDL NPDVNAFQRK FVNEVRRCDE    60
MERKLRYIEA EVHKDGVHIP AVKEAPRAPN PREIIDLEAH LEKTENEILE LSHNAVNLKQ   120
NYLELTELRH VLEKTEAFFI AQEEIGMDSM TKSLISDETG QQAATRGRLG FVAGVVNRER   180
VPAFERMLWR ISRGNVFLRR AELDKPLEDP ATGNEIYKTV FVAFFQGEQL KSRIKKVCSG   240
FHASLYPCPP SNTERQDMVK GVRTRLEDLN MVLNQTSDHR QRKALADGSN ACGSSIPSFL   300
NCIETDEEPP TFNRTNRFTR GFQNLIDAYG VASYRECNPA LYTTITFPFL FAVMFGDLGH   360
GCIMALFGAW MVCNEVKLAA KKSNNEIWNI FFAGRYIIDL MQCFSMYTGL VYNDIFSKSM   420
NIFGSSWSVP YDNDTMEHNA ALTMDPKTSY NNNPYFIGID PVWQSADNKI IFLNSYKMKL   480
SIIFGVLHMI FGVCMSVVNY NFFRRRYSIV LEFLPQVIFL CLLFLYMVFM MFYKWVAYSA   540
FSEEQAYTPG CAPSVLILFI NMMLFSSTAP PEGCNEYMFE AQASIQRVFV LVALCCIPVM   600
LLGKPLYLLA AGKKKKEAKP EHSNGSVNPG IEMQEQTGIK DGVPKPEAKP AASGHDHEDE   660
PFSEIMIHQA IHTIEYVLST ISHTASYLRL WALSLAHAEL SEVLWNMVLT FGLKDHDYIG   720
GIKLYVAFCF WALFTLAILV MMEGLSAFLH TLRLHWVEFM SKFYSGLGYI FQPFCFKTIL   780
EQEDNKDD                                                           788

SEQ ID NO: 34           moltype = AA  length = 1174
FEATURE                 Location/Qualifiers
source                  1..1174
                        mol_type = protein
                        organism = Spodoptera frugiperda
SEQUENCE: 34
MENNIQNQCV PYNCLNNPEV EILNEERSTG RLPLDISLSL TRFLLSEFVP GVGVAFGLFD    60
LIWGFITPSD WSLFLLQIEQ LIEQRIETLE RNRAITTLRG LADSYEIYIE ALREWEANPN   120
NAQLREDVRI RFANTDDALI TAINNFTLTS FEIPLLSVYV QAANLHLSLL RDAVSFGQGW   180
GLDIATVNNH YNRLINLIHR YTKHCLDTYN QGLENLRGTN TRQWARFNQF RRDLTLTVLD   240
IVALFPNYDV RTYPIQTSSQ LTREIYTSSV IEDSPVSANI PNGFNRAEFG VRPPHLMDFM   300
NSLFVTAETV RSQTVWGGHL VSSRNTAGNR INFPSYGVFN PGGAIWIADE DPRPFYRTLS   360
```

```
DPVFVRGGFG NPHYVLGLRG VAFQQTGTNH TRTFRNSGTI DSLDEIPPQD NSGAPWNDYS   420
HVLNHVTFVR WPGEISGSDS WRAPMFSWTH RSATPTNTID PERITQIPLV KAHTLQSGTT   480
VVRGPGFTGG DILRRTSGGP FAYTIVNING QLPQRYRARI RYASTTNLRI YVTVAGERIF   540
AGQFNKTMDT GDPLTFQSFS YATINTAFTF PMSQSSFTVG ADTFSSGNEV YIDRFELIPV   600
TATFEAEYDL ERAQKAVNAL FTSINQIGIK TDVTDYHIDQ VSNLVDCLSD EFCLDEKREL   660
SEKVKHAKRL SDERNLLQDP NFKGINRQLD RGWRGSTDIT IQRGDDVFKE NYVTLPGTFD   720
ECYPTYLYQK IDESKLKPYT RYQLRGYIED SQDLEIYLIR YNAKHETVNV LGTGSLWPLS   780
VQSPIRKCGE PNRCAPHLEW NPDLDCSCRD GEKCAHHSHH FSLDIDVGCT DLNEDLDVWV   840
IPKIKTQDGH ARLGNLEFLE EKPLVGEALA RVKRAEKKWR DKREKLELET NIVYKEAKES   900
VDALFVNSQY DQLQADTNIA MIHAADKRVH RIREAYLPEL SVIPGVNVDI FEELKGRIFT   960
AFFLYDARNV IKNGDFNNGL SCWNVKGHVD VEEQNNHRSV LVVPEWEAEV SQEVRVCPGR  1020
GYILRVTAYK EGYGEGCVTI HEIENNTDEL KFSNCVEEEV YPNNTVTCND YTANQEEYGG  1080
AYTSRNRGYD ETYGSNSSVP ADYASVYEEK SYTDGRRDNP CESNRGYGDY TPLPAGYVTK  1140
ELEYFPETDK VWIEIGETEG TFIVDSVELL LMEE                             1174

SEQ ID NO: 35           moltype = AA  length = 427
FEATURE                 Location/Qualifiers
source                  1..427
                        mol_type = protein
                        organism = Spodoptera frugiperda
SEQUENCE: 35
GEFLDRLSAT DEDGLHAGRV TFSIAGNDEA AEYFNVLNDG DNSAMLTLKQ ALPAGVQQFE    60
LVIRATDGGT EPGPRSTDCS VTVVFVMTQG DPVFDDNAAS VRFVEKEAGM SEKFQLPQAD   120
DPKNYRCMDD CHTIYYSIVD GNDGDHFAVE PETNVIYLLK PLDRSQQEQY RVVVAASNTP   180
GGTSTLSSSL LTVTIGVREA NPRPIFESEF YTAGVLHTDS IHKELVYLAA KHSEGLPIVY   240
SIDQETMKID ESLQTVVEDA FDINSATGVI SLNFQPTSVM HGSFDFEVVA SDTRGASDRA   300
KVSIYMISTR VRVAFLFYNT EAEVNERRNF IAQTFANAFG MTCNIDSVLP ATDANGVIRE   360
GYTELQAHFI RDDQPVPADY IEGLFTELNT LRDIREVLST QQLTLLDFAA GGSAVLPGGE   420
YALAVYI                                                            427

SEQ ID NO: 36           moltype = AA  length = 9
FEATURE                 Location/Qualifiers
source                  1..9
                        mol_type = protein
                        note = SYNTHESIZED
                        organism = synthetic construct
SEQUENCE: 36
GGGGSGGGG                                                            9

SEQ ID NO: 37           moltype = AA  length = 796
FEATURE                 Location/Qualifiers
source                  1..796
                        mol_type = protein
                        organism = Spodoptera frugiperda
SEQUENCE: 37
SPESASTTPT PAPIVSPTTD SDGSSGTTEG PTSPLTPSTT PSTTSTTTTT TTTTTTTTTT    60
TTETPPDESP GQLDLEEIID GVFSPPSFNA TWATGSELMF RNDNGDLVLY DVDSDTPMPI   120
VSNTSKILQE ASRVMQLSPE GKDVMLAHSV APVYRYSFIA RYTAVNIENE EEVPITPPSV   180
PREQALLQNL VWGPSGTSLA FVYYNNIYYQ PSLKEAPRQI TTDGVLNVIY NGIPDWVYEE   240
EVFGSNNAIW FSKDGTKMAY VTFDDSHVEV MRVPHYGIPG ETQYTRHRQI RYPKPNTTNP   300
TVKVTLWNLI TDTPSVVEAP NDLNQPILKT VKFINNDDIA VVWTNREQTS LRVQKCRASG   360
NTAECTTIYN YVENGGWIDN IPFFFNDAGN SFITILPFAV DGVRFKQIVQ VTEGTATAPA   420
TVKNRVNNPH TVLEILAWGT DDVIWYKATS VSDSREQHIF SVNSQDVISC FTCNIRRTDG   480
GLCLYNEGTI STAGDRITIN CAGPDVPQIF IYKTNGELVR VWDEGADLSN LMHNRTLPVT   540
LRAQITSPLG QASTDIHIQA PADYAHRTNV PLLVYVYGGP DTALVTRQWS LDWGSSLVSR   600
WGIAVAHIDG RGSGLRGVEN MFALNRKLGT VEIEDQIAGA KYRYIQDNFP WIDANRTCIW   660
GWSYGGYAAS KALAEGGDVF RCAAAIAPVV DWRFYVDTIY TERYMGLPTA EDNAEGYEVS   720
SLLTKAEALR EKSYFLVHGT ADDNVHYQHA MLLSRLLQRR DVFFTQMSYT DEDHGLVGVR   780
PHLYHALERF LQEYML                                                  796

SEQ ID NO: 38           moltype = AA  length = 847
FEATURE                 Location/Qualifiers
source                  1..847
                        mol_type = protein
                        organism = Spodoptera frugiperda
SEQUENCE: 38
MAQDNSNSTM EMGTSDQVLV ATKRKKTIGY IIGTIAMLAV GGVVIALIVV LSPESASTTP    60
TPAPIVSPTT DSDGSSGTTE GPTSPLTPST TPSTTSTTTT TTTETPPDES             120
PGQLDLEEII DGVFSPPSFN ATWATGSELM FRNDNGDLVL YDVDSDTPMP IVSNTSKILQ   180
EASRVMQLSP EGKDVMLAHS VAPVYRYSFI ARYTAVNIEN EEEVPITPPS VPREQALLQN   240
LVWGPSGTSL AFVYYNNIYY QPSLKEAPRQ ITTDGVLNVI YNGIPDWVYE EEVFGSNNAI   300
WFSKDGTKMA YVTFDDSHVE VMRVPHYGIP GETQYTRHRQ IRYPKPNTTN PTVKVTLWNL   360
ITDTPSVVEA PNDLNQPILK TVKFINNDDI AVVWTNREQT SLRVQKCRAS GNTAECTTIY   420
NYVENGGWID NIPFFFNDAG NSFITILPFA VDGVRFKQIV QVTEGTATAP ATVKNRVNNP   480
HTVLEILAWG TDDVIWYKAT SVSDSREQHI FSVNSQDVIS CFTCNIRRTD GGLCLYNEGT   540
ISTAGDRITI NCAGPDVPQI FIYKTNGELV RVWDEGADLS NLMHNRTLPV TLRAQITSPL   600
GQASTDIHIQ APADYAHRTN VPLLVYVYGG PDTALVTRQW SLDWGSSLVS RWGIAVAHID   660
GRGSGLRGVE NMFALNRKLG TVEIEDQIAG AKYRYIQDNF PWIDANRTCI WGWSYGGYAA   720
SKALAEGGDV FRCAAAIAPV VDWRFYVDTI YTERYMGLPT AEDNAEGYEV SSLLTKAEAL   780
```

```
REKSYFLVHG TADDNVHYQH AMLLSRLLQR RDVFFTQMSY TDEDHGLVGV RPHLYHALER    840
FLQEYML                                                              847

SEQ ID NO: 39           moltype = AA  length = 209
FEATURE                 Location/Qualifiers
source                  1..209
                        mol_type = protein
                        organism = Spodoptera frugiperda
SEQUENCE: 39
LPTYGTPVSE GLAQLRVYNG YNCNFTLNTA NLNTLEENAT RDFEIGPLSA YENLHIFADD     60
FVDLPYYLQG EPATECAGIA YSGYFNLKEK TANSFFIKKD GLYNFTDNND KAIDGVNVRF    120
LSNINSVVDI SIENDQKNKT LLSIQSNDTS QKSIAKGVSN VTVGGFVVLS DFNFKSGAVY    180
TINIYEDRAG VYYANTVMIT PSNSIHILW                                      209

SEQ ID NO: 40           moltype = AA  length = 584
FEATURE                 Location/Qualifiers
source                  1..584
                        mol_type = protein
                        organism = Spodoptera frugiperda
SEQUENCE: 40
MEFTIVALLL IAFGTGGIKP CVSAFGGDQF KLPEQERYLG YFFSLFYFAI NAGSLISTFL     60
TPILRADVHC FGDNDCYSLA FGVPGILMVV SIVFFVAGKR LYVIKKPAGN VLGKVSTCIG    120
HAVVKSCKSK EKREHWLDHA DDKYDSNLIE DVKALLRVLV LFIPLPVFWA LFDQQGSRWT    180
FQADRMEQDI GSWTLKADQM QVLNPLLILI FIPIFEVAIY PFLTWCKLVR KPLHKMIWGG    240
ILAACAFIIS GIVELNLLPT YGTPVSEGLA QLRVYNGYNC NFTLNTANLN TLEENATRDF    300
EIGPLSAYEN LHIFADDFVD LPYYLQGEPA TECAGIAYSG YFNLKEKTAN SFFIKKDGLY    360
NFTDNNDKAI DGVNVRFLSN INSVVDISIE NDQKNKTLLS IQSNDTSQKS IAKGVSNVTV    420
GGFVVLSDFN FKSGAVYTIN IYEDRAGVYY ANTVMITPSN SIHILWLIPQ YVVMTMGEVM    480
FSVTGLEFSF TQAPASMKSV LQSVWLLTVA FGNLIVVLIV EGNFLDAQWK EFFLFAGLML    540
IDMLIFTTMA FRYKYKELSS SDENLAIEEI KMPEKTSQDK HEKN                     584

SEQ ID NO: 41           moltype = DNA  length = 23
FEATURE                 Location/Qualifiers
source                  1..23
                        mol_type = other DNA
                        note = primers annealing to the common CH2 exon of the
                          heavy chain llama immunoglobulins and to the leader
                          sequence
                        organism = synthetic construct
SEQUENCE: 41
gtcctggctg ctcttctaca agg                                             23

SEQ ID NO: 42           moltype = DNA  length = 23
FEATURE                 Location/Qualifiers
source                  1..23
                        mol_type = other DNA
                        note = primer annealing to the common CH2 exon of the heavy
                          chain llama immunoglobulins and to the leader sequence
                        organism = synthetic construct
SEQUENCE: 42
ggtacgtgct gttgaactgt tcc                                             23

SEQ ID NO: 43           moltype = AA  length = 1260
FEATURE                 Location/Qualifiers
source                  1..1260
                        mol_type = protein
                        organism = Spodoptera frugiperda
SEQUENCE: 43
MKDSKGNAWQ LKPGEKENEN KLPDPLNEDV QKGQFSDTSS EPSEAKAEEV PSIPFITLFR     60
FASTRDKLFI ICALICSAVA AISTPLNTLL LAYLLEAMVN YSIFGDADAF MKSLLNFAIY    120
NAAVGAALVV LSYAATTLMN IAAYNQVYVI RQEYLKAALN QDFGYFDVHK NAEIANKMNS    180
DIMKLEEGIG EKLATFFFYQ ASFLSSVIMA LVKGWKLALL CLISFPVTMT LVGVAGLIAA    240
SLSKKEAIAT GKAGAIAEEV ISAIRTVYAF SGQEKELDRY EGHLNDARKI NVKKSLFNGL    300
AMGCLFFCIF CAYALSFWFG YRLMVTGDYD VSTMIAVFFG VMTGSANFGI SSTLMEVFGS    360
ARGAGAHIFN MIDNVPTINP LQNRGTVPSD IEGNIELKNV EFHYPSRPDV PVLKGVSIKV    420
KRGQSVALVG HSGCGKSTII QLISRFYDVV EGSVAIDGND VRDLSVRWLR EQIGLVGQEP    480
VLFNTTVREN IRYGRENATN EEIEACARQA NAHQFIMKLP KGYDTLVGER GASLSGGQKQ    540
RIAIARALVR NPKILLLDEA TSALDTSSEA KVQKALDKAQ EGRTTIVVAH RLSTIRNVDV    600
IYVFKAGLVV ECGNHTELMA SKGHYYDMVM LQNLPGVDEQ SPEKTKLSRE TSIISEKDDE    660
DEFLEFRNDV KEDAAEAPDI SFMRVLKLNK PEWKSVTLAS ICSLMSGFCM PLFAVIFGDF    720
LALLDGDDPD EIQKGVSRLA LIFVGIGVFS GITNFIVVFF YGIAGEALTK RLRLMMFRKL    780
LEMDIGFYDD KDNSTGALCA RLSGEAAAVQ GATGQRIGTV VQAVGTFGFA LVLSLIFEWR    840
VGLVALTFVP IIIFVLYKEG RMTYAATSGT VKVMETSSKI AVEAVANVRT VASLGREETF    900
RREYSKQLRP ALDTAVRSSH WRGLVFGMSR GVFNFVIASS LYYGGTIIVN EGVPFEQVFK    960
SAQALLMGAT SAAQAFAFAP NFQKGIKAAG RVIVLLGRQS KITDPAEPAV KNFNGTEAS    1020
LQGIQFRYPT RPLVRVLKDL NLEIQRGKTV ALVGASGCGK STVIQLLERY YDPEDGIVAQ   1080
DGVPLPKLNL VDARRAIGFV QQEPILFDRT IGENIAYGNN EARVSNDEVI EAAQQANIHN   1140
FITSLPLGYD TNIGSKGTQL SGGQKQRVAI ARALIRRPKM LLLDEATSAL DTESEKVVQE   1200
ALDKAKAGRT CVMIAHRLST VRDADVICVI HEGQVAEMGT HNELLEKLGL YYNLNRRGYA   1260
```

```
SEQ ID NO: 44          moltype = AA  length = 25
FEATURE                Location/Qualifiers
source                 1..25
                       mol_type = protein
                       organism = Spodoptera frugiperda
SEQUENCE: 44
YLLEAMVNYS IFGDADAFMK SLLNF                                        25

SEQ ID NO: 45          moltype = DNA  length = 4178
FEATURE                Location/Qualifiers
source                 1..4178
                       mol_type = genomic DNA
                       organism = Bacillus thuringiensis
SEQUENCE: 45
ttacaattca agatgaattg caggtaaatg gttctaacat gtataagtgt aagtatttct  60
acattaccac aaattctcaa tttgtatatg taaaatagga aaagtggatt ttatatataa  120
gtataaaaag taataagact ttaaaataag ttaacggaat acaaaccctt aatgcattgg  180
ttaaacattg taaagtctaa agcatggata atgggcgaga agtaagtaga ttgttaacac  240
cctgggtcaa aaattgatat ttagtaaaat tagttgcact ttgtgcattt tttcataaga  300
tgagtcatat gttttaaatt gtagtaatga aaaacagtat tatatcataa tgaattggta  360
tcttaataaa agagatggag gtaacttatg gataacaatc cgaacatcaa tgaatgcatt  420
ccttataatt gtttaagtaa ccctgaagta gaagtattag gtggagaaag aatagaaact  480
ggttacaccc caatcgatat ttccttgtcg ctaacgcaat ttcttttgag tgaatttgtt  540
cccggtgctg gatttgtgtt aggactagtt gatataaatat ggggaatttt tggtccctct  600
caatgggacg catttcttgt acaaattgaa cagttaatta accaaagaat agaagaattc  660
gctaggaacc aagccatttc tagattagaa ggactaagca atctttatca aatttacgca  720
gaatctttta gagagtggga agcagatcct actaatccag cattaagaga agagatgcgt  780
attcaattca atgacatgaa cagtgccctt acaaccgcta ttcctctttt tgcagttcaa  840
aattatcaag ttcctctttt atcagtatat gttcaagctg caaatttaca tttatcagtt  900
ttgagagatg tttcagtgtt tggacaaagg tggggatttg atgccgcgac tatcaatagt  960
cgttataatg atttaactag gcttattggc aactatacag attatgctgt acgctggtac  1020
aatacgggat tagaacgtgt atggggaccg gattctagag attgggtaag gtataatcaa  1080
tttagaagag aattaacact aactgtatta gatatcgttg ctctgttccc gaattatgat  1140
agtagaagat atccaattcg aacagtttcc caattaacaa gagaaattta tacaaaccca  1200
gtattagaaa attttgatgg tagttttcga ggctcggctc agggcataga aagaagtatt  1260
aggagtccac atttgatgga tatacttaac agtataacca tctatacgga tgctcatagg  1320
ggttattatt attggtcagg gcatcaaata atggcttctc ctgtcggttt ttcggggcca  1380
gaattcacgt ttccgctata tggaaccatg ggaaatgcag ctccacaaca acgtattgtt  1440
gctcaactag gtcagggcgt gtatagaaca ttatcgtcca ctttatatag aagacctttt  1500
aatataggga taaataatca acaactatct gttcttgacg ggacagaatt tgcttatgga  1560
acctcctcaa atttgccatc cgctgtatac agaaaaagcg gaacggtaga ttcgctggat  1620
gaaataccgc cacagaataa caacgtgcca cctaggcaag gatttagtca tcgattaagc  1680
catgtttcaa tgtttcgttc aggctttagt aatagtagtg taagtataat aagagctcct  1740
atgttctctt ggatacatcg tagtgctgaa tttaataata taattgcatc ggatagtatt  1800
actcaaatcc ctgcagtgaa gggaaacttt ctttttaatg gttctgtaat ttcaggacca  1860
ggatttactg gtggggactt agttagatta aatagtagtg gaaataacat tcagaataga  1920
gggtatattg aagttccaat tcacttccca tcgacatcta ccagatatcg agttcgtgta  1980
cggtatgctt ctgtaacccc gattcacctc aacgttaatt ggggtaattc atccattttt  2040
tccaatacag taccagctac agctacgtca ttagataatc tacaatcaag tgattttggt  2100
tattttgaaa gtgccaatgc ttttacatct tcattaggta atatagtagg tgttagaaat  2160
tttagtggga ctgcaggagt gataatagac agatttgaat ttattccagt tactgcaaca  2220
ctcgaggctg aatataatct ggaaagagcg cagaaggcgg tgaatgcgct gtttacgtct  2280
acaaaccaac tagggctaaa aacaaatgta acggattatc atattgatca agtgtccaat  2340
ttagttacgt atttatcgga tgaattttgt ctggatgaaa agcgagaatt gtccgagaaa  2400
gtcaaacatg cgaagcgact cagtgatgaa cgcaatttac tccaagattc aaatttcaaa  2460
gacattaata ggcaaccaga acgtgggtgg ggcggaagta cagggattac catccaagga  2520
ggggatgacg tatttaaaga aaattacgtc acactatcag gtacctttga tgagtgctat  2580
ccaacatatt tgtatcaaaa aatcgatgaa tcaaaattaa aagcctttac ccgttatcaa  2640
ttaagagggt atatcgaaga tagtcaagac ttagaaatct atttaattcg ctacaatgca  2700
aaacatgaaa cagtaaatgt gccaggtacg ggttccttat ggccgctttc agcccaaagt  2760
ccaatcggaa agtgtggaga gccgaatcga tgcgcgccac accttgaatg gaatcctgac  2820
ttagattgtt cgtgtaggga tggagaaaag tgtgcccatc attcgcatca tttctcctta  2880
gacattgatg taggatgtac agacttaaat gaggacctag gtgtatgggt gatctttaag  2940
attaagacgc aagatgggca cgcaagacta gggaatctag agtttctcga agagaaacca  3000
ttagtaggag aagcgctagc tcgtgtgaaa agagcggaga aaaaatggag agacaaacgt  3060
gaaaaattgg aatgggaaac aaatatcgtt tataaagagg caaaagaatc tgtagatgct  3120
ttatttgtaa actctcaata tgatcaatta caagcggata cgaatattgc catgattcat  3180
gcggcagata aacgtgttca tagcattcga gaagcttatc tgcctgagct gtctgtgatt  3240
ccgggtgtca atgcggctat ttttgaagaa ttagaagggc gtattttcac tgcattctcc  3300
ctatatgatg cgagaaatgt cattaaaaat ggtgatttta ataatggctt atcctgctgg  3360
aacgtgaaag ggcatgtaga tgtagaagaa caaaacaacc aacgttcggt ccttgttgtt  3420
ccggaatggg aagcagaagt gtcacaagaa gttcgtgtct gtccgggtcg tggctatatc  3480
cttcgtgtca cagcgtacaa ggagggatat ggagaaggtt gcgtaaccat tcatgagatc  3540
gagaacaata cagacgaact gaagtttagc aactgcgtag aagaggaaat ctatccaaat  3600
aacacggtaa cgtgtaatga ttatactgta aatcaagaag aatacggagg tgcgtacact  3660
tctcgtaatc gaggatataa cgaagctcct tccgtaccag ctgattatgc gtcagtctat  3720
gaagaaaaat cgtatacaga tggacgaaga gagaatcctt gtgaatttaa cagagggtat  3780
agggattaca cgccactacc agttggttat gtgacaaaag aattagaata cttcccagaa  3840
```

```
accgataagg tatggattga gattggagaa acggaaggaa catttatcgt ggacagcgtg  3900
gaattactcc ttatggagga atagtctcat gcaaactcag gtttaaatat cgttttcaaa  3960
tcaattgtcc aagagcagca ttacaaatag ataagtaatt tgttgtaatg aaaaacggac  4020
atcacctcca ttgaaacgga gtgatgtccg ttttactatg ttattttcta gtaatacata  4080
tgtatagagc aacttaatca agcagagata ttttcaccta tcgatgaaaa tatctctgct  4140
ttttcttttt ttatttggta tatgctttac ttgtaatc                         4178

SEQ ID NO: 46           moltype = DNA   length = 2983
FEATURE                 Location/Qualifiers
source                  1..2983
                        mol_type = genomic DNA
                        organism = Bacillus thuringiensis
SEQUENCE: 46
aagcttaatt aaagataata tctttgaatt gtaacgcccc tcaaaagtaa gaactacaaa  60
aaaagaatac gttatataga aatatgtttg aaccttcttc agattacaaa tatattcgga  120
cggactctac ctcaaatgct tatctaacta tagaatgaca tacaagcaca accttgaaaa  180
tttgaaaata taactaccaa tgaacttgtt catgtgaatt atcgctgtat ttaattttct  240
caattcaata tataatatgc caatacattg ttacaagtag aaattaagac acccttgata  300
gccttactat acctaacatg atgtagtatt aaatgaatat gtaaatatat ttatgataag  360
aagcgactta tttataatca ttacatattt ttctattgga atgattaaga ttccaataga  420
atagtgtata aattatttat cttgaaagga gggatgccta aaaacgaaga acattaaaaa  480
catatatttg caccgtctaa tggatttatg aaaaatcatt ttatcagttt gaaaatttat  540
tattatgata agaaagggag gaagaaaaat gaatccgaac aatcgaagtg aacatgatac  600
aataaaaact actgaaaata atgaggtgcc aactaaccat gttcaatatc ctttagcgga  660
aactccaaat ccaacactag aagatttaaa ttataaagag tttttaagaa tgactgcaga  720
taataacacg gaagcactag atagctctac aacaaaagat gtcattcaaa aaggcatttc  780
cgtagtaggt gatctcctag gcgtagtagg tttcccgttt ggtggagcgc ttgtttcgtt  840
ttatacaaac tttttaaata ctatttggcc aagtgaagac ccgtggaagg cttttatgga  900
acaagtagaa gcattgatgg atcagaaaat agctgattat gcaaaaaata aagctcttgc  960
agagttacag ggccttcaaa ataatgtcga agattatgta agtgcattga gttcatggca  1020
aaaaaatcct gtgagttcac gaaatccaca tagccagggg cggataagag agctgttttc  1080
tcaagcagaa agtcattttc gtaattcaat gccttcgttt gcaatttctg gatacgaggt  1140
tctatttcta acaacatatg cacaagctgc caacacacat ttattttac taaaagacgc  1200
tcaaatttat ggagaagaat ggggatacga aaaagaagat attgctgaat tttataaaag  1260
acaactaaaa cttacgcaag aatatactga ccattgtgtc aaatgtata atgttggatt  1320
agataaatta agaggttcat cttatgaatc ttgggtaaac tttaaccgtt atcgcagaga  1380
gatgacatta acagtattag atttaattgc actatttcca ttgtatgatg ttcggctata  1440
cccaaaagaa gttaaaaccg aattaacaag agacgtttta acagatccaa ttgtcggagt  1500
caacaacctt aggggctatg gaacaacctt tctaatata gaaaattata ttcgaaaacc  1560
acatctattt gactatctgc atagaattca atttcacacg cggttccaac caggatatta  1620
tggaaatgac tctttcaatt attggtccgg taattatgtt tcaactagac caagcatagg  1680
atcaaatgat ataatcacat ctccattcta tggaaataaa tccagtgaac ctgtacaaaa  1740
tttagaattt aatggagaaa aagtctatag agccgtagca aatacaaatc ttgcggttcg  1800
gccgtccgct gtatattcag gtgttacaaa agtggaattt agccaatata atgatcaaac  1860
agatgaagca agtacacaaa cgtacgactc aaaaagaaat gttggcgcgg tcagctggga  1920
ttctatcgat caattgcctc cagaaacaac agatgaacct ctagaaaagg gatatagcca  1980
tcaactcaat tatgtaatgt gcttttaat gcagggtagt agaggaacaa tcccagtgtt  2040
aacttggaca cataaaagtg tagacttttt taacatgatt gattcgaaaa aaattacaca  2100
acttccgtta gtaaaggcat ataagttaca atctggtgct tccgttgtcg caggtcctag  2160
gtttacagga ggagatatca ttcaatgcac agaaaatgga agtgcggcaa ctatttacgt  2220
tacaccggat gtgtcgtact ctcaaaaata tcgagctaga attcattatg cttctacatc  2280
tcagataaca tttacactca gtttagacgg ggcaccattt aatcaatact atttcgataa  2340
aacgataaat aaaggagaca cattaacgta taattcattt aatttagcaa gtttcagcac  2400
accattcgaa ttatcaggga ataacttaca aataggcgtc acaggattaa gtgctggaga  2460
taagttat atagacaaaa ttgaatttat tccagtgaat taaattaact agaaagtaaa  2520
gaagtagtga ccatctatga tagtaagcaa aggataaaaa aatgagttca taaatgaat  2580
aacatagtgt tcttcaactt tcgcttttg aaggtagatg aagaacacta ttttatttt  2640
caaaatgaag gaagttttaa atatgtaatc atttaaaggg aacaatgaaa gtaggaaata  2700
agtcattatc tataacaaaa taacattttt atatagccaa aaatgaatta taatattaat  2760
cttttctaaa ttgacgtttt tctaaacgtt ctatagcttc aagacgctta gaatcatcaa  2820
tatttgtata cagagctgtt gtttccatcg agttatgtcc catttgattc gctaatagaa  2880
caagatcttt attttcgtta taatgattgg ttgcataagt atggcgtaat ttatgagggc  2940
ttttcttttc atcaaaagcc ctcgtgtatt tctctgtaag ctt                   2983

SEQ ID NO: 47           moltype = DNA   length = 2370
FEATURE                 Location/Qualifiers
source                  1..2370
                        mol_type = genomic DNA
                        organism = Bacillus thuringiensis
SEQUENCE: 47
atgaacaaga ataatactaa attaagcaca agagccttac caagtttat tgattatttt  60
aatggcattt atggatttgc cactggtatc aaagacatta tgaacatgat ttttaaaacg  120
gatacaggtg gtgatctaac cctagacgaa atttaaaga atcagcagtt actaaatgat  180
atttctggta aattggatgg ggtgaatgga agcttaaatg atcttatcgc acagggaaac  240
ttaaatacag aattatctaa ggaaatatta aaaattgcaa atgaacaaaa tcaagtttta  300
aatgatgtta ataacaaact cgatgcgata aatacgatgc ttcgggtata tctacctaaa  360
attacctcta tgttgagtga tgtaatgaaa caaaattatg cgctaagtct gcaaatagaa  420
tacttaagta aacaattgca agagatttct gataagttgg atattattaa tgtaaatgta  480
cttattaact ctacacttac tgaaattaca cctgcgtatc aaaggattaa atatgtgaac  540
```

```
gaaaaatttg aggaattaac ttttgctaca gaaactagtt caaaagtaaa aaaggatggc   600
tctcctgcag atattcttga tgagttaact gagttaactg aactagcgaa aagtgtaaca   660
aaaaatgatg tggatggttt tgaatttac cttaatacat tccacgatgt aatggtagga   720
aataattat tcgggcgttc agctttaaaa actgcatcgg aattaattac taagaaaat   780
gtgaaaacaa gtggcagtga ggtcgaaaat gtttataact tcttaattgt attaacagct   840
ctgcaagcaa aagcttttct tactttaaca acatgccgaa aattattagg cttagcagat   900
attgattata cttctattat gaatgaacat ttaaataagg aaaagagga atttagagta   960
aacatcctcc ctacactttc taatactttt tctaatccta attatgcaaa agttaaagga  1020
agtgatgaag atgcaaagat gattgtggaa gctaaaccag gacatgcatt gattgggttt  1080
gaaattagta atgattcaat tacagtatta aaagtatatg aggctaagct aaaacaaaat  1140
tatcaagtcg ataaggattc cttatcggaa gttatttatg gtgatatgga taaattattg  1200
tgcccagatc aatctgaaca aatctattat acaaataaca tagtatttcc aaatgaatat  1260
gtaattacta aaattgattt cactaaaaaa atgaaaactt taagatatga ggtaacagcg  1320
aatttttatg attcttctac aggagaaatt gacttaaata agaaaaaagt agaatcaagt  1380
gaagcggagt atagaacgtt aagtgctaat gatgatgggg tgtatatgcc gttaggtgtc  1440
atcagtgaaa cattttgac tccgattaat gggtttggcc tccaagctga tgaaaattca  1500
agattaatta ctttaacatg taaatcatat ttaagagaac tactgctagc aacagactta  1560
agcaataaag aaactaaatt gatcgtcccg ccaagtggtt ttattagcaa tattgtagag  1620
aacgggtcca tagaagagga caatttagag ccgtgaaaag caaataataa gaatgcgtat  1680
gtagatcata caggcggagt gaatggaact aaagctttat atgttcataa ggacggagga  1740
atttcacaat ttattggaga taagttaaaa ccgaaaactg agtatgtaat ccaatatact  1800
gttaaaggaa aaccttctat tcatttaaaa gatgaaaata ctggaatata tcattatgaa  1860
gatacaaata ataatttaga agattatcaa actattaata aacgttttac tacaggaact  1920
gatttaaagg gagtgtattt aattttaaaa agtcaaaatg gagatgaagc ttgggggat  1980
aactttatta ttttggaaat tagtccttct gaaaagttat taagtccaga attaattaat  2040
acaaataatt ggacgagtac gggatcaact aatattgaat acactt cactctttat  2100
cagggaggac gagggattct aaaacaaaac cttcaattag atagttttc aacttataga  2160
gtgtattttt ctgtgtccgg agatgctaat gtaaggatta gaaattctag ggaagtgtta  2220
tttgaaaaaa gatatatgag cggtgctaaa gatgtttctg aaatgttcac tacaaaattt  2280
gagaaagata acttttatat agagctttct caagggaata atttatatgg tggtcctatt  2340
gtacattttt acgatgtctc tattaagtaa                                    2370

SEQ ID NO: 48         moltype = AA  length = 299
FEATURE               Location/Qualifiers
source                1..299
                      mol_type = protein
                      note = SYNTHESIZED
                      organism = synthetic construct
SEQUENCE: 48
MSPILGYWKI KGLVQPTRLL LEYLEEKYEE HLYERDEGDK WRNKKFELGL EFPNLPYYID   60
GDVKLTQSMA IIRYIADKHN MLGGCPKERA EISMLEGAVL DIRYGVSRIA YSKDFETLKV  120
DFLSKLPEML KMFEDRLCHK TYLNGDHVTH PDFMLYDALD VVLYMDPMCL DAFPKLVCFK  180
KRIEAIPQID KYLKSSKYIA WPLQGWQATF GGGDHPPKSD GSGSHHHHHH GSGSLEVLFQ  240
GPLPTLPWSV CQEEWGDCLP SDPDLDPVGT ITNETKSSAE LYFLKTVLQQ KDGIEDGLG   299

SEQ ID NO: 49         moltype = AA  length = 448
FEATURE               Location/Qualifiers
source                1..448
                      mol_type = protein
                      note = SYNTHESIZED
                      organism = synthetic construct
SEQUENCE: 49
MGSGSHHHHH HGSGSNLYFQ GGEFLDRLSA TDEDGLHAGR VTFSIAGNDE AAEYFNVLND   60
GDNSAMLTLK QALPAGVQQF ELVIRATDGG TEPGPRSTDC SVTVVFVMTQ GDPVFDDNAA  120
SVRFVEKEAG MSEKFQLPQA DDPKNYRCMD DCHTIYYSIV DGNDGDHFAV EPETNVIYLL  180
KPLDRSQQEQ YRVVVAASNT PGGTSTLSSS LLTVTIGVRE ANPRPIFESE FYTAGVLHTD  240
SIHKELVYLA AKHSEGLPIV YSIDQETMKI DESLQTVVED AFDINSATGV ISLNFQPTSV  300
MHGSFDFEVV ASDTRGASDR AKVSIYMIST RVRVAFLFYN TEAEVNERRN FIAQTFANAF  360
GMTCNIDSVL PATDANGVIR EGYTELQAHF IRDDQPVPAD YIEGLFTELN TLRDIREVLS  420
TQQLTLLDFA AGGSAVLPGG EYALAVYI                                      448

SEQ ID NO: 50         moltype = AA  length = 642
FEATURE               Location/Qualifiers
source                1..642
                      mol_type = protein
                      note = SYNTHESIZED
                      organism = synthetic construct
SEQUENCE: 50
MNNVLNSGRT TICDAYNVVA HDPFSFEHKS LDTIQKEWME WKRTDHSLYV APVVGTVSSF   60
LLKKVGSLIG KRILSELWGI IFPSGSTNLM QDILRETEQF LNQRLNTDTL ARVNAELIGL  120
QANIREFNQQ VDNFLNPTQN PVPLSITSSV NTMQQLFLNR LPQFQIQGYQ LLLLPLFAQA  180
ANMHLSFIRD VILNADEWGI SAATLRTYRD YLRNYTRDYS NYCINTYQTA FRGLNTRLHD  240
MLEFRTYMFL NVFEYVSIWS LFKYQSLMVS SGRTYPIQTS SQLTREIYTS SVIEDSPVSA  300
NIPNGFNRAE FGVRPPHLMD FMNSLFVTAE TVRSQTVWGG HLVSSRNTAG NRINFPSYGV  360
FNPGGAIWIA DEDPRPFYRT LSDPVFVRGG FGNPHYVLGL RGVAFQQTGT NHTRTFRNSG  420
TIDSLDEIPP QDNSGAPWND YSHVLNHVTF VRWPGEISGS DSWRAPMFSW THRSATPTNT  480
IEIYAANENG TMIHLAPEDY TGFTISPIHA TQVNNQTRTF ISEKFGNQGD SLRFEQSNTT  540
ARYTLRGNGN SYNLYLRVSS IGNSTIRVTI NGRVYTVSNV NTTTNNDGVN DNGARFSDIN  600
IGNIVASDNT NVTLDINVTL NSGTPFDLMN IMFVPTNLPP LY                      642
```

```
SEQ ID NO: 51          moltype = AA  length = 1176
FEATURE                Location/Qualifiers
source                 1..1176
                       mol_type = protein
                       organism = Bacillus thuringiensis
SEQUENCE: 51
MDNNPNINEC IPYNCLSNPE VEVLGGERIE TGYTPIDISL SLTQFLLSEF VPGAGFVLGL  60
VDIIWGIFGP SQWDAFLVQI EQLINQRIEE FARNQAISRL EGLSNLYQIY AESFREWEAD  120
PTNPALREEM RIQFNDMNSA LTTAIPLLAV QNYQVPLLSV YVQAANLHLS VLRDVSVFGQ  180
RWGFDAATIN SRYNDLTRLI GNYTDYAVRW YNTGLERVWG PDSRDWVRYN QFRRELTLTV  240
LDIVALFSNY DSRRYPIRTV SQLTREIYTN PVLENFDGSF RGMAQRIEQN IRQPHLMDIL  300
NSITIYTDVH RGFNYWSGHQ ITASPVGFSG PEFAFPLFGN AGNAAPPVLV SLTGLGIFRT  360
LSSPLYRRII LGSGPNNQEL FVLDGTEFSF ASLTTNLPST IYRQRGTVDS LDVIPPQDNS  420
VPPRAGFSHR LSHVTMLSQA AGAVYTLRAP TFSWQHRSAE FNNIIPSSQI TQIPLTKSTN  480
LGSGTSVVKG PGFTGGDILR RTSPGQISTL RVNITAPLSQ RYRVRIRYAS TTNLQFHTSI  540
DGRPINQGNF SATMSSGSNL QSGSFRTVGF TTPFNFSNGS SVFTLSAHVF NSGNEVYIDR  600
IEFVPAEVTF EAEYDLERAQ KAVNELFTSS NQIGLKTDVT DYHIDQVSNL VECLSDEFCL  660
DEKQELSEKV KHAKRLSDER NLLQDPNFRG INRQLDRGWR GSTDITIQGG DDVFKENYVT  720
LLGTFDECYP TYLYQKIDES KLKAYTRYQL RGYIEDSQDL EIYLIRYNAK HETVNVPGTG  780
SLWPLSAQSP IGKCGEPNRC APHLEWNPDL DCSCRDGEKC AHHSHHFSLD IDVGCTDLNE  840
DLGVWVIFKI KTQDGHARLG NLEFLEEKPL VGEALARVKR AEKKWRDKRE KLEWETNIVY  900
KEAKESVDAL FVNSQYDQLQ ADTNIAMIHA ADKRVHSIRE AYLPELSVIP GVNAAIFEEL  960
EGRIFTAFSL YDARNVIKNG DFNNGLSCWN VKGHVDVEEQ NNQRSVLVVP EWEAEVSQEV  1020
RVCPGRGYIL RVTAYKEGYG EGCVTIHEIE NNTDELKFSN CVEEEIYPNN TVTCNDYTVN  1080
QEEYGGAYTS RNRGYNEAPS VPADYASVYE EKSYTDGRRE NPCEFNRGYR DYTPLPVGYV  1140
TKELEYFPET DKVWIEIGET EGTFIVDSVE LLLMEE                            1176

SEQ ID NO: 52          moltype = AA  length = 652
FEATURE                Location/Qualifiers
source                 1..652
                       mol_type = protein
                       organism = Bacillus thuringiensis
SEQUENCE: 52
MNPNNRSEHD TIKVTPNSEL QTNHNQYPLA DNPNSTLEEL NYKEFLRMTE DSSTEVLDNS  60
TVKDAVGTGI SVVGQILGVV GVPFAGALTS FYQSFLNTIW PSDADPWKAF MAQVEVLIDK  120
KIEEYAKSKA LAELQGLQNN FEDYVNALNS WKKTPLSLRS KRSQDRIREL FSQAESHFRN  180
SMPSFAVSKF EVLFLPTYAQ AANTHLLLLK DAQVFGEEWG YSSEDVAEFY HRQLKLTQQY  240
TDHCVNWYNV GLNGLRGSTY DAWVKFNRFR REMTLTVLDL IVLFPFYDIR LYSKGVKTEL  300
TRDIFTDPIF SLNTLQEYGP TFLSIENSIR KPHLFDYLQG IEFHTRLQPG YFGKDSFNYW  360
SGNYVETRPS IGSSKTITSP FYGDKSTEPV QKLSFDGQKV YRTIANTDVA AWPNGKVYLG  420
VTKVDFSQYD DQKNETSTQT YDSKRNNGHV SAQDSIDQLP PETTDEPLEK AYSHQLNYAE  480
CFLMQDRRGT IPFFTWTHRS VDFFNTIDAE KITQLPVVKA YALSSGASII EGPGFTGGNL  540
LFLKESSNSI AKFKVTLNSA ALLQRYRVRI RYASTTNLRL FVQNSNNDFL VIYINKTMNK  600
DDDLTYQTFD LATTNSNMGF SGDKNELIIG AESFVSNEKI YIDKIEFIPV QL          652

SEQ ID NO: 53          moltype = AA  length = 789
FEATURE                Location/Qualifiers
source                 1..789
                       mol_type = protein
                       organism = Bacillus thuringiensis
SEQUENCE: 53
MNKNNTKLST RALPSFIDYF NGIYGFATGI KDIMNMIFKT DTGGDLTLDE ILKNQQLLND  60
ISGKLDGVNG SLNDLIAQGN LNTELSKEIL KIANEQNQVL NDVNNKLDAI NTMLRVYLPK  120
ITSMLSDVMK QNYALSLQIE YLSKQLQEIS DKLDIINVNV LINSTLTEIT PAYQRIKYVN  180
EKFEELTFAT ETSSKVKKDG SPADILDELT ELTELAKSVT KNDVDGFEFY LNTFHDVMVG  240
NNLFGRSALK TASELITKEN VKTSGSEVGN VYNFLIVLTA LQAKAFLTLT TCRKLLGLAD  300
IDYTSIMNEH LNKEKEEFRV NILPTLSNTF SNPNYAKVKG SDEDAKMIVE AKPGHALIGF  360
EISNDSITVL KVYEAKLKQN YQVDKDSLSE VIYGDMDKLL CPDQSEQIYY TNNIVFPNEY  420
VITKIDFTKK MKTLRYEVTA NFYDSSTGEI DLNKKKVESS EAEYRTLSAN DDGVYMPLGV  480
ISETFLTPIN GFGLQADENS RLITLTCKSY LRELLLATDL SNKETKLIVP PSGFISNIVE  540
NGSIEEDNLE PWKANNKNAY VDHTGGVNGT KALYVHKDGG ISQFIGDKLK PKTEYVIQYT  600
VKGKPSIHLK DENTGYIHYE DTNNNLEDYQ TINKRFTTGT DLKGVYLILK SQNGDEAWGD  660
NFIILEISPS EKLLSPELIN TNNWTSTGST NISGNTLTLY QGGRGILKQN LQLDSFSTYR  720
VYFSVSGDAN VRIRNSREVL FEKRYMSGAK DVSEMFTTKF EKDNFYIELS QGNNLYGGPI  780
VHFYDVSIK                                                          789

SEQ ID NO: 54          moltype = AA  length = 18
FEATURE                Location/Qualifiers
source                 1..18
                       mol_type = protein
                       note = SYNTHESIZED
                       organism = synthetic construct
SEQUENCE: 54
GSTSGSGKPG SGEGSTKG                                                18

SEQ ID NO: 55          moltype = DNA  length = 54
FEATURE                Location/Qualifiers
source                 1..54
```

```
                            mol_type = other DNA
                            note = SYNTHESIZED
                            organism = synthetic construct
SEQUENCE: 55
ggctcaactt ctggatctgg gaagccaggg agcggcgaag gttcgactaa gggc        54

SEQ ID NO: 56               moltype = AA   length = 17
FEATURE                     Location/Qualifiers
source                      1..17
                            mol_type = protein
                            note = SYNTHESIZED
                            organism = synthetic construct
SEQUENCE: 56
AEAAAKEAAA KEAAAKA                                                 17

SEQ ID NO: 57               moltype = DNA   length = 51
FEATURE                     Location/Qualifiers
source                      1..51
                            mol_type = other DNA
                            note = SYNTHESIZED
                            organism = synthetic construct
SEQUENCE: 57
gcggaggccg ctgcaaagga agctgctgcg aaggaagcag cggccaaggc g           51

SEQ ID NO: 58               moltype = AA   length = 17
FEATURE                     Location/Qualifiers
source                      1..17
                            mol_type = protein
                            note = SYNTHESIZED
                            organism = synthetic construct
SEQUENCE: 58
ESGSVSSEQL AQFRSLD                                                 17

SEQ ID NO: 59               moltype = DNA   length = 51
FEATURE                     Location/Qualifiers
source                      1..51
                            mol_type = other DNA
                            note = SYNTHESIZED
                            organism = synthetic construct
SEQUENCE: 59
gaaagcggca gcgtgagcag cgaacagctg gcgcagtttc gcagcctgga t           51

SEQ ID NO: 60               moltype = AA   length = 15
FEATURE                     Location/Qualifiers
source                      1..15
                            mol_type = protein
                            note = SYNTHESIZED
                            organism = synthetic construct
SEQUENCE: 60
GGGGSGGGGS GGGGS                                                   15

SEQ ID NO: 61               moltype = DNA   length = 45
FEATURE                     Location/Qualifiers
source                      1..45
                            mol_type = other DNA
                            note = SYNTHESIZED
                            organism = synthetic construct
SEQUENCE: 61
ggtggcggcg ggagtggcgg gggtggtagt ggcggtgggg gctcc                  45

SEQ ID NO: 62               moltype = AA   length = 8
FEATURE                     Location/Qualifiers
source                      1..8
                            mol_type = protein
                            note = SYNTHESIZED
                            organism = synthetic construct
SEQUENCE: 62
GGGGGGGG                                                            8

SEQ ID NO: 63               moltype = DNA   length = 24
FEATURE                     Location/Qualifiers
source                      1..24
                            mol_type = other DNA
                            note = SYNTHESIZED
                            organism = synthetic construct
SEQUENCE: 63
ggtggcggcg ggggcggggg tggt                                         24

SEQ ID NO: 64               moltype = AA   length = 12
```

```
FEATURE                   Location/Qualifiers
source                    1..12
                          mol_type = protein
                          note = SYNTHESIZED
                          organism = synthetic construct
SEQUENCE: 64
PTPTTPTPTT PT                                                               12

SEQ ID NO: 65             moltype = DNA  length = 36
FEATURE                   Location/Qualifiers
source                    1..36
                          mol_type = other DNA
                          note = SYNTHESIZED
                          organism = synthetic construct
SEQUENCE: 65
ccgactccga ctactcccac acctaccacg cccacc                                     36

SEQ ID NO: 66             moltype = AA  length = 20
FEATURE                   Location/Qualifiers
source                    1..20
                          mol_type = protein
                          note = SYNTHESIZED
                          organism = synthetic construct
SEQUENCE: 66
MKYLLPTAAA GLLLLAAQPA                                                       20

SEQ ID NO: 67             moltype = DNA  length = 402
FEATURE                   Location/Qualifiers
source                    1..402
                          mol_type = other DNA
                          note = SYNTHESIZED
                          organism = synthetic construct
SEQUENCE: 67
atggcccagg tgcagctgca ggagtctggg ggaggcttgg tgcagccggg ggggtctctg           60
agactctcct gtgcagcctc tggattcacc ttcagtagcg ctgccatgag ctgggtccgc          120
caggctccag gaaaggggct cgagtgggtc tcagttatta atagtggcgg tgatagtaca          180
agttatacag gctccgtgaa gggccgattc accatctcca gggacaacgc caaggcgaca          240
ctgtatctgc aaatgaacaa cctgaaacct gaggacacgg ccgtgtatta ttgtgcaaga          300
gggagtaccc gcggccaggg gacccaggtc accgtctcct cagcggccgc atacccgtac          360
gacgttccgg actacggttc ccaccaccat caccatcact ag                             402

SEQ ID NO: 68             moltype = AA  length = 133
FEATURE                   Location/Qualifiers
source                    1..133
                          mol_type = protein
                          note = SYNTHESIZED
                          organism = synthetic construct
SEQUENCE: 68
MAQVQLQESG GGLVQPGGSL RLSCAASGFT FSSAAMSWVR QAPGKGLEWV SVINSGGDST           60
SYTGSVKGRF TISRDNAKAT LYLQMNNLKP EDTAVYYCAR GSTRGQGTQV TVSSAAAYPY         120
DVPDYGSHHH HHH                                                             133

SEQ ID NO: 69             moltype = DNA  length = 444
FEATURE                   Location/Qualifiers
source                    1..444
                          mol_type = other DNA
                          note = SYNTHESIZED
                          organism = synthetic construct
SEQUENCE: 69
atggcccagg tgcagctgca ggagtctggg ggaggctcgg tgcagcctgg ggggtctcta           60
aaactctcct gtgcagcctc tggattcacc ttcagtaact atgccatgag ctgggtccgc          120
caggctccag gaaaggggct cgagtgggtc tcaggtatta atgctggtgg tgatacgaca          180
aactatgcag actccgtgaa ggaccgattc accatctcca gagacaacgc caagaacacg          240
ctgtatctcc aaatgaacag cctgaaacct gaggacacgg ccatatatta ctgtctaaag          300
cttgagacca gtgtggttcc tagtagtagt tactaccgca atcgcggttc caggggccag          360
ggaacccagg tcaccgtctc ctcagcggcc gcatacccgt acgacgttcc ggactacggt          420
tcccaccacc atcaccatca ctag                                                 444

SEQ ID NO: 70             moltype = AA  length = 147
FEATURE                   Location/Qualifiers
source                    1..147
                          mol_type = protein
                          note = SYNTHESIZED
                          organism = synthetic construct
SEQUENCE: 70
MAQVQLQESG GGSVQPGGSL KLSCAASGFT FSNYAMSWVR QAPGKGLEWV SGINAGGDTT           60
NYADSVKDRF TISRDNAKNT LYLQMNSLKP EDTAIYYCLK LETSVVPSSS YYRNRGSRGQ         120
GTQVTVSSAA AYPYDVPDYG SHHHHHH                                              147
```

| SEQ ID NO: 71 | moltype = DNA length = 444 |
|---|---|
| FEATURE | Location/Qualifiers |
| source | 1..444 |
| | mol_type = other DNA |
| | note = SYNTHESIZED |
| | organism = synthetic construct |

SEQUENCE: 71
```
atggcccagg tgcagctgca ggagtctggg ggaggattgg tgcaggctgg ggactctctg    60
agactctcct gtgcagcctc tgaacaatcc ttcaatatgg aaattatggg ctggttccgc   120
caggctccag ggaaggagcg tgagtttgta gcagctatta cctatagtgg tagtatcaca   180
aaatatgcag actccgcgaa gggccgattc accatctcca gagacaacgc caagaacacg   240
gtgtatctgc aaatgaacag tttgaaccct gaggacacgg ccctttatta ctgtgccctt   300
aacaaagggg gactgtatac tgactaccga tcttgggcga cgtatgacta ccgcggccag   360
gggacccagg tcaccgtctc ctcagcggcc gcataccccgt acgacgttcc ggactacggt   420
tcccaccacc atcaccatca ctag                                          444
```

| SEQ ID NO: 72 | moltype = AA length = 147 |
|---|---|
| FEATURE | Location/Qualifiers |
| source | 1..147 |
| | mol_type = protein |
| | note = SYNTHESIZED |
| | organism = synthetic construct |

SEQUENCE: 72
```
MAQVQLQESG GGLVQAGDSL RLSCAASEQS FNSEIMGWFR QAPGKEREFV AAITYSGSIT    60
KYADSAKGRF TISRDNAKNT VYLQMNSLNP EDTALYYCAL NKGGLYTDYR SWATYDYRGQ   120
GTQVTVSSAA AYPYDVPDYG SHHHHHH                                       147
```

| SEQ ID NO: 73 | moltype = DNA length = 429 |
|---|---|
| FEATURE | Location/Qualifiers |
| source | 1..429 |
| | mol_type = other DNA |
| | note = SYNTHESIZED |
| | organism = synthetic construct |

SEQUENCE: 73
```
atggcccagg tgcagctgca ggagtctggg ggaggattgg tgcaggctgg ggctctctg     60
agactctcct gtgcagcctc tggacgcacc ttcagtaggt atgccatggg ctggtttcgc   120
caggctctag ggaaggagcg tgagttcgta gcaggtatta ctggagtggg tagtatgaca   180
tactatgcag actccgtgaa gggccgattc accatctcca gagacaacgc caagaacatg   240
ctgtatctgc aaatgaacag tctgaaatct gaggacacgg ccgtgtatta ctgtgccgga   300
gtgacggtag taggtggtgc accagccttt gactactggg gccaggggac ccaggtcacc   360
gtctcctcag cggccgcata cccgtacgac gttccggact acggttccca ccaccatcac   420
catcactag                                                           429
```

| SEQ ID NO: 74 | moltype = AA length = 142 |
|---|---|
| FEATURE | Location/Qualifiers |
| source | 1..142 |
| | mol_type = protein |
| | note = SYNTHESIZED |
| | organism = synthetic construct |

SEQUENCE: 74
```
MAQVQLQESG GGLVQAGGSL RLSCAASGRT FSRYAMGWFR QALGKEREFV AGINWSGSMT    60
YYADSVKGRF TISRDNAKNM LYLQMNSLKS EDTAVYYCAG VTVVGGAPAF DYWGQGTQVT   120
VSSAAAYPYD VPDYGSHHHH HH                                            142
```

| SEQ ID NO: 75 | moltype = DNA length = 417 |
|---|---|
| FEATURE | Location/Qualifiers |
| source | 1..417 |
| | mol_type = other DNA |
| | note = SYNTHESIZED |
| | organism = synthetic construct |

SEQUENCE: 75
```
atggcccagg tgcagctgca ggagtctgga ggaggagtgg tgcagactgg gggctccctg    60
acactctcct gtaaagcctc tagacgcacc agtggctttg ccatggcctg gttccgccag   120
gctccaggga tggaacgtga atttgtagcg ggcattgtgc ggactgggga taatatccac   180
tatttagatt ctgtgaaggg ccgattcacc atctctagag ataataccaa gaacacgctg   240
tctctgcaaa tgaacagcct gagacctggg gacacggccg tctattactg tgcagcagac   300
gtgacaaaga gtggatttat ttattggggc caggggaccc aggtcaccgt ctcctcagcg   360
gccgcatacc cgtacgacgt tccggactac ggttccacc accatcacca tcactag       417
```

| SEQ ID NO: 76 | moltype = AA length = 138 |
|---|---|
| FEATURE | Location/Qualifiers |
| source | 1..138 |
| | mol_type = protein |
| | note = SYNTHESIZED |
| | organism = synthetic construct |

SEQUENCE: 76
```
MAQVQLQESG GGVVQTGGSL TLSCKASRRT SGFAMAWFRQ APGMEREFVA GIGRTGDNIH    60
YLDSVKGRFT ISRDNTKNTL SLQMNSLRPG DTAVYYCAAD VTKSGFIYWG QGTQVTVSSA   120
AAYPYDVPDY GSHHHHHH                                                 138
```

```
SEQ ID NO: 77            moltype = DNA  length = 444
FEATURE                  Location/Qualifiers
source                   1..444
                         mol_type = other DNA
                         note = SYNTHESIZED
                         organism = synthetic construct
SEQUENCE: 77
atggcccagg tgcagctgca ggagtctggg ggaggcttgg tgcagcctgg ggggtctctg      60
agactcgcct gtgtactctc cggaggcccc tcgagtagtt atggtgtggg ctggttccga     120
cagcgatcag ggacagagcg tgaatttgta gcagctatca gtgggagtgg tcgtactatc     180
cattatgtag acgacgtgaa gggccgattc gccatctcca gagacagcgc caagaatgcg     240
gtggatctgc aaatgaacaa cctgaaacct gaggacacgc cgttattta ctgtgcggca      300
ctcgcgctcg ttactactca tccgacgagc aatgtgggtg aatgggacta ctgggggcag     360
gggacccagg tcaccgtctc ctcagcggcc gcatacccgt acgacgttcc ggactacggt     420
tcccaccacc atcaccatca ctag                                            444

SEQ ID NO: 78            moltype = AA  length = 147
FEATURE                  Location/Qualifiers
source                   1..147
                         mol_type = protein
                         note = SYNTHESIZED
                         organism = synthetic construct
SEQUENCE: 78
MAQVQLQESG GGLVQPGGSL RLACVLSGGP SSSYGVGWFR QRSGTEREFV AAISGSGRTI      60
HYVDDVKGRF AISRDSAKNA VDLQMNNLKP EDTAVYYCAA LALVTTHPTS NVGEWDYWGQ     120
GTQVTVSSAA AYPYDVPDYG SHHHHHH                                         147

SEQ ID NO: 79            moltype = DNA  length = 426
FEATURE                  Location/Qualifiers
source                   1..426
                         mol_type = other DNA
                         note = SYNTHESIZED
                         organism = synthetic construct
SEQUENCE: 79
atggcccagg tgcagctgca ggagtctgga ggaggagtgg tgcagactgg ggctccctg       60
acactctcct gtaaagcctc tagacgcacc agtggctttg ccatggcctg gttccgccag     120
gctccaggga tggaacgtga atttgtagcg ggcattggtc ggactgggga taatatccac     180
tatttagatt ctgtgaaggg ccgattcacc atctctagag ataataccaa gaacacgctg     240
tctctgcaaa tgaacagtct gaaatctgag gacacggccg tgtattactg tgcaaaagtg     300
gtggtagtag ctggttcacc atctttcgac gcatggggcc aggggaccca ggtcaccgtc     360
tcctcagcgg ccgcataccc gtacgacgtt ccggactacg gttccaccac ccatcaccat     420
cactag                                                                426

SEQ ID NO: 80            moltype = AA  length = 141
FEATURE                  Location/Qualifiers
source                   1..141
                         mol_type = protein
                         note = SYNTHESIZED
                         organism = synthetic construct
SEQUENCE: 80
MAQVQLQESG GGVVQTGGSL TLSCKASRRT SGFAMAWFRQ APGMEREFVA GIGRTGDNIH      60
YLDSVKGRFT ISRDNTKNTL SLQMNSLKSE DTAVYYCAKV VVVAGSPSFD AWGQGTQVTV     120
SSAAAYPYDV PDYGSHHHHH H                                               141

SEQ ID NO: 81            moltype = DNA  length = 423
FEATURE                  Location/Qualifiers
source                   1..423
                         mol_type = other DNA
                         note = SYNTHESIZED
                         organism = synthetic construct
SEQUENCE: 81
atggcccagg tgcagctgca ggagtctggg ggaggattgg tgcaggctgg gggctctctg      60
acgctctcct gcgcattctc tggtcgcacc ttcactcatt atgccatggc ctggttccgc     120
caggctccag ggaaggagcg taagttcgta gctggtgtta cacggagtgg cccgaacaca     180
tattatgacg actccgtgca gggccgattc accatctcaa gagacaacgc caagaacacg     240
gtttatctgc acatgaacag cctgaaacct gaggacacgg ccgttattta ctgtgctgca     300
aattcggggg tagtatccgg atatgactac tggggccagg gaacccaggt caccgtctcc     360
tcagcggccg cataccgta cgacgttccg gactacggtt ccaccaccat caccatcac      420
tag                                                                   423

SEQ ID NO: 82            moltype = AA  length = 140
FEATURE                  Location/Qualifiers
source                   1..140
                         mol_type = protein
                         note = SYNTHESIZED
                         organism = synthetic construct
SEQUENCE: 82
MAQVQLQESG GGLVQAGGSL TLSCAFSGRT FTHYAMAWFR QAPGKERKFV AGVTRSGPNT      60
```

```
YYDDSVQGRF TISRDNAKNT VYLHMNSLKP EDTAVYYCAA NSGVVSGYDY WGQGTQVTVS    120
SAAAYPYDVP DYGSHHHHHH                                                140

SEQ ID NO: 83           moltype = DNA  length = 414
FEATURE                 Location/Qualifiers
source                  1..414
                        mol_type = other DNA
                        note = SYNTHESIZED
                        organism = synthetic construct
SEQUENCE: 83
atggcccagg ttcagttgca ggaaagcggt ggcggcgtag ttcaaactgg cggttcgctg    60
acactttctt gtaaggcttc tcgtcgcact tccgggtttg caatggcctg gttccgtcag    120
gctccgggga tggagcgtga gtttgtcgcg ggattgggc gcacggggga caacatccat    180
taccttgatt cggtcaaagg ccgcttcact atttctcgtg ataacacaaa gaacactctg    240
agcttacaaa tgaataatct taaaccggag gacacggctg tttattattg cttgcgtact    300
atgggaggga cctggtcgga aaggggcaa ggcacgcagg tcacggttag ctcagcggcc    360
gcataccccgt acgacgttcc ggactacggt tccaccacc atcaccatca ctag         414

SEQ ID NO: 84           moltype = AA   length = 137
FEATURE                 Location/Qualifiers
source                  1..137
                        mol_type = protein
                        note = SYNTHESIZED
                        organism = synthetic construct
SEQUENCE: 84
MAQVQLQESG GGVVQTGGSL TLSCKASRRT SGFAMAWFRQ APGMEREFVA GIGRTGDNIH    60
YLDSVKGRFT ISRDNTKNTL SLQMNNLKPE DTAVYYCLRT MGGTWSEKGQ GTQVTVSSAA    120
AYPYDVPDYG SHHHHHH                                                   137

SEQ ID NO: 85           moltype = DNA  length = 453
FEATURE                 Location/Qualifiers
source                  1..453
                        mol_type = other DNA
                        note = SYNTHESIZED
                        organism = synthetic construct
SEQUENCE: 85
atggcccagg tgcagctgca ggagtctggg gaggattgg tgcaggctgg ggcctctctg    60
agactctcct gtgcagcctc tagacgcacc ggcagtagtc ttaccatggg ctggttccgc    120
caggctccag ggaaggagcg tgagtttgta gcagctatta gccggagtgg tattagaaca    180
tactacgcag actttgtgaa gggccggttc accatctcca gagacaacgc caagaacacg    240
ctctatctgc aaatgaacag cctgaaacct gaggacacgg ccgtgtatta ctgtgcggct    300
aacgacaaaa catacggtag tggtcttgac gtctacacaa ggcgacaaaa ctattactac    360
tggggcccgg gaacccaggt caccgtctcc tcagcggccg cataccccgta cgacgttccg    420
gactacggtt cccaccacca tcaccatcac tag                                 453

SEQ ID NO: 86           moltype = AA   length = 150
FEATURE                 Location/Qualifiers
source                  1..150
                        mol_type = protein
                        note = SYNTHESIZED
                        organism = synthetic construct
SEQUENCE: 86
MAQVQLQESG GGLVQAGASL RLSCAASRRT GSSLTMGWFR QAPGKEREFV AAISRSGIRT    60
YYADFVKGRF TISRDNAKNT LYLQMNSLKP EDTAVYYCAA NDKTYGSGLD VYTRRQNYYY    120
WGPGTQVTVS SAAAYPYDVP DYGSHHHHHH                                     150

SEQ ID NO: 87           moltype = DNA  length = 453
FEATURE                 Location/Qualifiers
source                  1..453
                        mol_type = other DNA
                        note = SYNTHESIZED
                        organism = synthetic construct
SEQUENCE: 87
atggcccagg tgcagctgca ggagtctgga ggaggattgg cgcaggctgg ggcctctctg    60
agactctcct gtgcagcctc tagacgcacc ggcagtagtc ttaccatggg ctggttccgc    120
caggctccag ggaaggagcg tgagtttgta gcagctatta gccggagtgg tattagaaca    180
tactacgcag actttgtgaa gggccggttc accatctcca gagacaacgc caagaacacg    240
ctctatctgc aaatgaacag cctgaaacct gaggacacgg ccgtgtatta ctgtgcggct    300
aacgacaaaa catacggtag tggtcttgac gtctacacaa ggcgacaaga ctattactac    360
tggggcccgg gaacccaggt caccgtctcc tcagcggccg cataccccgta cgacgttccg    420
gactacggtt cccaccacca tcaccatcac tag                                 453

SEQ ID NO: 88           moltype = AA   length = 150
FEATURE                 Location/Qualifiers
source                  1..150
                        mol_type = protein
                        note = SYNTHESIZED
                        organism = synthetic construct
SEQUENCE: 88
```

```
MAQVQLQESG GGLAQAGASL RLSCAASRRT GSSLTMGWFR QAPGKEREFV AAISRSGIRT    60
YYADFVKGRF TISRDNAKNT LYLQMNSLKP EDTAVYYCAA NDKTYGSGLD VYTRRQDYYY   120
WGPGTQVTVS SAAAYPYDVP DYGSHHHHHH                                   150

SEQ ID NO: 89              moltype = DNA  length = 414
FEATURE                    Location/Qualifiers
source                     1..414
                           mol_type = other DNA
                           note = SYNTHESIZED
                           organism = synthetic construct
SEQUENCE: 89
atggcccagg tgcagctgca ggagtctggg ggaggctcgg tgcaggctgg ggggtctctg    60
aaactctcct gtgcagcttc tggaaccgaa agcattttca tcgtgatggg ctggtaccgc   120
caggctccag ggaaagagcg cgagttggtc gcggcaatgt catttggtgg tggtacaaat   180
gttacagacg gcgtgagggg ccgattcacc atctccagag actttgacaa gaacacggtg   240
gatctacaaa tgaacaacct aaaaactgag gacacggccg tctattactg taatgcagtc   300
cagtggggcc ctcgtgacta ctggggccag gggacccagg tcaccgtctc ctcagcggcc   360
gcataccgt acgacgttcc ggactacggt tccaccacca tcaccatca ctag           414

SEQ ID NO: 90              moltype = AA  length = 137
FEATURE                    Location/Qualifiers
source                     1..137
                           mol_type = protein
                           note = SYNTHESIZED
                           organism = synthetic construct
SEQUENCE: 90
MAQVQLQESG GGSVQAGGSL KLSCAASGTE SIFIVMGWYR QAPGKERELV AAMSFGGGTN    60
VTDGVRGRFT ISRDFDKNTV DLQMNNLKTE DTAVYYCNAV QWGPRDYWGQ GTQVTVSSAA   120
AYPYDVPDYG SHHHHHH                                                 137

SEQ ID NO: 91              moltype = DNA  length = 453
FEATURE                    Location/Qualifiers
source                     1..453
                           mol_type = other DNA
                           note = SYNTHESIZED
                           organism = synthetic construct
SEQUENCE: 91
atggcccagg tgcagctgca ggagtctgga ggaggattgg tgcaggctgg ggcctctctg    60
agactctcct gtgcagcctc tagacgcacc ggcagtagtc ttaccatggg ctggttccgc   120
caggctccag ggagggagcg tgagtttgta gcagctatta gcggagtgg tattagaaca   180
tactacgcag actttgtgaa gggccggttc accatctcca gagacaacgc caagaacacg   240
ctctatctgc aaatgaacag cctgaaacct gaggacacgg ccgtgtatta ctgtgcggct   300
aacgacaaaa catacggtag tggtcttgac gtctcacaca ggcacaaga ctattactac   360
tggggcccgg ggacccaggt caccgtctcc tcagcggccg catacccgta cgacgttccg   420
gactacggtt cccaccacca tcaccatcac tag                                453

SEQ ID NO: 92              moltype = AA  length = 150
FEATURE                    Location/Qualifiers
source                     1..150
                           mol_type = protein
                           note = SYNTHESIZED
                           organism = synthetic construct
SEQUENCE: 92
MAQVQLQESG GGLVQAGASL RLSCAASRRT GSSLTMGWFR QAPGREREFV AAISRSGIRT    60
YYADFVKGRF TISRDNAKNT LYLQMNSLKP EDTAVYYCAA NDKTYGSGLD VYTRRQDYYY   120
WGPGTQVTVS SAAAYPYDVP DYGSHHHHHH                                   150

SEQ ID NO: 93              moltype = DNA  length = 441
FEATURE                    Location/Qualifiers
source                     1..441
                           mol_type = other DNA
                           note = SYNTHESIZED
                           organism = synthetic construct
SEQUENCE: 93
atggcccagg tgcagctgca ggagtctggg ggaggattgg tgcaggctgg ggcctctctg    60
agactctcct gtgcagcctc tagacgcacc ggcagtagtc ttaccatggg ctggttccgc   120
caggctccag ggaaggagcg tgagtttgta gcagctatta gcggagtgg tattagaaca   180
tactacgcag actttgtgaa gggccggttc accatctcca gagataacgg cgagaatacg   240
ctgtatctgc aaatcaacag cctgaaacct gaggacacgg ccgtttatta ctgtgcggca   300
tccagcaacc cgggatacta tcgtacagct cccaaccagt ataacttctg ggcccgggg    360
acccaggtca ccgtctcctc tgcggccgca tacccgtacg acgttccgga ctacggttcc   420
caccaccatc accatcacta g                                             441

SEQ ID NO: 94              moltype = AA  length = 146
FEATURE                    Location/Qualifiers
source                     1..146
                           mol_type = protein
                           note = SYNTHESIZED
                           organism = synthetic construct
```

```
SEQUENCE: 94
MAQVQLQESG GGLVQAGASL RLSCAASRRT GSSLTMGWFR QAPGKEREFV AAISRSGIRT      60
YYADFVKGRF TISRDNGENT LYLQINSLKP EDTAVYYCAA SSNPGYYRTA PNQYNFWGPG    120
TQVTVSSAAA YPYDVPDYGS HHHHHH                                        146

SEQ ID NO: 95             moltype = DNA   length = 828
FEATURE                   Location/Qualifiers
source                    1..828
                          mol_type = other DNA
                          note = SYNTHESIZED
                          organism = synthetic construct
SEQUENCE: 95
atggcccagg tgcagctgca ggagtctggg ggaggattgg tgcaggctgg ggactctctg     60
agactctcct gtgcagcctc tgaacaatcc ttcaatagcg aaattatgca ctggttccgc    120
caggctccag ggaaggagcg tgagtttgta gcagctatta cctatagtgg tagtatcaca    180
aaatatgcag actccgcgaa gggccgattc accatctcca gagacaacgc caagaacacg    240
gtgtatctgc aaatgaacag tttgaaccct gaggacacgg ccctttatta ctgtgccctt    300
aacaaagggg gactgtatac tgactaccga tcttgggcga cgtatgacta ccgcggccag    360
gggacccagg tcaccgtctc ctcaccgact ccgactactc ccacacctac cacgcccacc    420
caggtcagct gcaggagtc tggaggagga gtggtgcaga ctgggggctc cctgacactc    480
tcctgtaaag cctctagacg caccagtggc tttgccatgg cctggttccg ccaggctcca    540
gggatgaac gtgaatttgt agcgggcatt ggtcggactg gggataatat ccactattta    600
gattctgtga agggccgatt caccatctct agagataata ccaagaacac gctgtctctg    660
caaatgaaca acctgaaacc tgaggacacg gccgtgtatt actgcctacg tacgatgggt    720
ggtacctggt ctgagaaggg ccaggggacc caggtcaccg tctcctcagc ggccgcatac    780
ccgtacgacg ttccggacta cggttcccac caccatcacc atcactag              828

SEQ ID NO: 96             moltype = AA   length = 275
FEATURE                   Location/Qualifiers
source                    1..275
                          mol_type = protein
                          note = SYNTHESIZED
                          organism = synthetic construct
SEQUENCE: 96
MAQVQLQESG GGLVQAGDSL RLSCAASEQS FNSEIMGWFR QAPGKEREFV AAITYSGSIT     60
KYADSAKGRF TISRDNAKNT VYLQMNSLNP EDTALYYCAL NKGGLYTDYR SWATYDYRGQ   120
GTQVTVSSPT PTTPTPTTPT QVQLQESGGG VVQTGGSLTL SCKASRRTSG FAMAWFRQAP   180
GMEREFVAGI GRTGDNIHYL DSVKGRFTIS RDNTKNTLSL QMNNLKPEDT AVYYCLRTMG   240
GTWSEKGQGT QVTVSSAAAY PYDVPDYGSH HHHHH                              275

SEQ ID NO: 97             moltype = DNA   length = 867
FEATURE                   Location/Qualifiers
source                    1..867
                          mol_type = other DNA
                          note = SYNTHESIZED
                          organism = synthetic construct
SEQUENCE: 97
atggcccagg tgcagctgca ggagtctggg ggaggattgg tgcaggctgg ggactctctg     60
agactctcct gtgcagcctc tgaacaatcc ttcaatagcg aaattatggg ctggttccgc    120
caggctccag ggaaggagcg tgagtttgta gcagctatta cctatagtgg tagtatcaca    180
aaatatgcag actccgcgaa gggccgattc accatctcca gagacaacgc caagaacacg    240
gtgtatctgc aaatgaacag tttgaaccct gaggacacgg ccctttatta ctgtgccctt    300
aacaaagggg gactgtatac tgactaccga tcttgggcga cgtatgacta ccgcggccag    360
gggacccagg tcaccgtctc ctcaccgaca ccgaccaccc cacgccccac tactcccacc    420
caagtccagt tacaggagtc aggaggtggt ctggtccaga cgggtggcag tttcgtctt    480
agttgcgcgg cctcacgccg tactggtagt agtctgacta tggggtggtt tcgccaagcc    540
caggtcgtg aacgtgaatt tgtcgcagcg attagccgta gcggtatccg tacctattat    600
gcggactttg tcaagggccg tttcactatc tcccgcgaca atgcgaaaaa cacttttgtac    660
cttcaaatga actcattgaa accagaggat accgcggtgt actattgtgc ggcgaacgac    720
aagacgtatg gtcggggct ggatgtatat acgcgtcgtc aggattatta ctactggggt    780
cccggtaccc aggtaacagt gtcatcagcg gccgcatacc cgtacgacgt tccggactac    840
ggttcccacc accatcacca tcactag                                        867

SEQ ID NO: 98             moltype = AA   length = 288
FEATURE                   Location/Qualifiers
source                    1..288
                          mol_type = protein
                          note = SYNTHESIZED
                          organism = synthetic construct
SEQUENCE: 98
MAQVQLQESG GGLVQAGDSL RLSCAASEQS FNSEIMGWFR QAPGKEREFV AAITYSGSIT     60
KYADSAKGRF TISRDNAKNT VYLQMNSLNP EDTALYYCAL NKGGLYTDYR SWATYDYRGQ   120
GTQVTVSSPT PTTPTPTTPT QVQLQESGGG LVQAGASLRL SCAASRRTGS SLTMGWFRQA   180
PGREREFVAA ISRSGIRTYY ADFVKGRFTI SRDNAKNTLY LQMNSLKPED TAVYYCAAND   240
KTYGSGLDVY TRRQDYYYWG PGTQVTVSSA AAYPYDVPDY GSHHHHHH                288

SEQ ID NO: 99             moltype = DNA   length = 867
FEATURE                   Location/Qualifiers
source                    1..867
```

```
                        mol_type = other DNA
                        note = SYNTHESIZED
                        organism = synthetic construct
SEQUENCE: 99
atggcccagg tgcagctgca ggagtctggg ggaggattgg tgcaggctgg ggactctctg    60
agactctcct gtgcagcctc tgaacaatcc ttcaatagcg aaattatggg ctggttccgc   120
caggctccag ggaaggagcg tgagtttgta gcagctatta cctatagtgg tagtatcaca   180
aaatatgcag actccgcgaa gggccgattc accatctcca gagacaacgc caagaacacg   240
gtgtatctgc aaatgaacag tttgaaccct gaggacacgg ccctttatta ctgtgccctt   300
aacaaagggg gactgtatac tgactaccga tcttgggcga cgtatgacta ccgcggccag   360
gggacccagg tcaccgtctc ctcaccgacg ccgacaaccc ctacaccgac tactccgact   420
caagttcaat acaggaatc aggcggaggc ttggtacagg ctggtgcatc gttacgtctt   480
tcttgcgcag cttcccgtcg cacgggctct tctttaacga tgggctggtt tcgtcaggcg   540
ccgggcaaag agcgtgaatt cgtggcggcc atctcgcgta gcggaattcg tacttattat   600
gccgactttg tcaaaggccg cttcactatt agtcgtgata atgcaaagaa cacccttta   660
ctgcaaatga atagcttgaa gccggaagac actgccgttt actactgcgc ggcaaacgac   720
aagacatatg ggtctggcct tgacgtttat acccgtcgtc aaaattatta ttattggggg   780
cctggtactc aagttaccgt gtcgtcagcg gccgcatacc cgtacgacgt tccggactac   840
ggttcccacc accatcacca tcactag                                        867

SEQ ID NO: 100         moltype = AA  length = 288
FEATURE                Location/Qualifiers
source                 1..288
                       mol_type = protein
                       note = SYNTHESIZED
                       organism = synthetic construct
SEQUENCE: 100
MAQVQLQESG GGLVQAGDSL RLSCAASEQS FNSEIMGWFR QAPGKEREFV AAITYSGSIT    60
KYADSAKGRF TISRDNAKNT VYLQMNSLNP EDTALYYCAL NKGGLYTDYR SWATYDYRGQ   120
GTQVTVSSPT PTTPTPTTPT QVQLQESGGG LVQAGASLRL SCAASRRTGS SLTMGWFRQA   180
PGKEREFVAA ISRSGIRTYY ADFVKGRFTI SRDNAKNTLY LQMNSLKPED TAVYYCAAND   240
KTYGSGLDVY TRRQNYYYWG PGTQVTVSSA AAYPYDVPDY GSHHHHHH                288

SEQ ID NO: 101         moltype = DNA  length = 855
FEATURE                Location/Qualifiers
source                 1..855
                       mol_type = other DNA
                       note = SYNTHESIZED
                       organism = synthetic construct
SEQUENCE: 101
atggcccagg tgcagctgca ggagtctggg ggaggattgg tgcaggctgg ggactctctg    60
agactctcct gtgcagcctc tgaacaatcc ttcaatagcg aaattatggg ctggttccgc   120
caggctccag ggaaggagcg tgagtttgta gcagctatta cctatagtgg tagtatcaca   180
aaatatgcag actccgcgaa gggccgattc accatctcca gagacaacgc caagaacacg   240
gtgtatctgc aaatgaacag tttgaaccct gaggacacgg ccctttatta ctgtgccctt   300
aacaaagggg gactgtatac tgactaccga tcttgggcga cgtatgacta ccgcggccag   360
gggacccagg tcaccgtctc ctcaccgacc ccacaaccgac caacgccgac tactccgaca   420
caagtacaat acaagaatc aggaggaggt tagttcaag ctggcgcttc tttacgttta   480
agttgtgcgg cctcccgtcg taccggctcc tcattgacaa tggggtggtt tcgtcaggct   540
cctgggaagg agcgtgaatt tgtcgccgca attagccgtt ctggcattcg tacctactac   600
gcagattttg tcaaggggcg tttcaccatt tcacgcgata acggggagaa tacgctttac   660
ttgcagatca attctctgaa gcctgaagat accgcggtgt actattgcgc cgcctcttct   720
aatccgggtt attatcgcac agcaccaac caatataact tctggggtcc tgggacacaa   780
gtgacggttt cttctgcggc cgcataccccg tacgacgttc cggactacgg ttcccaccac   840
catcaccatc actag                                                    855

SEQ ID NO: 102         moltype = AA  length = 284
FEATURE                Location/Qualifiers
source                 1..284
                       mol_type = protein
                       note = SYNTHESIZED
                       organism = synthetic construct
SEQUENCE: 102
MAQVQLQESG GGLVQAGDSL RLSCAASEQS FNSEIMGWFR QAPGKEREFV AAITYSGSIT    60
KYADSAKGRF TISRDNAKNT VYLQMNSLNP EDTALYYCAL NKGGLYTDYR SWATYDYRGQ   120
GTQVTVSSPT PTTPTPTTPT QVQLQESGGG LVQAGASLRL SCAASRRTGS SLTMGWFRQA   180
PGKEREFVAA ISRSGIRTYY ADFVKGRFTI SRDNGENTLY LQINSLKPED TAVYYCAASS   240
NPGYYRTAPN QYNFWGPGTQ VTVSSAAAYP YDVPDYGSHH HHHH                    284

SEQ ID NO: 103         moltype = DNA  length = 855
FEATURE                Location/Qualifiers
source                 1..855
                       mol_type = other DNA
                       note = SYNTHESIZED
                       organism = synthetic construct
SEQUENCE: 103
atggcccagg tgcagctgca ggagtctggg ggaggattgg tgcaggctgg ggactctctg    60
agactctcct gtgcagcctc tgaacaatcc ttcaatagcg aaattatggg ctggttccgc   120
caggctccag ggaaggagcg tgagtttgta gcagctatta cctatagtgg tagtatcaca   180
```

```
aaatatgcag actccgcgaa gggccgattc accatctcca gagacaacgc caagaacacg    240
gtgtatctgc aaatgaacag tttgaaccct gaggacacgg cccttttatta ctgtgccctt   300
aacaaagggg gactgtatac tgactaccga tcttgggcga cgtatgacta ccgcggccag   360
gggacccagg tcaccgtctc ctcaggtggc ggcggaggtg gaggtggtca ggtgcagctt   420
caagaatcag gggggggatt ggcacaagcc ggggctagct tacgcctgtc ctgcgcggcg   480
agccgccgta caggctcaag tcttacgatg ggctggtttc gtcaggcacc tgggaaagag   540
cgtgagtttg ttgccgccat ctcgcgctcg ggtatccgta cctactatgc agatttcgtt   600
aaaggacgct tcacgatttc tcgcgataat gctaaaaaca cgctgtatct gcagatgaat   660
tccttaaagc cggaagatac agcggtgtac tactgtgcgg caaatgataa gacctatggt   720
tctggtctgg atgtttatac acgtcgtcaa gattattact actgggggcc cggcacgcag   780
gttactgtgt cgtcagcggc cgcataccccg tacgacgttc cggactacgg ttcccaccac   840
catcaccatc actag                                                    855

SEQ ID NO: 104            moltype = AA   length = 284
FEATURE                   Location/Qualifiers
source                    1..284
                          mol_type = protein
                          note = SYNTHESIZED
                          organism = synthetic construct
SEQUENCE: 104
MAQVQLQESG GGLVQAGDSL RLSCAASEQS FNSEIMGWFR QAPGKEREFV AAITYSGSIT    60
KYADSAKGRF TISRDNAKNT VYLQMNSLNP EDTALYYCAL NKGGLYTDYR SWATYDYRGQ   120
GTQVTVSSGG GGGGGGQVQL QESGGGLAQA GASLRLSCAA SRRTGSSLTM GWFRQAPGKE   180
REFVAAISRS GIRTYYADFV KGRFTISRDN AKNTLYLQMN SLKPEDTAVY YCAANDKTYG   240
SGLDVYTRRQ DYYWGPGTQ VTVSSAAAYP YDVPDYGSHH HHHH                     284

SEQ ID NO: 105            moltype = DNA   length = 816
FEATURE                   Location/Qualifiers
source                    1..816
                          mol_type = other DNA
                          note = SYNTHESIZED
                          organism = synthetic construct
SEQUENCE: 105
atggcccagg tgcagctgca ggagtctggg ggaggattgg tgcaggctgg ggactctctg    60
agactctcct gtgcagcctc tgaacaatcc ttcaatagcg aaattatggg ctggttccgc   120
caggctccag ggaaggagcg tgagtttgta gcagctatta cctatagtgg tagtatcaca   180
aaatatgcag actccgcgaa gggccgattc accatctcca gagacaacgc caagaacacg   240
gtgtatctgc aaatgaacag tttgaaccct gaggacacgg cccttttatta ctgtgccctt   300
aacaaagggg gactgtatac tgactaccga tcttgggcga cgtatgacta ccgcggccag   360
gggacccagg tcaccgtctc ctcaggtggt ggcggcggag gaggcggaca ggtgcagctt   420
caagagtcag gaggcggttc tgtacaagcc gggggatctc tgaaattaag ttgcgcagcc   480
tctgggacag agtcgatttt tattgttatg ggctggtatc gtcaggcacc tggcaaggaa   540
cgtgagctgg tcgccgccat gagttttggg ggcgggacga atgtgactga cggagttcgt   600
ggtcgcttta ccatttcccg tgatttttgac aagaacacgg tcgacctgca aatgaacaat   660
cttaaaaccg aggacaccgc agtttactat tgtaatgctg tgcaatgggg cccgcgcgac   720
tactggggac agggcactca ggtcacagta tcctcagcgg ccgcataccc gtacgacgtt   780
ccggactacg gttcccacca ccatcaccat cactag                            816

SEQ ID NO: 106            moltype = AA   length = 271
FEATURE                   Location/Qualifiers
source                    1..271
                          mol_type = protein
                          note = SYNTHESIZED
                          organism = synthetic construct
SEQUENCE: 106
MAQVQLQESG GGLVQAGDSL RLSCAASEQS FNSEIMGWFR QAPGKEREFV AAITYSGSIT    60
KYADSAKGRF TISRDNAKNT VYLQMNSLNP EDTALYYCAL NKGGLYTDYR SWATYDYRGQ   120
GTQVTVSSGG GGGGGQVQL QESGGGSVQA GGSLKLSCAA SGTESIFIVM GWYRQAPGKE   180
RELVAAMSFG GTNVTDGVR GRFTISRDFD KNTVDLQMNN LKTEDTAVYY CNAVQWGPRD   240
YWGQGTQVTV SSAAAYPYDV PDYGSHHHHH H                                 271

SEQ ID NO: 107            moltype = DNA   length = 843
FEATURE                   Location/Qualifiers
source                    1..843
                          mol_type = other DNA
                          note = SYNTHESIZED
                          organism = synthetic construct
SEQUENCE: 107
atggcccagg tgcagctgca ggagtctggg ggaggctcgg tgcagcctgg ggggtctcta    60
aaactctcct gtgcagcctc tggattcacc ttcagtaact atgccatgag ctgggtccgc   120
caggctccag aaaggggct cgagtgggtc tcagtattat atgctggtgg tgatacgaca   180
aactatgcag actccgtgaa ggaccgattc accatctcca gagacaacgc caagaacacg   240
ctgtatctcc aaatgaacag cctgaaacct gaggacacgg ccatatatta ctgtctaaag   300
cttgagacca gtgtggttcc tagtagtagt tactaccgca atcgcggttc cagggggcag   360
ggaacccagg tcaccgtctc ctcaccgacg cctactaccc cgactccgac cactcctact   420
caggtcagc ttcaggagtc aggtggaggt cttgttcagg ctggtggatc tcttcgcttg   480
tcttgcgctc cgtcgggtcg tacattctcg cgctacgcga tgggctggtt ccgtcaggct   540
ttgggtaaag agcgcgagtt tgtggcaggg attaactggt ccgggtctat gacgtactac   600
gcagattctg ttaaaggtcg cttcactatt tctcgtgata acgcgaaaaa catgttgtat   660
```

```
ctgcaaatga attctcttaa atcggaggat accgcagttt actattgcgc aggagtcacc   720
gtcgtcggag gtgcgccagc ttttgactat tggggtcaag gcactcaagt aaccgtctca   780
tcagcggccg catacccgta cgacgttccg gactacggtt cccaccacca tcaccatcac   840
tag                                                                  843

SEQ ID NO: 108          moltype = AA  length = 280
FEATURE                 Location/Qualifiers
source                  1..280
                        mol_type = protein
                        note = SYNTHESIZED
                        organism = synthetic construct
SEQUENCE: 108
MAQVQLQESG GGSVQPGGSL KLSCAASGFT FSNYAMSWVR QAPGKGLEWV SGINAGGDTT    60
NYADSVKDRF TISRDNAKNT LYLQMNSLKP EDTAIYYCLK LETSVVPSSS YYRNRGSRGQ   120
GTQVTVSSPT PTTPTPTTPT QVQLQESGGG LVQAGGSLRL SCAASGRTFS RYAMGWFRQA   180
LGKEREFVAG INWSGSMTYY ADSVKGRFTI SRDNAKNMLY LQMNSLKSED TAVYYCAGVT   240
VVGGAPAFDY WGQGTQVTVS SAAAYPYDVP DYGSHHHHHH                         280

SEQ ID NO: 109          moltype = DNA  length = 831
FEATURE                 Location/Qualifiers
source                  1..831
                        mol_type = other DNA
                        note = SYNTHESIZED
                        organism = synthetic construct
SEQUENCE: 109
atggcccagg tgcagctgca ggagtctggg ggaggctcgg tgcagcctgg ggggtctcta    60
aaactctcct gtgcagcctc tggattcacc ttcagtaact atgccatgag ctgggtccgc   120
caggctccag aaaggggct cgagtgggtc tcaggtatta tgctggtgg tgatacgaca    180
aactatgcag actccgtgaa ggaccgattc accatctcca gagacaacgc caagaacacg   240
ctgtatctcc aaatgaacag cctgaaacct gaggacacgg ccatatatta ctgtctaaag   300
cttgagacca gtgtggttcc tagtagtagt tactaccgca atcgcggttc caggggccag   360
ggaacccagg tcaccgtctc ctcaccgacc caaccactc cgacgccac aacgccact     420
caggtacaat acaggaatc aggggtggt gtagttcaaa cggggggctc attgactctt   480
tcttgcaaag cgtctcgccg tacctccggt tttgcgatgg cctggttccg ccaagcacca   540
gggatggaac gtgaatttgt tgccgatatt ggtcgcactg gtgataacat ccactacctt   600
gactcggtga agggtcgttt caccatttcc cgcgacaaca ccaaaatac cttatccttg   660
caaatgaatt ctcttcgtcc aggtgatacc gccgtttatt actgtgctgc tgatgtcact   720
aagtcgggct catctactg gggtcagggc acacaggtca ccgtttcatc agcggccgca   780
tacccgtacg acgttccgga ctacggttcc caccaccatc accatcacta g            831

SEQ ID NO: 110          moltype = AA  length = 276
FEATURE                 Location/Qualifiers
source                  1..276
                        mol_type = protein
                        note = SYNTHESIZED
                        organism = synthetic construct
SEQUENCE: 110
MAQVQLQESG GGSVQPGGSL KLSCAASGFT FSNYAMSWVR QAPGKGLEWV SGINAGGDTT    60
NYADSVKDRF TISRDNAKNT LYLQMNSLKP EDTAIYYCLK LETSVVPSSS YYRNRGSRGQ   120
GTQVTVSSPT PTTPTPTTPT QVQLQESGGG VVQTGGSLTL SCKASRRTSG FAMAWFRQAP   180
GMEREFVAGI GRTGDNIHYL DSVKGRFTIS RDNTKNTLSL QMNSLRPGDT AVYYCAADVT   240
KSGFIYWGQG TQVTVSSAAA YPYDVPDYGS HHHHHH                             276

SEQ ID NO: 111          moltype = DNA  length = 837
FEATURE                 Location/Qualifiers
source                  1..837
                        mol_type = other DNA
                        note = SYNTHESIZED
                        organism = synthetic construct
SEQUENCE: 111
atggccagg tgcagctgca ggagtctggg ggaggctcgg tgcagcctgg ggggtctcta     60
aaactctcct gtgcagcctc tggattcacc ttcagtaact atgccatgag ctgggtccgc   120
caggctccag aaaggggct cgagtgggtc tcaggtatta tgctggtgg tgatacgaca    180
aactatgcag actccgtgaa ggaccgattc accatctcca gagacaacgc caagaacacg   240
ctgtatctcc aaatgaacag cctgaaacct gaggacacgg ccatatatta ctgtctaaag   300
cttgagacca gtgtggttcc tagtagtagt tactaccgca atcgcggttc caggggccag   360
ggaacccagg tcaccgtctc ctcaccgaca cccacgactc ccactccac cactcctacc   420
caagtgcagt tacaggaatc aggtggtgga ctggtccaag caggcgggtc ccttacgctt   480
tcatgtcgt tcagcggacg tacgtttaca cactatgcta tggcgtggtt ccgccaagca   540
cctgggaaag aacgtaaatt cgtagcaggg gtaacccgct caggaccgaa tacttattat   600
gatgactccg tccaagggcg tttcactatc agccgtgata tgcaaagaa tactgtgtac   660
cttcacatga attccttgaa gcctgaagac acggcggtat attattgcgc tgccaattcc   720
ggtgtggttt ctgatatgat tactggggg caaggcacg aagtcacggt gtcgtcagcg    780
gccgcatacc cgtacgacgt tccggactac ggttcccacc accatcacca tcactag      837

SEQ ID NO: 112          moltype = AA  length = 278
FEATURE                 Location/Qualifiers
source                  1..278
                        mol_type = protein
```

-continued

```
                        note = SYNTHESIZED
                        organism = synthetic construct
SEQUENCE: 112
MAQVQLQESG GGSVQPGGSL KLSCAASGFT FSNYAMSWVR QAPGKGLEWV SGINAGGDTT    60
NYADSVKDRF TISRDNAKNT LYLQMNSLKP EDTAIYYCLK LETSVVPSSS YYRNRGSRGQ   120
GTQVTVSSPT PTTPTPTTPT QVQLQESGGG LVQAGGSLTL SCAFSGRTFT HYAMAWFRQA   180
PGKERKFVAG VTRSGPNTYY DDSVQGRFTI SRDNAKNTVY LHMNSLKPED TAVYYCAANS   240
GVVSGYDYWG QGTQVTVSSA AAYPYDVPDY GSHHHHHH                           278

SEQ ID NO: 113          moltype = DNA  length = 846
FEATURE                 Location/Qualifiers
source                  1..846
                        mol_type = other DNA
                        note = SYNTHESIZED
                        organism = synthetic construct
SEQUENCE: 113
atggcccagg tgcagctgca ggagtctggg ggaggattgg tgcaggctgg ggactctctg    60
agactctcct gtgcagcctc tgaacaatcc ttcaatagcg aaattatgcc ctggttccgc   120
caggctccag ggaaggagcg tgagtttgta gcagctatta cctatagtgg tagtatcaca   180
aaatatgcag actccgcgaa gggccgattc accatctcca gagacaacgc caagaacacg   240
gtgtatctgc aaatgaacag tttgaaccct gaggacacgg ccctttatta ctgtgccctt   300
aacaaagggg gactgtatac tgactaccga tcttgggcga cgtatgacta ccgcggccag   360
gggacccagg tcaccgtctc ctcaggtggg ggaggaggtg gtggtggtca ggtacagttg   420
caggagagtg gaggcggtct tgtgcaacct ggcgggtcgt tgcgcttagc ttgtgtattg   480
tcgggcggtc cctcgtcgtc ctatggggta gggtggtttc gtcagcgcag tggcacagaa   540
cgcgaattcg tggctgctat ctctgggtcc ggtcgcacaa tccattatgt tgacgatgta   600
aaaggacgct tcgcaatttc acgcgatagc gctaagaatg cagtggactt gcagatgaac   660
aatctgaaac cggaggatac agcagtttat tactgtgctg ctcttgcact ggtaacgacg   720
catccgacgt ctaacgtcgg agaatgggac tactggggtc aaggcaccca ggttaccgtg   780
agttcagcgg ccgcataccc gtacgacgtt ccggactacg gttcccacca ccatcaccat   840
cactag                                                              846

SEQ ID NO: 114          moltype = AA  length = 281
FEATURE                 Location/Qualifiers
source                  1..281
                        mol_type = protein
                        note = SYNTHESIZED
                        organism = synthetic construct
SEQUENCE: 114
MAQVQLQESG GGLVQAGDSL RLSCAASEQS FNSEIMGWFR QAPGKEREFV AAITYSGSIT    60
KYADSAKGRF TISRDNAKNT VYLQMNSLNP EDTALYYCAL NKGGLYTDYR SWATYDYRGQ   120
GTQVTVSSGG GGGGGGQVQL QESGGGLVQP GGSLRLACVL SGGPSSSYGV GWFRQRSGTE   180
REFVAAISGS GRTIHYVDDV KGRFAISRDS AKNAVDLQMN NLKPEDTAVY YCAALALVTT   240
HPTSNVGEWD YWGQGTQVTV SSAAAYPYDV PDYGSHHHHH H                       281

SEQ ID NO: 115          moltype = DNA  length = 828
FEATURE                 Location/Qualifiers
source                  1..828
                        mol_type = other DNA
                        note = SYNTHESIZED
                        organism = synthetic construct
SEQUENCE: 115
atggcccagg tgcagctgca ggagtctggg ggaggattgg tgcaggctgg ggactctctg    60
agactctcct gtgcagcctc tgaacaatcc ttcaatagcg aaattatggg ctggttccgc   120
caggctccag ggaaggagcg tgagtttgta gcagctatta cctatagtgg tagtatcaca   180
aaatatgcag actccgcgaa gggccgattc accatctcca gagacaacgc caagaacacg   240
gtgtatctgc aaatgaacag tttgaaccct gaggacacgg ccctttatta ctgtgccctt   300
aacaaagggg gactgtatac tgactaccga tcttgggcga cgtatgacta ccgcggccag   360
gggacccagg tcaccgtctc ctcaggtggc ggaggtggag gcgaggtcag agttcaactt   420
caggaatccg gtggggtgt agtacaaacg ggagggtctc ttacgctgtc ctgcaaggca   480
tctcgccgca cctcagggtt cgctatggcc tggtttcgtc aagcgccagg atggaacgc    540
gagttcgttg ctggaatcgg acgtactggt gacaacatcc attatcttga cagtgtgaaa   600
ggacgcttca ccatcagccg cgataataca aaaaacacct taagccttca aatgaattct   660
ctgaagagcg aggacaccgc agtttattat tgtgccaagt tggttgttgt agcggggtca   720
cctagtttcg acgcgtgggg ccagggcacg caggttaccg tgtcctcagc ggccgcatac   780
ccgtacgacg ttccggacta cggttcccac caccatcacc atcactag                828

SEQ ID NO: 116          moltype = AA  length = 275
FEATURE                 Location/Qualifiers
source                  1..275
                        mol_type = protein
                        note = SYNTHESIZED
                        organism = synthetic construct
SEQUENCE: 116
MAQVQLQESG GGLVQAGDSL RLSCAASEQS FNSEIMGWFR QAPGKEREFV AAITYSGSIT    60
KYADSAKGRF TISRDNAKNT VYLQMNSLNP EDTALYYCAL NKGGLYTDYR SWATYDYRGQ   120
GTQVTVSSGG GGGGGGQVQL QESGGGVVQT GGSLTLSCKA SRRTSGFAMA WFRQAPGMER   180
EFVAGIGRTG DNIHYLDSVK GRFTISRDNT KNTLSLQMNS LKSEDTAVYY CAKVVVVAGS   240
PSFDAWGQGT QVTVSSAAAY PYDVPDYGSH HHHH                               275
```

```
SEQ ID NO: 117              moltype = DNA  length = 453
FEATURE                     Location/Qualifiers
source                      1..453
                            mol_type = other DNA
                            note = SYNTHESIZED
                            organism = synthetic construct
SEQUENCE: 117
atggcccagg tgcagctgca ggagtctggg ggaggattgg tgcaggctgg ggcctctctg    60
agactctcct gtgcagcctc tagacgcacc ggcagtagtc ttaccatggg ctggttccgc   120
caggctccag ggaaggagcg tgagtttgta gcagctatta gcggagtgg tattagaaca    180
tactacgcag actttgtgaa gggccggttc accatctcca gagacaacgc caagaacacg   240
ctctatctgc aaatgaacag cctgaaacct ggggacacgg ccgtgtatta ctgtgcggct   300
aacgacaaaa catacggtag tggtcttgac gtctcacaga gccacaaga ctattactac    360
tggggcccgg ggacccaggt caccgtctcc tcagcggccg cataccgta cgacgttccg    420
gactacggtt cccaccacca tcaccatcac tag                                453

SEQ ID NO: 118              moltype = AA  length = 150
FEATURE                     Location/Qualifiers
source                      1..150
                            mol_type = protein
                            note = SYNTHESIZED
                            organism = synthetic construct
SEQUENCE: 118
MAQVQLQESG GGLVQAGASL RLSCAASRRT GSSLTMGWFR QAPGKEREFV AAISRSGIRT    60
YYADFVKGRF TISRDNAKNT LYLQMNSLKP GDTAVYYCAA NDKTYGSGLD VYTRRQDYYY   120
WGPGTQVTVS SAAAYPYDVP DYGSHHHHHH                                    150

SEQ ID NO: 119              moltype = DNA  length = 414
FEATURE                     Location/Qualifiers
source                      1..414
                            mol_type = other DNA
                            note = SYNTHESIZED
                            organism = synthetic construct
SEQUENCE: 119
atggcccagg tgcagctgca ggagtctggg ggaggctcgg tgcaggctgg ggggtctctg    60
aaaactctcct gtgcagcctc tggaaccgaa agcattttca tcgtgatggg ctggtaccgc  120
caggctccag ggaagagcg cgagttggtc gcggcaatga catttggtgg tggtacaaat   180
gtgacagacg gcgtgagggg ccgattcacc atctccagag accttgacaa gaacacggtg   240
gatctgcaaa tgaacaacct aaaaactgag gacacggccg tctattactg taatgcagtc   300
cgttggggcc ctcgtgacta ctggggccag gggacccagg tcaccgtctc ctcagcggcc   360
gcataccgt acgacgttcc ggactacggt tccaccacc atcaccatca ctag           414

SEQ ID NO: 120              moltype = AA  length = 137
FEATURE                     Location/Qualifiers
source                      1..137
                            mol_type = protein
                            note = SYNTHESIZED
                            organism = synthetic construct
SEQUENCE: 120
MAQVQLQESG GSVQAGGSL KLSCAASGTE SIFIVMGWYR QAPGKERELV AAMTFGGGTN     60
VTDGVRGRFT ISRDLDKNTV DLQMNNLKTE DTAVYYCNAV RWGPRDYWGQ GTQVTVSSAA   120
AYPYDVPDYG SHHHHHH                                                  137

SEQ ID NO: 121              moltype = DNA  length = 450
FEATURE                     Location/Qualifiers
source                      1..450
                            mol_type = other DNA
                            note = SYNTHESIZED
                            organism = synthetic construct
SEQUENCE: 121
atggcccagg tgcagctgca ggagtctggg ggaggattgg tgcaggctgg gggctctctg    60
agactctcct gtgcagcctc tggacgcact ttcagtagcg cgcccatggc ctggttccgc   120
caggctccag ggaaggagcg tgaatttgtc gccgctatta gcagtaatga tggtagtaca   180
aggtatggag actccgtgaa gggccgattc accatctcca gagacaacgc caagaacgcg   240
ctgtggctgc aaatgaacag cctgaaacct gaggacacgg ccgtgtatta ctgtgcggcc   300
cggcgaacat acggagtgg tagttacacg cccggcgcaa catattacta tgactcatgg    360
ggcccgggga cccaggtcac cgtctcctca gcggccgcat acccgtacga cgttccggac   420
tacggttccc accaccatca ccatcactag                                    450

SEQ ID NO: 122              moltype = AA  length = 149
FEATURE                     Location/Qualifiers
source                      1..149
                            mol_type = protein
                            note = SYNTHESIZED
                            organism = synthetic construct
SEQUENCE: 122
MAQVQLQESG GGLVQAGGSL RLSCAASGRT FSSAPMAWFR QVPGKEREFV AAISSNDGST    60
RYGDSVKGRF TISRDNAKNA LWLQMNSLKP EDTAVYYCAA RRTLRSGSYT PGATYYYDSW   120
```

```
GPGTQVTVSS AAAYPYDVPD YGSHHHHHH                                              149

SEQ ID NO: 123          moltype = DNA   length = 432
FEATURE                 Location/Qualifiers
source                  1..432
                        mol_type = other DNA
                        note = SYNTHESIZED
                        organism = synthetic construct
SEQUENCE: 123
atggcccagg tgcagctgca ggagtctgga ggaggcttgg tgcaggctgg ggggtctctg   60
agactctcct gtgtagcctc tggaagcatc ttcagtggcg atgccatggg ctggtaccgc  120
caggctccag ggaagcagcg cgagttggtc gcaactatta ctcgtggtgg gattacaaac  180
tatgccgact ccgcgaaggg ccgattcacc atctccagag acaatgccaa gaacacggtg  240
tctctgcaaa tgaacagcct gaaacctgag gacacgtcg tctattactg tcatgcagaa   300
gacccgggtt ggggtgtcta ccggggggcgt cgtggctact ggggccaggg gacccaggtc  360
accgtctcct cagcggccgc atacccgtac gacgttccgg actacggttc ccaccaccat  420
caccatcact ag                                                        432

SEQ ID NO: 124          moltype = AA    length = 141
FEATURE                 Location/Qualifiers
source                  1..141
                        mol_type = protein
                        note = SYNTHESIZED
                        organism = synthetic construct
SEQUENCE: 124
QVQLQESGGG LVQAGGSLRL SCVASGSIFS GDAMGWYRQA PGKQRELVAT ITRGGITNYA    60
DSAKGRFTIS RDNAKNTVSL QMNSLKPEDT AVYYCHAEDP GWGVYRGRRG YWGQGTQVTV   120
SSAAAYPYDV PDYGSHHHHH H                                              141

SEQ ID NO: 125          moltype = DNA   length = 453
FEATURE                 Location/Qualifiers
source                  1..453
                        mol_type = other DNA
                        note = SYNTHESIZED
                        organism = synthetic construct
SEQUENCE: 125
atggcccagg tgcagctgca ggagtctgga ggaggattgg tgcaggctgg ggcctctctg    60
agactctcct gtgcagcctc tagacgcacc ggcagtagtc ttaccatggg ctggttccgc   120
caggctccag ggaaggagcg tgagtttgta gcagctattg gccggagtgg tattagaaca   180
tactacgcag gctttgtgaa gggccggttc accatctcca gagacaacgc caagaacacg   240
ctctatctgc aaatgaacag cctgaaacct gaggacacgg ccgtgtatta ctgtgcggct   300
aacgacaaaa catacggtag tggtcttgac gtctacacaa ggcgacaaga ctattactac   360
tggggcccgg gaacccaggt caccgtctcc tcagcggccg catacccgta cgacgttccg   420
gactacggtt cccaccacca tcaccatcac tag                                 453

SEQ ID NO: 126          moltype = AA    length = 150
FEATURE                 Location/Qualifiers
source                  1..150
                        mol_type = protein
                        note = SYNTHESIZED
                        organism = synthetic construct
SEQUENCE: 126
MAQVQLQESG GGLVQAGASL RLSCAASRRT GSSLTMGWFR QAPGKEREFV AAISRSGIRT    60
YYAGFVKGRF TISRDNAKNT LYLQMNSLKP EDTAVYYCAA NDKTYGSGLD VYTRRQDYYY  120
WGPGTQVTVS SAAAYPYDVP DYGSHHHHHH                                    150

SEQ ID NO: 127          moltype = DNA   length = 414
FEATURE                 Location/Qualifiers
source                  1..414
                        mol_type = other DNA
                        note = SYNTHESIZED
                        organism = synthetic construct
SEQUENCE: 127
atggcccagg tgcagctgca ggagtctggg ggaggctcgg tgcaggctgg ggggtctctg    60
aaactctcct gtgcagcctc tggaaccgaa agcatttca tcgtgatggg ctggtaccgc   120
caggctccag ggaaagagcg cgaattggtc gcggcaatgt catttggtgg tggagcaaat  180
gttacagacg cgtgaggggg ccgattcacc atctccagag accttgacaa gaacacgta   240
gatctgcaaa tgaacaacct aaaacctgag gacacggccg tctattactg taatgcagtc  300
cggtggggcc ctcgtgacta ctgggtcag gggacccagg tcaccgtctc ctcagcggcc   360
gcatacccgt acgacgttcc ggactacggt tccaccacc atcaccatca ctag          414

SEQ ID NO: 128          moltype = AA    length = 137
FEATURE                 Location/Qualifiers
source                  1..137
                        mol_type = protein
                        note = SYNTHESIZED
                        organism = synthetic construct
SEQUENCE: 128
MAQVQLQESG GGSVQAGGSL KLSCAASGTE SIFIVMGWYR QAPGKERELV AAMSFGGGAN    60
```

```
VTDGVRGRFT ISRDLDKNTV DLQMNNLKPE DTAVYYCNAV RWGPRDYWGQ GTQVTVSSAA    120
AYPYDVPDYG SHHHHHH                                                  137

SEQ ID NO: 129          moltype = DNA  length = 411
FEATURE                 Location/Qualifiers
source                  1..411
                        mol_type = other DNA
                        note = SYNTHESIZED
                        organism = synthetic construct
SEQUENCE: 129
atggcccaag ttcaactgca ggagtccggc gggggtgtag tgcagactgg aggcagcttg    60
acgctttcct gtaaggcttc acgtcgcacg tctggatttg cgatggcctg gttccgtcag    120
gcccctggga tggaacgcga gttcgttgct ggtatcgggc gcacgggtga taacatccac    180
tacttggatt ctgttaaagg gcgtttcgct atttcccgtg acaacacaaa gaatacgtta    240
tatcttcaga tgaataattt gcagccagag gatacagcgg tctattactg ctgcttggct    300
aaagctgctg atccttttg cgatcaaggt actcaggtaa cggtctcctc agcggccgca    360
tacccgtacg acgttccgga ctacggttcc caccaccatc accatcacta g            411

SEQ ID NO: 130          moltype = AA  length = 136
FEATURE                 Location/Qualifiers
source                  1..136
                        mol_type = protein
                        note = SYNTHESIZED
                        organism = synthetic construct
SEQUENCE: 130
MAQVQLQESG GGVVQTGGSL TLSCKASRRT SGFAMAWFRQ APGMEREFVA GIGRTGDNIH    60
YLDSVKGRFA ISRDNTKNTL YLQMNNLQPE DTAVYYCCLA KAADPFCDQG TQVTVSSAAA    120
YPYDVPDYGS HHHHHH                                                   136

SEQ ID NO: 131          moltype = DNA  length = 420
FEATURE                 Location/Qualifiers
source                  1..420
                        mol_type = other DNA
                        note = SYNTHESIZED
                        organism = synthetic construct
SEQUENCE: 131
atggcccaat tgcaagaatc aggtggcggt gttgttcaaa ccggaggatc attaacatta    60
tcgtgcaaag cgtcccgtcg cacatcaggc ttcgcaatgg cgtggtttcg tcaggcacct    120
gggatggagc gcgagtttgt ggctgggatt gggcgcactg tgataatat ccattacctt     180
gattcagtaa aaggacgttt cacgatctca cgtgataata ctaagaacac gcttagttta    240
cagatgaaca acctgaaacc ggaagacact gcagtgtact actgcgcagc gaatccttgg    300
atcaatacgg gaacgggatg gaactactgg ggacaaggga cccaagtgac ggtatctca     360
gcggccgcat acccgtacga cgttccggac tacggttccc accaccatca ccatcactag    420

SEQ ID NO: 132          moltype = AA  length = 139
FEATURE                 Location/Qualifiers
source                  1..139
                        mol_type = protein
                        note = SYNTHESIZED
                        organism = synthetic construct
SEQUENCE: 132
MAQLQESGGG VVQTGGSLTL SCKASRRTSG FAMAWFRQAP GMEREFVAGI GRTGDNIHYL    60
DSVKGRFTIS RDNTKNTLSL QMNNLKPEDT AVYYCAANPW INTGTGWNYW GQGTQVTVSS    120
AAAYPYDVPD YGSHHHHHH                                                139

SEQ ID NO: 133          moltype = DNA  length = 417
FEATURE                 Location/Qualifiers
source                  1..417
                        mol_type = other DNA
                        note = SYNTHESIZED
                        organism = synthetic construct
SEQUENCE: 133
atggcccagg tgcagctgca ggagtctggg ggaggcttgg tgcagcctgg ggggtctctg    60
agactctcct gtgcagcctc tggaagcatc ttcagtatcc ctgccatggg ctggtaccgt    120
caggctccag ggaagcagcg cgagttggtc gcagttatta ctagagatgg tagcacgcac    180
tatgcagact ccgtgaaggg ccgattcacc atctccagag acaacgccaa aaacacgctg    240
tatctgcaaa tgaacagtct gaaatctgag gacacggccg tgtattactg tgccaaactg    300
ggtactagcc gatcgtatga ctactgggc aggggaccc aggtcaccgt ctcctcagcc      360
gccgcatacc cgtacgacgt tccggactac ggttcccacc accatcacca tcactag       417

SEQ ID NO: 134          moltype = AA  length = 138
FEATURE                 Location/Qualifiers
source                  1..138
                        mol_type = protein
                        note = SYNTHESIZED
                        organism = synthetic construct
SEQUENCE: 134
MAQVQLQESG GGLVQPGGSL RLSCAASGSI FSIPAMGWYR QAPGKQRELV AVITRDGSTH    60
YADSVKGRFT ISRDNAKNTL YLQMNSLKSE DTAVYYCAKL GTSRSYDYWG QGTQVTVSSA    120
```

| | | |
|---|---|---|
| AAYPYDVPDY GSHHHHHH | | 138 |
| SEQ ID NO: 135<br>FEATURE<br>source | moltype = AA   length = 13<br>Location/Qualifiers<br>1..13<br>mol_type = protein<br>organism = synthetic construct | |
| SEQUENCE: 135<br>AASGRTFSRY AMG | | 13 |
| SEQ ID NO: 136<br>FEATURE<br>source | moltype = AA   length = 10<br>Location/Qualifiers<br>1..10<br>mol_type = protein<br>organism = synthetic construct | |
| SEQUENCE: 136<br>GINWSGSMTY | | 10 |
| SEQ ID NO: 137<br>FEATURE<br>source | moltype = AA   length = 14<br>Location/Qualifiers<br>1..14<br>mol_type = protein<br>organism = synthetic construct | |
| SEQUENCE: 137<br>AGVTVVGGAP AFDY | | 14 |
| SEQ ID NO: 138<br>FEATURE<br>source | moltype = AA   length = 12<br>Location/Qualifiers<br>1..12<br>mol_type = protein<br>organism = synthetic construct | |
| SEQUENCE: 138<br>KASRRTSGFA MA | | 12 |
| SEQ ID NO: 139<br>FEATURE<br>source | moltype = AA   length = 10<br>Location/Qualifiers<br>1..10<br>mol_type = protein<br>organism = synthetic construct | |
| SEQUENCE: 139<br>GIGRTGDNIH | | 10 |
| SEQ ID NO: 140<br>FEATURE<br>source | moltype = AA   length = 11<br>Location/Qualifiers<br>1..11<br>mol_type = protein<br>organism = synthetic construct | |
| SEQUENCE: 140<br>AADVTKSGFI Y | | 11 |
| SEQ ID NO: 141<br>FEATURE<br>source | moltype = AA   length = 10<br>Location/Qualifiers<br>1..10<br>mol_type = protein<br>organism = synthetic construct | |
| SEQUENCE: 141<br>LRTMGGTWSE | | 10 |
| SEQ ID NO: 142<br>FEATURE<br>source | moltype = AA   length = 13<br>Location/Qualifiers<br>1..13<br>mol_type = protein<br>organism = synthetic construct | |
| SEQUENCE: 142<br>AFSGRTFTHY AMA | | 13 |
| SEQ ID NO: 143<br>FEATURE<br>source | moltype = AA   length = 10<br>Location/Qualifiers<br>1..10<br>mol_type = protein<br>organism = synthetic construct | |
| SEQUENCE: 143<br>GVTRSGPNTY | | 10 |
| SEQ ID NO: 144<br>FEATURE<br>source | moltype = AA   length = 12<br>Location/Qualifiers<br>1..12<br>mol_type = protein<br>organism = synthetic construct | |

```
SEQUENCE: 144
AANSGVVSGY DY                                                      12

SEQ ID NO: 145          moltype = AA  length = 13
FEATURE                 Location/Qualifiers
source                  1..13
                        mol_type = protein
                        organism = synthetic construct
SEQUENCE: 145
AASGRTVNNY PMA                                                     13

SEQ ID NO: 146          moltype = AA  length = 10
FEATURE                 Location/Qualifiers
source                  1..10
                        mol_type = protein
                        organism = synthetic construct
SEQUENCE: 146
GISRNGATTA                                                         10

SEQ ID NO: 147          moltype = AA  length = 9
FEATURE                 Location/Qualifiers
source                  1..9
                        mol_type = protein
                        organism = synthetic construct
SEQUENCE: 147
AADPPTWTY                                                           9

SEQ ID NO: 148          moltype = AA  length = 13
FEATURE                 Location/Qualifiers
source                  1..13
                        mol_type = protein
                        organism = synthetic construct
SEQUENCE: 148
AASGFTFSNY AMS                                                     13

SEQ ID NO: 149          moltype = AA  length = 10
FEATURE                 Location/Qualifiers
source                  1..10
                        mol_type = protein
                        organism = synthetic construct
SEQUENCE: 149
GINAGGDTTN                                                         10

SEQ ID NO: 150          moltype = AA  length = 19
FEATURE                 Location/Qualifiers
source                  1..19
                        mol_type = protein
                        organism = synthetic construct
SEQUENCE: 150
LKLETSVVPS SSYYRNRGS                                               19

SEQ ID NO: 151          moltype = AA  length = 13
FEATURE                 Location/Qualifiers
source                  1..13
                        mol_type = protein
                        organism = synthetic construct
SEQUENCE: 151
AASEQSFNSE IMG                                                     13

SEQ ID NO: 152          moltype = AA  length = 10
FEATURE                 Location/Qualifiers
source                  1..10
                        mol_type = protein
                        organism = synthetic construct
SEQUENCE: 152
AITYSGSITK                                                         10

SEQ ID NO: 153          moltype = AA  length = 19
FEATURE                 Location/Qualifiers
source                  1..19
                        mol_type = protein
                        organism = synthetic construct
SEQUENCE: 153
ALNKGGLYTD YRSWATYDY                                               19

SEQ ID NO: 154          moltype = AA  length = 13
FEATURE                 Location/Qualifiers
source                  1..13
                        mol_type = protein
```

```
                                    -continued organism = synthetic construct
SEQUENCE: 154
AASRRTGSSL TMG                                                              13

SEQ ID NO: 155          moltype = AA   length = 10
FEATURE                 Location/Qualifiers
source                  1..10
                        mol_type = protein
                        organism = synthetic construct
SEQUENCE: 155
AISRSGIRTY                                                                  10

SEQ ID NO: 156          moltype = AA   length = 22
FEATURE                 Location/Qualifiers
source                  1..22
                        mol_type = protein
                        organism = synthetic construct
SEQUENCE: 156
AANDKTYGSG LDVYTRRQNY YY                                                    22

SEQ ID NO: 157          moltype = AA   length = 22
FEATURE                 Location/Qualifiers
source                  1..22
                        mol_type = protein
                        organism = synthetic construct
SEQUENCE: 157
AANDKTYGSG LDVYTRRQDY YY                                                    22

SEQ ID NO: 158          moltype = AA   length = 13
FEATURE                 Location/Qualifiers
source                  1..13
                        mol_type = protein
                        organism = synthetic construct
SEQUENCE: 158
VASGSIFSGD AMG                                                              13

SEQ ID NO: 159          moltype = AA   length = 9
FEATURE                 Location/Qualifiers
source                  1..9
                        mol_type = protein
                        organism = synthetic construct
SEQUENCE: 159
TITRGGITN                                                                    9

SEQ ID NO: 160          moltype = AA   length = 16
FEATURE                 Location/Qualifiers
source                  1..16
                        mol_type = protein
                        organism = synthetic construct
SEQUENCE: 160
HAEDPGWGVY RGRRGY                                                           16

SEQ ID NO: 161          moltype = AA   length = 13
FEATURE                 Location/Qualifiers
source                  1..13
                        mol_type = protein
                        organism = synthetic construct
SEQUENCE: 161
AASGFTFSSA AMS                                                              13

SEQ ID NO: 162          moltype = AA   length = 10
FEATURE                 Location/Qualifiers
source                  1..10
                        mol_type = protein
                        organism = synthetic construct
SEQUENCE: 162
VINSGGDSTS                                                                  10

SEQ ID NO: 163          moltype = AA   length = 5
FEATURE                 Location/Qualifiers
source                  1..5
                        mol_type = protein
                        organism = synthetic construct
SEQUENCE: 163
ARGST                                                                        5

SEQ ID NO: 164          moltype = AA   length = 609
FEATURE                 Location/Qualifiers
source                  1..609
```

```
                        mol_type = protein
                        organism = Spodoptera frugiperda
SEQUENCE: 164
MSLRLTRERQ SGETNNGFDA SPEDGKAAAL NDKSLVNGAT EKSPEKKDEP ERAVWGNQIE    60
FLMSCIATSV GLGNVWRFPF VAYQNGGGAF LIPYIIVLLL IGKPMYYLEC VLGQFSSKNS   120
VTVWSLSPAM KGAGYATALG CGYILSYYVS IVALCLYYLA MSFLPTLPWS VCQEEWGDCL   180
PSDPDLDPVG TITNETKSLP IWYLVVCLFG SWFIIFVIVS RGVKSSGKAA YFLALFPYVV   240
MLILLITTSI LPGAGTGILF FLTPQWDKLI ELDVWYAAVT QVFFSLSVCT GAIIMFSSYN   300
GFRQNVYRDA MIVTTLDTFT SLLSGFTIFG ILGNLAYELD KDVDDVTGSA GTGLAFISYP   360
DAISKTFQPQ LFAVLFFLMM TVLGIGSAVA LLSTINTVMM DAFPRIKTIY MSAFCCTIGF   420
AIGLIYVTPG GQYILELVDY FGGTFLILFC AIAEIIGVFW IYGLENLCLD IEYMLGVKTS   480
FYWRCCWGVI MPAMMITVFI YALATSETLK FGEDYYYPTA GYVAGYMMLF VGVAFVPISI   540
GLTMYKNKTG DCAETAKRSF RPKESWGPRE EFERLNWIEF RREAEAERAQ KRTSWLQHIR   600
YSLFGGYRR                                                           609

SEQ ID NO: 165          moltype = AA   length = 35
FEATURE                 Location/Qualifiers
source                  1..35
                        mol_type = protein
                        organism = Spodoptera frugiperda
SEQUENCE: 165
LPTLPWSVCQ EEWGDCLPSD PDLDPVGTIT NETKS                               35

SEQ ID NO: 166          moltype = AA   length = 601
FEATURE                 Location/Qualifiers
source                  1..601
                        mol_type = protein
                        organism = Spodoptera frugiperda
SEQUENCE: 166
MLANILKIIL NFQPEKKDEP ERAVWGNQIE FLMSCIATSV GLGNVWRFPF VAYQNGGGAF    60
LIPYIIVLLL IGKPMYYLEC VLGQFSSKNS VTVWSLSPAM KGAGYATALG CGYILSYYVS   120
IVALCLYYLA MSFLPTLPWS VCQEEWGNCL PSDPDLDPVG TITNETKSSA ELYFLKTVLQ   180
QKDGIEDGLG LPIWYLVVCL FGSWFIIFVI VSRGVKSSGK AAYFLALFPY VVMLILLITT   240
SILPGAGTGI LFFLTPQWDK LIELDVWYAA VTQVFFSLSV CTGAIIMFSS YNGFRQNVYR   300
DAMIVTTLDT FTSLLSGFTI FGILGNLAYE LDKDVDDVTG SAGTGLAFIS YPDAISKTFQ   360
PQLFAVLFFL MMTVLGIGSA VALLSTINTV MMDAFPRIKT IYMSAFCCTI GPAIGLIYVT   420
PGGQYILELV DYFGGTFLIL FCAIVEIIGV FWIYGLENLC LDIEYMLGVK TSFYWRCCWG   480
VIMPAMMITV FIYALATSET LKFGEDYYYP TAGYVAGYMM LFVGVAFVPI SIGLTMYKNK   540
TGDCAETAKR SFRPKESWGP REEFERLNWI EFRREAEAER AQKRTSWLQH IRYSLFGGYR   600
R                                                                   601

SEQ ID NO: 167          moltype = AA   length = 57
FEATURE                 Location/Qualifiers
source                  1..57
                        mol_type = protein
                        organism = Spodoptera frugiperda
SEQUENCE: 167
LPTLPWSVCQ EEWGNCLPSD PDLDPVGTIT NETKSSAELY FLKTVLQQKD GIEDGLG       57

SEQ ID NO: 168          moltype = AA   length = 622
FEATURE                 Location/Qualifiers
source                  1..622
                        mol_type = protein
                        organism = Spodoptera frugiperda
SEQUENCE: 168
MSGETNNGFD ASPEDGKAAA LNDKSLVNGA SEKSPEKKDE PERAVWGNQI EFLMSCIATS    60
VGLGNVWRFP FVAYQNGGGA FLIPYIIVLL LIGKPMYYLE CVLGQFSSKN SVTVWSLSPA   120
MKGAGYATAL GCGYILSYYV SIVALCLYYL AMSFLPTLPW SVCQEEWGDC LPSDPDLDPV   180
GTITNETKSS AELYFLKTVL QQKDGIEGGL GLPIWYLVVC FGSWFIIFV ISRGVKSSG     240
KAAYFLALFP YVVMLILLIT TSILPGAGTG ILFFLTPQWD KLIELDVWYA AVTQVFFSLS   300
VCTGAIIMFS SYNGFRQNVY RDAMIVTTLD TFTSLLSGFT IFGILGNLAY ELDKDVDDVT   360
GSAGTGLAFI SYPDAISKTF QPQLFAVLFF LMMTVLGIGS AVALLSTINT VMMDAFPRIK   420
TIYMSAFCCT IGFAIGLIYV TPGGQYILEL VDYFGGTFLI LFCAIVEIIG VFWIYGLENL   480
CLDIEYMLGV KTSFYWRCCW GVIMPAMMIT VFIYALATSE TLKFGEDYYY PTAGYVAGYM   540
MLFVGVAFVP ISIGLTMYKN KTGDCAETAK RSFRPKESWG PREEFERLNW IEFRREAEAE   600
RAQKRTSWLQ HIRYSLFGGY RR                                            622

SEQ ID NO: 169          moltype = AA   length = 57
FEATURE                 Location/Qualifiers
source                  1..57
                        mol_type = protein
                        organism = Spodoptera frugiperda
SEQUENCE: 169
LPTLPWSVCQ EEWGDCLPSD PDLDPVGTIT NETKSSAELY FLKTVLQQKD GIEGGLG       57

SEQ ID NO: 170          moltype = AA   length = 638
FEATURE                 Location/Qualifiers
source                  1..638
                        mol_type = protein
```

```
                          organism = Helicoverpa armigera
SEQUENCE: 170
MSGENNEGFD LSSEDPGQGS RVGVGAQPIP PLTEKAPVNG VSGNNEKKID PETAVPERAV    60
WDNQLEFLMS CIATSVGLGN VWRFPPFIAYQ NGGGAFLIPY VIVLLLIGKP MYYLECALGQ  120
FSSRNSVKVW SLSPAMKGTG YATALGCGYI LSYYVSIVAL CLFYLAMSFQ ATLPWGICQP  180
EWDDCVPSDP SQEVGVVTEN ATSSAELYFL KTVLQQKDGI EGGLGLPVWH LVLCLAGAWF  240
VIFVIVARGV KSSGKAAYFL ALFPYVVMIV LLITTVILPG AGDGILFFLT PQWDKLIELD  300
VWYAAVTQVF FSLSVCTGAI IMFSSYNGFR QNVYRDAMIV TTLDTFTSLL SGITIFGILG  360
NLAVELNQEV KDVIGSAGTG LAFISYPDAI SKTFLPQLFS VLFFLMMSVL GVGSAVALLS  420
TINTVMMDAF PRIRTVFMSA FCCTIGFAVG LIYVTPGGQY ILELVDYYGG TFLILFCAIA  480
EIIGVVWIYG LENLCVDIEF MLGIKTGFYW RFCWGLIMPA MMITVFVYAF ASYEALLFGG  540
YYTYPTAGYV SGYMMLIVGI LFVPISISLT MYKNKTGNFI QTIKQAFKAK SSWGPRGPNE  600
YNDWVQFKAE AKQQRVAMRT SWARHIWLSL TGGYRKRL                           638

SEQ ID NO: 171             moltype = AA  length = 56
FEATURE                    Location/Qualifiers
source                     1..56
                           mol_type = protein
                           organism = Helicoverpa armigera
SEQUENCE: 171
QATLPWGICQ PEWDDCVPSD PSQEVGVVTE NATSSAELYF LKTVLQQKDG IEGGLG        56

SEQ ID NO: 172             moltype = AA  length = 531
FEATURE                    Location/Qualifiers
source                     1..531
                           mol_type = protein
                           organism = Heliothis virescens
SEQUENCE: 172
MSCIATSVGL GNVWRFPFVA YQNGGGAFLI PYIIVLLLIG KPMYYLECFL GQFSSRNSIR   60
VWALAPAMKG TGYATALVCG YVVSYYVSIV ALCLFYLSMS FQETLPWGIC QPEWNDCVPS  120
DPNQEVGVVT ENATSSAELY FLNTVLQQKD GLEGGLGLPV WHLVVCLAAS WIVIFMVVAR  180
GVKSSGKAAY FLALFPYVVM IILLISTVIL PGAGDGILFF LTPQWDRLIS LEVWYAAVTQ  240
VFFSLSVCTG AIIMFSSYNG FRQNVYRDSM IVTTLDTFTS LLSGITIFGI LGNLAFELQK  300
EVKDVVGSAG TGLAFISYPD AISKTFLPQL FSVLFFLMMT VLGVGSAVAL LSTINTVMMD  360
APFRIRTIFM SAFCCTMGFA VGLIYVTPGG QYVLELVDYF GGTFLLLFCA IAEIMGVVWI  420
YGLENLCEDI EFMLGFKTGF YWRFCWGIIM PVMMIVVFIY AFASYEALKF GGYYYYPTAG  480
YVSGYMMLIL GMLFVPLSIS LTMYKNRTGN FIQVSYSFNF NIVNNDLCYV I            531

SEQ ID NO: 173             moltype = AA  length = 570
FEATURE                    Location/Qualifiers
source                     1..570
                           mol_type = protein
                           organism = Heliothis virescens
SEQUENCE: 173
MSCIATSVGL GNVWRFPFVA YQNGGGAFLI PYIIVLLLIG KPMYYLECFL GQFSSRNSIR   60
VWALAPAMKG TGYATALVCG YVVSYYVSIV ALCLFYLSMS FQETLPWGIC QPEWNDCVPS  120
DPNQEVGVVT ENATSSAELY FLNTVLQQKD GLEGGLGLPV WHLVVCLAAS WIVIFMVVAR  180
GVKSSGKAAY FLALFPYVVM IILLISTVIL PGAGDGILFF LTPQWDRLIS LEVWYAAVTQ  240
VFFSLSVCTG AIIMFSSYNG FRQNVYRDSM IVTTLDTFTS LLSGITIFGI LGNLAFELQK  300
EVKDVVGSAG TGLAFISYPD AISKTFLPQL FSVLFFLMMT VLGVGSAVAL LSTINTVMMD  360
APFRIRTIFM SAFCCTMGFA VGLIYVTPGG QYVLELVDYF GGTFLLLFCA IAEIMGVVWI  420
YGLENLCEDI EFMLGFKTGF YWRFCWGIIM PVMMIVVFIY AFASYEALKF GGYYYYPTAG  480
YVSGYMMLIL GMLFVPLSIS LTMYKNRTGN FIQTMKQAFK PKSSWGPRAP SDYNDWKQFK  540
AEAKEQRVAK RTSWCNHIWL SLTGGYRKQL                                    570

SEQ ID NO: 174             moltype = AA  length = 56
FEATURE                    Location/Qualifiers
source                     1..56
                           mol_type = protein
                           organism = Heliothis virescens
SEQUENCE: 174
QETLPWGICQ PEWNDCVPSD PNQEVGVVTE NATSSAELYF LNTVLQQKDG LEGGLG        56

SEQ ID NO: 175             moltype = AA  length = 642
FEATURE                    Location/Qualifiers
source                     1..642
                           mol_type = protein
                           organism = Heliothis virescens
SEQUENCE: 175
MSGENNEGFD LSPESQGQQG SPANVNEKVP FNGVSGNNEK KVDPENALPE RAVDPENALP    60
ERAVWDNQLE FLMSCIATSV GLGNVWRFPF VAYQNGGGAF LIPYIIVLLL IGKPLYYLEC  120
FLGQFSSRNS VRVWALAPAM KGAGYASALV CGYVLSYYVS IVALCLFYLS MSFQETLPWG  180
ICQPEWNDCV PSDPNQEGV ITENATSSAE LYFLNTVLQQ NDGLEGGLGL PVWHLVLCLA  240
ASWIVIFVVV ARGVKSSGKA AYFLALFPYV VMIILLITTA TLPGAGDGIL FFFTPQWDKI  300
LSLQVWYDAV TQVFFSLSVG MGAIIMFSSY NGFKQNVYRD SMIVTTLDTF TSLLSGITIF  360
GILGNLAFEL KQEVKDVVGS AGTGLAFISY PDAISKTFLP QLFSVLFFLM LSVLGVGSAV  420
ALLSTINTVM MDAFPRIRTI FMSAFCCTIG FAVGLIYVTP GGQYVLQLVD HFGGTFLLLF  480
CGIAEVMGFV WIYGLENLCE DIEFMLGFKT GFYWRFCWGI ITPIMMIVVF IYAFASFEDL  540
KFGEDYYYPT AGYVSGYMML IVGMLFVPIS ISLTMKNKNT GNFIQTMKQA FKPKSSWGPR  600
```

```
APSDYNDWKQ FKAEAKEQRV AKRTSWCNHI WLSLTGGYRK QL                642

SEQ ID NO: 176          moltype = AA  length = 56
FEATURE                 Location/Qualifiers
source                  1..56
                        mol_type = protein
                        organism = Heliothis virescens
SEQUENCE: 176
QETLPWGICQ PEWNDCVPSD PNQEVGVITE NATSSAELYF LNTVLQQNDG LEGGLG   56

SEQ ID NO: 177          moltype = AA  length = 567
FEATURE                 Location/Qualifiers
source                  1..567
                        mol_type = protein
                        organism = Ostrinia furnacalis
SEQUENCE: 177
MSCIATSVGL GNVWRFPFVA YQNGGGAFLV PYIIVLFLIG KPMYYLECVI GQFSTRNSVK 60
VWALAPAMKG TGYAQALTCG YILSYYVSII ALCLYYFAMS FQPTLPWALC EPEWENCVPS 120
APGHNITITN ESTSSAELFF LKTVLRQREG IEGGLGLPLW DLTLCLLASW VIIFVIVARG 180
VKSSGKAAYF LALFPYVVMI ILLISTSILN GAGNGILFFL TPQWEKILEL DVWYAAVTQL 240
FFSLSVCTGA LVMFSSYNGF RQNVYRDAMI VTTLDTFTSL LSGITIFGIL GNLAYELNQD 300
VADVVGSAGT GLAFVSYPDA IAKTFLPQLY SVLFFLMMSV LGVGSGVALL STINTVLMDS 360
FPRIRTVYMS AICCTAGFAI GLIYVTPGGQ FILELVDYYG GTFLALFSAI VEIIGIFWIY 420
GLENITLDIE FMLGIKTSFY WRCCWGFITP ALMIVVFVYA LISYEALEFG GYYIYPDAGY 480
VAGYLMLLAG IAFVPIFMFI TMYKNRTGNC TETAKKSFRP KKTWGPRDPV LREEWNMFKL 540
NARADRQIQG ASFFRHIWNI MTGGYRR                                   567

SEQ ID NO: 178          moltype = AA  length = 55
FEATURE                 Location/Qualifiers
source                  1..55
                        mol_type = protein
                        organism = Ostrinia furnacalis
SEQUENCE: 178
QPTLPWALCE PEWENCVPSA PGHNITITNE STSSAELFFL KTVLRQREGI EGGLG    55

SEQ ID NO: 179          moltype = AA  length = 350
FEATURE                 Location/Qualifiers
source                  1..350
                        mol_type = protein
                        organism = Ostrinia furnacalis
SEQUENCE: 179
MSGENNNGFT MEDPPPTTSA DSTWIPDSTP PLTTAPSGPA PEYSKMKWST NGHDQPMSPP 60
PIIKVPLEQS ETAKQDADAE KAEPQRAMWD NQIEFLMSCI ATSVGLGNVW RFPPFVAYKNG 120
GGAFLIPYII VLFLVGKPMY YLECIVGQFS SRNSVKVWSL SPAMRGIGYA QALSCSYIVT 180
YYVSIVGLCL YYLAMSFQAE LPWSKCDPEW ANCVPSAPNH DIITTNESRS SAELYFVHTV 240
LQQNKGLEEG LGAPVWYLAL CLFASWVIIF VIVARGVKSS GKAAYFLAIF PYVVMLILLI 300
TTLLLNGAGK GILFFITPQW DKLLKLEVNV KNIKALLSLT ISTVENIFAI          350

SEQ ID NO: 180          moltype = AA  length = 55
FEATURE                 Location/Qualifiers
source                  1..55
                        mol_type = protein
                        organism = Ostrinia furnacalis
SEQUENCE: 180
QAELPWSKCD PEWANCVPSA PNHDIITTNE SRSSAELYFV HTVLQQNKGL EEGLG    55

SEQ ID NO: 181          moltype = AA  length = 642
FEATURE                 Location/Qualifiers
source                  1..642
                        mol_type = protein
                        organism = Plutella xylostella
SEQUENCE: 181
MINKLVESEG QTNLAFEESP EKDLNKSEAP EVVKSTPGFV LEKGDNNNAA REEEEEEPER 60
AMWGNQIEFL MSCIATSVGL GNVWRFPFVA YQNGGGAFLI PYVIVLFIIG KPMYYLECAI 120
GQFSSRNSVK VWSLSPAMKG TGYAQALGCG YILSYYVAII ALCLFYLVKS FSAELPWAVC 180
DPAWGATCVP SGAGGGTPVA GGVSSAELYF TKTVLQQSDG IEGGLGAPIW YLTLCLFASW 240
LIIFVIVARG VKSSGKASYF LALFPYVVML ILLIRSATLT GAGDGILFFL TPQWDKLIQL 300
DVWYAAVTQV FFSLSVGTGA IIMPFSSYNGF RQNIYRDAMI VTTLDTFTSL MSGITIFGIL 360
GNLAYELGYD DVNSVIGSGG TGLAFISYPD AIAKSPFVPQ LFAVLFFLMM SVLGVGSAVA 420
LLSTINTVMM DSFRRVPTVA MSAICCSAGF LIGLVYVTPG GQYILELVDY YGGTFMRLFA 480
AIVETIGVFW IYGLENLCID IEFMLGIKTS WYWRVCWSIV TPAIMITVFM YTLITTESLV 540
FGDGYVYPNG AYVAGTLLQY AGIALIPIFI MFSLWKYRSG TLVETVKRAF RKKASYGPAD 600
RDKFAEYQEF RKDAKLERDM RRDGFFQHIG LSLSGGYRKS KY                  642

SEQ ID NO: 182          moltype = AA  length = 55
FEATURE                 Location/Qualifiers
source                  1..55
                        mol_type = protein
                        organism = Plutella xylostella
```

```
SEQUENCE: 182
SAELPWAVCD PAWGATCVPS GAGGGTPVAG GVSSAELYFT KTVLQQSDGI EGGLG          55

SEQ ID NO: 183          moltype = AA  length = 636
FEATURE                 Location/Qualifiers
source                  1..636
                        mol_type = protein
                        organism = Plutella xylostella
SEQUENCE: 183
MSEGQTNLAF EESPEKDLNK SEAPEVVKST PGIGFVLEKG DNNNAEREEE EEPERAMWGN      60
QIEFLMSCIA TSVGLGNVWR FPPFVAYQNGG GAFLIPYVIV LFLIGKPMYY LECAIGQFSS    120
RNSVKVWSLS PAMKGTGYAQ ALGCGYILSY YVAIIALCLF YLVKSFSAEL PWAVCDPAWG    180
ATCVPSGAGG GAPVAGGVSS AELYFTKTVL QQSDGIEGGL GAPIWYLTLC LFASWLIIFV    240
IVARGVKSSG KASYFLALFP YVVMLILLIR SATLTGAGDG ILFFLTPQWD KLIQLDVWYA    300
AVTQVFFSLS VGTGAIIMFS SYNGFRQNIY RDAMIVTTLD TFTSLMSGIT IFGILGNLAY    360
ELGYDDVNSV IGSGGTGLAF ISYPDAIAKS PFVPQLFAVL FFLMMSVLGV GSAVALLSTI    420
NTVMMDSFRR VPTVAMSAIC CSAGFLIGLV YVTPGGQYIL ELVDYYGGTF LVLFGAIAEI    480
VGVFWIYGLQ NICLDIEFML GIKTSVYWRF CWGIITPLMM IAVFIYALIS FEALVFGEDY    540
VYPTAGYVAG YMILLVGVAL VPLFIIITVT KYRTGDFPET LKKAFSPKAS WGPSRRSDKR    600
EWQAFKEQAK AEQDKAYTTK LNHLWTSLVG GYKRPF                               636

SEQ ID NO: 184          moltype = AA  length = 55
FEATURE                 Location/Qualifiers
source                  1..55
                        mol_type = protein
                        organism = Plutella xylostella
SEQUENCE: 184
SAELPWAVCD PAWGATCVPS GAGGGAPVAG GVSSAELYFT KTVLQQSDGI EGGLG          55

SEQ ID NO: 185          moltype = AA  length = 646
FEATURE                 Location/Qualifiers
source                  1..646
                        mol_type = protein
                        organism = Plutella xylostella
SEQUENCE: 185
MAQCEWTTDH TDASNRDLSP NKGETNAAFE DVFENNTTTK RESQPHGEDI KLPTAKDVED      60
NQERAVWGNQ IEFLLSCIAT SVGLGNVWRF PFVAYQNGGG AFLIPYIIVL LVIGKPMYYL    120
ECALGQFSSR NSVRIWALAP AMKGTGYAQA IGSSYMLSYY VAIIALCLFY LVQSFSPQLP    180
WAVCAPEWGD TCVPSGGGAT PGPGAVSSAE LYFTKTVVQL SDGIEGGLGA PIWYLSLCLL    240
ASWLIIFLIV VRGVKSSGKA SYFLAIFPYF IMIILLARSV TLEGASTGIL FFLTPQWDKL    300
LEINVWYAAV TQVFFSLGVG TGAIIMFSSY NGFRQNIYRD AMIVTTLDTF TSLMSGITIF    360
GILGNLAFEL GYEDIDSVIG SGGTSLAFVS YPDAIAKSPF LPQLFSLLFF LMMCVLGVGS    420
AVAVLSTITT LVTDAFPRVP PAVVAAGCSA VGFLVGLVYV TPGGQYILEL VDYYGATFLI    480
LFGAIIEIIG VFWIYGLENV CLDIEQMLGV RTSAYWRLCW GLLTPCLMIA VFVYSLVSFE    540
PLVFGEDYVY PFAGYVAGFT LLLAGVVVVP IYIITTLYKY RTGRFPETVA KAFSMKSSWG    600
PRRTDDRRDW LAFREQTLAE RQKLGIGRFR HIYLSLTGGY KRQTDI                    646

SEQ ID NO: 186          moltype = AA  length = 54
FEATURE                 Location/Qualifiers
source                  1..54
                        mol_type = protein
                        organism = Plutella xylostella
SEQUENCE: 186
SPQLPWAVCA PEWGDTCVPS GGGATPGPGA VSSAELYFTK TVVQLSDGIE GGLG           54

SEQ ID NO: 187          moltype = AA  length = 575
FEATURE                 Location/Qualifiers
source                  1..575
                        mol_type = protein
                        organism = Plutella xylostella
SEQUENCE: 187
MSCIATSVGL GNVWRFPFVA YQNGGGAFLI PYVIVLIVIG KPMYYLETVL GQFSSSNCVK      60
IWALSPAMKG TGYAQALGAS YVLSYYVSII ALCLYYLAMS FNSTLPWATC REEWGANCVP    120
SGATGLDTSA INGTLVSSAE LYFTKTVLKQ SDGIDDGIGL PLWDLTLCLF ASWLIIFIIV    180
ARGVKSSGKA AYFLAIFPYV VMLILLIRAV TLEGASKGIL FFITPQWEKI LQLQVWYAAV    240
TQVFFSLSVC SGALIMFASY NGFKTNVYRD SMIVTTLDTF TSLISGITIF GVLGNLAFEL    300
GYDDVGEVIG SGGTGLAFIS YPDAIAKSPF VPQLFSVLFF SMMAVLGIGS GVALLSTVTT    360
VLMDAFPRVP TIYMSALGCA VGFLVGLVYV TPGGQYILEL VDYYGGTFMR LFAAIVETIG    420
VFWIYGLENL CIDIEFMLGI KTSWYWRVCW SIVTTPAIMIT VFMYTLITTE SLVFGDYVY    480
PNGAYVAGTL LQYAGIALIP IFIMFSLWKY RSGTLVETVK RAFRKKASYG PADRDKFAEY    540
QEFRKDAKLE RDMRRDGFFQ HIGLSLSGGY RKSKY                                575

SEQ ID NO: 188          moltype = AA  length = 638
FEATURE                 Location/Qualifiers
source                  1..638
                        mol_type = protein
                        organism = Plutella xylostella
SEQUENCE: 188
MGDSVKVADA GNDNAGFDPV PEKGFTKEAK AEALEDPQPP QDAAAATDQQ PARAQWDNPL      60
```

```
EFLMSCIATS VGLGNVWRFP FVAYQNGGGA FLIPYVIVLI VIGKPMYYLE TVLGQFSSSN    120
CVKIWALSPA MKGTGYAQAL GASYVLSYYV SIIALCLYYL AMSFNSTLPW ATCREEWGAN    180
CVPSGATGLD TSAINGTLVS SAELYFTKTV LKQSDGIDDG IGLPLWDLTL CLFASWLIIF    240
IIVARGVKSS GKAAYFLAIF PYVVMLILLI RAVTLEGASK GILFFITPQW EKILQLQVWY    300
AAVTQVFFSL SVCSGALIMF ASYNGFKTNV YRDSMIVTTL DTFTSLISGI TIFGVLGNLA    360
FELGYDDVGE VIGSGGTGLA FISYPDAIAK SPFVPQLFSV LFFSMMAVLG IGSGVALLST    420
VTTVLMDAFP RVPTIYMSAL GCAVGFLVGL VYVTPGGQYI LELVDYYGGT FMRLFAAIVE    480
TIGVFWIYGL ENLCIDIEFM LGIKTSWYWR VCWSIVTPAI MITVFMYTLI TTESLVFGDG    540
YVYPNGAYVA GTLLQYAGIA LIPIFIMFSL WKYRSGTLVE TVKRAFRKKA SYGPADRDKF    600
AEYQEFRKDA KLERDMRRDG FFQHIGLSLS GGYRKSKY                            638

SEQ ID NO: 189          moltype = AA  length = 495
FEATURE                 Location/Qualifiers
source                  1..495
                        mol_type = protein
                        organism = Plutella xylostella
SEQUENCE: 189
MGDSVKVADA GNDNAGFDPV PEKGFTKEAK AEALEDPQPP QDAAAATDQQ PARAQWDNPL     60
EFLMSCIATS VGLGNVWRFP FVAYQNGGGA FLIPYVIVLI VIGKPMYYLE TVLGQFSSSN    120
CVKIWALSPA MKGTGYAQAL GASYVLSYYV SIIALCLYYL AMSFNSTLPW ATCREEWGAN    180
CVPSGATGLD TSAINGTLVS SAELYFTKTV LKQSDGIDDG IGLPLWDLTL CLFASWLIIF    240
IIVARGVKSS GKAAYFLAIF PYVVMLILLI RAVTLEGASK GILFFITPQW EKILQLQVWY    300
AAVTQVFFSL SVCSGALIMF ASYNGFKTNV YRDSMIVTTL DTFTSLISGI TIFGVLGNLA    360
FELGYDDVGE VIGSGGTGLA FISYPDAIAK SPFVPQLFSV LFFSMMAVLG IGSGVALLST    420
VTTVLMDAFP RVPTIYMSAL GCAVGFLVGL VYVTPGGQYI LELVDYYGGT FMRLFAAIVE    480
TIGVFWIYGT HLLIY                                                    495

SEQ ID NO: 190          moltype = AA  length = 58
FEATURE                 Location/Qualifiers
source                  1..58
                        mol_type = protein
                        organism = Plutella xylostella
SEQUENCE: 190
NSTLPWATCR EEWGANCVPS GATGLDTSAI NGTLVSSAEL YFTKTVLKQS DGIDDGIG      58

SEQ ID NO: 191          moltype = AA  length = 574
FEATURE                 Location/Qualifiers
source                  1..574
                        mol_type = protein
                        organism = Heliothis virescens
SEQUENCE: 191
MSCIATSVGL GNVWRFPFIA YQNGGGAFLI PYIIVLILIG KPMYYLETSL GQFSSSNCVK     60
VWALSPAMKG TGYAQALSAL YVVSYYMSIV GLCLYYLVMS FQSTLPWALC QPEWENCVPS    120
GQTANDTEGL TGEPVSSAEL YFTKTILKQS DGIHDGIGAP LWDLTLSLFI SWLIIFLIVA    180
RGVKSSGKAA YFLALFPYVV MFILLIRAVT LPGAEMGILF FITPKWEKIM ERVWYAAVT    240
QVFFSLSTCS GALIMFSSYN NFSQNVYRDS MIVTTLDTFT SLISGITIFG ILGNLAFQLG    300
YDNINDVIGS GGSSLAFISY PDAIAQSPFV PQLFAALFFL MMAVLGVGSG VALFSTVNTI    360
LLDAFPRVPT IYMSAINCSI GFLVGLVYVT PGGQYILELV DYYGGTFMRL FAAIIETMGV    420
FWVYGLENMC LDIEYMLGLK SSFYWRMCWG IVTPLMMMVV FFYSLITTEE LLFGGTYEYP    480
QGAYIAGAIL QYFGIALIPI FMLATLWKYK SGSFAETVKR SFRPKKTYGP KIPQKREEWL    540
EFRRNAKYER ELKRKNWFHH IGLSLIGGYR RGRK                               574

SEQ ID NO: 192          moltype = AA  length = 57
FEATURE                 Location/Qualifiers
source                  1..57
                        mol_type = protein
                        organism = Heliothis virescens
SEQUENCE: 192
QSTLPWALCQ PEWENCVPSG QTANDTEGLT GEPVSSAELY FTKTILKQSD GIHDGIG        57

SEQ ID NO: 193          moltype = AA  length = 638
FEATURE                 Location/Qualifiers
source                  1..638
                        mol_type = protein
                        organism = Helicoverpa armigera
SEQUENCE: 193
MEPNGVNVVE DGSRVNPGFN PEPENGDVSK KKDLTTDFLE SQITDAAKPA TENERQQWDN     60
QYQFLMSCIA TSVGLGNVWR PPFIAYQNGG GAPLIPYMYY LILIGKPMYY LETSLGQFSS    120
SNCVKVWALS PAMKGTGYAQ ALSALYVVSY YMSIVGLCLY YLVMSFQSTL PWALCRPEWE    180
NCVPSGQTAN DTELTGEPVS SAELYFTKTI LRQSDGIHDG IGAPIWDLTL SLFVSWLIIF    240
LIVARGVKSS GKAAYFLALF PYVVMFILLI RAVTLPGAEM GILFFITPKW EKILEMRVWY    300
AAVTQVFFSL SACSGALIMF SSFNNFSQNV YRDSMIVTTL DTFTSLISGI TIFGILGNLA    360
FQLGYDNIND VIGSGGSSLA FISYPDAIAQ SPFVPQLFFL MMAVLG VGSSV ALFST VNTI    420
INTILIDAFP KVPIIYMSAI NCTICFLVGL VYVTPGGQYI LELVDYYGGT FMRLFAAIIE    480
TMGVFWIYGL ENMCLDIEYM LGLKSSIYWR VCWGIVTPIM MMVVFFYSLI TTEELLFGGT    540
YEYPQGAYIA GAILQYFGIA LIPIFMLATL WKYKSDTFVD TVKRSFRKKA TYGPRNLQKR    600
EEWKEFRRNA KYERELKRKN WFHHIGLSLI GGYRRGQK                           638

SEQ ID NO: 194          moltype = AA  length = 56
```

```
FEATURE                  Location/Qualifiers
source                   1..56
                         mol_type = protein
                         organism = Helicoverpa armigera
SEQUENCE: 194
QSTLPWALCR PEWENCVPSG QTANDTELTG EPVSSAELYF TKTILRQSDG IHDGIG         56

SEQ ID NO: 195           moltype = AA   length = 626
FEATURE                  Location/Qualifiers
source                   1..626
                         mol_type = protein
                         organism = Plutella xylostella
SEQUENCE: 195
MVQKGETNAA FEDDPENYET KRPSQLHGEV TTLPTTKDVE DNQERAVWGN QIEFLLSCIA     60
TSVGLGNVWR FPFVAYQNGG GAFLIPYVIV LLVIGKPMYY LECALGQFSS RNSVRIWALA    120
PAMKGTGYAQ AIGSSYMLSY YVAIIALCLF YLVQSFSPQL PWAVCAPQWD ACVPSGGGAT    180
PGPGAVSSAE LYFTKTVVQL SDGIEGGLGA PIWYLALCLL ASWVVIFLIV VRGVRSSGKA    240
SYFLAIFPYF IMIILLIRSV TLEGASTGIL FFLTPQWDKL LEINVWYAAV TQVFFSLGVG    300
TGAIIMFSSY NGFRQNIYRD AMIVTTLDTF TSLMSGITIF GILGNLAFEL GYEDVDSVIG    360
SGGTSLAFVS YPDAIAKSPF LPQLFSILFF LMMCVLGVGS AVAVLSTITT LVTDACPRAP    420
PAVVAAGCCA AGFLVGLVYV TPGGQYILEL VDYYGATFLI LFGAIVEIIG VFWIYGLENV    480
CLDIELMLGV RTSAYWRVCW GLATPGLMVA VFVYSLISFK PLVFGGDYVY PFAGYVAGFT    540
LLLAGVVVVP IFLITTLYKY RTGRFSETVA KAFSMKSSWG PRRTDDRRDW LAFREQTLAE    600
RQKLGIGRFR HIYLSLTGGY RRQTDI                                        626

SEQ ID NO: 196           moltype = AA   length = 642
FEATURE                  Location/Qualifiers
source                   1..642
                         mol_type = protein
                         organism = Plutella xylostella
SEQUENCE: 196
MRKAEDRVLW RSLGEAYVQK GETNAAFEDD PENYETKRPS QLHGEVTTLP TTKDVEDNQE     60
RAVWGNQIEF LLSCIATSVG LGNVWRFPFV AYQNGGGAFL IPYVIVLLVI GKPMYYLECA    120
LGQFSSRNSV RIWALAPAMK GTGYAQAIGS SYMLSYYVAI IALCLFYLVQ SFSPQLPWAV    180
CAPQWDACVP SGGGATPGPG AVSSAELYFT KTVVQLSDGI EGGLGAPIWY LALCLLASWV    240
VIFLIVVRGV RSSGKASYFL AIFPYFIMII LLIRSVTLEG ASTGILFFLT PQWDKLLEIN    300
VWYAAVTQVF FSLGVGTGAI IMFSSYNGFR QNIYRDAMIV TTLDTFTSLM SGITIFGILG    360
NLAFELGYED VDSVIGSGGT SLAFVSYPDA IAKSPFLPQL FSILFFLMMC VLGVGSAVAV    420
LSTITTLVTD ACPRAPPAVV AAGCCAAGFL VGLVYVTPGG QYILELVDYY GATFLILFGA    480
IVEIIGVFWI YGLENVCLDI ELMLGVRTSA YWRVCWGLAT PGLMVAVFVY SLISFKPLVF    540
GGDYVYPFAG YVAGFTLLLA GVVVVPIFLI TTLYKYRTGR FSETVAKAFS MKSSWGPRRT    600
DDRRDWLAFR EQTLAERQKL GIGRFRHIYL SLTGGYRRQT DI                       642

SEQ ID NO: 197           moltype = AA   length = 53
FEATURE                  Location/Qualifiers
source                   1..53
                         mol_type = protein
                         organism = Plutella xylostella
SEQUENCE: 197
SPQLPWAVCA PQWDACVPSG GGATPGPGAV SSAELYFTKT VVQLSDGIEG GLG             53

SEQ ID NO: 198           moltype = AA   length = 641
FEATURE                  Location/Qualifiers
source                   1..641
                         mol_type = protein
                         organism = Ostrinia furnacalis
SEQUENCE: 198
MDSEKQTAEN GTQENKAFDA SPENGVSNMS KLDVKKQDLK DTDLENTKPT NEGKTQERPK     60
WDNQIEFLMS CIATSVGLGN VWRFPFVAYQ NGGGAFLIPY IIVLLVIGKP MYYLETVLGQ    120
FSSSNCVKIW ALSPAMKGTG YAQALGASFV LSYYVSIIAL CLYYLAMSFQ STLPWALCDP    180
EWESDKVYCV PSGYTAPPGI NGTSSAELYF TQTVLRQSDG IDDGIGAPIW DLTLCLLASW    240
IIIFVIVARG VKSSGKAAYF LAIFPYIVMF ILLIRAVTLE GAGKGIMFFL TPEWAKILEI    300
KVMYAAVTQV FFSLSVCSGA LIMFSSYNGF RQNVYRDSMI VTTLDTFTSL MSGITIFGIL    360
GNLAHQLNQD DVGEVIGSGG SSLAFISYPD AIAQSPFVPQ LFSVLFFLMM AVLGIGSGVA    420
LLSTVNTILM DSFPRVPTIY MSAIACSAGF LLGLVYVTPG GQYILELVDY YGGTFMRLFA    480
AIAETIGVFW IYGLENICLD IEFMLGVKSS FYWRICWSII TPAIMIAVFM YALITTEALV    540
YGGTYRYPEG AYIAGNMLQY IGIALIPLFI IAALWKYRSG DIIETIKVSF RKKETYGPSD    600
EELREQWRQF RSDAKFDRSV QRKNWFHHLG MILIGGYRWG K                         641

SEQ ID NO: 199           moltype = AA   length = 57
FEATURE                  Location/Qualifiers
source                   1..57
                         mol_type = protein
                         organism = Ostrinia furnacalis
SEQUENCE: 199
QSTLPWALCD PEWESDKVYC VPSGYTAPPG INGTSSAELY FTQTVLRQSD GIDDGIG        57

SEQ ID NO: 200           moltype = AA   length = 641
FEATURE                  Location/Qualifiers
```

```
source                   1..641
                         mol_type = protein
                         organism = Spodoptera frugiperda
SEQUENCE: 200
MDSDNVKVEN GSRENTGFDS APEYDDKSKK FPPDYNGTEK DLPSDYPDKS VDGASPEVER    60
PTWDNQYQFL MSCIATSVGL GNVWRFPFIA YQNGGGAFLI PYIIVLILIG KPMYYLETAL   120
GQFSSSNCVK VWALSPAMKG TGYAQALSAL YIVSYYMSIV GLCLYYLLMS FQSVLPWSVC   180
QPDWVDCVPS GEVANSSLII DRPITSAQLY FQKVILRQSD GIHDGIGAPL WDLTLSLFIS   240
WLIVFVIVAK GIKSSGKAAY FLALFPYVVM FILLIRAVTL PGAGKGILFF ITPQWEKILE   300
LKVWYAATTQ VFFSLSTCSG ALIMFSSFNK FTQNVYRDSM IVTTLDTFTS LISGITIFGI   360
LGNLAFQMGE DDISTIIRGG GSSLAFVSYP DAIAQSPFVP QLFSALFFLM MAVLGVGSGV   420
ALFSTVNTIL LDAFPKVPTI VMSGVMCSAC FLVGLVYVTP GGQYILELVD HYGGTFMRLF   480
AAIVEIIGVF WIYGLENMCL NIEFMLGLKT SFYWRICWGI VTPFMMMTVF FYALITTDQL   540
TFNDYVYPDI AYIAGSLLQY FGIALVPIFM AATLWKYRTS SFVETVKTSF RAKKKYGPSI   600
PQKKEEWREF RRNAKYERNL IRKNQLHHIG LSLIGGYRRR K                      641

SEQ ID NO: 201           moltype = AA length = 56
FEATURE                  Location/Qualifiers
source                   1..56
                         mol_type = protein
                         organism = Spodoptera frugiperda
SEQUENCE: 201
QSVLPWSVCQ PDWVDCVPSG EVANSSLIID RPITSAQLYF QKVILRQSDG IHDGIG        56

SEQ ID NO: 202           moltype = AA length = 664
FEATURE                  Location/Qualifiers
source                   1..664
                         mol_type = protein
                         organism = Spodoptera frugiperda
SEQUENCE: 202
MPCKKENLQG GNSSDDFSCY GLGERENNVK VENGSRENPG FDSAPEYDDK SKKFPPDYNG    60
TEKDLPSDYP DKSVDGASPE VERPTWDNQY QFLMSCIATS VGLGNVWRFP FIAYQNGGGA   120
FLIPYIIVLI LIGKPMYYLE TALGQFSSSN CVKVWALSPA MKGTGYAQAL SALYIVSYYM   180
SIVGLCLYYL LMSFQSVLPW SVCQPDWVDC VPSGEVANSS LIIDRPITSA QLYFQKVILR   240
QSDGIHDGIG APLWDLTLSL FISWLIVFVI VAKGIKSSGK AAYFLALFPY VVMFILLIRA   300
VTLPGAGKGI LFFITPQWEK ILELKVWYAA TTQVFFSLST CSGALIMFSS FNKFTQNVYR   360
DSMIVTTLDT FTSLISGITI FGILGNLAFQ MGEDDISTII RGGGSSLAFV SYPDAIAQSP   420
FVPQLFSALF FLMMAVLGVG SGVALFSTVN TILLDAFPKV PTIVMSGVMC SACFLVGLVY   480
VTPGGQYILE LVDHYGGTFM RLFAAIVEII GVFWIYGLEN MCLNIEFMLG LKTSFYWRIC   540
WGIVTPFMMM TVFFYALITT DQLTFNDYVY PDIAYIAGSL LQYFGIALVP IFMAATLWKY   600
RTSSFVETVK TSFRAKKKYG PSIPQKKEEW REFRRNAKYE RNLIRKNQLH HIGLSLIGGY   660
RRRK                                                                664

SEQ ID NO: 203           moltype = AA length = 662
FEATURE                  Location/Qualifiers
source                   1..662
                         mol_type = protein
                         organism = Spodoptera frugiperda
SEQUENCE: 203
MTSPVLGKAR GSVRLLLTKN HPDSDNVKVE NGSRENPGFD SAPEYDDKSK KFPPDYNGTE    60
KDLPSDYPDK SVVGASPEVE RPTWDNQYQF LMSCIATSVG LGNVWRFPFI AYQNGGGAFL   120
IPYIIVLILI GKPMYYLETA LGQFSSSNCV KVWALSPAMK GTGYAQALSA LYIVSYYMSI   180
VGLCLYYLLM SFQSVLPWSV CQPDWVDCVP SGEVANQSLI IDRPITSAQL YFQKVILRQS   240
DGIHDGIGAP LWDLTLSLFI SWLIVFVIVA KGIKSSGKAA YFLALFPYVV MFILLIRAVT   300
LPGAGKGILF FITPQWEKIL ELKVWYAATT QVFFSLSTCS GALIMFSSFN KFTQNVYRDS   360
MIVTTLDTFT SLISGITIFG ILGNLAFQMG EDDISTIIRG GGSSLAFVSY PDAIAQSPFV   420
PQLFSALFFL MMAVLGVGSG VALFSTVNTI LLDAFPKVPT IVMSGVMCSA CFLVGLVYVT   480
PGGQYILELV DHYGGTFMRL FAAIVEIIGV FWIYGLENMC LNIEFMLGLK TSFYWRICWG   540
IVTPFMMMTV FFYALITTDQ LTFNDYVYPD IAYIAGSLLQ YFGIALVPIF MAATLWKYRT   600
SSFVETVKTS FRAKKKYGPS IPQKKEEWRE FRRNAKYERN LIRKNQLHHI GLSLIGGYRR   660
RK                                                                  662

SEQ ID NO: 204           moltype = AA length = 56
FEATURE                  Location/Qualifiers
source                   1..56
                         mol_type = protein
                         organism = Spodoptera frugiperda
SEQUENCE: 204
QSVLPWSVCQ PDWVDCVPSG EVANQSLIID RPITSAQLYF QKVILRQSDG IHDGIG        56

SEQ ID NO: 205           moltype = AA length = 638
FEATURE                  Location/Qualifiers
source                   1..638
                         mol_type = protein
                         organism = Diabrotica virgifera virgifera
SEQUENCE: 205
MVRVEGQSQD SIIMDKDFPV GLENLGFQKE PSDYEKERNG DLTAVTVTTN EEAKERSQWG    60
NSTEFLMSCI AMSVGLGNIW RFPFIANKNG GGAFLIPYLI ILTFIGRPMY YMEMALGQFS   120
NRGSIKMYTK LSPVLKGIGY GQVVGSFCVA SYYCIIMAIT LVYLFNSFTS NFPWATCQES   180
```

```
WQEYLDSRNL TCLDQSNTSI TGVETISSSE MYFRREVLKE VDDISDGIGL PDWKLAILVL    240
VTWLITYLVS VRGVKSSGKA SYFLAIFPYV VMFILFIRAA TLEGATEGML YFIKADFTKL    300
LDAEVWYAAV TQCFFSLGVG FGSIITLSSY NKFDHNINRD ALVVTTLDTF TSLLSGFTIF    360
GILGNLAHEM NVPPSEVISA GGGTGLAFIS YPDALSKFTF VPWLFSITFF FMLFVLGVGS    420
LVATHATLNT AIKDAFNIAD WKIAAFTSMV LFLVGMIYIT PGGQYILDLV DHFGGTFVIF    480
VCAILEVFAI TFLYGVENFC IDLEFMTKKK VGVYWRISWG VVMPLLLIVI FIYFVSTLKP    540
LVYGIYSLYY PTELTILGWS IIGIVIVQLF VWLLYFLGKN GHCSITKMFR DTFSTETWGP    600
EDDPKAKEDWK KFRENRISER GLYSYPWLKR KMKILTGR                           638

SEQ ID NO: 206           moltype = AA    length = 61
FEATURE                  Location/Qualifiers
source                   1..61
                         mol_type = protein
                         organism = Diabrotica virgifera virgifera
SEQUENCE: 206
TSNFPWATCQ ESWQEYLDSR NLTCLDQSNT SITGVETISS SEMYFRREVL KEVDDISDGI    60
G                                                                    61

SEQ ID NO: 207           moltype = AA    length = 661
FEATURE                  Location/Qualifiers
source                   1..661
                         mol_type = protein
                         organism = Diabrotica virgifera virgifera
SEQUENCE: 207
MKHVVNNLLS EVTLHQRGKY VKFKYCEIPL EHCLFVFSQE YTFDNPVFII SPEDVDHKSN    60
GKIPDVEEND KSPQRSQWGN DTQFLMSCVA MSVGLGNVWR FPPIARSNGG GAFLIPYLIV    120
LTVVGRPMYY MEMVLGQFCS RGPGQMYSKM SPVLKGIGIG QVFGATCVAS YYCILMAITL    180
LYLVNSFTIN FPWATCWESW EEYLNERNFT CVDKDTVNFS SNNTISSAEM YFRREVLKEK    240
DDISDGLGAP DWKLSLFLLV SWFATFLVSI KGVKSSGKAS YFLAIFPYIV MLVLLIRAST    300
LPGAAEGMKY FVDADFSRLK DAEVWYAAVT QCFFSLGVGF GNIVTLASYN KFSHNINRDA    360
FIIITTLDTFT SLLSGVTIFG ILGNLAYEMK IPPSEVIAAG GGTALAFISY PDALSKFTFA    420
PWLFAITFFV MLFVLGLGSL QGLHGNLNGL IKEYLPYTPD WKIAGCSSIV LFFVGLIYVT    480
QGGQYTLDLV DFFGGTFVIF VCAICEVFVI AYIYGIDRLC LDIEFMSKRK VGIYWRLTWG    540
LLMPLLLILI FLYFIWTLKP IVYGIDSLRL PLGLEIFGWS ILAVTVIQLM GWFFYYLYAN    600
RKYPGIQKLT ETFSFKTWGP EGRQRTEEWK KFLEEKNTIL QGKRSRIPTK IKAIFLDPYK    660
S                                                                    661

SEQ ID NO: 208           moltype = AA    length = 628
FEATURE                  Location/Qualifiers
source                   1..628
                         mol_type = protein
                         organism = Diabrotica virgifera virgifera
SEQUENCE: 208
MGKNKKEYTF DNPVFIISPE DVDHKSNGKI PDVEENDKSP QRSQWGNDTQ FLMSCVAMSV    60
GLGNVWRFPF IARSNGGGAF LIPYLIVLTV VGRPMYYMEM VLGQFCSRGP GQMYSKMSPV    120
LKGIGIGQVF GATCVASYYC ILMAITLLYL VNSFTINFPW ATCWESWEEY LNERNFTCVD    180
KDTVNFSSNN TISSAEMYFR REVLKEKDDI SDGLGAPDWK LSLFLLVSWF ATFLVSIKGV    240
KSSGKASYFL AIFPYIVMLV LLIRASTLPG AAEGMKYFVD ADFSRLKDAE VWYAAVTQCF    300
FSLNVGFGNI VTLASYNKFS HNINRDAFII TTLDTFTSLL SGVTIFGILG NLAYEMKIPP    360
SEVIAAGGGT ALAFISYPDA LSKFTFAPWL FAITFFVMLF VLGLGSLQGL HGNLNGLIKE    420
YLPYTPDWKI AGCSSIVLFF VGLIYVTQGG QYTLDLVDFF GGTFVIFVCA ICEVFVIAYI    480
YGIDRLCLDI EFMSKRKVGI YWRLTWGLLM PLLLILIFLY FIWTLKPIVY GIDSLRLPLG    540
LEIFGWSILA VTVIQLMGWF FYYLYANRKY PGIQKLTETF SFKTWGPEGR QRTEEWKKFL    600
EEKNTILQGK RSRIPTKIKA IFLDPYKS                                       628

SEQ ID NO: 209           moltype = AA    length = 61
FEATURE                  Location/Qualifiers
source                   1..61
                         mol_type = protein
                         organism = Diabrotica virgifera virgifera
SEQUENCE: 209
TINFPWATCW ESWEEYLNER NFTCVDKDTV NFSSNNTISS AEMYFRREVL KEKDDISDGL    60
G                                                                    61

SEQ ID NO: 210           moltype = AA    length = 710
FEATURE                  Location/Qualifiers
source                   1..710
                         mol_type = protein
                         organism = Frankliniella occidentalis
SEQUENCE: 210
MALLLLLLLL LLLHCCTAAL LHRPLQAGRA VEREPCPPVK MSEQMYYWGE EKETVDPDQT    60
FIEFSAKSAP SREVTAADSG GPAGAAAPAA GPAGPGGPGG PHEERPGWGH KLDFLFSCIS    120
VSVGLGNVWR FPPYLCYKNGG GAFLVTYGIA MVFCGVPIFF QEVAIGQYLG SGGMTLVGQL    180
CPILQGVGYA TMTLVFFLDI YYCIIIAWTL YYLITTFIAL PELPWSSCDN EWNTPRCYDH    240
RANGTLHAAL NGTDHGNRSS PVEEYWDRRV LHITDGIHDL GGMQWELFMC LALGWVLVYF    300
IIYRGLHQSG KIIWFTALFP YAILAVLLVR SVTLEGASDG LLYYVTPRWE ELLGPGPWID    360
GATQIFFAYS IGMGALPTLG SYNAYNHNSY KDALITCVVN TLTSLVAGVV TFSILGHVAL    420
GKGTSVASVV TSGPGLVFLT YPEVVLRLPG APVVSAVFFT MLVVLGIDSE FCIVEALVAG    480
LADQWPVLKT HRKKFTAAMC GLMFLLGLPM VTHVSVVVKG SSNIQKTISS HFLIACSISP    540
```

```
QGGAYIFQLM DFYSVSGMSL LWVCFFQTIA IGWIFGAKNF SACIKSMMGV EVNKFWYACW   600
VVFAPAVMVA IFVFYVLQYQ PLTYGKDYMY PMWAQGIGIA ISFSSMVWIP AYAVYYMIKS   660
KGTFKERLLR GLRPDFKCKA KIPAGQKGPV IPMSESSAGL LTKNSSFLNQ              710

SEQ ID NO: 211          moltype = AA  length = 642
FEATURE                 Location/Qualifiers
source                  1..642
                        mol_type = protein
                        organism = Frankliniella occidentalis
SEQUENCE: 211
MSEQMYYWGE EKETVDPDQT FIEFSAKSAP SREVTAADSG GPAGAAAPAA GPAGPGGPGG    60
PHEERPGWGH KLDFLFSCIS VSVGLGNVWR FPYLCYKNGG GAFLVTYGIA MVFCGVPIFF   120
QEVAIGQYLG SGGMTLVGQL CPILQGVGYA TMTLVFFLDI YYCIIIAWTL YYLITTFIAL   180
PELPWSSCDN EWNTPRCYDH RANGTLHAAL NGTDHGNRSS PVEEYWDRRV LHITDGIHDL   240
GGMQWELFMC LALGWVLVYF IIYRGLHQSG KIIWFTALFP YAILAVLLVR SVTLEGASDG   300
LLYYVTPRWE ELLGPGPWID GATQIFFAYS IGMGALPTLG SYNAYNHNSY KDALITCVVN   360
TLTSLVAGVV TFSILGHVAL GKGTSVASVV TSGPGLVFLT YPEVVLRLPG APVWSAVFFT   420
MLVVLGIDSE FCIVEALVAG LADQWPVLKT HRKKFTAAMC GLMFLLGLPM VTHGGAYIFQ   480
LMDFYSVSGM SLLWVCFFQT IAIGWIFGAK NFSACIKSMM GVEVNKFWYA CWVVFAPAVM   540
VAIFVFYVLQ YQPLTYGKDY MYPMWAQGIG IAISFSSMVW IPAYAVYYMI KSKGTFKERL   600
LRGLRPDFKC KAKIPAGQKG PVIPMSESSA GLLTKNSSFL NQ                     642

SEQ ID NO: 212          moltype = AA  length = 62
FEATURE                 Location/Qualifiers
source                  1..62
                        mol_type = protein
                        organism = Frankliniella occidentalis
SEQUENCE: 212
LPELPWSSCD NEWNTPRCYD HRANGTLHAA LNGTDHGNRS SPVEEYWDRR VLHITDGIHD    60
LG                                                                  62

SEQ ID NO: 213          moltype = AA  length = 640
FEATURE                 Location/Qualifiers
source                  1..640
                        mol_type = protein
                        organism = Leptinotarsa decemlineata
SEQUENCE: 213
MNKEQMNGNI EGNTKNEVEE ITVYDNPSYM RDTNEVEIQQ KAEKEIENDN AVKGVPQDRP    60
QWGRSIEFLM SCVAMNVGLG NIWRFPFVAY ENGGGAFVIP YLLVLTFFGR PMYYLEMCLG   120
QFTSRGNVKM FESLAPILKG IGYGQLIGDF SVATYYCTLM AISLFYLIQS FTSDLPWTEC   180
RDEWKTNPFL QGKTCVSSKS VNVSNNISVC SSELYFRIEV LRESPDISEG LGIPDWRLAL   240
YLLASWIVTF LICSKGVKSS GKVSYFLALF PYIILFSLLI RATTLEGSVE GIAFFFLPQW   300
EKLLEAKVWY AAITQCMFSL NIGFGTVTMC ASYNSFRHNT YRDAIIVSIL DTGTSMLAGT   360
IIFGILGNLA LKLNVDIDKV VTSGTGLAFI SYPEAIARFE SVPWVFAVLF FSMLFILGVG   420
SLIALYGSAS TVIMDSYPHL NISYVSFGTA VVGPIIGLVY ITPGGQWIFT MVDFYAGTAI   480
FFFFMNTSEII IIAWWYGIED ICKDIEFMLG RKTGIYWRMS WGLIIPVALL AVMVYFLSNL   540
EPLRYADHIY PITVEAGGYA LFAFGVLQPF FWFFIELCKR KRKERLYSEV LESMLSHESW   600
GPKDMTENTA WREFKQEARM KRVSKRRNCL VDKLCVLIGY                        640

SEQ ID NO: 214          moltype = AA  length = 61
FEATURE                 Location/Qualifiers
source                  1..61
                        mol_type = protein
                        organism = Leptinotarsa decemlineata
SEQUENCE: 214
TSDLPWTECR DEWKTNPFLQ GKTCVSSKSV NVSNNISVCS SELYFRIEVL RESPDISEGL    60
G                                                                   61

SEQ ID NO: 215          moltype = AA  length = 638
FEATURE                 Location/Qualifiers
source                  1..638
                        mol_type = protein
                        organism = Helicoverpa zea
SEQUENCE: 215
MSGENNEGFD LSSEDPGQGS RVGVGALPIP PLTEKAPVNG VSGNNEKKVD PETVVPERAV    60
WDNQLEFLMS CIATSVGLGN VWRFPFVAYQ NGGGAFLIPY VIVLLLIGKP MYYLECALGQ   120
FSSRNSVKVW SLSPAMKGTG YATALGCYIL SYYVSIVAL CLFYLAMSFQ ATLPWGICQP   180
EWDDCVPSDP SQEVGVVTEN ATSSAELYFL KTVLQQKDGI EGGLGLPVWH LVLCLAGAWF   240
VIFVIVARGV KSSGKAAYFL ALFPYVVMIV LLITTVILPG AGDGILFFLT PQWDKLIELD   300
VWYAAVTQVF FSLSVCTGAI IMFSSYNGFR QNVYRDAMIV TTLDTFTSLL SGITIFGILG   360
NLAVELNQEV KDVIGSAGTG LAFISYPDAI SKTFLPQLFS VLFFLMMSVL GVGSAVALLS   420
TINTVMMDAF PRIRTVFMSA FCCTIGFAVG LIYVTPGGQY ILELVDYYGG TFLILFCAIA   480
EIIGVVWIYG LENLCVDIEF MLGIKTGFYW RFCWGLIMPA MMITVFIYAF ASYEALLFGG   540
YYTYPTAGYV SGYMMLIVGI LFVPISISLT MYKNKTGNFI QTIKQAFKAK SSWGPRTPSD   600
YNDWVQFKAE AKQQRVAMRT SWARHIWLSL TGGYRKRL                          638

SEQ ID NO: 216          moltype = AA  length = 56
FEATURE                 Location/Qualifiers
source                  1..56
```

```
                        mol_type = protein
                        organism = Helicoverpa zea
SEQUENCE: 216
QATLPWGICQ PEWDDCVPSD PSQEVGVVTE NATSSAELYF LKTVLQQKDG IEGGLG        56

SEQ ID NO: 217          moltype = AA  length = 638
FEATURE                 Location/Qualifiers
source                  1..638
                        mol_type = protein
                        organism = Helicoverpa armigera
SEQUENCE: 217
MSGENNEGFD LSSEDPGQGS RVGVGALPIP PLTEKAPVNG VSGNNEKKVD PETAVPERAV    60
WDNQLEFLMS CIATSVGLGN VWRFPFIAYQ NGGGAFLIPY VIVLLLIGKP MYYLECALGQ   120
FSSRNSVKVW SLSPAMKGTG YATALGCYYI LSYYVSIVAL CLFYLAMSFQ ATLPWGICQP   180
EWDDCVPSDP SQEVGVVTEN ATSSAELYFL KTVLQQKDGI EGGLGLPVWH LVLCLAGAWF   240
VIFVIVARGV KSSGKAAYFL ALFPYVVMIV LLITTVILPG AGDGILFFLT PQWDKLIELD   300
VWYAAVTQVF FSLSVCTGAI IMFSSYNGFR QNVYRDAMIV TTLDTFTSLL SGITIFGILG   360
NLAVELNQEV KDVIGSAGTG LAFISYPDAI SKTFLPQLFS VLFFLMMSVL GVGSAVALLS   420
TINTVMMDAF PRIRTVFMSA FCCTIGFAVG LIYVTPGGQY ILELVDYYGG TFLILFCAIA   480
EIIGVVWIYG LENLCVDIEF MLGIKTGFYW RFCWGLIMPA MMITVFIYAF ASYEALLFGG   540
YYTYPTAGYV SGYMMLIVGI LFVPISISLT MYKNKTGNFI QTIKQAFKAK SSWGPRGPSE   600
YNDWVQFKAE AKQQRVAMRT SWARHIWLSL TGGYRKRL                          638

SEQ ID NO: 218          moltype = AA  length = 56
FEATURE                 Location/Qualifiers
source                  1..56
                        mol_type = protein
                        organism = Helicoverpa armigera
SEQUENCE: 218
QATLPWGICQ PEWDDCVPSD PSQEVGVVTE NATSSAELYF LKTVLQQKDG IEGGLG        56

SEQ ID NO: 219          moltype = AA  length = 634
FEATURE                 Location/Qualifiers
source                  1..634
                        mol_type = protein
                        organism = Trichoplusia ni
SEQUENCE: 219
MSGQGNDGFD ISPEDPQSKA GFKSPPTLIV SSPEKVPVDD DNNEKGDLEA DEPERAVWGN    60
QIEFLMSCIA TSVGLGNVWR FPPFIAYLNGG GAFLIPYIIV LILIGKPMYY LECALGQFSS  120
KNSIRVWSLS PAMKGTGYAT ALGCSYILSY YVSIVALCLY YLAMSFQSTL PWSVCQPEWV   180
DCLPSDPSID AGPISENASS SAELYFLKTV LQQKDGLEGG LGLPIWYLVL CLFASWLVIF   240
LIVAQGVKSS GKAAYFLALF PYVVMIILLI VTLTLDGSGD GILFFLTPQW DKLIELDVWY   300
AAVTQVFFSL SVSTGAIIMF SSYNGFRQNV YRDSMIVTTL DTFTSLLSGI SAVALLSTVN   360
FELNKDVSDV IGKAGTGLAF VSYPDAISKT FLPQLFAVLF FLMMTVLGIG SAVALLSTVN   420
TVLIDKFPRI RVVFMSAFSC TVGFAVGLIY VTPGGQYVLE LVDYFGGTFL ILFCAIVEVI   480
TVFWIYGLEN VCVDIEYMLG MKTGPYWRFC WGLITPLMMI VVFMYALVSS EQLKFGDYVY   540
PTAGYVSGYL MLVIGMIFVP VAISITMYKR WNGNFMESVK LSFRSKSTWG PRDAKERRGW   600
EEFKRQAKEE RAPLKTSWPK HIWMSLYGGY RRKL                              634

SEQ ID NO: 220          moltype = AA  length = 56
FEATURE                 Location/Qualifiers
source                  1..56
                        mol_type = protein
                        organism = Trichoplusia ni
SEQUENCE: 220
QSTLPWSVCQ PEWVDCLPSD PSIDAGPISE NASSSAELYF LKTVLQQKDG LEGGLG        56

SEQ ID NO: 221          moltype = AA  length = 634
FEATURE                 Location/Qualifiers
source                  1..634
                        mol_type = protein
                        organism = Manduca sexta
SEQUENCE: 221
MNDGQVNGGF ESSEPKMEPK RSSQISLPPA NLKATMDNID DMDLEAEPPE RMVWSNNIEF    60
LMSCIATSVG LGNVWRFPFI AYQNGGGAFL VPYIIVLLLV GKPVYYLECV LGQFSSRNSV   120
KIWSISPAMK GTGYAQAVGC GYILSYYVVI CGLCLFYLAM SFQATLPWAI CQPEWENCVP   180
SDPTLAAGVG NITNGTSSAE LYFLRTVLQQ SDGIEGGLGA PIWYLVLCLF IAWLMVFGVV   240
ARGVKSSGKA AYFLALFPYV VMITLFITTV LLPGATDGIL FFVTPDWWKL LELGVWYAAI   300
TQVFFSLSVC TGAIIMFSSY NGFKQNVYRD ALIVTTLDTF TSFLSGCTIF GILGNLAYEL   360
NSDVGDVIGS GGTSLAFISY PDAIAKTFQP QLFSVLFFLM MSVLGIGSSV ALLSTLNTVV   420
MDAFPRVPTV YMSALSCTCG FLLGLVYCTP GGQFILELVD HYGGTFLVLF CAISELAGVF   480
WIYGLENLCL DIEFMMGKTT GFYWRLCWGI VTPGMMIIVF IYALLSFENL VFGDFYVYPV   540
AGYVAGYMML FLGIVLVPIG IVVTLYKYRT GNFRETVKKA FHSKPSWGPR SPRLRREWMQ   600
FRIEAKALRQ KMNTSRVKHL WYSITGAYRR NINK                              634

SEQ ID NO: 222          moltype = AA  length = 57
FEATURE                 Location/Qualifiers
source                  1..57
                        mol_type = protein
```

```
                          organism = Manduca sexta
SEQUENCE: 222
QATLPWAICQ PEWENCVPSD PTLAAGVGNI TNGTSSAELY FLRTVLQQSD GIEGGLG          57

SEQ ID NO: 223            moltype = AA   length = 567
FEATURE                   Location/Qualifiers
source                    1..567
                          mol_type = protein
                          organism = Ostrinia furnacalis
SEQUENCE: 223
MSCIATSVGL GNVWRFPFVA YQNGGGAFLV PYIIVLFLIG KPMYYLECVI GQFSTRNSVK       60
VWALAPAMKG TGYAQALTCG YILSYYVSII ALCLYYFAMS FQPTLPWALC EPEWENCVPS      120
APGHNITITN ESTSSAELFF LKTVLRQREG IEGGLGLPLW DLTLCLLASW VIIFVIVARG      180
VKSSGKAAYF LALFPYVVMI ILLISTSILN GAGNGILFFL TPQWEKILEL DVWYAAVTQL      240
FFSLSVCTGA LVMFSSYNGF RQNVYRDAMI VTTLDTFTSL LSGITIFGIL GNLAYELNQD      300
VADVVGSAGT GLAFVSYPDA IAKTFLPQLY SVLFFLMMSV LGVGSGVALL STINTVLMDS      360
FPRIRTVYMS AICCTAGFAI GLIYVTPGGQ FILELVDYYG GTFLALFSAI VEIIGIFWIY      420
GLENITLDIE FMLGIKTSFY WRCCWGFITP ALMIVVFVYA LISYEALEFG GYYIYPDAGY      480
VAGYLMLLAG IAFVPIFMFI TMYKNRTGNC TETAKKSFRP KKTWGPRDPV LREEWNMFKL      540
NARADRQIQG ASFFRHIWNI MTGGYRR                                          567

SEQ ID NO: 224            moltype = AA   length = 55
FEATURE                   Location/Qualifiers
source                    1..55
                          mol_type = protein
                          organism = Ostrinia furnacalis
SEQUENCE: 224
QPTLPWALCE PEWENCVPSA PGHNITITNE STSSAELFFL KTVLRQREGI EGGLG            55

SEQ ID NO: 225            moltype = AA   length = 636
FEATURE                   Location/Qualifiers
source                    1..636
                          mol_type = protein
                          organism = Plutella xylostella
SEQUENCE: 225
MSEGQTNLAF EESPEKDLNK SEAPEVVKST PGIGFVLEKG DNNNAEREEE EEPERAMWGN       60
QIEFLMSCIA TSVGLGNVWR FPFVAYQNGG GAFLIPYVIV LFLIGKPMYY LECAIGQFSS      120
RNSVKVWSLS PAMKGTGYAQ ALGCGYILSY YVAIIALCLF YLVKSFSAEL PWAVCDPAWG      180
ATCVPSGAGG GAPVAGGVSS AELYFTKTVL QQSDGIEGGL GAPIWYLTLC LFASWLIIFV      240
IVARGVKSSG KASYFLALFP YVVMLILLIR SATLTGAGDG ILFFLTPQWD KLIQLDVWYA      300
AVTQVFFSLS VGTGAIIMFS SYNGFRQNIY RDAMIVTTLD TFTSLMSGIT IFGILGNLAY      360
ELGYDDVNSV IGSGGTGLAF ISYPDAIAKS PFVPQLFAVL FFLMMSVLGV GSAVALLSTI      420
NTVMMDSFRR VPTVAMSAIC CSAGFLIGLV YVTPGGQYIL ELVDYYGGTF LVLFGAIAEI      480
VGVFWIYGLQ NICLDIEFML GIKTSVYWRF CWGIITPLMM IAVFIYALIS FEALVFGEDY      540
VYPTAGYVAG YMILLVGVAL VPLFIIITVT KYRTGDFPET LKKAFSPKAS WGPSRRSDKR      600
EWQAFKEQAK AEQDKAYTTK LNHLWTSLVG GYKRPF                                636

SEQ ID NO: 226            moltype = AA   length = 55
FEATURE                   Location/Qualifiers
source                    1..55
                          mol_type = protein
                          organism = Plutella xylostella
SEQUENCE: 226
SAELPWAVCD PAWGATCVPS GAGGGAPVAG GVSSAELYFT KTVLQQSDGI EGGLG            55

SEQ ID NO: 227            moltype = AA   length = 638
FEATURE                   Location/Qualifiers
source                    1..638
                          mol_type = protein
                          organism = Diabrotica virgifera
SEQUENCE: 227
MVRVEGQSQD SIIMDKDFPV GLENLGFQKE PSDYEKERNG DLTAVTVTTN EEAKERSQWG       60
NSTEFLMSCI AMSVGLGNIW RFPFIANKNG GGAFLIPYLI ILTFIGRPMY YMEMALGQFS      120
NRGSIKMYTK LSPVLKGIGY GQVVGSFCVA SYYCIIMAIT LVYLFNSFTS NFPWATCQFS      180
WQEYLDSRNL TCLDQSNTSI TGVETISSSE MYFRREVLKE VDDISDGIGL PDWKLAILVL      240
VTWLITYLVS VRGVKSSGKA SYFLAIFPYV VMFILFIRAA TLKGATEGML YFIKADFTKL      300
LDAEVWYAAV TQCFFSLGVG FGSIITLSSY NKFDHNINRD ALVVTTLDTF TSLLSGFTIF      360
GILGNLAHEM NVPPSEVISA GGGTGLAFIS YPDALSKPTF VPWLFSITFF FMLFVLGVGS      420
LVATHATLNT AIKDAFNIAD WKIAAFTSMV LFLVGMIYIT PGGQYILDLV DHFGGTFVIF      480
VCAILEVFAI TFLYGVENFC IDLEFMTKKK VGVYWRISWG VVMPLLLIVI FIYFVSTLKP      540
LVYGIYSLYY PTELTILGWS IIGIVIVQLF VWLLYFLGKN GHCSITKMFR DTFSTETWGP      600
EDPKAKEDWK KFRENRISER GLYSYPWLKR KMKILTGR                              638

SEQ ID NO: 228            moltype = AA   length = 61
FEATURE                   Location/Qualifiers
source                    1..61
                          mol_type = protein
                          organism = Diabrotica virgifera
SEQUENCE: 228
```

```
TSNFPWATCQ ESWQEYLDSR NLTCLDQSNT SITGVETISS SEMYFRREVL KEVDDISDGI    60
G                                                                    61

SEQ ID NO: 229          moltype = AA   length = 641
FEATURE                 Location/Qualifiers
source                  1..641
                        mol_type = protein
                        organism = Drosophila melanogaster
SEQUENCE: 229
MELKGVQPSN GSSNGSGNGA TNAASTEKTD AEKPTAERTN WGNGLEFLMS CISVSVGLGN    60
VWRFPPTAYE NGGGAFLIPY IIVLFLIGKP MYYLEMIMGQ FTSQGTVKIW SVVPGFVGVG   120
YGQAFGTICI ISYYSSLLAL TLYYLFVSFQ SELPWSYCRD EWTNCVNSRP QEYVDNLLTG   180
VSLANESARN LSGIVANDET EKLQSSSELY FLNVVIKEKL DISDGVGDPD WKLTLALFVA   240
WVVIFLVIMR GVKSSGKAAY FLALFPYVVL FVLLIRAVTL EGARDGILFF LEPQWGELLN   300
PTVWKEAVVQ CFFSLAVGSG PIIMFASYNR FDHGIYRDAM IVTTLDTLTS LLGGITIFAI   360
LGNLAHNLQI ENIRDVVRSG TGLAFISYPD AISKFQAVPQ LFSVLFFFML FVLGIGSIVA   420
LQSTIVTIIC DQFKGWKYWK VALTTSVCGF LMGLVYVTPG GQWILTLVDF YGGTYVVFIL   480
AIFELAGIVW VYGLQNFCDD IEFMCNRRVS LYWRVCWSFF TPVMMIIIFI YSMVTIEPIK   540
YSELYFPEAA NIAGWLLFAI GAAQFPPLWGL WYISRHPQGT YWKSLKASLK PSDRWGPANP   600
EIRREWVIFK NQKAAQRATQ KDTSKLGFFW RKVANFCGSN K                       641

SEQ ID NO: 230          moltype = AA   length = 78
FEATURE                 Location/Qualifiers
source                  1..78
                        mol_type = protein
                        organism = Drosophila melanogaster
SEQUENCE: 230
QSELPWSYCR DEWTNCVNSR PQEYVDNLLT GVSLANESAR NLSGIVANDE TEKLQSSSEL    60
YFLNVVIKEK LDISDGVG                                                  78

SEQ ID NO: 231          moltype = AA   length = 620
FEATURE                 Location/Qualifiers
source                  1..620
                        mol_type = protein
                        organism = Halyomorpha sp.
SEQUENCE: 231
MDVPLHHHHD CYHSDEECEA EDDIDTKRGR SGSLRRFSVP PRRESGSEAR TMDAAIRRPS    60
LAALADRGTW GSPWEFLLSC VGLSVGIGNV WRFPYLAYQN GGGKLIIDRV GCAMITVSLI   120
VCIYYNVIMS YTVFYMVASF DSEVPWSKCD PAWADMATCY VRGEPQSLAM NVTIPNRTIA   180
ENSSRETASL QYWERYVLKL SDGIENLGPI KWDLALCLLV SWCVVVLCLI KGIKTSGKVV   240
YFAATFPYVI LFTLLITGLL QEGAMSGVIY FIYPTWSKLL DIQVWQAAAG QMFFSLSVSM   300
GGLIMYSSYN DFRNNVYRDA LVVSVMDTVT SIISGIVTFS ILGAMAHDLQ VPISQVVKEG   360
PGLAFIAYPE ALLRLPAPQL WSVLFFLMLF ILGLDSEFAL LENVLTSLSD EFPILRKTKL   420
GFCIGTATFC YLIGLTCVTY GGNYVLTLMD VYGGGMAVLF IAIAESIALV WIYGLKNLCR   480
DMKFMLGFRP SFYWRITWVF TTPVILSVIF IYSLIEYKPL HYENYDYPDW ADGIGWVLAG   540
LSVLQIPFWA IVVVSRKKSD TFLGKVKEAI KPTKEWGPAD PRNKERWAEV VDATNSSKLK   600
YHNGMIMVSP EAEACLRKPV                                                620

SEQ ID NO: 232          moltype = AA   length = 68
FEATURE                 Location/Qualifiers
source                  1..68
                        mol_type = protein
                        organism = Halyomorpha sp.
SEQUENCE: 232
DSEVPWSKCD PAWADMATCY VRGEPQSLAM NVTIPNRTIA ENSSRETASL QYWERYVLKL    60
SDGIENLG                                                             68

SEQ ID NO: 233          moltype = AA   length = 605
FEATURE                 Location/Qualifiers
source                  1..605
                        mol_type = protein
                        organism = Halyomorpha sp.
SEQUENCE: 233
MGHATTPMGS TTKLVTDPNK GAGCWFCPSF STILAALSLS FSLGNTLRLP RLVLSHGGGT    60
FLVIYIGITV LFGIPLAFLE IVLGQFCQQG TTKLWRAVPL LKGVGYVKVL CSFLLAIYYP   120
VVMAISLFYG LWTVKGPLPF IECAHPLLHQ EVLGDSCLEK TFLTPPYKDI MWFSVNVTLL   180
FLLWAFVMLC VCRGSKSYRT AALFLTLPLI GLIAALLSMK LTQGYEGLNA LLTFSWEPVL   240
RFDTWYYAMV QFFFSTHIGF GNLTTCAGNI YSKSSAFWVA VGYIFCNIAA GIGMVVLVYS   300
WLGDNFATWH QIPILFVLTL IYDAASLQSN NGQLWASLAY LMIVLSGFTS MVALIYTIVV   360
SIVVETKNKW RSWLITAAIC AIGFILGVAI MLPEKLKFLH MLDHYVIGHM VAMSTALELV   420
GFLWVYGVDT LCNDFEFVLG YKLSKIWNTI WFTTPIFLVV VEVSSLFLLP LNGEDVEDDR   480
WVYLTGWFMY MFLWLIIIVV GLWQLCAQVD YNLAQKLHSS LKPTRNWGPV DPLYRHGWVQ   540
WRDSYQNTGE RDFTLKRRGT RDYTHSIKSE QRYNTMSLPR PNSTYVVQLP ENYWPKAQQK   600
KSTLS                                                                605

SEQ ID NO: 234          moltype = AA   length = 42
FEATURE                 Location/Qualifiers
source                  1..42
                        mol_type = protein
```

```
                            organism = Halyomorpha sp.
SEQUENCE: 234
KGPLPFIECA HPLLHQEVLG DSCLEKTFLT PPYKDIMWFS VN                    42
```